US007612075B2

(12) United States Patent
Ewing et al.

(10) Patent No.: US 7,612,075 B2
(45) Date of Patent: Nov. 3, 2009

(54) SUBSTITUTED OXOAZAHETEROCYCLYL COMPOUNDS

(75) Inventors: William R. Ewing, Yardley, PA (US); Michael R. Becker, Norristown, PA (US); Yong Mi Choi-Sledeski, Belle Mead, NJ (US); Heinz W. Pauls, Oakville, CA (US); Wei He, Audobon, PA (US); Stephen M. Condon, Newton, MA (US); Roderick S. Davis, West Chester, PA (US); Barbara A. Hanney, Pennsburg, PA (US); Alfred P. Spada, Carlsbad, CA (US); Christopher J. Burns, Malvern, PA (US); John Z. Jiang, Collegeville, PA (US); Michael R. Myers, Fishers, IN (US); Wan F. Lau, Groton, CT (US); Aiwen Li, Audubon, PA (US); Gregory B. Poli, Perkasie, PA (US); Mark A. Bobko, Exton, PA (US); Robert L. Morris, Wayne, PA (US); Joseph M. Karpinski, Douglassville, PA (US); Timothy F. Gallagher, Harleysville, PA (US); Kent W. Neuenschwander, Schwenksville, PA (US); Robert D. Groneberg, Boulder, CO (US); Jean-Francois Sabuco, Paris (FR)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 1162 days.

(21) Appl. No.: 10/628,093

(22) Filed: Jul. 25, 2003

(65) Prior Publication Data
US 2004/0102450 A1 May 27, 2004

Related U.S. Application Data

(63) Continuation of application No. 09/363,196, filed on Jul. 28, 1999, now abandoned, which is a continuation-in-part of application No. PCT/US99/01682, filed on Jan. 27, 1999.

(60) Provisional application No. 60/072,707, filed on Jan. 27, 1998.

(51) Int. Cl.
*A61K 31/497* (2006.01)
*C07D 401/06* (2006.01)
(52) U.S. Cl. .................... 514/252.13; 544/362
(58) Field of Classification Search .............. 544/362, 544/386; 514/252.13
See application file for complete search history.

(56) References Cited

U.S. PATENT DOCUMENTS

| 3,935,214 | A  | 1/1976  | Zellner |
| 5,559,232 | A  | 9/1996  | Ackermann et al. |
| 5,612,353 | A  | 3/1997  | Ewing et al. |
| 5,798,352 | A  | 8/1998  | Danilewicz |
| 5,877,174 | A  | 3/1999  | Ono et al. |
| 6,093,718 | A  | 7/2000  | Waterson et al. |
| 6,300,330 | B1 | 10/2001 | Sticker et al. |
| 6,335,341 | B1 | 1/2002  | Johnson et al. |
| 6,359,134 | B1 | 3/2002  | Tawada et al. |
| 6,369,063 | B1 | 4/2002  | Su et al. |
| 6,403,595 | B1 | 6/2002  | Tawada et al. |
| 6,525,042 | B1 | 2/2003  | Kobayashi et al. |

FOREIGN PATENT DOCUMENTS

| EP | 0365992     | 5/1990  |
| EP | 0783500     | 7/1998  |
| EP | 1048652     | 11/2000 |
| EP | 1054005     | 11/2000 |
| WO | WO 96/10022 | 4/1996  |
| WO | WO 97/06802 | 2/1997  |
| WO | WO 97/28129 | 8/1997  |
| WO | WO 97/29104 | 8/1997  |
| WO | WO 97/38984 | 10/1997 |
| WO | WO 98/09987 | 3/1998  |
| WO | WO 98/21188 | 5/1998  |
| WO | WO 98/46591 | 10/1998 |
| WO | WO 98/46626 | 10/1998 |
| WO | WO 98/46627 | 10/1998 |
| WO | WO 98/46628 | 10/1998 |

(Continued)

OTHER PUBLICATIONS

Abad-Zapatero, et al., Structure of a Secreted Aspartic Protease From Candida Albicans Complexed with a Potent Inhibitor: Implications for the Design Of Antifungal Agents, Chemical Abstract, 124:311048, XP-002195405, RN 176200-48-9, Protein Sci (1996) 5(4) 640-52.

(Continued)

*Primary Examiner*—James O. Wilson
*Assistant Examiner*—Ebenezer Sackey
(74) *Attorney, Agent, or Firm*—Ronald G. Ort; Jiang Lin

(57) ABSTRACT

This invention is directed to oxoazaheterocycyl compounds which inhibit Factor Xa, to oxoazaheterocycyl compounds which inhibit both Factor Xa and Factor IIa, to pharmaceutical compositions comprising these compounds, to intermediates useful for preparing these compounds, to a method of directly inhibiting Factor Xa and to a method of simultaneously directly inhibiting Factor Xa and Factor IIa.

15 Claims, No Drawings

FOREIGN PATENT DOCUMENTS

| WO | WO 98/54164 | 12/1998 |
| --- | --- | --- |
| WO | WO 99/06371 | 2/1999 |
| WO | WO 99/06395 | 2/1999 |
| WO | WO 99/09027 | 2/1999 |
| WO | WO 99/46267 | 9/1999 |

OTHER PUBLICATIONS

Struve, et al., Syntheses Of And Structural Assignments For Some N-Phosphono-2-iminoimidazolidines (Cyclic Guanidines), J. Org. Chem., vol. 42, No. 25, 1977 (4035-4040).

Yamawaki, et al., 1-Halophenyl-4-acyl-2-piperazinones, Chemical Abstract, 82:171054, XP002195404, JP 49 110680, Oct. 22, 1974.

1-Cyclohexyl-4-p-tolylsulfonyl-2-Piperazin one, Database Crossfire Beilstein, 565750, XP002195407, Collect. Czech. Chem. Commun. (1960), 25, 2651-2661.

4-(4-Methylphenyl) Sulfonyl I-1-Phenyl-2,6-Piperazinedione, Database Crossfire Beilstein, 838927, XP002195406, Nippon Kagaku Kaishi (1978), (12), 1661-5.

Tawada, et al. et al., Preparation of Sulfonamides As Inhibitors of Blood Coagulation Factor X, Chemical Abstract, vol. 131:170361, 1999.

SUBSTITUTED OXOAZAHETEROCYCLYL COMPOUNDS

This application is a continuation-in-part of International Patent Application No. PCT/US99/01682, filed on Jan. 27, 1999, which is, in turn, a continuation-in-part of U.S. Patent Application No. 60/072,707, filed Jan. 27, 1998, now abandoned.

FIELD OF THE INVENTION

This invention is directed to oxoazaheterocyclyl compounds which inhibit Factor Xa, to pharmaceutical compositions comprising these compounds, to intermediates useful for preparing these compounds and to a method of inhibiting Factor Xa. This invention is also directed to oxoazaheterocyclyl compounds which directly inhibit both Factor Xa and Factor IIa (thrombin), to pharmaceutical compositions comprising these compounds, to intermediates useful for preparing these compounds and to a method of simultaneously directly inhibiting both Factor Xa and Factor IIa (thrombin).

BACKGROUND OF THE INVENTION

Factor Xa and Factor Xa assembled in the prothrombinase complex (Factor Xa, Factor Va, calcium and phospholipid) activate prothrombin (Factor II) to generate thrombin (Factor IIa). Factor Xa is strategically located at the intersection of extrinsic and intrinsic pathways of the blood coagulation system. Thus, an inhibitor of Factor Xa inhibits the formation of thrombin and, therefore, is useful for preventing or treating disorders related to blood coagulation in mammals.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting (CABG) of the coronary or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening clots throughout the microvasculature of several organ systems.

In addition to their use in anticoagulant therapy, Factor Xa inhibitors are useful in the treatment or prevention of other diseases in which the generation of thrombin has been implicated as playing a physiologic role. For example, thrombin has been proposed to contribute to the morbidity and mortality of such chronic and degenerative diseases as arthritis, cancer, atherosclerosis and Alzheimer's disease by virtue of its ability to regulate many different cell types through specific cleavage and activation of a cell surface thrombin receptor, mitogenic effects, diverse cellular functions such as cell proliferation, for example, abnormal proliferation of vascular cells resulting in restenosis or angiogenesis, release of PDGF and DNA syntheses. Inhibition of Factor Xa will effectively block thrombin generation and therefore neutralize any physiologic effects of thrombin on various cell types.

The representative indications discussed above include some, but not all, of the possible clinical situations amenable to treatment with a Factor Xa inhibitor.

Oxoazaheterocyclyl Factor Xa inhibitors are disclosed in International Patent Application Numbers PCT/US98/07158, published Oct. 22, 1998; PCT/US98/07159, published Oct. 22, 1998; PCT/US98/07160, published Oct. 22, 1998; PCT/US98/07161, published Oct. 22, 1998; and PCT/US96/09290, published Dec. 19, 1996. Oxoazaheterocyclyl fibrinogen antagonists are disclosed in International Patent Application Number PCT/US92/09467, published May 13, 1993.

Vascular injury, caused by biochemical or physical perturbations, results in the activation of the coagulation system, culminating in the generation of thrombin. Thrombin promotes thrombus formation by catalyzing the transformation of fibrinogen to fibrin, by activating Coagulation Factor XIII, which stabilizes the thrombus, and by activating platelets. Thrombin promotes further thrombus growth by positive feedback to the coagulation cascade (activation of Coagulation Factors V and VIII), resulting in the explosive production of thrombin. Thrombin is present, and active, in the thrombi of patients with thrombotic vascular disease. Thrombin inhibition prevents the action of thrombin after thrombin has been activated from prothrombin. An inhibitor of thrombin inhibits cleavage of fibrinogen to fibrin, activation of Factor XIIIa, activation of platelets, and feedback of thrombin to the coagulation cascade to generate more thrombin. Consequently, inhibition of thrombin activity with a direct thrombin inhibitor would be useful for preventing or treating disorders related to blood coagulation in mammals.

The combined inhibitors of Factor Xa and Factor IIa described herein inhibit thrombin activity (via IIa inhibition) and thrombin production (via Factor Xa inhibition). Therefore, these agents inhibit any thrombin that may be present and also inhibit the further production of thrombin. Other agents which have this dual activity include heparin and low molecular weight heparins (LMWHs), which have demonstrated efficacy in thrombotic diseases. However, heparin and LMWHs act indirectly through a cofactor, antithrombin-III (ATIII), to inhibit Xa and IIa. The heparin/ATIII complex is too large, however, to inhibit thrombus-bound Xa and IIa, thus limiting its efficacy. Direct inhibitors of Factor Xa and Factor IIa, as described herein, are capable of inhibiting soluble and thrombus-bound Xa and IIa, thus providing an important therapeutic advantage over currently available Xa/IIa inhibitors.

SUMMARY OF THE INVENTION

This invention is directed to a compound of formula I

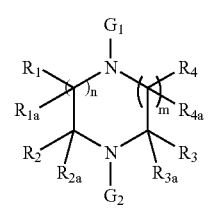

I or a pharmaceutically acceptable salt thereof, pharmaceutically acceptable prodrug thereof, an N-oxide thereof, a hydrate thereof or a solvate thereof wherein G$_1$ and G$_2$ are L$_1$-Cy$_1$ or L$_2$-Cy$_2$, provided that when R$_1$ and R$_{1a}$ or R$_4$ and R$_{4a}$ taken together form O or S, then G$_1$ is L$_2$-Cy$_2$ and G$_2$ is L$_1$-Cy$_1$, or when R$_2$ and R$_{2a}$ or R$_3$ and R$_{3a}$ taken together form O or S, then G$_1$ is L$_1$-Cy$_1$ and G$_2$ is L$_2$-Cy$_2$;

Cy$_1$ and Cy$_2$ are independently selected from optionally substituted aryl, optionally substituted heteroaryl, optionally substituted cycloalkyl, optionally substituted cycloalkenyl, optionally substituted heterocyclyl, optionally substituted heterocyclenyl, optionally substituted fused arylcycloalkyl, optionally substituted fused arylcycloalkenyl, optionally substituted fused arylheterocyclyl, optionally substituted fused arylheterocyclenyl, optionally substituted fused heteroarylcycloalkyl, optionally substituted fused heteroarylcycloalkenyl, optionally substituted fused heteroarylheterocyclyl and optionally substituted fused heteroarylheterocyclenyl;

L$_1$ is absent, O, NR$_5$, —S(O)p-, —S(O)pNR$_5$—, —C(X)Y— or -L$_3$-Q-L$_4$-Q'-L$_5$-, —C(O)Y—C(X)Y—, —C(X)YC(O)—, —C(C)NR$_5$—S(O)p-, or —C(O)C(O)NR$_5$S(O)p-;

L$_2$ is absent or a group of formula

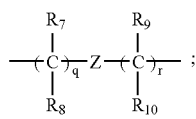

L$_3$ and L$_5$ are independently absent, optionally substituted alkylene, optionally substituted alkenylene or optionally substituted alkynylene;

L$_4$ is optionally substituted alkylene, optionally substituted alkenylene, or optionally substituted alkynylene;

Q and Q' are independently absent, O, S, NR$_5$, —S(O)p-, —S(O)pNR$_5$— or —C(X)Y—;

A is CH or N;

R$_1$, R$_{1a}$, R$_2$, R$_{2a}$, R$_3$, R$_3$a, R$_4$ and R$_{4a}$ are independently selected from hydrogen, carboxy, alkoxycarbonyl, Y$_1$Y$_2$NC(O)—, optionally substituted alkyl, optionally substituted aryl, optionally substituted aralkyl, optionally substituted heteroaryl and optionally substituted heteroaralkyl, or R$_1$ and R$_{1a}$, R$_2$ and R$_{2a}$, R$_3$ and R$_{3a}$, or R$_4$ and R$_{4a}$ taken together form O or S; or R$_1$ and R$_2$ together with the carbon atoms through which R$_1$ and R$_2$ are linked form a cycloalkyl group, cycloalkenyl group, heterocyclyl group, or heterocyclenyl group; or R$_3$ and R$_4$ together with the carbon atoms through which R$_3$ and R$_4$ are linked form a cycloalkyl group, cycloalkenyl group, heterocyclyl group, or heterocyclenyl group; or R$_{1a}$ and R$_{2a}$ are absent and R$_1$ and R$_2$ together with the carbon atoms through which R$_1$ and R$_2$ are linked form an aryl or heteroaryl group; or R$_{3a}$ and R$_{4a}$ are absent and R$_3$ and R$_4$ together with the carbon atoms through which R$_3$ and R$_4$ are linked form an aryl or heteroaryl group; or one or more of the pairs R$_1$ and R$_{1a}$ taken together with the carbon atom through which they are linked form a 3 to 7 membered cycloalkyl or cycloalkenyl group; or R$_2$ and R$_{2a}$ taken together with the carbon atom through which they are linked form a 3 to 7 membered cycloalkyl or cycloalkenyl group; or R$_3$ and R$_{3a}$ taken together with the carbon atom through which they are linked form a 3 to 7 membered cycloalkyl or cycloalkenyl group; or R$_4$ and R$_{4a}$ taken together with the carbon atom through which they are linked form a 3 to 7 membered cycloalkyl or cycloalkenyl group;

m and n are independently 0, 1 or 2, provided that m and n are not both 0 and further provided that when R$_1$ and R$_{1a}$ taken together form O or S, n is 1, and when R$_4$ and R$_{4a}$ taken together form O or S, m is 1;

R$_5$ is hydrogen, optionally substituted alkyl, optionally substituted aralkyl, optionally substituted heteroaralkyl, R$_6$O(CH$_2$)v-, R$_6$O$_2$C(CH$_2$)x-,Y$_1$Y$_2$NC(O)(CH$_2$)x-, or Y$_1$Y$_2$N(CH$_2$)v-;

R$_6$ is hydrogen, optionally substituted alkyl, optionally substituted aralkyl or optionally substituted heteroaralkyl;

Y$_1$ and Y$_2$ are independently hydrogen, optionally substituted alkyl, optionally substituted alkoxy, optionally substituted aryloxy, optionally substituted aryl, optionally substituted aralkyl or optionally substituted heteroaralkyl, or Y$_1$ and Y$_2$ taken together with the N through which Y$_1$ and Y$_2$ are linked form a monocyclic heterocyclyl;

R$_7$, R$_8$, R$_9$ and R$_{10}$ are independently selected from hydrogen, hydroxy, alkoxy, optionally substituted alkyl, optionally substituted aryl, optionally substituted heteroaryl, optionally substituted aralkyl and optionally substituted heteroaralkyl, provided that only one of R$_7$ and R$_8$ or one of R$_9$ and R$_{10}$ is hydroxy or alkoxy, and further provided when any of R$_7$, R$_8$, R$_9$ and R$_{10}$ is hydroxy or alkoxy, then the hydroxy or alkoxy is not α substituted to an N, O or S in Z;

X is O or S;

Y is absent or is selected from O, S and NR$_5$;

Z is absent or is selected from optionally substituted lower alkenylene, optionally substituted lower alkynylene, O, —C(O)—, S(O)p, NR$_5$, —NR$_5$C(O)— and —C(O)NR$_5$—;

x is 1, 2, 3 or 4;

v is 2, 3 or 4;

p is 1 or 2; and q and r are independently 0, 1, 2 or 3, provided that q and r are not both 0.

In another aspect, this invention is directed to a pharmaceutical composition comprising a therapeutically effective amount of the compound of formula I or formula II and a pharmaceutically acceptable carrier.

In another aspect, this invention is directed to a method of treating a physiological disorder capable of being modulated by inhibiting Factor Xa comprising administering to a patient in need of such treatment a therapeutically effective amount of a compound of formula I or formula II.

In another aspect, this invention is directed to a compound of formula III

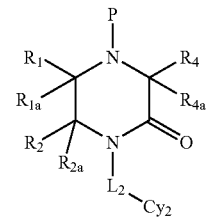

wherein

P is H or a nitrogen protecting group;

R$_1$, R$_{1a}$, R$_2$, R$_{2a}$, R$_4$ and R$_{4a}$ are independently selected from hydrogen, carboxy, alkoxycarbonyl, Y$_1$Y$_2$NC(O)—, optionally substituted alkyl, optionally substituted aryl, optionally substituted aralkyl, optionally substituted heteroaryl and optionally substituted heteroaralkyl, or R$_1$ and R$_{1a}$, R$_2$ and R$_{2a}$ or R$_4$ and R$_{4a}$ taken together form O or S;

or $R_1$ and $R_2$ together with the carbon atoms through which $R_1$ and $R_2$ are linked form a cycloalkyl group, cycloalkenyl group, heterocyclyl group, or heterocyclenyl group; or $R_{1a}$ and $R_{2a}$ are absent and $R_1$ and $R_2$ together with the carbon atoms through which $R_1$ and $R_2$ are linked form an aryl or heteroaryl group; or $R_1$ and $R_{1a}$ taken together with the carbon atom through which they are linked form a 3 to 7 membered cycloalkyl or cycloalkenyl group; or $R_2$ and $R_{2a}$ taken together with the carbon atom through which they are linked form a 3 to 7 membered cycloalkyl or cycloalkenyl group; or $R_4$ and $R_{4a}$ taken together with the carbon atom through which they are linked form a 3 to 7 membered cycloalkyl or cycloalkenyl group;

$L_2$ is absent or a group of formula

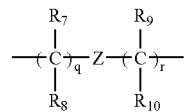

$Cy_2$ is selected from optionally substituted aryl, optionally substituted heteroaryl, optionally substituted cycloalkyl, optionally substituted cycloalkenyl, optionally substituted heterocyclyl, optionally substituted heterocyclenyl, optionally substituted fused arylcycloalkyl, optionally substituted fused arylcycloalkenyl, optionally substituted fused arylheterocyclyl, optionally substituted fused arylheterocyclenyl, optionally substituted fused heteroarylcycloalkyl, optionally substituted fused heteroarylcycloalkenyl, optionally substituted fused heteroarylheterocyclyl and optionally substituted fused heteroarylheterocyclenyl;

$R_5$ is hydrogen, optionally substituted alkyl, optionally substituted aralkyl, optionally substituted heteroaralkyl, $R_6O(CH_2)v$-, $R_6O_2C(CH_2)x$-, $Y_1Y_2NC(O)(CH_2)x$-, or $Y_1Y_2N(CH_2)v$-;

$R_6$ is hydrogen, optionally substituted alkyl, optionally substituted aralkyl or optionally substituted heteroaralkyl;

$Y_1$ and $Y_2$ are independently hydrogen, optionally substituted alkyl, optionally substituted aryl, optionally substituted aralkyl or optionally substituted heteroaralkyl, or $Y_1$ and $Y_2$ taken together with the N through which $Y_1$ and $Y_2$ are linked form a monocyclic heterocyclyl;

$R_7$, $R_8$, $R_9$ and $R_{10}$ are independently selected from hydrogen, hydroxy, alkoxy, optionally substituted alkyl, optionally substituted aryl, optionally substituted heteroaryl, optionally substituted aralkyl and optionally substituted heteroaralkyl, provided that only one of $R_7$ and $R_8$ or one of $R_9$ and $R_{10}$ is hydroxy or alkoxy, and further provided when $R_7$, $R_8$, $R_9$ and $R_{10}$ is hydroxy or alkoxy, then the hydroxy or alkoxy is not α substituted to a N, O or S in Z;

Z is absent or is selected from optionally substituted lower alkenylene, optionally substituted lower alkynylene, O, S(O)p, —C(O)—, $NR_5$, —$NR_5C(O)$— and —C(O)$NR_5$—;

x is 1, 2, 3 or 4;

v is 2, 3 or 4; and q and r are independently 0, 1, 2 or 3, provided that q and r are not both 0, which is an intermediate useful in the preparation of the compound of formula I or formula II

DETAILED DESCRIPTION OF THE INVENTION

Definitions

As used above, and throughout the description of the invention, the following terms, unless otherwise indicated, shall be understood to have the following meanings:

"Derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

"Patient" includes both human and other mammals.

"Alkyl" means an aliphatic hydrocarbon group, which may be straight or branched chain, having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl may be substituted with one or more "alkyl group substituents" which may be the same or different, and include halo, cycloalkyl, cycloalkenyl, heterocyclyl, heterocyclenyl, hydroxy, oxime, alkylthio, alkylsulfinyl, alkylsulfonyl, arylthio, arylsulfinyl, arylsulfonyl, heteroarylthio, heteroarylsulfinyl, heteroarylsulfonyl, isourea, guanidino, acylhydrazino, alkoxy, amino, carbamoyl, acylamino, aroylamino, carboxy, alkoxycarbonyl, aralkyloxycarbonyl and heteroaralkyloxycarbonyl. Representative alkyl groups include methyl, trifluoromethyl, cyclopropylmethyl, cyclopentylmethyl, ethyl, n-propyl, i-propyl, n-butyl, t-butyl, n-pentyl, 3-pentyl, methoxyethyl, carboxymethyl, methoxycarbonylethyl, benzyloxycarbonylmethyl, and pyridylmethyloxycarbonylmethyl.

"Alkenyl" means a straight or branched aliphatic hydrocarbon group containing a carbon-carbon double bond and having about 2 to about 15 carbon atoms in the chain. Preferred alkenyl groups have 2 to about 6 carbon atoms in the chain. Branched means that one or more lower alkyl groups such as methyl, ethyl or propyl are attached to a linear alkenyl chain. "Lower alkenyl" means about 2 to about 4 carbon atoms in the chain which may be straight or branched. The alkenyl group may be substituted by one or more alkyl group substituents as defined herein. Representative alkenyl groups include ethenyl, propenyl, n-butenyl, i-butenyl, 3-methylbut-2-enyl, n-pentenyl, heptenyl, octenyl, decenyl, and the like.

"Alkylene" means a straight or branched bivalent hydrocarbon chain having from 1 to about 20 carbon atoms. The preferred alkylene groups are the lower alkylene groups having from 1 to about 6 carbon atoms. Alkylene may be substituted with 1 or more alkyl group substituents as defined herein. Representative alkylene groups include methylene, ethylene, and the like.

"Alkenylene" means a bivalent group derived from a straight or branched chain hydrocarbon containing at least one carbon-carbon triple bond. The preferred alkenylene groups are the lower alkenylene groups having from 1 to about 6 carbon atoms. Alkenylene group may be substituted by one or more alkyl group substituents as defined herein. Representative alkenylene groups include —CH=CH—, —CH$_2$CH=CH—, —C(CH$_3$)=CH—, —CH$_2$CH=CHCH$_2$—, and the like.

"Alkynylene" means a bivalent group derived from a straight or branched chain hydrocarbon containing at least one carbon-carbon double bond. Preferred alkynylene groups are the lower alkynylene groups having from 1 to about 6 carbon atoms. Alkynylene may be substituted by one or more alkyl group substituents as defined herein. Representative akynylene include —CH≡CH—, —CH≡CH—CH₂—, —CH≡CH—CH(CH₃)—, and the like.

"Aralkylamino" means a (arylalkyl)(Y₂)N— group wherein the arylalkyl portion and Y₂ are as herein defined.

"Heteroaralkylamino" means a (heteroaralkyl)(Y₂)N— group wherein the heteroaralkyl portion and Y₂ are as defined herein.

"Heterocyclylalkyl" means a heterocyclyl-alkylene- group wherein the heterocyclyl portion and alkylene portion are as defined herein.

"Heterocyclylalkylamino" means a (heterocyclylalkyl)(Y₂)N— group wherein the heterocyclylalkyl portion and Y₂ are as defined herein.

"Heterocyclenylalkyl" means a heterocyclenyl-alkylene- group wherein the heterocyclenyl portion and alkylene portion are as defined herein.

"Heterocyclenylalkylamino" means a (heterocyclenylalkyl)(Y₂)N— group wherein the heterocyclenylalkyl portion and Y₂ are as defined herein.

"Alkoxyalkyl" means an alkoxy-alkylene- group wherein the alkoxy portion and alkylene portion are as defined herein.

"Alkylthioalkyl" means an alkylthio-alkylene- group wherein the alkylthio portion and alkylene portion are as defined herein.

"Alkylsulfinylalkyl" means an alkylsulfinyl-alkylene- group wherein the alkylsulfinyl portion and alkylene portion are as defined herein.

"Alkylsulfonylalkyl" means an alkylsulfinyl-alkylene- group wherein the alkylsulfinyl portion and alkylene portion are as defined herein.

"Acylalkyl" means an acyl-alkylene- group wherein the acyl portion and alkylene portion are as defined herein.

"Acylaminoalkyl" means an acyl-NH-alkylene- group wherein the acyl portion and alkylene portion are as defined herein.

"Carbamoylalkyl" means an carbamoyl-alkylene- group wherein the carbamoyl portion and alkylene portion are as defined herein.

"Heterocyclylalkyloxycarbonyl" means a heterocyclylalkyl-O—C(O)— group wherein the heterocyclylalkyl portion is as defined herein.

"Isourea" means a group of formula

wherein $R_{11}$ is as defined herein and $R_{11a}$ is hydrogen, optionally substituted lower alkyl, optionally substituted aryl, or optionally substituted heteroaryl.

"Acylhydrazino" means a group of formula $Y_1Y_2N$—NHC(O)—, wherein $Y_1$ and $Y_2$ are as defined herein.

"Guanidino" or "guanidine" means a group of formula

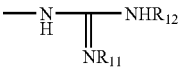

wherein $R_{11}$ and $R_{12}$ are as defined herein.

"Amidino" or "amidine" means a group of formula

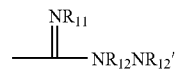

wherein $R_{11}$ is selected from hydrogen, $R_6O_2C$—, $R_6O$—, $R_6C(O)$—, cyano, optionally substituted lower alkyl, nitro or $Y_1Y_2N$— and $R_{12}$ and $R_{12}'$ are independtly selected from hydrogen, optionally substituted lower alkyl, optionally substituted aralkyl and optionally substituted heteroaralkyl. Preferred amidino groups are those in which $R_{11}$ is hydrogen, $R_6O$, or optionally substituted lower alkyl and $R_{12}$ is as defined above. Most preferred amidino groups are those in which $R_{11}$ and $R_{12}$ are hydrogen.

"Carbamate" means a group of formula $Y_1Y_2C(O)NH$— wherein $Y_1$ is as defined herein; $Y_2$ is selected from optionally substituted alkoxy or optionally substituted aryloxy. "Alkylcarbamate" means a group of formula $Y_1Y_2C(O)NH$— wherein $Y_1$ and $Y_2$ are independently alkyl. More prefered alkylcarbamate groups are methylcarbamate, ethylcarbamate, t-butylcarbamate, benzylcarbamate and phenylcarbamate.

"Aminoalkylamino" means a $Y_1Y_2N$-alkylene-$(Y_2)N$— group wherein $Y_1$, $Y_2$ and alkylene are as defined herein.

"Aryloxycarbonylalkyl" means a aryl-O—C(O)-alkylene group wherein the aryl portion and alkylene portion are as defined herein.

"Heteroaryloxycarbonylalkyl" means a hetoaryl-O—C(O)-alkylene group wherein the heteroaryl portion and alkylene portion are as defined herein.

"Heterocycloxycarbonylalkyl" means a heterocyclyl-O—C(O)-alkylene group wherein the heterocyclyl portion and alkylene portion are as defined herein.

"Heterocyclenyloxycarbonylalkyl" means a heterocyclenyl-O—C(O)-alkylene group wherein the heterocyclenyl portion and alkylene portion are as defined herein.

"Basic nitrogen atom" means an $sp^2$ or $sp^3$ hybridized nitrogen atom having a non-bonded pair of electrons which is capable of being protonated. Examples of basic nitrogen atoms, which may be optionally substituted where possible, include those in heteroaryl, heterocyclyl, heterocyclenyl, fused arylheterocyclyl, fused arylheterocyclenyl, fused heteroarylcycloalkyl, fused heteroarylcycloalkenyl, fused heteroarylheterocyclyl, fused heterocyclylheterocyclenyl, imino, amino, isourea, acylhydrazino, guanidino and amidino groups.

"Cycloalkyl" means a non-aromatic mono- or multicyclic hydrocarbon ring system of about 3 to about 10 carbon atoms. Representative monocyclic cycloalkyl rings include cyclopentyl, cyclohexyl, cycloheptyl, and the like. Representative multicyclic cycloalkyl rings include decalinyl, norbornyl, adamantyl, and the like. The cycloalkyl group is optionally substituted with one or more "cycloalkyl group substituents" which may be the same or different, where "cycloalkyl group substituent" includes oxo (O=), thioxo (S=), methylene (H₂C=), oxime (HO—N=), alkyl, aryl, heteroaryl, heterocyclyl, heterocyclenyl, cycloalkyl, cycloalkenyl, acylhydrazino, aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, acylamino, aroylamino, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amidino, amino, carbamoyl, or sulfamoyl. Preferred cycloalkyl group substituents are amino and amidino.

"Cycloalkenyl" means a non-aromatic monocyclic or multicyclic hydrocarbon ring system containing a carbon-carbon double bond and having about 3 to about 10 carbon atoms. The cycloalkenyl group is optionally substituted by one or more cycloalkyl group substituents as defined herein. Representative monocyclic cycloalkenyl rings include cyclopentenyl, cyclohexenyl or cycloheptenyl, and the like. A representative multicyclic cycloalkenyl ring is norbornylenyl. Preferred cycloalkenyl group substituents are amino and amidino.

"Carboxy" means a group of formula HO(O)C— (carboxylic acid group).

"Heterocyclyl" means a non-aromatic saturated monocyclic or multicyclic ring system of about 3 to about 10 ring atoms wherein the ring system contains one or more element(s) other than carbon. Preferred heterocyclyl comprise about 5 to about 7 ring atoms, more preferred 5 to 6 ring atoms, wherein one or two of the ring atoms is/are independently selected from oxygen, nitrogen or sulfur respectively. "Aza", "oxa" or "thia", when used as a prefix before heterocyclyl means that the ring system contains at lease one nitrogen, oxygen and sulfur atom. For example, "azaheterocyclyl" means a heterocyclyl group wherein one or more of the atoms in the ring system is/are nitrogen. The heterocyclyl group is optionally substituted with one or more heterocyclyl group substituents which may be the same or different, where "heterocyclyl group substituent" "includes oxo (O=), thioxo (S=), methylene ($H_2C$=), oxime (HO—N=), alkyl, aryl, heteroaryl, heterocyclyl, heterocyclenyl, cycloalkyl, cycloalkenyl, acylhydrazino, aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, acylamino, aroylamino, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amino, carbamoyl, and sulfamoyl. Preferred heterocyclyl group substituents include amino, amidino, halogen, hydroxy, alkoxycarbonylalkyl and carboxyalkyl. Representative heterocyclyl groups include piperidyl, pyrrolidinyl, piperazinyl, pyrazolidinyl, imidazolinyl, hexamethyleneimine, homopiperazine, tetrahydrofuryl, morpholinyl, thiomorpholinyl, thiazolidinyl, 1,3-dioxolanyl, 1,4-dioxanyl, 1,4-dithianyl, 1,3,5-triathianyl, tetrahydrothienyl, tetrahydrothiopyranyl, quinuclidinyl, and the like. The thio or nitrogen moiety of the heterocyclyl may also be optionally oxidized to the corresponding S-oxide, S,S-dioxide or N-oxide.

"Heterocyclenyl" means a heterocyclyl group as defined herein which contains at least one carbon-carbon or carbon-nitrogen double bond. "Aza", "oxa" or "thia", when used as a prefix before heterocyclenyl group means that the ring system contains at lease one nitrogen, oxygen or sulfur atom respectively. The heterocyclenyl group is optionally substituted with one or more heterocyclyl group substituents as defined herein. Representative heterocyclenyl groups include 2H-pyrrolyl, 2-pyrrolinyl, 3-pyrrolinyl, 2-imidazolinyl, 2-pyrazolinyl, 2H-pyranyl, 1,2-dihydropyridyl, 1,4-dihydropyridyl, 1,2,3,4-tetrahydropyridyl, tetrahydrothiophenyl, tetrahydrothiopyranyl, and the like. Preferred heterocyclenyl group substituents include amino, amidino, halogen, hydroxy, oxo, thioxo, methylene, oxime, alkoxycarbonylalkyl and carboxyalkyl. The thio or nitrogen moiety of the heterocyclyl may also be optionally oxidized to the corresponding N-oxide, S-oxide or S,S-dioxide.

"Aryl" means a 6 to 10 membered aromatic monocyclic or multicyclic hydrocarbon ring system. The aryl group is optionally substituted with one or more "aryl group substituents" which may be the same or different, where "aryl group substituent" includes alkyl, aryl, heteroaryl, heterocyclyl, heterocyclenyl, cycloalkyl, cycloalkenyl, acylhydrazino, aralkyl, heteroaralkyl, aryldiazo, heteroaryldiazo, hydroxy, alkylcarbamate, acylhydrazino, alkoxy, aryloxy, aralkoxy, acyl, aroyl, halo, nitro, cyano, carboxy, alkoxycarbonyl, aryloxycarbonyl, aralkoxycarbonyl, acylamino, aroylamino, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, arylazo, heteroarylazo, amino, amidino, alkylamino, carbamoyl, and sulfamoyl. Preferred aryl groups are optionally substituted phenyl or optionally substituted naphthyl. Preferred aryl group substituents include alkyl, aryl, heteroaryl, heterocyclyl, heterocyclenyl, cycloalkyl, cycloalkenyl, acylhydrazino, carboxy, sulfamoyl, alkylcarbamate, hydroxy, acyl, aroyl, halo, nitro, cyano, alkoxycarbonyl, acylamino, alkylthio, alkylamino, amino, carbamoyl, thiocarbamoyl and amidino.

"Heteroaryl" means about a 5- to about a 10-membered aromatic monocyclic or multicyclic ring system wherein one or more of the atoms in the ring system is/are element(s) other than carbon. Preferred heteroaryl groups contain one to about 4 heteroatoms selected from oxygen, nitrogen and sulfur. "Aza", "oxa" or "thia", when used as a prefix before heteroaryl means that the ring system contains at lease one nitrogen, oxygen or sulfur atom. The heteroaryl group is optionally substituted with one or more aryl group substituents as defined herein. Representative heteroaryl groups include pyrrolyl, pyrazinyl, furyl, thienyl, pyridyl, pyrimidyl, pyridazinyl, isoxazolyl, isothiazolyl, oxazolyl, thiazolyl, pyrazolyl, triazolyl, oxadiazolyl, thiadiazolyl, thienopyridyl, thienopyrolyl, thieno[3,2-d]pyrimidyl, pyrrolopyridyl, furanopyridyl, furazanyl, quinoxalinyl, quinazolinyl, quinolizinyl, imidazo[1,2-a]pyridyl, phthalazinyl, imidazo[2,1-b]thiazolyl, benzofuranyl, indolyl, isoindolyl, indolizinyl, indazolyl, azaindolyl, benzimidazolyl, benzothienyl, benzisoxazolyl, benzothiazolyl, purinyl, benzotriazolyl, 1,8-naphthyridinyl, pteridinyl, quinolinyl, imidazolyl, isoquinolinyl, cinnolinyl, triazinyl, benzotriazinyl, and the like. Preferred heteroaryl group substituents include hydrogen, alkyl, aryl, heteroaryl, heterocyclyl, heterocyclenyl, cycloalkyl, cycloalkenyl, acylhydrazino, hydroxy, acyl, aroyl, halo, nitro, cyano, carboxy, acylhydrazino, alkoxycarbonyl, acylamino, alkylthio, alkylamino, amino, carbamoyl, thiocarbamoyl and amidino. When the heteroaryl groups contains a nitrogen atom, the nitrogen atom may be oxidized to the N-oxide.

"Fused arylcycloalkyl" means a fused aryl and cycloalkyl, wherein the ayl and cycloalkyl portions are as defined herein. Preferred fused arylcycloalkyls groups are those wherein the aryl thereof is phenyl and the cycloalkyl consists of about 5 to about 6 carbon atoms. Representative fused phenylcycloalkyl groups include 1,2,3,4-tetrahydronaphthyl, indanyl, and the like. The fused arylcycloalkyl group is optionally substituted with one or more fused arylcycloalkyl group substituents selected from, alkyl, aryl, heteroaryl, heterocyclyl, heterocyclenyl, cycloalkyl, cycloalkenyl, acylhydrazino, aralkyl, heteroaralkyl, aryldiazo, heteroaryldiazo, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, acylamino, aroylamino, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, arylazo, heteroarylazo, amino, alkylamino, carbamoyl and sulfamoyl. The cycloalkyl moiety is further optionally substituted with oxo (O=), thioxo (S=), methylene (H$_2$C=), or oxime (HO—N=). Preferred fused phenylcycloalkyl group substituents include alkyl, aryl, heteroaryl, heterocyclyl, heterocyclenyl, cycloalkyl, cycloalkenyl, acylhydrazino, hydroxy, acyl, aroyl, halo, nitro, cyano, alkoxycarbonyl, acylamino, alkylthio, alkylamino, amino, carbamoyl, thiocarbamoyl and amidino.

"Fused arylcycloalkenyl" means a fused aryl and cycloalkenyl, wherein the aryl and cycloalkenyl portions are as defined herein. Preferred fused arylcycloalkyenl groups are those wherein the aryl thereof is phenyl and the cycloalkenyl consists of about 5 to about 6 carbon atoms. The fused arylcycloalkenyl is optionally substituted with one or more fused arylcycloalkyl group substituents as defined herein. Representative fused phenylcycloalkenyl groups include 1,2-dihydronaphthylenyl, indenyl, and the like. The cycloalkyl moiety is further optionally substituted with oxo (O=), thioxo (S=), methylene (H$_2$C=), oxime (HO—N=). Preferred substituents include alkyl, aryl, heteroaryl, heterocyclyl, heterocyclenyl, cycloalkyl, cycloalkenyl, acylhydrazino, hydroxy, acyl, aroyl, halo, nitro, cyano, alkoxycarbonyl, acylamino, alkylthio, alkylamino, amino, carbamoyl, thiocarbamoyl and amidino.

"Fused arylheterocyclyl" means a fused aryl and heterocyclyl, wherein the aryl and heterocyclyl portions are as defined herein. Preferred fused arylheterocyclyl groups are those wherein the aryl portion thereof is phenyl and the heterocyclyl portion consists of about 5 to about 7 ring atoms, more preferred 5 to 6 ring atoms, wherein one or two of the ring atoms is/are independently selected from oxygen, nitrogen and sulfur. "Aza", "oxa" or "thia", when used as a prefix before the heterocyclyl portion of the fused arylheterocyclyl means that the heterocyclyl contains at lease one nitrogen, oxygen or sulfur atom. Representative preferred fused phenylheterocyclyl ring systems include indolinyl, 1,2,3,4-tetrahydroisoquinolinyl, 1,2,3,4-tetrahydroquinolinyl, 2,3-dihydrobenzofuran, 1H-2,3-dihydroisoindolyl, 2,3-dihydrobenz[f]isoindolyl, 1,2,3,4-tetrahydrobenz[g]isoquinolinyl, and the like. The fused phenylheterocyclyl group is optionally substituted with one or more fused phenylcycloalkyl group substituents as defined herein. The heterocyclyl portion is further optionally substituted with oxo (O=), thioxo (S=), methylene (H$_2$C=) or oxime (HO—N=). Preferred substituents include alkyl, aryl, heteroaryl, heterocyclyl, heterocyclenyl, cycloalkyl, cycloalkenyl, acylhydrazino, hydroxy, acyl, aroyl, halo, nitro, cyano, alkoxycarbonyl, acylamino, alkylthio, alkylamino, amino, carbamoyl, thiocarbamoyl and amidino. The nitrogen or sulphur atom of the heterocyclyl may also be optionally oxidized to the corresponding N-oxide, S-oxide or S,S-dioxide.

"Fused arylheterocyclenyl" means a fused aryl and heterocyclenyl, wherein the aryl and hterocyclenyl portions are as defined herein. "Aza", "oxa" or "thia", when used as a prefix before the heterocyclenyl portion of the fused arylheterocyclenyl group means that the heterocyclenyl portion contains at lease one nitrogen, oxygen or sulfur atom. Preferred fused arylheterocyclyl groups are those wherein the aryl thereof is phenyl and the heterocyclyl consists of about 5 to 6 ring atoms wherein one or two of the ring atoms is/are independently selected from oxygen, nitrogen and sulfur. Representative preferred fused arylheterocycloalkenyl ring systems include 3H-indolinyl, 3H-quinazolin-4-one, 1,1-dioxobenzo[d]isothiazolyl, 1H-2-oxoquinolyl, 2H-1-oxoisoquinolyl, and the like. The fused arylheterocyclenyl group is optionally substituted with one or more fused arylcycloalkyl group substituents as defined herein. The heterocyclyl portion is further optionally substituted with oxo (O=), thioxo (S=), methylene (H$_2$C=) or oxime (HO—N=). Preferred substituents include alkyl, aryl, heteroaryl, heterocyclyl, heterocyclenyl, cycloalkyl, cycloalkenyl, acylhydrazino, hydroxy, acyl, aroyl, halo, nitro, cyano, alkoxycarbonyl, acylamino, alkylthio, alkylamino, amino, carbamoyl, thiocarbamoyl and amidino. The nitrogen or sulphur atom of the heterocyclenyl is optionally oxidized to the corresponding N-oxide, S-oxide or S,S-dioxide.

"Fused heteroarylcycloalkyl" means a fused heteroaryl and cycloalkyl, wherein the heteroaryl and cycloalkyl portions are as defined herein. "Aza", "oxa" or "thia", when used as a prefix before the heteroaryl portion of the fused heteroarylcycloalkyl group means that the heteroaryl portion contains at lease one nitrogen, oxygen or sulfur atom. Preferred fused heteroarylcycloalkyl groups are those wherein the heteroaryl portion thereof consists of about 5 to about 6 ring atoms in which one or two of the ring atoms are independently selected from oxygen, nitrogen and sulfur and the cycloalkyl consists of about 5 to about 6 ring atoms. Representative preferred fused heteroarylcycloalkyl groups include 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, 5,6,7,8-tetrahydrobenzothiazolyl, 5,6-dihydro-4H-benzothiazol-7-one, and the like. The fused heteroarylcycloalkyl group is optionally substituted with one or more fused phenylcycloalkyl group substituents as defined herein. The cycloalkyl moiety is further optionally substituted with oxo (O=), thioxo (S=), methylene (H$_2$C=) or oxime (HO—N=). Preferred substituents include alkyl, aryl, heteroaryl, heterocyclyl, heterocyclenyl, cycloalkyl, cycloalkenyl, acylhydrazino, hydroxy, acyl, aroyl, halo, nitro, cyano, alkoxycarbonyl, acylamino, alkylthio, alkylamino, amino, carbamoyl, thiocarbamoyl and amidino. The nitrogen atom of the heteroaryl portion of the fused heteroarylcycloalkyl group is optionally oxidized to the N-oxide.

"Fused heteroarylcycloalkenyl" means a 5- or 6-membered heteroaryl fused with a cycloalkenyl ring. "Aza", "oxa" or "thia", when used as a prefix before the heteroaryl portion of the fused heteroarylcycloalkenyl means that the cycloalkenyl contains at lease one nitrogen, oxygen or sulfur atom. Preferred fused heteroarylcycloalkenyls are those wherein the heteroaryl thereof consists of about 5 to about 6 ring atoms in which one or two of the ring atoms are independently selected from oxygen, nitrogen and sulfur and the cycloalkenyl consists of about 5 to about 6 ring atoms. Representative preferred fused heteroarylcycloalkenyl include 5,6-dihydroisoquinolyl, 5,6-dihydroquinoxalinyl, 5,6-dihydroquinazolinyl, 4,5-dihydro-1H-benzimidazolyl, 4,5-dihydrobenzoxazolyl, and the like. The fused heteroarylcycloalkenyl is optionally substituted with one or more fused phenylcycloalkyl group substituents as defined herein. The cycloalkenyl moiety is further optionally substituted with oxo (O=), thioxo (S=), methylene (H$_2$C=) or oxime (HO—N=). Preferred substituents include alkyl, aryl, heteroaryl, heterocyclyl, heterocyclenyl, cycloalkyl, cycloalkenyl, acylhydrazino, hydroxy, acyl, aroyl, halo, nitro, cyano, alkoxycarbonyl, acylamino, alkylthio, alkylamino, amino, carbamoyl, thiocarbamoyl and amidino. The nitrogen atom of the heteroaryl portion of the fused heteroarylcycloalkyl is optionally oxidized to the N-oxide.

"Fused heteroarylheterocyclyl" means a heteroaryl ring fused with a heterocyclyl ring wherein the heteroaryl and heterocyclyl portions are as defined herein. "Aza", "oxa" or "thia", when used as a prefix before the heteroaryl or heterocyclyl portion of the fused heteroarylheterocyclyl group means that the heteroaryl or heterocyclyl potion contains at lease one nitrogen, oxygen or sulfur atom. Preferred fused heteroarylheterocyclyl groups are ring systems wherein one or two of the ring atoms of the heteroaryl are independently selected from oxygen, nitrogen and sulfur and the heterocyclyl portion consists of about 5 to about 6 ring atoms in which one or two of the ring atoms are independently selected from oxygen, nitrogen and sulfur. Representative fused heteroarylheterocyclyl groups include 4,7-dihydro-5H-thiazolo[5,4-c]pyridin-6-one, 5,6,7,8-tetrahydro-thiazolo[4,5-c]azepin-4-one, 2,3-dihydro-1H pyrrol[3,4-b]quinolin-2-yl, 1,2,3,4-tetrahydrobenz[b][1,7]naphthyridin-2-yl, 1,2,3,4-tetrahydrobenz[b][1,6]naphthyridin-2-yl, 1,2,3,4-tetrahydro-9H-pyrido[3,4-b]indol-2-yl, 1,2,3,4-tetrahydro-9H-pyrido[4,3-b]indol-2yl, 2,3,-dihydro-1H-pyrrolo[3,4-b]indol-2-yl, 1H-2,3,4,5-tetrahydroazepino[3,4-b]indol-2-yl, 1H-2,3,4,5-tetrahydroazepino[4,3-b]indol-3-yl, 1H-2,3,4,5-tetrahydroazepino[4,5-b]indol-2 yl, 5,6,7,8-tetrahydro[1,7]napthyridinyl, 1,2,3,4-tetrhydro[2,7]naphthyridyl, 2,3-dihydro[1,4]dioxino[2,3-b]pyridyl, 2,3-dihydro[1,4]dioxino[2,3-b]pyridyl, 3,4-dihydro-2H-1-oxa-4,6-diazanaphthalenyl, 4,5,6,7-tetrahydro-3H-imidazo[4,5-c]pyridyl, 6,7-dihydro-5,8-diazanaphthalenyl, and the like. The fused heteroarylheterocyclyl group is optionally substituted with one or more fused arylcycloalkyl group substituents as defined herein. The heterocyclyl portion is further optionally substituted with oxo (O=), thioxo (S=), methylene (H$_2$C=) or oxime (HO—N=). Preferred substituents include alkyl, aryl, heteroaryl, heterocyclyl, heterocyclenyl, cycloalkyl, cycloalkenyl, acylhydrazino, hydroxy, acyl, aroyl, halo, nitro, cyano, alkoxycarbonyl, acylamino, alkylthio, alkylamino, amino, carbamoyl, thiocarbamoyl and amidino. The nitrogen atom of the heteroaryl portion is optionally oxidized to the N-oxide. The nitrogen or sulphur atom of the heterocyclyl portion is optionally oxidized to the corresponding N-oxide, S-oxide or S,S-dioxide.

"Fused heteroarylheterocyclenyl" means a fused heteroaryl and heterocyclenyl, wherein the heteoayl and heterocyclenyl portions are as defined herein. "Aza", "oxa" or "thia", when used as a prefix before the heteroaryl or heterocyclenyl portion of the fused heteroarylheterocyclenyl group means that the heteroaryl or heterocyclenyl portion contains at lease one nitrogen, oxygen or sulfur atom. Preferred fused heteroarylcycloalkenyl groups are ring systems wherein the heteroaryl portion thereof consists of about 5 to about 6 ring atoms in which one or two of the ring atoms are independently selected from oxygen, nitrogen and sulfur and the heterocyclenyl portion consists of about 5 to about 6 ring atoms in which one or two of the ring atoms are independently selected from oxygen, nitrogen and sulfur. Representative fused heteroarylheterocyclenyl groups include 7,8-dihydro[1,7]naphthyridinyl, 1,2-dihydro[2,7]naphthyridinyl, 6,7-dihydro-3H-imidazo[4,5-c]pyridyl, and the like. The fused heteroarylheterocyclenyl group is optionally substituted with one or more fused arylcycloalkyl group substituents as defined herein. The heterocyclenyl portion is further optionally substituted with oxo (O=), thioxo (S=), methylene (H$_2$C=) or oxime (HO—N=). Preferred substituents include alkyl, aryl, heteroaryl, heterocyclyl, heterocyclenyl, cycloalkyl, cycloalkenyl, acylhydrazino, hydroxy, acyl, aroyl, halo, nitro, cyano, alkoxycarbonyl, acylamino, alkylthio, alkylamino, amino, carbamoyl, thiocarbamoyl and amidino. The nitrogen atom of the heteroaryl portion is optionally oxidized to the N-oxide. The nitrogen or sulphur atom of the heterocyclenyl is optionally oxidized to the corresponding N-oxide, S-oxide or S,S-dioxide.

"Aralkyl" means an aryl-alkyl- group in which the aryl portion and alkyl portion are as defined herein. Preferred aralkyl groups contain a lower alkyl moiety. Representative aralkyl groups include benzyl, 2-phenethyl and naphthlenemethyl.

"Heteroaralkyl" means a heteroaryl-alkyl- group in which the heteroaryl portion and alkyl portion are as defined herein. Preferred heteroaralkyl groups contain a lower alkyl moiety. Representative heteroaralkyl groups may contain thienylmethyl, pyridylmethyl, imidazolylmethyl and pyrazinylmethyl.

"Aralkenyl" means an aryl-alkenyl- group in which the aryl portion and alkenyl portion are as defined herein. Preferred aralkenyl groups contain a lower alkenyl moiety. An representative aralkenyl group is 2-phenethenyl.

"Heteroaralkenyl" means a heteroaryl-alkenyl- group in which the heteroaryl portion and alkenyl portion are as defined herein. Preferred heteroaralkenyls contain a lower alkenyl moiety. Representative heteroaralkenyl groups may contain thienylethenyl, pyridylethenyl, imidazolylethenyl and pyrazinylethenyl.

"Hydroxyalkyl" means a HO-alkylene- group in which the alkylene portion is as defined herein. Preferred hydroxyalkyl groups contain lower alkylene. Representative hydroxyalkyl groups include hydroxymethyl and 2-hydroxyethyl.

"Acyl" means an H—CO— or alkyl-CO— group in which the alkyl portion is as defined herein. Preferred acyl groups contain a lower alkyl. Representative acyl groups include formyl, acetyl, propanoyl, 2-methylpropanoyl, butanoyl and palmitoyl.

"Aroyl" means an aryl-CO— group in which the aryl portion is as defined herein. Representative aroyl groups include benzoyl and 1- and 2-naphthoyl.

"Aryldiazo" means an aryl-N=N— group in which the aryl portion is as defined herein. Representative aryldiazo groups include phenyldiazo and naphthyldiazo.

"Heteroaroyl" means an means a heteroaryl-CO— group in which the heteroaryl portion is as defined herein. Representative heteroaryl groups include thiophenoyl and pyridinoyl.

"Heteroaryldiazo" means a heteroaryl-N=N— group in which the heteroaryl group is as defined herein. Representative heteroaryldiazo groups include pyridyldiazo and thienyldiazo.

"Alkoxy" means an alkyl-O— group in which the alkyl portion is as defined herein. Representative alkoxy groups include methoxy, ethoxy, n-propoxy, i-propoxy, n-butoxy and heptoxy.

"Aryloxy" means an aryl-O— group in which the aryl portion is as defined herein. Representative aryloxy groups include phenoxy and naphthoxy.

"Aralkyloxy" means an aralkyl-O— group in aralkyl portion is as defined herein. Representative aralkyloxy groups include benzyloxy and 1- or 2-naphthalenemethoxy.

"Alkylthio" means an alkyl-S— group in which alkyl portion is as defined herein. Representative alkylthio groups include methylthio, ethylthio, i-propylthio and heptylthio.

"Arylthio" means an aryl-S— group in which the aryl portion is as defined herein. Representative arylthio groups include phenylthio and naphthylthio.

"Aralkylthio" means an aralkyl-S— group in which the aralkyl portion is as defined herein. A representative aralkylthio group is benzylthio.

"Amino" means a group of formula Y$_1$Y$_2$N— wherein Y$_1$ and Y$_2$ are defined herein. Preferred amino groups include amino (H₂N—), methylamino, dimethylamino, diethylamino, benzylamino, phenethylamino, 5-aminoindolyl, 2-amino-2-thiazolinyl, N-(2-aminoethyl)morpholine, 2(aminomethyl)pyridine, or 4(aminomethyl)pyridine.

"Aminoalkyl" means a $Y_1Y_2N$-alkylene- group wherein $Y_1$, $Y_2$ and the alkylene portion are defined herein.

"Alkoxycarbonyl" and "alkyloxycarbonyl" means an alkyl-O—CO— group wherein the alkyl portion is as defined herein. Representative alkoxycarbonyl groups include methoxycarbonyl, ethoxycarbonyl, or t-butyloxycarbonyl.

"Heterocyclylalkyloxycarbonyl" means an heterocyclylalkyloxycarbonyl group wherein the heterocyclyl portion and alkyloxycarbonyl portion are as defined herein. A represenaivie example of a heterocyclylalkyloxycarbonyl group is pyrrolidinylethoxycarbonyl.

"Heterocyclenylalkyloxycarbonyl" means an heterocyclenyl-alkyloxycarbonyl group wherein the heterocyclenyl portion and alkyloxycarbonyl portion are as defined herein. A representaivie example of a heterocyclenylalkyloxycarbonyl group is pyrrolinylethoxycarbonyl.

"Heteroaralkyloxycarbonyl" means an heteroaryl-alkyloxycarbonyl group wherein the heteroaryl portion and alkyloxycarbonyl portion are as defined herein. A representaivie example of a heteroaralkyloxycarbonyl group is pyridylethoxycarbonyl.

"Arylalkyloxycarbonyl" means an aryl-alkyloxycarbonyl group wherein the aryl portion and alkyloxycarbonyl portion are as defined herein. A representaivie example of a aralkyloxycarbonyl group is phenylethoxycarbonyl.

"Cycloalkylalkyloxycarbonyl" means a cycloalkyl-alkyloxycarbonyl group wherein the cycloalkyl portion and alkyloxycarbonyl portion are as defined herein. A representaivie example of a ar cycloalkylalkyloxycarbonyl group is cyclohexylethoxycarbonyl.

"Cycloalkenylalkyloxycarbonyl" means a cycloalkenyl-alkyloxycarbonyl group wherein the cycloalkenyl portion and alkyloxycarbonyl portion are as defined herein. A representaivie example of a ar cycloalkenylalkyloxycarbonyl group is cyclohexenylethoxycarbonyl.

"Alkoxycarbonylalkyl" means an alkyl-O—CO-alkylene-group wherein alkyl portion and alkylene portion are defined herein.

"Aryloxycarbonyl" means an aryl-O—CO— group wherein aryl portion is as defined herein. Representative aryloxycarbonyl groups include phenoxycarbonyl and naphthoxycarbonyl.

"Aralkoxycarbonyl" means an aralkyl-O—CO— group wherein aralkyl portion is as defined herein. A representative aralkoxycarbonyl group is benzyloxycarbonyl.

"Carbamoyl" means a group of formula $Y_1Y_2NCO$— wherein $Y_1$ and $Y_2$ are defined herein. Representative carbamoyl groups are carbamoyl (H₂NCO—) and dimethylaminocarbamoyl (Me₂NCO—).

"Heterocyclylalkylcarbamoyl" means a heterocyclyl-alkylene-carbamoyl wherein the heterocyclyl, alkylene and carbamoyl portions are as defined herein. A representative example of a heterocyclylalkylenecarbamoyl group is pyrrolidinylethylcarbamoyl. "Heterocyclenylalkylcarbamoyl" means a heterocyclenyl-alkylene-carbamoyl wherein the heterocyclenyl, alkylene and carbamoyl portions are as defined herein. A representative example of a heterocyclyenlalkylenecarbamoyl group is pyrrolinylethylcarbamoyl.

"Heteroaralkylcarbamoyl" means a heteroaryl-alkylene-carbamoyl wherein the heteroaryl, alkylene and carbamoyl portions are as defined herein. A representative example of a heteroaralkylenecarbamoyl group is pyridinylethylcarbamoyl.

"Arylalkylcarbamoyl" means an aryl-alkylene-carbamoyl wherein the aryl, alkylene and carbamoyl portions are as defined herein. A representative example of an aralkylenecarbamoyl group is phenylethylcarbamoyl.

"Cycloalkylalkylcarbamoyl" means an cycloalkyl-alkylene-carbamoyl wherein the cycloalkyl, alkylene and carbamoyl portions are as defined herein. A representative example of an cycloalkylalkylcarbamoyl group is cyclohexylethylcarbamoyl.

"Cycloalkenylcarbamoyl" means an cycloalkenyl-alkylene-carbamoyl wherein the cycloalkenyl, alkylene and carbamoyl portions are as defined herein. A representative example of an cycloalkylalkenylcarbamoyl group is cyclohexenylethylcarbamoyl.

"Sulfamoyl" means a group of formula $Y_1Y_2NSO_2$— wherein $Y_1$ and $Y_2$ are defined herein. Representative sulfamoyl groups are aminosulfamoyl (H₂NSO₂—) and dimethylaminosulfamoyl (Me₂NSO₂—).

"Acylamino" means an acyl-NH— group wherein the acyl portion is as defined herein.

"Aroylamino" means an aroyl-NH— group wherein the aroyl portion is as defined herein.

"Alkylsulfonyl" means an alkyl-SO₂— group wherein the alkyl portion is as defined herein. Preferred alkylsulfonyl groups are those in which the alkyl group is lower alkyl.

"Alkylsulfinyl" means an alkyl-SO— group wherein the alkyl portion is as defined herein. Preferred alkylsulfinyl groups are those in which the alkyl portion is lower alkyl.

"Arylsulfonyl" means an aryl-SO₂— group wherein the aryl portion is as defined herein.

"Arylsulfinyl" means an aryl-SO— group wherein the aryl portion is as defined herein.

"Halo" or "halogen" means fluoro, chloro, bromo, or iodo. Preferred are fluoro, chloro or bromo, and more preferred are fluoro or chloro.

"Nitrogen protecting group" means an easily removable group which is known in the art to protect an amino group against undesirable reaction during synthetic procedures and to be selectively removable. The use of N-protecting groups is well known in the art for protecting groups against undesirable reactions during a synthetic procedure and many such protecting groups are known, CF, for example, T. H. Greene and P. G. M. Wuts, Protective Groups in Organic Synthesis, 2nd edition, John Wiley & Sons, New York (1991), incorporated herein by reference. Preferred N-protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxycarbonyl, 9-fluorenylmethoxycarbonyl, 2,2,2-trifluoroethoxycarbonyl, 2-trimethylsilylethxoycarbonyl, vinyloxycarbonyl, allyloxycarbonyl, t-butyloxycarbonyl (BOC), 1,1-dimethylpropynyloxycarbonyl, benzyloxycarbonyl (CBZ), p-nitrophenylsulfinyl, p-nitrobenzyloxycarbony, 2,4-dichlorobenzyloxycarbonyl, allyloxycarbonyl (Alloc), and the like.

"Compounds of the invention", and equivalent expressions, are meant to embrace compounds of general formula I or formula II as hereinbefore described, which expression includes the prodrugs, the pharmaceutically acceptable salts, and the solvates, e.g. hydrates, where the context so permits. It is understood that the activity of individual compounds of formula I or formula II will vary depending on the individual compound and assay employed. Compounds of the invention as used herein includes all compounds of formula I or formula II having an in-vitro activity of greater than 10% at 3.9 µM in the Factor Xa in vitro enzyme assay described herein. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

"Prodrug" means a form of the compound of formula I or formula II which may or may not itself be biologically active but which may be converted, for example by metabolic, solvolytic, or other physiological means, to a biologically active chemical entity, and is suitable for administration to a patient without undue toxicity, irritation, allergic response, and the like, and effective for their intended use, including ketal, ester and zwitterionic forms. A prodrug is transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A. C. S. Symposium Series, and in Edward B. Roche, ed., *Bioreversible Carriers in Drug Design*, American Pharmaceutical Association and Pergamon Press, 1987, both of which are incorporated herein by reference.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include ethanolates, methanolates, and the like. "Hydrate" is a solvate wherein the solvent molecule(s) is/are $H_2O$.

In a specific embodiment, the term "about" or "approximately" means within 20%, preferably within 10%, and more preferably within 5% of a given value or range Where the compound of this invention is substituted with a basic moiety, acid addition salts may be formed. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrohalides, e.g. hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-β-hydroxynaphthoates, gentisates, mesylates, isethionates and di-p-toluoyltartratesmethanesulfonate, ethanesulfonate, benzenesulfonate, p-toluenesulfonate, cyclohexylsulfamate and quinate, respectively.

Acid addition salts of the compounds of this invention are prepared by reaction of the free base with the appropriate acid by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds of this invention can be regenerated from the acid addition salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial effects inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, n-methylglucamine, lysine, arginine, ornithine, choline, N,N'-dibenzylethylenediamine, chloroprocaine, diethanolamine, procaine, n-benzylphenethylamine, diethylamine, piperazine, tris(hydroxymethyl)aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The compounds of this invention can be regenerated from the base addition salts by the application or adaptation of known methods. For example, parent compounds of the invention can be regenerated from their base addition salts by treatment with an acid, e.g. hydrochloric acid.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

It will be appreciated that compounds useful according to the present invention may contain asymmetric centers. These asymmetric centers may independently be in either the R or S configuration. It will be apparent to those skilled in the art that certain compounds useful according to the invention may also exhibit geometrical isomerism. It is to be understood that the present invention includes individual stereoisomers and mixtures thereof, including racemic mixtures, of compounds of formula I or formula II hereinabove. Such isomers can be separated from their mixtures, by the application or adaptation of known methods, for example chromatographic techniques and recrystallisation techniques, or they are separately prepared from the appropriate isomers of their intermediates.

Compounds of this invention may also exhibit geometrical isomerism. Geometrical isomers include the cis and trans forms of compounds of the invention having alkenyl or alkenylenyl moieties. The present invention comprises the individual geometrical isomers and stereoisomers and mixtures thereof.

For the propose herein it is understood that tautermeric forms are included in the recitation of a given group, e.g., thio/mercapto or oxo/hydroxyl.

Preferred Embodiments

Another preferred aspect of the invention is a compound of formula I, wherein q is 0 and Z is absent.

Another preferred aspect of the invention is a compound of formula I, wherein q is 0, r is 1 and Z is absent.

Another preferred aspect of the invention is a compound of formula I, wherein $Cy_2$ is optionally substituted heteroaryl, optionally substituted heterocyclyl, optionally substituted heterocyclenyl, optionally substituted cycloalkyl, optionally substituted cycloalkenyl, optionally substituted fused heteroarylheterocyclyl, optionally substituted fused heteroarylheterocyclenyl, optionally substituted fused heteroarylcycloalkenyl, optionally substituted fused heteroarylcycloalkyl, fused arylheteroclyl, optionally substituted fused arylheterocyclenyl, or optionally substituted aryl.

Another preferred aspect of the invention is a compound of formula I, wherein $Cy_2$ is optionally substituted azaheteroaryl, optionally substituted azaheterocyclyl, optionally substituted azaheterocyclenyl, optionally substituted fused arylazaheteroclylyl, optionally substituted fused arylazaheterocyclenyl, optionally substituted fused heteroarylazaheteroclylyl, optionally substituted fused heteroarylazaheterocyclenyl, optionally substituted fused azaheteroarylcycloalkyl, optionally substituted fused azaheteroarylcycloalkenyl, optionally substituted azaheterocyclyl, or optionally substituted heterocyclenyl.

Another preferred aspect of the invention is a compound of formula I, wherein $Cy_2$ is optionally substituted with one or more groups selected from amino, carbamoyl, acylamino, heteroaryl, heterocyclenyl, heterocyclyl, alkyl, alkyloxycarbonyl, amidino, hydroxy, alkoxy, aryl, isourea, guanidino, acylhydrazino, acyl, cyano, carboxy, sulfamoyl, or halo.

Another preferred aspect of the invention is a compound of formula I, wherein $Cy_2$ is optionally substituted with one of more groups selected from aralkylamino, heteroaralkylamino, heterocyclylalkylamino, heterocyclenylalkylamino, alkylcarbamate, aminoalkylamino, aryloxycarbonylalkyl, heteroaryloxycarbonylalkyl, heterocycloxycarbonylalkyl, heterocyclenyloxycarbonylalkyl, and alkoxycarbonylalkyl.

Another preferred aspect of the invention is a compound of formula I, wherein $Cy_2$ optionally contains at least substituent selected from oxime and oxo when $Cy_2$ is cycloalkyl, cycloalkenyl, heterocyclyl, heterocyclenyl, fused arylcycloalkyl, fused arylcycloalkenyl, fused arylheterocyclyl, fused arylheterocyclenyl, fused heteroarylcycloalkyl, fused heteroarylcycloalkenyl, fused heteroarylheterocyclyl or fused heteroarylheterocyclenyl.

Another preferred aspect of the invention is a compound of formula I, wherein $R_1$, $R_{1a}$, $R_2$, $R_{2a}$, $R_4$, or $R_{4a}$ are hydrogen.

Another preferred aspect of the invention is a compound of formula I, wherein $R_4$, and $R_{4a}$ taken together form O or S.

Another preferred aspect of the invention is a compound of formula I, wherein $R_4$, and $R_{4a}$ taken together form O.

Another preferred aspect of the invention is a compound of formula I, wherein $R_1$, $R_{1a}$, $R_2$ and $R_{2a}$ are hydrogen.

Another preferred aspect of the invention is a compound of formula I, wherein $R_1$, $R_{1a}$, $R_4$ and $R_{4a}$ are hydrogen.

Another preferred aspect of the invention is a compound of formula I, wherein $R_4$ and $R_{4a}$ are hydrogen.

Another preferred aspect of the invention is a compound of formula I, wherein $R_4$ is optionally substituted lower alkyl.

Another preferred aspect of the invention is a compound of formula I, wherein $R_4$ is alkoxyalkyl, alkylthioalkyl, alkylsulfinylalkyl, alkylsulfonylalkyl, alkoxycarbonylalkyl, hydroxyalkyl, acylalkyl, acylaminoalkyl or carbamoylalkyl.

Another preferred aspect of the invention is a compound of formula I, wherein $R_2$ is optionally substituted lower alkyl.

Another preferred aspect of the invention is a compound of formula I, wherein $R_2$ and $R_{2a}$ are hydrogen.

Another preferred aspect of the invention is a compound of formula I, wherein $R_2$ alkoxyalkyl, alkoxycarbonylalkyl, carboxyalkyl, hydroxyalkyl or heterocyclylalkyloxycarbonyl, and $R_{2a}$ is hydrogen.

Another preferred aspect of the invention is a compound of formula I, wherein $R_1$ and $R_{1a}$ are hydrogen.

Another preferred aspect of the invention is a compound of formula I, wherein $R_1$ is lower alkyl, carboxy, alkoxycarbonyl or carbamoyl, and $R_{1a}$ is hydrogen.

Another preferred aspect of the invention is a compound of formula I, wherein $R_1$ is alkoxyalkyl, carboxyalkyl, alkoxycarbonylalkyl or carbamoylalkyl.

Another preferred aspect of the invention is a compound of formula I, wherein $R_1$ and $R_{1a}$ taken together with the carbon atom through which they are linked form a 3 to 7 membered cycloalkyl or cycloalkenyl group.

Another preferred aspect of the invention is a compound of formula I, wherein $R_2$ and $R_{2a}$ taken together with the carbon atom through which they are linked form a 3 to 7 membered cycloalkyl or cycloalkenyl group.

Another preferred aspect of the invention is a compound of formula I, wherein $R_4$ and $R_{4a}$ taken together with the carbon atom through which they are linked form a 3 to 7 membered cycloalkyl or cycloalkenyl group.

Another preferred aspect of the invention is a compound of formula I, wherein $R_{1a}$ and $R_{2a}$ are absent and $R_1$ and $R_2$ together with the carbon atoms through which $R_1$ and $R_2$ are linked form an aryl or heteroaryl group.

Another preferred aspect of the invention is a compound of formula I, wherein $R_1$ and $R_2$ together with the carbon atoms through which $R_1$ and $R_2$ are linked form a cycloalkyl group, cycloalkenyl group, heterocyclyl group, or heterocyclenyl group.

Another preferred aspect of the invention is a compound of formula I, wherein $R_1$ and $R_2$ together with the carbon atoms through which $R_1$ and $R_2$ are linked form a cyclohexyl group.

Another preferred aspect of the invention is a compound of formula I, wherein $R_1$ and $R_2$ together with the carbon atoms through which $R_1$ and $R_2$ are linked form a cyclohexenyl group.

Another preferred aspect of the invention is a compound of formula I, wherein $L_1$ is absent, optionally substituted alkylene, optionally substituted alkenylene, —C(O)NR$_5$—, —S(O)p-, —C(O)—, —C(O)Y—C(X)Y—, —C(O)O—, C(O)NR$_5$—S(O)p-, —C(O)—C(O)NR$_5$S(O)p-, —S(O)pNR$_5$—, —C(O)-alkylene-O—, —C(O)-alkenylene-O—, —S(O)p-alkenylene-, —S(O)p-alkylene-, —C(O)-alkenylene-C(O)—, —C(O)-alkylene-S(O)p-, —S(O)p-alkylene-C(O)—, —C(O)-alkylene, —C(O)-alkenylene-, -alkylene-C(O)NR$_5$—, or —C(O)CH(OH)-alkylene-.

Another preferred aspect of the invention is a compound of formula I, wherein L$_1$ is methylene, —C(O)-alkylene-O—, —C(O)-alkenylene-, —S(O)p-alkenylene-, —C(O)C(O)NR$_5$— or —S(O)p-.

Another preferred aspect of the invention is a compound of formula I, wherein Cy$_1$ is optionally substituted aryl, heteroaryl, optionally substituted heterocyclyl, optionally substituted heterocyclenyl, optionally substituted cycloalkyl, optionally substituted cycolalkenyl, optionally substituted fused arylcycloalkyl, optionally substituted fused arylcycloalkenyl, optionally substituted fused arylheterocyclyl, optionally substituted fused arylheterocyclenyl, optionally substituted fused heteroarylcycloalkyl, optionally substituted fused heteroarylcycloalkenyl, optionally substituted fused heteroarylheterocyclyl or optionally substituted fused heteroarylheterocyclenyl.

Another preferred aspect of the invention is a compound of formula I, wherein Cy$_1$ is optionally substituted aryl, heteroaryl, optionally substituted heterocyclyl, optionally substituted heterocyclenyl, optionally substituted cycloalkyl or optionally substituted cycolalkenyl.

Another preferred aspect of the invention is a compound of formula I, wherein Cy$_1$ is optionally substituted with one of more groups selected from amino, halo, hydroxyl, aryl, heteroaryl, amidino, alkyl, acylamino, carbamoyl, cyano, alkoxy, nitro, carbamate, sulfamyl.

Another preferred aspect of the invention is a compound of formula I, wherein Cy$_1$ is optionally substituted with one of more groups selected from —NH$_2$, chloro, carbamate or aminosulfamyl.

Another preferred aspect of the invention is a compound of formula I, wherein Cy$_1$ optionally contains at least substituent selected from oxime and oxo when Cy$_1$ is cycloalky, cycloalkenyl, heterocyclyl, heterocyclenyl, fused arylcycloalkyl, fused arylcycloalkenyl, fused arylheterocyclyl, fused arylheterocyclenyl, fused heteroarylcycloalkyl fused heteroarylcycloalkenyl, fused heteroarylheterocyclyl or fused heteroarylheterocyclenyl.

Another preferred aspect of the invention is a compound of formula I, wherein R$_1$ is alkyl, hydrogen or alkoxycarbonyl.

Another preferred aspect of the invention is a compound of formula I, wherein R$_1$ is alkoxycarbonylalkyl.

Another preferred aspect of the invention is a compound of formula I, wherein R$_1$ is alkyl, R$_4$ is alkyl, L$_1$ is —S(O)$_2$—, —S(O)$_2$-alkenylene- or —S(O)$_2$-alkylene- and Cy$_1$ is optionally substituted heteroaryl.

Another preferred aspect of the invention is a compound of formula I, wherein R$_1$, R$_{1a}$, R$_4$, and R$_{4a}$, are hydrogen, L$_1$ is —S(O)$_2$—, —S(O)$_2$-alkenylene- or —S(O)$_2$-alkylene-, and Cy$_1$ is optionally substituted aryl.

Another preferred aspect of the invention is a compound of formula I, wherein R$_1$, R$_{1a}$, R$_4$, and R$_{4a}$, are hydrogen, L$_1$ is —S(O)$_2$—, —S(O)$_2$-alkenylene- or —S(O)$_2$-alkylene-, and Cy$_1$ is optionally substituted heteroaryl.

Another preferred aspect of the invention is a compound of formula I, wherein R$_1$, R$_{1a}$, R$_4$, and R$_{4a}$, are hydrogen, L$_1$ is —S(O)$_2$—, —S(O)$_2$-alkenylene- or —S(O)$_2$-alkylene-, and Cy$_1$ is optionally substituted azaheteroaryl.

Another preferred aspect of the invention is a compound of formula I, wherein R$_1$, R$_{1a}$, R$_{1a}$, R$_4$, and R$_{4a}$, are hydrogen, L$_1$ is —S(O)$_2$—, —S(O)$_2$-alkenylene- or —S(O)$_2$-alkylene-, and Cy$_1$ is optionally substituted thiaheteroaryl.

Another preferred aspect of the invention is a compound of formula I, wherein R$_1$, R$_{1a}$, R$_{1a}$, R$_4$, and R$_{4a}$, are hydrogen, L$_1$ is —S(O)$_2$—, —S(O)$_2$-alkenylene- or —S(O)$_2$-alkylene-, and Cy$_1$ is optionally substituted benzothiophenyl.

Another preferred aspect of the invention is a compound of formula I, wherein R$_1$, R$_{1a}$, R$_{1a}$, R$_4$, and R$_{4a}$, are hydrogen, L$_1$ is —S(O)$_2$—, —S(O)$_2$-alkenylene or —S(O)$_2$-alkylene, and Cy$_1$ is optionally substituted indolyl.

Another preferred aspect of the invention is a compound of formula I, wherein R$_1$, R$_{1a}$, R$_{1a}$, R$_4$, and R$_{4a}$, are hydrogen, L$_1$ is —S(O)$_2$—, —S(O)$_2$-alkenylene or —S(O)$_2$-alkylene, and Cy$_1$ is optionally substituted benzimidazolyl.

Another preferred aspect of the invention is a compound of formula I, wherein R$_1$, R$_{1a}$, R$_{1a}$, R$_4$, and R$_{4a}$, are hydrogen, L$_1$ is —S(O)$_2$—, —S(O)$_2$-alkenylene or —S(O)$_2$-alkylene, and Cy$_1$ is optionally substituted thienyl.

Another preferred aspect of the invention is a compound of formula I, wherein R$_1$, R$_{1a}$, R$_{1a}$, R$_4$, and R$_{4a}$, are hydrogen, L$_1$ is —S(O)$_2$—, —S(O)$_2$-alkenylene or —S(O)$_2$-alkylene, L$_2$ is alkylene, Cy$_1$ is optionally substituted heteroaryl, and Cy$_2$ is optionally substituted aryl, optionally substituted cycloalkyl, optionally substituted cycloalkenyl, optionally substituted heteroaryl, optionally substituted heterocyclyl or optionally substituted heterocyclenyl.

Another preferred aspect of the invention is a compound of formula I, wherein R$_1$, R$_{1a}$, R$_{1a}$, R$_4$, and R$_{4a}$, are hydrogen, L$_1$ is —S(O)$_2$—, —S(O)$_2$-alkenylene or —S(O)$_2$-alkylene, L$_2$ is alkylene, Cy$_1$ is optionally substituted heteroaryl, and Cy$_2$ is optionally substituted heteroaryl.

Another preferred aspect of the invention is a compound of formula I, wherein R$_1$, R$_{1a}$, R$_{1a}$, R$_4$, and R$_{4a}$, are hydrogen, L$_1$ is —S(O)$_2$—, —S(O)$_2$-alkenylene or —S(O)$_2$-alkylene, L$_2$ is alkylene, Cy$_1$ is heteroaryl, and Cy$_2$ is optionally substituted azaindolyl, optionally substituted quinazolinyl or optionally substituted piperdinyl.

Another preferred aspect of the invention is a compound of formula I, wherein R$_1$, R$_{1a}$, R$_{1a}$, R$_4$, and R$_{4a}$, are hydrogen, L$_1$ is —S(O)$_2$—, —S(O)$_2$-alkenylene or —S(O)$_2$-alkylene, L$_2$ is alkylene, Cy$_1$ is optionally substituted azaheteroaryl, and Cy$_2$ is optionally substituted azaheteroaryl.

Another preferred aspect of the invention is a compound of formula I, wherein R$_1$, R$_{1a}$, R$_{1a}$, R$_4$, and R$_{4a}$, are hydrogen, L$_1$ is —S(O)$_2$—, —S(O)$_2$-alkenylene or —S(O)$_2$-alkylene, L$_2$ is alkylene, Cy$_1$ is optionally substituted thiaheteroaryl, and Cy$_2$ is optionally substituted azaindolyl, optionally substituted quinazolinyl or optionally substituted piperdinyl.

Another preferred aspect of the invention is a compound of formula I, wherein R$_1$, R$_{1a}$, R$_{1a}$, R$_4$, and R$_{4a}$, are hydrogen, L$_1$ is —S(O)$_2$—, —S(O)$_2$-alkenylene or —S(O)$_2$-alkylene, L$_2$ is alkylene, Cy$_1$ is optionally substituted benzothiophenyl, and Cy$_2$ is optionally substituted azaindolyl, optionally substituted quinazolinyl or optionally substituted piperdinyl.

Another preferred aspect of the invention is a compound of formula I, wherein R$_1$, R$_{1a}$, R$_{1a}$, R$_4$, and R$_{4a}$, are hydrogen, L$_1$ is —S(O)$_2$—, —S(O)$_2$-alkenylene or —S(O)$_2$-alkylene, L$_2$ is alkylene, Cy$_1$ is optionally substituted indolyl, and Cy$_2$ is optionally substituted azaindolyl, optionally substituted quinazolinyl or optionally substituted piperdinyl.

Another preferred aspect of the invention is a compound of formula I, wherein R$_1$, R$_{1a}$, R$_{1a}$, R$_4$, and R$_{4a}$, are hydrogen, L$_1$ is —S(O)$_2$—, —S(O)$_2$-alkenylene or —S(O)$_2$-alkylene, L$_2$ is alkylene, Cy$_1$ is optionally substituted benzimidazolyl, and Cy$_2$ is optionally substituted azaindolyl, optionally substituted quinazolinyl or optionally substituted piperdinyl.

Another preferred aspect of the invention is a compound of formula I, wherein R$_1$, R$_{1a}$, R$_{1a}$, R$_4$ and R$_{4a}$, are hydrogen, L$_1$ is —S(O)$_2$—, —S(O)$_2$-alkenylene or —S(O)$_2$-alkylene, L$_2$ is alkylene, Cy$_1$ is optionally substituted thienyl, and Cy$_2$ is optionally substituted azaindolyl or optionally substituted quinazolinyl.

Another preferred aspect of the invention is a compound of formula I, wherein Cy$_2$ is quinazolinyl substituted by an amino substituent.

Another preferred aspect of the invention is a compound of formula I, wherein Cy$_2$ is quinazolinyl substituted by —NH$_2$ or —N(alkyl)$_2$.

Another preferred aspect of the invention is a compound of formula I, wherein R$_2$ is hydrogen, carboxyalkyl, alkoxyalkyl, hydroxyalkyl, alkoxycarbonylalkyl, acylamino or carbamoyl.

Another preferred aspect of the invention is a compound of formula I, wherein Cy$_2$ is piperdinyl.

Another preferred aspect of the invention is a compound of formula I, wherein Cy$_2$ is N-substituted piperdinyl.

Another preferred aspect of the invention is a compound of formula I, wherein Cy$_2$ is N-substituted piperdinyl and the piperdinyl moiety is attached to the parent moiety at the 4-position of the piperdinyl ring.

Another preferred aspect of the invention is a compound of formula I, wherein Cy$_2$ is a piperdinyl moiety substituted on the nitrogen ring atom by a group selected from aryl or heteroaryl.

Another preferred aspect of the invention is a compound of formula I, wherein Cy$_2$ is a piperdinyl moiety substituted on the nitrogen ring atom by an azaheteroaryl group.

Another preferred aspect of the invention is a compound of formula I, wherein Cy$_2$ is a piperdinyl moiety substituted on the nitrogen ring atom by a group selected from 2-pyridyl, 4-pyridyl or 4-pyrimidyl.

Another preferred aspect of the invention is a compound of formula I, wherein Cy$_2$ is a piperdinyl moiety substituted on the nitrogen ring atom by an optionally substituted pyrimidyl group.

Another preferred aspect of the invention is a compound of formula I, wherein Cy$_2$ is a piperdinyl moiety substituted on the nitrogen ring atom by a pyrimidyl group wherein said pyrimidyl group is attached to the piperdinyl moiety at the 4-position of said pyrimidyl group.

Another preferred aspect of the invention is a compound of formula I, wherein Cy$_2$ is a piperdinyl moiety substituted on the nitrogen ring atom by a pyrimidyl group wherein said pyrimidyl group is substituted by an aryl group substituent, more preferably, said pyrimidyl group is substituted at its 2-position by a group selected from halogen, alkoxy, alkylthio and Y$_1$Y$_2$N—, wherein Y$_1$ and Y$_2$ are independently, hydrogen, alkyl or aralkyl.

Another preferred aspect of the invention is a compound of formula I, wherein Cy$_2$ is optionally susbutituted thiazolyl.

Another preferred aspect of the invention is a compound of formula I, wherein Cy$_2$ is thiazolyl substituted by at least one substituent selected from lower alkyl, aryl, heteroaryl, amino, acylaminoalkyl, alkoxycarbonylalkyl, carbamoylalkyl and alkoxyalkyl.

Another preferred aspect of the invention is a compound of formula I, wherein Cy$_2$ is a group of formula

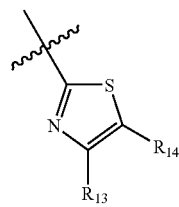

wherein R$_{13}$ and R$_{14}$ are independently hydrogen, lower alkyl, aryl, heteroaryl, amino, acylaminoalkyl,alkoxycarbonylalkyl, carbamoylalkyl or alkoxyalkyl; or R$_{13}$ and R$_{14}$ together with the carbon atoms through which R$_{13}$ and R$_{14}$ are linked form a cycloalkyl group, cycloalkenyl group, heterocyclyl group, heterocyclenyl group, aryl group or heteroaryl group.

Another preferred aspect of the invention is a compound of formula I, wherein Cy$_2$ is a group of formula

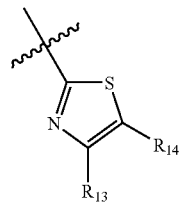

wherein R$_{13}$ and R$_{14}$ together with the carbon atoms through which R$_{13}$ and R$_{14}$ are linked form a cycloalkyl group, cycloalkenyl group, heterocyclyl group or heterocyclenyl group, optionally substituted with an oxo moeity.

Another preferred aspect of the invention is a compound of formula I, wherein Cy$_2$ is a piperdinyl moiety substituted on the nitrogen ring atom by a pyrimidyl group of formula

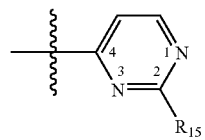

wherein R$_{15}$ is selected from halogen, alkoxy, alkylthio and Y$_1$Y$_2$N—, wherein Y$_1$ and Y$_2$ are independently, hydrogen, alkyl and aralkyl.

Another preferred aspect of the invention is a compound of formula I, wherein Cy$_2$ is a piperdinyl moiety substituted on the nitrogen ring atom by a group selected from alkoxycarbonyl, carbamoyl, acyl, alkyl and amidino.

Another preferred aspect of the invention is a compound of formula I, wherein Cy$_2$ is a piperdinyl moiety substituted on the nitrogen ring atom by

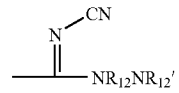

wherein R$_{12}$ and R$_{12}$' are independently selected from hydrogen or optionally substituted lower alkyl.

Other preferred compounds have formula I wherein m is 1; and n is 1.

Other preferred compounds have formula I wherein A is N.

Other preferred compounds have formula I wherein $R_3$ and $R_{3a}$ taken together are O; and $R_1$, $R_{1a}$, $R_2$, $R_{2a}$, $R_4$ and $R_{4a}$ are hydrogen.

Other preferred compounds have formula I wherein $R_3$ and $R_{3a}$ taken together are O; $R_1$, $R_{1a}$, $R_2$, $R_{2a}$ and $R_4$ are hydrogen; and $R_{4a}$ is optionally substituted alkyl.

Other preferred compounds have formula I wherein $R_3$ and $R_{3a}$ taken together are O; $R_1$, $R_{1a}$, $R_2$ and $R_4$ are hydrogen; and $R_{2a}$ and $R_{4a}$ are optionally substituted alkyl.

Other preferred compounds have formula I wherein $R_3$ and $R_{3a}$ taken together are O; $R_1$, $R_2$, $R_{2a}$ and $R_4$ are hydrogen; and $R_{1a}$ and $R_{4a}$ are optionally substituted alkyl.

Other preferred compounds have formula I wherein $R_3$ and $R_{3a}$ taken together are O; $R_1$, $R_2$, $R_{2a}$, $R_4$ and $R_{4a}$ are hydrogen; and $R_{1a}$ is carboxy, alkoxycarbonyl, $Y_1Y_2NCO$ or optionally substituted alkyl.

Other preferred compounds have formula I wherein $R_3$ and $R_{3a}$ taken together are O; and $R_1$, $R_{1a}$, $R_2$, $R_4$ and $R_{4a}$ are hydrogen; and $R_{2a}$ is carboxy, alkoxycarbonyl, $Y_1Y_2NCO$ or optionally substituted alkyl.

Another preferred aspect of the invention is directed to a compound of formula II

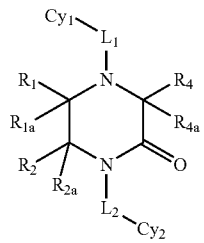

II or a pharmaceutically acceptable salt thereof, pharmaceutically acceptable prodrug thereof, an N-oxide thereof, a hydrate thereof or a solvate thereof, wherein $R_1$, $R_{1a}$, $R_2$, $R_{2a}$, $R_4$, $R_{4a}$, $Cy_1$, $Cy_2$, $L_1$, and $L_2$ are as defined in formula I.

Preferred compounds have formula I or formula II wherein $Cy_2$ contains at least one nitrogen atom and when $Cy_2$ is optionally substituted aryl, optionally substituted cycloalkyl, optionally substituted cycloalkenyl, optionally substituted fused phenylcycloalkyl or optionally substituted fused phenylcycloalkenyl, then said nitrogen atom is a basic nitrogen atom.

Another preferred aspect of the invention is a compound of formula I or formula II, wherein Z is absent or is selected from O, $S(O)_p$ and $NR_5$.

Another preferred aspect of the invention is a compound of formula I or formula II, wherein Z is —$NR_5C(O)$— or —$C(O)NR_5$—.

Another preferred aspect of the invention is a compound of formula IIa,

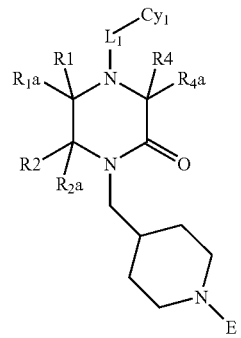

IIa wherein $R_1$, $R_{1a}$, $R_2$, $R_{2a}$, $R_3$, $R_{3a}$, $R_4$, $R_{4a}$, $Cy_1$, and $L_1$, are as defined in formula I, E is alkoxycarbonyl, carbamoyl, acyl, alkyl, amidino;

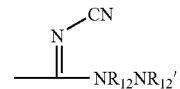

wherein $R_{12}$ and $R_{12}'$ are independently selected from hydrogen or optionally substituted lower alkyl; or wherein $R_{15}$ is selected from halogen, alkoxy, alkylthio and $Y_1Y_2N$—, wherein $Y_1$ and $Y_2$ are independently, hydrogen, alkyl and aralkyl.

Another preferred aspect of the invention is a compound of formula I or formula II, wherein $L_1$ is —$S(O)_p$—, —$C(X)Y$— or -$L_3$-Q-$L_4$-Q'-$L_5$-.

Another preferred aspect of the invention is a compound of formula I or formula II, wherein $Cy_1$ is optionally substituted aryl or optionally substituted heteroaryl.

Another preferred aspect of the invention is a compound of formula I wherein $R_1$, $R_2$, $R_3$ and $R_4$ are independently heterocyclyl, heterocyclenyl, heteroaryl, aryl, cycloalkyl, or cycloalkenyl.

More preferred compounds are those having a structure of formula I or formula II, wherein $L_2$ is alkylene of one to three carbon atoms.

Other more preferred compounds are those having a structure of formula I or formula II, wherein $L_2$ is —$CH_2$—.

Other more preferred compounds are those having a structure of formula I or formula II, wherein $L_2$ is a group of formula

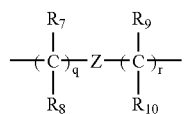

wherein Z is NR$_5$; q is 2; r is 0; R$_5$ is hydrogen or optionally substituted alkyl; and R$_7$ and R$_8$ are hydrogen.

Other more preferred compounds are those having a structure of formula I or formula II, wherein R$_5$ is hydrogen.

Other more preferred compounds are those having a structure of formula I or formula II, wherein Cy$_2$ is optionally substituted aryl or optionally substituted heteroaryl.

Other more preferred compounds are those having a structure of formula I or formula II, wherein L$_1$ is —S(O)$_2$—.

Other more preferred compounds are those having a structure of formula I or formula II, wherein L$_1$ is —C(X)Y—; X is O; and Y is NH.

Other more preferred compounds are those having a structure of formula I or formula II, wherein L$_1$ is -L$_3$-Q-L4-Q'-L5-; Q is —S(O)$_2$— or —C(O)—; and L$_4$ is optionally substituted alkenylene.

Other more preferred compounds are those having a structure of formula I or formula II, wherein L$_1$ is -L$_3$-Q-L4-Q'-L5-; and L$_4$ is optionally substituted alkylene.

Other more preferred compounds are those having a structure of formula I or formula II, wherein L$_1$ is -L$_3$-Q-L4-Q'-L5-; Q is —C(O)—; Q' is O; and L$_4$ is optionally substituted alkylene.

Other more preferred compounds are those having a structure of formula I or formula II, wherein L$_1$ is -L$_3$-Q-L4-Q'-L5-; L$_3$ is optionally substituted alkylene; and L$_4$ is optionally substituted alkenylene.

Other more preferred compounds are those having a structure of formula I or formula II, wherein Cy$_1$ is optionally substituted phenyl, optionally substituted thienyl, optionally substituted benzothienyl, optionally substituted isoquinolinyl, optionally substituted indolyl, optionally substituted thienopyridyl, optionally substituted furanyl, optionally substituted pyridyl, or optionally substituted benzimidazolyl.

Other more preferred compounds are those having a structure of formula I or formula II, wherein Cy$_2$ is optionally substituted phenyl, optionally substituted pyridyl, optionally substituted imidazolyl, optionally substituted quinolinyl, optionally substituted isoquinolinyl, optionally substituted quinazolinyl, optionally substituted cinnolinyl, optionally substituted azaindolyl, or optionally substituted thienopyridyl.

Another preferred aspect of the invention is a compound of formula IIb

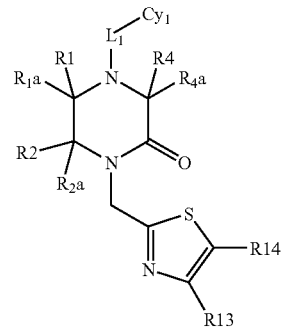

or a pharmaceutically acceptable salt thereof, pharmaceutically acceptable prodrug thereof, an N-oxide thereof, a hydrate thereof or a solvate thereof, wherein L$_1$, Cy$_1$, R$_1$, R$_{1a}$, R$_2$, R$_{2a}$, R$_4$ and R$_{4a}$ are as described in compound of formula I, R$_{13}$ and R$_{14}$ are independently hydrogen, lower alkyl, aryl, heteroaryl, amino, acylaminoalkyl, alkoxycarbonylalkyl, carbamoylalkyl or alkoxyalkyl; or R$_{13}$ and R$_{14}$ together with the carbon atoms through which R$_{13}$ and R$_{14}$ are linked form a cycloalkyl group, cycloalkenyl group, heterocyclyl group, heterocyclenyl group, aryl group or heteroaryl group.

Another preferred aspect of the invention is a compound of formula IIb wherein R$_{13}$ and R$_{14}$ together with the carbon atoms through which R$_{13}$ and R$_{14}$ are linked form a cycloalkyl group, cycloalkenyl group, heterocyclyl group or heterocyclenyl group, optionally substituted with an oxo moiety.

Other preferred compounds are those which inhibit both Factor Xa and Factor IIa (thrombin) activity, having a structure of formula IIc

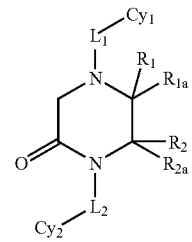

or a pharmaceutically acceptable salt thereof, pharmaceutically acceptable prodrug thereof, an N-oxide thereof, a hydrate thereof or a solvate thereof,
wherein:
Cy$_1$ is thiaheteroaryl or azaheteroaryl,
L$_1$; is —S(O)$_2$—, —S(O)$_2$-alkylene-, —S(O)$_2$-alkyenlene- or —S(O)$_2$-alkynylene-;
R$_1$, R$_{1a}$, R$_2$, R$_{2a}$ are independently hydrogen, alkyl, carboxyl, alkoxycarbonyl, or carbamoyl;
L$_2$ is methylene; and
Cy$_2$ is azaheteroaryl, azaheterocyclyl, azaheterocyclenyl, fused azaheteroarylcycloalkyl, fused azaheteroarylcycloalkenyl, fused heteroarylazacycloalkyl or fused heteroarylazacycloalkenyl.

Other preferred compounds which inhibit both Factor Xa and Factor IIa (thrombin) activity are those having a structure of formula IIc wherein:

Cy$_1$ is thiaheteroaryl or azaheteroaryl,

L$_1$ is —S(O)$_2$—, —S(O)$_2$-alkylene-, —S(O)$_2$-alkenylene- or —S(O)$_2$-alkynylene-;

R$_1$, R$_{1a}$, R$_2$, R$_{2a}$ are independently hydrogen, alkoxyalkyl, hydroxyalkyl, aminoalkyl, alkylaminoalkyl, carboxyl, alkoxycarbonyl, or carbamoyl;

L$_2$ is methylene; and

Cy$_2$ is azaheteroaryl, azaheterocyclyl, azaheterocyclenyl, fused azaheteroarylcycloalkyl, fused azaheteroarylcycloalkenyl, fused heteroarylazacycloalkyl or fused heteroarylazacycloalkenyl.

Other preferred compounds which inhibit both Factor Xa and Factor IIa (thrombin) activity are those having a structure of formula IIc wherein Cy$_2$ is optionally substituted azaindolyl, optionally substituted quinazolinyl or optionally substituted piperdinyl.

Other preferred compounds which inhibit both Factor Xa and Factor IIa (thrombin) activity are those having a structure of formula IIc wherein R$_1$, R$_{1a}$, R$_2$, and R$_{2a}$ are independently aryl, heteroaryl, cycloalkyl, cycloalkenyl, heterocyclyl or heterocyclenyl.

Other preferred compounds which inhibit both Factor Xa and Factor IIa (thrombin) activity are those having a structure of formula IIc wherein Cy$_2$ is an optionally substituted thiazolyl.

Other preferred compounds which inhibit both Factor Xa and Factor IIa (thrombin) activity are those having a structure of formula IIc wherein Cy$_2$ is is a group of formula wherein R$_{13}$ and R$_{14}$ are independently hydrogen, lower alkyl, aryl, heteroaryl, amino, acylaminoalkyl, alkoxycarbonylalkyl, carbamoylalkyl or alkoxyalkyl; or R$_{13}$ and R$_{14}$ together with the carbon atoms through which R$_{13}$ and R$_{14}$ are linked form a cycloalkyl group, cycloalkenyl group, heterocyclyl group, heterocyclenyl group, aryl group or heteroaryl group.

Other preferred compounds which inhibit both Factor Xa and Factor IIa (thrombin) activity are those having a structure of formula IIc wherein Cy$_2$ is a group of formula wherein R$_{13}$ and R$_{14}$ together with the carbon atoms through which R$_{13}$ and R$_{14}$ are linked form a cycloalkyl group, cycloalkenyl group, heterocyclyl group or heterocyclenyl group, optionally substituted with an oxo or oxime substituent.

Other preferred compounds which inhibit both Factor Xa and Factor IIa (thrombin) activity are those having a structure of formula IIc wherein Cy$_2$ is optionally substituted azaindolyl.

More preferred compounds which inhibit both Factor Xa and Factor IIa (thrombin) activity are those having a structure of formula IIc wherein Cy$_2$ is optionally substituted 5-azaindolyl.

More preferred compounds which inhibit both Factor Xa and Factor IIa (thrombin) activity are those having a structure of formula IIc wherein, when Cy$_2$ is optionally substituted azaindolyl, the parent molecule is attached to the azaindolyl group at the 2-position.

More preferred compounds which inhibit both Factor Xa and Factor IIa (thrombin) activity are those having a structure of formula IIc wherein Cy$_2$ is wherein R$_{19}$ is hydrogen or optionally substituted alkyl.

More preferred compounds which inhibit both Factor Xa and Factor IIa (thrombin) activity are those having a structure of formula IIc wherein Cy$_2$ is optionally substituted azaindolyl;

L$_1$ is —S(O)$_2$—, —S(O)$_2$-alkenylene;

Cy$_1$ is optionally substituted thienyl or optionally substituted benzothiophenyl, R$_1$ and R$_2$ are hydrogen;

R$_{1a}$ and R$_{2a}$ are independently hydrogen, alkyl, carboxyl, alkoxycarbonyl, or carbamoyl.

More preferred compounds which inhibit both Factor Xa and Factor IIa (thrombin) activity are those having a structure of formula IIc wherein R$_1$, R$_{1a}$ and R$_2$ are hydrogen; and R$_{2a}$ is alkyl, carboxyl, alkoxycarbonyl, or carbamoyl.

More preferred compounds which inhibit both Factor Xa and Factor IIa (thrombin) activity are those having a structure of formula IIc wherein Cy$_2$ is optionally substituted azaindolyl;

L$_1$ is —S(O)$_2$—, or —S(O)$_2$-alkenylene;

Cy$_1$ is optionally substituted thienyl or optionally substituted benzothiophenyl, optionally substituted, optionally substituted bemzimidazolyl, or optionally substituted indolyl, R$_1$, R$_{1a}$ and R$_2$ are hydrogen; and R$_{2a}$ is alkyl, carboxyl, alkoxycarbonyl, or carbamoyl.

More preferred compounds which inhibit both Factor Xa and Factor IIa (thrombin) activity are those having a structure of formula IIc wherein R$_1$, R$_2$ and R$_{2a}$ are hydrogen; and R$_{1a}$ is alkyl, carboxyl, alkoxycarbonyl, or carbamoyl.

More preferred compounds which inhibit both Factor Xa and Factor IIa (thrombin) activity are those having a structure of formula IIc wherein Cy$_2$ is optionally substituted azaindolyl;

L$_1$ is —S(O)$_2$—, or —S(O)$_2$-alkenylene;

Cy$_1$ is optionally substituted thienyl or optionally substituted benzothiophenyl, R$_{1a}$ is alkyl, carboxyl, alkoxycarbonyl, or carbamoyl; and R$_1$, R$_2$ and R$_{2a}$ are hydrogen.

Other preferred compounds which inhibit both Factor Xa and Factor IIa (thrombin) activity are those having a structure of formula IId

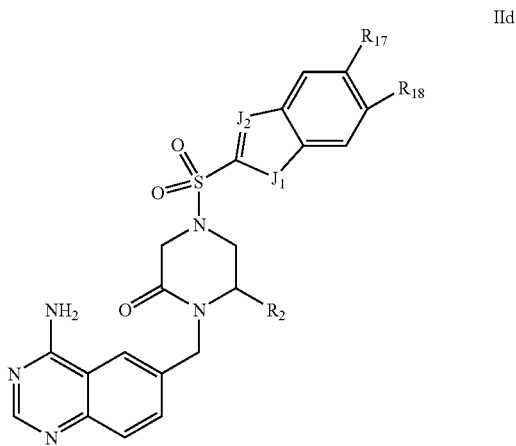

wherein $R_{17}$ and $R_{18}$ are independently hydrogen or halogen;
$J_1$ is S or NH;
$J_2$ is CH or N; and
$R_2$ is hydrogen, alkyl, carboxyl, alkoxycarbonyl, or carbamoyl.

Another preferred aspect of the invention is a compound of formula IId wherein $R_2$ is heterocyclylalkyloxycarbonyl, heterocyclenylalkyloxycarbonyl, heteroaralkyloxycarbonyl, arylalkyloxycarbonyl, cycloalkylalkyloxycarbonyl, or cycloalkenylalkyloxycarbonyl.

Another preferred aspect of the invention is a compound of formula IId wherein $R_2$ is heterocyclylalkylcarbamoyl, heterocyclenylalkylcarbamoyl, heteroaralkylcarbamoyl, arylalkylcarbamoyl, cycloalkylcarbamoyl, or cycloalkenylcarbamoyl.

Another preferred aspect of the invention is a compound of formula IId wherein $R_2$ is heterocyclyl, heterocyclenyl, heteroaryl, aryl, cycloalkyl, or cycloalkenyl.

Another preferred aspect of the invention is a compound of formula IId wherein $R_2$ is heterocyclylalkyloxycarbonylalkyl, heterocyclenylalkyloxycarbonylalkyl, heteroaralkyloxycarbonylalkyl, arylalkyloxycarbonylalkyl, cycloalkylalkyloxycarbonylalkyl, or cycloalkenylalkyloxycarbonylalkyl.

Another preferred aspect of the invention is a compound of formula IId wherein $R_2$ is heterocyclylalkylcarbamoylalkyl, heterocyclenylalkylcarbamoylalkyl, heteroaralkylcarbamoylalkyl, arylalkylcarbamoylalkyl, cycloalkylcarbamoylalkyl, or cycloalkenylcarbamoylalkyl.

Another preferred aspect of the invention is a compound of formula IId wherein $R_2$ is alkoxyalkyl, hydroxyalkyl or aminoalkyl.

Another preferred aspect of the invention is a compound of formula IId wherein $R_2$ is alkyl(H)N-alkyl-.

Compounds contemplated as falling within the scope of this invention, include, but are not limited to
4-[4-(6-Chlorobenzo[b]thiophene-2-sulfonyl)-2-oxo-piperazine-1-ylmethyl]benzamidine,
4-[4-(4-Methoxy-benzenesulfonyl)-2-oxo-piperazin-1-ylmethyl]-benzamidine,
4-[4-(5-Chloro-thieno[3,2-b]pyridine-2-sulfonyl)-2-oxo-piperazin-1-ylmethyl]-benzamidine,
4-[4-(6-Chloro-thieno[2,3-b]pyridine-2-sulfonyl)-2-oxo-piperazin-1-ylmethyl]-benzamidine,
4-[2-Oxo-4-(thieno[2,3-c]pyridine-2-sulfonyl)-piperazin-1-ylmethyl]-benzamidine,
4-[4-(7-Chloro-thieno[2,3-c]pyridine-2-sulfonyl)-2-oxo-piperazin-1-ylmethyl]-benzamidine,
4-[4-(5'-Chloro-[2,2']bithiophenyl-5-sulfonyl)-2-oxo-piperazin-1-ylmethyl]-benzamidine,
4-[4-(4-Chloro-thieno[3,2-c]pyridine-2-sulfonyl)-2-oxo-piperazin-1-ylmethyl]-benzamidine,
4-[2-Oxo-4-(toluene-4-sulfonyl)-piperazin-1-ylmethyl]-benzamidine,
4-[4-(Benzo[b]thiophene-2-sulfonyl)-2-oxo-piperazin-1-ylmethyl]-benzamidine,
4-Amino-3-[4-(6-chloro-benzo[b]thiophene-2-sulfonyl)-2-oxo-piperazin-1-ylmethyl]-benzamidine,
3-[2-Oxo-4-(toluene-4-sulfonyl)-piperazin-1-ylmethyl]-benzamidine,
3-[4-(6-Fluoro-benzo[b]thiophene-2-sulfonyl)-2-oxo-piperazin-1-ylmethyl]-benzamidine,
3-[4-(4-Chloro-benzo[b]thiophene-2-sulfonyl)-2-oxo-piperazin-1-ylmethyl]-benzamidine,
3-[4-(5-Chloro-benzo[b]thiophene-2-sulfonyl)-2-oxo-piperazin-1-ylmethyl]-benzamidine,
3-[4-(6-Methoxy-naphthalene-2-sulfonyl)-2-oxo-piperazin-1-ylmethyl]-benzamidine,
3-{4-[5-(5-Nitro-pyridine-2-sulfonyl)-thiophene-2-sulfonyl]-2-oxo-piperazin-1-ylmethyl}-benzamidine,
3-[4-(6-Chloro-benzo[b]thiophene-2-sulfonyl)-2-oxo-piperazin-1-ylmethyl]-benzamidine,
3-{4-[2-(3-Chloro-phenyl)-ethenesulfonyl]-2-oxo-piperazin-1-ylmethyl}-benzamidine,
3-[2-Oxo-4-(4-phenylazo-benzenesulfonyl)-piperazin-1-ylmethyl]-benzamidine,
3-[4-(Benzo[b]thiophene-2-sulfonyl)-2-oxo-piperazin-1-ylmethyl]-benzamidine,
4-[4-(6-Chloro-1H-benzoimidazol-2-ylmethyl)-2-oxo-piperazin-1-ylmethyl]-benzamidine,
4-{4-[3-(5-Chloro-thiophen-2-yl)-(E)-acryloyl]-2-oxopiperazin-1-ylmethyl}benzamidine,
3-{4-[3-(5-Chloro-thiophen-2-yl)-(E)-acryloyl]-2-oxopiperazin-1-ylmethyl}benzamidine,
3-[4-(6-Chloro-1H-benzoimidazol-2-ylmethyl)-2-oxo-piperazin-1-ylmethyl]-benzamidine,
1-(2-Aminoquinolin-6-ylmethyl)-4-(5'-chloro-[2,2']bithiophenyl-5-sulfonyl)piperazin-2-one,
6-[4-(6-Chlorobenzo[b]thiophene-2-sulfonyl)-2-oxopiperazin-1-ylmethyl]-1H-quinolin-2-one,
4-(6-Chloro-benzo[b]thiophene-2-sulfonyl)-1-thieno[2,3-c]pyridin-3-ylmethyl-piperazin-2-one,
1-(2-Amino-quinoxalin-6-ylmethyl)-4-(6-chloro-benzo[b]thiophene-2-sulfonyl)-piperazin-2-one,
4-(6-Chloro-benzo[b]thiophene-2-sulfonyl)-1-thieno[2,3-c]pyridin-2-ylmethyl-piperazin-2-one,
4-(6-Chloro-benzo[b]thiophene-2-sulfonyl)-1-thieno[3,2-c]pyridin-2-ylmethyl-piperazin-2-one,
1-(2-Amino-quinolin-6-ylmethyl)-4-(6-chloro-thieno[2,3-b]pyridine-2-sulfonyl)-piperazin-2-one,
4-(6-Chloro-benzo[b]thiophene-2-sulfonyl)-1-(1-hydroxy-isoquinolin-6-ylmethyl)-piperazin-2-one,
4-(6-Chloro-benzo[b]thiophene-2-sulfonyl)-1-(1-chloro-isoquinolin-6-ylmethyl)-piperazin-2-one,
7-[4-(6-Chloro-benzo[b]thiophene-2-sulfonyl)-2-oxo-piperazin-1-ylmethyl]-2H-isoquinolin-1-one,
4-(6-Chloro-benzo[b]thiophene-2-sulfonyl)-1-(1-chloro-isoquinolin-7-ylmethyl)-piperazin-2-one, 1-(7-Amino-thieno[2,3-c]pyridin-2-ylmethyl)-4-(6-chloro-benzo[b]thiophene-2-sulfonyl)-piperazin-2-one,
4-(6-Chloro-benzo[b]thiophene-2-sulfonyl)-1-(2-chloro-quinolin-6-ylmethyl)-piperazin-2-one,
4-(6-Chloro-benzo[b]thiophene-2-sulfonyl)-1-quinolin-6-ylmethyl-piperazin-2-one,
7-[4-(6-Chloro-benzo[b]thiophene-2-sulfonyl)-2-oxo-piperazin-1-ylmethyl]-1H-quinolin-2-one,
1-(2-Amino-quinolin-7-ylmethyl)-4-(6-chloro-benzo[b]thiophene-2-sulfonyl)-piperazin-2-one,
1-(4-Amino-thieno[3,2-c]pyridin-2-ylmethyl)-4-(6-chloro-benzo[b]thiophene-2-sulfonyl)-piperazin-2-one,
4-(6-Chloro-benzo[b]thiophene-2-sulfonyl)-1-(1,2,3,4-tetrahydro-isoquinolin-6-ylmethyl)-piperazin-2-one,
4-(6-Chloro-benzo[b]thiophene-2-sulfonyl)-1-isoquinolin-6-ylmethyl-piperazin-2-one,
1-(2-Amino-quinolin-6-ylmethyl)-4-(6-chloro-benzo[b]thiophene-2-sulfonyl)-piperazin-2-one,
4-(6-Chloro-benzo[b]thiophene-2-sulfonyl)-1-(decahydro-isoquinolin-6-ylmethyl)-piperazin-2-one,
1-(1-Amino-isoquinolin-6-ylmethyl)-4-(6-chloro-benzo[b]thiophene-2-sulfonyl)-piperazin-2-one,
4-(6-Chloro-benzo[b]thiophene-2-sulfonyl)-1-(decahydro-isoquinolin-7-ylmethyl)-piperazin-2-one,
1-(1-Amino-isoquinolin-7-ylmethyl)-4-(6-chloro-benzo[b]thiophene-2-sulfonyl)-piperazin-2-one,
1-(4-Amino-thieno[3,2-c]pyridin-3-ylmethyl)-4-(6-chloro-benzo[b]thiophene-2-sulfonyl)-piperazin-2-one,
(+/−)-[1-(6-Chloro-benzo[b]thiophene-2-sulfonyl)-3-oxo-4-thieno[3,2-c]pyridin-2-ylmethyl-piperazin-2-yl]-acetic acid,
(+/−)-[1-(6-Chloro-benzo[b]thiophene-2-sulfonyl)-3-oxo-4-thieno[2,3-c]pyridin-2-ylmethyl-piperazin-2-yl]-acetic acid,
1-(1-Amino-isoquinolin-6-ylmethyl)-4-[3-(5-chloro-thiophen-2-yl)-(E)-acryloyl]-3-(S)-methoxymethyl-piperazin-2-one,
1-(1-Amino-isoquinolin-6-ylmethyl)-4-[(5-chloro-thiophen-2-yloxy)-acetyl]-3-(S)-methoxymethyl-piperazin-2-one,
(3S)-1-(7-Chloro-isoquinolin-3-ylmethyl)-4-[(5-chloro-thiophen-2-yloxy)-acetyl]-3-methoxmethyl-piperazin-2-one,
(3S)-1-(7-Chloro-isoquinolin-3-ylmethyl)-4-[3-(5-chloro-thiophen-2-yl)-(E)-acryloyl]-3-methoxymethyl-piperazin-2-one,
(S)-4-[3-(5-Chloro-thiophen-2-yl)-acryloyl]-3-ethyl-1-(4-hydroxy-quinolin-7-ylmethyl)-piperazin-2-one,
1-(2-Amino-quinolin-6-ylmethyl)-4-[3-(5-chloro-thiophen-2-yl)-(E)-acryloyl]-piperazin-2-one,
1-(2-Aminoquinolin-6-ylmethyl)-4-(4-methoxybenzyl)piperazin-2-one,
1-(2-Aminoquinolin-6-ylmethyl)-4-6-chlorobenzo[b]thiophen-2-ylmethyl)piperazin-2-one,
1-(2-Aminoquinolin-6-ylmethyl)-4-(5-methoxy-1H-benzoimidazol-2-ylmethyl)piperazin-2-one,
1-(2-Aminoquinolin-6-ylmethyl)-4-(5′-chloro-[2,2′]bithiophenyl-5-ylmethyl)piperazin-2-one,
1-(2-Aminoquinolin-6-ylmethyl)-4-[3-(5-chloro-thiophen-2-yl)-allyl]-piperazin-2-one,
1-(2-Aminoquinolin-6-ylmethyl)-4-[3-(3,5-dibromo-4-methoxy-phenyl)-[1,2,4]oxadiazol-5-ylmethyl]piperazin-2-one,
3-[4-(2-Aminoquinolin-6-ylmethyl)-3-oxo-piperazin-1-ylmethyl]-7-fluoro-1H-quinolin-2-one,
1-(2-Aminoquinolin-6-ylmethyl)-4-(6-chloro-naphthalen-2-ylmethyl)-piperazin-2-one,
3-(4-Biphenyl-3-ylmethyl-3-oxo-piperazin-1-ylmethyl)-benzamidine,
4-(5-Chloro-1H-indol-2-ylmethyl)-1-(4-chloro-quinolin-7-ylmethyl)-piperazin-2-one,
1,4-Bis-(5-chloro-1H-indol-2-ylmethyl)-piperazin-2-one,
1-(4-Amino-thieno[3,2-d]pyrimidin-6-ylmethyl)-4-(7-chloro-isoquinolin-3-ylmethyl)-piperazin-2-one,
1-(4-Amino-thieno[3,3,2-d]pyrimidin-6-ylmethyl)-4-(6-chloro-benzo[b]thiophen-2-ylmethyl)-piperazin-2-one,
1-(4-Amino-thieno[3,2-d]pyrimidin-6-ylmethyl)-4-[3-(5-chloro-thiophen-2-yl)-allyl]-piperazin-2-one,
1-(3-Amino-1H-indazol-6-ylmethyl)-4-[3-(5-chloro-thiophen-2-yl)-allyl]-piperazin-2-one,
1-(3-Amino-1H-indazol-6-ylmethyl)-4-(6-chloro-benzo[b]thiophen-2-ylmethyl)-piperazin-2-one,
1-(4-Amino-thieno[2,3-d]pyrimidin-6-ylmethyl)-4-(6-chloro-benzo[b]thiophen-2-ylmethyl)-piperazin-2-,
4-[4-(6-Chloro-benzo[b]thiophen-2-ylmethyl)-2-oxo-piperazin-1-ylmethyl]-benzamidine,
4-[4-(6-Chloro-benzo[b]thiophen-2-ylmethyl)-3-oxo-piperazin-1-ylmethyl]-benzamidine,
4-(4-Cyclohexylmethyl-2-oxo-piperazin-1-ylmethyl)-benzamidine,
1-(1-Amino-isoquinolin-6-ylmethyl)-4-(6-chloro-benzo[b]thiophen-2-ylmethyl)-piperazin-2-one,
1-(1-Amino-isoquinolin-6-ylmethyl)-4-[3-(5-chloro-thiophen-2-yl)-allyl]-3-(S)-methoxymethyl-piperazin-2-one,
4-[3-(5-Chloro-thiophen-2-yl)-allyl]-1-[4-(6-methoxy-pyridin-3-yl)-benzyl]-3-(S)-methyl-piperazin-2-one,
4-[3-(5-Chloro-thiophen-2-yl)-allyl]-3-(S)-methyl-1-[4-(6-oxo-1,6-dihydro-pyridin-3-yl)-benzyl]-piperazin-2-one,
(S)-4-(5-Chloro-1H-indol-2-ylmethyl)-1-(4-chloro-quinolin-7-ylmethyl)-3-methoxymethyl-piperazin-2-one,
(S)-4-(5-Chloro-1H-indol-2-ylmethyl)-1-(4-chloro-quinolin-7-ylmethyl)-3-methyl-piperazin-2-one,
1-(4-Aminoquinazolin-7-ylmethyl)-4-(6-chlorobenzo[b]thiophene-2-sulfonyl)piperazin-2-one,
4-(4-Amino-quinazolin-7-ylmethyl)-3-oxo-piperazine-1-sulfonic acid 3-chloro-benzylamide,
1-(4-Amino-quinazolin-7-ylmethyl)-4-(6-chloro-thieno[2,3-b]pyridine-2-sulfonyl)-piperazin-2-one,
1-(4-Amino-quinazolin-7-ylmethyl)-4-(5′-chloro-[2,2′]bithiophenyl-5-sulfonyl)-piperazin-2-one,
4-(4-Amino-quinazolin-7-ylmethyl)-3-oxo-piperazine-1-sulfonic acid 4-chloro-benzylamide,
1-(4-Amino-quinazolin-7-ylmethyl)-4-(5-isoxazol-3-yl-thiophene-2-sulfonyl)-piperazin-2-one,
1-(4-Amino-quinazolin-7-ylmethyl)-4-(thieno[3,2-b]pyridine-2-sulfonyl)-piperazin-2-one,
4-(4-Amino-quinazolin-7-ylmethyl)-3-oxo-piperazine-1-sulfonic acid [2-(3-chloro-phenyl)-ethyl]-amide,
4-(4-Amino-quinazolin-7-ylmethyl)-3-oxo-piperazine-1-sulfonic acid [2-(4-chloro-phenyl)-ethyl]-amide,
1-(4-Amino-quinazolin-7-ylmethyl)-4-(6-chloro-1H-benzoimidazole-2-sulfonyl)-piperazin-2-one,
1-(4-Amino-quinazolin-7-ylmethyl)-4-[2-(5-chloro-thiophen-2-yl)-ethenesulfonyl]-piperazin-2-one,
4-(3-Amino-benzenesulfonyl)-1-(4-amino-quinazolin-7-ylmethyl)-piperazin-2-one,
1-(4-Amino-quinazolin-7-ylmethyl)-4-[2-(5-chloro-thiophen-2-yl)-ethenesulfonyl]-3-(S)-ethyl-piperazin-2-one,
1-(4-Amino-quinazolin-7-ylmethyl)-4-(6-chloro-benzo[b]thiophene-2-sulfonyl)-3-(S)-ethyl-piperazin-2-one,
1-(4-Amino-quinazolin-7-ylmethyl)-4-(5′-chloro-[2,2′]bithiophenyl-5-sulfonyl)-3-(S)-ethyl-piperazin-2-one, 1-(4-Amino-quinazolin-7-ylmethyl)-4-(5'-chloro-[2,2']bithiophenyl-5-sulfonyl)-3-(S)-methyl-piperazin-2-one,
1-(4-Amino-quinazolin-7-ylmethyl)-4-(6-chloro-benzo[b]thiophene-2-sulfonyl)-3-(S)-methyl-piperazin-2-one,
(+/−)-1-(4-Amino-quinazolin-7-ylmethyl)-4-(6-chloro-benzo[b]thiophene-2-sulfonyl)-6-methyl-piperazin-2-one,
(+/−)-[4-(4-Amino-quinazolin-7-ylmethyl)-1-(6-chloro-benzo[b]thiophene-2-sulfonyl)-3-oxo-piperazin-2-yl]-acetic acid,
1-(4-Amino-thieno[3,2-d]pyrimidin-6-ylmethyl)-4-[2-(5-chloro-thiophen-2-yl)-ethenesulfonyl]-piperazin-2-one,
1-(4-Amino-thieno[3,2-d]pyrimidin-6-ylmethyl)-4-(6-chloro-benzo[b]thiophene-2-sulfonyl)-piperazin-2-one,
1-(4-Amino-thieno[2,3-d]pyrimidin-6-ylmethyl)-4-(6-chloro-benzo[b]thiophene-2-sulfonyl)-piperazin-2-one,
4-(6-Chloro-benzo[b]thiophene-2-sulfonyl)-1-(4-hydroxy-quinazolin-6-ylmethyl)-piperazin-2-one,
1-(4-Amino-thieno[3,2-d]pyrimidin-7-ylmethyl)-4-(6-chloro-benzo[b]thiophene-2-sulfonyl)-piperazin-2-one,
1-(4-Amino-quinazolin-6-ylmethyl)-4-(6-chloro-benzo[b]thiophene-2-sulfonyl)-piperazin-2-one,
4-(6-Chloro-benzo[b]thiophene-2-sulfonyl)-1-(4-hydroxy-quinazolin-7-ylmethyl)-piperazin-2-one,
1-(4-Amino-thieno[3,2-d]pyrimidin-6-ylmethyl)-4-[3-(4-bromo-thiophen-2-yl)-acryloyl]-piperazin-2-one,
1-(4-Amino-thieno[3,2-d]pyrimidin-6-ylmethyl)-4-[3-(5-chloro-thiophen-2-yl)-acryloyl]-piperazin-2-one,
4-[2-(5-Chloro-thiophen-2-yl)-ethenesulfonyl]-1-(1H-pyrrolo[3,2-c]pyridin-2-ylmethyl)piperazin-2-one,
4-(6-Chlorobenzo[b]thiophene-2-sulfonyl)-1-(1H-pyrrolo[3,2-c]pyridin-2-ylmethyl)piperazin-2-one,
4-(6-Chlorobenzo[b]thiophene-2-sulfonyl)-1-(5-oxy-1H-pyrrolo[3,2-c]pyridin-2-ylmethyl)piperazin-2-one,
4-(6-Chlorobenzo[b]thiophene-2-sulfonyl)-1-(1-methyl-1H-pyrrolo[3,2-c]pyridin-2-ylmethyl)piperazin-2-one,
4-(3-Chlorobenzo[b]thiophene-2-sulfonyl)-1-(1H-pyrrolo[3,2-c]pyridin-2-ylmethyl)piperazin-2-one,
4-(6-Chlorothieno[2,3-b]pyridine-2-sulfonyl)-1-(1H-pyrrolo[3,2-c]pyridin-2-ylmethyl)piperazin-2-one,
4-(6-Bromobenzo[b]thiophene-2-sulfonyl)-1-(1H-pyrrolo[3,2-c]pyridin-2-ylmethyl)piperazin-2-one,
2-[3-Oxo-4-(1H-pyrrolo[3,2-c]pyridin-2-ylmethyl)piperazine-1-sulfonyl]-benzo[b]thiophene-6-carbonitrile,
4-(5'-Chloro-[2,2']bithiophenyl-5-sulfonyl)-1-(1H-pyrrolo[3,2-c]pyridin-2-ylmethyl)piperazin-2-one,
4-[2-(4-Chlorophenyl)ethenesulfonyl]-1-(1H-pyrrolo[3,2-c]pyridin-2-ylmethyl)piperazin-2-one,
{2-[4-(6-Chlorobenzo[b]thiophene-2-sulfonyl)-2-oxopiperazin-1-ylmethyl]pyrrolo[3,2-c]pyridin-1-yl}acetic acid,
4-(5-Pyridin-4-ylthiophene-2-sulfonyl)-1-(1H-pyrrolo[3,2-c]pyridin-2-ylmethyl)piperazin-2-one,
{2-[4-(6-Chlorobenzo[b]thiophene-2-sulfonyl)-2-oxopiperazin-1-ylmethyl]pyrrolo[3,2-c]pyridin-1-yl}acetic acid ethyl ester,
4-(6-Chlorobenzo[b]thiophene-2-sulfonyl)-1-[1-(2-methoxyethyl)-1H-pyrrolo[3,2-c]pyridin-2-ylmethyl]piperazin-2-one,
4-(6-Chlorothieno[3,2-b]pyridine-2-sulfonyl)-1-(1H-pyrrolo[3,2-c]pyridin-2-ylmethyl)piperazin-2-one,
{2-[4-(6-Chloro-benzo[b]thiophene-2-sulfonyl)-2-oxopiperazin-1-ylmethyl]pyrrolo[2,3c]pyridin-1-yl}acetic acid methyl ester,
2-[3-Oxo-4-(1H-pyrrolo[3,2-c]pyridin-2-ylmethyl)piperazine-1-sulfonyl]benzo[b]thiophene-5-carbonitrile,
4-(5-Aminomethylbenzo[b]thiophene-2-sulfonyl)-1-(1H-pyrrolo[3,2-c]pyridin-2-ylmethyl)piperazin-2-one,
2-{2-[4-(6-Chlorobenzo[b]thiophene-2-sulfonyl)-2-oxopiperazin-1-ylmethyl]pyrrolo[3,2-c]pyridin-1-yl}acetamide,
4-(6-Chlorobenzo[b]thiophene-2-sulfonyl)-1-[1-(2-hydroxyethyl)-1H-pyrrolo[3,2-c]pyridin-2-ylmethyl]piperazin-2-one,
4-(6-Chloro-1H-benzoimidazole-2-sulfonyl)-1-(1H-pyrrolo[3,2-c]pyridin-2-ylmethyl)-piperazin-2-one,
4-(1H-Benzoimidazole-2-sulfonyl)-1-(1H-pyrrolo[3,2-c]pyridin-2-ylmethyl)-piperazin-2-one,
4-(6-Aminomethyl-benzo[b]thiophene-2-sulfonyl)-1-(1H-pyrrolo[3,2-c]pyridin-2-ylmethyl)-piperazin-2-one,
1-(1H-Pyrrolo[3,2-c]pyridin-2-ylmethyl)-4-(thieno[2,3-b]pyridine-2-sulfonyl)-piperazin-2-one,
1-(1H-Pyrrolo[3,2-c]pyridin-2-ylmethyl)-4-(thieno[3,2-b]pyridine-2-sulfonyl)-piperazin-2-one,
4-[2-(5-Chloro-thiophen-2-yl)-ethanesulfonyl]-1-(1H-pyrrolo[3,2-c]pyridin-2-ylmethyl)-piperazin-2-one,
4-(2-Benzo[b]thiophen-2-yl-ethenesulfonyl)-1-(1H-pyrrolo[3,2-c]pyridin-2-ylmethyl)-piperazin-2-one,
4-[2-(5-Chloro-4-methoxy-thiophen-2-yl)-ethenesulfonyl]-1-(1H-pyrrolo[3,2-c]pyridin-2-ylmethyl)-piperazin-2-one,
4-(6-Chloro-benzo[b]thiophene-2-sulfonyl)-1-furo[3,2-c]pyridin-2-ylmethyl-piperazin-2-one,
4-(6-Fluoro-benzo[b]thiophene-2-sulfonyl)-1-furo[3,2-c]pyridin-2-ylmethyl-piperazin-2-one,
4-(6-Chlorobenzo[b]thiophene-2-sulfonyl)-1-(1H-pyrrolo[2,3-c]pyridin-2-ylmethyl)piperazin-2-one,
4-(6-Chlorothieno[2,3-b]pyridine-2-sulfonyl)-1-(1H-pyrrolo[2,3-c]pyridin-2-ylmethyl)-piperazin-2-one,
{2-[4-(6-Chloro-benzo[b]thiophene-2-sulfonyl)-2-oxo-piperazin-1-ylmethyl]-pyrrolo[2,3-c]pyridin-1-yl}-acetic acid methyl ester,
4-(6-Chloro-benzo[b]thiophene-2-sulfonyl)-1-(1H-pyrrolo[3,2-b]pyridin-2-ylmethyl)-piperazin-2-one,
1-(4-Amino-1H-pyrrolo[3,2-c]pyridin-2-ylmethyl)-4-(6-chloro-benzo[b]thiophene-2-sulfonyl)piperazin-2-one,
4-[2-(5-Chloro-thiophen-2-yl)-ethenesulfonyl]-5-(±)-hydroxymethyl-1-(1H-pyrrolo[3,2-c]pyridin-2-ylmethyl)-piperazin-2-one,
(±)-1-(6-Chloro-benzo[b]thiophene-2-sulfonyl)-5-oxo-4-(1H-pyrrolo[3,2-c]pyridin-2-ylmethyl)-piperazine-2-carboxylic acid methyl ester,
(±)-1-[2-(5-Chloro-thiophen-2-yl)-ethenesulfonyl]-5-oxo-4-(1H-pyrrolo[3,2-c]pyridin-2-ylmethyl)-piperazine-2-carboxylic acid methyl ester,
(±)-1-(6-Chloro-benzo[b]thiophene-2-sulfonyl)-5-oxo-4-(1H-pyrrolo[3,2-c]pyridin-2-ylmethyl)-piperazine-2-carboxylic acid,
(±)-4-(6-Chloro-benzo[b]thiophene-2-sulfonyl)-5-hydroxymethyl-1-(1H-pyrrolo[3,2-c]pyridin-2-ylmethyl)-piperazin-2-one,
(−)-1-[2-(5-Chloro-thiophen-2-yl)-ethenesulfonyl]-5-oxo-4-(1H-pyrrolo[3,2-c]pyridin-2-ylmethyl)-piperazine-2-carboxylic acid methyl ester,
(±)-1-[2-(5-Chloro-thiophen-2-yl)-ethenesulfonyl]-5-oxo-4-(1H-pyrrolo[3,2-c]pyridin-2-ylmethyl)-piperazine-2-carboxylic acid methyl ester,
4-[2-(5-Chloro-thiophen-2-yl)-ethenesulfonyl]-6-(R)-hydroxymethyl-1-(1H-pyrrolo[3,2-c]pyridin-2-ylmethyl)-piperazin-2-one,
4-(6-Chloro-benzo[b]thiophene-2-sulfonyl)-6-(R)-hydroxymethyl-1-(1H-pyrrolo[3,2-c]pyridin-2-ylmethyl)-piperazin-2-one,
(±)-4-[2-(5-Chloro-thiophen-2-yl)-ethenesulfonyl]-6-oxo-1-(1H-pyrrolo[3,2-c]pyridin-2-ylmethyl)-piperazine-2-carboxylic acid methyl ester, (±)-4-(6-Chloro-benzo[b]thiophene-2-sulfonyl)-6-oxo-1-(1H-pyrrolo[3,2-c]pyridin-2-ylmethyl)-piperazine-2-carboxylic acid methyl ester,
(±)-4-[2-(5-Chloro-thiophen-2-yl)-ethenesulfonyl]-6-oxo-1-(1H-pyrrolo[3,2-c]pyridin-2-ylmethyl)-piperazine-2-carboxylic acid,
(±)-4-(6-Chloro-benzo[b]thiophene-2-sulfonyl)-6-oxo-1-(1H-pyrrolo[3,2-c]pyridin-2-ylmethyl)-piperazine-2-carboxylic acid,
(±)-4-(6-Chloro-benzo[b]thiophene-2-sulfonyl)-6-hydroxymethyl-1-(1H-pyrrolo[3,2-c]pyridin-2-ylmethyl)-piperazin-2-one,
(±)-4-[2-(5-Chloro-thiophen-2-yl)-ethenesulfonyl]-6-hydroxymethyl-1-(1H-pyrrolo[3,2-c]pyridin-2-ylmethyl)-piperazin-2-one,
(±)-4-(6-Chloro-benzo[b]thiophene-2-sulfonyl)-6-oxo-1-(1H-pyrrolo[3,2-c]pyridin-2-ylmethyl)-piperazine-2-carboxylic acid amide,
4-[2-(5-Chloro-thiophen-2-yl)-ethenesulfonyl]-3-(S)-methoxymethyl-1-(1H-pyrrolo[3,2-c]pyridin-2-ylmethyl)-piperazin-2-one,
4-(6-Chloro-benzo[b]thiophene-2-sulfonyl)-3-(S)-methoxymethyl-1-(1H-pyrrolo[3,2-c]pyridin-2-ylmethyl)-piperazin-2-one,
4-(5'-Chloro-[2,2']bithiophenyl-5-sulfonyl)-3-(S)-methoxymethyl-1-(1H-pyrrolo[3,2-c]pyridin-2-ylmethyl)-piperazin-2-one,
4-[2-(4-Chloro-phenyl)-ethenesulfonyl]-3-(S)-methoxymethyl-1-(1H-pyrrolo[3,2-c]pyridin-2-ylmethyl)-piperazin-2-one,
1-(4-Aminoquinazolin-7-ylmethyl)-4-(6-chlorobenzo[b]thiophene-2-ylmethyl)piperazin-2-one,
1-(4-Aminoquinazolin-7-ylmethyl)-4-(6-chloro-1H-benzoimidazol-2-ylmethyl)piperazin-2-one,
1-(4-Amino-quinazolin-7-ylmethyl)-4-(6-chloro-benzothioazol-2-ylmethyl)-piperazin-2-one,
1-(4-Amino-quinazolin-7-ylmethyl)-4-(6-chloro-benzooxazol-2-ylmethyl)-piperazin-2-one,
1-(4-Amino-quinazolin-7-ylmethyl)-4-(5-chloro-benzothioazol-2-ylmethyl)-piperazin-2-one,
3-[4-(4-Aminoquinazoline-7-ylmethyl)-3-oxopiperazin-1-ylmethyl]-7-chloro1H-quinolin-2-one,
1-(4-Amino-quinazolin-7-ylmethyl)-4-(3-chloro-1H-indol-6-ylmethyl)-piperazin-2-one,
1-(4-Amino-quinazolin-7-ylmethyl)-4-[3-(5-chloro-thiophen-2-yl)-(E)-allyl]-piperazin-2-one,
1-(4-Amino-quinazolin-7-ylmethyl)-4-[3-(5-chloro-thiophen-2-yl)-but-2-(E)-enyl]-piperazin-2-one ditrifluoroacetate,
1-(4-Amino-quinazolin-7-ylmethyl)-4-[3-(5-chloro-thiophen-2-yl)-2-methyl-(E)-allyl]-pipeazin-2-one ditrifluoroacetate,
1-(4-Amino-quinazolin-7-ylmethyl)-4-[3-(4-bromo-furan-2-yl)-(E)-allyl]-piperazin-2-one,
1-(4-Amino-quinazolin-7-ylmethyl)-4-[3-(6-methoxy-pyridin-3-yl)-(E)-allyl]-piperazin-2-one,
1-(4-Amino-quinazolin-7-ylmethyl)-4-[3-(5-chloro-thiophen-2-yl)-(E)-allyl]-4-oxy-piperazin-2-one,
1-(4-Amino-quinazolin-7-ylmethyl)-4-[3-(5-chloro-thiophen-2-yl)-prop-2-ynyl]-piperazin-2-one,
1-(4-Amino-quinazolin-7-ylmethyl)-4-[3-(5-chloro-thiophen-2-yl)-propyl]-piperazin-2-one,
1-(4-Amino-quinazolin-7-ylmethyl)-4-prop-2-ynyl-piperazin-2-one,
1-(4-Amino-quinazolin-7-ylmethyl)-4-(3-biphenyl-2-yl-prop-2-ynyl)-piperazin-2-one,
1-(4-Amino-quinazolin-7-ylmethyl)-4-(1H-pyrrolo[3,2-c]pyridin-2-ylmethyl)-piperazin-2-one,
1-(4-Amino-quinazolin-7-ylmethyl)-4-[2-(5-chloro-thiophen-2-yloxy)-ethyl]-piperazin-2-one,
1-(4-Amino-quinazolin-7-ylmethyl)-4-(5-chloro-1-methyl-1H-indol-2-ylmethyl)-piperazin-2-one,
1-(4-Amino-quinazolin-7-ylmethyl)-4-[3-(4-chloro-thiophen-2-yl)-allyl]-piperazin-2-one,
1-(4-Amino-quinazolin-7-ylmethyl)-4-[3-(6-chloro-benzo[b]thiophen-2-yl)-allyl]-piperazin-2-one,
1-(4-Amino-quinazolin-7-ylmethyl)-4-[3-(5-chloro-4-methyl-thiophen-2-yl)-allyl]-piperazin-2-one,
1-(4-Amino-quinazolin-7-ylmethyl)-4-(5-chloro-benzofuran-2-ylmethyl)-piperazin-2-one,
1-(4-Amino-quinazolin-7-ylmethyl)-4-(3-chloro-1H-indol-5-ylmethyl)-piperazin-2-one,
1-(4-Amino-quinazolin-7-ylmethyl)-4-(5-chloro-1H-indol-2-ylmethyl)-piperazin-2-one,
1-(4-Amino-quinazolin-7-ylmethyl)-4-(5,7-dichloro-1H-indol-2-ylmethyl)-piperazin-2-one,
1-(4-Amino-quinazolin-7-ylmethyl)-4-(6-chloro-1H-indol-2-ylmethyl)-piperazin-2-one,
1-(4-Amino-quinazoin-7-ylmethyl)-4-(3-p-tolyl-prop-2-ynyl)-piperazin-2-one,
1-(4-Amino-quinazolin-7-ylmethyl)-4-(3-m-tolyl-prop-2-ynyl)-piperazin-2-one,
1-(4-Amino-quinazolin-7-ylmethyl)-4-[3-(4-chloro-phenyl)-prop-2-ynyl]-piperazin-2-one,
1-(4-Amino-quinazolin-7-ylmethyl)-4-[3-(3-chloro-phenyl)-prop-2-ynyl]-piperazin-2-one,
1-(4-Amino-quinazolin-7-ylmethyl)-4-[3-(2-chloro-phenyl)-prop-2-ynyl]-piperazin-2-one,
1-(4-Amino-quinazolin-7-ylmethyl)-4-(3-biphenyl-4-yl-prop-2-ynyl)-piperazin-2-one,
1-(4-Amino-quinazolin-7-ylmethyl)-4-[3-(4,5-dibromo-thiophen-2-yl)-allyl]-piperazin-2-one,
1-(4-Amino-quinazolin-7-ylmethyl)-4-(3-biphenyl-3-yl-prop-2-ynyl)-piperazin-2-one,
1-(4-Amino-quinazolin-7-ylmethyl)-4-[3-(2,5-dichloro-thiophen-3-yl)-prop-2-ynyl]-piperazin-2-one,
1-(4-Amino-quinazolin-7-ylmethyl)-4-[3-(3-chloro-phenyl)-propyl]-piperazin-2-one,
1,4-Bis-(4-amino-quinazolin-7-ylmethyl)-piperazin-2-one,
1-(4-Amino-quinazolin-7-ylmethyl)-4-(1H-pyrrolo[2,3-c]pyridin-2-ylmethyl)-piperazin-2-one,
1-(4-Amino-quinazolin-7-ylmethyl)-4-[3-(5-nitro-thiophen-2-yl)-allyl]-piperazin-2-one,
1-(4-Amino-quinazolin-7-ylmethyl)-4-[3-(6-chloro-pyridin-3-yl)-allyl]-piperazin-2-one,
1-(4-Amino-quinazolin-7-ylmethyl)-4-(1H-pyrrolo[3,2-c]pyridin-2-ylmethyl)-piperazin-2-one,
1-(4-Amino-quinazolin-7-ylmethyl)-4-[3-(5-chloro-thiophen-3-yl)-allyl]-piperazin-2-one,
1-(4-Amino-quinazolin-7-ylmethyl)-4-[3-(5-bromo-furan-2-yl)-allyl]-piperazin-2-one,
1-(4-Amino-quinazolin-7-ylmethyl)-4-[5-(5-methyl-thiophen-2-yl)-penta-2,4-dienyl]-piperazin-2-one,
1-(4-Amino-quinazolin-7-ylmethyl)-4-(2-chloro-benzo[b]thiophen-5-ylmethyl)-piperazin-2-one,
1-(4-Amino-quinazolin-7-ylmethyl)-4-[3-(5-methyl-thiophen-2-yl)-allyl]-piperazin-2-one,
1-(4-Amino-quinazolin-7-ylmethyl)-4-[3-(5-methoxy-thiophen-2-yl)-allyl]-piperazin-2-one,
4-(1-Amino-7-chloro-isoquinolin-3-ylmethyl)-1-(4-amino-quinazolin-7-ylmethyl)-piperazin-2-one,
2-[4-(4-Amino-quinazolin-7-ylmethyl)-3-oxo-piperazin-1-yl]-N-(5-chloro-thiophen-2-yl)-acetamide, 1-(4-Amino-quinazolin-7-ylmethyl)-4-(7-chloro-isoquinolin-3-ylmethyl)-piperazin-2-one,
1-(4-Amino-quinazolin-7-ylmethyl)-4-[2-(3-chloro-phenyl)-2-(S)-hydroxy-ethyl]-piperazin-2-one,
1-(4-Amino-quinazolin-7-ylmethyl)-4-[2-(3-chloro-phenylsulfanyl)-ethyl]-piperazin-2-one,
1-(4-Amino-quinazolin-7-ylmethyl)-4-(2-methylene-1,1-dioxo-2,3-dihydro-1H-11 6-benzo[b]thioiphen-3-yl)-piperazin-2-one,
1-(4-Amino-quinazolin-7-ylmethyl)-4-[3-(4-nitro-phenyl)-allyl]-piperazin-2-one,
1-(4-Amino-quinazolin-7-ylmethyl)-4-(2-chloro-benzo[b]thiophen-6-ylmethyl)-piperazin-2-one,
2-[4-(4-Amino-quinazolin-7-ylmethyl)-3-oxo-piperazin-1-yl]-N-(4-chloro-phenyl)-acetamide,
1-(4-Amino-quinazolin-7-ylmethyl)-4-[1-(4-chloro-phenyl)-pyrrolidin-3-yl]-piperazin-2-one,
1-(4-Amino-quinazolin-7-ylmethyl)-4-[2-(5-chloro-thiophen-2-yl)-ethyl]-piperazin-2-one,
1-(4-Amino-quinazolin-7-ylmethyl)-4-[3-(4-chloro-phenyl)-propyl]-piperazin-2-one,
2-[4-(4-Aminoquinazoline-7-ylmethyl)-3-oxo-piperazin-1-ylmethyl]-3-(4-chlorophenyl)-acrylic acid,
1-(4-Amino-quinazolin-7-ylmethyl)-4-(7-chloro-1-hydroxy-isoquinolin-3-ylmethyl)-piperazin-2-one,
1-(4-Amino-quinazolin-7-ylmethyl)-4-(6-chloro-naphthalen-2-ylmethyl)-piperazin-2-one,
1-(4-Amino-quinazolin-7-ylmethyl)-4-isoquinolin-3-ylmethyl-piperazin-2-one,
1-(4-Amino-quinazolin-7-ylmethyl)-4-[1-(3-chloro-phenyl)-pyrrolidin-3-yl]-piperazin-2-one,
1-(4-Amino-quinazolin-7-ylmethyl)-4-(1,7-dichloro-isoquinolin-3-ylmethyl)-piperazin-2-one,
4-(2-Amino-7-chloro-quinolin-3-ylmethyl)-1-(4-amino-quinazolin-7-ylmethyl)-piperazin-2-one,
1-(4-Aminoquinazolin-7-ylmethyl)-4-(5-chloro-benzo[b]thiophene-2-ylmethyl)piperazin-2-one,
1-(4-Amino-quinazolin-7-ylmethyl)-4-[2-(4-chloro-phenylsulfanyl)-ethyl]-piperazin-2-one,
1-(4-Amino-quinazolin-7-ylmethyl)-4-[2-(6-chloro-benzo[b]thiophen-2-yl)-ethyl]-piperazin-2-one,
1-(4-Aminoquinazolin-7-ylmethyl)-4-[2-(4-chloro-phenoxy)-ethyl]-piperazine-2-one,
2-[4-(4-Amino-quinazolin-7-ylmethyl)-3-oxo-piperazin-1-ylmethyl]-6-chloro-4H-benzo[1,4]thiazin-3-one,
1-(4-Amino-quinazolin-7-ylmethyl)-4-(2,7-dichloro-quinolin-3-ylmethyl)-piperazin-2-one,
2-[[4-(4-Amino-quinazolin-7-ylmethyl)-3-oxo-piperazin-1-yl]-(4-chloro-phenyl)-methyl]-acrylic acid ethyl ester,
2-[4-(4-Amino-quinazolin-7-ylmethyl)-3-oxo-piperazin-1-ylmethyl]-3-(4-chloro-phenyl)-acrylic acid ethyl ester,
1-(4-Amino-quinazolin-7-ylmethyl)-4-[3-(4-chloro-phenyl)-allyl]-piperazin-2-one,
1-(4-Amino-quinazolin-7-ylmethyl)-4-[3-(3-chloro-phenyl)-allyl]-piperazin-2-one,
1-(4-Amino-quinazolin-7-ylmethyl)-4-[3-(5-bromo-thiophen-2-yl)-allyl]-piperazin-2-one,
1-(4-Amino-quinazolin-7-ylmethyl)-4-[3-(4-bromo-thiophen-2-yl)-allyl]-piperazin-2-one,
3-[4-(4-Amino-quinazolin-7-ylmethyl)-3-oxo-piperazin-1-ylmethyl]-7-fluoro-1H-quinolin-2-one,
3-[4-(4-Amino-quinazolin-7-ylmethyl)-3-oxo-piperazin-1-ylmethyl]-6-chloro-1H-quinoxalin-2-one,
1-(4-Amino-quinazolin-7-ylmethyl)-4-(5-chloro-1-methyl-1H-benzoimidazol-2-ylmethyl)-piperazin-2-one,
2-[4-(4-Amino-quinazolin-7-ylmethyl)-3-oxo-piperazin-1-ylmethyl]-6-chloro-3H-quinazolin-4-one,
1-(4-Amino-quinazolin-7-ylmethyl)-4-(3-thiophen-2-yl-propyl)-piperazin-2-one,
1-(4-Amino-quinazolin-7-ylmethyl)-4-(7-chloro-quinolin-3-ylmethyl)-piperazin-2-one,
3-[4-(4-Amino-quinazolin-7-ylmethyl)-3-oxo-piperazin-1-ylmethyl]-5,7-dichloro-1H-quinolin-2-one,
1-(4-Amino-quinazolin-7-ylmethyl)-4-(6,7-dichloro-benzo[b]thiophen-2-ylmethyl)-piperazin-2-one,
3-[4-(4-Amino-quinazolin-7-ylmethyl)-3-oxo-piperazin-1-ylmethyl]-5-chloro-1H-quinolin-2-one,
1-(4-Amino-quinazolin-7-ylmethyl)-4-(5-chloro-[2,3']bithiophenyl-5'-ylmethyl)-piperazin-2-one,
4-(6-Amino-benzo[b]thiophen-2-ylmethyl)-1-(4-amino-quinazolin-7-ylmethyl)-piperazin-2-one,
1-(4-Amino-quinazolin-7-ylmethyl)-4-(2-chloro-quinolin-6-ylmethyl)-piperazin-2-one,
1-(4-Amino-quinazolin-7-ylmethyl)-4-(6-bromo-1H-benzoimidazol-2-ylmethyl)-piperazin-2-one,
1-(4-Amino-quinazoin-7-ylmethyl)-4-(6-nitro-benzo[b]thiophen-2-ylmethyl)-piperazin-2-one,
1-(4-Amino-quinazolin-7-ylmethyl)-4-[5-(3-chloro-phenyl)-thiophen-2-ylmethyl]-piperazin-2-one,
1-(4-Amino-quinazolin-7-ylmethyl)-4-(6-chloro-3-methoxy-benzo[b]thiophen-2-ylmethyl)-piperazin-2-one,
3-[4-(4-Amino-quinazolin-7-ylmethyl)-3-oxo-piperazin-1-ylmethyl]-6-chloro-1H-quinolin-2-one,
1-(4-Amino-quinazolin-7-ylmethyl)-4-(6-trifluoromethyl-1H-benzoimidazol-2-ylmethyl)-piperazin-2-one,
1-(4-Amino-quinazolin-7-ylmethyl)-4-(5'-methyl-[2,2']bithiophenyl-5-ylmethyl)-piperazin-2-one,
1-(4-Amino-quinazolin-7-ylmethyl)-4-(5-methyl-benzo[b]thiophen-2-ylmethyl)-piperazin-2-one,
1-(4-Amino-quinazolin-7-ylmethyl)-4-(5'-chloro-3,3'-dimethyl-[2,2']bithiophenyl-5-ylmethyl)-piperazin-2-one,
1-(4-Amino-quinazolin-7-ylmethyl)-4-[3-(3,5-dibromo-4-methoxy-phenyl)-[1,2,4]oxadiazol-5-ylmethyl]-piperazin-2-one,
1-(4-Amino-quinazolin-7-ylmethyl)-4-(6-methyl-benzo[b]thiophen-2-ylmethyl)-piperazin-2-one,
1-(4-Amino-quinazolin-7-ylmethyl)-4-(4-methyl-benzo[b]thiophen-2-ylmethyl)-piperazin-2-one,
1-(4-Amino-quinazolin-7-ylmethyl)-4-(7-chloro-benzo[b]thiophen-2-ylmethyl)-piperazin-2-one,
1-(4-Amino-quinazolin-7-ylmethyl)-4-(5'-chloro-3'-methyl-[2,2']bithiophenyl-5-ylmethyl)-piperazin-2-one,
1-(4-Amino-quinazolin-7-ylmethyl)-4-(1H-benzoimidazol-2-ylmethyl)-piperazin-2-one,
1-(4-Amino-quinazolin-7-ylmethyl)-4-(5'-bromo-[2,2']bithiophenyl-5-ylmethyl)-piperazin-2-one,
1-(4-Amino-quinazolin-7-ylmethyl)-4-[5-(2,3-dihydro-benzo[1,4]dioxin-6-yl)-oxazol-2-ylmethyl]-piperazin-2-one,
1-(4-Amino-quinazolin-7-ylmethyl)-4-(5,6-dichloro-benzo[b]thiophen-2-ylmethyl)-piperazin-2-one,
1-(4-Amino-quinazolin-7-ylmethyl)-4-(4,5-dichloro-benzo[b]thiophen-2-ylmethyl)-piperazin-2-one,
1-(4-Amino-quinazolin-7-ylmethyl)-4-(5-chloro-benzooxazol-2-ylmethyl)-piperazin-2-one,
1-(4-Amino-quinazolin-7-ylmethyl)-4-(6-chloro-5-fluoro-benzo[b]thiophen-2-ylmethyl)-piperazin-2-one,
1-(4-Amino-quinazolin-7-ylmethyl)-4-(4-chloro-5-fluoro-benzo[b]thiophen-2-ylmethyl)-piperazin-2-one,
1-(4-Amino-quinazolin-7-ylmethyl)-4-(5'-chloro-3-methyl-[2,2']bithiophenyl-5-ylmethyl)-piperazin-2-one,
1-(4-Amino-quinazolin-7-ylmethyl)-4-(5-chloro-thieno[3,2-b]pyridin-2-ylmethyl)-piperazin-2-one, 1-(4-Amino-quinazolin-7-ylmethyl)-4-(5,6-dichloro-1H-benzoimidazol-2-ylmethyl)-piperazin-2-one,
1-(4-Amino-quinazolin-7-ylmethyl)-4-(3-benzooxazol-2-yl-benzyl)-piperazin-2-one,
1-(4-Amino-quinazolin-7-ylmethyl)-4-[5-(4-chloro-phenyl)-thiophen-2-ylmethyl]-piperazin-2-one,
1-(4-Amino-quinazolin-7-ylmethyl)-4-(6-methyl-1H-benzoimidazol-2-ylmethyl)-piperazin-2-one,
1-(4-Amino-quinazolin-7-ylmethyl)-4-[2,2']bithiophenyl-5-ylmethyl-piperazin-2-one,
1-(4-Amino-quinazolin-7-ylmethyl)-4-(4-fluoro-benzo[b]thiophen-2-ylmethyl)-piperazin-2-one,
1-(4-Aminoquinazolin-7-ylmethyl)-4-(6-fluoro-benzo[b]thiophene-2-ylmethyl)piperazin-2-one,
1-(4-Amino-quinazolin-7-ylmethyl)-4-[5-(1-methyl-5-trifluoro-methyl-1H-pyrazol-3-yl)-thiophen-2-ylmethyl]-piperazin-2-one,
1-(4-Amino-quinazolin-7-ylmethyl)-4-(3,4-dimethyl-thieno[2,3-b]thiophen-2-ylmethyl)-piperazin-2-one,
1-(4-Amino-quinazolin-7-ylmethyl)-4-(4-chloro-3-methyl-benzo[b]thiophen-2-ylmethyl)-piperazin-2-one,
1-(4-Amino-quinazolin-7-ylmethyl)-4-(6-chloro-3-methyl-benzo[b]thiophen-2-ylmethyl)-piperazin-2-one,
1-(4-Amino-quinazolin-7-ylmethyl)-4-[5-(2-methyl-5-trifluoromethyl-2H-pyrazol-3-yl)thiophen-2-ylmethyl]piperazin-2-one,
1-(4-Amino-quinazolin-7-ylmethyl)-4-[5-(3-nitro-phenyl)-furan-2-ylmethyl]-piperazin-2-one,
1-(4-Amino-quinazolin-7-ylmethyl)-4-(5-chloro-thieno[3,2-b]pyridin-6-ylmethyl)-piperazin-2-one,
1-(4-Amino-quinazolin-7-ylmethyl)-4-[5-(4-methoxy-phenyl)-thiophen-2-ylmethyl]-piperazin-2-one,
1-(4-Amino-quinazolin-7-ylmethyl)-4-(4-hydroxy-2-pyridin-2-yl-pyrimidin-5-ylmethyl)-piperazin-2-one,
1-(4-Amino-quinazolin-7-ylmethyl)-4-[3-(4-fluoro-phenoxy)-benzyl]-piperazin-2-one,
1-(4-Amino-quinazolin-7-ylmethyl)-4-[2-(4-chloro-phenyl)-thiazol-4-ylmethyl]-piperazin-2-one,
1-(4-Amino-quinazolin-7-ylmethyl)-4-(6-bromo-benzo[b]thiophen-2-ylmethyl)-piperazin-2-one,
1-(4-Amino-quinazolin-7-ylmethyl)-4-benzo[b]thiophen-2-ylmethyl-piperazin-2-one,
1-(4-Amino-quinazolin-7-ylmethyl)-4-(5'-chloro-[2,2']bithiophenyl-5-ylmethyl)-piperazin-2-one,
1-(4-Amino-quinazolin-7-ylmethyl)-4-(3,5-bis-trifluoromethyl-benzyl)-piperazin-2-one,
1-(4-Amino-quinazolin-7-ylmethyl)-4-biphenyl-4-ylmethyl-piperazin-2-one,
1-(4-Amino-quinazolin-7-ylmethyl)-4-naphthalen-2-ylmethyl-piperazin-2-one,
1-(4-Amino-quinazolin-7-ylmethyl)-4-(5-chloro-benzo[b]thiophen-3-ylmethyl)-piperazin-2-one,
1-(4-Amino-quinazolin-7-ylmethyl)-4-(6-chloro-thieno[2,3-b]pyridin-2-ylmethyl)-piperazin-2-one,
1-(4-Aminoquinazolin-7-ylmethyl)-4-[3-(5-chloro-thiophen-2-yl)-(E)-acryloyl]piperazin-2-one,
1-(4-Amino-quinazolin-7-ylmethyl)-4-(4-chloro-thiophene-2-carbonyl)-piperazin-2-one,
4-[3-(3-Amino-4-chloro-phenyl)-(E)-acryloyl]-1-(4-amino-quinazolin-7-ylmethyl)-piperazin-2-one,
1-(4-Amino-quinazolin-7-ylmethyl)-4-(3-chloro-1H-indole-6-carbonyl)-piperazin-2-one,
1-(4-Amino-quinazolin-7-ylmethyl)-4-[(5-chloro-thiophen-2-yloxy)-acetyl]piperazin-2-one,
1-(4-Amino-quinazolin-7-ylmethyl)-4-[3-(5-bromo-thiophen-2-yl)-(E)-acryloyl]-piperazin-2-one,
5-Chloro-thiophene-2-carboxylic acid {2-[4-(4-amino-quinazolin-7-ylmethyl)-3-oxo-piperazin-1-yl]-2-oxo-ethyl}-amide,
1-(4-Amino-quinazolin-7-ylmethyl)-4-[3-(4-chloro-thiophen-2-yl)-(E)-acryloyl]-piperazin-2-one,
1-(4-Amino-quinazolin-7-ylmethyl)-4-(5-chloro-1H-indole-2-carbonyl)-piperazin-2-one,
1-(4-Amino-quinazolin-7-ylmethyl)-4-[3-(6-chloro-benzo[b]thiophen-2-yl)-(E)-acryloyl]-piperazin-2-one,
1-(4-Amino-quinazolin-7-ylmethyl)-4-[3-(4-bromo-thiophen-2-yl)-(E)-acryloyl]-piperazin-2-one,
5-Chloro-thiophene-2-carboxylic acid {2-[4-(4-amino-quinazolin-7-ylmethyl)-3-oxo-piperazin-1-yl]-1-methyl-2-oxo-ethyl}-amide,
5-Chloro-thiophene-2-carboxylic acid {3-[4-(4-amino-quinazolin-7-ylmethyl)-3-oxo-piperazin-1-yl]-3-oxo-propyl}-amide,
1-(4-Amino-quinazolin-7-ylmethyl)-4-[(4-chloro-phenoxy)-acetyl]-piperazin-2-one,
1-(4-Amino-quinazolin-7-ylmethyl)-4-[(4-chloro-2-methyl-phenoxy)-acetyl]-piperazin-2-one,
1-(4-Amino-quinazolin-7-ylmethyl)-4-(5'-chloro-[2,2']bithiophenyl-5-carbonyl)-piperazin-2-one,
1-(4-Amino-quinazolin-7-ylmethyl)-4-[3-(5-chloro-thiophen-2-yl)-propionyl]-piperazin-2-one,
1-(4-Amino-quinazolin-7-ylmethyl)-4-[3-(3-chloro-phenyl)-(E)-acryloyl]-piperazin-2-one,
N-[2-[4-(4-Amino-quinazolin-7-ylmethyl)-3-oxo-piperazin-1-yl]-1-(5-chloro-thiophen-2-ylmethyl)-2-oxo-ethyl]-benzamide,
N-[1-[4-(4-Amino-quinazolin-7-ylmethyl)-3-oxo-piperazine-1-carbonyl]-2-(5-chloro-thiophen-2-yl)-vinyl]-benzamide,
N-[1-[4-(4-Amino-quinazolin-7-ylmethyl)-3-oxo-piperazine-1-carbonyl]-2-(5-chloro-thiophen-2-yl)-vinyl]-acetamide,
1-(4-Amino-quinazolin-7-ylmethyl)-4-[3-(4-chloro-phenyl)-(E)-acryloyl]-piperazin-2-one,
1-(4-Amino-quinazolin-7-ylmethyl)-4-[(5-chloro-thiophen-2-yl)-acetyl]-piperazin-2-one,
1-(4-Amino-quinazoin-7-ylmethyl)-4-(6-chloro-benzo[b]thiophene-2-carbonyl)-piperazin-2-one,
2-[4-(4-Amino-quinazolin-7-ylmethyl)-3-oxo-piperazine-1-carbonyl]-6-chloro-4H-benzo[1,4]thiazin-3-one,
1-(4-Amino-quinazolin-7-ylmethyl)-4-[(6-chloro-benzo[b]thiophen-2-yl)-acetyl]-piperazin-2-one
4-(4-Aminoquinazolin-7-ylmethyl)-3-oxopiperazine-1-carboxylic acid 4-chloro-benzylamide,
4-(4-Aminoquinazolin-7-ylmethyl)-3-oxopiperazine-1-carboxylic acid (5-chloro-thiophen-2-ylmethyl)amide,
4-(4-Aminoquinazolin-7-ylmethyl)-3-oxopiperazine-1-carboxylic acid (5-chloro-thiophen-2-yl)amide,
4-(4-Amino-quinazolin-7-ylmethyl)-3-oxo-piperazine-1-carboxylic acid (4-chloro-thiophen-2-yl)-amide,
4-(4-Amino-quinazolin-7-ylmethyl)-3-oxo-piperazine-1-carboxylic acid (5-bromo-thiophen-2-yl)-amide,
4-(4-Amino-quinazolin-7-ylmethyl)-3-oxo-piperazine-1-carboxylic acid (3-amino-4-chloro-phenyl)-amide,
4-(4-Amino-quinazolin-7-ylmethyl)-3-oxo-piperazine-1-carboxylic acid (4-bromo-phenyl)-amide,
4-(4-Amino-quinazolin-7-ylmethyl)-3-oxo-piperazine-1-carboxylic acid (4-chloro-phenyl)-amide,
4-(4-Amino-quinazolin-7-ylmethyl)-3-oxo-piperazine-1-carboxylic acid (4-methoxy-phenyl)-amide,
4-(4-Amino-quinazolin-7-ylmethyl)-3-oxo-piperazine-1-carboxylic acid (3,4-dichloro-phenyl)-amide, 4-(4-Amino-quinazolin-7-ylmethyl)-3-oxo-piperazine-1-carboxylic acid 5-chloro-thiophen-2-ylmethyl ester,
4-(4-Amino-quinazolin-7-ylmethyl)-3-oxo-piperazine-1-carboxylic acid 6-chloro-benzooxazol-2-ylmethyl ester,
4-(4-Amino-quinazolin-7-ylmethyl)-3-oxo-piperazine-1-carboxylic acid 1-(3-chloro-phenyl)-pyrrolidin-3-yl ester,
1-(4-Amino-quinazolin-7-ylmethyl)-4-(7-chloro-isoquinolin-3-ylmethyl)-3-(S)-methyl-piperazin-2-one,
4-(4-Amino-quinazolin-7-ylmethyl)-4-(3-chloro-1H-indol-6-ylmethyl)-3-(S)-methyl-piperazin-2-one,
1-(4-Amino-quinazolin-7-ylmethyl)-4-[3-(4-chloro-thiophen-2-yl)-allyl]-3-(S)-methyl-piperazin-2-one,
1-(4-Amino-quinazolin-7-ylmethyl)-4-[3-(6-chloro-benzo[b]thiophen-2-yl)-allyl]-3-(S)-methyl-piperazin-2-one,
1-(4-Amino-quinazolin-7-ylmethyl)-4-[3-(5-chloro-thiophen-2-yl)-propyl]-3-(S)-methyl-piperazin-2-one,
1-(4-Amino-quinazolin-7-ylmethyl)-4-(5-chloro-1H-indol-2-ylmethyl)-3-(S)-methyl-piperazin-2-one,
1-(4-Amino-quinazolin-7-ylmethyl)-4-[3-(5-chloro-thiophen-2-yl)-but-2-enyl]-3-(S)-methyl-piperazin-2-one,
1-(4-Amino-quinazolin-7-ylmethyl)-4-(5'-chloro-[2,2']bithiophenyl-5-ylmethyl)-3-(S)-methyl-piperazin-2-one,
1-(4-Amino-quinazolin-7-ylmethyl)-4-(5-chloro-1H-benzoimidazol-2-ylmethyl)-3-(S)-methyl-piperazin-2-one,
1-(4-Amino-quinazolin-7-ylmethyl)-4-[3-(5-chloro-thiophen-2-yl)-allyl]-3-(S)-methyl-piperazin-2-one,
1-(4-Amino-quinazolin-7-ylmethyl)-4-(6-chloro-naphthalen-2-ylmethyl)-3-(S)-methyl-piperazin-2-one,
1-(4-Amino-quinazolin-7-ylmethyl)-4-(6-chloro-thieno[2,3-b]pyridin-2-ylmethyl)-3-(S)-methyl-piperazin-2-one,
1-(4-Amino-quinazolin-7-ylmethyl)-4-(6-chloro-benzo[b]thiophen-2-ylmethyl)-3-(S)-methyl-piperazin-2-one,
1-(4-Amino-quinazolin-7-ylmethyl)-4-(5-chloro-benzo[b]thiophen-2-ylmethyl)-3-(S)-methyl-piperazin-2-one,
1-(4-Amino-quinazolin-7-ylmethyl)-4-(5-chloro-benzo[b]thiophen-2-ylmethyl)-3-(R)-methyl-piperazin-2-one,
1-(4-Amino-quinazolin-7-ylmethyl)-4-(6-chloro-benzo[b]thiophen-2-ylmethyl)-3-(R)-methyl-piperazin-2-one,
1-(4-Amino-quinazolin-7-ylmethyl)-4-[3-(4-chloro-thiophen-2-yl)-acryloyl]-3-(S)methyl-piperazin-2-one,
1-(4-Amino-quinazolin-7-ylmethyl)-4-[(5-chloro-thiophen-3-yloxy)-acetyl]-3-(S)-methyl-piperazin-2-one,
1-(4-Amino-quinazolin-7-ylmethyl)-4-[(4-chloro-thiophen-2-yloxy)-acetyl]-3-(S)-methyl-piperazin-2-one,
1-(4-Amino-quinazolin-7-ylmethyl)-4-[3-(5-bromo-thiophen-2-yl)-acryloyl]-3-(S)-methyl-piperazin-2-one,
1-(4-Amino-quinazolin-7-ylmethyl)-4-(3-chloro-1H-indole-6-carbonyl)-3-(S)-methyl-piperazin-2-one,
1-(4-Amino-quinazolin-7-ylmethyl)-4-(7-chloro-isoquinoline-3-carbonyl)-3-(S)-methyl-piperazin-2-one,
1-(4-Amino-quinazolin-7-ylmethyl)-4-[(5-chloro-thiophen-2-yloxy)-acetyl]-3-(S)-methyl-piperazin-2-one,
1-(4-Amino-quinazolin-7-ylmethyl)-4-[3-(4-bromo-thiophen-2-yl)-acryloyl]-3-(S)-methyl-piperazin-2-one,
1-(4-Amino-quinazolin-7-ylmethyl)-4-[(4-chloro-phenoxy)-acetyl]-3-(S)-methyl-piperazin-2-one,
1-(4-Amino-quinazolin-7-ylmethyl)-4-(5'-chloro-[2,2']bithiophenyl-5-carbonyl)-3-(S)-methyl-piperazin-2-one,
1-(4-Amino-quinazolin-7-ylmethyl)-4-[3-(5-chloro-thiophen-2-yl)-but-2-enoyl]-3-(S)-methyl-piperazin-2-one,
1(4-Amino-quinazolin-7-ylmethyl)-4-(6-chloro-benzo[b]thiophene-2-carbonyl)-3-(S)-methyl-piperazin-2-one,
1-(4-Amino-quinazolin-7-ylmethyl)-4-[3-(5-chloro-thiophen-2-yl)-acryloyl]-3-(S)-methyl-piperazine-2-one,
1-(4-Amino-quinazolin-7-ylmethyl)-4-[3-(5-chloro-thiophen-2-yl)-propyl]-3-(S)-ethyl-piperazin-2-one,
1-(4-Amino-quinazolin-7-ylmethyl)-4-[3-(4-chloro-thiophen-2-yl)-allyl]-3-(S)-ethyl-piperazin-2-one,
1-(4-Amino-quinazolin-7-ylmethyl)-4-[3-(5-chloro-thiophen-2-yl)-but-2-enyl]-3-(S)-ethyl-piperazin-2-one,
1-(4-Amino-quinazolin-7-ylmethyl)-4-(7-chloro-isoquinolin-3-ylmethyl)-3-(S)-ethyl-piperazin-2-one,
1-(4-Amino-quinazolin-7-ylmethyl)-4-[3-(5-chloro-thiophen-2-yl)-allyl]-3-(S)-ethyl-piperazin-2-one,
1-(4-Amino-quinazolin-7-ylmethyl)-4-(6-chloro-naphthalen-2-ylmethyl)-3-(S)-ethyl-piperazin-2-one,
1-(4-Amino-quinazolin-7-ylmethyl)-4-(6-chloro-benzo[b]thiophen-2-ylmethyl)-3-(S)-ethyl-piperazin-2-one,
1-(4-Amino-quinazolin-7-ylmethyl)-4-(6-chloro-thieno[2,3-b]pyridin-2-ylmethyl)-3-(S)-ethyl-piperazin-2-one,
1-(4-Amino-quinazolin-7-ylmethyl)-4-[3-(5-chloro-thiophen-2-yl)-acryloyl]-3-(S)-ethyl-piperazin-2-one,
1-(4-Amino-quinazolin-7-ylmethyl)-4-[(4-chloro-thiophen-2-yloxy)-acetyl]-(S)-3-ethyl-piperazin-2-one,
1-(4-Amino-quinazolin-7-ylmethyl)-4-[(5-chloro-thiophen-3-yloxy)-acetyl]-(S)-3-ethyl-piperazin-2-one,
1-(4-Amino-quinazolin-7-ylmethyl)-4-[3-(5-chloro-thiophen-3-yl)-acryloyl]-(S)-3-ethyl-piperazin-2-one,
2-(2-{2-[4-(4-Amino-quinazolin-7-ylmethyl)-(S)-2-ethyl-3-oxo-piperazin-1-yl]-2-oxo-ethoxy}-5-chloro-thiophen-3-yl)-acetamide,
(2-{2-[4-(4-Amino-quinazolin-7-ylmethyl)-(S)-2-ethyl-3-oxo-piperazin-1-yl]-2-oxo-ethoxy}-5-chloro-thiophen-3-yl)-acetic acid,
1-(4-Amino-quinazolin-7-ylmethyl)-4-(2,3-dichloro-benzo[b]thiophene-6-carbonyl)-(S)-3-ethyl-piperazin-2-one,
1-(4-Amino-quinazolin-7-ylmethyl)-4-(2-chloro-benzo[b]thiophene-6-carbonyl)-(S)-3-ethyl-piperazin-2-one,
(2-{2-[4-(4-Amino-quinazolin-7-ylmethyl)-(S)-2-ethyl-3-oxo-piperazin-1-yl]-2-oxo-ethoxy}-5-chloro-thiophen-3-yl)-acetic acid ethyl,
1-(4-Amino-quinazolin-7-ylmethyl)-4-[(3,5-dichloro-thiophen-2-yloxy)-acetyl]-(S)-3-ethyl-piperazin-2-one,
(2-{2-[4-(4-Amino-quinazolin-7-ylmethyl)-(S)-2-ethyl-3-oxo-piperazin-1-yl]-2-oxo-ethoxy}-5-chloro-thiophen-3-yl)-acetic acid methyl ester,
1-(4-Amino-quinazolin-7-ylmethyl)-4-(3-chloro-1H-indole-6-carbonyl)-(3S)-ethyl-piperazin-2-one,
1-(4-Amino-quinazolin-7-ylmethyl)-4-(7-chloro-isoquinoline-3-carbonyl)-3-(S)-ethyl-piperazin-2-one,
1-(4-Amino-quinazolin-7-ylmethyl)-4-[(5-chloro-thiophen-2-yloxy)-acetyl]-3-(S)-ethyl-piperazin-2-one,
1-(4-Amino-quinazolin-7-ylmethyl)-4-[3-(5-bromo-thiophen-2-yl)-acryloyl]-3-(S)-ethyl-piperazin-2-one,
1-(4-Amino-quinazolin-7-ylmethyl)-4-[3-(4-chloro-thiophen-2-yl)-acryloyl]-3-(S)-ethyl-piperazine-2-one,
1-(4-Amino-quinazolin-7-ylmethyl)-4-[3-(4-bromo-thiophen-2-yl)-acryloyl]-3-(S)-ethyl-piperazin-2-one,
1-(4-Amino-quinazolin-7-ylmethyl)-4-[3-(5-chloro-thiophen-2-yl)-propionyl]-3-(S)-ethyl-piperazin-2-one,
1-(4-Amino-quinazolin-7-ylmethyl)-4-[1-(4-chloro-phenyl)-1H-pyrrole-2-carbonyl]-3-(S)-ethyl-piperazin-2-one,
1-(4-Amino-quinazolin-7-ylmethyl)-4-[(4-chloro-phenyl-sulfanyl)-acetyl]-3-(S)-ethyl-piperazin-2-one,
1-(4-Amino-quinazolin-7-ylmethyl)-4-[3-(5-chloro-thiophen-2-yl)-but-2-enoyl]-3-(S)-ethyl-piperazin-2-one,
1-(4-Amino-quinazolin-7-ylmethyl)-4-[(4-chloro-phenoxy)-acetyl]-3-(S)-ethyl-piperazin-2-one,
1-(4-Amino-quinazolin-7-ylmethyl)-4-[3-(4-chloro-phenyl)-acryloyl]-3-(S)-ethyl-piperazin-2-one,
1-(4-Amino-quinazolin-7-ylmethyl)-4-(5-chloro-1H-indole-2-carbonyl)-3-(S)-ethyl-piperazin-2-one, 1-(4-Amino-quinazolin-7-ylmethyl)-4-[3-(4-chloro-phenyl)-propionyl]-3-(S)-ethyl-piperazin-2-one,
1-(4-Amino-quinazolin-7-ylmethyl)-3-(S)-ethyl-4-[3-(4-methoxy-phenyl)-propionyl]-piperazin-2-one,
1-(4-Amino-quinazolin-7-ylmethyl)-4-(6-chloro-benzo[b]thiophene-2-carbonyl)-3-(S)-ethyl-piperazin-2-one,
1-(4-Amino-quinazolin-7-ylmethyl)-4-[(5-chloro-thiophen-2-yloxy)-acetyl]-3-(S)-propyl-piperazin-2-one,
4-[3-(6-Amino-pyridin-3-yl)-acryloyl]-1-(4-amino-quinazolin-7-ylmethyl)-3-(S)-propyl-piperazin-2-one,
1-(4-Amino-quinazolin-7-ylmethyl)-4-[(2,5-dichloro-thiophen-3-yloxy)-acetyl]-3-(S)-propyl-piperazin-2-one,
1-(4-Amino-quinazolin-7-ylmethyl)-4-[(4-chloro-thiophen-2-yloxy)-acetyl]-3-(S)-propyl-piperazin-2-one,
1-(4-Amino-quinazolin-7-ylmethyl)-4-[3-(4-bromo-thiophen-2-yl)-acryloyl]-3-(S)-propyl-piperazin-2-one,
1-(4-Amino-quinazolin-7-ylmethyl)-4-[3-(4-chloro-thiophen-2-yl)-acryloyl]-3-(S)-propyl-piperazin-2-one,
1-(4-Amino-quinazolin-7-ylmethyl)-4-[(3-chloro-phenoxy)-acetyl]-3-(S)-propyl-piperazin-2-one,
1-(4-Amino-quinazolin-7-ylmethyl)-4-[(5-chloro-thiophen-3-yloxy)-acetyl]-3-(S)-propyl-piperazin-2-one,
1-(4-Amino-quinazolin-7-ylmethyl)-4-[(3-chloro-5-methoxy-phenoxy)-acetyl]-3-(S)-propyl-piperazin-2-one,
1-(4-Amino-quinazolin-7-ylmethyl)-4-[3-(5-chloro-thiophen-3-yl)-acryloyl]-3-(S)-propyl-piperazin-2-one,
1-(4-Amino-quinazolin-7-ylmethyl)-4-[3-(5-chloro-thiophen-2-yl)-acryloyl]-3-(S)-propyl-piperazin-2-one,
1-(4-Amino-quinazolin-7-ylmethyl)-4-[3-(5-chloro-thiophen-2-yl)-allyl]-3-(S)-methoxymethyl-piperazin-2-one,
1-(4-Amino-quinazolin-7-ylmethyl)-4-(3-chloro-1H-indol-6-ylmethyl)-3-(S)-methoxymethyl-piperazin-2-one,
1-(4-Amino-quinazolin-7-ylmethyl)-4-[2-(5-chloro-thiophen-2-yloxy)-ethyl]-3-(S)-methoxymethyl-piperazin-2-one,
1-(4-Amino-quinazolin-7-ylmethyl)-4-(5-chloro-1H-indol-2-ylmethyl)-3-(S)-methoxymethyl-piperazin-2-one,
1-(4-Amino-quinazolin-7-ylmethyl)-4-(7-chloro-isoquinolin-3-ylmethyl)-3-(R)-methoxymethyl-piperazin-2-one,
1-(4-Amino-quinazolin-7-ylmethyl)-4-(7-chloro-isoquinolin-3-ylmethyl)-3-(S)-methoxymethyl-piperazin-2-one,
1-(4-Amino-quinazolin-7-ylmethyl)-4-(6-chloro-naphthalen-2-ylmethyl)-3-(S)-methoxymethyl-piperazin-2-one,
1-(4-Amino-quinazolin-7-ylmethyl)-4-(6-chloro-benzo[b]thiophen-2-ylmethyl)-3-(S)-methoxymethyl-piperazin-2-one,
1-(4-Amino-quinazolin-7-ylmethyl)-4-[(5-chloro-thiophen-2-yloxy)-acetyl]-3-(S)-methoxymethyl-piperazin-2-one,
1-(4-Amino-quinazolin-7-ylmethyl)-4-(6-chloro-1H-benzoimidazole-2-carbonyl)-3-(S)-methoxymethyl-piperazin-2-one,
1-(4-Amino-quinazolin-7-ylmethyl)-4-[(4-chloro-thiophen-2-yloxy)-acetyl]-3-(S)-methoxymethyl-piperazin-2-one,
4-[3-(4-Amino-phenyl)-acryloyl]-1-(4-amino-quinazolin-7-ylmethyl)-3-(S)-methoxymethyl-piperazin-2-one,
1-(4-Amino-quinazolin-7-ylmethyl)-4-(3-3H-imidazol-4-yl-acryloyl)-3-(S)-methoxymethyl-piperazin-2-one,
1-(4-Amino-quinazolin-7-ylmethyl)-4-[(2,5-dichloro-thiophen-3-yloxy)-acetyl]-3-(S)-methoxymethyl-piperazin-2-one,
(1-(4-Amino-quinazolin-7-ylmethyl)-4-(6-chloro-1H-benzoimidazole-2-carbonyl)-3-(S)-methoxymethyl-piperazin-2-one,
1-(4-Amino-quinazolin-7-ylmethyl)-4-(5-chloro-thiophene-2-carbonyl)-3-(S)-methoxymethyl-piperazin-2-one,
1-(4-Amino-quinazolin-7-ylmethyl)-4-[3-(5-bromo-furan-2-yl)-acryloyl]-3-(S)-methoxymethyl-piperazin-2-one,
1-(4-Amino-quinazolin-7-ylmethyl)-4-[3-(4-bromo-phenyl)-acryloyl]-3-(S)-methoxymethyl-piperazin-2-one,
1-(4-Amino-quinazolin-7-ylmethyl)-4-[3-(4-chloro-phenyl)-acryloyl]-3-(S)-methoxymethyl-piperazin-2-one,
1-(4-Amino-quinazolin-7-ylmethyl)-4-[3-(3-bromo-phenyl)-acryloyl]-3-(S)-methoxymethyl-piperazin-2-one,
1-(4-Amino-quinazolin-7-ylmethyl)-4-[3-(3-chloro-phenyl)-acryloyl]-3-(S)-methoxymethyl-piperazin-2-one,
1-(4-Amino-quinazolin-7-ylmethyl)-4-[3-(5-bromo-thiophen-2-yl)-acryloyl]-3-(S)-methoxymethyl-piperazin-2-one,
1-(4-Amino-quinazolin-7-ylmethyl)-4-[(5-chloro-thiophen-3-yloxy)-acetyl]-3-(S)--methoxymethyl-piperazin-2-one,
1-(4-Amino-quinazoin-7-ylmethyl)-4-[(5-chloro-pyridin-3-yloxy)-acetyl]-3-(S)-methoxymethyl-piperazin-2-one,
1-(4-Amino-quinazolin-7-ylmethyl)-4-[(6-chloro-pyridin-2-yloxy)-acetyl]-3-(S)-methoxymethyl-piperazin-2-one,
4-[3-(6-Amino-pyridin-3-yl)-acryloyl]-1-(4-amino-quinazolin-7-ylmethyl)-3-(S)-methoxymethyl-piperazin-2-one,
1-(4-Amino-quinazolin-7-ylmethyl)-4-[(3-chloro-5-methoxy-phenoxy)-acetyl]-3-(S)-methoxymethyl-piperazin-2-one,
1-(4-Amino-quinazolin-7-ylmethyl)-4-[3-(5-chloro-thiophen-3-yl)-acryloyl]-3-(S)-methoxymethyl-piperazin-2-one,
1-(4-Amino-quinazolin-7-ylmethyl)-4-[(2,5-dichloro-phenoxy)-acetyl]-3-(S)-methoxymethyl-piperazin-2-one,
1-(4-Amino-quinazolin-7-ylmethyl)-4-[(5-fluoro-thiophen-2-yloxy)-acetyl]-3-(S)-methoxymethyl-piperazin-2-one,
1-(4-Amino-quinazolin-7-ylmethyl)-4-[(3-fluoro-phenoxy)-acetyl]-3-(S)-methoxymethyl-piperazin-2-one,
1-(4-Amino-quinazolin-7-ylmethyl)-4-[2-(3-chloro-phenoxy)-propionyl]-3-(S)-methoxymethyl-piperazin-2-one,
1-(4-Amino-quinazolin-7-ylmethyl)-4-[(6-chloro-pyridin-3-yloxy)-acetyl]-3-(S)-methoxymethyl-piperazin-2-one,
1-(4-Amino-quinazolin-7-ylmethyl)-3-(S)-methoxymethyl-4-[(4-trifluoromethylsulfanyl-phenoxy)-acetyl]-piperazin-2-one,
1-(4-Amino-quinazolin-7-ylmethyl)-4-[(3-chloro-phenylamino)-acetyl]-3-(S)-methoxymethyl-piperazin-2-one,
1-(4-Amino-quinazolin-7-ylmethyl)-4-[(4-chloro-phenylamino)-acetyl]-3-(S)-methoxymethyl-piperazin-2-one,
1-(4-Amino-quinazolin-7-ylmethyl)-4-[(3-chloro-phenoxy)-acetyl]-3-(S)-methoxymethyl-piperazin-2-one,
(2-{2-[4-(4-Amino-quinazolin-7-ylmethyl)-2-(S)-methoxymethyl-3-oxo-piperazin-1-yl]-2-oxo-ethoxy}-5-chloro-thiophen-3-yl)-acetic acid,
1-(4-Amino-quinazolin-7-ylmethyl)-4-[(5-chloro-thiophen-2-ylsulfanyl)-acetyl]-3-(S)-methoxymethyl-piperazin-2-one,
1-(4-Amino-quinazolin-7-ylmethyl)-4-[(6-chloro-pyridin-3-ylamino)-acetyl]-3-(S)-methoxymethyl-piperazin-2-one,
2-(2-{2-[4-(4-Amino-quinazolin-7-ylmethyl)-2-(S)-methoxymethyl-3-oxo-piperazin-1-yl]-2-oxo-ethoxy}-5-chloro-thiophen-3-yl)-,
1-(4-Amino-quinazolin-7-ylmethyl)-4-(2-chloro-benzo[b]thiophene-6-carbonyl)-3-(S)-methoxymethyl-piperazin-2-one,
1-(4-Amino-quinazolin-7-ylmethyl)-4-(2,3-dichloro-benzo[b]thiophene-6-carbonyl)-3-(S)-methoxymethyl-piperazin-2-one,
1-(4-Amino-quinazolin-7-ylmethyl)-4-[(3,5-dichloro-thiophen-2-yloxy)-acetyl]-3-(S)-methoxymethyl-piperazin-2-one, (2-{2-[4-(4-Amino-quinazolin-7-ylmethyl)-2-(S)-methoxymethyl-3-oxo-piperazin-1-yl]-2-oxo-ethoxy}-5-chloro-thiophen-3-yl)-acetic acid methyl ester,
(2-{2-[4-(4-Amino-quinazolin-7-ylmethyl)-2-(S)-methoxymethyl-3-oxo-piperazin-1-yl]-2-oxo-ethoxy}-5-chloro-thiophen-3-yl)-acetic acid ethyl ester,
1-(4-Amino-quinazolin-7-ylmethyl)-4-[(2-chloro-pyridin-3-ylamino)-acetyl]-3-(S)-methoxymethyl-piperazin-2-one,
1-(4-Amino-quinazolin-7-ylmethyl)-4-[(2,3-dichloro-phenoxy)-acetyl]-3-(S)-methoxymethyl-piperazin-2-one,
1-(4-Amino-quinazolin-7-ylmethyl)-4-[(4-fluoro-phenoxy)-acetyl]-3-(S)-methoxymethyl-piperazin-2-one,
1-(4-Amino-quinazolin-7-ylmethyl)-4-[(4-chloro-2-methyl-phenoxy)-acetyl]-3-(S)-methoxymethyl-piperazin-2-one,
1-(4-Amino-quinazolin-7-ylmethyl)-4-[(2,4-dichloro-phenoxy)-acetyl]-3-(S)-methoxymethyl-piperazin-2-one,
1-(4-Amino-quinazolin-7-ylmethyl)-4-(7-chloro-isoquinoline-3-carbonyl)-3-(S)-methoxymethyl-piperazin-2-one,
(1-(4-Amino-quinazolin-7-ylmethyl)-4-[3-(4-bromo-thiophen-2-yl)-acryloyl]-3-(S)-methoxmethyl-piperazin-2-one,
1-(4-Amino-quinazolin-7-ylmethyl)-4-[3-(4-chloro-thiophen-2-yl)-acryloyl]-3-(S)-methoxymethyl-piperazin-2-one,
1-(4-Amino-quinazolin-7-ylmethyl)-4-[3-(5-chloro-thiophen-2-yl)-acryloyl]-3-(R)-methoxymethyl-piperazin-2-one,
1-(4-Amino-quinazolin-7-ylmethyl)-4-[3-(5-chloro-thiophen-2-yl)-acryloyl]-3-(S)-methoxymethyl-piperazin-2-one,
1-(4-Amino-quinazolin-7-ylmethyl)-4-(6-chloro-benzo[b]thiophene-2-carbonyl)-3-(S)-methoxymethyl-piperazin-2-one,
1-(4-Amino-quinazolin-7-ylmethyl)-4-[(4-chloro-phenoxy)-acetyl]-3-(S)-methoxymethyl-piperazin-2-one,
1-(4-Amino-quinazolin-7-ylmethyl)-4-[(6-chloro-pyridin-3-yloxy)-acetyl]-3-(S)-ethoxymethyl-piperazin-2-one,
1-(4-Amino-quinazolin-7-ylmethyl)-3-(S)-ethoxymethyl-4-[(3-fluoro-phenoxy)-acetyl]-piperazin-2-one,
1-(4-Amino-quinazolin-7-ylmethyl)-4-[3-(5-chloro-thiophen-2-yl)-acryloyl]-3-(S)-ethoxymethyl-piperazin-2-one,
1-(4-Amino-quinazolin-7-ylmethyl)-4-[(2-chloro-pyridin-3-ylamino)-acetyl]-3-(S)-ethoxymethyl-piperazin-2-one,
1-(4-Amino-quinazolin-7-ylmethyl)-4-[(6-chloro-pyridin-3-ylamino)-acetyl]-3-(S)-ethoxymethyl-piperazin-2-one,
1-(4-Amino-quinazolin-7-ylmethyl)-4-[(5-chloro-thiophen-2-yloxy)-acetyl]-3-(S)-ethoxymethyl-piperazin-2-one,
1-(4-Amino-quinazolin-7-ylmethyl)-3-(S)-benzyl-4-[3-(5-chloro-thiophen-2-yl)-acryloyl]-piperazin-2-one,
1-(4-Amino-quinazolin-7-ylmethyl)-3-(S)-benzyl-4-(6-chloro-benzo[b]thiophene-2-carbonyl)-piperazin-2-one,
1-(4-Amino-quinazolin-7-ylmethyl)-3-(S)-benzyl-4-[3-(5-chloro-thiophen-2-yl)-allyl]-piperazin-2-one,
1-(4-Amino-quinazolin-7-ylmethyl)-3-(S)-benzyl-4-(6-chloro-benzo[b]thiophen-2-ylmethyl)-piperazin-2-one,
1-(4-Amino-quinazolin-7-ylmethyl)-3-(S)-benzyl-4-[(4-chloro-phenoxy)-acetyl]-piperazin-2-one,
1-(4-Amino-quinazolin-7-ylmethyl)-3-(S)-benzyl-4-(6-chloro-naphthalen-2-ylmethyl)-piperazin-2-one,
1-(4-Amino-quinazolin-7-ylmethyl)-3-(S)-benzyl-4-[3-(5-chloro-thiophen-2-yl)-propyl]-piperazin-2-one,
1-(4-Amino-quinazolin-7-ylmethyl)-4-[(5-chloro-thiophen-2-yloxy)-acetyl]-3-(S)-((R)-1-methoxy-ethyl)-piperazin-2-one,
1-(4-Amino-quinazolin-7-ylmethyl)-4-[3-(5-chloro-thiophen-2-yl)-allyl]-3-(S)-((R)-1-methoxy-ethyl)-piperazin-2-one,
1-(4-Amino-quinazolin-7-ylmethyl)-4-[3-(5-chloro-thiophen-2-yl)-acryloyl]-3-(S)-((R)-1-methoxy-ethyl)-piperazin-2-one,
1-(4-Amino-quinazolin-7-ylmethyl)-4-[3-(4-bromo-thiophen-2-yl)-acryloyl]-3-(S)-((R)-1-methoxy-ethyl)-piperazin-2-one,
1-(4-Amino-quinazolin-7-ylmethyl)-4-(7-chloro-isoquinolin-3-ylmethyl)-3-(S)-((R)-1-methoxy-ethyl)-piperazin-2-one,
1-(4-Amino-quinazolin-7-ylmethyl)-4-(6-chloro-benzo[b]thiophen-2-ylmethyl)-3-(S)-isopropyl-piperazin-2-one,
1-(4-Amino-quinazolin-7-ylmethyl)-4-(6-chloro-benzo[b]thiophen-2-ylmethyl)-3,3-dimethyl-piperazin-2-one,
1-(4-Amino-quinazolin-7-ylmethyl)-4-[3-(5-chloro-thiophen-2-yl)-allyl]-3,3-dimethyl-piperazin-2-one,
1-(4-Amino-quinazolin-7-ylmethyl)-4-[3-(5-chloro-thiophen-2-yl)-acryloyl]-3,3-dimethyl-piperazin-2-one,
1-(4-Amino-quinazolin-7-ylmethyl)-4-(6-chloro-benzo[b]thiophene-2-carbonyl)-3,3-dimethyl-piperazin-2-one,
1-(4-Amino-quinazolin-7-ylmethyl)-4-[(5-chloro-thiophen-2-yloxy)-acetyl]-3-(S)-(2-methoxy-ethyl)-piperazin-2-one,
4-(4-Amino-quinazolin-7-ylmethyl)-2-(S)-(2-methoxy-ethyl)-3-oxo-piperazine-1-carboxylic acid (4-chloro-phenyl)-amide,
1-(4-Amino-quinazoin-7-ylmethyl)-4-[(5-chloro-thiophen-3-yloxy)-acetyl]-3-(S)-(2-methoxy-ethyl)-piperazin-2-one,
1-(4-Amino-quinazolin-7-ylmethyl)-4-(6-chloro-benzo[b]thiophene-2-carbonyl)-3-(S)-(2-methoxy-ethyl)-piperazin-2-one,
1-(4-Amino-quinazolin-7-ylmethyl)-4-(6-chloro-naphthalen-2-ylmethyl)-3-(S)-methoxymethyl-6-(S)-methyl-piperazin-2-one,
1-(4-Amino-quinazolin-7-ylmethyl)-4-[3-(5-chloro-thiophen-2-yl)-propyl]-3-(S)-ethyl-6-methyl-piperazin-2-one,
1-(4-Amino-quinazolin-7-ylmethyl)-4-(6-chloro-naphthalen-2-ylmethyl)-3-(S)-methoxymethyl-6-(R)-methyl-piperazin-2-one,
1-(4-Amino-quinazolin-7-ylmethyl)-4-[3-(5-chloro-thiophen-2-yl)-allyl]-3-(S)-methoxymethyl-6-methyl-piperazin-2-one,
(1-(4-Amino-quinazolin-7-ylmethyl)-4-(7-chloro-isoquinolin-3-ylmethyl)-3-(S)-methoxymethyl-6-methyl-piperazin-2-one,
1-(4-Amino-quinazolin-7-ylmethyl)-4-[3-(5-chloro-thiophen-2-yl)-allyl]-3-(S)-6-dimethyl-piperazin-2-one,
1-(4-Amino-quinazolin-7-ylmethyl)-4-(6-chloro-naphthalen-2-ylmethyl)-6-methyl-piperazin-2-one,
1-(4-Amino-quinazolin-7-ylmethyl)-4-[3-(5-chloro-thiophen-2-yl)-allyl]-6-methyl-piperazin-2-one,
1-(4-Amino-quinazolin-7-ylmethyl)-4-[(5-chloro-thiophen-2-yloxy)-acetyl]-3(S)-methoxymethyl-6-methyl-piperazin-2-one,
1-(4-Amino-quinazolin-7-ylmethyl)-4-[(4-chloro-thiophen-2-yloxy)-acetyl]-(S)-3-methoxymethyl-6-methyl-piperazin-2-one,
1-(4-Amino-quinazolin-7-ylmethyl)-4-[(5-chloro-thiophen-3-yloxy)-acetyl]-(S)-3-methoxymethyl-6-methyl-piperazin-2-one,
1-(4-Amino-quinazolin-7-ylmethyl)-4-[(3-chloro-4-fluoro-phenoxy)-acetyl]-3(S)-methoxymethyl-6-methyl-piperazin-2-one, 1-(4-Amino-quinazolin-7-ylmethyl)-4-[(3,5-dichloro-phenoxy)-acetyl]-3(S)-methoxymethyl-6-methyl-piperazin-2-one, 1-(4-Amino-quinazolin-7-ylmethyl)-4-[3-(2,5-dichlorophenyl)-acryloyl]-3(S)-methoxymethyl-6-methyl-piperazin-2-one, 1-(4-Amino-quinazolin-7-ylmethyl)-4-[(5-chloro-2-methylphenoxy)-acetyl]-3(S)-methoxymethyl-6-methyl-piperazin-2-one, 1-(4-Amino-quinazolin-7-ylmethyl)-4-[(2,5-dichloro-phenoxy)-acetyl]-3(S)-methoxymethyl-6-methyl-piperazin-2-one, 1-(4-Amino-quinazolin-7-ylmethyl)-4-[(3-chloro-phenoxy)-acetyl]-3-(S)-methoxymethyl-6-methyl-piperazin-2-one, 1-(4-Amino-quinazolin-7-ylmethyl)-4-[3-(5-chloro-thiophen-2-yl)-propionyl]-3(S)-ethyl-6-methyl-piperazin-2-one, 1-(4-Amino-quinazolin-7-ylmethyl)-4-[(5-chloro-thiophen-2-yloxy)-acetyl]-3(S)-ethyl-6-methyl-piperazin-2-one, 1-(4-Amino-quinazolin-7-ylmethyl)-4-[3-(4-bromo-thiophen-2-yl)-acryloyl]-3(S)-ethyl-6-methyl-piperazin-2-one, 1-(4-Amino-quinazolin-7-ylmethyl)-4-[3-(5-chloro-thiophen-2-yl)-acryloyl]-3(S)-ethyl-6-methyl-piperazin-2-one, (S)-1-(4-Amino-quinazolin-7-ylmethyl)-4-[3-(5-chloro-thiophen-2-yl)-acryloyl]-3-methoxymethyl-6-methyl-piperazin-2-one, (S)-1-(4-Amino-quinazolin-7-ylmethyl)-4-[3-(4-bromo-thiophen-2-yl)-acryloyl]-3-methoxymethyl-6-methyl-piperazin-2-one, 1-(4-Amino-quinazolin-7-ylmethyl)-4-(6-chloro-benzo[b]thiophene-2-carbonyl)-3(S)-6-dimethyl-piperazin-2-one, 1-(4-Amino-quinazolin-7-ylmethyl)-4-[3-(4-bromo-thiophen-2-yl)-acryloyl]-3(S)-6-dimethyl-piperazin-2-one, 1-(4-Amino-quinazolin-7-ylmethyl)-4-[3-(5-chloro-thiophen-2-yl)-acryloyl]-3(S)-6-dimethyl-piperazin-2-one, 1-(4-Amino-quinazolin-7-ylmethyl)-4-[3-(5-chloro-thiophen-2-yl)-acryloyl]-6-methyl-piperazin-2-one, 4-(4-Amino-quinazolin-7-ylmethyl)-2-(S)-methoxymethyl-3-oxo-piperazine-1-carboxylic acid (4-chloro-phenyl)-amide, 4-(4-Amino-quinazolin-7-ylmethyl)-2-(S)-methyl-3-oxo-piperazine-1-carboxylic acid (5-chloro-thiophen-2-yl)-amide, 4-(4-Amino-quinazolin-7-ylmethyl)-(2S)-methoxymethyl-3-oxo-piperazine-1-carboxylic acid (5-chloro-thiophen-2-yl)-amide, 4-(4-Amino-quinazolin-7-ylmethyl)-2(S)-(2-methoxyethyl)-3-oxo-piperazine-1-carboxylic acid (4-chloro-phenyl)-amide, 4-(4-Amino-quinazolin-7-ylmethyl)-2-(S)-butyl-3-oxo-piperazine-1-carboxylic acid (4-chloro-phenyl)-amide, 4-(4-Amino-quinazolin-7-ylmethyl)-(2S)-methoxymethyl-3-oxo-piperazine-1-carboxylic acid (5-bromo-thiophen-2-yl)-amide, 4-(4-Amino-quinazolin-7-ylmethyl)-(2S)-methoxymethyl-3-oxo-piperazine-1-carboxylic acid (5-chloro-thiophen-3-yl)-amide, 4-(4-Amino-quinazolin-7-ylmethyl)-(2S)-methoxymethyl-3-oxo-piperazine-1-carboxylic acid (4-chloro-thiophen-2-yl)-amide, 4-(4-Amino-quinazolin-7-ylmethyl)-3-oxo-(S)-2-propyl-piperazine-1-carboxylic acid (4-chloro-phenyl)-amide, 4-(4-Amino-quinazolin-7-ylmethyl)-(2S)-methoxymethyl-3-oxo-piperazine-1-carboxylic acid (3-bromo-phenyl)-amide, 4-(4-Amino-quinazolin-7-ylmethyl)-3-oxo-(2S)-propyl-piperazine-1-carboxylic acid (4-chloro-thiophen-2-yl)-amide, 4-(4-Amino-quinazolin-7-ylmethyl)-3-oxo-(S)-2-propyl-piperazine-1-carboxylic acid (5-chloro-2-methoxy-phenyl)-amide, 4-(4-Amino-quinazolin-7-ylmethyl)-2-(S)-methoxymethyl-3-oxo-piperazine-1-carboxylic acid (4-bromo-2-chloro-phenyl)-amide, 4-(4-Amino-quinazolin-7-ylmethyl)-2-(S)-methoxymethyl-3-oxo-piperazine-1-carboxylic acid (4-trifluoromethoxy-phenyl)-amide, 4-(4-Amino-quinazolin-7-ylmethyl)-2-(S)-methoxymethyl-3-oxo-piperazine-1-carboxylic acid (4-fluoro-phenyl)-amide, 4-(4-Amino-quinazolin-7-ylmethyl)-2-(S)-methoxymethyl-3-oxo-piperazine-1-carboxylic acid (2,4-dichloro-phenyl)-amide, 4-(4-Amino-quinazolin-7-ylmethyl)-2-(S)-methoxymethyl-3-oxo-piperazine-1-carboxylic acid (2,4-difluoro-phenyl)-amide, 4-(4-Amino-quinazolin-7-ylmethyl)-(2S)-methoxymethyl-3-oxo-piperazine-1-carboxylic acid (3-chloro-phenyl)-amide, 4-(4-Amino-quinazolin-7-ylmethyl)-3-oxo-(2S)-propyl-piperazine-1-carboxylic acid (5-chloro-thiophen-2-yl)-amide, 4-(4-Amino-quinazolin-7-ylmethyl)-(2S)-methyl-3-oxo-piperazine-1-carboxylic acid (6-chloro-pyridin-3-yl)-amide, 4-(4-Amino-quinazolin-7-ylmethyl)-(2S)-methoxymethyl-3-oxo-piperazine-1-carboxylic acid (4-bromo-phenyl)-amide, 4-(4-Amino-quinazolin-7-ylmethyl)-(2S)-methyl-3-oxo-piperazine-1-carboxylic acid (4-bromo-phenyl)-amide, 4-(4-Amino-quinazolin-7-ylmethyl)-2-(S)-methoxymethyl-5-(R,S)-methyl-3-oxo-piperazine-1-carboxylic acid (4-chloro-phenyl)-amide, 4-(4-Amino-quinazolin-7-ylmethyl)-(2S)-ethyl-3-oxo-piperazine-1-carboxylic acid (4-bromo-phenyl)-amide, 4-(4-Amino-quinazolin-7-ylmethyl)-(2S)-methyl-3-oxo-piperazine-1-carboxylic acid (4-chloro-phenyl)-amide, 4-(4-Amino-quinazolin-7-ylmethyl)-(2S)-ethyl-3-oxo-piperazine-1-carboxylic acid (4-chloro-phenyl)-amide, 4-(4-Amino-quinazolin-7-ylmethyl)-(S)-2-methoxymethyl-3-oxo-piperazine-1-carboxylic acid (5-chloro-4-methoxy-thiophen-2-yl)-amide, (3S, 5RS)-1-(4-Amino-quinazolin-7-ylmethyl)-4-(6-chloro-benzo[b]thiophen-2-ylmethyl)-3,5-dimethyl-piperazin-2-one, (3S, 5S)-1-(4-Amino-quinazolin-7-ylmethyl)-4-[3-(5-chloro-thiophen-2-yl)-allyl]-3,5-dimethyl-piperazin-2-one, (3S,5R)-1-(4-Amino-quinazolin-7-ylmethyl)-4-[3-(5-chloro-thiophen-2-yl)-allyl]-3,5-dimethyl-piperazin-2-one, (3S, 5R)-1-(4-Amino-quinazolin-7-ylmethyl)-4-[2-(5-chloro-thiophen-2-yl)-ethenesulfonyl]-3,5-dimethyl-piperazin-2-one, (3S, 5S)-1-(4-Amino-quinazolin-7-ylmethyl)-4-[2-(5-chloro-thiophen-2-yl)-ethenesulfonyl]-3,5-dimethyl-piperazin-2-one, (3S, 5S)-1-(4-Amino-quinazolin-7-ylmethyl)-4-(6-chloro-benzo[b]thiophen-2-sulfonyl)-3,5-dimethyl-piperazin-2-one,
(3S, 5S)-1-(4-Amino-quinazolin-7-ylmethyl)-4-[3-(5-chloro-thiophen-2-yl)-acryloyl]-3,5-dimethyl-piperazin-2-one,
(3S, 5R)-4-(4-Amino-quinazolin-7-ylmethyl)-2,6-dimethyl-oxo-piperazine-1-carboxylic acid (4-bromo-phenyl)-amide,
(3S, 5S)-4-(4-Amino-quinazolin-7-ylmethyl)-2,6-dimethyl-oxo-piperazine-1-carboxylic acid (4-bromo-phenyl)-amide,
(3S, 5S)-4-(4-Amino-quinazolin-7-ylmethyl)-2,6-dimethyl-oxo-piperazine-1-carboxylic acid (4-chloro-phenyl)-amide,
1-(4-Aminoquinolin-7-ylmethyl)-4-(6-chlorobenzo[b]thiophen-2-sulfonyl)-piperazin-2-one,
1-(4-Amino-quinolin-7-ylmethyl)-4-[2-(5-chloro-thiophen-2-yl)-ethenesulfonyl]-piperazin-2-one,
(S)-1-(4-Amino-quinolin-7-ylmethyl)-4-(6-chloro-benzo[b]thiophene-2-sulfonyl)-3-methyl-piperazin-2-one,
(3S,5S)-1-(4-Amino-quinolin-7-ylmethyl)-4-[2-(5-chloro-thiophen-2-yl)-ethenesulfonyl]-3,5-dimethyl-piperazin-2-one,
(3S,5R)-1-(4-Amino-quinolin-7-ylmethyl)-4-[2-(5-chloro-thiophen-2-yl)-ethenesulfonyl]-3,5-dimethyl-piperazin-2-one,
(S,R)-1-(4-Amino-quinolin-7-ylmethyl)-4-(6-chloro-benzo[b]thiophene-2-sulfonyl)-6-oxo-piperazine-2-carboxylic acid,
1-(4-Amino-quinolin-7-ylmethyl)-4-(6-chloro-benzo[b]thiophene-2-sulfonyl)-6-oxo-piperazine-2-carboxylic acid methylamide,
1-(4-Amino-quinolin-7-ylmethyl)-4-(6-chloro-benzo[b]thiophene-2-sulfonyl)-6-oxo-piperazine-2-carboxylic acid ethylamide,
1-(4-Amino-quinolin-7-ylmethyl)-4-(6-chloro-benzo[b]thiophene-2-sulfonyl)-6-oxo-piperazine-2-carboxylic acid dimethylamide,
1-(4-Amino-quinolin-7-ylmethyl)-4-(6-chloro-benzo[b]thiophene-2-sulfonyl)-6-(morpholine-4-carbonyl)-piperazin-2-one,
(S)-1-(4-Aminoquinolin-7-ylmethyl)-4-[3-(5-chlorothiophen-2-yl)-allyl]-3-methylpiperazin-2-one,
1-(4-Amino-quinolin-7-ylmethyl)-4-[3-(5-chloro-thiophen-2-yl)-allyl]-piperazin-2-one,
(3S, 5R)-1-(4-Amino-quinolin-7-ylmethyl)-4-(6-chloro-benzo[b]thiophen-2-ylmethyl)-3,5-dimethyl-piperazin-2-one,
(3S, 5S)-1-(4-Amino-quinolin-7-ylmethyl)-4-(6-chloro-benzo[b]thiophen-2-ylmethyl)-3,5-dimethyl-piperazin-2-one,
(S)-1-(4-Amino-quinolin-7-ylmethyl)-4-(7-chloro-iso-quinolin-3-ylmethyl)-3-methyl-piperazin-2-one,
(S)-1-(4-Amino-quinolin-7-ylmethyl)-4-(6-chloro-naphthalen-2-ylmethyl)-3-methyl-piperazin-2-one,
(3S,5S)-1-(4-Amino-quinolin-7-ylmethyl)-4-[3-(5-chloro-thiophen-2-yl)-allyl]-3,5-dimethyl-piperazin-2-one,
(3S,5R)-1-(4-Amino-quinolin-7-ylmethyl)-4-[3-(5-chloro-thiophen-2-yl)-allyl]-3,5-dimethyl-piperazin-piperazine-2-one,
1-(4-Amino-quinolin-7-ylmethyl)-4-(5-chloro-1H-indol-2-ylmethyl)-piperazin-2-one,
(S)-1-(4-Amino-quinolin-7-ylmethyl)-4-(6-chloro-naphthalen-2-ylmethyl)-3-ethyl-piperazin-2-one,
1-(4-Amino-quinolin-7-ylmethyl)-4-[3-(5-chloro-thiophen-2-yl)-allyl]-(S)-3-((R)-1-methoxy-ethoxyl)-piperazin-2-one,
1-(4-Amino-quinolin-7-ylmethyl)-4-(7-chloro-isoquinolin-3-ylmethyl)-(S)-3-((R)-1-methoxy-ethyl)-piperazin-2-one,
(S)-1-(4-Amino-quinolin-7-ylmethyl)-4-(5-chloro-1H-indol-2-ylmethyl)-3-methoxymethyl-piperazin-2-one,
(S)-1-(4-Amino-quinolin-7-ylmethyl)-4-(5-chloro-1H-indol-2-ylmethyl)-3-methyl-piperazin-2-one,
4-(5-Chloro-1H-indol-2-ylmethyl)-1-[4-(2-hydroxy-ethylamino)-quinolin-7-ylmethyl]-piperazin-2-one,
(S)-4-(5-Chloro-1H-indol-2-ylmethyl)-1-(4-ethylamino-quinolin-7-ylmethyl)-3-methyl-piperazin-2-one,
(S)-4-(5-Chloro-1H-indol-2-ylmethyl)-1-(4-ethylamino-quinolin-7-ylmethyl)-3-methoxymethyl-piperazin-2-one,
(S)-4-(5-Chloro-1H-indol-2-ylmethyl)-3-methyl-1-(4-methylamino-quinolin-7-ylmethyl)-piperazin-2-one,
(S)-4-(5-Chloro-1H-indol-2-ylmethyl)-3-methoxymethyl-1-(4-methylamino-quinolin-7-ylmethyl)-piperazin-2-one,
(S)-1-(4-Amino-quinolin-7-ylmethyl)-4-[3-(5-chloro-thiophen-2-yl)-allyl]-3-methyl-4-oxy-piperazin-2-one,
(S)-1-(4-Aminoquinolin-7-ylmethyl)-4-[3-(4-bromothiophen-2-yl)acryloyl]-3-methyl-piperazin-2-one,
1-(4-Amino-quinolin-7-ylmethyl)-4-[3-(5-chloro-thiophen-2-yl)-acryloyl]-3(S)-ethyl-6-methyl-piperazin-2-one,
4-[3-(5-Chloro-thiophen-2-yl)-acryloyl]-(S)-3-ethyl-1-(4-hydroxyamino-quinolin-7-ylmethyl)-piperazin-2-one,
1-(4-Amino-quinolin-7-ylmethyl)-4-[3-(5-chloro-thiophen-2-yl)-acryloyl]-piperazin-2-one,
(S)-1-(4-Amino-quinolin-7-ylmethyl)-4-[3-(5-chloro-thiophen-2-yl)-acryloyl]-3-ethyl-piperazin-2-one,
(S)-1-(4-Amino-quinolin-7-ylmethyl)-4-[3-(5-chloro-thiophen-2-yl)-acryloyl]-3-methyl-piperazin-2-one,
1-(4-Amino-quinolin-7-ylmethyl)-4-[3-(4-bromo-thiophen-2-yl)-acryloyl]-piperazin-2-one,
(S)-1-(4-Amino-quinolin-7-ylmethyl)-4-[3-(5-chloro-thiophen-2-yl)-acryloyl]-3-methoxymethyl-piperazin-2-one,
(S)-1-(4-Amino-quinolin-7-ylmethyl)-4-[3-(4-bromo-thiophen-2-yl)-acryloyl]-3-ethyl-piperazin-2-one,
(S)-1-(4-Amino-quinolin-7-ylmethyl)-4-[(5-chloro-thiophen-2-yloxy)-acetyl]-3-ethyl-piperazin-2-one,
(S)-1-(4-Amino-quinolin-7-ylmethyl)-4-[(5-chloro-thiophen-2-yloxy)-acetyl]-3-methoxymethyl-6-methyl-piperazin-2-one,
1-(4-Amino-quinolin-7-ylmethyl)-4-[3-(5-chloro-thiophen-2-yl)-acryloyl]-(S)-3-(1-(R)-methoxy-ethyl)-piperazin-2-one,
1-(4-Aminoquinolin-7-ylmethyl)-4-[3-(4-bromothiophen-2-yl)-acryl-oyl]-3-(S)-(1-(R)-methoxyethyl)-piperazin-2-one trifluoroacetate,
1-(4-Aminoquinolin-7-ylmethyl)-4-[(5-chlorothiophen-2-yloxy-acetyl]-3-(S)-(1-(R)-methoxyethyl)-piperazin-2-one trifluoroacetate,
(S)-1-(4-Amino-quinolin-7-ylmethyl)-4-[3-(5-chloro-thiophen-2-yl)-acryloyl]-3-ethyl-piperazin-2-one,
1-(4-Aminocinnolin-7-ylmethyl)-4-[2-(5-chlorothiophen-2-yl)-ethenesulfonyl]-piperazin-2-one,
4-(6-Chloro-thieno[2,3-b]pyridine-2-sulfonyl)-1-[2-(pyridin-4-ylamino)-ethyl]-piperazin-2-one,
4-(6-Chloro-benzo[b]thiophene-2-sulfonyl)-1-[2-(methyl-pyridin-4-yl-amino)-ethyl]-piperazin-2-one,
4-[2-(5-Chloro-thiophen-2-yl)-ethenesulfonyl]-1-[2-(3-methyl-pyridin-4-ylamino)-ethyl]-piperazin-2-one,
4-(6-Chloro-benzo[b]thiophene-2-sulfonyl)-1-[2-(pyridin-4-ylamino)-ethyl]-piperazin-2-one, 1-[2-(Pyridin-4-ylamino)-ethyl]-4-(thieno[2,3-b]pyridine-2-sulfonyl)-piperazin-2-one,
4-(5'-Chloro-[2,2']bithiophenyl-5-sulfonyl)-1-[2-(pyridin-4-ylamino)-ethyl]-piperazin-2-one
1-[2-(Pyridin-4-ylamino)-ethyl]-4-(thieno[3,2-b]pyridine-2-sulfonyl)-piperazin-2-one,
4-[2-(5-Chloro-thiophen-2-yl)-ethenesulfonyl]-1-[2-(pyridin-4-ylamino)-ethyl]-piperazin-2-one,
4-[2-(5-Chloro-thiophen-2-yl)-ethenesulfonyl]-1-[2-(methylpyridin-4-ylamino)-ethyl]-piperazin-2-one,
4-(2-Benzo[b]thiophen-2-yl-ethenesulfonyl)-1-[2-(pyridin-4-ylamino)-ethyl]-piperazin-2-one,
4-(6-Chloro-benzo[b]thiophene-2-sulfonyl)-1-[2-(3-methyl-pyridin-4-ylamino)-ethyl]-piperazin-2-one,
4-[2-(5-Chloro-thiophen-2-yl)-ethenesulfonyl]-1-(2-pyrrolo[3,2-c]pyridin-1-yl-ethyl)-piperazin-2-one,
1-[2-(2-Amino-3-chloro-pyridin-4-ylamino)-ethyl]-4-[2-(5-chloro-thiophen-2-yl)-ethenesulfonyl]-piperazin-2-one,
1-[2-(2-Amino-5-chloro-pyridin-4-ylamino)-ethyl]-4-[2-(5-chloro-thiophen-2-yl)-ethenesulfonyl]-piperazin-2-one,
4-[2-(5-Chloro-thiophen-2-yl)-ethenesulfonyl]-1-[2-(2,3,5,6-tetrachloro-pyridin-4-ylamino)-ethyl]-piperazin-2-one,
1-[2-(2-Amino-3,5,6-trichloro-pyridin-4-ylamino)-ethyl]-4-[2-(5-chloro-thiophen-2-yl)-ethenesulfonyl]-piperazin-2-one,
4-[3-(5-Chloro-thiophen-2-yl)-acryloyl]-1-[2-(pyridin-4-ylamino)-ethyl]-piperazin-2-one,
4-(6-Chloro-benzo[b]thiophene-2-sulfonyl)-1-[2-(pyridazin-4-yl-amino)-ethyl]-piperazin-2-one,
1-[3-(4-Amino-pyridin-3-yl)-propenyl]-4-[2-(5-chloro-thiophen-2-yl)-ethenesulfonyl]-piperazin-2-one,
1-[3-(4-Amino-pyridin-3-yl)-propenyl]-4-(6-chloro-benzo[b]thiophene-2-sulfonyl)-piperazin-2-one,
1-[3-(4-Amino-pyridin-3-yl)-allyl]-4-(6-chloro-benzo[b]thiophene-2-sulfonyl)-piperazin-2-one,
1-[3-(4-Amino-pyridin-3-yl)-allyl]-4-[2-(5-chloro-thiophen-2-yl)-ethenesulfonyl]-piperazin-2-one,
1-[3-(4-Amino-pyridin-3-yl)-propyl]-4-(6-chloro-benzo[b]thiophene-2-sulfonyl)-piperazin-2-one,
1-[3-(4-Amino-pyridin-3-yl)-propyl]-4-[2-(5-chloro-thiophen-2-yl)-ethenesulfonyl]-piperazin-2-one,
4-[2-(5-Chlorothiophen-2-yl)-ethenesulfonyl]-1-(2-pyrrolo[3,2-c]pyridin-1-ylethyl)-piperazin-2-one,
4-Prop-2-ynyl-1-(1H-pyrrolo[3,2-c]pyridin-2-ylmethyl)-piperazin-2-one.
1,4-Bis-(1H-pyrrolo[3,2-c]pyridin-2-ylmethyl)-piperazin-2-one,
4-(6-Chloro-1H-benzoimidazol-2-ylmethyl)-1-(1H-pyrrolo[3,2-c]pyridin-2-ylmethyl)-piperazin-2-one,
4-(5'-Chloro-[2,2']bithiophenyl-5-ylmethyl)-1-(1H-pyrrolo[3,2-c]pyridin-2-ylmethyl)-piperazin-2-one,
4-[3-(5-Chloro-thiophen-2-yl)-allyl]-1-(1H-pyrrolo[3,2-c]pyridin-2-ylmethyl)-piperazin-2-one,
4-(5-Chloro-1H-indol-2-ylmethyl)-1-(1H-pyrrolo[3,2-c]pyridin-2-ylmethyl)-piperazin-2-one,
4-(6-Chloro-naphthalen-2-ylmethyl)-1-(1H-pyrrolo[3,2-c]pyridin-2-ylmethyl)-piperazin-2-one,
4-(7-Chloro-isoquinolin-3-ylmethyl)-1-(1H-pyrrolo[3,2-c]pyridin-2-ylmethyl)-piperazin-2-one,
4-(5'-Chloro-[2,2']bithiophenyl-5-ylmethyl)-6-oxo-1-(1H-pyrrolo[3,2-c]pyridin-2-ylmethyl)-piperazine-2-(±)-carboxylic acid methyl ester,
1-(5-Chloro-1H-indol-2-ylmethyl)-5-oxo-4-(1H-pyrrolo[3,2-c]pyridin-2-ylmethyl)-piperazine-2-(±)-carboxylic acid methyl ester,
1-[(5-Chloro-thiophen-2-yloxy)-acetyl]-5-oxo-4-(1H-pyrrolo[3,2-c]pyridin-2-ylmethyl)-piperazine-2-carboxylic acid methyl ester,
1-(6-Chloro-benzo[b]thiophene-2-carbonyl)-5-oxo-4-(1H-pyrrolo[3,2-c]pyridin-2-ylmethyl)-piperazine-2-carboxylic acid methyl ester,
1-[1-(3,5-Dichloro-phenyl)-2,5-dimethyl-1H-pyrrole-3-carbonyl]-5-oxo-4-(1H-pyrrolo[3,2-c]pyridin-2-ylmethyl)-piperazine-2-carboxylic acid methyl ester,
1-(1H-Pyrrolo[3,2-c]pyridin-2-ylmethyl)-4-(1H-pyrrolo[2,3-c]pyridin-2-ylmethyl)-piperazin-2-one,
4-(3-Phenyl-prop-2-ynyl)-1-(1H-pyrrolo[3,2-c]pyridin-2-ylmethyl)-piperazin-2-one,
4-[3-(5-Chloro-thiophen-2-yl)-prop-2-ynyl]-1-(1H-pyrrolo[3,2-c]pyridin-2-ylmethyl)-piperazin-2-one,
4-[3-(5-Chloro-thiophen-2-yl)-allyl]-3-(S)-methoxymethyl-1-(1H-pyrrolo[3,2-c]pyridin-2-ylmethyl)-piperazin-2-one,
4-(5-Chloro-1H-indol-2-ylmethyl)-3-(S)-methoxymethyl-1-(1H-pyrrolo[3,2-c]pyridin-2-ylmethyl)-piperazin-2-one,
4-(5'-Chloro-[2,2']bithiophenyl-5-ylmethyl)-3-(S)-methoxymethyl-1-(1H-pyrrolo[3,2-c]pyridin-2-ylmethyl)-piperazin-2-one,
4-(6-Chloro-benzo[b]thiophene-2-carbonyl)-3-(S)-methoxymethyl-1-(1H-pyrrolo[3,2-c]pyridin-2-ylmethyl)-piperazin-2-one,
4-[1-(3,5-Dichloro-phenyl)-2,5-dimethyl-1H-pyrrole-3-carbonyl]-3-(S)-methoxymethyl-1-(1H-pyrrolo[3,2-c]pyridin-2-ylmethyl)-piperazin-2-one,
4-[3-(4-Chloro-phenyl)-(E)-acryloyl]-3-(S)-methoxymethyl-1-(1H-pyrrolo[3,2-c]pyridin-2-ylmethyl)-piperazin-2-one,
(S)-2-Methoxymethyl-3-oxo-4-(1H-pyrrolo[3,2-c]pyridin-2-ylmethyl)-piperazine-1-carboxylic acid (4-chloro-phenyl)-amide,
(S)-4-[3-(5-Chloro-thiophen-2-yl)-(E)-acryloyl]-3-methoxymethyl-1-(1H-pyrrolo[3,2-c]pyridin-2-ylmethyl)-piperazin-2-one,
4-(6-Chloro-benzo[b]thiophene-2-carbonyl)-1-(1H-pyrrolo[3,2-c]pyridin-2-ylmethyl)piperazin-2-one,
4-[3-(6-Chloro-benzo[b]thiophen-2-yl)-(E)-acryloyl]-1-(1H-pyrrolo[3,2-c]pyridin-2-ylmethyl)-piperazin-2-one,
4-[(5-Chloro-thiophen-2-yloxy)-acetyl]-1-(1H-pyrrolo[3,2-c]pyridin-2-ylmethyl)-piperazin-2-one,
4-[1-(3,5-Dichloro-phenyl)-2,5-dimethyl-1H-pyrrole-3-carbonyl]-1-(1H-pyrrolo[3,2-c]pyridin-2-ylmethyl)-piperazin-2-one,
4-(5'-Chloro-[2,2']bithiophenyl-5-carbonyl)-1-(1H-pyrrolo[3,2-c]pyridin-2-ylmethyl)-piperazin-2-one,
4-(5-Chloro-1H-indole-2-carbonyl)-1-(1H-pyrrolo[3,2-c]pyridin-2-ylmethyl)-piperazin-2-one,
4-[4-(6-Methoxy-pyridin-3-yl)-benzoyl]-1-(1H-pyrrolo[3,2-c]pyridin-2-ylmethyl)-piperazin-2-one,
4-(4-Pyridin-3-yl-benzoyl)-1-(1H-pyrrolo[3,2-c]pyridin-2-ylmethyl)-piperazin-2-one,
4-[3-(4-Bromo-thiophen-2-yl)-(E)-acryloyl]-1-(1H-pyrrolo[3,2-c]pyridin-2-ylmethyl)-piperazin-2-one,
4-[3-(5-Chloro-thiophen-2-yl)-propionyl]-1-(1H-pyrrolo[3,2-c]pyridin-2-ylmethyl)-piperazin-2-one,
4-[(5-Chloro-3-methyl-benzo[b]thiophen-2-yl)-acetyl]-1-(1H-pyrrolo[3,2-c]pyridin-2-ylmethyl)-piperazin-2-one,
4-[2-(4-Chloro-phenyl)-2-methyl-propionyl]-1-(1H-pyrrolo[3,2-c]pyridin-2-ylmethyl)-piperazin-2-one,
4-[3-(3,4-Dichloro-phenyl)-(E)-acryloyl]-1-(1H-pyrrolo[3,2-c]pyridin-2-ylmethyl)-piperazin-2-one,
4-[(4-Chloro-phenyl)-acetyl]-1-(1H-pyrrolo[3,2-c]pyridin-2-ylmethyl)-piperazin-2-one, 4-[3-(4-Chloro-phenyl)-(E)-acryloyl]-1-(1H-pyrrolo[3,2-c]pyridin-2-ylmethyl)-piperazin-2-one, 4-[3-(5-Chloro-thiophen-2-yl)-(E)-acryloyl]-1-(1H-pyrrolo[3,2-c]pyridin-2-ylmethyl)-piperazin-2-one, (±)-1-(4-Amino-quinazolin-7-ylmethyl)-4-(5-chloro-1H-indol-2-ylmethyl)-6-oxo-piperazine-2-carboxylic acid methyl ester, (±)-1-(4-Amino-quinazolin-7-ylmethyl)-4-(5-chloro-1H-indol-2-ylmethyl)-6-oxo-piperazine-2-carboxylic acid, (±)-1-(4-Amino-quinazolin-7-ylmethyl)-4-(5-chloro-1H-indol-2-ylmethyl)-6-oxo-piperazine-2-carboxylic acid methylamide, (+/−)-1-(4-Amino-quinazolin-7-ylmethyl)-4-(5-chloro-1H-indol-2-ylmethyl)-6-oxo-piperazine-2-carboxylic acid ethylamide, (+/−)-1-(4-Amino-quinazolin-7-ylmethyl)-4-(5-chloro-1H-indol-2-ylmethyl)-6-oxo-piperazine-2-carboxylic acid dimethylamide, (+/−)-1-(4-Amino-quinazolin-7-ylmethyl)-4-(5-chloro-1H-indol-2-ylmethyl)-6-oxo-piperazine-2-carboxylic acid benzylamide, (+/−)-1-(4-Amino-quinazolin-7-ylmethyl)-4-(5-chloro-1H-indol-2-ylmethyl)-6-oxo-piperazine-2-carboxylic acid (2-hydroxy-ethyl)-amide, (+/−)-1-(4-Amino-quinazolin-7-ylmethyl)-4-(5-chloro-1H-indol-2-ylmethyl)-6-oxo-piperazine-2-carboxylic acid bis-(2-hydroxy-ethyl)-amide, (+/−)-1-(4-Amino-quinazolin-7-ylmethyl)-4-(5-chloro-1H-indol-2-ylmethyl)-6-(morpholine-4-carbonyl)-piperazin-2-one, (+/−)-1-(4-Amino-quinazolin-7-ylmethyl)-4-(5-chloro-1H-indol-2-ylmethyl)-6-oxo-piperazine-2-carboxylic acid methylcarbamoylmethyl-amide, (+/−)-1-(4-Amino-quinazolin-7-ylmethyl)-4-[3-(5-chloro-thiophen-2-yl)-allyl]-6-oxo-piperazine-2-carboxylic acid, (+/−)-1-(4-Amino-quinazolin-7-ylmethyl)-4-[3-(5-chloro-thiophen-2-yl)-allyl]-6-oxo-piperazine-2-carboxylic acid methyl ester, (+/−)-1-(4-Amino-quinazolin-7-ylmethyl)-4-[3-(5-chloro-thiophen-2-yl)-allyl]-6-oxo-piperazine-2-carboxylic acid amide, (+/−)-1-(4-Amino-quinazolin-7-ylmethyl)-4-[3-(5-chloro-thiophen-2-yl)-allyl]-6-oxo-piperazine-2-carboxylic acid ethylamide, (+/−)-1-(4-Amino-quinazolin-7-ylmethyl)-4-[3-(5-chloro-thiophen-2-yl)-allyl]-6-(4-methyl-piperazine-1-carbonyl)-piperazin-2-one, (±)-1-(4-Amino-quinazolin-7-ylmethyl)-4-(6-chloro-benzo[b]thiophene-2-sulfonyl)-6-oxo-piperazine-2-carboxylic acid methyl ester, (±)-1-(4-Amino-quinazolin-7-ylmethyl)-4-(6-chloro-benzo[b]thiophene-2-sulfonyl)-6-oxo-piperazine-2-carboxylic acid, (±)-1-(4-Amino-quinazolin-7-ylmethyl)-4-(6-chloro-benzo[b]thiophene-2-sulfonyl)-6-oxo-piperazine-2-carboxylic acid amide, (+/−)-1-(4-Amino-quinazolin-7-ylmethyl)-4-(6-chloro-benzo[b]thiophene-2-sulfonyl)-6-oxo-piperazine-2-carboxylic acid ethyl ester, (+/−)-1-(4-Amino-quinazolin-7-ylmethyl)-4-(6-chloro-benzo[b]thiophene-2-sulfonyl)-6-oxo-piperazine-2-carboxylic acid, (+/−)-1-(4-Amino-quinolin-7-ylmethyl)-4-(6-chloro-benzo[b]thiophene-2-sulfonyl)-6-oxo-piperazine-2-carboxylic acid methylamide, (+/−)-1-(4-Amino-quinolin-7-ylmethyl)-4-(6-chloro-benzo[b]thiophene-2-sulfonyl)-6-oxo-piperazine-2-carboxylic acid ethylamide, (+/−)-1-(4-Amino-quinolin-7-ylmethyl)-4-(6-chloro-benzo[b]thiophene-2-sulfonyl)-6-oxo-piperazine-2-carboxylic acid dimethylamide, (+/−)1-(4-Amino-quinolin-7-ylmethyl)-4-(6-chloro-benzo[b]thiophene-2-sulfonyl)-6-(morpholine-4-carbonyl)-piperazin-2-one, (±)-1-(4-Amino-quinazolin-7-ylmethyl)-4-[(5-chloro-thiophen-2-yloxy)-acetyl]-6-oxo-piperazine-2-carboxylic acid methyl ester, (±)-1-(4-Amino-quinazolin-7-ylmethyl)-4-[(5-chloro-thiophen-2-yloxy)-acetyl]-6-oxo-piperazine-2-carboxylic acid methylamide, (+/−)1-(4-Amino-quinazolin-7-ylmethyl)-4-[(5-chloro-thiophen-2-yloxy)-acetyl]-6-oxo-piperazine-2-carboxylic acid ethylamide, (+/−)-1-(4-Amino-quinazolin-7-ylmethyl)-4-[(5-chloro-thiophen-2-yloxy)-acetyl]-6-oxo-piperazine-2-carboxylic acid, 4-Prop-2-ynyl-1-(1H-pyrrolo[3,2-c]pyridin-2-ylmethyl)-piperazin-2-one.

1,4-Bis-(1H-pyrrolo[3,2-c]pyridin-2-ylmethyl)-piperazin-2-one,

2-Amino-4-[4-(6-chloro-1H-benzoimidazol-2-ylmethyl)-2-oxo-piperidin-1-ylmethyl]-benzonitrile, 4-[4-(6-Chloro-1H-benzoimidazol-2-ylmethyl)-2-oxo-piperidin-1-ylmethyl]-benzamidine, 1-(4-Amino-quinazolin-7-ylmethyl)-4-(6-chloro-1H-benzoimidazol-2-ylmethyl)-piperidin-2-one, 4-(6-Chloro-1H-benzoimidazol-2-ylmethyl)-1-(2,4-diamino-quinazolin-7-ylmethyl)-piperidin-2-one, 1-(4-Amino-2-methyl-quinazolin-7-ylmethyl)-4-(6-chloro-1H-benzoimidazol-2-ylmethyl)-piperidin-2-one, (3S, 5R)-4-[4-(6-Chloro-benzo[b]thiophen-2-ylmethyl)-3,5-dimethyl-2-oxo-piperazin-1-ylmethyl]-benzamidine, (3S,5S)-4-[4-(6-Chloro-benzo[b]thiophen-2-ylmethyl)-3,5-dimethyl-2-oxo-piperazin-1-ylmethyl]-benzamidine, 4-{4-[3-(5-Chloro-thiophen-2-yl)-acryloyl]-3,5-dimethyl-2-oxo-piperazin-1-ylmethyl}-benzamidine, (3R,5S)-4-[4-(6-Chloro-benzo[b]thiophen-2-ylmethyl)-3,5-dimethyl-2-oxo-piperazin-1-ylmethyl]-benzamidine, 2-[4-(6-Chlorobenzo[b]thiophene-2-sulfonyl)-2-oxopiperazin-1-yl]-N-[2-(3H-imidazol-4-yl)-ethyl]acetamide, 2-[4-(6-Chloro-benzo[b]thiophene-2-sulfonyl)-2-oxo-piperazin-1-yl]-N-pyridin-4-yl-acetamide, 2-[4-(6-Chloro-benzo[b]thiophene-2-sulfonyl)-2-oxo-piperazin-1-yl]-N-pyridin-3-ylmethyl-acetamide, 2-[4-(6-Chloro-benzo[b]thiophene-2-sulfonyl)-2-oxo-piperazin-1-yl]-N-piperidin-4-yl-acetamide, N-(1-Carbamimidoyl-piperidin-4-yl)-2-[4-(6-chloro-benzo[b]thiophene-2-sulfonyl)-2-oxo-piperazin-1-yl]-acetamide, 5-(2-{2-[4-(6-Chloro-benzo[b]thiophene-2-sulfonyl)-2-oxo-piperazin-1-yl]-acetylamino}-ethyl)-imidazole-1-carboxylic acid ethyl ester, 2-[4-(6-Chloro-benzo[b]thiophene-2-sulfonyl)-2-oxo-piperazin-1-yl]-N-pyrimidin-4-yl-acetamide, 2-[4-(6-Chloro-benzo[b]thiophene-2-sulfonyl)-2-oxo-piperazin-1-yl]-N-phenyl-acetamide, 2-[4-(6-Chloro-benzo[b]thiophene-2-sulfonyl)-2-oxo-piperazin-1-yl]-N-(9H-purin-6-yl)-acetamide, N-(4-Amino-2-methyl-pyrimidin-5-ylmethyl)-2-[4-(6-chloro-benzo[b]thiophene-2-sulfonyl)-2-oxo-piperazin-1-yl]-acetamide, 2-[4-(6-Chloro-benzo[b]thiophene-2-sulfonyl)-2-oxo-piperazin-1-yl]-N-(3-imidazol-1-yl-propyl)-acetamide,
2-[4-(6-Chloro-benzo[b]thiophene-2-sulfonyl)-2-oxo-piperazin-1-yl]-N-[2-(1-methyl-1H-imidazol-4-yl)-ethyl]-acetamide,
2-[4-(6-Chloro-benzo[b]thiophene-2-sulfonyl)-2-oxo-piperazin-1-yl]-N-(2-pyridin-4-yl-ethyl)-acetamide,
2-[4-(6-Chloro-benzo[b]thiophene-2-sulfonyl)-2-oxo-piperazin-1-yl]-N-[2-(3-methyl-3H-imidazol-4-yl)-ethyl]-acetamide,
2-[4-(6-Chloro-benzo[b]thiophene-2-sulfonyl)-2-oxo-piperazin-1-yl]-N-(2-pyridin-2-yl-ethyl)-acetamide,
2-[4-(6-Chloro-benzo[b]thiophene-2-sulfonyl)-2-oxo-piperazin-1-yl]-N-(2-pyridin-3-yl-ethyl)-acetamide,
2-[4-(6-Chloro-benzo[b]thiophene-2-sulfonyl)-2-oxo-piperazin-1-yl]-N-(2-imidazol-1-yl-ethyl)-acetamide,
2-[4-(6-Chloro-benzo[b]thiophene-2-sulfonyl)-2-oxo-piperazin-1-yl]-N-[2-(1-methyl-1H-pyrrol-2-yl)-ethyl]-acetamide,
2-[4-(6-Chloro-benzo[b]thiophene-2-sulfonyl)-2-oxo-piperazin-1-yl]-N-[2-(5-methyl-1H-imidazol-4-yl)-ethyl]-acetamide,
2-[4-(6-Chloro-benzo[b]thiophene-2-sulfonyl)-2-oxo-piperazin-1-yl]-N-(4-dimethylamino-[1,3,5]triazin-2-yl)-acetamide,
2-[4-(6-Chloro-benzo[b]thiophene-2-sulfonyl)-2-oxo-piperazin-1-yl]-N-methyl-N-pyridin-4-yl-acetamide,
N-[2-(2-Amino-pyridin-4-yl)-ethyl]-2-[4-(6-chloro-benzo[b]thiophene-2-sulfonyl)-2-oxo-piperazin-1-yl]-acetamide,
2-[4-(6-Chloro-benzo[b]thiophene-2-sulfonyl)-2-oxo-piperazin-1-yl]-N-[2-(4-methyl-thiazol-5-yl)-ethyl]-acetamide,
2-[4-(6-Chloro-benzo[b]thiophene-2-sulfonyl)-2-oxo-piperazin-1-yl]-N-(2-thiazol-4-yl-ethyl)-acetamide,
2-[4-(6-Chloro-benzo[b]thiophene-2-sulfonyl)-2-oxo-piperazin-1-yl]-N-(3-guanidino-propyl)-acetamide trifluoroacetic acid salt,
N-(3-Amino-propyl)-2-[4-(6-chloro-benzo[b]thiophene-2-sulfonyl)-2-oxo-piperazin-1-yl]-acetamide,
2-[4-(6-Chloro-benzo[b]thiophene-2-sulfonyl)-2-oxo-piperazin-1-yl]-N-[2-(2-mercapto-1H-imidazol-4-yl)-ethyl]-acetamide,
N-[2-(2-Amino-thiazol-4-yl)-ethyl]-2-[4-(6-chloro-benzo[b]thiophene-2-sulfonyl)-2-oxo-piperazin-1-yl]-acetamide,
2-[4-(6-Chloro-benzo[b]thiophene-2-sulfonyl)-2-oxo-piperazin-1-yl]-N-methyl-N-(2-pyridin-4-yl-ethyl)-acetamide,
2-[4-(6-Chloro-benzo[b]thiophene-2-sulfonyl)-2-oxo-piperazin-1-yl]-N-[2-(2-methylsulfanyl-1H-imidazol-4-yl)-ethyl]-acetamide,
4-(6-Chloro-benzo[b]thiophene-2-sulfonyl)-1-[3-(3H-imidazol-4-yl)-propyl]-piperazin-2-one,
4-[4-(6-Chloro-benzo[b]thiophene-2-sulfonyl)-2-oxo-piperazin-1-ylmethyl]-piperidine-1-carboxamidine,
4-(6-Chloro-benzo[b]thiophene-2-sulfonyl)-1-(3-piperazin-1-yl-propyl)-piperazin-2-one,
4-(6-Chloro-benzo[b]thiophene-2-sulfonyl)-1-(3-pyridin-4-yl-propyl)-piperazin-2-one,
4-(6-Chloro-benzo[b]thiophene-2-sulfonyl)-1-(4-piperidin-4-yl-butyl)-piperazin-2-one,
4-(6-Chloro-benzo[b]thiophene-2-sulfonyl)-1-(2-piperidin-4-yl-ethyl)-piperazin-2-one,
4-(6-Chloro-benzo[b]thiophene-2-sulfonyl)-1-(3-piperidin-4-yl-propyl)-piperazin-2-one,
4-[(5-Chloro-thiophen-2-yloxy)-acetyl]-3-(S)-methoxymethyl-1-[4-(6-methoxy-pyridin-3-yl)-benzyl]-piperazin-2-one,
4'-[4-(6-Chloro-benzo[b]thiophene-2-sulfonyl)-2-oxo-piperazin-1-ylmethyl]-biphenyl-2-carbonitrile,
4-(6-Chloro-benzo[b]thiophene-2-sulfonyl)-1-(4-chloro-3-hydroxy-benzyl)-piperazin-2-one,
1-Benzyl-4-(6-chloro-benzo[b]thiophene-2-sulfonyl)-piperazin-2-one,
4-(6-Chloro-benzo[b]thiophene-2-sulfonyl)-1-(4-chloro-benzyl)-piperazin-2-one,
4-[(4-Chloro-thiophen-2-yloxy)-acetyl]-3-(S)-methoxymethyl-1-[4-(6-methoxy-pyridin-3-yl)-benzyl]-piperazin-2-one,
4-[(5-Chloro-thiophen-3-yloxy)-acetyl]-1-[4-(6-hydroxy-pyridin-3-yl)-benzyl]-3-(S)-methoxymethyl-piperazin-2-one,
4-[(5-Chloro-thiophen-3-yloxy)-acetyl]-3-(S)-methoxymethyl-1-[4-(6-methoxy-pyridin-3-yl)-benzyl]-piperazin-2-one,
4-[(5-Chloro-thiophen-2-yloxy)-acetyl]-1-[4-(6-hydroxy-pyridin-3-yl)-benzyl]-3-(S)-methoxymethyl-piperazin-2-one,
4-[3-(5-Chloro-thiophen-2-yl)-(E)-acryloyl]-1-[4-(6-methoxy-pyridin-3-yl)-benzyl]-3-(S)-methyl-piperazin-2-one,
4-[3-(5-Chloro-thiophen-2-yl)-(E)-acryloyl]-3-(S)-methyl-1-[4-(6-oxo-1,6-dihydro-pyridin-3-yl)-benzyl]-piperazin-2-one,
1-Biphenyl-4-ylmethyl-4-[3-(5-chloro-thiophen-2-yl)-(E)-acryloyl]-3-(S)-ethyl-6-methyl-piperazin-2-one,
4-[3-(5-Chloro-thiophen-2-yl)-(E)-acryloyl]-1-[4-(6-hydroxy-pyridin-3-yl)-benzyl]-3-(S)-methoxymethyl-piperazin-2-one,
4-[3-(5-Chloro-thiophen-2-yl)-(E)-acryloyl]-3-(S)-methoxymethyl-1-[4-(6-methoxy-pyridin-3-yl)-benzyl]-piperazin-2-one,
1-(3-Amino-1H-indazol-6-ylmethyl)-4-(6-chloro-benzo[b]thiophen-2-ylmethyl)-piperazin-2-one,
1-(3-Amino-1H-indazol-6-ylmethyl)-4-[3-(5-chloro-thiophen-2-yl)]-piperazin-2-one,
1-(3-Amino-1H-indazol-6-ylmethyl)-4-(6-chloro-benzo[b]thiophene-2-sulfonyl)-piperazin-2-one,
4-[4-(6-Chloro-benzo[b]thiophen-2-ylmethyl)-2-(S)-methyl-3,6-dioxo-piperazin-1-ylmethyl]-benzamidine,
4-[4-(6-Chloro-benzo[b]thiophen-2-ylmethyl)-2-(R)-methyl-3,6-dioxo-piperazin-1-ylmethyl]-benzamidine,
3-[4-(6-Chloro-benzo[b]thiophen-2-ylmethyl)-2,5-dioxo-piperazin-1-ylmethyl]-benzamidine and
4-[4-(6-Chloro-benzo[b]thiophen-2-ylmethyl)-2,5-dioxo-piperazin-1-ylmethyl]-benzamidine.

Preferred compounds which inhibit both Factor Xa and Factor IIa (thrombin) activity are selected from the group consisting of:

(+/−)-1-(4-Amino-quinazolin-7-ylmethyl)-4-(6-chloro-benzo[b]thiophene-2-sulfonyl)-6-oxo-piperazine-2-carboxylic acid;
(+/−)-1-(4-Amino-quinazolin-7-ylmethyl)-4-(6-chloro-benzo[b]thiophene-2-sulfonyl)-6-oxo-piperazine-2-carboxylic acid methyl ester;
(+/−)-1-(4-Amino-quinazolin-7-ylmethyl)-4-(6-chloro-benzo[b]thiophene-2-sulfonyl)-6-oxo-piperazine-2-carboxylic acid ethyl ester;
1-(4-Amino-quinazolin-7-ylmethyl)-4-(6-chloro-benzo[b]thiophene-2-sulfonyl)--oxo-piperazine-2-carboxylic acid 2-pyrrolidin-1-yl-ethyl ester;

1-(4-Amino-quinazolin-7-ylmethyl)-4-(6-chloro-benzo[b]thiophene-2-sulfonyl)--oxo-piperazine-2-carboxylic acid 2-pyrrolidin-1-yl-ethyl amide;

(+/−)-1-(4-Amino-quinazolin-7-ylmethyl)-4-(6-chloro-1H-indole-2-sulfonyl)-6-oxo-piperazine-2-carboxylic acid methyl ester;

(+/−)-1-(4-Amino-quinazolin-7-ylmethyl)-4-(5-chloro-1H-indole-2-sulfonyl)-6-oxo-piperazine-2-carboxylic acid methyl ester;

(+/−)-1-(4-Amino-quinazolin-7-ylmethyl)-4-(6-chloro-1H-benzoimidazole-2-sulfonyl)-6-oxo-piperazine-2-carboxylic acid methyl ester;

(S)-[1-(4-Amino-quinazolin-7-ylmethyl0-4-(6-chloro-benzo[b]thiophene-2-sulfonyl)-6-oxo-piperazin-2-yl]acetic acid;

(S)-[1-(4-Amino-quinazolin-7-ylmethyl0-4-(6-chloro-benzo[b]thiophene-2-sulfonyl)-6-oxo-piperazin-2-yl]acetic acid tert-butyl ester;

(+/−)-1-(4-Amino-quinazolin-7-ylmethyl)-4-(6-chloro-benzo[b]thiophene-2-sulfonyl)-6-methyl-piperazin-2-one;

(S)-1-(4-Amino-quinazolin-7-ylmethyl)-4-(6-chloro-benzo[b]thiophene-2-sulfonyl)-6-methyl-piperazin-2-one;

(R)-1-(4-Amino-quinazolin-7-ylmethyl)-4-(6-chloro-benzo[b]thiophene-2-sulfonyl)-6-methyl-piperazin-2-one;

(S)-1-(4-Amino-quinazolin-7-ylmethyl)-4-(6-chloro-benzo[b]thiophene-2-sulfonyl)-6-isopropyl-piperazin-2-one;

(R)-1-(4-Amino-quinazolin-7-ylmethyl)-4-(6-chloro-benzo[b]thiophene-2-sulfonyl)-6-isopropyl-piperazin-2-one;

(S)-1-(4-Amino-quinazolin-7-ylmethyl)-4-(6-chloro-benzo[b]thiophene-2-sulfonyl)-6-isobutyl-piperazin-2-one;

(R)-1-(4-Amino-quinazolin-7-ylmethyl)-4-(6-chloro-benzo[b]thiophene-2-sulfonyl)-6-isobutyl-piperazin-2-one;

(R)-1-(4-Amino-quinazolin-7-ylmethyl)-4-(6-chloro-benzo[b]thiophene-2-sulfonyl)-6-methoxymethyl-piperazin-2-one;

(S)-1-(4-Amino-quinazolin-7-ylmethyl)-4-(6-chloro-benzo[b]thiophene-2-sulfonyl)-6-methoxymethyl-piperazin-2-one;

(S)-1-(4-Amino-quinazolin-7-ylmethyl)-4-(6-chloro-benzo[b]thiophene-2-sulfonyl)-6-isopropylaminomethyl-piperazin-2-one;

(S)-1-(4-Amino-quinazolin-7-ylmethyl)-4-(6-chloro-1H-indole-2-sulfonyl)-6-methyl-piperazin-2-one;

(R)-1-(4-Amino-quinazolin-7-ylmethyl)-4-(6-chloro-1H-indole-2-sulfonyl)-6-methyl-piperazin-2-one;

(S)-1-(4-Amino-quinazolin-7-ylmethyl)-4-(6-chloro-1H-indole-2-sulfonyl)-6-isopropyl-piperazin-2-one;

(R)-1-(4-Amino-quinazolin-7-ylmethyl)-4-(6-chloro-1H-indole-2-sulfonyl)-6-isopropyl-piperazin-2-one;

(S)-1-(4-Amino-quinazolin-7-ylmethyl)-4-(6-chloro-1H-indole-2-sulfonyl)-6-isobutyl-piperazin-2-one;

(R)-1-(4-Amino-quinazolin-7-ylmethyl)-4-(6-chloro-1H-indole-2-sulfonyl)-6-isobutyl-piperazin-2-one;

(R)-1-(4-Amino-quinazolin-7-ylmethyl)-4-(6-chloro-1H-indole-2-sulfonyl)-6-methoxymethyl-piperazin-2-one;

(S)-1-(4-Amino-quinazolin-7-ylmethyl)-4-(6-chloro-1H-indole-2-sulfonyl)-6-methoxymethyl-piperazin-2-one;

(S)-1-(4-Amino-quinazolin-7-ylmethyl)-4-(5-chloro-1H-indole-2-sulfonyl)-6-methyl-piperazin-2-one;

(R)-1-(4-Amino-quinazolin-7-ylmethyl)-4-(5-chloro-1H-indole-2-sulfonyl)-6-methyl-piperazin-2-one;

(S)-1-(4-Amino-quinazolin-7-ylmethyl)-4-(5-chloro-1H-indole-2-sulfonyl)-6-isopropyl-piperazin-2-one;

(R)-1-(4-Amino-quinazolin-7-ylmethyl)-4-(5-chloro-1H-indole-2-sulfonyl)-6-isopropyl-piperazin-2-one;

(S)-1-(4-Amino-quinazolin-7-ylmethyl)-4-(5-chloro-1H-indole-2-sulfonyl)-6-isobutyl-piperazin-2-one;

(R)-1-(4-Amino-quinazolin-7-ylmethyl)-4-(5-chloro-1H-indole-2-sulfonyl)-6-isobutyl-piperazin-2-one;

(R)-1-(4-Amino-quinazolin-7-ylmethyl)-4-(5-chloro-1H-indole-2-sulfonyl)-6-methoxymethyl-piperazin-2-one;

(S)-1-(4-Amino-quinazolin-7-ylmethyl)-4-(5-chloro-1H-indole-2-sulfonyl)-6-methoxymethyl-piperazin-2-one;

(S)-1-(4-Amino-quinazolin-7-ylmethyl)-4-(6-chloro-1H-benzoimidazole-2-sulfonyl)-6-methyl-piperazin-2-one;

(R)-1-(4-Amino-quinazolin-7-ylmethyl)-4-(6-chloro-1H-benzoimidazole-2-sulfonyl)-6-methyl-piperazin-2-one;

(S)-1-(4-Amino-quinazolin-7-ylmethyl)-4-(6-chloro-1H-benzoimidazole-2-sulfonyl)-6-isopropyl-piperazin-2-one;

(R)-1-(4-Amino-quinazolin-7-ylmethyl)-4-(6-chloro-1H-benzoimidazole-2-sulfonyl)-6-isopropyl-piperazin-2-one;

(S)-1-(4-Amino-quinazolin-7-ylmethyl)-4-(6-chloro-1H-benzoimidazole-2-sulfonyl)-6-isobutyl-piperazin-2-one;

(R)-1-(4-Amino-quinazolin-7-ylmethyl)-4-(6-chloro-1H-benzoimidazole-2-sulfonyl)-6-isobutyl-piperazin-2-one;

(R)-1-(4-Amino-quinazolin-7-ylmethyl)-4-(6-chloro-1H-benzoimidazole-2-sulfonyl)-6-methoxymethyl-piperazin-2-one;

(S)-1-(4-Amino-quinazolin-7-ylmethyl)-4-(6-chloro-1H-benzoimidazole-2-sulfonyl)-6-methoxymethyl-piperazin-2-one;

4-(6-Chloro-benzo[b]thiophene-2-sulfonyl)-1-(3,4,5,6-tetrahydro-2H-[1,2']bipyridinyl-4-ylmethyl)-piperazin-2-one;

4-(6-Chloro-benzo[b]thiophene-2-sulfonyl)-1-[1-(2-dimethylamino-pyrimidin-4-yl)-piperidin-4-ylmethyl]-piperazin-2-one;

N,N-Dimethyl-N4{[(chlorobenzo[b]thiophene-2-sulfonyl)-2-(keto)piperazin-1-yl]methylpiperdinyl]} cyanoguanidine;

4-(6-Chloro-benzo[b]thiophene-2-sulfonyl)-1-{1-[2-(2-hydroxy-ethylamino)-pyrimidin-4-yl]-piperidin-4-ylmethyl}-piperazin-2-one;

4-(6-Chloro-benzo[b]thiophene-2-sulfonyl)-1-[-pyrimidin-4-yl)-piperidin-4-ylmethyl]-piperazin-2-one;

3-{2-[4-(6-Chloro-benzo[b]thiophene-2-sulfonyl)-2-oxo-piperazin-1-ylmethyl]-thiazol-4-yl}-3-methyl-butyric acid ethyl ester;

(R)-2-[4-(6-Chloro-benzo[b]thiophene-2-sulfonyl)-2-methoxymethyl-6-oxo-piperazin-1-ylmethyl]-4,5,6,7-tetrahydro-benzothiazole-4-carboxylic acid amide;

2-[4-(6-Chloro-benzo[b]thiophene-2-sulfonyl)-2-oxo-piperazin-1-ylmethyl]-4,5,6,7-tetrahydro-benzothiazole-4-carboxylic acid ethyl ester;

4-(6-Chloro-benzo[b]thiophene-2-sulfonyl)-1-(4,5,6,7-tetrahydro-benzothiazol-2-ylmethyl)-piperazin-2-one;

(R)-4-(6-Chloro-benzo[b]thiophene-2-sulfonyl)-6-methoxymethyl-1-(4-pyridin-3-yl-thiazol-2-ylmethyl)-piperazin-2-one;

4-(6-Chloro-benzo[b]thiophene-2-sulfonyl)-1-(4-hydroxy-4,5,6,7-tetrahydro-benzothiazol-2-ylmethyl)-piperazin-2-one;

2-[4-(6-Chloro-benzo[b]thiophene-2-sulfonyl)-2-oxo-piperazin-1-ylmethyl]-thiazole-4-carboxylic acid isopropyl-methyl-amide;

2-[4-(6-Chloro-benzo[b]thiophene-2-sulfonyl)-2-oxo-piperazin-1-ylmethyl]-4,5,6,7-tetrahydro-benzothiazole-4-carboxylic acid amide;

2-[4-(6-Chloro-benzo[b]thiophene-2-sulfonyl)-2-oxo-piperazin-1-ylmethyl]-6,7-dihydro-5H-benzothiazol-4-one oxime;

2-[4-(6-Chloro-benzo[b]thiophene-2-sulfonyl)-2-oxo-piperazin-1-ylmethyl]-thiazole-4-carboxylic acid methoxy-methyl-amide;
2-[4-(6-Chloro-benzo[b]thiophene-2-sulfonyl)-2-oxo-piperazin-1-ylmethyl]-6,7-dihydro-5H-benzothiazol-4-one;
(R)-2-[4-(6-Chloro-benzo[b]thiophene-2-sulfonyl)-2-methoxymethyl-6-oxo-piperazin-1-ylmethyl]-thiazole-4-carboxylic acid dimethylamide;
1-[2-(5-Chloro-thiophen-2-yl)-ethenesulfonyl]-5-oxo-4-(1H-pyrrolo[3,2-c]pyridin-2-ylmethyl)-piperazine-2-carboxylic acid methyl ester;
1-[2-(5-Chloro-thiophen-2-yl)-ethenesulfonyl]-5-oxo-4-(1H-pyrrolo[3,2-c]pyridin-2-ylmethyl)-piperazine-2-carboxylic acid methyl ester;
1-(6-Chloro-benzo[b]thiophene-2-sulfonyl)-5-oxo-4-(1H-pyrrolo[3,2-c]pyridin-2-ylmethyl)-piperazine-2-carboxylic acid methyl ester;
4-(6-Chloro-benzo[b]thiophene-2-sulfonyl)-6-hydroxymethyl-1-(1-methyl-1H-pyrrolo[3,2-c]pyridin-2-ylmethyl)-piperazin-2-one;
4-(6-Chloro-benzo[b]thiophene-2-sulfonyl)-6-oxo-1-(1H-pyrrolo[3,2-c]pyridin-2-ylmethyl)-piperazine-2-carboxylic acid methyl ester;
4-(6-Chloro-benzo[b]thiophene-2-sulfonyl)-6-methoxymethyl-1-(1H-pyrrolo[3,2-c]pyridin-2-ylmethyl)-piperazin-2-one; and
4-(6-Chloro-benzo[b]thiophene-2-sulfonyl)-1-(1H-pyrrolo[3,2-c]pyridin-2-ylmethyl)-piperazin-2-one;

Preferred compounds wherein Z is —NR$_5$C(O)— or —C(O)NR$_5$— are selected from
2-[4-(6-Chlorobenzo[b]thiophene-2-sulfonyl)-2-oxopiperazin-1-yl]-N-[2-(3H-imidazol-4-yl)-ethyl]acetamide,
2-[4-(6-Chloro-benzo[b]thiophene-2-sulfonyl)-2-oxo-piperazin-1-yl]-N-pyridin-4-yl-acetamide,
2-[4-(6-Chloro-benzo[b]thiophene-2-sulfonyl)-2-oxo-piperazin-1-yl]-N-pyridin-3-ylmethyl-acetamide,
2-[4-(6-Chloro-benzo[b]thiophene-2-sulfonyl)-2-oxo-piperazin-1-yl]-N-piperidin-4-yl-acetamide,
N-(1-Carbamimidoyl-piperidin-4-yl)-2-[4-(6-chloro-benzo[b]thiophene-2-sulfonyl)-2-oxo-piperazin-1-yl]-acetamide,
5-(2-{2-[4-(6-Chloro-benzo[b]thiophene-2-sulfonyl)-2-oxo-piperazin-1-yl]-acetylamino}-ethyl)-imidazole-1-carboxylic acid ethyl ester,
2-[4-(6-Chloro-benzo[b]thiophene-2-sulfonyl)-2-oxo-piperazin-1-yl]-N-pyrimidin-4-yl-acetamide,
2-[4-(6-Chloro-benzo[b]thiophene-2-sulfonyl)-2-oxo-piperazin-1-yl]-N-phenyl-acetamide,
2-[4-(6-Chloro-benzo[b]thiophene-2-sulfonyl)-2-oxo-piperazin-1-yl]-N-(9H-purin-6-yl)-acetamide,
N-(4-Amino-2-methyl-pyrimidin-5-ylmethyl)-2-[4-(6-chloro-benzo[b]thiophene-2-sulfonyl)-2-oxo-piperazin-1-yl]-acetamide,
2-[4-(6-Chloro-benzo[b]thiophene-2-sulfonyl)-2-oxo-piperazin-1-yl]-N-(3-imidazol-1-yl-propyl)-acetamide,
2-[4-(6-Chloro-benzo[b]thiophene-2-sulfonyl)-2-oxo-piperazin-1-yl]-N-[2-(1-methyl-1H-imidazol-4-yl)-ethyl]-acetamide,
2-[4-(6-Chloro-benzo[b]thiophene-2-sulfonyl)-2-oxo-piperazin-1-yl]-N-(2-pyridin-4-yl-ethyl)-acetamide,
2-[4-(6-Chloro-benzo[b]thiophene-2-sulfonyl)-2-oxo-piperazin-1-yl]-N-[2-(3-methyl-3H-imidazol-4-yl)-ethyl]-acetamide,
2-[4-(6-Chloro-benzo[b]thiophene-2-sulfonyl)-2-oxo-piperazin-1-yl]-N-(2-pyridin-2-yl-ethyl)-acetamide,
2-[4-(6-Chloro-benzo[b]thiophene-2-sulfonyl)-2-oxo-piperazin-1-yl]-N-(2-pyridin-3-yl-ethyl)-acetamide,
2-[4-(6-Chloro-benzo[b]thiophene-2-sulfonyl)-2-oxo-piperazin-1-yl]-N-(2-imidazol-1-yl-ethyl)-acetamide,
2-[4-(6-Chloro-benzo[b]thiophene-2-sulfonyl)-2-oxo-piperazin-1-yl]-N-[2-(1-methyl-1H-pyrrol-2-yl)-ethyl]-acetamide,
2-[4-(6-Chloro-benzo[b]thiophene-2-sulfonyl)-2-oxo-piperazin-1-yl]-N-[2-(5-methyl-1H-imidazol-4-yl)-ethyl]-acetamide,
2-[4-(6-Chloro-benzo[b]thiophene-2-sulfonyl)-2-oxo-piperazin-1-yl]-N-(4-dimethylamino-[1,3,5]triazin-2-yl)-acetamide,
2-[4-(6-Chloro-benzo[b]thiophene-2-sulfonyl)-2-oxo-piperazin-1-yl]-N-methyl-N-pyridin-4-yl-acetamide,
N-[2-(2-Amino-pyridin-4-yl)-ethyl]-2-[4-(6-chloro-benzo[b]thiophene-2-sulfonyl)-2-oxo-piperazin-1-yl]-acetamide,
2-[4-(6-Chloro-benzo[b]thiophene-2-sulfonyl)-2-oxo-piperazin-1-yl]-N-[2-(4-methyl-thiazol-5-yl)-ethyl]-acetamide,
2-[4-(6-Chloro-benzo[b]thiophene-2-sulfonyl)-2-oxo-piperazin-1-yl]-N-(2-thiazol-4-yl-ethyl)-acetamide,
2-[4-(6-Chloro-benzo[b]thiophene-2-sulfonyl)-2-oxo-piperazin-1-yl]-N-(3-guanidino-propyl)-acetamide trifluoroacetic acid salt,
N-(3-Amino-propyl)-2-[4-(6-chloro-benzo[b]thiophene-2-sulfonyl)-2-oxo-piperazin-1-yl]-acetamide,
2-[4-(6-Chloro-benzo[b]thiophene-2-sulfonyl)-2-oxo-piperazin-1-yl]-N-[2-(2-mercapto-1H-imidazol-4-yl)-ethyl]-acetamide,
N-[2-(2-Amino-thiazol-4-yl)ethyl]-2-[4-(6-chloro-benzo[b]thiophene-2-sulfonyl)-2-oxo-piperazin-1-yl]-acetamide,
2-[4-(6-Chloro-benzo[b]thiophene-2-sulfonyl)-2-oxo-piperazin-1-yl]-N-methyl-N-(2-pyridin-4-yl-ethyl)-acetamide, or
2-[4-(6-Chloro-benzo[b]thiophene-2-sulfonyl)-2-oxo-piperazin-1-yl]-N-[2-(2-methylsulfanyl-1H-imidazol-4-yl)-ethyl]-acetamide, or a pharmaceutically acceptable salt thereof, pharmaceutically acceptable prodrug thereof, an N-oxide thereof, a hydrate thereof or a solvate thereof.

Still more preferred compounds are selected from
4-[3-(6-Amino-pyridin-3-yl)-acryloyl]-1-(4-amino-quinazolin-7-ylmethyl)-3-(S)-methoxymethyl-piperazin-2-one,
1-(1-Amino-isoquinolin-7-ylmethyl)-4-(6-chloro-benzo[b]thiophene-2-sulfonyl)-piperazin-2-one,
4-(5'-Chloro-[2,2']bithiophenyl-5-ylmethyl)-3-(S)-methoxymethyl-1-(1H-pyrrolo[3,2-c]pyridin-2-ylmethyl)-piperazin-2-one,
1-(4-Amino-quinazolin-7-ylmethyl)-4-(6-chloro-benzo[b]thiophene-2-sulfonyl)-piperazin-2-one,
(S)-1-(4-Amino-quinazolin-7-ylmethyl)-4-[3-(5-chloro-thiophen-2-yl)-acryloyl]-3-methyl-piperazin-2-one,
1-(4-Amino-quinazolin-7-ylmethyl)-4-[3-(5-chloro-thiophen-2-yl)-allyl]-piperazin-2-one,
1-(4-Amino-quinazolin-7-ylmethyl)-4-(3-chloro-1H-indol-6-ylmethyl)-piperazin-2-one,
1-(4-Amino-quinazolin-7-ylmethyl)-4-(7-chloro-isoquinolin-3-ylmethyl)-3-(S)-methyl-piperazin-2-one,
1-(4-Amino-quinazolin-7-ylmethyl)-4-[3-(5-chloro-thiophen-2-yl)-allyl]-4-oxy-piperazin-2-one,
4-[2-(5-Chloro-thiophen-2-yl)-ethenesulfonyl]-1-[2-(pyridin-4-ylamino)-ethyl]-piperazin-2-one,
1-(4-Amino-quinazolin-7-ylmethyl)-4-[3-(5-chloro-thiophen-2-yl)-allyl]-3-(S)-methyl-piperazin-2-one, 4-(4-Amino-quinazolin-7-ylmethyl)-2-(S)-methoxymethyl-3-oxo-piperazine-1-carboxylic acid (4-chloro-phenyl)-amide, 1-(4-Amino-quinazolin-7-ylmethyl)-4-(6-chloro-1H-benzoimidazol-2-ylmethyl)-piperazin-2-one, 1-(4-Amino-thieno[3,2-d]pyrimidin-6-ylmethyl)-4-[2-(5-chloro-thiophen-2-yl)-ethenesulfonyl]-piperazin-2-one, 1-(4-Amino-quinazolin-7-ylmetyl)-4-[3-(5-chloro-thiophen-2-yl)-allyl]-3-(S)-methoxymethyl-piperazin-2-one, 1-(4-Amino-quinazolin-7-ylmethyl)-4-[3-(5-bromo-furan-2-yl)-acryloyl]-3-(S)-methoxymethyl-piperazin-2-one, 1-(4-Amino-quinolin-7-ylmethyl)-4-[3-(5-chloro-thiophen-2-yl)-allyl]-3-(S)-methyl-4-oxo-piperazin-2-one, 1-(1-Amino-isoquinolin-6-ylmethyl)-4-[(5-chloro-thiophen-2-yloxy)-acetyl]-3-(S)-methoxymethyl-piperazin-2-one, 1-(4-Amino-quinazolin-7-ylmethyl)-4-[3-(5-chloro-thiophen-2-yl)-allyl]-3-(S)-ethoxymethyl-piperazin-2-one, 1-(4-Amino-quinazolin-7-ylmethyl)-4-[3-(4-chloro-thiophen-2-yl)-acryloyl]-3-(S)-methyl-piperazin-2-one, 1-(4-Amino-quinolin-7-ylmethyl)-4-[3-(5-chloro-thiophen-2-yl)-acryloyl]-3-((S)-1-(R)-methoxy-ethyl)-piperazin-2-one, 1-(4-Amino-quinazolin-7-ylmethyl)-4-(6-chloro-benzo[b]thiophene-2-sulfonyl)-6-oxo-piperazine-2-(R)-carboxylic acid ethyl ester, 1-(4-Amino-quinazolin-7-ylmethyl)-4-(7-chloro-isoquinolin-3-ylmethyl)-piperazin-2-one, 1-(4-Amino-quinolin-7-ylmethyl)-4-[3-(5-chloro-thiophen-2-yl)-allyl]-piperazin-2-one, 3-[4-(4-Amino-quinazolin-7-ylmethyl)-3-oxo-piperazin-1-ylmethyl]-7-chloro-1H-quinolin-2-one, 1-(4-Amino-quinazolin-7-ylmethyl)-3-(S)-butyl-4-[(5-chloro-thiophen-3-yloxy)-acetyl]-piperazin-2-one, 4-[3-(6-Amino-pyridin-3-yl)-acryloyl]-1-(4-amino-quinazolin-7-ylmethyl)-3-(S)-propyl-piperazin-2-one, 1-(4-Amino-quinazolin-7-ylmethyl)-4-(3-chloro-1H-indol-6-ylmethyl)-3-(S)-methyl-piperazin-2-one, 1-(4-Amino-quinolin-7-ylmethyl)-4-(5-chloro-1H-indol-2-ylmethyl)-piperazin-2-one, 1-(4-Amino-quinazolin-7-ylmethyl)-4-[(5-chloro-thiophen-2-yloxy)-acetyl]-3-(S)-ethyl-piperazin-2-one, 1-(4-Amino-quinazolin-7-ylmethyl)-4-[3-(4-chloro-thiophen-2-yl)-acryloyl]-3-(S)-ethyl-piperazin-2-one, 4-(6-Chloro-benzo[b]thiophene-2-sulfonyl)-6-oxo-1-(1H-pyrrolo[3,2-c]pyridin-2-ylmethyl)-piperazine-2-carboxylic acid methyl ester, (3S,5R)-1-(4-Amino-quinazolin-7-ylmethyl)-4-[3-(5-chloro-thiophen-2-yl)-allyl]-3,5-dimethyl-piperazin-2-one, 1-(4-Amino-quinazolin-7-ylmethyl)-4-[3-(4-bromo-thiophen-2-yl)-acryloyl]-3-(S)-ethyl-piperazin-2-one, 1-(4-Amino-quinazolin-7-ylmethyl)-4-[3-(5-chloro-thiophen-2-yl)-acryloyl]-3-(S)-methoxymethyl-piperazin-2-one, 1-(4-Amino-quinazolin-7-ylmethyl)-4-(5'-chloro-[2,2']bithiophenyl-5-sulfonyl)-piperazin-2-one, 1-(4-Amino-quinazolin-7-ylmethyl)-4-[3-(5-bromo-thiophen-2-yl)-acryloyl]-3-(S)-methoxymethyl-piperazin-2-one, 1-(4-Amino-quinazolin-7-ylmethyl)-4-[(5-chloro-thiophen-3-yloxy)-acetyl]-3-(S)-propyl-piperazin-2-one, 4-[(5-Chloro-thiophen-2-yloxy)-acetyl]-1-[4-(6-hydroxy-pyridin-3-yl)-benzyl]-3-(S)-methoxymethyl-piperazin-2-one, 1-(4-Amino-quinazolin-7-ylmethyl)-4-[(5-chloro-thiophen-2-yloxy)-acetyl]-3-(S)-ethoxymethyl-piperazin-2-one, 1-(4-Amino-quinolin-7-ylmethyl)-4-(5-chloro-1H-indol-2-ylmethyl)-3-(S)-methyl-piperazin-2-one, 1-(4-Amino-quinolin-7-ylmethyl)-4-(5-chloro-1H-indol-2-ylmethyl)-3-(S)-methoxymethyl-piperazin-2-one, 1-(4-Amino-quinolin-7-ylmethyl)-4-[3-(5-chloro-thiophen-2-yl)-acryloyl]-3-(S)-ethyl-6-methyl-piperazin-2-one, (3S, 5S)-1-(4-Amino-quinazolin-7-ylmethyl)-4-(6-chloro-benzo[b]thiophene-2-sulfonyl)-3,5-dimethyl-piperazin-2-one, (3S, 5R)-1-(4-Amino-quinazolin-7-ylmethyl)-4-[2-(5-chloro-thiophen-2-yl)-ethenesulfonyl]-3,5-dimethyl-piperazin-2-one, 1-(4-Amino-quinazolin-7-ylmethyl)-4-[3-(5-bromo-thiophen-2-yl)-acryloyl]-3-(S)-ethyl-piperazin-2-one, 1-(4-Amino-quinazolin-7-ylmethyl)-4-[3-(4-bromo-thiophen-2-yl)-acryloyl]-3-(S)-6-dimethyl-piperazin-2-one, 1-(4-Amino-quinolin-7-ylmethyl)-4-[3-(5-chloro-thiophen-2-yl)-allyl]-3-(S)-methyl-piperazin-2-one, 1(4-Amino-quinolin-7-ylmethyl)-4-(7-chloro-isoquinolin-3-ylmethyl)-3-(S)-methyl-piperazin-2-one, (4-Amino-quinazolin-7-ylmethyl)-4-[3-(5-chloro-thiophen-2-yl)-acryloyl]-3-(S)-ethyl-piperazin-2-one, 4-(6-Chloro-benzo[b]thiophene-2-sulfonyl)-1-(1-ethyl-1H-pyrrolo[3,2-c]pyridin-2-ylmethyl)-piperazin-2-one, 4-[4-(6-Chloro-benzo[b]thiophene-2-sulfonyl)-2-oxo-piperazin-1-ylmethyl]-piperidine-1-carboxamidine, 4-(6-Chloro-thieno[2,3-b]pyridine-2-sulfonyl)-1-(1H-pyrrolo[3,2-c]pyridin-2-ylmethyl)-piperazin-2-one, 4-(6-Chloro-benzo[b]thiophene-2-sulfonyl)-1-(1H-pyrrolo[3,2-c]pyridin-2-ylmethyl)-piperazin-2-one, 4-[(5-Chloro-thiophen-3-yloxy)-acetyl]-3-(S)-methoxymethyl-1-[4-(6-methoxy-pyridin-3-yl)-benzyl]-piperazin-2-one, 4-(4-Amino-quinazolin-7-ylmethyl)-3-oxo-2-(S)-propyl-piperazine-1-carboxylic acid (5-chloro-thiophen-2-yl)-amide, 1-(4-Amino-quinazolin-7-ylmetyl)-4-[3-(5-chloro-thiophen-3-yl)-acryloyl]-3-(S)-propyl-piperazin-2-one, 4-(6-Chloro-benzo[b]thiophene-2-sulfonyl)-6-hydroxymethyl-1-(1H-pyrrolo[3,2-c]pyridin-2-ylmethyl)-piperazin-2-one, 4-(4-Amino-quinazolin-7-ylmethyl)-2-(S)-methyl-3-oxo-piperazine-1-carboxylic acid (5-chloro-thiophen-2-yl)-amide, 1-(4-Amino-quinazolin-7-ylmethyl)-4-[(5-chloro-thiophen-2-yloxy)-acetyl]-3-(S)-ethyl-6-methyl-piperazin-2-one, 1-(4-Amino-quinolin-7-ylmethyl)-4-[3-(4-bromo-thiophen-2-yl)-acryloyl]-3-(S)-ethyl-piperazin-2-one, 1-(4-Amino-quinazolin-7-ylmethyl)-4-[3-(4-chloro-thiophen-2-yl)-acryloyl]-3-(S)-methoxymethyl-piperazin-2-one, 1-(4-Amino-quinolin-7-ylmethyl)-4-[3-(4-bromo-thiophen-2-yl)-acryloyl]-3-(S)-methyl-piperazin-2-one, 1-(4-Amino-quinazolin-7-ylmethyl)-4-(6-chloro-benzo[b]thiophene-2-sulfonyl)-6-methyl-piperazin-2-one, 1-(4-Amino-quinazolin-7-ylmethyl)-4-(6-chloro-1H-benzoimidazole-2-sulfonyl)-piperazin-2-one, 4-(6-Chloro-benzo[b]thiophene-2-sulfonyl)-1-[1-(2-hydroxy-ethyl)-1H-pyrrolo[3,2-c]pyridin-2-ylmethyl]-piperazin-2-one, 4-(6-Bromo-benzo[b]thiophene-2-sulfonyl)-1-(1H-pyrrolo[3,2-c]pyridin-2-ylmethyl)-piperazin-2-one, 4-(6-Chloro-benzo[b]thiophene-2-sulfonyl)-1-(1-methyl-1H-pyrrolo[3,2-c]pyridin-2-ylmethyl)-piperazin-2-one, 1-(4-Amino-quinazolin-7-ylmethyl)-4-[(5-chloro-thiophen-3-yloxy)-acetyl]-3-(S)-methoxymethyl-6-methyl-piperazin-2-one, 4-(6-Chloro-benzo[b]thiophene-2-sulfonyl)-6-oxo-1-(1H-pyrrolo[3,2-c]pyridin-2-ylmethyl)-piperazine-2-carboxylic acid, 1-(4-Amino-quinazolin-7-ylmethyl)-4-[3-(4-bromo-thiophen-2-yl)-acryloyl]-3-(S)-ethyl-6-methyl-piperazin-2-one, 1-(4-Amino-quinazolin-7-ylmethyl)-4-[3-(5-chloro-thiophen-2-yl)-acryloyl]-3-(S)-ethyl-6-methyl-piperazin-2-one, 1-(4-Amino-quinolin-7-ylmethyl)-4-[3-(5-chloro-thiophen-2-yl)-acryloyl]-3-(S)-methoxymethyl-piperazin-2-one, 1-(4-Amino-quinazolin-7-ylmethyl)-4-[3-(5-chloro-thiophen-2-yl)-acryloyl]-3-(S)-methoxymethyl-6-methyl-piperazin-2-one, 1-(4-Amino-quinazolin-7-ylmethyl)-4-[3-(4-bromo-thiophen-2-yl)-acryloyl]-3-(S)-methoxymethyl-6-methyl-piperazin-2-one, 1(4-Amino-quinazolin-7-ylmethyl)-4-[3-(4-bromo-thiophen-2-yl)-acryloyl]-3-(S)-methoxymethyl-piperazin-2-one, (3S, 5R)-1-(4-Amino-quinolin-7-ylmethyl)-4-[3-(5-chloro-thiophen-2-yl)-allyl]-3,5-dimethyl-piperazin-2-one, 4-[2-(5-Chloro-thiophen-2-yl)-ethenesulfonyl]-6-oxo-1-(1H-pyrrolo[3,2-c]pyridin-2-ylmethyl)-piperazine-2-carboxylic acid methyl ester, 1-(4-Amino-quinazolin-7-ylmethyl)-4-(6-chloro-benzo[b]thiophene-2-sulfonyl)-6-oxo-piperazine-2-(R)-carboxylic acid methyl ester, 1-(4-Amino-quinazolin-7-ylmethyl)-4-(6-chloro-benzo[b]thiophene-2-sulfonyl)-6-oxo-piperazine-2-(S)-carboxylic acid methyl ester, 1-(4-Amino-quinolin-7-ylmethyl)-4-[3-(5-chloro-thiophen-2-yl)-acryloyl]-3-(S)-ethyl-piperazin-2-one, 1-(4-Amino-quinazolin-7-ylmethyl)-4-[(5-chloro-thiophen-2-yloxy)-acetyl]-6-(R)-hydroxymethyl-3-(S)-methoxymethyl-piperazin-2-one, 1-(1-Amino-isoquinolin-6-ylmethyl)-4-(6-chloro-benzo[b]thiophene-2-sulfonyl)-piperazin-2-one, 1-(4-Amino-quinazolin-7-ylmethyl)-4-[(5-chloro-thiophen-3-yloxy)-acetyl]-3-(S)-methoxymethyl-piperazin-2-one, 4-[4-(6-Chloro-benzo[b]thiophene-2-sulfonyl)-2-oxo-piperazin-1-ylmethyl]-benzamidine, 1-(4-Amino-quinazolin-7-ylmethyl)-4-[(5-chloro-thiophen-2-yloxy)-acetyl]-3-(S)-propyl-piperazin-2-one, 4-(6-Chloro-benzo[b]thiophene-2-sulfonyl)-6-oxo-1-(1H-pyrrolo[3,2-c]pyridin-2-ylmethyl)-piperazine-2-carboxylic acid amide 4-[2-(5-Chloro-thiophen-2-yl)-ethenesulfonyl]-6-hydroxymethyl-1-(1H-pyrrolo[3,2-c]pyridin-2-ylmethyl)-piperazin-2-one, (+/−)-1-(4-Amino-quinolin-7-ylmethyl)-4-(6-chloro-benzo[b]thiophene-2-sulfonyl)-6-oxo-piperazine-2-carboxylic acid, 1-(4-Amino-quinolin-7-ylmethyl)-4-[(5-chloro-thiophen-2-yloxy)-acetyl]-3-(S)-methoxymethyl-6-methyl-piperazin-2-one, 4-(4-Amino-quinazolin-7-ylmethyl)-2-(S)-methoxymethyl-3-oxo-piperazine-1-carboxylic acid (5-bromo-thiophen-2-yl)-amide, 4-[4-(6-Chloro-thieno[2,3-b]pyridine-2-sulfonyl)-2-oxo-piperazin-1-ylmethyl]-benzamidine, 4-[2-(5-Chloro-thiophen-2-yl)-ethenesulfonyl]-1-(1H-pyrrolo[3,2-c]pyridin-2-ylmethyl)-piperazin-2-one, 1-(4-Amino-quinazoin-7-ylmethyl)-4-[3-(4-chloro-thiophen-2-yl)-acryloyl]-3-(S)-propyl-piperazin-2-one, 1-(4-Amino-quinolin-7-ylmethyl)-4-[(5-chloro-thiophen-2-yloxy)-acetyl]-3-(S)-ethyl-piperazin-2-one, 4-(4-Amino-quinazolin-7-ylmethyl)-2-(S)-methoxymethyl-3-oxo-piperazine-1-carboxylic acid (5-chloro-thiophen-2-yl)-amide, 1-(4-Amino-quinazolin-7-ylmethyl)-4-(6-chloro-benzo[b]thiophene-2-sulfonyl)-piperazin-2-one, 1-(4-Amino-quinazolin-7-ylmethyl)-4-[3-(4-bromo-thiophen-2-yl)-acryloyl]-3-(S)-propyl-piperazin-2-one, (+/−)-1-(4-Amino-quinazolin-7-ylmethyl)-4-(6-chloro-benzo[b]thiophene-2-sulfonyl)-6-oxo-piperazine-2-carboxylic acid amide, 1-(4-Amino-quinazolin-7-ylmethyl)-4-[(5-chloro-thiophen-2-yloxy)-acetyl]-3-(S)-methoxymethyl-piperazin-2-one, 1-(4-Amino-quinazolin-7-ylmethyl)-4-[3-(5-chloro-thiophen-2-yl)-acryloyl]-3-(S)-propyl-piperazin-2-one, 1-(4-Amino-cinnolin-7-ylmethyl)-4-[2-(5-chloro-thiophen-2-yl)-ethenesulfonyl]-piperazin-2-one, 1-(4-Amino-quinolin-7-ylmethyl)-4-(6-chloro-benzo[b]thiophene-2-sulfonyl)-6-(morpholine-4-carbonyl)-piperazin-2-one, 1-(4-Amino-quinolin-7-ylmethyl)-4-(6-chloro-benzo[b]thiophene-2-sulfonyl)-6-oxo-piperazine-2-carboxylic acid dimethylamide, 1-(4-Amino-quinolin-7-ylmethyl)-4-(6-chloro-benzo[b]thiophene-2-sulfonyl)-6-oxo-piperazine-2-carboxylic acid ethylamide, 1-(4-Amino-quinolin-7-ylmethyl)-4-(6-chloro-benzo[b]thiophene-2-sulfonyl)-6-oxo-piperazine-2-carboxylic acid methylamide, 1-(4-Amino-quinazolin-7-ylmethyl)-4-[(5-chloro-thiophen-2-yloxy)-acetyl]-3-(S)-methoxymethyl-6-methyl-piperazin-2-one, 1-(4-Amino-quinazolin-7-ylmethyl)-4-(6-chloro-benzo[b]thiophene-2-sulfonyl)-6-oxo-piperazine-2-(S)-carboxylic acid ethyl ester, 4-[2-(5-Chloro-thiophen-2-yl)-ethenesulfonyl]-6-(R)-hydroxymethyl-1-(1H-pyrrolo[3,2-c]pyridin-2-ylmethyl)-piperazin-2-one, 1-(4-Amino-quinolin-7-ylmethyl)-4-[2-(5-chloro-thiophen-2-yl)-ethenesulfonyl]-piperazin-2-one, (3S, 5S)-1-(4-Amino-quinolin-7-ylmethyl)-4-[2-(5-chloro-thiophen-2-yl)-ethenesulfonyl]-3,5-dimethyl-piperazin-2-one, 1-(4-Amino-quinazolin-7-ylmethyl)-4-(6-chloro-thieno[2,3-b]pyridine-2-sulfonyl)-piperazin-2-one, 1-(4-Amino-quinolin-7-ylmethyl)-4-(6-chloro-benzo[b]thiophene-2-sulfonyl)-piperazin-2-one, (3S, 5S)-1-(4-Amino-quinazolin-7-ylmethyl)-4-[2-(5-chloro-thiophen-2-yl)-ethenesulfonyl]-3,5-dimethyl-piperazin-2-one, 1-(4-Amino-quinazolin-7-ylmethyl)-4-[2-(5-chloro-thiophen-2-yl)-ethenesulfonyl]-piperazin-2-one, (+/−)-1-(4-Amino-quinazolin-7-ylmethyl)-4-(6-chloro-benzo[b]thiophene-2-sulfonyl)-6-oxo-piperazine-2-carboxylic acid, 1-(4-Amino-quinolin-7-ylmethyl)-4-(5-chloro-1H-indol-2-ylmethyl)-3-(S)-methyl-piperazin-2-one, 4-(5-Chloro-1H-indol-2-ylmethyl)-3-(S)-methyl-1-(4-methylamino-quinolin-7-ylmethyl)-piperazin-2-one, 4-(5-Chloro-1H-indol-2-ylmethyl)-3-(S)-methoxymethyl-1-(4-methylamino-quinolin-7-ylmethyl)-piperazin-2-one, 1-(4-Amino-quinolin-7-ylmethyl)-4-(6-chloro-benzo[b]thiophene-2-sulfonyl)-6-oxo-piperazine-2-carboxylic acid dimethylamide, 1-(4-Amino-quinazolin-7-ylmethyl)-4-(6-chloro-benzo[b]thiophene-2-sulfonyl)-6-oxo-piperazine-2-(S)-carboxylic acid methyl ester,
(+/−)-1-(4-Amino-quinazolin-7-ylmethyl)-4-(6-chloro-benzo[b]thiophene-2-sulfonyl)-6-oxo-piperazine-2-carboxylic acid amide,
1-(4-Amino-quinazolin-7-ylmethyl)-4-(1H-5 3-chloro-1-aza-inden-2-ylmethyl)-6-oxo-piperazine-2-carboxylic acid,
(+/−)-1-(4-Amino-quinazolin-7-ylmethyl)-4-(5-chloro-1H-indol-2-ylmethyl)-6-oxo-piperazine-2-carboxylic acid methylamide,
(+/−)-1-(4-Amino-quinazolin-7-ylmethyl)-4-(5-chloro-1H-indol-2-ylmethyl)-6-oxo-piperazine-2-carboxylic acid ethylamide,
1-(4-Amino-quinazolin-7-ylmethyl)-4-(5-chloro-1H-indol-2-ylmethyl)-6-oxo-piperazine-2-carboxylic acid (2-hydroxy-ethyl)-amide,
(+/−)-1-(4-Amino-quinazolin-7-ylmethyl)-4-[(5-chloro-thiophen-2-yloxy)-acetyl]-6-oxo-piperazin-2-carboxylic acid methyl ester,
(+/−)-1-(4-Amino-quinazolin-7-ylmethyl)-4-[3-(5-chloro-thiophen-2-yl)-allyl]-6-oxo-piperazine-2-carboxylic acid methyl ester,
(+/−)-1-(4-Amino-quinazolin-7-ylmethyl)-4-[3-(5-chloro-thiophen-2-yl)-allyl]-6-oxo-piperazine-2-carboxylic acid,
4-(5'-Chloro-[2,2']bithiophenyl-5-ylmethyl)-6-oxo-1-(1H-pyrrolo[3,2-c]pyridin-2-ylmethyl)-piperazine-2-carboxylic acid methyl ester,
4-[2-(5-Chloro-thiophen-2-yl)-ethenesulfonyl]-5-hydroxymethyl-1-(1H-pyrrolo[3,2-c]pyridin-2-ylmethyl)-piperazin-2-one,
1-[2-(5-Chloro-thiophen-2-yl)-ethenesulfonyl]-5-oxo-4-(1H-pyrrolo[3,2-c]pyridin-2-ylmethyl)-piperazine-2-carboxylic acid methyl ester, or a pharmaceutically acceptable salt thereof, pharmaceutically acceptable prodrug thereof, an N-oxide thereof, a hydrate thereof or a solvate thereof.

Still yet more preferred compounds are selected from
1-(4-Amino-quinazolin-7-ylmethyl)-4-[(5-chloro-thiophen-2-yloxy)-acetyl]-3-(S)-methoxymethyl-piperazin-2-one,
1-(4-Amino-quinazolin-7-ylmethyl)-4-[(5-chloro-thiophen-2-yloxy)-acetyl]-3-(S)-methoxymethyl-6-methyl-piperazin-2-one,
4-(6-Chloro-benzo[b]thiophene-2-sulfonyl)-1-(1H-pyrrolo[3,2-c]pyridin-2-ylmethyl)-piperazin-2-one,
4-[2-(5-Chloro-thiophen-2-yl)-ethenesulfonyl]-1-(1H-pyrrolo[3,2-c]pyridin-2-ylmethyl)-piperazin-2-one,
1-(4-Amino-quinazolin-7-ylmethyl)-4-[3-(5-chloro-thiophen-2-yl)-acryloyl]-3-(S)-methoxymethyl-piperazin-2-one,
1-(4-Amino-quinazolin-7-ylmethyl)-4-[3-(5-chloro-thiophen-2-yl)-allyl]-piperazin-2-one,
4-[2-(5-Chloro-thiophen-2-yl)-ethenesulfonyl]-6-(R)-hydroxymethyl-1-(1H-pyrrolo[3,2-c]pyridin-2-ylmethyl)-piperazin-2-one and
4-[3-(6-Amino-pyridin-3-yl)-acryloyl]-1-(4-amino-quinazolin-7-ylmethyl)-3-(S)-propyl-piperazin-2-one, or a pharmaceutically acceptable salt thereof, pharmaceutically acceptable prodrug thereof, an N-oxide thereof, a hydrate thereof or a solvate thereof.

Preferred intermediates according to this invention have formula III wherein $Cy_2$ contains at least one nitrogen atom and when $Cy_2$ is optionally substituted aryl, optionally substituted cycloalkyl, optionally substituted cycloalkenyl, optionally substituted fused phenylcycloalkyl or optionally substituted fused phenylcycloalkenyl, then said nitrogen atom is a basic nitrogen atom.

Other preferred intermediates according to this invention have formula III wherein Z is absent.

Other preferred intermediates according to this invention have formula III wherein $R_1$, $R_{1a}$, $R_2$, $R_{2a}$, $R_4$ and $R_{4a}$ are hydrogen.

More preferred intermediates according to this invention are selected from
(2S, 6RS)-4-(4-chloro-quinolin-7-ylmethyl)-2,6-dimethyl-3-oxo-piperazine-1-carboxylic acid benzyl ester,
(3S,5RS)-1-(4-chloro-quinolin-7-ylmethyl)-3,5-dimethyl-piperazin-2-one,
(3S, 5R)-1-(4-chloro-quinolin-7-ylmethyl)-3,5-dimethyl-piperazin-2-one,
(3S, 5S)-1-(4-chloro-quinolin-7-ylmethyl)-3,5-dimethyl-piperazin-2-one,
(3S, 5R)-1-(4-chloro-quinolin-7-ylmethyl)-3,5-dimethyl-piperazin-2-one,
(2S, 6R)-4-(4-chloro-quinolin-7-ylmethyl)-2,6-dimethyl-3-oxo-piperazine-1-carboxylic acid benzyl ester,
(3S, 5S)-1-(4-chloro-quinolin-7-ylmethyl)-4-[3-(5-chloro-thiophen-2-yl)-allyl]-3,5-dimethyl-piperazine-2-one,
(3S, 5R)-1-(4-chloro-quinolin-7-ylmethyl)-4-[3-(5-chloro-thiophen-2-yl)-allyl]-3,5-dimethyl-piperazine-2-one,
4-(2-Oxopiperazin-1-ylmethyl)benzamidine,
1-(2-Aminoquinolin-6-ylmethyl)piperazin-2-one,
1-(1-Aminoisoquinolin-6-ylmethyl)piperazin-2-one,
2-(2-Oxopiperazin-1-ylmethyl)pyrrolo[3,2-c]pyridin-1-carboxylic acid tert-butyl ester,
2-(5-(±)-Methoxycarbonyl-2-oxo-piperazin-1-ylmethyl)-pyrrolo[3,2-c]pyridine-1-carboxylic acid tert-butyl ester,
2-(2-(±)-Methoxycarbonyl-6-oxo-piperazin-1-ylmethyl)-pyrrolo[3,2-c]pyridine-1-carboxylic acid tert-butyl ester,
1-(4-Aminoquinazoline-7-ylmethyl)piperazine-2-one,
1-(4-Amino-thieno[2,3-d]pyrimidin-6-ylmethyl)-piperazin-2-one,
4-[3-(2-Oxo-piperazin-1-yl)-propyl]-piperidine-1-carboxylic acid tert-butyl ester,
1-(4-Amino-quinazoline-7-ylmethyl)-3-methoxymethyl-piperazine-2-one,
1-(4-Aminoquinazoline-7-ylmethyl)-3-butyl-piperazine-2-one,
1-(4-Aminoquinazoline-7-ylmethyl)-3-ethyl-piperazine-2-one,
1-(4-Aminoquinazoline-7-ylmethyl)-3-propyl-piperazine-2-one,
1-(4-Amino-quinazoline-7-ylmethyl)-3-ethoxymethyl-piperazine-2-one,
1-(4-Amino-quinazoline-7-ylmethyl)-3-methyl-piperazine-2-one,
1-(4-Amino-quinazoline-7-ylmethyl)-3-benzyl-piperazine-2-one,
1-(4-Amino-quinazoline-7-ylmethyl)-3-(1-methoxyethyl)-piperazine-2-one,
1-(4-Amino-quinazoline-7-ylmethyl)-3,3-dimethyl-piperazine-2-one,
1-(4-Amino-quinazoline-7-ylmethyl)-3-isopropyl-piperazine-2-one,
1-(4-Amino-quinazoline-7-ylmethyl)-3-isobutyl-piperazine-2-one,
1-(4-Amino-quinazoline-7-ylmethyl)-3-(2-methoxyethyl)1piperazine-2-one,
1-(4-Amino-quinazoline-7-ylmethyl)-3-methoxymethyl-6-methyl-piperazine-2-one,
(3S,5RS)-1-(4-amino-quinazolin-7-ylmethyl)-3,5-dimethyl-piperazin-2-one, 1-(4-Chloroquinolin-7-ylmethyl)-piperazin-2-one,
1-(4-Chloroquinolin-7-ylmethyl)-piperazin-2-one,
1-(4-Chloroquinolin-7-ylmethyl)-3-(S)-methylpiperazin-2-one,
1-[2-(Pyridin-4-ylamino)-ethyl]-piperazin-2-one,
1-[2-{(Methyl)-(pyridin-4-yl)-amino}-ethyl]-piperazin-2-one trifluroacetate,
1-[2-(3-Methylpyridin-4-yl-amino)-ethyl]-piperazin-2-one,
1-[2-(Pyridazin-4-ylamino)-ethyl]-piperazin-2-one,
4-[3-(4-tert-Butoxycarbonylamino-pyridin-3-yl)-propenyl]-3-oxo-piperazine-1-carboxylic acid tert-butyl ester,
4-[3-(4-tert-butoxycarbonylamino-pyridin-3-yl)-allyl]-3-oxo-piperazine-1-carboxylic acid tert-butyl ester
4-[3-(4-tert-Butoxycarbonylamino-pyridin-3-yl)-propyl]-3-oxo-piperazine-1-carboxylic acid tert-butyl ester.
4-(Benzyloxycarbonyl)-1-(2-pyrrolo[3,2-c]pyridin-1-yl-ethyl)-piperazin-2-one,
(±)-1-(3-Amino-4-cyano-benzyl)-4-(6-chloro-benzo[b]thiophene-2-sulfonyl)-6-oxo-piperazine-2-carboxylic acid methyl ester and
(±)-1-(3-Amino-4-cyano-benzyl)-4-(6-chloro-benzo[b]thiophene-2-sulfonyl)-6-oxo-piperazine-2-carboxylic acid.

Preparation of the Compounds of the Invention

A general route to the compounds of this invention wherein A is N and $R_1$, $R_{1a}$, $R_2$, $R_{2a}$, $R_3$, $R_{3a}$, $R_4$, $R_{4a}$, $L_1$, $L_2$, $Cy_1$, $Cy_2$, m and n are defined for Formula I above is outlined in Scheme 1.

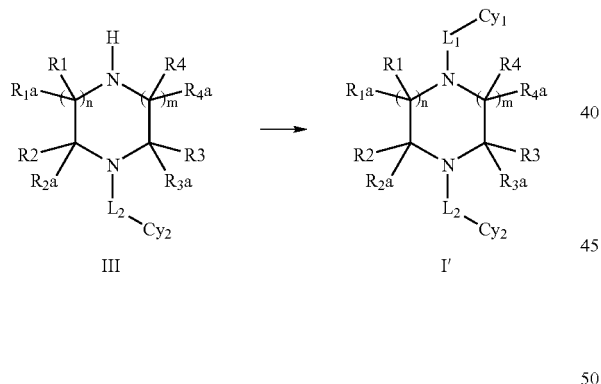

Scheme 1

As outlined in Scheme 1, coupling of a compound of formula III with a sulfonyl chloride, an alkyl halide, an acid or an activated derivative thereof, such as an acid anhydride or acid chloride, an isocyanate, chloroformate or activated sulfamoyl ester in an appropriate solvent, generates the compound of formula I in which the $L_1$-$Cy_1$ portion is a sulfonamide, alkyl amine, amide, urea, carbamate or sulfamyl urea, respectively. Sulfonamide formation is accomplished with a base such as a trialkylamine in an inert solvent such as dichloromethane, THF or acetonitrile at about 0° C. to about 100° C. in the presence or absence of an activating agent such as dimethylaminopyridine (DMAP). Alkyl amine formation can be achieved with a suitable base such as $K_2CO_3$ or trialkylamine in an appropriate solvent such as DMF or acetonitrile at about 0° C. to about 100° C. Amide, urea, carbamate and sulfamyl urea formation can be conducted with acids and coupling reagents such as EDC or TBTU or with any variant of reactive acid derivatives and the use of an appropriate base additive such as triethylamine, N-methylmorpholine or diisopropylethylamine.

The preparation of a compound of formula III wherein $R_1$, $R_{1a}$, $R_2$, $R_{2a}$, $R_3$, $R_{3a}$, $R_4$, $R_{4a}$, $L_2$, $Cy_2$, m and n are as defined herein from formula 1, is outlined in Scheme 2.

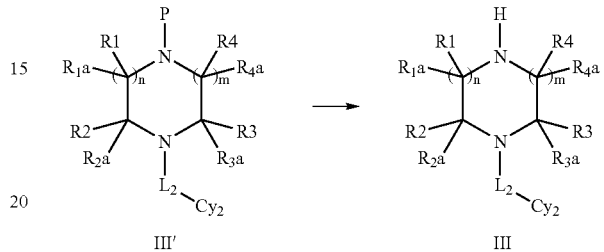

Scheme 2

As outlined in Scheme 2, a compound of formula III is prepared by removing a nitrogen protecting group P from the compound of formula III'. In a preferred aspect, P is an alkyl, aralkyl or aryl carbamate moiety, which is removed using strong acid, strong base or catalytic hydrogenation in an appropriate solvent such as methanol or ethanol.

The preparation of a compound of formula III' wherein $R_1$, $R_{1a}$, $R_2$, $R_{2a}$, $R_3$, $R_{3a}$, $R_4$, $R_{4a}$, $L_1$, $L_2$, $Cy_1$, $Cy_2$, m and n and P are defined herein is outlined in Scheme 3.

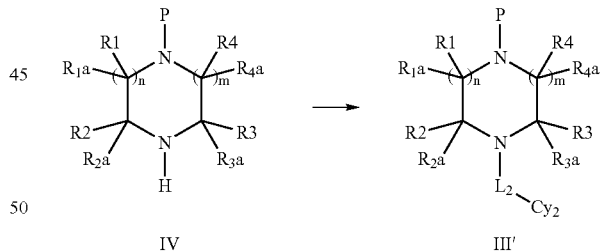

Scheme 3

As indicated in Scheme 3, the compound of formula III' is obtained by coupling a compound of formula IV with an appropriate $Cy_2$-$L_2$-LG compound wherein LG is a leaving group, such as chloro, bromo, iodo, or optionally substituted lower alkylsulfonyloxy or arylsulfonyloxy, in an inert organic solvent, such as THF, $Et_2O$ or DMF, in the presence of a strong base such as NaH, lithium hexamethyldisilylazide or lithium diisopropylamine. In a preferred aspect, P is an alkyl, aralkyl or aryl carbamate group.

The preparation of intermediate compounds of formula 7 and 10 is outlined in Scheme 4.

Scheme 4

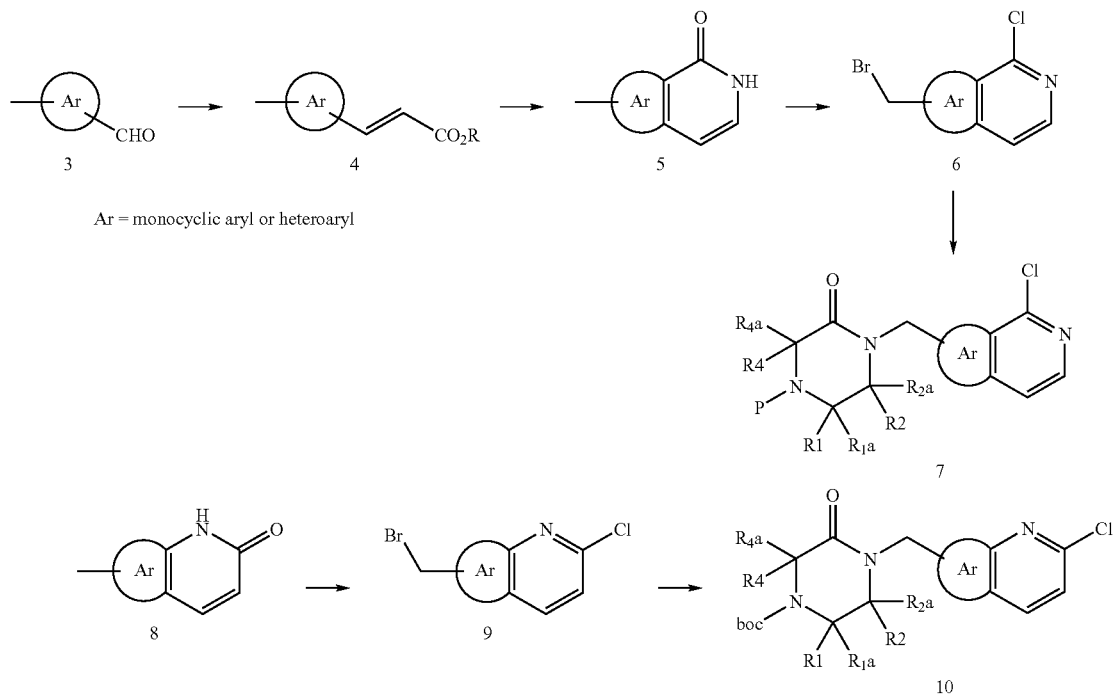

As indicated in Scheme 4, reacting a compound of formula 3 with an appropriate malonic acid in a polar, such as pyridine or ethanol, and a base, such as piperidine or pyridine, at reflux provides a compound of formula 4 wherein R is H. Alternatively, a compound of formula 3 may be reacted with a suitable Wittig or Horner-Emmons reagent in an inert solvent such as THF to give a compound of formula 4 wherein R is lower alkyl. When R is lower alkyl, the ester is hydrolyzed to the corresponding carboxylic acid (R is H) using an appropriate strong acid or alkali base. The corresponding acid is converted to the acid chloride using standard reagents such as thionyl chloride, or is converted to the mixed anhydride in a polar solvent, such as acetone or THF, to form an activated acyl compound. The activated acyl compound is then treated with a solution of NaN$_3$ in water at about –10° C. to about 25° C. to yield the corresponding acyl azide. The acyl azide compound is then heated slowly in an inert solvent such as benzene or toluene at about 60° C. to about 110° C. and then concentrated in vacuo and heated in a higher boiling inert solvent, such as 1,2-dichlorobenzene or phenyl ether, at about 180° C. to about 240° C. with a catalyst such as iodine or tributylamine to obtain a compound of formula 5. Alternatively the acyl azide compound can be added directly to a high boiling inert solvent, such as phenyl ether, at about 180° C. to about 240° C. with a catalyst such as iodine or tributylamine to obtain the compound of formula 5.

A compound of formula 8, prepared as described in Syn., 739 (1975), the contents of which are hereby incorporated herein by reference, or a compound of formula 5 above, may be chlorinated using standard reagents such as POCl$_3$ or POCl$_3$/PCl$_5$ and halogenated using standard conditions, such as N-halosuccinimide and benzoyl peroxide in an inert solvent such as carbon tetrachloride, to give the corresponding chloro-halomethyl compounds 6 and 9, respectively. Compounds of formula 6 or 9 are coupled to compounds of formula IV, in which R3 and R3a taken together form oxo, under basic condition employing NaH, or KOtBu or some other deprotonating base, to give compounds of formula 7 or 10.

The preparation of aminoquinazoline, quinazolinone or amino-thienopyrimidine intermediates is outlined in Scheme 5.

Scheme 5

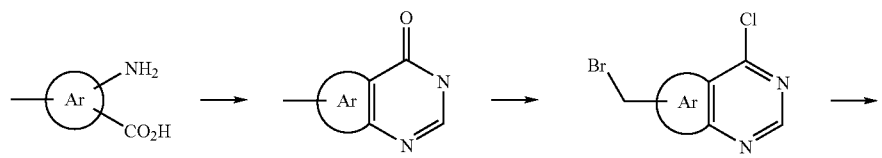

Ar = monocyclic aryl or heteroaryl

-continued

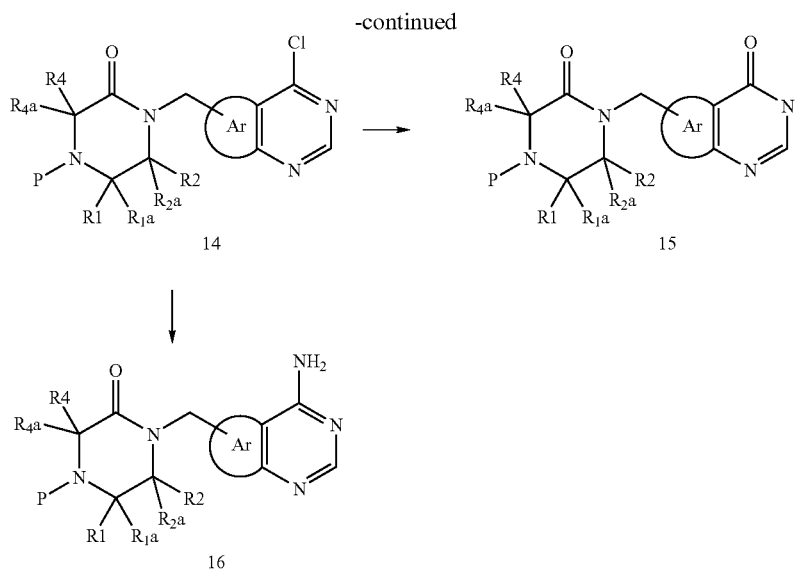

As shown in Scheme 5, an aminoheteroaryl carboxylic acid or an aminoarylcarboxylic acid of formula 11, in which the amino and carboxylic acid are ortho to each other, is treated with formamidine under heat to form the corresponding quinazolinone or thienopyrimidinone 12. The quinazolinone or thienopyrimidinone 12 is then converted to the chloroquinazoline or chlorothienopyrimidine using a chlorinating reagent such as P(O)Cl$_3$ and heat. The chloroquinazoline or chlorothienopyrimidine is brominated at the benzylic carbon using radical bromination conditions. Alternatively, a chloroquinazoline or chlorothienopyrimidine, containing a hydroxy-methylene group is converted to the corresponding bromide using CBr$_4$/PPh$_3$; or PBr$_3$. The bromide 13 is then reacted with the anion of the ring nitrogen of a compound of formula III, formed using NaH, LiN(SiMe$_3$)$_3$, NaN(SiMe$_3$)$_3$, LDA, lithium alkoxide, sodium alkoxide or an appropriate base, in an inert solvent such as THF, DMF, ether, or DME. This yields compounds of formula 14 which contain a chloroquinazoline or a chloro-thienopyrimidine group. The chloro group is converted to an amino group using NH$_3$ in ethanol in the presence of a catalytic amount of acid, such as HOAc to give compounds of formula 16. Alternatively, the chloro group is converted to a substituted amino group using a primary or secondary amine in an inert solvent. Alternatively, the chloro group is converted to a hydroxy group using acetic acid in water with heating or using a hydroxide source to give compounds of formula 15. Alternatively, the chloro is converted to an alkoxy group using an alcoholic solvent with heated in the presence of a base.

An alternative synthesis of quinazolines and thienoquinazolines is outlined in Scheme 6.

Scheme 6.

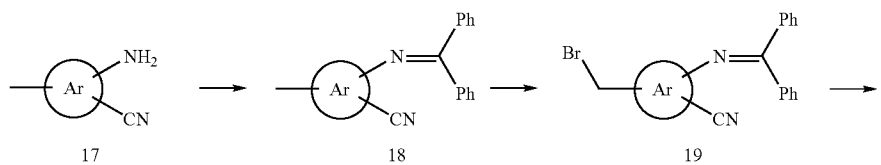

Ar = monocyclic aryl or heteroaryl

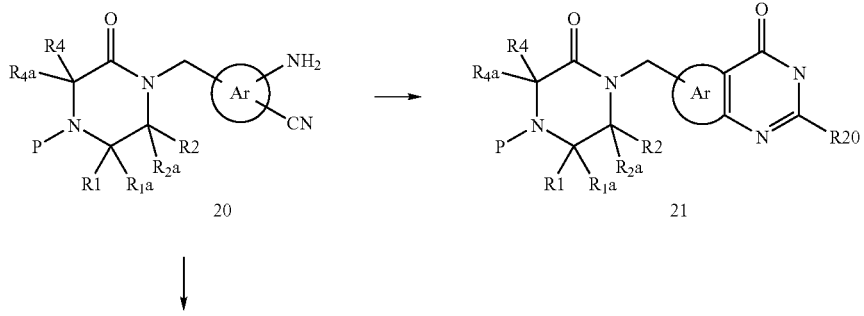

-continued

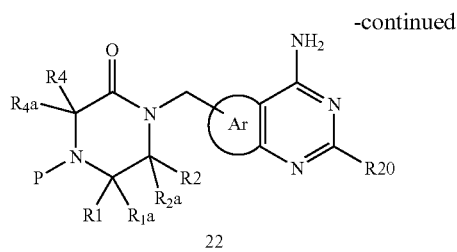

22

As shown in Scheme 6, an amino-aryl nitrile or an amino heteroaryl nitrile 17 is treated with an aldehyde or ketone under imine forming conditions. The corresponding aryl or heteroaryl imine is brominated using radical bromination with NBS. The bromide is then coupled with compounds of formula IV under basic conditions, such as NaH, LiN(SiMe$_3$)$_3$, NaN(SiMe$_3$)$_3$, LDA, lithium alkoxides, sodium alkoxides or an appropriate base, in an inert solvent, such as THF, DMF, ether, or DME. This yields compounds of formula 20 in which

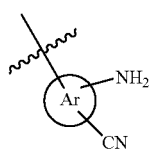

is an imino-aryl nitrile or an imino heteroaryl nitrile. The imine is deprotected using an acid such as HCl to give the corresponding aniline. The aniline-aryl-nitrile or the aniline-heteroaryl nitrile 20, is converted to the amino-quinazoline or thienopyrimidine, formula 22 (in which $R_{20}$=H), using triazine or formamidine. The quinazolinone or thienopyrimidinone, formula 21, in which $R_{20}$=H, is formed from a compound of formula 20 using formamide. Alternatively, compounds of formula 20 can be reacted under acid conditions, such as HCl (gas) in a solvent such as ethanol in the presence of a nitrile, to give compounds of formula 22 in which $R_{20}$ is alkyl, aryl or amino depending on the group attached to the nitrile.

The preparation of cinnoline (X=N) and quinoline (X=CH) intermediates is outlined in Scheme 7.

Scheme 7

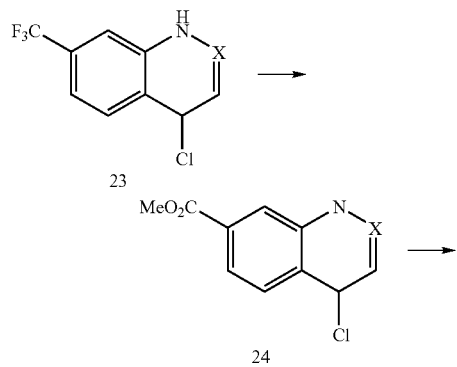

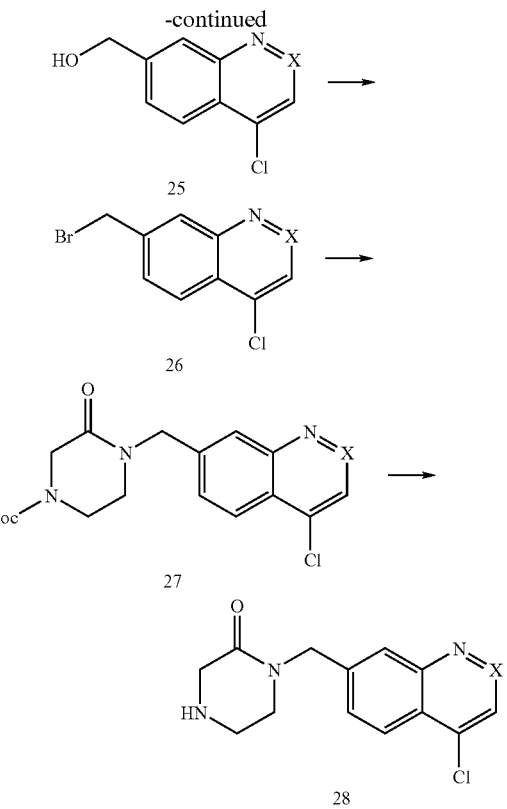

As shown in Scheme 7, halogenated azaarenes 23, exemplified by 4-chloro-7-trifluoromethylquinoline or cinnoline, are treated with H$_2$SO$_4$ (70-95%) at 180-220° C. for about 16 to 48 hours in a sealed reaction vessel. The solution is cooled, poured into water and neutralized with base to pH ~3-4. The product is dissolved in aqueous base and precipitated by acidification to yield 7-carboxy-4-chloroquinoline or cinnoline. This material is converted to the alkyl ester, such as methyl (24) or ethyl, by standard methods. 7-Alkyloxycarbonyl-4-chloroquinoline or cinnoline is dissolved in an anhydrous, aprotic solvent (THF or ether). The solution is cooled (–60 to –95° C.) and treated with a reducing agent such as lithium aluminum hydride. The solution is warmed (to approximately –40 to –50° C.) for about 15 to 30 minutes and quenched with a solvent such as ethyl acetate. Standard workup gives the product 7-hydroxymethyl-4-chloroquinoline, or cinnoline (25). Material 25 is treated with 45-50% HBr and heated to about 100-140° C. for about 45 to 90 minutes. After cooling and standard workup, 7-bromomethyl-4-chloroquinoline (or cinnoline) 26 is obtained. Alkylation as described before provides 4-chloroquinoline (or cinnoline) 27 followed by deprotection under the usual acidic conditions gives 4-chloroquinoline (or cinnoline) 28.

The preparation of pyrrolopyridine derivatives is outlined in Scheme 8.

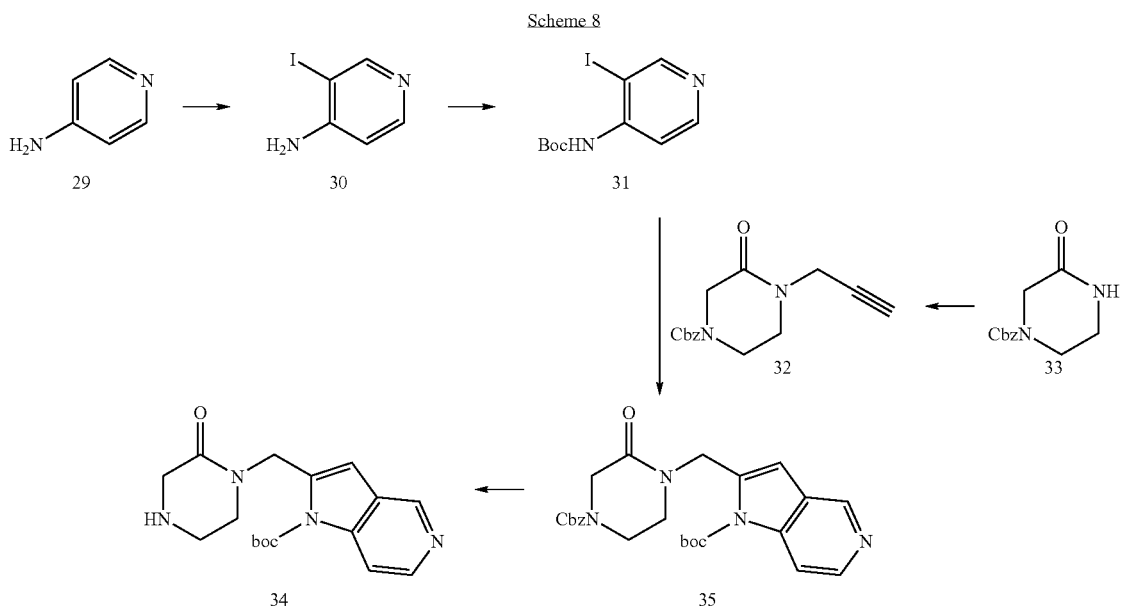

As indicated in Scheme 8, pyrrolopyridine derivatives are prepared by alkylation of a suitably protected oxopiperazine 33 with propargyl bromide in the presence of a base such as sodium hydride. The resulting alkyne 32 is heated (100-120° C.) with a halopyridine 31, optionally substituted with hydroxy, alkoxycarbonylamino, or sulfhydryl, a catalyst, such as $Pd(PPh_3)_2Cl_2$, copper iodide and triethylamine, in a suitable solvent, such as acetonitrile, in a sealed vessel or in DMF for 2-20 hours. When the pyridine is substituted with an alkoxycarbonylamino moiety, additional treatment with DBU at about 60° C. in DMF yields pyrrolopyridine 35. Subsequent carbamate deprotection using transfer hydrogenation conditions such as Pd black in formic acid yields the desired oxopiperazine pyrroloopyridines 34. After further reaction of 34 with the $L_1$-$Cy_1$ group, an additional deprotection step such as Boc removal using, for example, TFA, HCl is required for generating the oxopiperazine pyrrolopyridines with $L_1$-$Cy_1$ in place. Halopyridine 31 is prepared from iodination of 4-aminopyridine 29 to give iodo-aminopyridine 30 followed by Boc protection.

The preparation of compounds of formula 40 is outlined in Scheme 9.

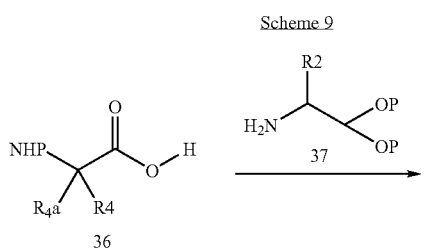

As shown in Scheme 9, compounds of formula 40 are prepared from an appropriately protected mono- or di-substituted amino-acid 36. To this is added an amino-acetaldehyde, protected as an acetal derivative 37, under standard peptide coupling procedures, employing activating reagents such as EDC, TBTU, or BOP. The resulting dipeptidyl moiety 38 is subjected to conditions which remove the acetal, such as acidic conditions (TsOH). The resulting cyclic material 39 is reduced using hydrogenating conditions to yield a compound of formula 40. This reduction, alternatively, can be carried out using a reagent which acts as a hydride source, such as LAH or NaH.

The preparation of compounds of formula 46a and 46b is outlined in scheme 10.

Scheme 10.

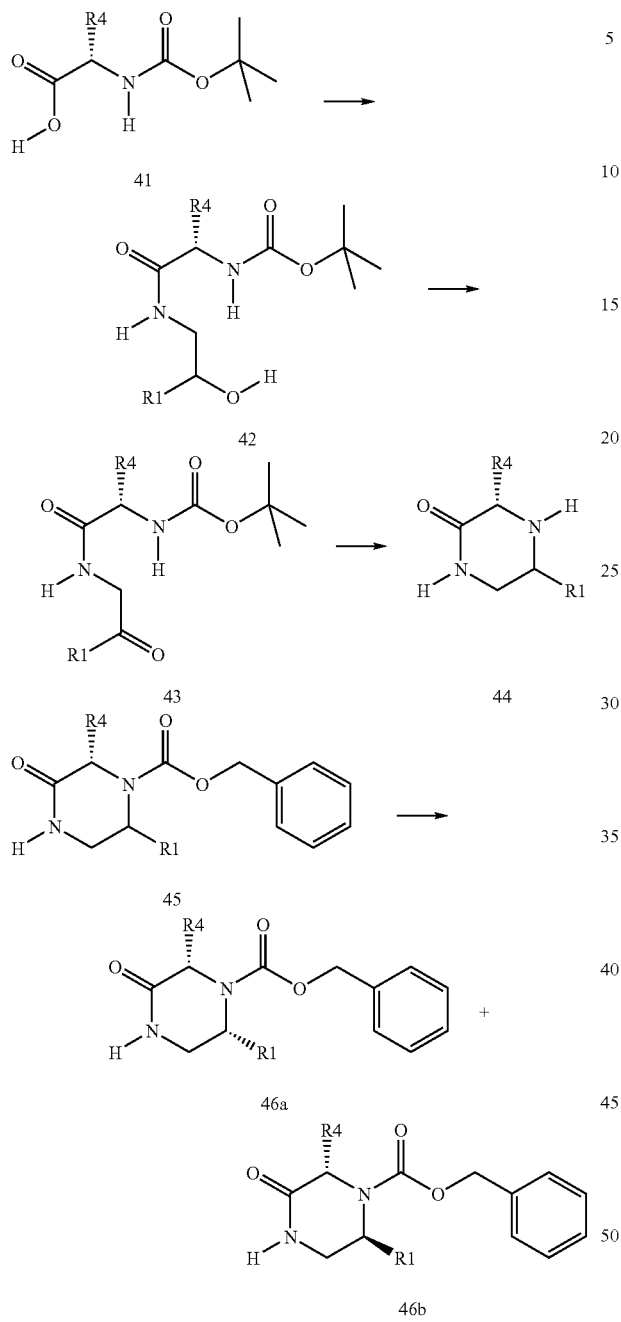

A chiral synthesis of compounds of formula 46a is outlined in Scheme 11.

Scheme 11

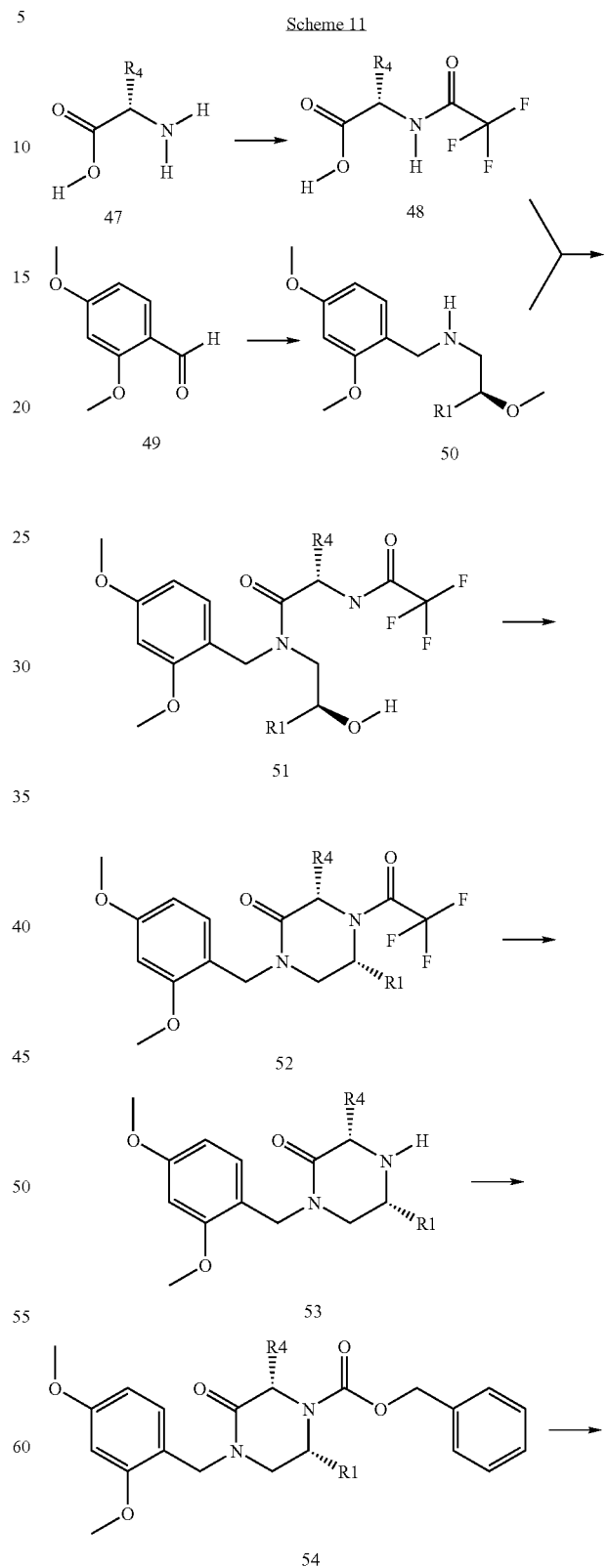

As indicated in Scheme 10, a protected amino acid 41 is coupled to a beta-aminoalcohol using standard peptide coupling procedures (iso-propyl chloroformate and triethylamine). The alcohol 42 is then oxidized to a ketone 43 using, for example, Swern oxidation conditions. The protecting group is removed with trifluoroacetic acid and the resulting cyclized compound is reduced under hydrogenation conditions to give the 2-piperidinone 44. The piperazin-2-one ketopiperazine is reacted with N-(benzyloxycarbonyloxyl) succinimide to give a mixture of diastereomers 45 which are separated by chromatographic methods, or in some cases by recrystallization, to give compounds 46a and 46b.

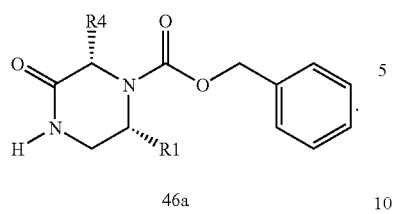

46a

As shown in Scheme 11, amino acid 47 is protected as its trifluoroacetate derivative using trifluoroacetic anhydride and a base to yield compound 48. Amino-alcohol 50 is obtained via reductive amination conditions using a benzaldehyde derivative, such as 2,4-dimethoxybenzaldehyde 49 and the corresponding primary amine. The resulting amino-alcohol 50 is then coupled to amino-acid 48 using standard peptide coupling procedures (iso-propyl chloroformate and triethylamine) to afford compound 51. Ring closure of compound 51 is then accomplished by utilizing Mitsinobu conditions to yield 2-piperidinone 52. The trifluoroacetate group of compound 52 is removed under basic conditions to give amine 53, which reacts with N-(benzyloxycarbonyloxy)succinimide to give carbamate 54. Deprotection of compound 54 is achieved with an aqueous solution of potassium persulfate and sodium phosphate and heat to produce compound 46a. All possible enantiomers of piperazin-2-one, shown in scheme 2c, can be made from the corresponding amino-alcohol 50 and amino acid 47.

The preparation of the compound of formula 58 wherein $R_1$, $R_2$, $R_{2a}$, $R_4$ and $R_{4a}$ are hydrogen and $R_{1a}$ is carbomethoxy, methoxymethyl, or a protected hydroxymethyl group is shown in Scheme 12.

Scheme 12

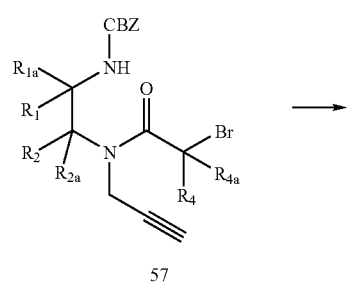

As shown in Scheme 12, alkynylating a compound of formula 55 with propargyl bromide in the presence of an amine base such as triethylamine provides the compound of formula 56. Coupling with bromoacetic acid using a standard reagent such as DCC gives the compound of formula 57, which can be cyclized using a non-nucleophilic strong base, such as NaH, in a solvent, such as THF, to yield the desired compound of formula 58.

The preparation of a compound of formula 59 is outlined in Scheme 13.

Scheme 13

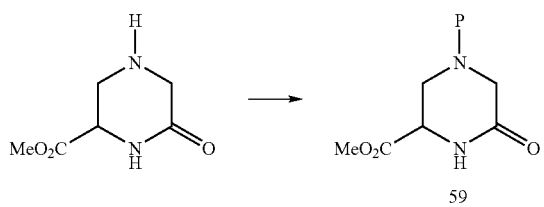

59

As indicated in Scheme 13, protection of methyl 6-oxopiperazine-2-carboxylate (Aebischer, B., Helv. Chim. Acta 1989, 72, 1043-1051) using, for example, benzyl chloroformate or allyl chloroformate under standard conditions provides compound 59. Alkynylation of 59 with propargyl bromide using a strong base such as NaH in polar solvents as THF or DMF provides the compound of formula 58 (Scheme 12).

The preparation of a compound of formula 61 wherein $R_1$, $R_2$, $R_4$, $R_{4a}$, $L_1$ and $Cy_1$ are as defined in formula I above, and $R_{1a}$ and $R_{2a}$ are independently carboxy, acetamido or hydroxymethyl, is outlined in Scheme 14.

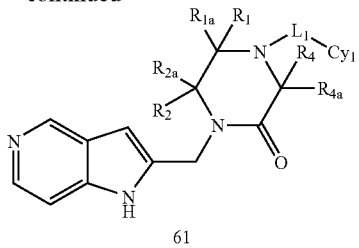

61

As shown in Scheme 14, the compound of formula 61 is prepared by hydrolysis of the corresponding ester 60 using a base such as NaOH or LiOH to yield the acid 61. Coupling the acid with a primary or secondary amine or ammonia using standard coupling reagents such as TBTU or EDC gives the amide 61. Alternatively, reduction of the ester 60 using a reducing agent such as $NaBH_4$ yields a hydroxymethyl resin of 61.

The preparation of diketopiperazine compounds of formula 66 is outlined in Scheme 15.

Scheme 15

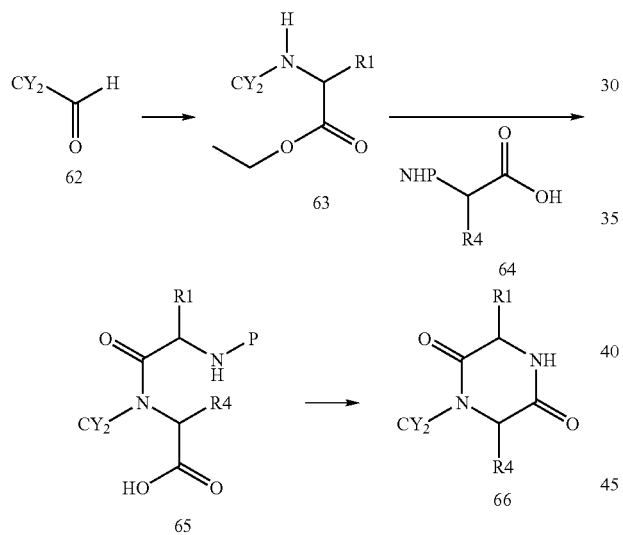

As shown in Scheme 15, an aldehyde 62 containing the $Cy_2$ group is condensed with an amino acid ester under reductive amination conditions. The resulting secondary amine 63 is then coupled to an N-protected amino acid 64. The resulting dipeptide 65 is deprotected which, in general, results in cyclization to the N—$Cy_2$ diketopiperazine 66. Alternatively, for dipeptides 65 which do not cyclize, diketopiperazine 66 formation can be achieved using a peptide coupling reagent such as EDC, TBTU, or BOP.

The preparation of sulfonyl chloride intermediates 69 and 72 is outlined in Scheme 16.

Scheme 16

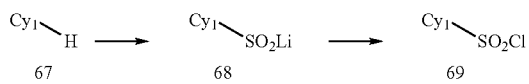

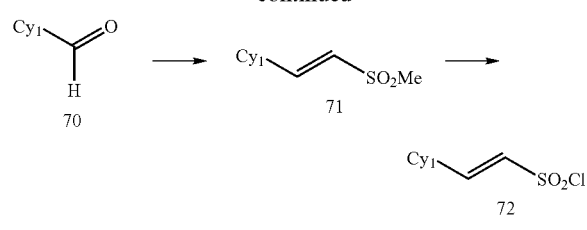

As shown in Scheme 16, $Cy_1$ substituted sulfonyl chlorides 69 and 72 are prepared by treatment of the appropriate aryl or heteroaryl compounds 67 with a strong base such as n-BuLi at −78° C. followed by the addition of $SO_2$ gas and treatment of the resulting lithium aryl or heteroaryl sulfonate 68 with a chlorinating agent such as NCS or $SO_2Cl_2$ to yield compound 69 or, alternatively, by homologation of the appropriate aryl or heteroaryl aldehydes 70 using, for example, ethylmethanesulfonate to yield compound 71 and ethylchlorophosphonate to yield compound 72.

The preparation of intermediate compounds 75 and 78 of formula $Cy_1$—$CO_2H$ is outlined in Scheme 17.

Scheme 17

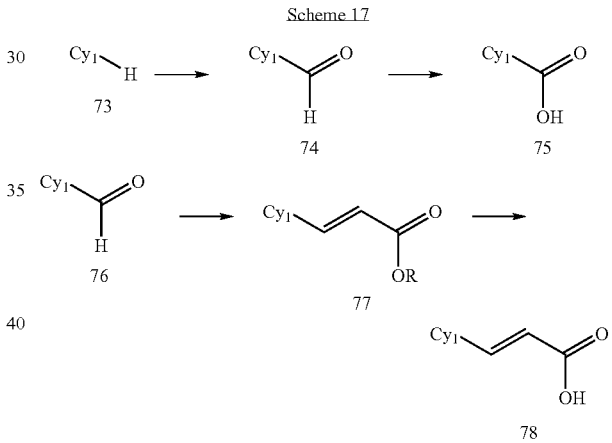

As shown in Scheme 17, the requisite $Cy_1$ acids 75 and 78 can be obtained by oxidation of the corresponding alcohols or the aldehydes 74 using, for example, $MnO_2$, PDC or $AgNO_3$ in an appropriate solvent, such as $CH_2Cl_2$ or $H_2O/EtOH$. The $Cy_1$ substituted aryl and heteroaryl groups 73 can be functionalized by deprotonation methods using an appropriate non-nucleophilic base such as n-BuLi in an appropriate solvent such as $Et_2O$ or THF and quenching with an appropriate carbonyl electrophile such as DMF, $CO_2$ or alkyl chloroformate. Alternatively, the acids can also be generated by hydrolysis of the corresponding esters 77 using, for example, NaOH or LiOH. For example, in the acrylic esters, the $Cy_1$-(alkenylene)- groups as defined above are generated by homologation of the $Cy_1$ aldehydes 76 using the usual Wittig type or Horner-Emmons type reagents in an appropriate solvent such as $CH_2Cl_2$ or THF.

The preparation of $Cy_1$ alkyl (81) and alkenyl (84) halides is outlined in Scheme 18.

Scheme 18

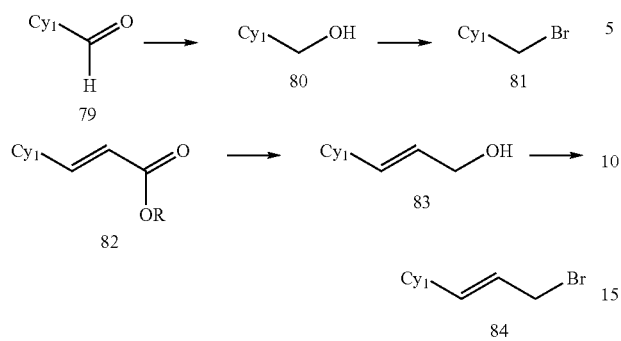

As shown in Scheme 18, $Cy_1$ alkyl and alkenyl halides 81 and 84 can be prepared by halogenation of the corresponding alcohols 80 and 83 using either $NBS, CBr_4$ or $PBr_3$ under standard solvent conditions. The alcohols are generated by reduction of the corresponding aldehydes 79 or esters 82 using $NaBH_4$ or DIBAL in an appropriate solvent.

The preparation of $Cy_1$ isocyanate intermediates 86, 88 and 91 is outlined in Scheme 19.

Scheme 19

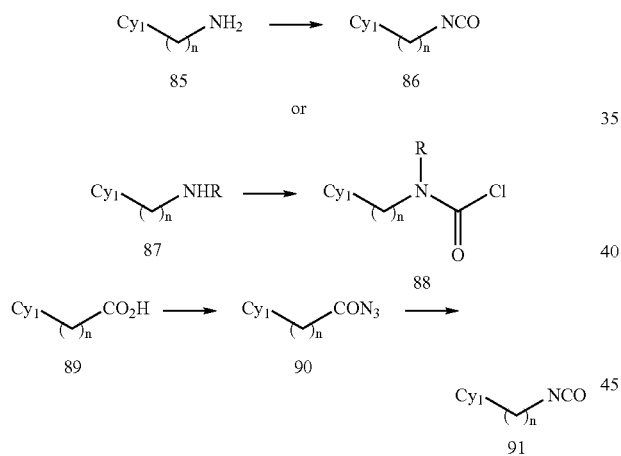

As shown in Scheme 19, $Cy_1$ isocyanates 86 and 88 are obtained by chlorocarbonylation methods using phosgene or triphosgene in an appropriate solvent such as $CH_2Cl_2$ with an appropriate base additive such as triethylamine or pyridine on the corresponding primary or secondary amines 85 and 87. Alternatively, the isocyanates 91 can also be generated by Curtius rearrangement in an appropriate solvent such as toluene, p-dioxane or DMF of the corresponding $Cy_1$ carbonyl azides 90. The carbonyl azides 90, in turn, are derived from the corresponding carboxylic acids 89 using either DPPA reagent or by proceeding through the mixed anhydride via an alkyl chloroformate reagent in an appropriate solvent such as DMF or acetone and using an appropriate base additive such as treithylamine.

The preparation of $Cy_1$ chloroformate intermediates 93 and sulfamoyl esters 95 is outlined in Scheme 20.

Scheme 20

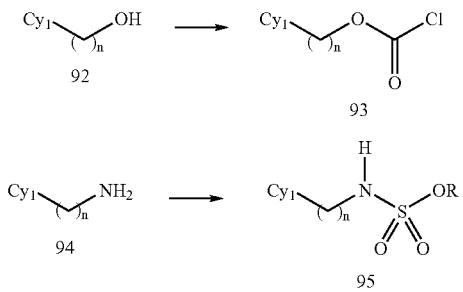

As indicated in Scheme 20, $Cy_1$ chloroformates 93 are obtained by chlorocarbonylation of the corresponding alcohols 92 using reagents such as phosgene, triphosgene or 1,1'-carbonyldiimidazole in an appropriate solvent such as $CH_2Cl_2$. Activated sulfamyl esters 95 are prepared from the corresponding amines 94 using catechol sulfate in an appropriate solvent.

The preparation of acetamido compounds 101 of this invention is outlined in Scheme 21.

Scheme 21

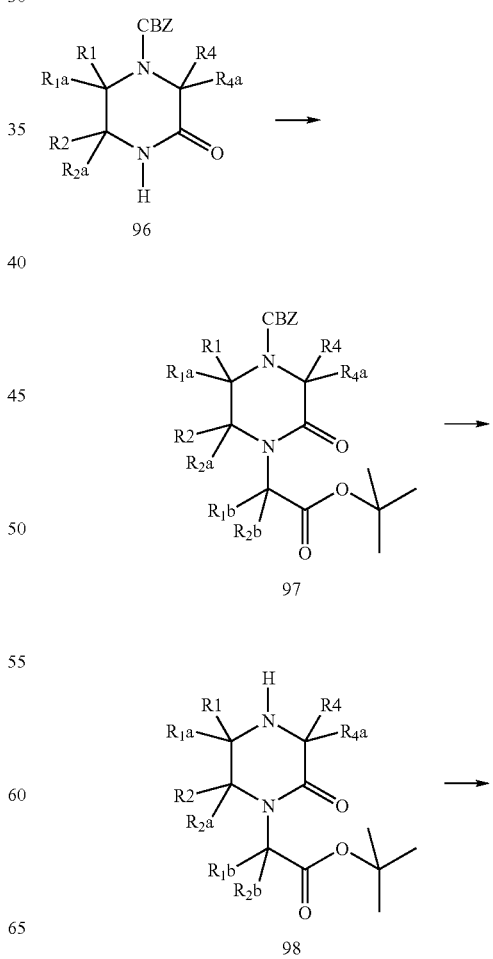

-continued

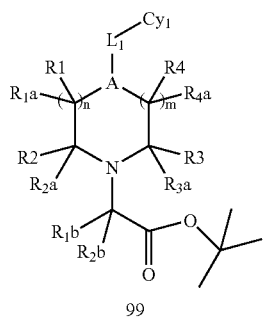
99

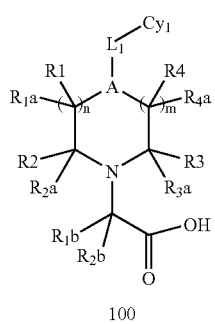
100

-continued

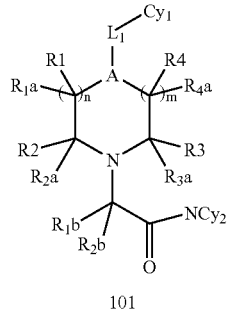
101

As indicated in Scheme 21, alkylation of piperazin-2-one 96 is achieved with a strong base such as NaH and a t-butyl ester of haloacetic acid to give the acetate 97. Pd-catalyzed hydrogenation effects removal of the CBZ group from the acetate 97 to give amine 98, which is converted to the $L_1$-$Cy_1$ derivative 99 as described in Scheme 1 above. Hydrolysis of t-butyl ester 99 to the corresponding acid 100 is accomplished using, for example, $TFA/CH_2Cl_2$. The resulting acid 100 is coupled with the optionally protected amine $HNCy_2$ under typical amide bond formation conditions to give acetamide 101.

The preparation of compounds 107 and 108 of this invention wherein $Cy_1$ is benzimidazol-2-yl is outlined in Scheme 22.

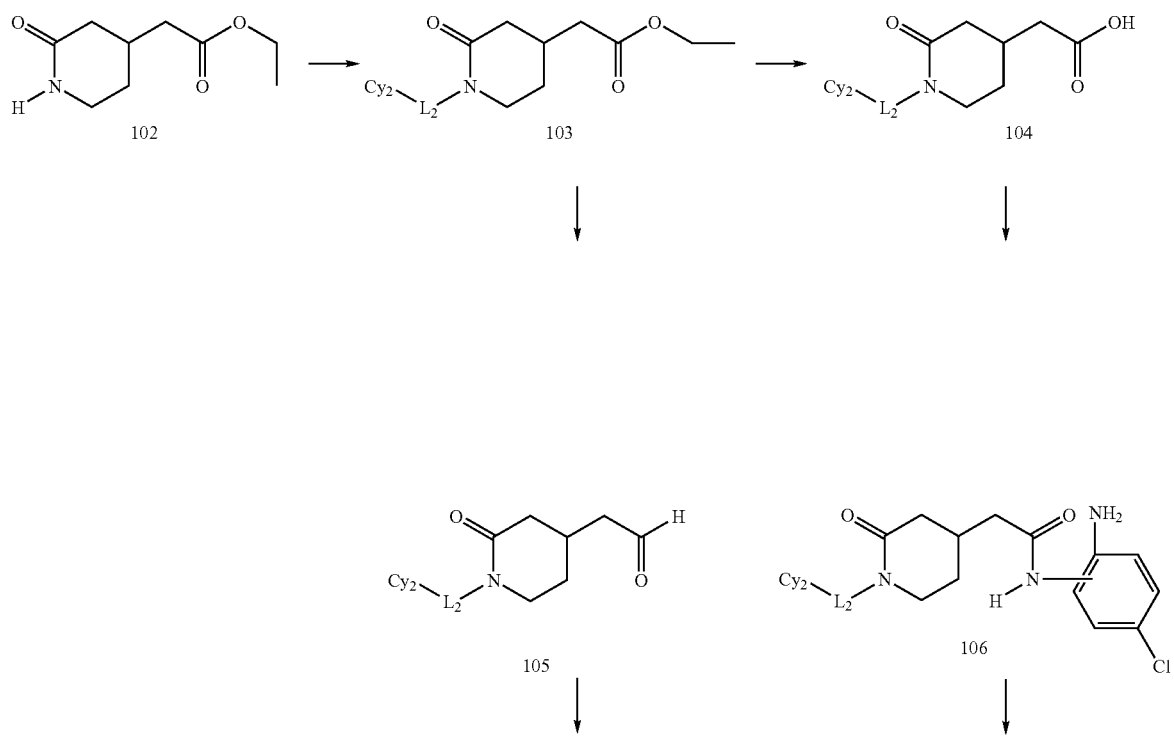

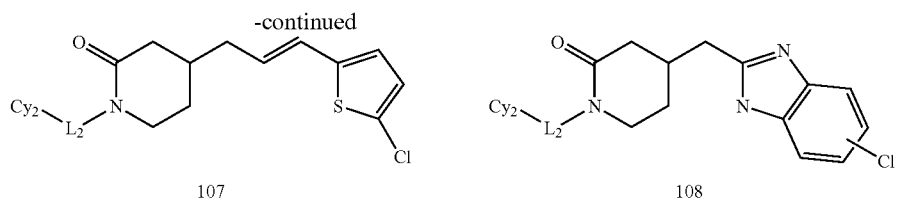

Piperidin-2-one 102 is alkylated by a procedure analgous to that described in Scheme 3 to give the N—Cy$_2$—L$_2$ ester derivative 103, which is hydrolyzed to give the acid 104 or reduced to give aldehyde 105. Coupling of the acid 104 with an amine affords amide 106, which is cyclized with acetic anhydride to give the compound 108. Wittig-coupling of aldehyde 105 produces compound 107.

The preparation of the compound of formula 114 is outlined in Scheme 23, wherein $R_1$, $R_{1a}$, $R_2$, $R_{2a}$, $R_4$, $R_{4a}$, $L_1$, $Cy_1$, P, are defined in formula I and $R_{13}$ and $R_{14}$ are defined herein.

lewis acid or a reagent such as trimethylsilyl iodide to provide a compound of formula 111. Coupling of a compound of formula 111 with an appropriate LG—L$_1$-Cy$_1$ can be performed as previously described in Scheme 1 to give a compound of formula 112 in which the L$_1$-Cy$_1$ portion is a sulfonamide, alkyl amine, amide, urea, carbamate or sulfamyl urea. Reaction of a compound of formula 112 with hydrogen sulfide dissolved in ethanol, methanol or another suitable solvent, in the presence of diisoproplyethylamine, triethylamine or another suitable base at an elevated temperature,

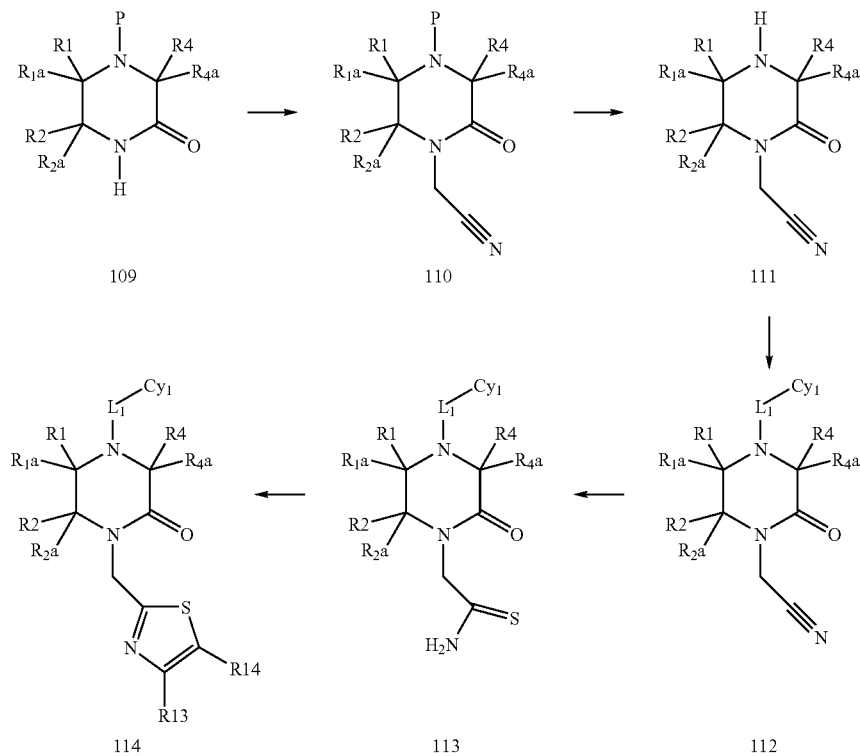

As shown in Scheme 23, alkylation of a compound of formula 109 with an appropriate LG—CH2—CN group wherein LG is a leaving group such as chloro, bromo, iodo, or optionally substituted lower alkylsulfonyloxy or arylsulfonyloxy in an inert organic solvent such as THF, Et$_2$O or DMF in the presence of a strong base such as NaH, lithium hexamethyldisilylazide or lithium diisopropylamine provides a compound of formula 110. In a preferred aspect, P a tertiary-alkyl or aralkyl carbamate moiety. Removal of the group P can be accomplished by either strong acid such as TFA, a preferably >80° C., provides a compound of formula 113. A compound of formula 114 can be prepared by heating ketone groups of the formula, R$_{13}$—C(O)—CH(LG)—R$_{14}$, with a compound of formula 113 in a suitable high boiling solvent. LG is a leaving group as previously defined. If R$_{13}$ or R$_{14}$ contains a protecting group, this group can be removed at this point.

An alternative preparation of a compound of formula 114 (Scheme 23) is shown in Scheme 24.

Scheme 24

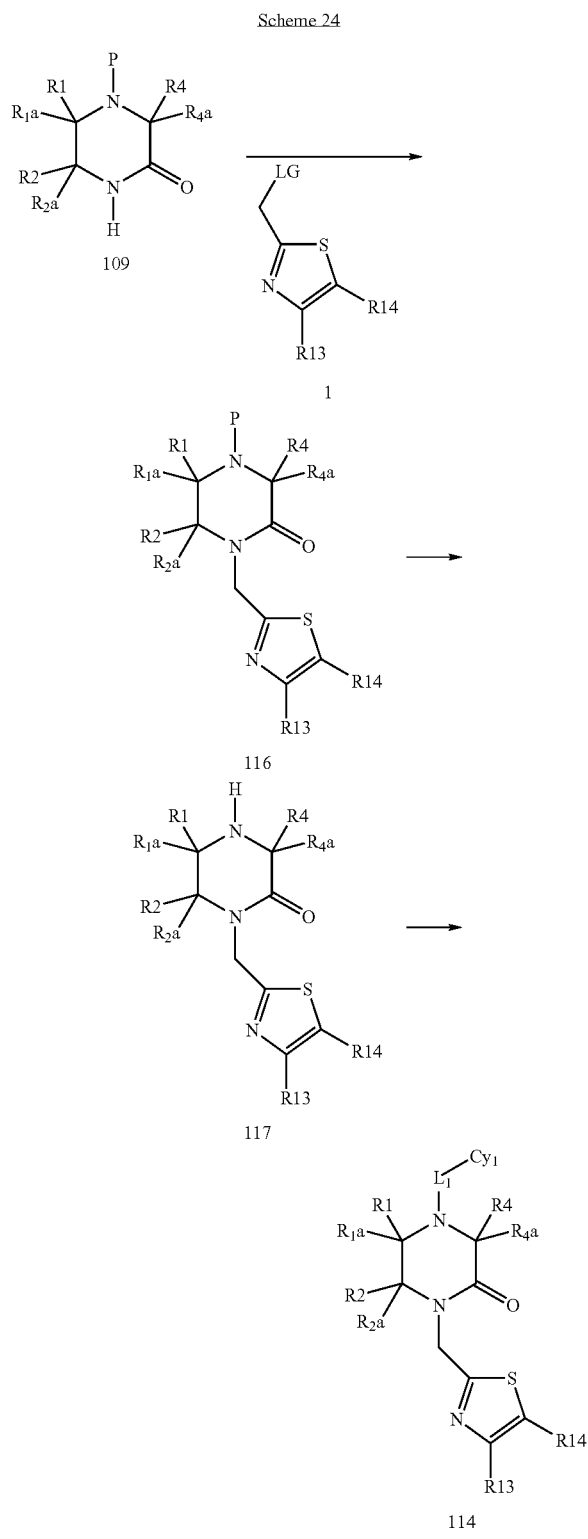

Scheme 25

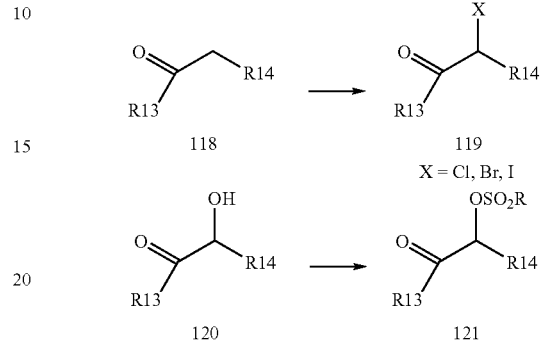

formula 114 is prepared from compound 117 using conditions previously described in Scheme 1.

The preparations of ketone groups of the formula, $R_{13}$—C(O)—CH(LG)—$R_{14}$ which are shown as compounds of formulas 119 and 121 are outlined in Scheme 25.

Halogenation of a compound of formula 118 with an appropriate reagent such as thionyl chloride, bromine, bromine/HOAc, NBS or iodine produces the corresponding halide of formula 119. A compound of formula 120 can be reacted with a sulfonyl chloride and a suitable base such as pyridine or triethylamine to provide a compound of formula 121.

Preparation of thiazole of formula 115 is outlined in Scheme 26.

Scheme 26

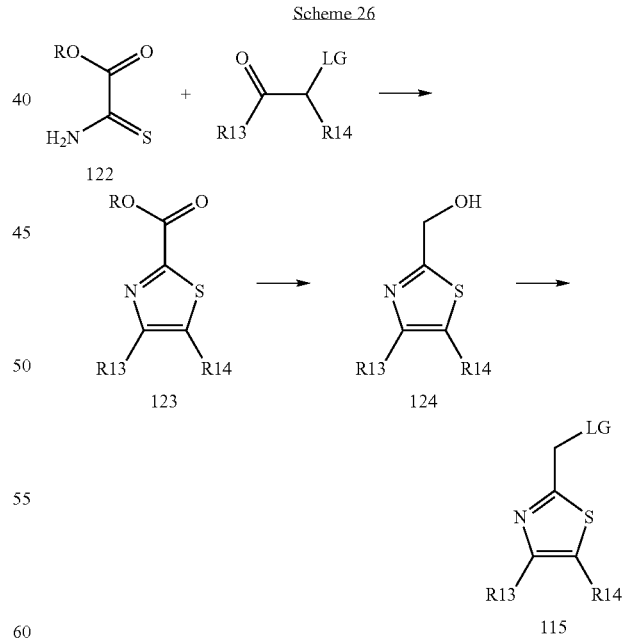

A compound of formula 116 can be prepared from a compound of formula 109 using conditions previously described in Scheme 3 for the alkylation of $Cy_2$—$Lg_2$—LG, which is represented by a compound of formula 115. Removal of the group P using a strong acid, strong base or reducing conditions provides a compound of formula 117. A compound of Condensation of a thioamide compound of formula 122 with a ketone of the formula, $R_{13}$—C(O)—CH(LG)—$R_{14}$ at elevated temperatures provides the thiazole compound of formula 123. Reduction with LAH, DIBAL or a similar reagent provides the alcohol of formula 124. Preparation of the compound of formula 115 can be acheived with PBr₃ to give the bromide (or with a sulfonyl chloride and base to provide the sulfonate ester).

An alternative preparation of a thiazole intermediate of formula 123 is outlined in Scheme 27

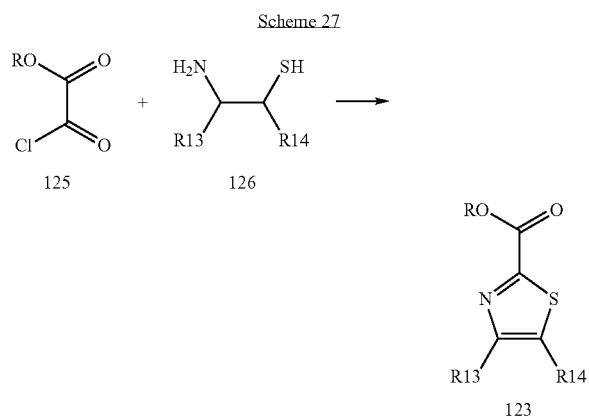

Condensation of a compound of formula 125 with an aminio-thiol compound of formula 126 with a base such as pyridine provides a thiazole of formula 123. This method is especially useful in cases where $R_{13}$ and $R_{14}$ are combined to form an aromatic ring system.

An alternative preparation of a thiazole intermediate of formula 115 is outlined in Scheme 28.

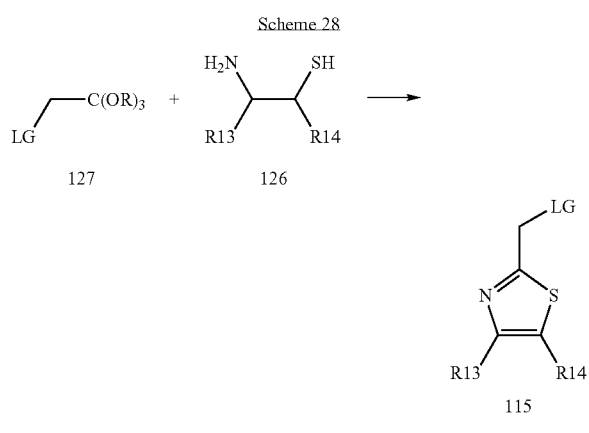

A compound of formula 127, such as 2-chloro-1,1,1-triethoxyethane, can be condensed with a compound of formula 126 at elevated temperatures to provide a compound of formula 115. This method is especially useful in cases where $R_{13}$ and $R_{14}$ are combined to form an aromatic ring system.

An alternative preparation of thiazole intermediate of formula 115 is outlined in Scheme 29.

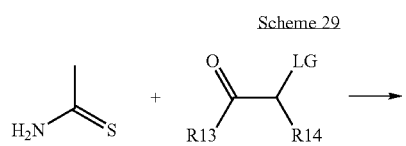

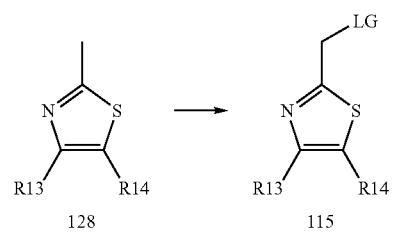

Condensation of thioacetamide with a ketone of the formula, $R_{13}$—C(O)—CH(LG)—$R_{14}$ at an elevated temperature provides a thiazole of formula 128. Functiononalization to provide a leaving group such as Br can be accomplished using NBS and an initiator at an elevated temperature in a solvent such as carbontetrachloride to provide a compound of formula 115. This method is especially useful in cases where $R_{13}$ and $R_{14}$ are combined to form an aromatic ring system.

Ring expansion of a compound of formula 128 to provide lactam products of formulas 130 and 131 is shown in Scheme 30.

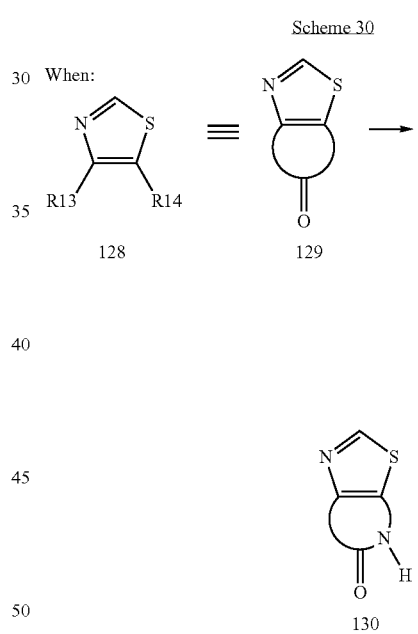

When $R_{13}$ and $R_{14}$ are combined to form a carbocyclic ring containing a ketone as shown in formula 21, then ring expansion to form the lactone products 130 and 131 can be achieved using the Schmidt reaction. At 0° C. to room temperature a mixture of the ketone 129 is stirred with sodium azide in sulfuric acid and chloroform. The Beckman ring expansion can also be used when the ketone 129 is first treated with hydroxylamine hydrochloride to give the intermediate oxime. An aniline byproduct can also be observed when the Semmler-Wolf aromatization mechanism predominates when thiazole-cycohexanone substrates are used.

Preparation of an intermediate of formula 133 is shown in scheme 31.

Scheme 31

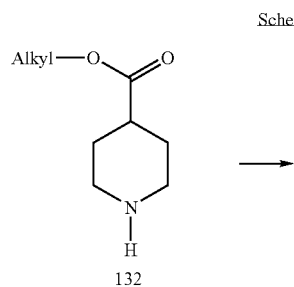

132 → 133

E = Aryl, heteroaryl, alkoxycarbonyl carbamyl, acyl, alkyl carbamyl, alkyl

When E of formula 133 aryl or heteroaryl, a compound of formula 133 can prepared using a Pd catalyzed aromatic carbon-nitrogen bond forming reaction developed by Buchwald and Hartwig. This reaction has been reviewed (*Acc. Chem. Res.* 1998 31, 805-818) and can be generalized to include the reaction of an aromatic bromide, chloride or triflate in an inert solvent in the presence of a Pd (0) catalyst and a base such as sodium tert-butoxide, at an elevated temperature, with a primary or secondary amine. When E of formula 133 is alkoxycarbonyl, acyl, alkyl carbamyl or alkyl, the corresponding halide can be used to couple to a compound of formula 132 in the presence of a base. When E of formula 133 is carbamyl, an isocyanate can be used to produce compound 133 from 132.

The preparation of a compound of formula 135 which can be used as an intermediate is outlined in Scheme 32.

Scheme 32

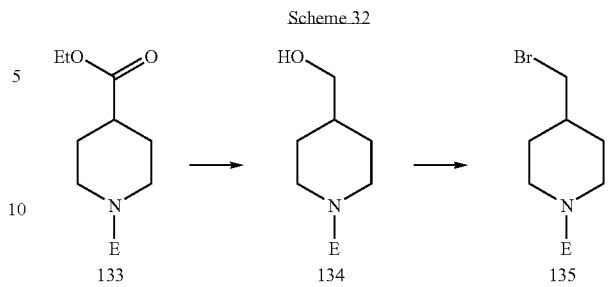

133 → 134 → 135

Reduction of a compound of formula 133 with a reducing agent such as LAH, DIBAL or another similar reagent in a nonprotic solvent can provide an alcohol of formula 134. Conversion of the alcohol 134 into a good leaving group, such as the bromide, can be acheived using $CBr_4/PPh_3$ or another similar reagent to provide a compound of formula 135.

The preparation of the compound of formula 140, wherein $R_1$, $R_{1a}$, $R_2$, $R_{2a}$, $R_4$, $R_{4a}$, $L_1$, $Cy_1$ are defined above is outlined in Scheme 33.

Scheme 33

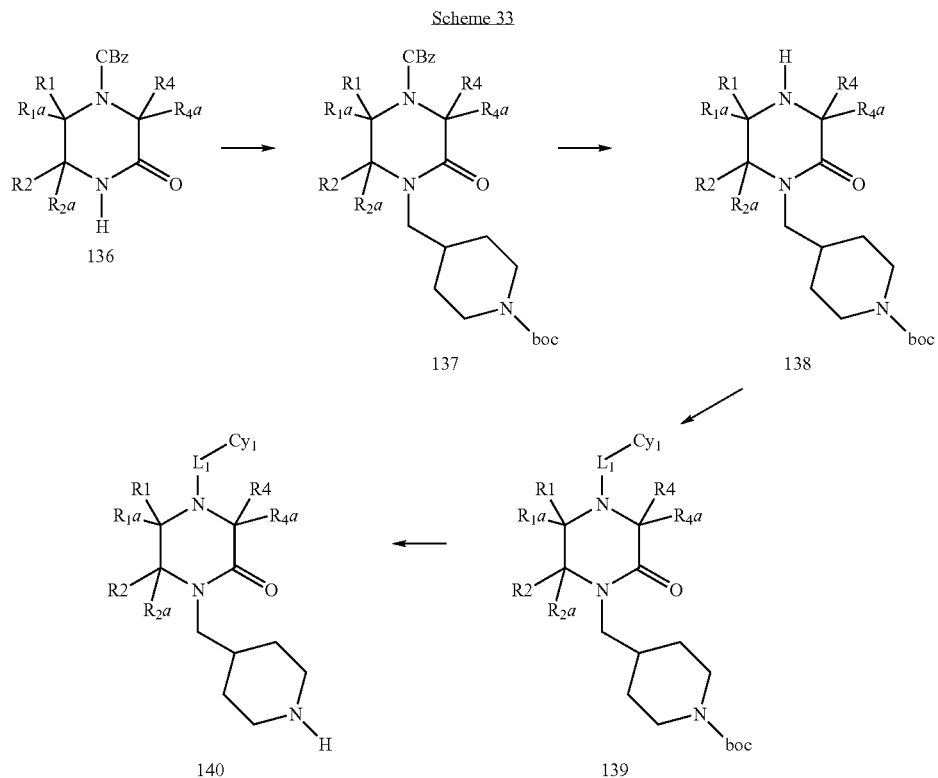

Alkylation of a compound of formula 136 with a compound of formula 135, where E is tert-butoxycarbonyl, in an inert organic solvent such as DMF in the presence of a strong base such as NaH, lithium hexamethyldisilylazide or lithium diisopropylamine, provides a compound of formula 137. Removal of the CBz (benzyloxycarbonyl) group by catalytic hydrogenation in an appropriate solvent such as ethanol provides a compound of formula 138. Coupling of a compound of formula 138 with $LG-L_1-Cy_1$ can be performed as previously described above to give a compound of formula 139 in which the $L_1$-$Cy_1$ portion is a sulfonamide, alkyl amine, amide, urea, carbamate or sulfamyl urea. Removal of the Boc (t-butoxycarbonyl) group with a strong acid, such as TFA, provides a compound of formula 140.

Preparation of a compound of formula 141, where Ar is an aromatic ring, is shown in scheme 34.

Scheme 34

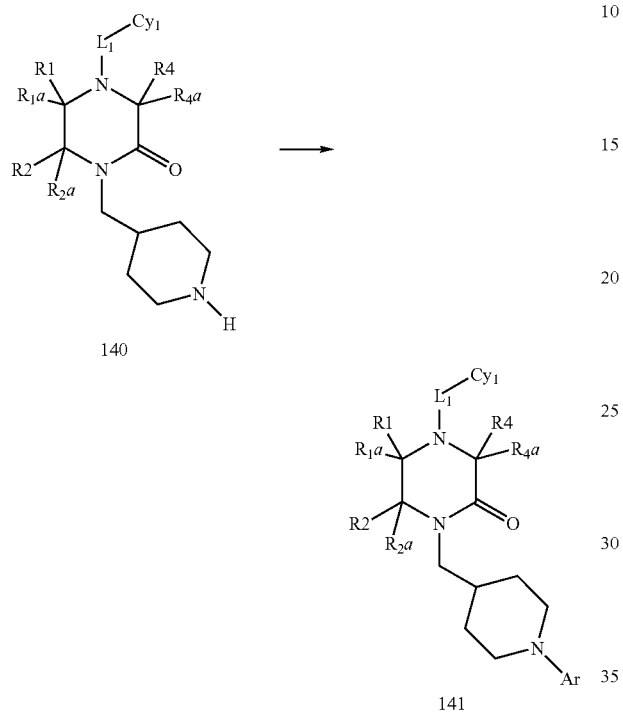

140

141

A compound of formula 140 can be converted to a compound of formula 141 using a Pd catalyzed aromatic carbon-nitrogen bond forming reaction developed by Buchwald and Hartwig. This reaction has been reviewed (*Acc. Chem. Res.* 1998 31, 805-818) and can be generalized to include the reaction of an aromatic bromide, chloride or triflate in an inert solvent in the presence of a Pd (0) catalyst and a base such as sodium tert-butoxide at an elevated temperature with a primary or secondary amine.

Preparation of a compound of formula 142, where AzaAr is an azaaromatic ring, is shown in scheme 35.

Scheme 35

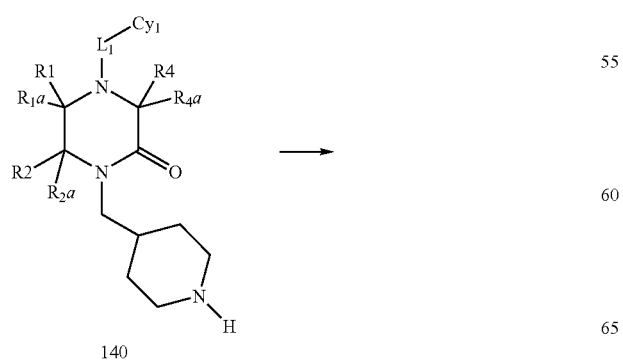

140

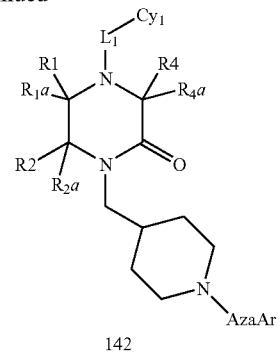

142

A compound of formula 142 can be prepared from a halo-substituted azaheteroaromatic compound by heating the halo substituted compound with a compound of formula 140 at an elevated temperature in an inert high boiling solvent such as n-butanol, xylene or NMP. The types of azaheteroaromatic compounds which are best suited for this reaction employ a halogen leaving group in a position of the ring which is activated toward displacement. Such systems are represented by, but not limited to, 2-fluoropyridine, 2-chloroquinoline, 2-chloro-pyrimidine, 4-chloro-pyrimidine and 2,4-dichloro-pyrimidine.

Preparation of a compound of formula 144, where R15 is alkylamine, alkylether or alkylthio, is shown in scheme 36.

Scheme 36

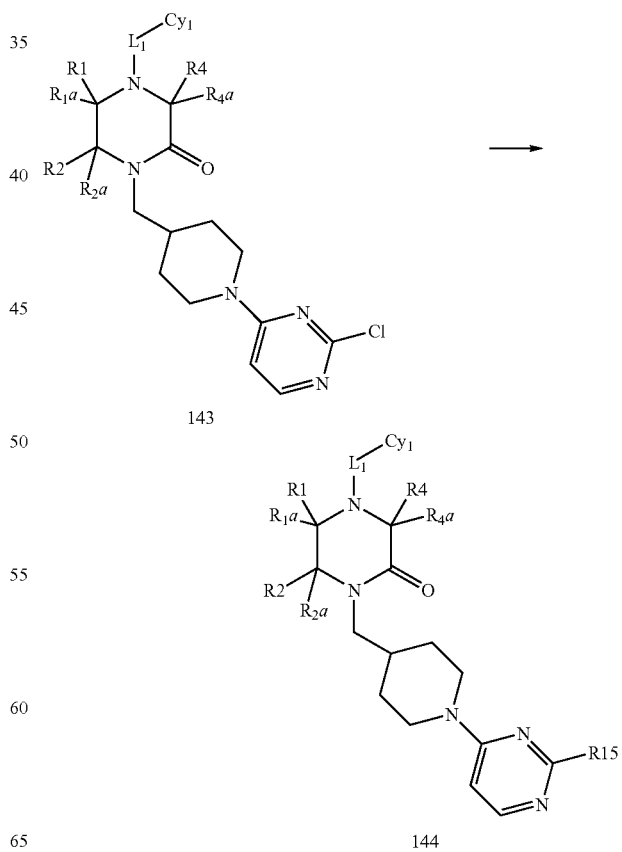

143

144

A compound of formula 143 can be heated with either an amine, alcohol or thiol in an inert solvent to give the corresponding compound of formula 144.

Preparation of a compound of formula 145 and conversion to a compound of formula 146, where each $R_{16}$ is independently H or alkyl, is outlined in scheme 37.

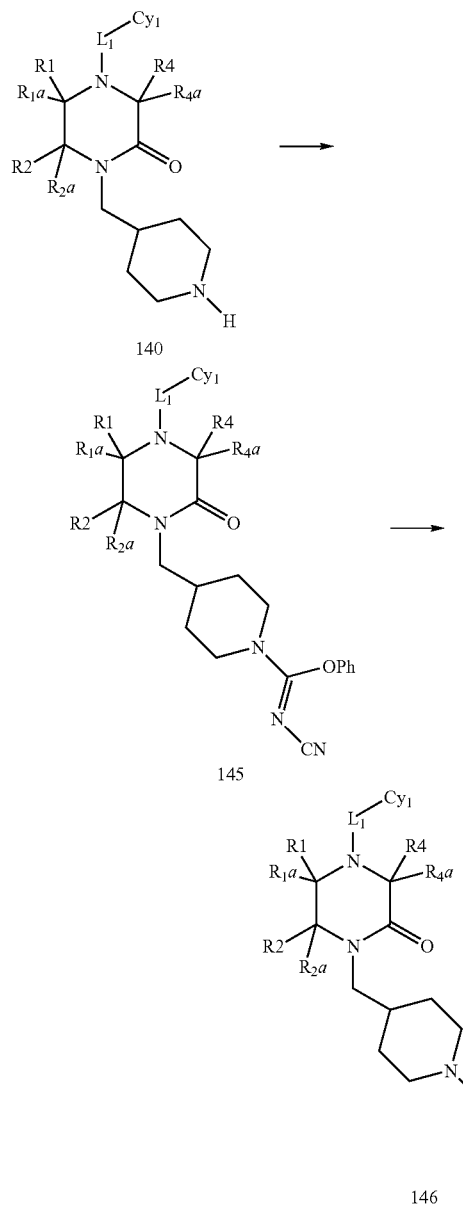

A compound of formula 145 can be prepared by combining a compound of formula 140 with a reagent such as diphenyl cyanocarbonimidate at ambient temperature or with heating. Heating compound 145 with amine $NH(R_{16})_2$, where each $R_{16}$ is independently H or alkyl, in an inert solvent provides a compound of formula 146.

General Methods for the preparation of 1-(alkyl,arly) amino-4-methylcyclohexyl-ketopiperazines of Formula 147 are outlined in Scheme 38.

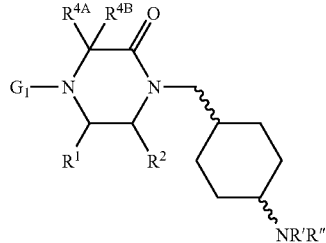

As indicated in the scheme 38, a preferred method of preparation of compounds of formula 147 involves construction of a ketopiperazine 152 containing the cyclic ketal of 4-methyl-cyclohexan-1-one as an N-1 substituent. Construction of intermediate 152 begins with reductive amination of intermediate 148 (prepared according to the method of Pearson et al.; *J. Org. Chem.* 62, 1997, 5284) with the substituted acetal of aminoacetaldehyde to provide intermediate 149. Intermediate 149 is then acylated with a suitably N-protected substituted α-amino acid to provide intermediate 150. Treatment of intermediate 150 with p-toluenesulphonic acid provides the unsaturated ketopiperazine 151. Deprotective hydrogenation of intermediate 151 provides intermediate 152. Attachment of the moiety $G_1$ provides intermediate 153. The acetal of the 4-substituted cyclohexanone is hydrolyzed under acidic conditions to provide intermediate 154. Reductive amination with the appropriate amine afford compounds of Formula 147. Reductive amination of the cyclohexanone with the selected amines can be achieved using standard methods known to those skilled in the art using borohydrides such as sodium borohydride or lithium tri-sec-butylborohydride in an appropriate solvent such as methanol or acetic acid at temperatures between 0 and 100° C. The isomeric cis/trans products of reductive amination can be separated by silica-gel chromatography or RP-HPLC.

Scheme 38

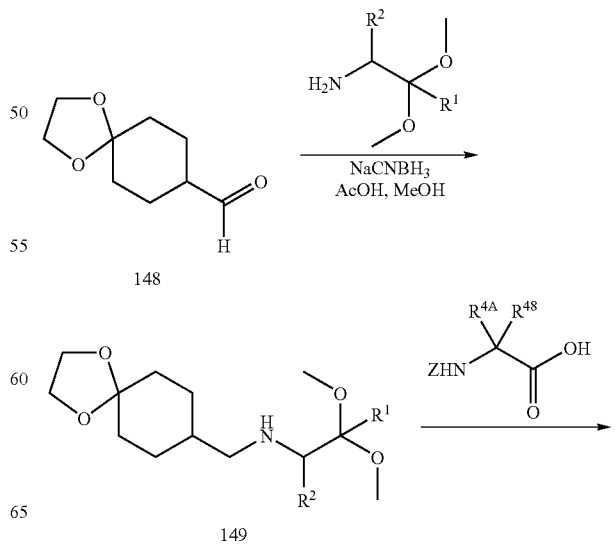

-continued

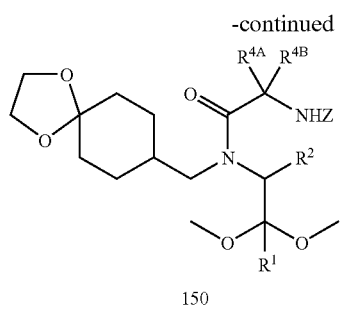

150

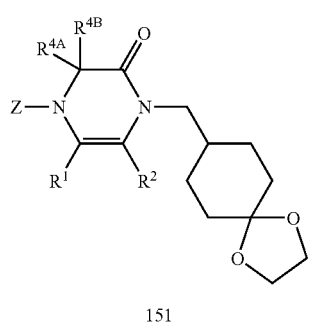

151

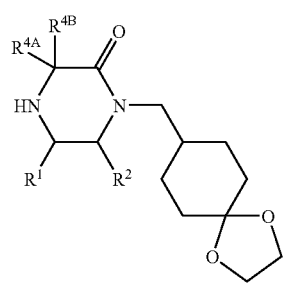

152

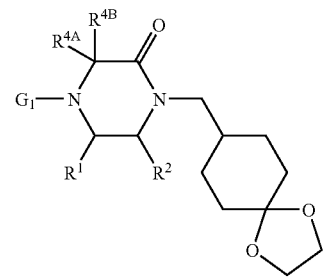

153

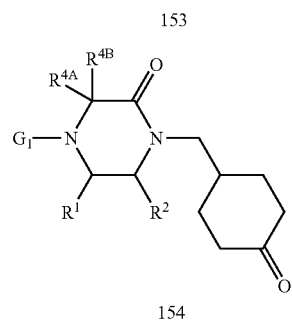

154

-continued

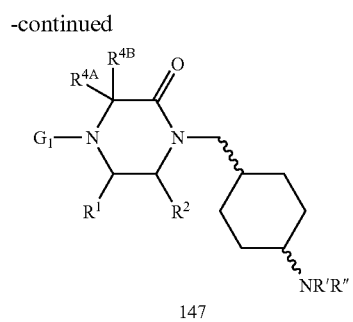

147

General Methods for the preparation of 1-(N,N'-aryl/alkyl-cyanoguanidine)-4-methylcyclohexyl-ketopiperazines of Formula 155 are outlined in scheme39.

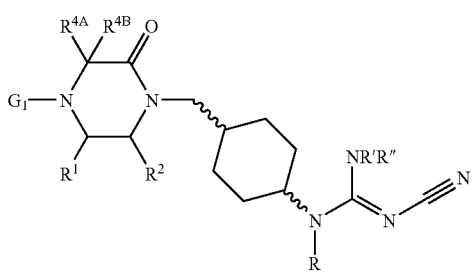

155

As shown in scheme 39, a preferred method of preparation of compounds of formula 155 involves construction of a ketopiperazine 152 containing the cyclic ketal of 4-methyl-cyclohexan-1-one as an N-1 substituent. Construction of intermediate 152 begins with reductive amination of intermediate 148 (prepared according to the method of Pearson et al.; J. Org. Chem. 62, 1997, 5284) with the substituted acetal of aminoacetaldehyde to provide intermediate 149. Intermediate 149 is then acylated with a suitably N-protected substituted α-amino acid to provide intermediate 150. Treatment of intermediate 150 with p-toluenesulphonic acid provides the unsaturated ketopiperazine 151. Deprotective hydrogenation of intermediate 151 provides intermediate 152. Attatchment of the moiety $G_1$ provides intermediate 153. The acetal of the 4-substituted cyclohexanone is hydrolyzed under acetic conditions to provide intermediate 154. Reductive amination with the appropriate primary amine provides intermediate 156. Reductive amination of the cyclohexanone with the selected amines can be achieved using standard methods known to those skilled in the art using borohydrides such as sodium borohydride or lithium tri-sec-butylborohydride in an appropriate solvent such as methanol or acetic acid at temperatures between 0 and 100° C. The isomeric cis/trans products of reductive amination can be separated by silica-gel chromatography or RP-HPLC. Intermediate 156 is reacted with diphenyl cyano-carbonimidate to provide intermediate 157. Intermediate 157 is reacted with appropriate primary and secondary amines to provide a compound of Formula 155.

Scheme 39
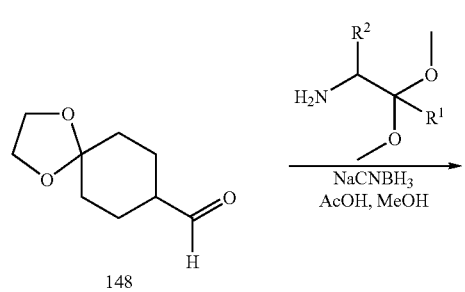
148
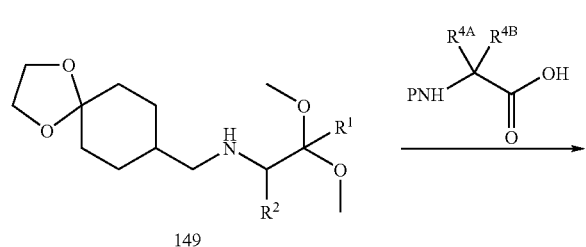
149
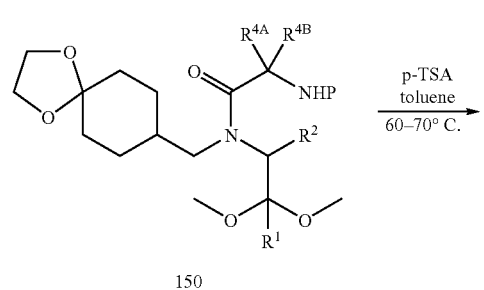
150
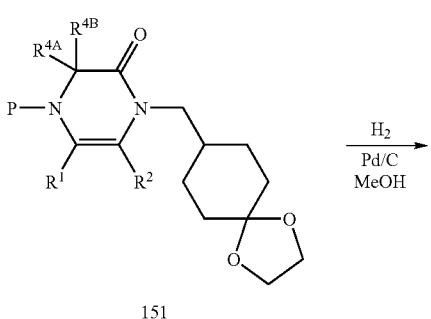
151
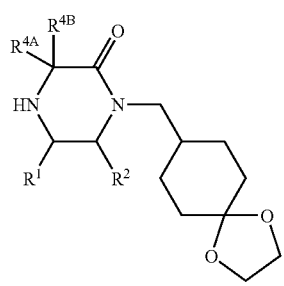
152
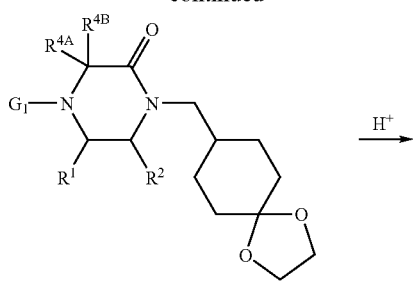
153
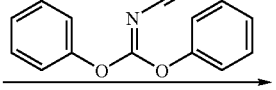
154
156
157
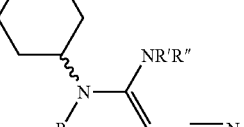
155
General Methods for the preparation of 2-substituted-4&5-methylpyrimidyl-ketopiperazines of Formulas 158 & 159 are outlined in Scheme 40 below.

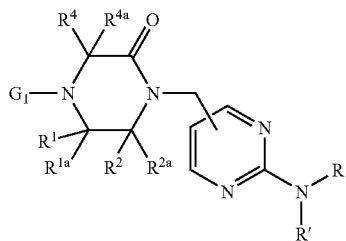

158

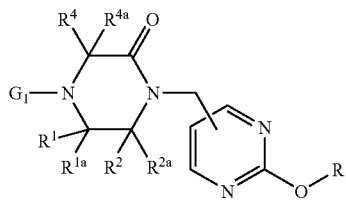

159

As shown in scheme 40, a preferred method of preparation of compounds of formula 158 and 159 involves alkylating a ketopiperazine intermediate 160 containing a desired N-4 substituent (designated G-1) with either 4 or 5-halomethyl 2-thiomethylpyrimidine to provide intermediate 161. Oxidation of the thiomethyl group of intermediate 161, to provide intermediate 162, followed by displacement with the appropriate amine or alkoxide affords compounds of Formula 158 or 159, respectively. Alkylation of the amide of intermediate 160 can be achieved using standard methods known to those skilled in the art such as deprotonation with NaH in DMF or t-butoxide in t-butanol at temperatures between −78 and 100° C. followed by addition of the halide intermediate 165 and stirring at 0 to 100° C. for 0.5 hours to 24 hours. Oxidation of the sulfide of intermediate 161 to the sufone of intermediate 162 can be accomplished in standard fashion, such as using oxone in a mixture of MeOH and H$_2$O or m-CPBA in CH$_2$Cl$_2$. Displacement of the sulfone of intermediate 162 with the appropriate amine can be acheived by simply stirring the components neat or in an unreactive solvent such as CH$_2$Cl$_2$ or DMF for 0.5 to 24 hours at 20 to 100° C. Similary, reaction of an alkoxide in an inert solvent leads to the desired displacement product.

Scheme 40

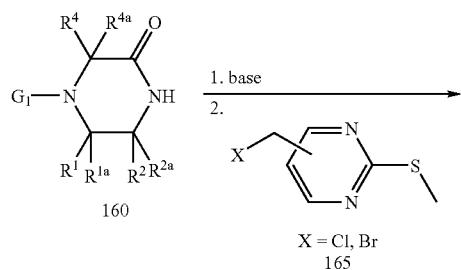

X = Cl, Br
165

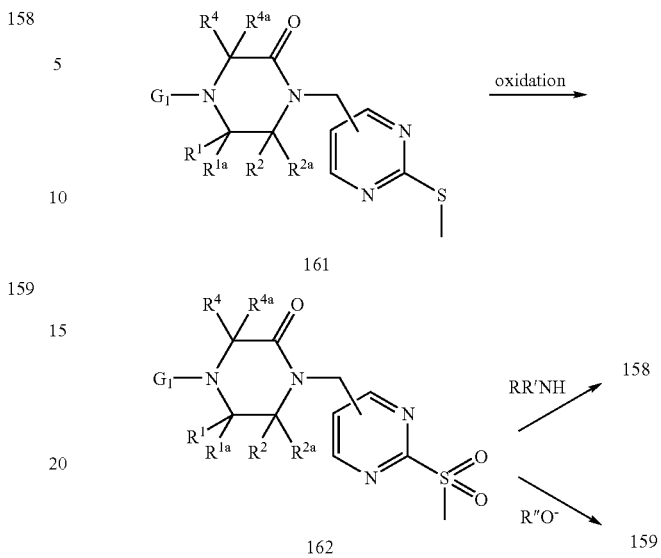

The 4&5-halomethyl-2-methylthiopyrimidines intermediates 165 can be prepared as illustrated in scheme 41 from the corresponding 4&5-carboxaldehydes intermediate 163, respectively. 2-Methylthiopyrimidine-4-carboxaldehyde can be prepared using the procedure of Bredereck et al. (*Chem. Ber.* 1964, 3407). 2-Methylthiopyrimidine-5-carboxaldehyde can be prepared by the procedure of Gupton et al. (*J. Het. Chem.* 28, 1991, 1281).

Scheme 41

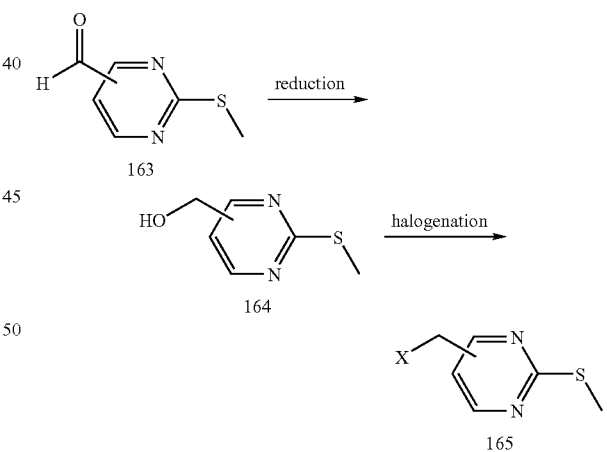

Alternatively, as illustrated in scheme 42, compounds of formula 158 and 159 can be prepared by alkylating suitably protected [at N-4 (designated P)] ketopiperazine intermediate 166, with either the 4- or 5-halomethyl-2-methylthiopyrimidine (intermediate 165) to provide intermediate 167. The protecting group of intermediate 167 can then be removed to provide intermediate 168 and the desired G-1 substituent added to provide intermediate 169. Suitable protecting groups include Boc, Cbz, Alloc and Fmoc, which can be manipulated in the usual manner.

Scheme 42

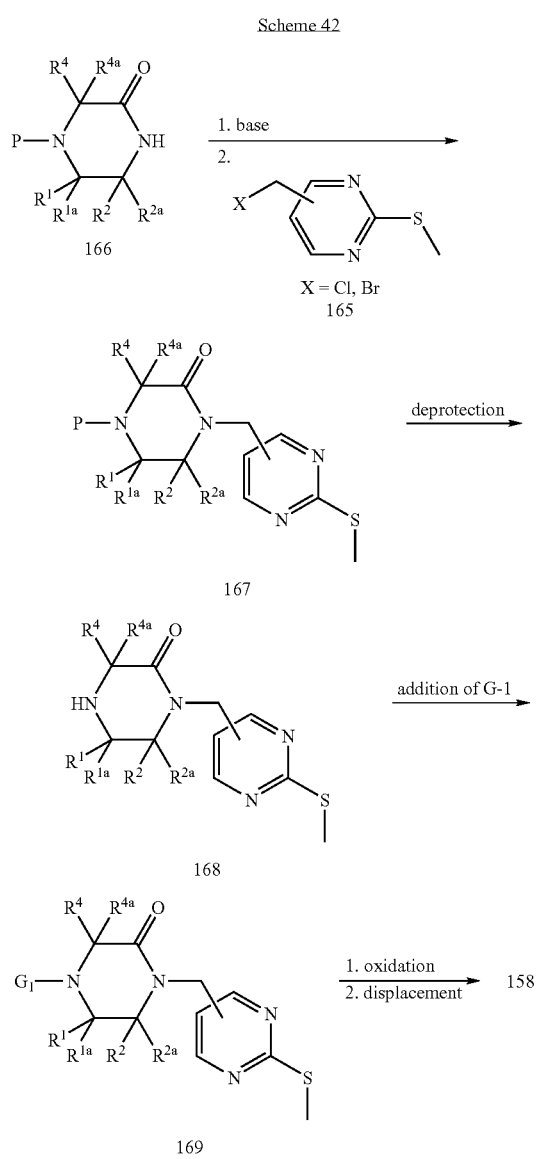

Diketopiperazine compounds of formula I, in which A is N, both $R_1$ and $R_{1a}$ taken together and $R_2$ and $R_{2a}$ taken together are oxygen, are prepared in general as described in *J. Org. Chem.* 1998, 63, 4131 and *Chem. Pharm. Bull.* 1981, 29, 684. The synthetic route used is outlined in Scheme 43 below.

Scheme 43

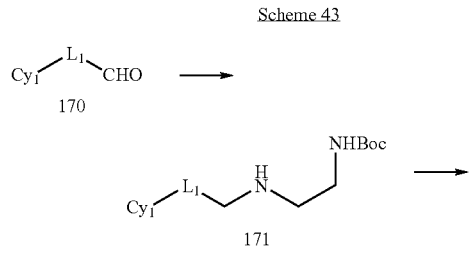

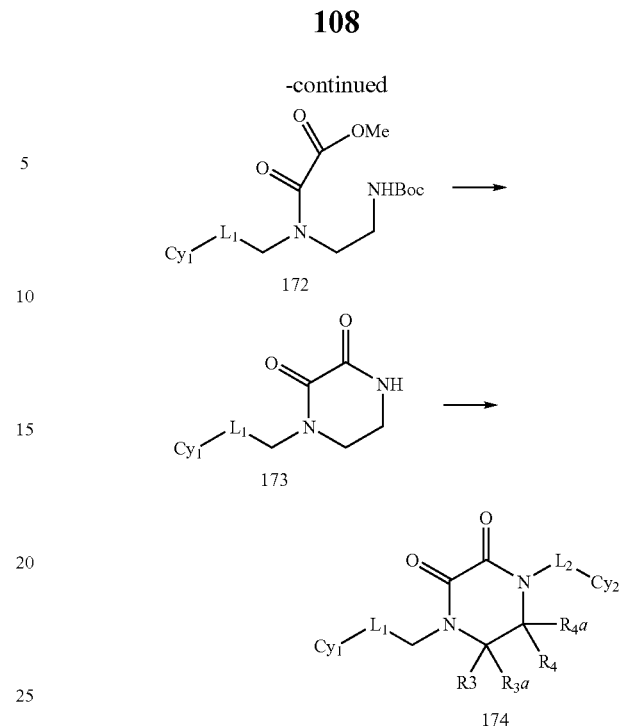

As shown in Scheme 43 above, an aryl, heteroaryl or biaryl aldehyde or alkenyl aldehyde derivatives representative of $Cy_1$—$L_1$ groups defined herein can be aminated with a suitably protected form of ethylenediamine using a reducing agent such as sodium borohydride. The secondary amine 171 is treated with an appropriate form of oxalyl chloride, notably methyl chlorooxoacetate, in the presence of base to form oxalamic ester intermediate 172. 2,3-Diketopiperazine 203 is formed by removal of the protecting group under acidic conditions (HCl or TFA) followed by cyclization under base conditions (TEA). Appropriate $Cy_2$—$L_2$ groups can be appended to compounds of formula 173 by alkylation with a suitable aryl chloromethyl or bromomethyl ring system, such as a compound of formula 179 using NaH, LiN(SiMe$_3$)$_3$, NaN(SiMe$_3$)$_3$, LDA, or an appropriate base, in an inert solvent such as THF or DMF to provide compounds of formula 174 in which $Cy_2$ is a chloroquinazoline, chloroquinoline, aminoquinazoline or another group defined herein.

Scheme 44

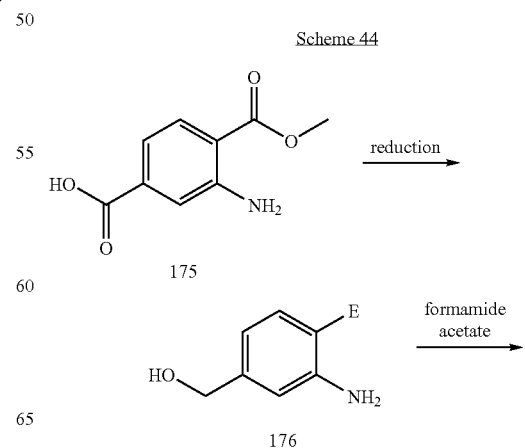

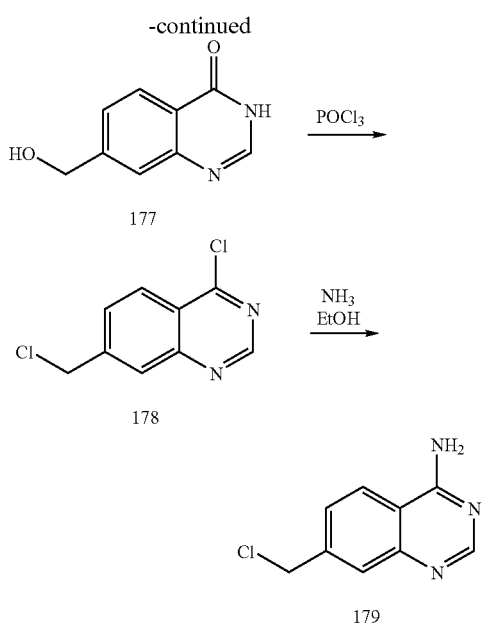

As shown in Scheme 44, the quinazoline 179 can be prepared by reduction of the acid 175 with Super Hydride in THF to afford the alcohol 176. The alcohol 176 is then reacted in formamide at about 180° C. to afford cyclised compound 177. The cyclised compound 177 is then converted to its chloro derivative 178, by reacting with POCl$_3$. The chloro derivative 178 is then converted to the amino compound 179 by using NH$_3$ in ethanol or NH$_4$OAc/PhOH.

This invention is further exemplified but not limited by the following examples which further illustrate the preparation of the compounds of this invention. The starting materials and intermediates are prepared by the application or adaptation of known methods, for example methods used heretofore or described in the literature, for example those described by R. C. Larock in Comprehensive Organic Transformations, VCH publishers, 1989.

The compounds of the invention, their methods or preparation and their biological activity will appear more clearly from the examination of the following examples which are presented as an illustration only and are not to be considered as limiting the invention in its scope.

EXAMPLE 1

6-Chlorobenzo[b]thiophene-2-sulfonyl chloride

A. 1-Chloro-3-(2,2-dimethoxyethylsulfanyl)benzene.

To a solution of 3-chlorothiophenol (2.4 g, 16.6 mmol) in THF (200 mL) at 0° C. is added bromoacetaldehyde dimethyl acetal (2.8 g, 16.6 mmol). To the solution is added sodium hydride (60% mineral oil dispersion, 0.70 g, 17.4 mmol). The reaction is stirred for 16 hours, and then is quenched by the addition of saturated NH$_4$Cl (aq.). The solution is diluted with EtOAc. The organic layer is washed with a saturated NaCl (aq.). The organic layer is dried over MgSO$_4$, filtered and concentrated. The crude product is purified by column chromatography eluting with hexanes. The title compound (3.7 g, 15.9 mmol) is obtained as an oil. $^1$H NMR (CDCl$_3$, 300 MHz) δ7.32 (m, 1H), 7.25 (m, 1H), 7.12 (m, 1H), 4.47 (m, 1H), 3.07 (s, 3H), 3.02 (s, 3H).

B. 4-Chlorobenzo[b]thiophene and 6-Chlorobenzo[b]thiophene.

A solution containing polyphosphoric acid (8 g) and chlorobenzene (50 mL) is heated at reflux. A solution containing 1-chloro-3-(2,2-dimethoxyethylsulfanyl)benzene (2.7 g, 11.6 mmol) in chlorobenzene (5 mL) is added dropwise to the refluxing polyphosphoric acid solution. After 6 hours, the solution is cooled to ambient temperature. The solution is diluted with CH$_2$Cl$_2$ and washed with water and saturated NaCl (aq.). The organic layer is dried over MgSO$_4$, filtered and concentrated. The crude product is purified by column chromatography eluting with hexanes to yield the title compounds (2.4 g, 9.0 mmol) as a 1:1 isomeric mixture. $^1$H NMR (CDCl$_3$, 300 MHz) δ7.88 (m, 1H), 7.75 (m, 2H), 7.42 (m, 2H). MS (EI): m/z 168, 170 (M+), Cl pattern.

C. 4-Chlorobenzo[b]thiophene-2-sulfonyl chloride and 6-Chlorobenzo[b]thiophene-2-sulfonyl chloride.

To a solution of 4-chloro-benzo[b]thiophene and 6-chlorobenzo[b]thiophene (11.8 g, 88.1 mmol), in 400 mL of THF at −78° C. is added n-BuLi (55 mL of a 1.6M solution in hexanes, 88.1 mmol). After 15 minutes, the solution is added by cannula to a precooled (−78° C.) solution of SO$_2$ (200 g) in 100 mL of THF. After addition, the solution is allowed to warm to ambient temperature. After 0.5 hour, the solution is concentrated. The residue is suspended in hexanes (400 mL) and is cooled to 0° C. To the solution is added SO$_2$Cl$_2$ (12.5 g, 92.5 mmol). After stirring for 15 minutes, the solution is concentrated. The residue is dissolved in EtOAc. The organic solution is washed with saturated NH$_4$Cl (aq.), H$_2$O and saturated NaCl (aq.). The organic layer is dried over MgSO$_4$, filtered and concentrated. The crude product is dissolved in CH$_2$Cl$_2$ and filtered through a plug of silica gel. The crude product is purified by column chromatography eluting with hexanes to yield the title compound as well as 4-chlorobenzo[b]thiophene-2-sulfonyl chloride as white solids.

4-Chlorobenzo[b]thiophene-2-sulfonyl chloride: $^1$H NMR (CDCl$_3$, 300 MHz) δ8.32 (m, 1H), 7.81 (m, 1H), 7.53 (m, 2H).

6-Chlorobenzo[b]thiophene-2-sulfonyl chloride: $^1$H NMR (CDCl$_3$, 300 MHz) δ8.11 (s, 1H), 7.88 (m, 2H), 7.50 (m, 1H).

EXAMPLE 2

5'-Chloro-[2,2']bithiophenyl-5-sulfonyl chloride

A. 5-Chloro-[2,2']bithiophene.

The title compound is prepared from 2-chloro-thiophene according to the procedure described in Bull. Chem. Soc. Japan, 1979, 1126. The crude product is purified by column chromatography eluting with a gradient of 5% EtOAc/hexanes to 10% EtOAc/hexanes to afford a white solid. $^1$H NMR (CDCl$_3$, 300 MHz) δ7.24 (m, 1H), 7.11 (d, 1H), 7.03 (dd, 1H), 6.94 (d, 1H), 6.83 (d, 1H). MS (EI) [M+]=200, 202, Cl pattern.

B. 5'-Chloro-[2.2']bithiophenyl-5-sulfonyl chloride.

The title compound is prepared as described in Example 1, Part C using 5-chloro-[2,2']bithiophene in place of 6-chlorobenzo[b]thiophene. The crude product is purified by column chromatography eluting with a gradient of 5% EtOAc/hexanes to 10% EtOAc/hexanes to give a white solid. $^1$H NMR (CDCl$_3$, 300 MHz) δ 7.76 (d, 1H), 7.14 (d, 1H), 7.09 (d, 1H), 6.92 (d, 1H). MS (EI): m/z 298, 300 (M+), Cl pattern.

EXAMPLE 3

2-(5-Chloro-thiophen-2-yl)-ethenesulfonyl chloride

A. 2-(5-Chloro-thiophen-2-yl)-ethenesulfonic acid ethyl ester.

n-Butyllithium (53.1 mL, 2.5M solution in hexanes) is added dropwise to a solution of ethylmethanesulfonate (12.9 mL, 0.12 mol) in THF (300 mL) at −78° C. The reaction mixture is stirred for 15 min then ethylchlorophosphonate (9.9 mL, 0.07 mol) is added dropwise. The solution is stirred at −78° C. for 30 minutes and then heated to 50° C. for 1 hour. The reaction mixture is then cooled to −78° C. and stirred for 1 h then 5-chlorothiophenecarboxaldehyde (7.1 mL, 0.07 mol) is added dropwise. The reaction mixture is allowed to slowly warm to RT overnight. Water (30 mL) is added to the mixture and stirred for 15 min then concentrated in vacuo. The residue is taken up in CH$_2$Cl$_2$ and washed with water, brine, dried over MgSO$_4$, filtered and concentrated to dryness. The crude product is purified by column chromatography eluting with 5% EtOAc/hexanes to give title product (11.3 g, 0.04 mol) as an oil. $^1$H NMR (CDCl$_3$, 300 MHz) δ 7.51 (d, 1H), 7.10 (d, 1H), 6.91 (d, 1H), 6.42 (d, 1H), 4.20 (q, 2H), 1.40 (t, 3H).

B. 2-(5-Chloro-thiophen-2-yl)-ethenesulfonyl chloride.

Tetrabutylammonium iodide (16.3 g, (44.2 mmol) is added to a solution of 2-(5-chloro-thiophen-2-yl)-ethenesulfonic acid ethyl ester (11.3 g, 40.2 mmol) in acetone (100 mL) at room temperature. The mixture is heated to reflux and stirred overnight then cooled to RT and conconcentrated in vacuo. The residue is taken up in CH$_2$Cl$_2$ then washed with water and brine. The organic layer is dried over MgSO$_4$, filtered and concentrated to dryness to give an oil (18.74 g, 40.2 mmol) which is taken on to the next step without further purification. Sulfuryl chloride (7.1 mL, 88.5 mmol) is added to a solution of triphenylphosphine (21.0 g, 86.42 mmol) in CH$_2$Cl$_2$ at 0° C. The ice bath is then removed and the product (18.74 g, 40.2 mmol) from the above reaction is added. After 2 h, the reaction mixture is concentrated in vacuo and the product purified by column chromatography eluting with 10% EtOAc/Hexanes to give the title compound (6.4 g, 26.3 mmol) as an off-white solid. $^1$H NMR (CDCl$_3$, 300 MHz) δ 7.70 (d, 1H), 7.23 (d, 1H), 7.00 (d, 1H), 6.91 (d, 1H).

EXAMPLE 4

3-Chlorobenzyl sulfamyl catechol

To a solution of 3-chlorobenzylamine (0.14 g, 1.0 mmol) in 3 mL of DMF is added Et$_3$N (0.10 g, 1.5 mmol). The solution is cooled to 0° C. Catechol sulfate (0.172 g, 1.0 mmol) is added. The solution is warmed to ambient temperatures. After 2.5 h, 30 mL of EtOAc is added. The solution is washed with 5% HCl, H$_2$O and saturated NaCl. The organic layer is dried over MgSO$_4$, filtered and concentrated to give the title compound (0.30 g, 0.97 mmol). $^1$H NMR (d6-DMSO, 300 MHz) δ 9.94 (s, 1H), 8.82 (m, 1H), 7.41 (m, 4H), 7.19 (d, 1H), 7.10 (m, 1H), 6.95 (d, 1H), 6.79 (m, 1H), 4.32 (AB, 2H).

EXAMPLE 5

2-Bromomethyl-6-chlorobenzo[b]thiophene

A. 6-Chlorobenzo[b]thiophene-2-carboxaldehyde.

To a solution of 6-chlorobenzo[b]thiophene (1.0 g, 5.93 mmol) in THF (60 mL) at −78° C. is added a 1.6 M solution of n-BuLi in THF (3.9 mL, 6.23 mmol). After 10 minutes, 0.5 mL of DMF is added. The solution is stirred for 0.5 hours, then allowed to warm to ambient temperature. The solution is poured into a solution of saturated NH$_4$Cl. The solution is diluted with ether and the layers are separated. The organic layer is washed with H$_2$O and saturated NaCl. The organic layer is dried over MgSO$_4$, filtered and concentrated. The title compound is obtained as a white solid. MS (EI): m/z 196 (M+).

B. 6-Chlorobenzo[b]thiophen-2-yl)methanol.

To a solution of 6-chlorobenzo[b]thiophene-2-carboxaldehyde in THF at 0° C. is added NaBH$_4$. After 1 hour, the solution is diluted with saturated NH$_4$Cl and ether. The organic layer is washed with H$_2$O and saturated NaCl, dried over MgSO$_4$, filtered and concentrated. $^1$H NMR (CDCl$_3$, 300 MHz) δ 7.82 (s, 1H), 7.60 (d, 1H), 7.40 (m, 2H), 4.91 (AB, 2H).

C. 2-Bromomethyl-6-chlorobenzo[b]thiophene.

To a solution of 6-chlorobenzo[b]thiophen-2-yl)-methanol (0.2 g, 1.01 mmol) in THF (10 mL) is added triphenyl phosphine (0.34 g, 1.31 mmol) followed by CBr$_4$ (0.42 g, 1.26 mmol). After 3 hours, the solution is concentrated. The product is purified by column chromatography eluting in a gradient of 5% EtOAc/hexanes to 10% EtOAc/hexanes. The product is obtained as a white solid (0.25 g, 0.53 mmol). $^1$H NMR (CDCl$_3$, 300 MHz) δ 7.82 (s, 1H), 7.62 (d, 1H), 7.40 (m, 2H), 4.76 (s, 2H).

EXAMPLE 6

5-Bromomethyl-5'-chloro-[2,2']bithiophenyl

A. (5'-Chloro-[2.2']bithiophenyl-5-yl)-methanol.

To a solution of 5-chloro-[2,2']bithiophenyl (3.00 g, 14.9 mmol) in 30 mL of THF at 0° C. is added n-BuLi (9.8 mL of a 1.6M solution in hexanes, 15.7 mmol) dropwise. DMF (2.30 mL, 30 mmol) is added dropwise and the resulting solution is heated at reflux for 1 hour. The solution is diluted with H$_2$O and extracted with Et$_2$O. The organic layer is washed with H$_2$O and saturated NaCl solution, then dried over MgSO$_4$, filtered and concentrated. The crude aldehyde is dissolved in 40 mL of anhydrous MeOH and sodium borohydride (0.85 g, 22.5 mmol) is added portionwise. The mixture is stirred at room temperature for 10 min, then quenched with water. The mixture is diluted with Et$_2$O and the layers separated. The organic layer is washed with H$_2$O, then dried over MgSO$_4$, filtered and concentrated to yield the title compound (2.23 g, 9.66 mmol) which is used in the subsequent step without further purification. $^1$H NMR (CDCl$_3$, 300 MHz) δ 6.95 (d, 1H), 6.90 (m, 2H), 6.86 (d, 1H), 4.82 (s, 2H), 1.88 (bs, 1H).

B. 5-Bromomethyl-5'-chloro-[2,2']bithiophenyl.

To a solution of (5'-chloro-[2,2']bithiophenyl-5-yl)-methanol (2.23 g, 9.66 mmol) in 65 mL of CH$_2$Cl$_2$ is added bromotrimethylsilane (3.82 mL, 29.0 mmol). After 4 h, the solution is concentrated in vacuo. The crude product is stirred in hot hexanes and filtered. The filtrate is concentrated and the title compound (1.67 g, 5.69 mmol) is obtained as a green solid. $^1$H NMR (CDCl$_3$, 300 MHz) δ 7.00 (d, 1H), 6.94 (m, 2H), 6.85 (d, 2H), 4.71 (s, 2H).

EXAMPLE 7

7-Bromomethyl-4-chloroquinazoline

A. 7-Methyl-3H-quinazolin-4-one.

A solution of 2-amino-4-methylbenzoic acid (31.6 g, 206 mmol) in formamide (60 mL) is heated to 130° C. for 1 hour, then at 175° C. for 3 hours. The solution is poured into 500 mL of ice water. The resulting solid is collected by filtration and further dried under reduced pressure. The title compound (26.2 g, 170 mmol) is obtained as a white solid. MS (EI): m/z 159 (M+).

B. 4-Chloro-7-methyl-quinazoline.

To a solution of 7-methyl-3H-quinazolin-4-one (10.6 g, 69 mmol) in toluene (350 mL) is added triethylamine (17.5 g, 173 mmol) followed by phosphorous oxychloride (12.3 g, 80 mmol). The resulting solution is heated to 80° C. After 4 hours, the solution is cooled to ambient temperature. The reaction mixture is poured into 500 mL of water. The layers are separated and the organic layer is washed with $H_2O$, saturated $NaHCO_3$, and saturated NaCl, dried over $MgSO_4$, filtered and concentrated. The resulting crude product is purified by recrystallization from EtOAc. The title compound is obtained as a white solid (10 g, 56 mmol). $^1$H NMR ($CDCl_3$, 300 MHz) δ9.02 (s, 1H), 8.16 (d, 1H), 7.87 (s, 1H), 7.55 (d, 1H), 2.62 (s, 3H).

C. 7-Bromomethyl-4-chloroquinazoline.

To a solution of 4-chloro-7-methylquinazoline (7.0 g, 39 mmol) in carbon tetrachloride (140 mL) is added N-bromosuccinimide (8.0 g, 45 mmol), and benzoyl peroxide (0.8 g, 3.3 mmol). The solution is refluxed for 8 hours. After this time, the solution is filtered. The filtrate is concentrated and the residue is stirred with ether to give the title compound as an off-white solid (5.1 g, 20 mmol). $^1$H NMR ($CDCl_3$, 300 MHz) δ9.10 (s, 1H), 8.30 (d, 1H), 8.10 (s, 1H), 7.82 (d, 1H), 4.68 (s, 2H). MS (EI): m/z 237 (M+).

EXAMPLE 8

3-Bromomethyl-7-chloro-1H-quinolin-2-one

A. N-(3-Chlorophenyl)-2-methyl-3-phenylacrylamide.

To a solution of 3-chloroaniline (0.98 mL, 9.3 mmol) in $CH_2Cl_2$ (25 mL) at 0° C. is added pyridine (0.78 mL, 9.5 mmol). To the resulting solution is added dropwise a solution of α-methyl cinnamic acid chloride (1.6 g, 9.3 mmol) in $CH_2Cl_2$ (8 mL). After 3 hours, the solution is concentrated. The crude product is purified by column chromatography eluting with 5% EtOAc/hexanes to 10% EtOAc/hexanes. The title compound is obtained as a solid (2.5 g, 9.2 mmol). $^1$H NMR ($CDCl_3$, 300 MHz) δ7.95 (m, 1H), 7.73 (s, 1H), 7.46 (m, 1H), 7.33 (m, 6H), 7.22 (m, 1H), 7.03 (m, 1H), 2.13 (s, 3H).

B. 7-Chloro-3-methyl-1H-quinolin-2-one.

To a solution of N-(3-chlorophenyl)-2-methyl-3-phenylacrylamide (2.5 g, 9.2 mmol) in chlorobenzene (50 mL) is added $AlCl_3$ (6.2 g, 46 mmol). The solution is heated to 120° C. After 4 hours the solution is poured onto ice. The solution is filtered. The organic layer is washed with 1N HCl, $H_2O$ and saturated NaCl. The crude product is purified by column chromatography eluting with 2% MeOH/$CH_2Cl_2$. The title compound is obtained as a white solid (1.5 g, 7.74 mmol). $^1$H NMR (d6-DMSO, 300 MHz) δ11.82 (bs, 1H), 7.73 (s, 1H), 7.52 (m, 1H), 7.21 (m, 2H), 2.08 (s, 3H).

C. 3-Bromomethyl-7-chloro-1H-quinolin-2-one.

The title compound is prepared as described in Example 7, Part C, substituting 7-chloro-3-methyl-1H-quinoline-2-one for 7-methyl-4-chloroquinazoline. The title compound is obtained as a white solid. $^1$H NMR (d6-DMSO, 300 MHz) δ12.00 (bs, 1H), 8.17 (s, 1H), 7.72 (d, 1H), 7.29 (m, 2H), 4.58 (s, 2H).

EXAMPLE 4

6-Bromomethyl-2-chloro-quinoline

A. 6-Methyl-1H-quinolin-2-one.

The title compound is prepared from p-toluidine and cinnamoyl chloride according to the procedure described in Synthesis 1975, 739. The crude product obtained is triturated in $Et_2O$/hexanes and filtered to give the title compound as a beige solid. $^1$H NMR (DMSO-$d_6$, 300 MHz) δ11.60 (bs, 1H), 7.82 (d, 1H), 7.41 (s, 1H), 7.30 (d, 1H), 7.18 (d, 1H), 6.45 (d, 1H), 2.30 (s, 3H).

B. 2-Chloro-6-methylquinoline.

6-Methyl-1H-isoquinolin-2-one (14.6 g, 91.7 mmol) in phosphorus oxychloride (160 mL) is heated at 60° C. for 17 hours. The mixture is cooled to room temperature, then concentrated to a beige residue. The residue is diluted with ice water and the pH is adjusted to about 8 by slow addition of 10 N NaOH. The crude product is precipitated out during neutralization of the aqueous solution and the solid is filtered, washed with water and dried. The solid is recrystallize from MeOH to afford the title compound (12.0 g, 67.5 mmol) as a beige solid. $^1$H NMR ($CDCl_3$, 300 MHz) δ8.02 (d, 1H), 7.92 (d, 1H), 7.60 (s, 1H), 7.58 (d, 1H), 7.33 (d, 1H), 2.53 (s, 3H).

C. 6-Bromomethyl-2-chloro-quinoline.

N-Bromosuccinimide (12.9 g, 72.5 mmol) and benzoyl peroxide (0.33 g, 1.30 mmol) are added to a solution of 2-chloro-6-methyl-quinoline (12.0 g, 67.5 mmol) in carbon tetrachloride (300 mL). The mixture is heated at reflux for 6 hours. At this time, the resulting mixture is cooled to room temperature, filtered, washed with $CH_2Cl_2$ and concentrated in vacuo. The crude residue is recrystallized from 50% EtOAc/hexanes to yield the title compound (8.80 g, 34.3 mmol) as a beige crystalline solid. $^1$H NMR ($CDCl_3$, 300 MHz) δ8.08 (d, 1H), 8.02 (d, 1H), 7.83 (s, 1H), 7.77 (dd, 1H), 7.40 (d, 1H), 4.65 (s, 2H). MS (EI): m/z 256, 258 (M+), Cl pattern.

EXAMPLE 10

3-Bromomethyl-1,7-dichloro-2H-isoquinoline

A. 3-(4-Chlorophenyl)-2-methyl-acryloyl azide.

To a solution of 3-(4-chlorophenyl)-2-methyl-acrylic acid (11.2 g, 57 mmol) in 500 mL of acetone at 0° C. is added triethyl amine (9.6 mL, 68 mmol) followed by ethyl chloroformate (6.2 mL, 63 mmol). The solution is allowed to warm to ambient temperatures. After 2 h, sodium azide (5.6 g, 86 mmol) in 35 mL of $H_2O$ is added. After addition, the solution is stirred for 2 hours. The solution is diluted with $H_2O$ (100 mL). The resulting solid is collected by filtration giving the title compound as a white solid (11.1 g, 50 mmol). $^1$H NMR ($CDCl_3$, 300 MHz) δ7.67 (s, 1H), 3.38 (m, 4H), 2.10 9s, 3H).

B. 7-Chloro-3-methyl-2H-isoquinoline-1-one.

3-(4-Chlorophenyl)-2-methyl-acryloyl azide (11.0 g, 50 mmol) is dissolved in 80 mL of diphenyl ether. The solution is added dropwise to a solution of tributyl amine (11.8 mL, 50 mmol) in 170 mL of diphenyl ether at 210° C. After 4 hours., the solution is cooled 50° C. and diluted with 1.5 L of hexanes. The resulting solid is collected by filtration giving the title compound as a white solid (7.2 g, 37 mmol). $^1$H NMR (d6-DMSO, 300 MHz) δ11.4 (bs, 1H), 8.02 (s, 1H), 7.67 (d, 1H), 7.55 (d, 1H), 6.34 (s, 1H), 2.18 (s, 3H).

C. 1,7-Dichloro-3-methyl-isoquinoline.

A solution of 7-chloro-3-methyl-2H-isoquinoline-1-one (7.1 g, 36.7 mmol) in 100 mL of phosphorous oxychloride is heated to 100° C. After 5 h, the solution is concentrated to dryness. The residue is dissolved in $CH_2Cl_2$. The solution is washed with $H_2O$. The organic layer is dried over $MgSO_4$, filtered and concentrated. The crude product is purified by column chromatography eluting with a gradient of 3% EtOAc/hexanes to 5% EtOAc/hexanes. The title compound is obtained as a white solid (6.0 g, 28 mmol). $^1H$ NMR ($CDCl_3$, 300 MHz) δ8.23 (s, 1H), 7.68 (m, 1H), 7.63 (m, 1H), 7.40 (s, 1H), 2.64 (s, 3H).

D. 3-Bromomethyl-1,7-dichloro-2H-isoquinoline.

The title compound is prepared as described in Example 7, part C, substituting 1,7-dichloro-3-methyl-isoquinoline for 4-chloro-7-methylquinazoline. $^1H$ NMR ($CDCl_3$, 300 MHz) δ8.29 (s, 1H), 7.82 (m, 1H), 7.76 (m, 2H), 4.68 (s, 2H).

EXAMPLE 11

3-Bromomethyl-7-chloroisoquinoline

A. 7-Chloro-3-methyl-isoquinoline.

To a solution of 1,7-dichloro-3-methyl-isoquinoline (0.50 g, 2.36 mmol), Example 10, part C, in 5.5 mL of 9:1 acetic acid:$H_2O$ at 75° C. is added zinc (0.23 g, 3.54 mmol) After 75 minutes, the solution is cooled to ambient temperatures. The solution is diluted with a 4:1 EtOAc:$CH_2Cl_2$ solution. To the solution is added 100 mL of a 1N NaOH solution. The aqueous solution is extracted with 4:1 EtOAc:$CH_2Cl_2$. The combined organic layers are washed with a saturated NaCl solution. The organic layer is dried over $MgSO_4$, filtered and concentrated. The crude product is purified by column chromatography eluting with a gradient of 5% EtOAc/hexanes to 15% EtOAc/hexanes. The title compound is obtained as a white solid (0.36 g, 1.97 mmol). $^1H$ NMR ($CDCl_3$, 300 MHz) δ9.09 (s, 1H), 7.89 (s, 1H), 7.61 (d, 1H), 7.55 (d, 1H), 7.44 (s, 1H) 2.68 (s, 3H). MS (EI): m/z 177, 179 (M+), Cl pattern.

B. 3-Bromomethyl-7-chloroisoquinoline.

The title compound is prepared as described in Example 7, part C, substituting 7-chloro-3-methyl-isoquinoline for 4-chloro-7-methylquinazoline. $^1H$ NMR ($CDCl_3$, 300 MHz) δ9.18 (s, 1H), 7.97 (s, 1H), 7.75 (m, 2H), 7.67 (m, 1H), 4.71 (s, 2H).

EXAMPLE 12

2-Bromomethyl-6-chloronaphthalene

A. 6-Chloro-3,4-dihydro-1H-naphthalene-2-one.

To a solution of (4-chlorophenyl)-acetyl chloride (17.3 g, 92 mmol) in 50 mL of $CH_2Cl_2$ at −20° C. is added a solution of $AlCl_3$ (24.4 g, 184 mmol) in 200 mL $CH_2Cl_2$ dropwise. After 20 minutes, ethylene (g) is bubbled through the solution for 30 minutes. The solution is stirred at −10° C. for 15 minutes. The reaction mixture is poured into 300 g of ice. The layers are separated. The organic layer is washed with $H_2O$, saturated $NaHCO_3$ and saturated NaCl. The organic layer is dried over $MgSO_4$, filtered and concentrated. The resulting solid is triturated with pentane (2×20 mL). The solid is then dried to give the title compound as a solid (15.2 g, 84.2 mmol). $^1H$ NMR ($CDCl_3$, 300 MHz) δ7.28 (m, 2H), 7.06 (m, 1H), 3.52 (s, 2H), 3.04 (m, 2H), 2.56 (m, 2H).

B. 6-Chloro-2-methyl-1,2,3,4-tetrahydronaphthalene-2-ol.

To a solution of $TiCl_4$ (95 mL, 1M in toluene) at −45° C. is added a solution of $CH_3MgBr$ (4.2 mL 3M in THF). The solution is stirred for 20 minutes. After this time, 6-chloro-3, 4-dihydro-1H-naphthalene-2-one (11.3 g, 63 mmol) in 80 mL of $CH_2Cl_2$ is added dropwise over 15 minutes. The reaction is stirred for an additional 15 min at −45° C. The solution is warmed to 0° C. After 2 h, the solution is diluted with $H_2O$ and $CH_2Cl_2$. The organic layer is dried over $MgSO_4$, filtered and concentrated. The title compound is obtained as an oil (11.3 g, 57.5 mmol). $^1H$ NMR ($CDCl_3$, 300 MHz) δ7.10 (m, 2H), 6.97 (m, 1H), 3.02 (m, 2H), 2.80 (s, 3H), 1.85 (m, 2H), 1.80 (m, 2H).

C. 2-Chloro-6-methyl naphthalene.

A solution of 6-chloro-2-methyl-1,2,3,4-tetrahydronaphthalene-2-ol (11.3 g, 57.5 mmol) and $Ph_3COH$ (16.5 g, 63 mmol) in 80 mL of TFA is stirred for 2.5 days. After this time, the solution is concentrated to dryness. The residue is dissolved in $CH_2Cl_2$. The organic layer is washed with $H_2O$, saturated $NaHCO_3$, and saturated NaCl. The organic layer is dried over $MgSO_4$, filtered and concentrated. The crude product is purified by column chromatography eluting with hexanes. The title compound is obtained as a white solid (4.05 g, 22.9 mmol). $^1H$ NMR ($CDCl_3$, 300 MHz) δ7.78 (s, 1H), 7.69 (m, 2H), 7.58 (s, 1H), 7.50 (m, 2H), 2.49 (s, 3H).

D. 2-Bromomethyl-6-chloronaphthalene.

The title compound is prepared as described in Example 7, part C, substituting 2-chloro-6-methyl naphthalene for 4-chloro-7-methylquinazoline. $^1H$ NMR ($CDCl_3$, 300 MHz) δ7.82 (m, 2H), 7.78 (s, 1H), 7.76 (m, 2H), 7.52 (d, 1H), 7.42 (d, 1H), 4.62 (s, 2H).

EXAMPLE 13

2-(Benzhydrylidene-amino)-4-bromomethyl-benzonitrile

A. 2-(Benzhydrylidene-amino)-4-methyl-benzonitrile.

To a solution of 2-amino-4-methyl benzonitrile (20 g, 151 mmol) in 1000 mL of dichloroethane is added benzophenone imine (30 g, 166 mmol). The solution is refluxed for 48 hours After this time, the solution is cooled to ambient temperatures. The solution is washed with sat. $NaHCO_3$, water and sat. NaCl. The organic layer is dried over $MgSO_4$, filtered and concentrated under vacuum. The product is further purified by recrystallization from t-butyl ether. The title compound (25.5 g, 118 mmol) is obtained as a yellow solid. $^1H$ NMR ($CDCl_3$, 300 MHz) δ7.88 (m, 2H), 7.42 (m, 3H), 7.32 (m, 7H), 6.79 (d, 1H), 6.58 (s, 1H), 2.23 (s, 3H).

B. 2-(Benzhydrylidene-amino)-4-bromomethyl-benzonitrile.

To a solution of 2-(benzhydrylidene-amino)-4-methyl-benzonitrile (11.2 g, 37.8 mmol) in 500 mL of $CCl_4$ is added N-bromosuccinimide (7.06 g, 39.7 mmol), and benzoyl peroxide (0.92 g, 3.8 mmol). The solution is heated to reflux for 16 hours. After this time, the solution is filtered and the organic solution is concentrated under vacuum. The residue is purified by column chromatography eluting with a gradient of 20% t-butyl ether/hexanes to 25% t-butyl ether/hexanes. The product is obtained as an oil containing a mixture of the desired monobromide, dibromide and unreacted starting material. The mixture is assayed by proton NMR and is found to have a purity between 60-75%. $^1H$ NMR ($CDCl_3$, 300 MHz) δ7.82 (m, 2H), 7.42 (m, 9H), 6.92 (d, 1H), 6.81 (s, 1H), 4.29 (s, 2H).

EXAMPLE 14

7-Bromomethyl-4-chloroquinoline

A. 7-Methyloxycarbonyl-4-chloroquinoline.

4-Chloro-7-trifluoromethylquinoline (5.0 g, 21.6 mmol) in 100 mL 80% $H_2SO_4$ is heated to 200° C. for 24 hours in a sealed tube. The solution is cooled, poured into water and neutralized with sodium hydroxide to pH~3-4. The precipitated solid is collected, washed with water and dissolved in 2 N sodium hydroxide. The aqueous solution is washed with ethyl acetate then acidified to pH~3-4. The precipitate is collected, washed with water and dried in a vacuum oven overnight to yield 7-carboxy-4-chloroquinoline as a solid (5.1 g, 24.6 mmol). A portion of this material (2.0 g, 9.6 mmol) is treated with anhydrous THF (200 mL) and DMF (2 mL) and 2 M oxalyl chloride in methylene chloride (14.5 mL, 29 mmol). The resulting suspension is stirred at room temperature for 2 h then treated with methanol (10 mL). After stirring 30 minutes the solution is concentrated and the residue is taken up in methylene chloride. The solution is washed with saturated sodium bicarbonate and dried (sodium sulfate) and concentrated to yield the title compound as a solid (2.1 g, 9.5 mmol). MS m/z: $M^+$=221; $^1$H NMR ($CDCl_3$, 300 MHz) δ8.6 (s, 1H), 8.2 (s, 1H), 7.9 (d, 1H), 7.65 (d, 1H), 7.45 (s, 1H), 3.95 (s. 3H).

B. 7-Hydroxymethyl-4-chloroquinoline.

7-Methyloxycarbonyl-4-chloroquinoline (2.1 g, 9.5 mmol) is dissolved in anhydrous THF (25 mL) and anhydrous ether (200 mL). The solution is cooled in a dry ice/acetone bath and treated 1M lithium aluminum hydride in THF (11.0 mL, 11 mmol). The solution is warmed (approximately −45° C.) for 20 minutes and quenched with ethyl acetate. The solution is diluted with ether (100 mL) and treated with water (36 mL), 15% NaOH (36 mL) and water (36 mL) in succession. The mixture is filtered and evaporated to yield the title compound as a residue (2.0 g, 9.7 mmol) which is dried under vacuum and used without further purification. MS m/z: $M^+$=193; $^1$H NMR ($CDCl_3$, 300 MHz) δ8.65 (d, 1H), 8.15 (d, 1H), 8.0 (d, 1H), 7.6 (d, 1H), 7.45 (d, 1H), 4.8 (s, 2H).

C. 7-Bromomethyl-4-chloroquinoline.

7-Hydroxymethyl-4-chloroquinoline (0.2 g, 0.97 mmol) is treated with 48% HBr and heated to 120° C. for 1 hours. The resulting solution is cooled with ice, diluted with water and treated with ethyl acetate and sodium bicarbonate until basic to pH paper. The layers are separated and the organic layer is washed with water, dried ($Na_2SO_4$) and concentrated to give 7-bromomethyl-4-chloroquinoline (0.23 g, 0.9 mmol). MS m/z: $M^+$=255; $^1$H NMR ($CDCl_3$, 300 MHz) δ8.75 (d, 1H), 8.25 (d, 1H), 8.1 (s, 1H), 7.7 (d, 1H), 7.5 (d, 1H), 4.7 (s. 2H).

EXAMPLE 15

7-Bromomethyl-4-chlorocinnoline

A. 4-methyl-2-nitrophenylethanone.

4-Fluro-3-nitrotoluene (7.5 g, 48.4 mmol) is treated with a solution of nitroethane (15.2 mL, 200 mmol) in ethyl acetate (100 mL) and DBU (21 mL, 145 mmol) and stirred overnight at ambient temperature. The solution is concentrated under vacuum, diluted with methanol, treated with 30% $H_2O_2$ (25 mL) and 10% sodium bicarbonate (25 ml) and stirred overnight at ambient temperature. The reaction mixture is concentrated in vacuo, acidified with 5% HCl and extracted with methylene chloride. The organic layer is dried (sodium sulfate) and chromatographed (35% ethyl acetate/hexane) to give the title compound (7.2 g, 40.2 mmol). MS m/z: $M^+$=279; $^1$H NMR ($CDCl_3$, 300 MHz) δ7.8 (s, 1H), 7.48 (d, 1H), 7.32 (d, 1H), 2.5 (s, 3H), 2.4 (s, 3H).

B. 2-Amino-4-methylphenylethanone.

A solution of 4-methyl-2-nitrophenylethanone (5.0 g, 28 mmol) in methanol (100 mL) is treated with ammonium formate (9.6 g, 140 mmol) and 5% palladium on carbon (1.5 g). The mixture is heated to 60° C. for 6 h then stirred at ambient temperature for 16 hours. The reaction mixture is filtered through Celite and the filtrate is concentrated in vacuo. The concentrate is treated with sodium bicarbonate and partitioned between water and ethyl acetate. The organic layer is separated, dried with sodium sulfate and concentrated to give crude title compound (4.5 g, 30.2 mmol) which is used without further purification. MS m/z: $M^+$=149; $^1$H NMR ($CDCl_3$, 300 MHz) δ8.05 (d, 1H), 7.4 (d, 1H), 7.25 (s, 1H), 2.8 (s, 3H), 2.45 (s, 3H).

C. 7-Methyl-1-H-cinnolin-4-one.

A solution of 2-amino-4-methylphenylethanone (5.0 g, 33.6 mmol) in concentrated HCl (100 mL) is treated, in portions, with a solution of sodium nitrite (5.7 g, 82.6 mmol) in water (~10 mL). The resulting solution is stirred at 60° C. for 2 hr, cooled to ambient temperature and diluted with a saturated solution of sodium acetate (~200 mL). Solid sodium acetate is added portionwise until the solution tested basic to pH paper. Upon stirring, the title compound precipitated as a white solid which is collected and air dried (2.3 g, 14.3 mmol). MS m/z: $[M+H]^+$=161; $^1$H NMR ($CDCl_3$, 300 MHz) δ8.1 (d, 1H), 7.85 (s, 1H), 7.45 (s, 1H) 7.3 (d, 1H), 2.55 (s, 3H).

D. 4-Chloro-7-methylcinnoline.

7-Methyl-1-H-cinnolin-4-one (1.3 g, 8.1 mmol) is treated with about 80 mL of chlorobenzene and heated until the solid dissolves. The resulting solution is cooled and treated with pyridine (0.16 mL, 2 mmol) and $POCl_3$ (1.13 mL, 12.2 mmol). The solution is heated to reflux for 1 h then concentrated to dryness. The residue is chromatographed (20% ethyl acetate/hexane) to yield the title compound as a tan solid (~1 g, 5.6 mmol). MS m/z (M+=178); $^1$H NMR ($CDCl_3$, 300 MHz) δ9.3 (s, 1H), 8.35 (s, 1H), 8.1 (d, 1H), 7.7 (d, 1H), 2.68 (s, 3H).

E. 7-Bromomethyl-4-chlorocinnoline.

A solution of 4-chloro-7-methylcinnoline (0.6 g, 3.37 mmol) in carbon tetrachloride (30 mL) is treated with N-bromosuccinimide (0.64 g, 3.4 mmol) and a catalytic amount of 70% benzoyl peroxide (0.22 g, 0.63 mmol). The solution is heated to 80° C. overnight, then filtered. The filtrate is concentrated in vacuo and the resulting residue is chromatographed (20% ethyl acetate/methyl chloride) to give the title compound (0.3 g, 1.2 mmol) and some unreacted starting material (0.1 g, 0.56 mmol). MS m/z: $[M+H]^+$=257; $^1$H NMR ($CDCl_3$, 300 MHz) δ9.35 (s, 1H), 8.55 (s, 1H), 8.2 (d, 1H), 8.85 (d, 1H), 4.75 (s, 2H).

EXAMPLE 16

6-Bromomethyl-3-chloro-1-(toluene-4-sulfonyl)-1H-indole

A. 1H-Indole-6-carboxylic acid methyl ester.

To a solution of 6-indole carboxylic acid (0.91 g, 5.67 mmol) in 33 mL of 2:1 THF/MeOH is added (trimethylsilyl) diazomethane (5.0 mL of a 2.0M solution in hexanes, 10.0 mmol). The mixture is stirred for 3 h and concentrated in vacuo to give the title compound (0.87 g, 4.97 mmol). The crude product is used in the next step without further purification. $^1$H NMR (CDCl$_3$, 300 MHz) δ8.70 (bs, 1H), 8.20 (s, 1H), 7.82 (dd, 1H), 7.67 (d, 1H), 7.45 (m, 1H), 6.60 (m, 1H), 3.95 (s, 3H).

B. 3-Chloro-1H-indole-6-carboxylic acid methyl ester.

To a solution of 1H-indole-6-carboxylic acid methyl ester (5.86 g, 33.5 mmol) in 30 mL of CH$_2$Cl$_2$ is added N-chlorosuccinimide (0.58, 4.33 mmol) portionwise over 1.5 hours. The mixture is stirred for 2 h, then diluted with water. The layers are separated and the organic phase is washed with water and saturated NaCl solution. The organic layer is dried over MgSO$_4$, filtered and concentrated in vacuo to give the title compound (5.74 g, 27.3 mmol). The crude product is used in the next step without further purification. $^1$H NMR (CDCl$_3$, 300 MHz) δ8.46 (bs, 1H), 8.19 (s, 1H), 7.90 (dd, 1H), 7.69 (d, 1H), 7.36 (d, 1H), 3.97 (s, 3H).

C. 3-Chloro-1-(toluene-4-sulfonyl)-1H-Indole-6-carboxylic acid methyl ester.

To a solution of 3-chloro-1H-indole-6-carboxylic acid methyl ester (3.00 g, 17.1 mmol) in 40 mL of THF at −78° C. is added LDA(8.55 mL of a 2.0M solution in hexanes, 17.1 mmol) dropwise. The solution is stirred at −78° C. for 30 minutes p-Toluenesulfonyl chloride (3.43 g, 18.0 mmol) in 15 mL of THF is added dropwise and the resulting solution is stirred at −78° C. for 3 hours. The mixture is warmed to 0° C., quenched with saturated NaHCO$_3$ solution and diluted with H$_2$O and Et$_2$O. The layers are separated. The organic phase is washed with saturated NaHCO$_3$ solution, H$_2$O and saturated NaCl solution, then dried over MgSO$_4$, filtered and concentrated. The crude residue is purified via flash column chromatography eluting with a gradient of 10% EtOAc/hexanes to 30% EtOAc/hexanes to provide the title compound (3.64 g, 10.0 mmol). $^1$H NMR (CDCl$_3$, 300 MHz) δ8.70 (s, 1H), 8.01 (dd, 1H), 7.80 (d, 2H), 7.70 (s, 1H), 7.60 (d, 1H), 7.38 (m, 2H), 4.00 (s, 3H), 2.49 (s, 3H).

D. [3-Chloro-1-(toluene-1-sulfonyl)-1H-indol-6-yl]-methanol.

To a solution of 3-chloro-1-(toluene-4-sulfonyl)-1H-Indole-6-carboxylic acid methyl ester (3.10 g, 8.53 mmol) in 50 mL of toluene at −78° C. is added DIBAL (13.8 mL of a 1.5M solution in toluene, 20.8 mmol) dropwise. The mixture is stirred at −78° C. for 2 h, then warmed to room temperature and stirred for 2 hours. The reaction mixture is quenched by the addition of MeOH and washed with saturated disodium tartrate solution. The aqueuos layer is extracted with Et$_2$O. The combined organics are washed with saturated disodium tartrate solution, water and saturated NaCl solution. The organic phase is then dried over anhydrous MgSO$_4$, filtered and concentrated to give the title compound (2.88 g). The crude product is used in the next step without further purification. $^1$H NMR (CDCl$_3$, 300 MHz) δ8.01 (s, 1H), 7.79 (d, 2H), 7.56 (s, 1H), 7.53 (d, 1H), 7.31 (d, 1H), 7.25 (d, 2H), 4.84 (s, 2H), 2.37 (s, 3H), 1.88 (bs, 1H).

E. 6-Bromomethyl-3-chloro-1-(toluene-4-sulfonyl)-1H-indole.

To a solution of [3-chloro-1-(toluene-1-sulfonyl)-1H-indol-6-yl]-methanol (0.45 g, 1.34 mmol) in 13 mL of Et$_2$O at 0° C. is added phosphorous tribromide (0.04 mL, 0.40 mmol). The mixture is stirred at 0° C. for 15 min, then at room temperature for 2 hours. The mixture is quenched by the addition of water/ice and diluted with Et$_2$O. The layers are separated and the organic phase is washed with saturated NaHCO$_3$ solution, water and saturated NaCl solution. The organic layer is dried over anhydrous MgSO$_4$, filtered and concentrated to provide the title compound (0.47 g, 1.18 mmol) as an oil. The crude product is used in the subsequent step without further purification. $^1$H NMR (CDCl$_3$, 300 MHz) δ8.09 (s, 1H), 7.79 (d, 2H), 7.59 (s, 1H), 7.50 (d, 1H), 7.35 (d, 1H), 7.27 (m, 2H), 4.66 (s, 2H), 2.39 (s, 3H).

EXAMPLE 17

2-(3-Bromo-(E)-propenyl)-5-chloro-thiophene

A. 3-(5-Chloro-thiophen-2-yl)-(E)-acrylic acid methyl ester.

To a solution of 5-chloro-2-thiophene-carboxaldehyde (5.10 g, 34.8 mmol) in 100 mL of dry CH$_2$Cl$_2$ is added methyl (triphenylphosphoranylidene)acetate (11.8 g, 35.3 mmol). The resulting brown-green mixture is stirred for 19 h at room temperature. The mixture is filtered through a Celite pad, concentrated in vacuo and triturated with hexane. The white precipitate (triphenylphosphine oxide) is filtered off and the filtrate is concentrated. The crude residue is purified via flash column chromatography eluting with a gradient of 5% EtOAc/hexanes to 10% EtOAc/hexanes to provide the title compound (6.20 g, 30.6 mmol) as a yellow solid. $^1$H NMR (CDCl$_3$, 300 MHz) δ7.65 (d, 1H), 7.05 (d, 1H), 6.89 (d, 1H), 6.10 (d, 1H), 3.80 (s, 3H).

B. 3-(5-Chloro-thiophen-2-yl)-prop-2-(E)-en-1-ol.

To a solution of 3-(5-chloro-thiophen-2-yl)-(E)-acrylic acid methyl ester (5.00 g, 24.7 mmol) in 80 mL of CH$_2$Cl$_2$ at 0° C. is added slowly a solution of DIBAL (36.2 mL of a 1.5M solution in toluene, 54.3 mmol). The mixture is stirred at 0° C. for 15 min, then quenched by the addition of 6 mL of MeOH. The mixture is allowed to warm to room temperature, diluted with water/ice and stirred for 15 minutes. The mixture is filtered through a pad of Celite and washed with CH$_2$Cl$_2$. The layers are separated and the aqueous layer is extracted with CH$_2$Cl$_2$. The combined organics are washed with saturated NaCl solution, dried over anhydrous Na$_2$SO$_4$, filtered and concentrated. The residue is purified via flash column chromatography eluting with a gradient of 15% EtOAc/hexanes to 25% EtOAc/hexanes to afford the title compound (4.18 g, 23.9 mmol) as an oil. $^1$H NMR (CDCl$_3$, 300 MHz) δ6.77 (d, 1H), 6.71 (d, 1H), 6.60 (d, 1H), 6.10 (m, 1H), 4.30 (d, 2H), 1.79 (bs, 1H).

C. 2-(3-Bromo-(E)-propenyl)-5-chloro-thiophene.

To a solution of 3-(5-chloro-thiophen-2-yl)-prop-2-(E)-en-1-ol (4.18 g, 23.9 mmol) in 140 mL of Et$_2$O at 0° C. is added phosphorous tribromide (1.34 mL, 14.3 mmol) in 10 mL of Et$_2$O. The mixture is stirred at 0° C. for 45 min, then at room temperature for 1.5 hours. The mixture is quenched by the addition of water/ice and diluted with Et$_2$O. The layers are separated and the organic phase is washed with water until neutral (3×) and once with saturated NaCl solution. The organic layer is dried over anhydrous MgSO$_4$, filtered and concentrated to provide the title compound (5.46 g, 23.0 mmol) as an oil. The crude material solidified upon storage in the freezer and can be used in the subsequent step without further purification. $^1$H NMR (CDCl$_3$, 300 MHz) δ6.80 (m, 2H), 6.65 (d, 1H), 6.10 (m, 1H), 4.10 (d, 2H).

EXAMPLE 18

3-(4-Bromo-furan-2-yl)-(E)-propenal

To a solution of 4-bromo-2-furfuraldehyde (0.5 g, 2.86 mmol) in 30 mL of dry CH$_2$Cl$_2$ is added (triphenylphosphoranylidene)acetaldehyde (0.87 g, 2.86 mmol). The resulting mixture is stirred for 16 h at room temperature. The crude mixture is concentrated in vacuo and the residue is purified via flash column chromatography eluting with $CH_2Cl_2$ to provide the title compound (0.15 g, 0.75 mmol) as a white solid. $^1$H NMR (CDCl$_3$, 300 MHz) δ9.62 (d, 1H), 7.59 (s, 1H), 7.18 (d, 1H), 6.81 (s, 1H), 6.60 (m, 1H).

EXAMPLE 19

Acetic acid 3-(6-methoxy-pyridin-3-yl)-(E)-allyl ester

To a solution of 3-(6-methoxy-pyridin-3-yl)-prop-2-(E)-en-1-ol (0.39 g, 2.36 mmol, prepared as described in EXAMPLE 17 from 6-methoxy-pyridine-3-carbaldehyde (J. Org. Chem. 1990, 72)) in 8 mL of $CH_2Cl_2$ at 0° C. is added triethylamine (0.66 mL, 4.72 mmol), DMAP (0.05 g, 0.40 mmol) and Ac$_2$O (0.33 mL, 3.54 mmol). The mixture is stirred at 0° C. for 45 min, then at room temperature for 16 hours. The mixture is diluted with Et$_2$O and washed with 1N HCl, water, saturated. NaHCO$_3$ solution and saturated NaCl solution. The organic layer is dried over anhydrous MgSO$_4$, filtered and concentrated. The residue is purified via flash column chromatography eluting with a gradient of 10% EtOAc/hexanes to 20% EtOAc/hexanes to afford the title compound (0.25 g, 1.21 mmol) as an oil. $^1$H NMR (CDCl$_3$, 300 MHz) δ8.12 (d, 1H), 7.68 (dd, 1H), 6.72 (d, 1H), 6.60 (d, 1H), 6.18 (dt, 1H), 4.73 (d, 2H), 3.95 (s, 3H), 2.10 (s, 3H).

EXAMPLE 20

2-(3-Bromo-prop-1-ynyl)-5-chloro-thiophene

A. 3-(5-Chloro-thiophen-2-yl)-prop-2-yn-1-ol.

Nitrogen (g) is bubbled through a solution of 5-bromo-2-chloro-thiophene (1.00 g, 5.06 mmol) in 8 mL of piperidine. After 5 min, propargyl alcohol (0.32 mL, 5.56 mmol), tetrakis (triphenylphosphine) palladium(0) (0.06 g) and CuI (catalytic amount) are added to the solution. The mixture is heated at 80° C. for 1 h in a sealed glass vessel. At this time, the mixture is cooled and diluted with EtOAc/Et$_2$O. The organic layer is washed 3N HCl, water, saturated NaHCO$_3$ solution and saturated NaCl solution. The organic layer is dried, filtered and concentrated. The crude residue is purified via flash column chromatography eluting with a gradient of 10% EtOAc/hexanes to 20% EtOAc/hexanes to give the title compound (0.8 g, 0.46 mmol) as an oil. $^1$H NMR (DMSO-d$_6$, 300 MHz) δ6.99 (d, 1H), 6.80 (d, 1H), 4.49 (s, 2H), 1.90 (bs, 1H). EI MS, [M]$^+$=172, 174 (Cl pattern).

B. 2-(3-Bromo-prop-1-ynyl)-5-chloro-thiophene.

The title compound is prepared as described in EXAMPLE 17, Part C, using 3-(5-chloro-thiophen-2-yl)-prop-2-yn-1-ol in place of 3-(5-chloro-thiophen-2-yl)-prop-2-(E)-en-1-ol. The crude product is used in the subsequent step without further purification. $^1$H NMR (CDCl$_3$, 300 MHz) δ7.04 (d, 1H), 6.80 (d, 1H), 4.98 (d, 2H).

EXAMPLE 21

2-Bromomethyl-5-chloro-indole-1-carboxylic acid tert-butyl ester

A. 5-Chloro-2-methyl-indole-1-carboxylic acid tert-butyl ester.

A solution containing 5-chloro-2-methylindole (4.0 g, 24.1 mmol) and DMAP (295 mg, 2.42 mmol) in anhydrous THF (100 mL) is cooled to 0° C. A solution containing (Boc)$_2$O (5.27 g, 24.1 mmol) in anhydrous THF (100 mL) is then added over a 20 min period. The reaction mixture is stirred for 2 h at 0° C. and then at ambient temperature for 16 hours. The reaction mixture is concentrated and the crude residue is purified by flash silica gel chromatography (2% EtOAc/hexane to 5% EtOAc/hexane) to provide 5.2 g (81%) of title compound as a pale yellow solid. $^1$H NMR (300 MHz, CDCl$_3$) δ1.67 (s, 9H), 2.57 (s, 3H), 6.24 (t, J=0.9 Hz, 1H), 7.16 (dd, J=8.8, 2.1 Hz, 1H), 7.38 (d, J=2.1 Hz, 1H), 8.01 (d, J=8.8 Hz, 1H) ppm; MS (EI): m/z 265 (M+).

B. 2-Bromomethyl-5-chloro-indole-1-carboxylic acid tert-butyl ester.

A solution containing 5-chloro-2-methyl-indole-1-carboxylic acid tert-butyl ester (3.0 g, 11.3 mmol), NBS (1.33 g, 11.3 mmol), and benzoyl peroxide (0.4 g, 1.13 mmol) in CCl$_4$ (100 mL) is heated at 80° C. for 3 hours. An additional portion of NBS (0.65 g, 5.65 mmol), and benzoyl peroxide (0.2 g, 0.56 mmol) is then added and the reaction mixture is heated for an additional 3 hours. After cooling to ambient temperature, the reaction mixture is filtered. The filtrate is concentrated to a brown oil which is triturated with hexane to remove residual succinimide, filtered, and concentrated. The resultant oil (4.5 g, >100%) is used directly in the next reaction without further purification. $^1$H NMR (300 MHz, CDCl$_3$) δ1.72 (s, 9H), 4.88 (s, 2H), 6.63 (s, 1H), 7.27 (dd, J=9.0, 2.0 Hz, 1H), 7.46 (d, J=2.0 Hz, 1H), 8.09 (d, J=9.0 Hz, 1H) ppm; MS (EI): m/z 343 (M+).

EXAMPLE 22

3-Bromomethyl-5-iodo-2-methoxy-pyridine

A. 5-Iodo-3-methyl-2-methoxy-pyridine.

To a solution containing 2-bromo-5-iodo-3-methyl-pyridine (4.80 g, 16.0 mmol) in DMSO (15 mL) is added methanolic NaOMe (3.33 M, 5.3 mL, 17.7 mmol) at 0° C. The solution is allowed to warm to ambient temperature and then heated at 70° C. for 1 hour. The reaction mixture is diluted with diethyl ether (300 mL) and water (200 mL) and the layers are separated. The organic phase is washed with brine, dried over anhydrous Na$_2$SO$_4$, filtered and concentrated. The crude product is purified by silica gel flash column chromatography (hexane/diethyl ether, 19:1) to provide 2.86 g (71%) of the title compound as a white solid. $^1$H NMR (300 MHz, CDCl$_3$) δ2.12 (s, 3H), 3.90 (s, 3H), 7.60 (d, J=2.1 Hz, 1H), 8.14 (d, J=2.1 Hz, 1H) ppm; MS (EI): m/z 249 (M+).

B. 3-Bromomethyl-5-iodo-2-methoxy-pyridine.

A solution containing 5-iodo-3-methyl-2-methoxy-pyridine (1.00 g, 4.00 mmol) and NBS (0.78 g, 4.40 mmol) in CCl$_4$ (20 mL) is warmed to reflux. AIBN is added in 5 mg portions (0.03 mmol) every hour. After 3 h, the reaction mixture is cooled and then concentrated in vacuo. The residue is dissolved in EtOAc (150 mL) and washed successively with aqueous Na$_2$S$_2$O$_3$ (100 mL), water (100 mL), brine then dried over anhydrous Na$_2$SO$_4$, filtered and concentrated. The crude product ispurified by silica gel flash column chromatography (hexane/diethyl ether, 19:1) to provide 0.72 g (55%) of the title compound as a white solid. $^1$H NMR (300 MHz, CDCl$_3$) δ3.97 (s, 3H), 4.38 (s, 2H), 7.83 (d, J=2.2 Hz, 1H), 8.27 (d, J=2.2 Hz, 1H) ppm; MS (EI): m/z 327 (M+).

EXAMPLE 23

5-Bromomethyl-6-methoxy-nicotinic acid methyl ester

A. 6-Methoxy-5-methyl-nicotinic acid methyl ester.

A solution containing 5-iodo-3-methyl-2-methoxy-pyridine (10.0 g, 40.0 mmol), $Et_3N$ (8.0 g, 80.0 mmol), and $(Ph_3P)_4PdCl_2$ (2.80 g, 4.00 mmol) in 1:1 DMF/MeOH (100 mL) is cooled to 0° C. Carbon monoxide is bubbled into the cooled solution for approx. 5 min at which time the reaction mixture is sealed under a balloon of CO. The reaction mixture is allowed to warm to ambient temperature and then stirred for 16 hours. The reaction mixture is concentrated in vacuo and the residue is partitioned between water (300 mL) and EtOAc (300 mL) and the layers are separated. The organic phase is washed with brine, dried over anhydrous $Na_2SO_4$, filtered and concentrated. The crude product is purified by silica gel flash column chromatography (hexane/diethyl ether, 19:1) to provide 4.10 g (57%) of the title compound as a white solid. $^1$H NMR (300 MHz, $CDCl_3$) δ2.20 (s, 3H), 3.88 (s, 3H), 4.00 (s, 2H), 7.96 (d, J=2.2 Hz, 1H), 8.65 (d, J=2.2 Hz, 1H) ppm; MS (ISP loop): m/z 182 (M+H).

B. 5-Bromomethyl-6-methoxy-nicotinic acid methyl ester.

A solution containing 6-methoxy-5-methyl-nicotinic acid methyl ester (4.00 g, 22.1 mmol), NBS (5.11 g, 28.7 mmol), and AIBN (0.90 g, 5.5 mmol) in $CCl_4$ (100 mL) is warmed to reflux. After 5 h, the reaction mixture is cooled and then concentrated in vacuo. The residue is dissolved in EtOAc (500 mL) and washed successively with aqueous $Na_2S_2O_3$ (300 mL), water (100 mL), brine then dried over anhydrous $Na_2SO_4$, filtered and concentrated. The crude product is purified by silica gel flash column chromatography (hexane/diethyl ether, 9:1) to provide 3.10 g (54%) of the title compound as a white solid. $^1$H NMR (300 MHz, $CDCl_3$) δ3.90 (s, 3H), 4.07 (s, 3H), 4.46 (s, 2H), 8.19 (d, J=2.2 Hz, 1H), 8.79 (d, J=2.2 Hz, 1H) ppm; MS (EI): m/z 259 (M+).

EXAMPLE 24

5-Chloro-2-thienyloxyacetic acid

A. 2-Hydroxy-thiophene.

Thiophene (42 g, 500 mmol) is dissolved in ether (250 mL). To the solution is added n-BuLi (200 mL of a 2.5N solution in hexanes, 500 mmol) at a rate which maintains a gentle reflux. After addition, the solution is stirred for 0.5 hour. The solution is then cooled to −78° C. and triethyl borate (102 g, 700 mL) is added dropwise. The solution is stirred for 3 hours. The cold bath is removed and 130 mL of a 30% $H_2O_2$ is added dropwise with rapid stirring. After addition, the solution is allowed to refluxed for an additional 20 minutes. The solution is then cooled to 0° C. and acidified to pH=3 with 6N HCl. The resulting solution is extracted with ether. The organic solution is washed with 10% ferric ammonium sulfate, water and saturated NaCl. The solution is dried over $MgSO_4$, filtered and concentrated under vacuum. The title compound (32 g, 320 mmol) is obtained as an oil. $^1$H NMR ($CDCl_3$, 300 MHz) δ7.60 (m, 1H), 6.35 (m, 1H), 4.12 (d, 2H).

B. Ethyl 2-thienyloxyacetate.

To a solution of 2-hydroxy-thiophene (32 g, 320 mmol) in $CHCl_3$ (500 mL) is added ethyl bromoacetate (53.4 g, 320 mmol). To the resulting solution is added a solution containing $n-Bu_4NHSO_4$ (25 g, 74 mmol) and NaOH (15.8 g, 394 mmol) in water (500 mL). After addition, the solution is stirred vigorously using mechanical stirring. The reaction is stirred for 12 hours. After this time, the layers are separated. The aqueous layer is extracted with $CHCl_3$. The combined organic layers are washed with water and saturated NaCl. The organic layer is dried over $MgSO_4$, filtered and concentrated under vacuum. The resulting crude product is purified by column chromatography eluting with a gradient of 30%$CH_2Cl_2$:hexanes to 60%$CH_2Cl_2$:hexanes. The title compound (11.5 g, 62 mmol) is obtained as $^1$H NMR ($CDCl_3$, 300 MHz) δ6.68 (dd, 1H), 6.60 (d, 1H), 6.22 (d, 1H), 4.62 (s, 2H), 4.30 (q, 2H), 1.31 (t, 3H).

C. Ethyl 5-chloro-2-thienyloxyacetate.

To a solution of ethyl 2-thienyloxyacetate (1.1 g, 5.9 mmol) in acetic acid (15 mL) is added N-chlorosuccinimide (0.78 g, 5.9 mmol). The solution is stirred for 1.5 hour. After this time the solution is concentrated. The resulting oil is dissolved in ether and washed with 1N NaOH, water and sat. NaCl. The organic layer is dried over $MgSO_4$, filtered and concentrated under vacuum. The title compound (1.26 g, 5.7 mmol) is obtained as an oil. $^1$H NMR ($CDCl_3$, 300 MHz) δ6.52 (d, 1H), 6.06 (d, 1H), 4.60 (s, 2H), 4.24 (q, 2H), 1.31 (t, 3H).

D. 5-Chloro-2-thienyloxyacetic acid.

To a solution of ethyl 5-chloro-2-thienyloxyacetate (0.39 g, 1.77 mmol) in 9 mL of a 1:1:1 mixture of $CH_3OH$:THF:water is added LiOH (0.38 g, 9.0 mmol). The solution is stirred for 16 hours. After this time, the solution is concentrated to ⅓ its volume. The resulting solution is acidified to pH=3 with 1N HCl. The aqueous solution is extracted with $CH_2Cl_2$. The organic layer is dried over $MgSO_4$, filtered and concentrated under vacuum. The title compound (0.32 g, 1.66 mmol) is obtained as a white solid. $^1$H NMR ($CDCl_3$, 300 MHz) δ6.50 (d, 1H), 6.07 (d, 1H), 4.66 (s, 2H).

EXAMPLE 25

3-(5-Chloro-thiophen-2-yl)-(E)-acrylic acid

To a mixture of 3-(5-chloro-thiophen-2-yl)-(E)-acrylic acid methyl ester (0.60 g, 2.96 mmol) in 15 mL of 1:1:1 THF/MeOH/$H_2O$ at 0° C. is added lithium hydroxide monohydrate (0.62 g, 14.7 mmol). The mixture is stirred at 0° C. for 1 h, then at room temperature for 1 h and concentrated in vacuo. The residue is diluted with EtOAc and washed with 1N HCl. The aqueous layer is extracted with EtOAc and the combined organics are washed with water (2×), dried, filtered and concentrated to provide the title compound (0.54 g, 2.86 mmol) as a white solid. The crude material can be used in the subsequent step without further purification. $^1$H NMR ($CDCl_3$, 300 MHz) δ7.65 (d, 1H), 7.05 (d, 1H), 6.90 (d, 1H), 6.10 (d, 1H).

EXAMPLE 26

3-(4-Chloro-thiophen-2-yl)-(E)-acrylic acid

A. 4-Chloro-2-thiophene-carboxaldehyde.

To a solution of 2-thiophene-carboxaldehyde (6.33 g, 56.4 mmol) in 100 mL of $CHCl_3$ at 0° C. is added aluminum trichloride (16.8 g, 126 mmol) portionwise over a few minutes. In a separate vessel, chlorine gas (4.00 g) is bubbled for about 2 min into 100 mL of $CCl_4$ at 0° C. and then added to the former mixture slowly at 0° C. The resulting mixture is stirred at 0° C. for 45 min, then allowed to warm to room temperature and stirred overnight. After 16 h, the reaction mixture is poured slowly into 6N HCl at 0° C., then stirred at room temperature for 2 hours. The layers are separated. The aqueous layer is extracted with CHCl$_3$. The combined organic layers are washed with H$_2$O and saturated NaCl solution, then dried over MgSO$_4$, filtered and concentrated. The crude product is purified by column chromatography eluting with 10% EtOAc/hexanes to yield the title compound (6.70 g, 45.9 mmol). $^1$H NMR (CDCl$_3$, 300 MHz) δ9.87 (s, 1H), 7.64 (s, 1H), 7.63 (s, 1H).

B. 3-(4-Chloro-thiophen-2-yl)-(E)-acrylic acid methyl ester.

The title compound is prepared as described in EXAMPLE 1, Part A from 4-chloro-2-thiophene-carboxaldehyde. $^1$H NMR (CDCl$_3$, 300 MHz) δ7.69 (d, 1H), 7.15 (s, 1H), 7.11 (s, 1H), 6.25 (d, 1H), 3.82 (s, 3H).

C. 3-(4-Chloro-thiophen-2-yl)-(E)-acrylic acid.

The title compound is prepared as described in EXAMPLE 1, Part B from 3-(4-chloro-thiophen-2-yl)-(E)-acrylic acid methyl ester. $^1$H NMR (CDCl$_3$, 300 MHz) δ7.77 (d, 1H), 7.19 (d, 2H), 6.25 (d, 1H).

EXAMPLE 27

(5-Chloro-thiophen-2-yl)-acetic acid

A. [2-(5-Chloro-thiophen-2-yl)-1-dimethylaminovinyl] phosphonic acid diethyl ester.

To a suspension of sodium hydride (0.25 g, 6.25 mmol, 60% mineral oil dispersion) in 10 mL of THF is added slowly a solution of tetraethyl dimethylaminomethylenediphosphonate (2.03 g, 6.14 mmol, prepared according to the procedure described in Psaume, Montury, and Cosmetic Comm. 1982, 12, 415) in 10 mL of THF. After stirring 1 h, a solution of 5-chloro-2-thiophene carboxaldehyde (0.90 g, 6.14 mmol) in 10 mL of THF is added. The resulting mixture is heated at reflux for 1 h, then cooled to room temperature. The reaction mixture is partitioned between Et$_2$O and water. The organic layer is washed sequentially with 1N HCl, water and saturated NaCl, then dried over MgSO$_4$, filtered and concentrated. The crude product is purified via flash column chromatography eluting with a gradient of 40% EtOAc/hexanes to 50% EtOAc/hexanes to afford the title compound (1.52 g, 4.69 mmol) as an oil. $^1$H NMR (CDCl$_3$, 300 MHz) δ7.20 (d, 1H), 6.95 (d, 1H), 6.82 (d, 1H), 4.15 (m, 4H), 2.62 (s, 6H), 1.60 (t, 6H).

B. (5-Chloro-thiophen-2-yl)-acetic acid.

A mixture of [2-(5-chloro-thiophen-2-yl)-1-dimethylaminovinyl]phosphonic acid diethyl ester (1.52 g, 4.69 mmol) and 30 mL of 6N HCl is heated at reflux for 2 hours. After cooling to room temperature, ice water is added and the mixture is partitioned between Et$_2$O and water. The organic layer is washed with water (2×), dried over MgSO$_4$, filtered and concentrated to give the title compound (0.62 g, 3.51 mmol) as a brown solid. The crude material can be used in the subsequent step without further purification. $^1$H NMR (CDCl$_3$, 300 MHz) δ8.30 (bs, 1H), 7.79 (d, 1H), 6.71 (d, 1H), 3.81 (s, 2H).

EXAMPLE 28

3-(5-Chloro-thiophen-2-yl)-propionic acid

A. 3-(5-Chloro-thiophen-2-yl)-propionaldehyde.

To a mixture of Pd(OAc)$_2$ (0.12 g, 0.53 mmol), NaHCO$_3$ (0.52 g, 6.19 mmol) and NaI (0.28 g, 1.87 mmol) in 5 mL of HMPA is added 5-bromo-2-chloro-thiophene (1.00 g, 5.06 mmol) and allyl alcohol (1.03 mL, 15.2 mmol). The mixture is heated to 90° C. and stirred for 16 hours. The reaction mixture is cooled to room temperature, diluted with Et$_2$O and washed with water. The organic layer is dried over MgSO$_4$, filtered and concentrated in vacuo. The crude residue is purified by flash column chromatography eluting with a gradient of 10% Et$_2$O/hexanes to 20% Et$_2$O/hexanes to provide the product (0.18 g, 1.03 mmol) as an oil. $^1$H NMR (CDCl$_3$, 300 MHz) δ9.81 (s, 1H), 6.71 (d, 1H), 6.58 (d, 1H), 3.07 (t, 2H), 2.81 (t, 2H).

B. 3-(5-Chloro-thiophen-2-yl)-propionic acid.

Silver nitrate (117 mg, 0.69 mmol) in 1 mL of H$_2$O is added to 1.36 mL of 1N NaOH at 0° C. and stirred for 5 minutes. To the brown suspension is added 3-(5-chloro-thiophen-2-yl)-propionaldehyde (60 mg, 0.34 mmol) and the resulting mixture is allowed to warm to room temperature over 2 hours. The precipitate is filtered and washed with hot water (2×). The combined aqueous layers are acidified with 6 N HCl and extracted with EtOAc (2×). The combined organic layers are washed with water (2×), then dried over MgSO$_4$, filtered and concentrated in vacuo to give the title compound (50 mg, 0.26 mmol) as a beige solid. The crude material can be used in the subsequent step without further purification. $^1$H NMR (CDCl$_3$, 300 MHz) δ6.72 (d, 1H), 6.60 (d, 1H), 3.07 (t, 2H), 2.71 (t, 2H).

EXAMPLE 29

3-Fluorophenoxy-acetic acid

A. 3-Fluorophenoxy-acetic acid ethyl ester.

To a solution of 3-fluorophenol (1.2 g, 11.8 mmol) in 20 mL of DMF at 0° C. is added sodium hydride (0.47 g, 10.7 mmol). After stirring for 10 minutes Ethyl bromoacetate (1.2 g, 10.7 mmol) is added dropwise. The reaction is allowed to warm to ambient temperatures and is stirred for 16 hours. To the reaction is added a saturated solution NH$_4$Cl (aq.). The resulting mixture is diluted with EtOAc and H$_2$O. The layers are separted. The organic layer is washed with H$_2$O and a saturated solution NaCl (aq.). The organic layer is dried over MgSO$_4$, filtered and concentrated to give the product (2 g, 10 mmol) as an oil. $^1$H NMR (CDCl$_3$, 300 MHz) δ7.22 (m, 1H), 6.65 (m, 3H), 4.61 (s, 2H), 4.27 (q, 2H), 1.24 (t, 3H).

B. 3-Fluorophenoxy-acetic acid.

To a solution of ethyl 3-fluorophenoxy-acetate (2 g, 10 mmol) in 24 mL of a 1:1:1 solution of MeOH:H$_2$O:THF is added lithium hydroxide monohydrate (2.25 g, 54 mmol). The solution is stirred for 16 hours. After this time, the solution is concentrated under reduced pressure to ⅓ of its volume. The remaining solution is acidified to pH=3 with 1N HCl (aq.). The aqueous solution is extracted with EtOAc. The organic layer is washed with a saturated solution NaCl (aq.). The organic layer is dried over MgSO$_4$, filtered and concentrated to give the product (1.65 g, 9.7 mmol) as a white solid. $^1$H NMR (CDCl$_3$, 300 MHz) δ9.8 (bs, 1H), 7.28 (m, 1H), 6.69 (m, 3H), 4.70 (s, 2H).

EXAMPLE 30

2-Chloropyrdin-3-ylamino-acetic acid

To a solution of 3-amino-2-chloropyridine (1.0 g, 7.8 mmol) in 20 mL of MeOH is added glyoxylic acid (0.86 mL of a 50% by weight solution in H$_2$O, 7.8 mmol). After stirring for 10 minutes, NaCNBH$_3$ (1.54 g, 23 mmol) is added. The reaction is stirred for 16 hours., then is concentrated under reduced pressure. The resulting residue is dissolved in H$_2$O. The solution is acidified to pH=3 with 1N HCl (aq.). The solution is extracted with EtOAc/CH$_2$Cl$_2$ (2:1). The organic layer is dried over MgSO$_4$, filtered and concentrated. The resulting product is obtained as a white solid (0.95 g, 5.1 mmol). $^1$H NMR (d6-DMSO, 300 MHz) δ12.7 (bs, 1H), 7.62 (m, 1H), 7.44 (m, 1H), 6.90 (m, 1H), 5.8 (bs, 1H), 3.95 (AB, 2H). 4.70 (s, 2H).

EXAMPLE 31

5-Chlorothiophen-2-yl-sulfanyl acetic acid

A. Thiophen-2-yl-sulfanyl acetic acid ethyl ester.

To a solution of thiophene-2-thiol (1.49 g, 116 mmol) in 40 mL of CH$_3$CN is added ethyl bromoacetate (2.14 g, 167 mmol) followed by K$_2$CO$_3$ (3.54 g, 138 mmol). The solution is stirred for 16 hours. After this time, the solution is filtered. The solvent is evaporate to give the product as an oil (2.4 g, 118 mmol). $^1$H NMR (CDCl$_3$, 300 MHz) δ7.37 (m, 1H), 7.21 (m, 1H), 6.94 (m, 1H), 4.15 (q, 2H), 3.48 (s, 2H), 1.20 (t, 3H). MS (EI): m/z 202 (M+).

B. 5-Chlorothiophen-2-yl sulfanyl acetic acid.

To a solution of thiophen-2-yl-sulfanyl acetic acid ethy (0.52 g, 2.6 mmol) in 25 mL of CH$_2$Cl$_2$ is added N-chlorosuccinimide (0.35 g, 2.6 mmol). The solution is stirred for 10 minutes. After this time, 1 drop of TFA is added. The solution is stirred for 16 hours. The reaction mixture is then diluted with 25 mL of CH$_2$Cl$_2$. The resulting solution is washed with 1N NaOH and a saturated NaCl solution. The organic layer is dried over MgSO$_4$, filtered and concentrated. The resulting product is obtained as an oil which is determined to contain 45% of the desired product. The oil is then dissolved in 60 mL of 1:1:1 THF:MeOH:H$_2$O. To the solution is added lithium hydroxide monohydrate (1.26 g, 30 mmol). The solution is stirred for 16 hours. After this time, the solution is acidified to pH=3 with 1N HCl. The aqueous solution is washed with H$_2$O and saturated NaCl solution. The solution is extracted with EtOAc/CH$_2$Cl$_2$ (2:1). The organic layer is dried over MgSO$_4$, filtered and concentrated. The resulting crude product is purified by column chromatography eluting with 20% MeOH:Et$_2$O to give the product as a white solid (0.4 g, 1.9 mmol). MS (EI): m/z 208, 210 (M+), Cl pattern.

EXAMPLE 32

5'-Chloro-[2,2']bithiophenyl-5-carboxylic acid

A. 5'-Chloro-[2,2']bithiophenyl-5-carbaldehyde.

To a solution of 5-chloro-[2,2']bithiophene (1.06 g, 5.28 mmol) in 12 mL of THF at −78° C. is added n-BuLi (4.4 mL of a 1.6M solution in hexanes, 6.99 mmol). After 15 minutes, DMF (0.97 mL, 14 mmol) is added and the resulting solution is allowed to warm to 0° C. After 15 min, the solution diluted with EtOAc and quenched with saturated NaHCO$_3$ solution. The organic solution is washed with H$_2$O and saturated NaCl solution, then dried over MgSO$_4$, filtered and concentrated. The crude product is purified by flash column chromatography eluting with a gradient of 10% Et$_2$O/hexanes to 20% Et$_2$O/hexanes to yield the title compound (0.89 g, 3.89 mmol) as a white solid. $^1$H NMR (CDCl$_3$, 300 MHz) δ9.87 (s, 1H), 7.70 (d, 1H), 7.20 (d, 1H), 7.15 (d, 1H), 6.91 (d, 1H).

B. 5'-Chloro-[2,2']bithiophenyl-5-carboxylic acid.

The title compound is prepared as described in EXAMPLE 28, Part B using 5'-chloro-[2,2']bithiophenyl-5-carbaldehyde. $^1$H NMR (CDCl$_3$, 300 MHz) δ7.69 (d, 1H), 7.09 (d, 1H), 7.06 (d, 1H), 6.89 (d, 1H). EI MS, [M]$^+$=243,245 (Cl pattern).

EXAMPLE 33

7-Chloro-isoquinoline-3-carboxylic acid

A. 7-Chloro-isoquinoline-3-carbaldehyde.

A 20 mL of 80% H$_2$SO$_4$ is added 7-chloro-3,3-dibromomethyl isoquinoline (0.69 g, 2.06 mmol) is heated to 150° C. for 16 hours. The solution is then cooled to ambient temperatures and diluted with 40 mL of H$_2$O. The resulting solution is basified to pH=11 with 1N NaOH. The aqueous solution is extracted with CH$_2$Cl$_2$. The organic solution is washed with H$_2$O and a saturated NaCl solution. The organic layer is dried over MgSO$_4$, filtered and concentrated to give the product as an oil (0.25 g, 1.3 mmol). $^1$H NMR (CDCl$_3$, 300 MHz) δ10.0 (s, 1H), 9.30 (s, 1H), 8.36 (s, 1H), 8.07 (s, 1H), 7.95 (d, 1H), 7.78 (d, 1H). MS (EI): m/z 191, 193 (M+), Cl pattern.

B. 7-Chloro-isoquinoline-3-carboxylic acid.

To 4.5 mL of a 1N NaOH solution at 0° C. is added a solution of AgNO$_3$ (0.31 g, 1.8 mmol) in 3 mL of H$_2$O, followed by a solution of of 7-chloro-isoquinoline-3-carbaldehyde (0.25 g, 1.3 mmol) in 3 of EtOH. The solution is stirred at 0° C. for 10 minutes, then at room temp. For 3 hours. The solution is acidified to pH=3 with 1H HCl. The resulting solution is extracted with CHCl$_3$. The organic layer is dried over MgSO$_4$, filtered and concentrated to give the product as a white solid (0.2 g, 0.96 mmol). $^1$H NMR (CD$_3$OD, 300 MHz) δ9.18 (s, 1H), 8.63 (s, 1H), 8.18 (m, 1H), 7.80 (m, 2H), 6.94 (m, 1H), 4.15 (q, 2H), 3.48 (s, 2H), 1.20 (t, 3H). MS (EI): m/z 208, 210 (M+), Cl pattern.

EXAMPLE 34

2-Acetylamino-3-(5-chloro-thiophen-2-yl)-acrylic acid

A. 4-(5-Chloro-thiophen-2-ylmethylene)-2-methyl-4H-oxazol-5-one.

A mixture consisting of 5-chlorothiophene-2-carboxaldehyde (1.00 g, 6.82 mmol), N-acetylglycine (0.96 g, 8.18 mmol), NaOAc (0.67 g, 8.18 mmol) in Ac$_2$O (5 mL) is warmed at reflux for 16 hours. The reaction mixture is cooled to ambient temperature and diluted with dilute aqueous NaOH (0.5 M, 100 mL) and CH$_2$Cl$_2$ (100 mL). The layers are separated and the organic phase is washed with aqueous NaHCO$_3$, brine, dried over anhydrous Na$_2$SO$_4$, filtered and concentrated to provide 1.5 g (100%) of the title compound as a colorless oil which is used without further purification in the next reaction. $^1$H NMR (300 MHz, CDCl$_3$) δ2.39 (s, 3H), 6.94 (d, J=4.0 Hz, 1H), 7.21 (s, 1H), 7.26 (d, J=4.0 Hz, 1H) ppm.

B. 2-Acetylamino-3-(5-chloro-thiophen-2-yl)-acrylic acid.

To a solution containing 4-(5-chloro-thiophen-2-ylmethylene)-2-methyl-4H-oxazol-5-one (1.5 g, 6.82 mmol) in MeOH (18 mL) is added 1.0 M NaOH (12.0 mL, 12 mmol) at ambient temperature. After 3 h, the reaction mixture is diluted with water (100 mL) and CH$_2$Cl$_2$ (100 mL) and the layers are separated. The basic, aqueous layer is washed with CH$_2$Cl$_2$ and then acidified using 1.0 M HCl (20 mL) to provide a crude solid which is collected on a Buchner funnel. Drying in vacuo provided 1.2 g (75%) of the title compound as a pale brown solid which is used without further purification. $^1$H NMR (300 MHz, DMSO-$d_6$) δ2.00 (s, 3H), 7.14 (d, J=4.01 Hz, 1H), 7.38 (d, J=4.01 Hz, 1H), 7.63 (s, 1H), 9.28 (s, 1H), 12.73 (br s, 1H) ppm; MS (EI): m/z 245 (M+).

EXAMPLE 35

2-Acetylamino-3-(5-chloro-thiophen-2-yl)-propionic acid

To a solution containing 2-acetylamino-3-(5-chloro-thiophen-2-yl)-acrylic acid (1.00 g, 4.08 mmol) and $K_2CO_3$ (1.70 g, 12.1 mmol) in DMF (20 mL) is added MeI (0.87 g, 6.12 mmol) at ambient temperature. After 2 h, the reaction mixture is diluted with water (100 mL) and EtOAc (100 mL) and the layers are separated. The aqueous layer is extracted with EtOAc (50 mL) and the combined organic phase is washed with brine, dried over anhydrous $Na_2SO_4$, filtered and concentrated to provide 0.92 g (83%) of the methyl ester which is used without further purification. $^1$H NMR (300 MHz, $CDCl_3$) δ2.19 (s, 3H), 3.77 (s, 3H), 6.86 (d, J=4.02 Hz, 1H), 6.99 (m, 1H), 7.05 (d, J=4.02 Hz, 1H), 7.64 (s, 1H) ppm.

A small Parr® vessel is charged with the crude ester (0.85 g, 3.13 mmol) and $(Ph_3P)_3RhCl$ (0.10 g, 0.10 mmol) in MeOH (50 mL). The vessel is pressurized to 50 PSI $H_2$ pressure and agitated for 7 h at ambient temperature. The reaction mixture is then filtered and concentrated to provide the desired compound, which is used without further purification. MS (EI): m/z 261 (M+).

The above-prepared saturated ester is dissolved in a 1:1:1 solution of water/THF/MeOH (15 mL). LiOH monohydrate (0.14 g, 3.23 mmol) is added and the heterogeneous mixture is stirred for 16 hours. The reaction mixture is diluted with water (100 mL) and EtOAc (100 mL) and the layers are separated. The aqueous layer is extracted with EtOAc (50 mL) and the combined organic phase is washed with brine, dried over anhydrous $Na_2SO_4$, filtered and concentrated to provide 0.62 g (81%) of the title compound as a colorless oil. $^1$H NMR (300 MHz, $CDCl_3$) δ2.02 (s, 3H), 3.30 (m, 2H), 4.81 (m, 1H), 6.45 (br d, J=6.45 Hz, 1H), 6.58 (d, J=3.68 Hz, 1H), 6.71 (d, J=3.68 Hz, 1H), 9.79 (br s, 1H) ppm; MS (EI): m/z 247 (M+).

EXAMPLE 36

3-(6-Amino-pyridin-3-yl)-acrylic acid

A. N-(5-Bromo-pyridin-2-yl)-acetamide.

Triethylamine (17.7 mL, 75 mmol) is added to a mixture of 2-amino-5-bromopyridine (5.0 g, 29 mmol) and acetic acid (7.1 mL, 75 mmol). The solution is heated to reflux for 48 hours. After this time, the solution is concentrated. The reside is dissolved in water and the pH is adjusted to 10 with 1N NaOH. The solids are collected by filtration. The crude product is recrystallized from boiling water to give the title compound (2.6 g 12.0 mmol) as a white solid. $^1$H NMR (300 MHz, $CDCl_3$) δ10.62 (1H, bs), 8.42 (s, 1H), 8.01 (m, 2H), 2.05 (s, 3H).

B. 3-(6-Acetylamino-pyridin-3-yl)-acrylic acid

To a mixture of N-(5-bromo-pyridin-2-yl)-acetamide (1.26 g, 5.86 mmol) and tri-n-butylamine in xylenes (10 mL) is added $Pd(OAc)_2$ (1.4 mg, 0.006 mmol) and triphenyl phosphine (15.4 mg, 0.06 mmol). Acrylic acid (0.48 mL, 7.03 mmol) is then added dropwise over 5 minutes. The mixture is heated to reflux for 5 hours. The solution is cooled to ambient temperatures. The mixture is diluted with water and the pH is adjusted to 4 with 1N HCl. The solution is extracted with EtOAc/$CH_2Cl_2$ (2:1). The resulting suspension is filtered to give the title compound (0.80 g, 3.88 mmol) as a white solid. MS (ion spray) 207, (M+H).

C. 3-(6-Amino-pyridin-3-yl)-acrylic acid

To 3-(6-acetylamino-pyridin-3-yl)-acrylic acid (0.80 g, 3.88 mmol) in ethanol (10 mL) is added 1N NaOH (20 mL). The solution is heated to reflux. After 16 h, the solution is concentrated to ⅓ its volume. The aqueous solution is diluted with water and acidified to pH=2 with 6N HCl. The solution is concentrated to dryness. The residue is dissolved in methanol. The solution is filtered. The organic solution is concentrated. The crude product is purified by RP-HPLC eluting with a gradient of 5%CH3CN/H2O (0.1% TFA) to 30% CH3CN/H2O (0.1%TFA) to give the product as a white solid (0.54 g, 1.93 mmol). $^1$H NMR (300 MHz, $CD_3OD$) δ8.34 (d, 1H), 8.07 (s, 1H), 7.54 (d, 2H), 7.06 (d, 1H), 6.47 (d, 1H). MS (ion spray) 165, (M+H).

EXAMPLE 37

4-Chloro-benzyl isocyanate

To a solution of triphosgene (0.54 g, 1.85 mmol) in 10 mL of dry $CH_2Cl_2$ at 0° C. is added 4-chloro-benzylamine (0.61 mL, 5.00 mmol) dropwise as a white precipitate forms. $Et_3N$ (1.39 mL, 10.0 mmol) in 5 mL of $CH_2Cl_2$ is added immediately and the resulting mixture is stirred at 0° C. for 5 min, then at room temperature for 3 hours. The mixture is concentrated in vacuo and triturated with EtOAc. The white precipitate (triethylamine hydrochloride) is filtered off and the filtrate is concentrated. The title compound (6.20 g, 30.6 mmol) is isolated as a crude yellow residue and used in the subsequent step without further purification. $^1$H NMR ($CDCl_3$, 300 MHz) δ7.35 (d, 2H), 7.25 (d, 2H), 4.50 (s, 2H).

EXAMPLE 38

5-Chloro-thiophene-2-carbonyl azide

To a solution of 5-chloro-2-thiophene-carboxylic acid (5.00 g, 30.7 mmol) in 130 mL of acetone is added $Et_3N$ (4.29 mL, 30.7 mmol). The mixture is cooled to 0° C. and ethyl chloroformate (3.23 mL, 33.8 mmol) is added. The mixture is stirred at 0° C. for 1 h and sodium azide (3.40 g, 52.3 mmol) is added. The mixture is stirred at 0° C. for 2 h, then poured into 300 mL of ice water and the aqueous layer is extracted with $CH_2Cl_2$ (2x). The combined organics are washed with water (2x) and brine, then dried, filtered and concentrated. The crude residue is purified via flash column chromatography eluting with 10% EtOAc/hexanes to provide the title compound (3.00 g, 16.0 mmol) as a white solid. $^1$H NMR ($CDCl_3$, 300 MHz) δ7.67 (d, 1H), 6.99 (d, 1H).

EXAMPLE 39

4-Nitro-2,3,5,6-tetrachloropyridine

Pentachloropyridine (80 g, 320 mmol) is treated with benzyl amine (104 mL, 96 mmol), dissolved in dioxane (1 L) and refluxed for 16 hours. The reaction mixture is cooled to ambient temperature and the precipitated white solid is removed by filtration. The filtrate is concentrated to a brown residue and triturated with 4% ethyl acetate in hexane (3×250 mL) to give 4-benzylamino-2,3,5,6-tetrachloropyridine as an off-white solid (40 g, 124 mmol). This material is dissolved in chloroform (400 mL), cooled in an ice bath and treated with trifluoroacetic acid (500 mL) and 30% hydrogen peroxide (100 mL). The reaction mixture is warmed to room temperature overnight and treated with additional trifluoroacetic acid (500 mL) and 30% hydrogen peroxide (100 mL). After stirring 24 hours the reaction is treated with water (1 L). The lower organic layer is separated and the aqueous layer is extracted with chloroform. The combined organic layers are concentrated to a solid residue and redissolved in ethyl acetate/hexane (30 mL). The suspended orange solid is removed and the filtrate is loaded on a silica flash column. The column is eluted with hexane and the title compound is collected as a white solid (15.6 g, 60 mmol). EI MS m/z 260, 262, 264 [M+].

EXAMPLE 40

4-(tert-Butyloxycarbonyl)-piperazin-2-one 4-(Benzyloxycarbonyl)-piperazin-2-one (2.2 g, 9.4 mmol) and Boc anhydride (2.5 g, 11.3 mmol) are dissolved in methanol (100 mL), treated with 5% Pd/C and shaken 16 h under hydrogen gas (30 PSI). The reaction vessel contents are filtered through Celite and the filtrate is concentrated to yield 4-(tert-Butyloxycarbonyl)-2-oxopiperazine (1.9 g, 9.4 mmol) which is used without further purification. EI MS m/z 200, M+; $^1$H NMR (CDCl$_3$, 300 MHz) δ6.17 (br, 1H), 4.20 (s, 2H), 3.55 (t, 2H), 3.38 (m, 2H), 1.48 (s, 9H).

EXAMPLE 41

2-Methoxymethyl-3-oxo-piperazine-1-carboxylic acid benzyl ester

A. N-Cbz-O-methylserine-aminoacetaldehyde dimethyl acetal.

To a solution of N-Cbz-O-methylserine (10.8 g, 41.8 mmol) in 500 mL of CH$_2$Cl$_2$ is added Et$_3$N (12.7 g, 125 mmol). The solution is cooled to 0° C. and TBTU (13.5 g, 42 mmol) and aminoacetaldehyde dimethyl acetal (4.83 g, 46 mmol) are added. The solution is stirred for 16 hours. The solution is diluted with 500 mL of ether. The resulting solution is washed with water, 1N KHSO$_4$, and sat. NaCl. The title compound (13.7 g, 41.8 mmol) is obtained as a white foam. $^1$H NMR (CDCl$_3$, 300 MHz) δ7.40 (m, 5H), 6.55 (bs, 1H), 5.66 (bs, 1H), 5.32 (m, 1H), 5.13 (s, 2H), 4.32 (m, 2H), 3.79 (dd, 1H), 3.44 (m, 2H), 3.40 (m, 9H).

B. N-Cbz-2-Oxo-3-(S)-methoxymethyl-(4,5-dihydro)piperazine.

To a solution of N-Cbz-O-methylserine-aminoacetaldehyde dimethyl acetal (13.7 g, 41.8 mmol) in 300 mL of toluene is added TsOH.H2O (0.80 g, 4.2 mmol). The solution is heated to 60° C. After 5 h, the solution is diluted with ether. The resulting organic solution is washed with water, sat. NaHCO3, and sat. NaCl. The organic layer is dried over MgSO$_4$, filtered and concentrated under vacuum. The resulting crude product is purified by column chromatography eluting with a gradient of 10%EtOAc:CH$_2$Cl$_2$ to 20%EtOAc:CH$_2$Cl$_2$. The title compound (10.7 g, 38 mmol) is obtained as a white solid. $^1$H NMR (CDCl$_3$, 300 MHz) δ7.36 (m, 5H), 6.45 and 6.30 (d, 1H rotational isomers), 5.61 and 5.50 (d, 1H rotational isomers), 5.20 (s, 2H), 4.92 and 4.83 (bs, 1H rotational isomers), 3.63 (m, 3H), 3.32 and 3.20 (s, 1H rotational isomers).

C. 2-Methoxymethyl-3-oxo-piperazine-1-carboxylic acid benzyl ester.

To a solution of N-Cbz-2-oxo-3-(S)-methoxymethyl-(4,5-dihydro)piperidine (10.7 g, 38 mmol) in 50 mL of methanol is added Pt/C (1 gm, 10% by weight). The atmosphere above the reaction is replaced by hydrogen. After 24 h, the solution is filtered and the filtrate is washed with methanol. The collected organic solutions are concentrated under vacuum. The resulting crude product is purified by column chromatography eluting with a gradient of 2%MeOH/CH$_2$Cl$_2$ to 5%MeOH/CH$_2$Cl$_2$. The title compound (6.0 g, 22 mmol) is obtained as a white solid. $^1$H NMR (CDCl$_3$, 300 MHz) δ7.35 (m, 5H), 6.42 (bs, 1H), 5.20 (AB, 2H), 4.58 (m, 1H), 4.18 (m, 1H), 3.95 (m, 1H), 3.50 (m, 4H), 3.27 (s, 3H).

EXAMPLE 42

2-Butyl-3-oxo-piperazine-1-carboxylic acid benzyl ester

The title compound is prepared as in EXAMPLE 41, substituting Cbz-norleucine for Cbz-O-methyl-serine. $^1$H NMR (CDCl$_3$, 300 mHz) δ7.32 (m, 5H), 5.13 (AB, 2H), 4.60 (m, 1H), 4.13 (m, 1H), 3.38 (m, 2H), 3.23 (m, 2H), 1.90 (m, 1H), 1.66 (m, 1H), 1.29 (m, 4H), 0.89 (m, 3H). MS (ion spray) m/z 291, (M+H).

EXAMPLE 43

2-Ethyl-3-oxo-piperazine-1-carboxylic acid benzyl ester

The title compound is prepared as in EXAMPLE 41, substituting Cbz-2-amino-butric acid for Cbz-O-methyl-serine. $^1$H NMR (CDCl$_3$, 300 mHz) δ7.37 (m, 5H), 6.55 (bs, 1H), 5.10 (AB, 2H), 4.57 (m, 1H), 4.24 (m, 1H), 3.42 (m, 1H), 3.26 (m, 2H), 2.20 (m, 1H), 1.81 (m, 1H), 0.96 (m, 3H).

EXAMPLE 44

2-Propyl-3-oxo-piperazine-1-carboxylic acid benzyl ester

The title compound is prepared as in EXAMPLE 41, substituting Cbz-norvaline for Cbz-O-methyl-serine. $^1$H NMR (CDCl$_3$, 300 mHz) δ7.32 (m, 5H), 7.00 (bs, 1H), 5.12 (AB, 2H), 4.58 (m, 1H), 4.21 (m, 1H), 3.40 (m, 1H), 3.19 (m, 2H), 1.88 (m, 1H), 1.73 (m, 1H), 1.37 (m, 2H), 0.91 (m, 3H). MS (ion spray) m/z 277, (M+H).

EXAMPLE 45

2-Ethoxymethyl-3-oxo-piperazine-1-carboxylic acid benzyl ester

The title compound is prepared as in EXAMPLE 41, substituting Cbz-O-ethyl-serine for Cbz-O-methyl-serine. $^1$H NMR (CDCl$_3$, 300 mHz) δ7.32 (m, 5H), 6.96 (bs, 1H), 5.17 (AB, 2H), 4.58 (m, 1H), 4.18 (m, 1H), 4.03 (m, 1H), 3.66 (m, 2H), 3.44 (m, 3H), 3.27 (s, 1H), 1.06 (m, 3H). MS (ion spray) m/z 293, (M+H).

EXAMPLE 46

2-Methyl-3-oxo-piperazine-1-carboxylic acid benzyl ester

The title compound is prepared as in EXAMPLE 41, substituting Cbz-alanine for Cbz-O-methyl-serine. $^1$H NMR (CDCl₃, 300 MHz) δ7.34 (m, 5H), 7.02 (bs, 1H), 5.17 (AB, 2H), 4.65 (m, 1H), 4.17 (m, 1H), 3.42 (m, 1H), 3.23 (m, 2H), 1.41 (d, 3H). MS (EI) m/z 248, (M+).

EXAMPLE 47

2-Benzyl-3-oxo-piperazine-1-carboxylic acid benzyl ester

The title compound is prepared as in EXAMPLE 41, substituting Cbz-phenylalanine for Cbz-O-methyl-serine. ¹H NMR (CDCl₃, 300 MHz) δ7.22 (m, 10H), 7.00 (bs, 1H), 5.10 (AB, 2H), 4.10 (m, 1H), 3.27 (m, 2H), 3.10 (m, 2H), 2.55 (m, 2H). MS (EI) m/z 324, (M+).

EXAMPLE 48

2-(1-Methoxyethyl)-3-oxo-piperazine-1-carboxylic acid benzyl ester

The title compound is prepared as in EXAMPLE 41, substituting Cbz-O-methyl-threonine for Cbz-O-methyl-serine. ¹H NMR (CDCl₃, 300 MHz) δ7.52 (bs, 1H), 7.22 (m, 5H), 5.12 (AB, 2H), 4.33 (m, 1H), 4.05 (m, 2H), 3.60 (m, 1H), 3.14 (s, 3H), 3.10 (m, 1H), 2.82 (m, 1H), 1.10 (d, 3H). MS (ion spray) m/z 293, (M+H).

EXAMPLE 49

2,2-Dimethyl-3-oxo-piperazine-1-carboxylic acid benzyl ester

The title compound is prepared as in EXAMPLE 41, substituting Cbz-2-amino-isobutryic acid for Cbz-O-methyl-serine. ¹H NMR (CDCl₃, 300 MHz) δ7.36 (m, 5H), 6.52 (bs, 1H), 5.12 (s, 2H), 3.72 (m, 2H), 3.33 (m, 2H), 1.68 (s, 3H), 1.64 (s, 3H). MS (EI) m/z 262, (M+).

EXAMPLE 50

2-Isopropyl-3-oxo-piperazine-1-carboxylic acid benzyl ester

The title compound is prepared as in EXAMPLE 41, substituting Cbz-valine for Cbz-O-methyl-serine. ¹H NMR (CDCl₃, 300 MHz) δ7.36 (m, 5H), 5.88 (bs, 1H), 5.10 (s, 2H), 4.35 (m, 1H), 3.44 (m, 1H), 3.27 (m, 2H), 2.31 (m, 1H), 1.00 (d, 3H), 0.94 (d, 2H).

EXAMPLE 51

2-Isobutyl-3-oxo-piperazine-1-carboxylic acid benzyl ester

The title compound is prepared as in EXAMPLE 41, substituting Cbz-leucine for Cbz-O-methyl-serine. ¹H NMR (CDCl₃, 300 MHz) δ7.35 (m, 5H), 6.50 (m, 1H), 5.15 (s, @H), 4.18 (m, 1H), 3.42 (m, 2H), 3.21 (m, 2H), 1.50 (m, 3H), 0.90 (m, 6H).

EXAMPLE 52

2-(2-Methoxyethyl)-3-oxo-piperazine-1-carboxylic acid benzyl ester

The title compound is prepared as in EXAMPLE 41, substituting Cbz-O-methyl-homo-serine for Cbz-O-methyl-serine. ¹H NMR (CDCl₃, 300 MHz) δ7.32 (m, 5H), 6.85 (bs, 1H), 5.14 (s, 2H), 4.75 (m, 2H), 4.20 (m, 2H), 3.42 (m, 1H), 3.21 (m, 3H), 2.12 (m, 4H).

EXAMPLE 53

2-Methoxymethyl-5-methyl-3-oxo-piperazine-1-carboxylic acid benzyl ester

The title compound is prepared as in EXAMPLE 41, substituting 2-amino-propionaldehyde dimethyl acetal for aminoacetaldehyde dimethyl acetal. ¹H NMR (CDCl₃, 300 MHz) δ7.42 (m, 5H), 6.96 (bs, 1H), 5.12 (AB, 2H), 4.52 (m, 1H), 4.21 (m, 1H), 3.92 (m, 1H), 3.58 (m, 2H), 3.22 (s, 3H), 3.10 (m, 1H), 0.95 (m, 3H).

EXAMPLE 54

3-(R)-(tert-Butyl-dimethyl-silanyloxymethyl)-5-oxo-piperazine-1-carboxylic acid benzyl ester A. 2-tert-Butoxcarbonylamino-3-(tert-butyl-dimethyl-silanyloxy)-propionic acid.

tert-Butyldimethylchlorosilane (32.3 g, 0.214 mol) in THF (50 mL) is added dropwise via cannula to a solution of BOC serine (20.0 g, 0.098 mol) and imidazole (15.3 g, 0.224 mol) in THF (360 mL) at RT. The resulting slurry is stirred for 2.5 h then the solvent is removed in vacuo. The crude product is dissolved in MeOH (180 mL) and 5N NaOH (58 mL) is slowly added at RT. The mixture is stirred for 3 h then diluted with water (180 mL) after which time the aqueous layer is washed with ether (180 mL×2). The aqueous layer is acidified to pH 4-5 with 2N HCl and extracted with diethyl ether. The organic layer is washed with saturated NaHCO₃ and brine then dried over MgSO₄, filtered and concentrated to dryness. The crude product (12.67 g, 0.040 mol) is used in the subsequent step without further purification. ¹H NMR (CDCl₃, 300 MHz) δ5.35 (bs, 1H), 4.30 (bs, 1H), 4.13 (dd, 1H), 3.80 (dd, 1H), 1.45 (s, 9H), 0.98 (s, 9H), 0.10 (s, 6H). EI MS, [M+H]⁺=320.

B. [2-(tert-Butyl-dimethyl-silanyloxy)-1-(methoxy-methyl-carbamoyl)-ethyl]-carbamic acid tert-butyl ester.

N,N-Dimethylaminopyridine (2.60 g, 21.3 mmol) and BOP reagent (18.15 g, 41.0 mmol) are added to a solution of 2-tert-butoxycarbonylamino-3-(tert-butyl-dimethyl-silanyloxy)-propionic acid (12.37 g, 38.7 mmol), diisopropylethylamine (8.1 mL, 46.4 mmol) and N,O-dimethylhydroxylamine hydrochloride (4.53 g, 46.4 mmol) in THF (260 mL) at RT. The resulting suspension is stirred at RT overnight then concentrated to dryness. The residue is diluted with EtOAc and washed with saturated NH₄Cl, saturated NaHCO₃ and brine. The organic layer is dried over MgSO₄, filtered and concentrated in vacuo to give the crude product which is purified by flash chromatography eluting with 10-30% EtOAc/Hexanes to yield the title compound (11.86 g, 30.37 mmol) as an oil. ¹H NMR (CDCl₃, 300 MHz) δ5.35 (bd, 1H), 4.71 (bs, 1H), 3.78-3.85 (m, 2H), 3.72 (s, 3H), 3.20 (s, 3H), 1.42 (s, 9H), 0.90 (s, 9H), 0.05 (s, 6H).

C. [1-(tert-Butyl-dimethyl-silanyloxymethyl)-2-oxo-ethyl]-carbamic acid tert-butyl ester.

A solution of [2-(tert-butyl-dimethyl-silanyloxy)-1-(methoxy-methyl-carbamoyl)-ethyl]-carbamic acid tert-butyl ester (11.86, 30.37 mmol) in Et₂O (100 mL) is added dropwise to a 1.0M solution of LAH in ether (35.5 mL) at −5° C.-0° C. The resulting mixture is stirred for 2.5 h then an aqueous solution of KHSO$_4$ is slowly added. The reaction mixture is stirred for 30 minutes and then washed with saturated NH$_4$Cl, saturated NaHCO$_3$ and brine. The organic layer is dried over MgSO$_4$, filtered and concentrated in vacuo to give the crude product which is purified by flash chromatography eluting with 30% EtOAc/Hexanes to yield the title compound (6.04 g, 19.9 mmol) as an oil. $^1$H NMR (CDCl$_3$, 300 MHz) δ9.65 (s, 1H), 5.30 (bs, 1H), 4.20 (m, 1H), 3.65 (4.90 (m, 2H), 1.48 (s, 9H), 0.90 (s, 9H), 0.05 (s, 6H). Ion spray MS, [M+H]$^+$=304.

D. [2-tert-Butoxycarbonylamino-3-(tert-butyl-dimethyl-silanyloxy)-propylamino]-acetic acid methyl ester.

Sodium cyanoborohydride (2.63 g, 41.9 mmol) is added to a solution of [1-(tert-butyl-dimethyl-silanyloxymethyl)-2-oxo-ethyl]-carbamic acid tert-butyl ester (6.04 g, 19.9 mmol) and glycine methyl ester hydrochloride (2.75 g, 32.9 mmol) in MeOH (500 mL). The mixture is stirred for 2 days at RT then concentrated to dryness. The crude product is purifed by flash chromatography eluting with 1-5% MeOH/CH$_2$Cl$_2$ to yield the title compound (3.06, 8.12 mmol) as a colorless oil. $^1$H NMR (CDCl$_3$, 300 MHz) δ5.00 (bs, 1H), 3.75 (s, 3H), 3.60-3.70 (m, 4H), 3.40 (d, 1H), 2.80 (dd, 1H), 2.68 (dd, 1H), 1.40 (s, 9H), 0.90 (s, 9H), 0.05 (s, 6H). Ion spray MS, [M+H]$^+$=377.

E. (Benzyloxycarbonyl-[2-tert-butoxycarbonylamino-3-(tert-butyl-dimethyl-silanyloxy)-propyl]-amino)-acetic acid methyl ester.

Benzylchloroformate (1.4 mL, 9.81 mmol) is added dropwise to a solution of N,N-dimethylaminopyridine (1.09 g, 8.93 mmol) and [2-tert-butoxycarbonylamino-3-(tert-butyl-dimethyl-silanyloxy)-propylamino]-acetic acid methyl ester (3.06 g, 8.12 mmol) in CH$_2$Cl$_2$ at RT. The resulting mixture is stirred overnight then concentrated to dryness. The crude product is purifed by flash chromatography eluting with 1% MeOH/CH$_2$Cl$_2$ to yield the title compound (3.52 g, 6.89 mmol) as a colorless oil. Ion spray MS, [M+H]$^+$=511.

F. 3-(tert-Butyl-dimethyl-silanyloxymethyl)-5-oxo-piperazine-1-carboxylic acid benzyl ester (Benzyloxycarbonyl-[2-tert-butoxycarbonylamino-3-(tert-butyl-dimethyl-silanyloxy)-propyl]-amino)-acetic acid methyl ester (3.52 g, 6.89 mmol) is stirred in 50% TFA/CH$_2$Cl$_2$ (40 mL) at RT for 40 minutes. The reaction mixture is concentrated in vacuo and the crude product is purifed by flash chromatography eluting with 1% MeOH/CH$_2$Cl$_2$ to yield the title compound (1.1 g, 2.9 mmol) as a colorless oil. Ion spray MS, [M+H]$^+$=379.

EXAMPLE 55

5-Oxo-piperazine-1,3(R or S)-dicarboxylic acid 1-benzyl ester 3-methyl ester

N,N-Dimethylaminopyridine (0.43 g, 3.5 mmol) and benzylchloroformate (0.55 g, 3.8 mmol) are added to a solution of methyl 6-oxopiperazine-2-carboxylate (0.50 g, 3.2 mmol) (Aebischer, B., Helv. Chim. Acta 1989, 72, 1043-1051) in CH$_2$Cl$_2$ at RT. After 1 h, the reaction mixture is poured into EtOAc and washed with saturated NaHCO$_3$ and brine then dried over MgSO$_4$, filtered and concentrated to dryness to give a solid (0.90 g, 3.1 mmol) which is used in subsequent reactions without further purification. $^1$H NMR (CDCl$_3$, 300 MHz) δ7.40 (bs, 5H), 6.32 (bs, 1H), 5.15 (s, 2H), 4.00-4.30 (m, 3H), 4.23 (s, 3H), 3.70-3.80 (m, 2H). MS (EI) m/z 292 (M+).

EXAMPLE 56

(S)-5-Oxo-piperazine-1,3-dicarboxylic acid 1-allyl ester 3-methyl ester

To a solution containing methyl (S)-6-oxopiperazine-2-carboxylate (1.32 g, 8.35 mmol), prepared by the method of Aebischer, in anhydrous dichloromethane (30 mL) at 0° C. is added triethylamine (1.26 g, 12.5 mmol) followed by allylchloroformate (1.20 g, 10.0 mmol). After 1 h, the reaction mixture is poured onto a 1:1 mixture of CH$_2$Cl$_2$/water (200 mL), acidified using 1 N HCl and the layers are separated. The organic phase is washed with brine, dried over anhydrous Na$_2$SO$_4$, filtered and concentrated. The crude residue is chromatographed on silica gel (CH$_2$Cl$_2$ to 1% MeOH/CH$_2$Cl$_2$) to provide 1.22 g (60%) of EXAMPLE 35 as a viscous oil. $^1$H NMR (300 MHz, CDCl$_3$) δ6.43 (bs, 1H), 5.90 (m, 1H), 5.26 (m, 2H), 4.61 (m, 2H), 4.05-4.26 (m, 3H), 3.80 (s, 3H), 3.72 (m, 2H); MS (ISP loop): m/z 243 (M+H).

EXAMPLE 57

(2S, 6R)-4-(2,6-dimethyl)-3-oxo-piperazine-1-carboxylic acid benzyl ester and

EXAMPLE 58

(2S, 6S)-2,6-dimethyl-3-oxo-piperazine-1-carboxylic acid benzyl ester

A. (2RS, 1S)-[1-(2-hydroxy-propylcarbamyl)-ethyl]-carbamic acid tert-butyl ester N-(tert-Butoxycarbonyl)-L-alanine (10.0 g, 52.8 mmol) is dissolved in 150 mL of THF. Once the triethylamine (11.0 ml, 79.2 mmol) is added, the solution is cooled to 0° C. Isopropyl chloroformate in toluene (1M) (52.8 ml, 52.8 mmol) is added slowly followed by the addition of (2RS) 1-amino-2-propanol (6.1 ml, 79.2 mmol). After stirring overnight, the mixture is washed with 1N sodium hydroxide and 1N hydrochloric acid. Concentration of the organic solvent afforded (2RS, 1S)-[1-(2-hydroxy-propylcarbamyl)-ethyl]-carbamic acid tert-butyl ester (9.92 g, 76% yield) as a clear oil.

B. (1S)-[1-(2-oxo-propylcarbamoyl)-ethyl]-carbamic acid tertbutyl ester

Dimethylsulfoxide (7.16 ml, 100.8 mmol) is added to a solution of oxalyl chloride (4.41 ml, 50.4 mmol) in 126 mL of methylene chloride at −78° C. The mixture is left to stir for fifteen minutes, and a solution of (2RS, 1S)-[1-(2-hydroxy-propylcarbamyl)-ethyl]-carbamic acid tert-butyl ester (9.92 g, 40.32 mmol) in 100 mL of CH$_2$Cl$_2$ is added dropwise. After stirring for 15 minutes at −78° C., the reaction is quenched with triethylamine (28 mL, 381 mmol), and the temperature is allowed to rise to room temperature. The volatile solvents are removed, and the residue is purified by flash column (SiO$_2$, 60% EtOAc/Hexane). The product (1S)-[1-(2-oxo-propylcarbamoyl)-ethyl]-carbamic acid tertbutyl ester (5.93 g, 60%) is isolated as a white solid. MS C$_{11}$H$_{20}$N$_2$O$_4$ MS m/z: 245.

C: (3S, 5RS)-3,5-dimethyl-piperazin-2-one.

(1S)-[1-(2-oxo-propylcarbamoyl)-ethyl]-carbamic acid tertbutyl ester (5.93 g, 24.3 mmol) is stirred in a solution of 30% trifluoroacetic acid in methylene chloride (100 mL) for three hours. The solvents are removed in vacuo. The residue is dissolved in 50 mL of MeOH and transferred to a par bottle. Palladium on carbon (10%, 1.0 g) is added, and the mixture is hydrogenated under pressure for 24 hours. The catalyst is filtered off; the MeOH is removed in vacuo to afford (3S, 5RS)-3,5-dimethyl-piperazin-2-one which is directly protected with a benzyl carbamate without further purification.

D: (2S, 6RS)-2,6-Dimethyl-3-oxo-piperazine-1-carboxylic acid benzyl ester.

To a solution of (3S, 5RS)-3,5-dimethyl-piperazin-2-one (24.3 mmol) in 100 mL of methylenechloride is added triethylamine (8.45 mL, 60.75 mmol) and N-(benzyloxycarbonyloxy)succinimide (12.1 g, 48.6 mmol). After stirring overnight, the $CH_2Cl_2$ is removed, and the crude mixture is chromatographed (50% EtOAc/Hexane). (2S, 6RS)-2,6-Dimethyl-3-oxo-piperazine-1-carboxylic acid benzyl ester (3.3 g, 52% yield over three steps) is isolated as a white powder. MS $C_{14}H_{18}N_2O_3$ MS m/z: 263.

E. (2S, 6R)-2,6-dimethyl-3-oxo-piperazine-1-carboxylic acid benzyl ester and (2S, 6S)-2,6-dimethyl-3-oxo-piperazine-1-carboxylic acid benzyl ester The two single enantiomers [(2S, 6R)-2,6-dimethyl-3-oxo-piperazine-1-carboxylic acid benzyl ester and (2S, 6S)-2,6-dimethyl-3-oxo-piperazine-1-carboxylic acid benzyl ester] can be seperated by column chromatography from (2S, 6RS)-2,6-dimethyl-3-oxo-piperazine-1-carboxylic acid benzyl ester, which can also be used directly in combination or separation of its derivatives as shown below.

EXAMPLE 59

(2S, 6R)-4-(2,4-Dimethoxy-benzyl)-2,6-dimethyl-3-oxo-piperazine-1-carboxylic acid benzyl ester A. (2S, 2S)-N-(2,4-dimethoxy-benzyl)-N-(2-hydroxy-propyl)-2-(2,2,2-trifluoroacelylamino)-propionamide.

To a slurry of (2S)-2-(2,2,2-trifluoroacetylamino)-propionic acid (15.3 g, 53.4 mmol) in 120 mL of methylene chloride is added triethylamine (5.6 mL, 40.0 mmol). The heterogeneous mixture is cooled to 0° C. and isopropyl chloroformate (27 mL, 27.0 mmol) is added slowly. After stirring for 20 minutes at room temperature, a solution of the (2S)-1-(2,4-dimethoxy-benzylamino)-propan-2-ol (6.0 g, 26.7 mmol, obtained from the reductive amination of the corresponding aldehyde and aminoalcohol) in 5 mL of methylene chloride is added. The resulting mixture is left to stir overnight. Ethyl acetate (500 mL) is added, and the organic solution is washed with 1N hydrochloric acid (50 mL) and 1N sodium hydroxide (50 mL). The ethyl acetate is dried with magnesium sulfate, filtered and condensed. The resulting residue is chromatographed on silica gel (25% ethyl acetate/hexane) to give (2S, 2S)-N-(2,4-dimethoxy-benzyl)-N-(2-hydroxy-propyl)-2-(2,2,2-trifluoroacetylamino)-propionamide (6.29 g, 60% yield) as a clear oil. MS $C_{17}H_{23}F_3N_2O_5$ MS m/z: 393.

B. (3S, 5R)-1-(2,4-dimethoxy-benzyl)-3,5-dimethyl-4-trifluoroacetyl-piperazin-2-one.

(2S, 2S)-N-(2,4-Dimethoxy-benzyl)-N-(2-hydroxypropyl)-2-(2,2,2-trifluoroacetylamino)-propionamide (3.64 g, 9.29 mmol) is dissolved in 25 mL of tetrahydrofuran. Triphenylphosphate (3.65 g, 14.0 mmol) is added, and the resulting mixture is cooled to 0° C. before diethyl azodicarboxylate (2.2 mL, 14 mmol) is added slowly. The resulting mixture is left to stir overnight. The reaction mixture is condensed, and the residue is purified by column chromatography ($SiO_2$, 25% ethyl acetate/hexane). The desired product, (3S, 5R)-1-(2,4-dimethoxy-benzyl)-3,5-dimethyl-4-trifluoroacetyl-piperazin-2-one (1.5 g, 43% yield), is isolated as a clear oil.

C. (3S, 5R)-1-(2,4-Dimethoxy-benzyl)-3,5-dimethyl-piperazin-2-one.

(3S, 5R)-1-(2,4-Dimethoxy-benzyl)-3,5-dimethyl-4-trifluoroacetyl-piperazin-2-one (575 mg, 1.54 mmol) is dissolved in 30 mL of methanol and 3 mL of $H_2O$. Potassium carbonate (883 mg, 6.4 mmol) is added to the solution, and the reaction is refluxed for one and half hours before concentration. Ethyl acetate (3×50 mL) is used to extract the aqueous layer. Removal of Ethyl acetate afforded the crude amine (387 mg, 91% yield) as a clear oil. $C_{15}H_{22}N_2O_3$ MS m/z: 279.

D. (2S, 6R)-4-(2,4-dimethoxy-benzyl)-2,6-dimethyl-3-oxo-piperazine-1-carboxylic acid benzyl ester.

Triethylamine (0.4 mL, 2.8 mmol) and N-(benzyloxycarbonyloxy)-succinimide (1.04 g, 4.2 mmol) is added to a solution of the above crude amine (387 mg, 1.4 mmol) in 15 mL of methylene chloride. The reaction mixture is left to stir overnight. The residue after concentration is chromatographed on silica gel (30% ethyl acetate/hexane) to give (2S, 6R)-4-(2,4-dimethoxy-benzyl)-2,6-dimethyl-3-oxo-piperazine-1-carboxylic acid benzyl ester (450 mg, 78% yield) as a clear oil.

E. (2S, 6R)-2,6-Dimethyl-3-oxo-piperazine-1-carboxylic acid benzyl ester.

(2S,6R)-4-(2,4-Dimethoxy-benzyl)-2,6-dimethyl-3-oxo-piperazine-1-carboxylic acid benzyl ester (1.13 g, 2.74 mmol) is dissolved in 20 mL of acetonitrile. An aqueous solution of potassium persulfate (2.2 g, 8.23 mmol) and sodium phosphate (2.3 g, 16.5 mmol) in 12 mL of $H_2O$ is added, and the resulting mixture is heated to 95-100° C. for two hours. After cooling to room temperature, ethyl acetate (200 mL) is used to extract the aqueous layer and dried over magnesium sulfate. The residue after filtration and concentration is chromatographed ($SiO_2$, 60% ethyl acetate/hexane) to give (2S, 6R)-2,6-Dimethyl-3-oxo-piperazine-1-carboxylic acid benzyl ester (480 mg, 67% yield) as a yellow oil.

EXAMPLE 60

(2S, 6RS)-4-(4-chloro-quinolin-7-ylmethyl)-2,6-dimethyl-3-oxo-piperazine-1-carboxylic acid benzyl ester (2S,6RS)-2,6-Dimethyl-3-oxo-piperazine-1-carboxylic acid benzyl ester (380 mg, 1.45 mmol) is dissolved in 10 mL of THF and 1 mL of DMF. Sodium hydride (60%, 72 mg, 3.14 mmol) is added at 0° C. and left to stir at room temperature for thirty minutes before 7-bromomethyl-4-chloro-quinoline (257 mg, 1.0 mmol) is added. The reaction is stirred for four hours. Ethyl acetate is added to the mixture, and the reaction is quenched with 3 mL of $H_2O$. The two layers are separated and ethyl acetate (2×30 ml) is used to extract before dried over magnesium sulfate. The residue after filtration and concentration is chromatographed on silica gel (60% EtOAc/Hexane) to give (2S, 6RS)-4-(4-chloro-quinolin-7-ylmethyl)-2,6-dimethyl-3-oxo-piperazine-1-carboxylic acid benzyl ester (417 mg, 95% yield). $C_{22}H_{20}ClN_3O_3$ MS m/z: 438, 440.

EXAMPLE 61

(3S,5RS)-1-(4-chloro-quinolin-7-ylmethyl)-3,5-dimethyl-piperazin-2-one and

EXAMPLE 62

(3S, 5R)-1-(4-chloro-quinolin-7-ylmethyl)-3,5-dimethyl-piperazin-2-one and

EXAMPLE 63

(3S, 5S)-1-(4-chloro-quinolin-7-ylmethyl)-3,5-dimethyl-piperazin-2-one (2S, 6RS)-4-(4-Chloro-quinolin-7-ylmethyl)-2,6-dimethyl-3-oxo-piperazine-1-carboxylic acid benzyl ester (417 mg, 1.0 mmol) is taken up in 7 mL of acetonitrile, and iodotrimethyl-silane (0.43 mL, 3.0 mmol) is added. The resulting mixture is stirred for one hour at room temperature before quenched with methanol (1 mL). The residue after concentration is taken up in 2N hydrochloric acid (3 mL) and is extracted with ether (2×30 mL). The aqueous layer is condensed to dryness and the residue is recrystalized from isopropanol and ether to give a mixture (1:4 ratio) of (3S, 5RS)-1-(4-chloro-quinolin-7-ylmethyl)-3,5-dimethyl-piperazin-2-one as a yellow solid (290 mg). The two epimers are separated using a flash column ($SiO_2$, 1% triethylamine/3% methanol/methylene chloride). $C_{16}H_{18}ClN_3O$ MS m/z: 304, 306. The minor isomer (3S, 5R)-1-(4-chloro-quinolin-7-ylmethyl)-3,5-dimethyl-piperazin-2-one.is (3S, 5R)-1-(4-chloro-quinolin-7-ylmethyl)-3,5-dimethyl-piperazin-2-one while the major isomer is (3S, 5S)-1-(4-chloro-quinolin-7-ylmethyl)-3,5-dimethyl-piperazin-2-one. Alternatively, (3S, 5R)-1-(4-chloro-quinolin-7-ylmethyl)-3,5-dimethyl-piperazin-2-one and (3S, 5S)-1-(4-chloro-quinolin-7-ylmethyl)-3,5-dimethyl-piperazin-2-one can be made via the same chemistry shown below from pure (2S, 6S)-2,6-dimethyl-3-oxo-piperazine-1-carboxylic acid benzyl ester and (2S, 6RS)-4-(4-chloro-quinolin-7-ylmethyl)-2,6-dimethyl-3-oxo-piperazine-1-carboxylic acid benzyl ester, respectively.

Alternative synthesis of (3S, 5R)-1-(4-chloro-quinolin-7-ylmethyl)-3,5-dimethyl-piperazin-2-one.

A. (2S, 6R)-4-(4-chloro-quinolin-7-ylmethyl)-2,6-dimethyl-3-oxo-piperazine-1-carboxylic acid benzyl ester.

(2S, 6R)-2,6-Dimethyl-3-oxo-piperazine-1-carboxylic acid benzyl ester (750 mg, 2.86 mmol) is dissolved in 20 mL of THF and 2 mL of DMF. Sodium hydride (60%, 142.6 mg, 6.20 mmol) is added at 0° C., and the reaction is left to stir at room temperature for thirty minutes at which time the 7-bromomethyl-4-chloro-quinoline (952 mg, 3.72 mmol) is added. The reaction is complete after stirring for four hours. Ethyl acetate (200 mL) is added to the mixture, and the reaction is quenched with 3 mL of $H_2O$. The two layers are separated, and ethyl acetate (2×30 mL) is used to extract and dried over magnesium sulfate. The residue after filtration and concentration is chromatographed on silica gel (60% EtOAc/Hexane) to give (2S,6R)-4-(4-chloro-quinolin-7-ylmethyl)-2,6-dimethyl-3-oxo-piperazine-1-carboxylic acid benzyl ester (1.04 g, 83%).

B. (3S, 5R)-1-(4-chloro-quinolin-7-ylmethyl)-3,5-dimethyl-piperazin-2-one.

A 33% solution of hydrogen bromide in acetic acid (10 mL) is added to (2S,6R)-4-(4-chloro-quinolin-7-ylmethyl)-2,6-dimethyl-3-oxo-piperazine-1-carboxylic acid benzyl ester (1.04 g, 2.38 mmol). The reaction is left to stir at room temperature for one hour. The reaction mixture is diluted with ethyl acetate and stirred vigorously to force the product to precipitate out of solution. The ethyl acetate is decanted off and the precipitate is purified on a silica gel column (1% triethylamine/3% methanol/methylene chloride) to 582 mg (81% yield) of (3S,5R)-1-(4-chloro-quinolin-7-ylmethyl)-3,5-dimethyl-piperazin-2-one as a white solid.

EXAMPLE 64

(3S, 5S)-1-(4-chloro-quinolin-7-ylmethyl)-4-[3-(5-chloro-thiophen-2-yl)-allyl]-3,5-dimethyl-piperazine-2-one and

EXAMPLE 65

(3S, 5R)-1-(4-chloro-quinolin-7-ylmethyl)-4-[3-(5-chloro-thiophen-2-yl)-allyl]-3,5-dimethyl-piperazine-2-one The crude (3S,5RS)-1-(4-chloro-quinolin-7-ylmethyl)-3,5-dimethyl-piperazin-2-one (69 mg, 0.20 mmol) obtained from above is dissolved in 1 mL of DMF. Potassium carbonate (76 mg, 0.60 mmol) is added followed by the addition of 2-(3-bromopropenyl)-5-chloro-thiophene (56 mg, 0.24 mmol). The reaction is left to stir overnight. The potassium carbonate is filtered off, and the crude material is purified. The two epimers are separated at this stage by preparative thin layer chromatography (80% EtOAc/hexane) to give a major epimer (3S, 5R)-1-(4-chloro-quinolin-7-ylmethyl)-4-[3-(5-chloro-thiophen-2-yl)-allyl]-3,5-dimethyl-piperazine-2-one (25 mg, 26% yield) and a minor epimer (3S, 5S)-1-(4-chloro-quinolin-7-ylmethyl)-4-[3-(5-chloro-thiophen-2-yl)-allyl]-3,5-dimethyl-piperazine-2-one (7 mg, 7.5% yield).

EXAMPLE 66

4-(2-Oxopiperazin-1-ylmethyl)benzamidine

A. 4-(4-Cyanobenzyl)-3-oxopiperazine-1-carboxylic acid benzyl ester.

To a solution of 3-oxo-piperazine-1-carboxylic acid benzyl ester (3.0 g, 12.8 mmol) and 4-bromomethyl tolylnitrile (2.76 g, 14.1 mmol) in 135 mL of THF and 15 mL of DMF at 0° C. is added a 60% dispersion in mineral oil of NaH (0.49 g, 12.8 mmol). After 5 hours, the solution is diluted with saturated $NH_4Cl$ and EtOAc. The organic layer is washed with $H_2O$ and saturated NaCl. The organic layer is dried over $MgSO_4$, filtered and concentrated. The crude product is purified by column chromatography over silca gel eluting with 20% EtOAc/$CH_2Cl_2$. The title compound is obtained as a white solid (4.01 g, 11.4 mmol). $^1$H NMR ($CDCl_3$, 300 MHz) δ7.62 (d, 2H), 7.39 (m, 7H), 5.14 (s, 2H), 4.68 (s, 2H), 4.27 (s, 2H), 3.73 (m, 2H), 3.30 (m, 2H).

B. 4-(4-Carbamimidoylbenzyl)-3-oxo-piperazine-1-carboxylic acid benzyl ester.

A solution of 4-(4-cyanobenzyl)-3-oxopiperazine-1-carboxylic acid benzyl ester (2.4 g, 6.87 mmol) in 30 mL of pyridine and 3 ml of $Et_3N$ is saturated with $H_2S$. The resulting mixture is sealed and stirred for 16 hours. After this time, the solution is concentrated. The residue is dissolved in 30 mL of acetone and methyl iodide (19.4 g, 137 mmol) is added. The solution is refluxed for 2 hours. After this time, the solution is concentrated. The residue is dissolved in MeOH (40 mL) and $NH_4OAc$ (5.0 g, 65 mol) is added. The solution is reluxed for 3 hours. After this time, the solution is concentrated. The crude product is purified by RP-HPLC eluting in a gradient of CH$_3$CN to 60% CH$_3$CN/H$_2$O(0.1%TFA). The appropriate collected fractions are lyophilized to give the product as a white foam. MS (FAB) m/z 367, (M+H).

C. 4-(2-Oxopiperazin-1-ylmethyl)benzamidine.

To a solution of 4-(4-carbamimidoylbenzyl)-3-oxopiperazine-1-carboxylic acid benzyl ester (2.0 g, 5.0 mmol) in 40 mL of MeOH and 4 mL of AcOH is added 10% Pd/C (0.4 g). The atmosphere above the reaction is replaced by hydrogen. After 4 hours, the solution is filtered through a pad of Celite. The organic layer is concentrated. The resulting crude product is purified by RP-HPLC eluting in a gradient of 10% CH$_3$CN/H$_2$O (0.1%TFA) to 40% CH$_3$CN/H$_2$O (0.1% TFA). The title compound is obtained as a white foam. $^1$H NMR (d$^6$-DMSO, 300 MHz) δ9.3 (bs, 4H), 9.1 (bs, 2H), 7.83 (d, 2H), 7.42 (d, 2H), 4.78 (s, 2H), 3.80 (s, 2H), 3.44 (m, 2H), 3.32 (m, 2H).

EXAMPLE 67

1-(2-Aminoquinolin-6-ylmethyl)piperazin-2-one

A. 4-(2-Chloro-quinolin-6-ylmethyl)-3-oxo-piperazine-1-carboxylic acid benzyl ester.

To a solution of 3-oxopiperazine-1-carboxylic acid benzyl ester (4.65 g, 19.8 mmol) and 6-bromomethyl-2-chloroquinoline (5.40 g, 21.0 mmol) in 80 mL of a 3:1 mixture of THF:DMF at 0° C. is added sodium hydride (0.81 g, 20.2 mmol, 60% mineral oil dispersion). The resulting mixture is stirred for 1 hour at 0° C. then at room temperature for 18 hours. The reaction mixture is quenched with saturated NH$_4$Cl solution, then diluted with EtOAc. The organic layer is washed sequentially with 1N HCl, water, saturated NaHCO$_3$ and saturated NaCl, then dried over MgSO$_4$, filtered and concentrated. The crude product is triturated in Et$_2$O/hexanes/EtOAc and filtered to afford the title compound (6.96 g, 17.0 mmol) as a white solid. $^1$H NMR (CDCl$_3$, 300 MHz) δ8.08 (d, 1H), 8.00 (d, 1H), 7.69 (s, 1H), 7.63 (dd, 1H), 7.41 (d, 1H), 7.35 (s, 5H), 5.15 (s, 2H), 4.78 (s, 2H), 4.28 (s, 2H), 3.70 (m, 2H), 3.32 (bs, 2H).

B. 4-(2-Phenoxyquinolin-6-ylmethyl)-3-oxopiperazine-1-carboxylic acid benzyl ester.

A mixture of phenol (15.1 g, 160 mmol) and 4-(2-chloroquinolin-6-ylmethyl)-3-oxopiperazine-1-carboxylic acid benzyl ester (6.60 g, 16.1 mmol) is melted together at 70° C. until a homogeneous mixture is obtained. Potassium hydroxide (3.15 g, 56.1 mmol) is added and the resulting mixture is heated overnight at 120° C. After 24 hours, the brown/black residue is cooled to room temperature, diluted with CH$_2$Cl$_2$ and stirred with 1N NaOH (100 mL) for 30 minutes. The two layers are separated and the aqueous layer is extracted with CH$_2$Cl$_2$. The combined organic layers are washed with 1N NaOH, saturated NaCl, dried over Na$_2$SO$_4$, filtered and concentrated. The crude title compound (6.92 g, 14.8 mmol) is obtained as a beige foam and used in the subsequent step without further purification. $^1$H NMR (CDCl$_3$, 300 MHz) δ8.07 (d, 1H), 7.76 (d, 1H), 7.63 (s, 1H), 7.50 (dd, 1H), 7.42 (m, 2H), 7.34 (m, 6H), 7.25 (m, 2), 7.09 (d, 1H), 5.14 (s, 2), 4.75 (s, 2H), 4.27 (s, 2H), 3.66 (m, 2H), 3.30 (bs, 2H).

C. 4-(2-Aminoquinolin-6-ylmethyl)-3-oxopiperazine-1-carboxylic acid benzyl ester A mixture of ammonium acetate (18.7 g, 242 mmol) and 4-(2-phenoxyquinolin-6-ylmethyl)-3-oxopiperazine-1-carboxylic acid benzyl ester (6.92 g, 14.8 mmol) is heated overnight at 150° C. After 21 hours, an additional 3 g of ammonium acetate is added and the heating is continued. After 5 hours, the mixture is cooled to room temperature, diluted with CH$_2$Cl$_2$ and stirred with 1N NaOH (100 mL) for 30 minutes. The two layers are separated and the aqueous layer is extracted with CH$_2$Cl$_2$. The combined organic layers are washed with 1N NaOH, saturated NaCl, dried over Na$_2$SO$_4$, filtered and concentrated. The crude mixture of the title compounds (5.50 g, 14.1 mmol) is obtained as a beige foam and used in the subsequent step without further purification.

Major component (4-(2-aminoquinolin-6-ylmethyl)-3-oxopiperazine-1-carboxylic acid benzyl ester): $^1$H NMR (CDCl$_3$, 300 MHz) δ7.86 (d, 1H), 7.63 (d, 1H), 7.48 (d, 1H), 7.45 (d, 1H), 7.35 (s, 5H), 6.74 (d, 1H), 5.14 (s, 2H), 4.79 (bs, 2H), 4.71 (s, 2H), 4.26 (s, 2H), 3.66 (s, 2H), 3.30 (s, 2H).

Minor component (3-oxo-4-(2-oxo-1,2-dihydroquinolin-6-ylmethyl)piperazine-1-carboxylic acid benzyl ester): $^1$H NMR (CDCl$_3$, 300 MHz) δ7.75 (d, 1H), 7.48 (m, 2H), 7.37 (m, 6H), 6.70 (d, 1H), 5.14 (s, 2H), 4.66 (s, 2H), 4.26 (s, 2H), 3.66 (s, 2H), 3.30 (s, 2H).

D. 1-(2-Aminoquinolin-6-ylmethyl)piperazin-2-one.

To a solution of a mixture of 4-(2-aminoquinolin-6-ylmethyl)-3-oxopiperazine-1-carboxylic acid benzyl ester and 3-oxo-4-(2-oxo-1,2-dihydro-quinolin-6-ylmethyl)piperazine-1-carboxylic acid benzyl ester (5.50 g, 14.1 mmol) in 100 mL of 10:1 MeOH/HOAc is added a catalytic amount of 10% palladium on activated carbon. The heterogenous mixture is hydrogenated at room temperature under a balloon of H$_2$ for 18 hours. The reaction mixture is filtered through a pad of Celite, washed with MeOH, and the filtrate is concentrated in vacuo. The crude mixture of products is purified by RP-HPLC eluting in a gradient of 2% CH$_3$CN/H$_2$O (0.1% TFA) to 20% CH$_3$CN/H$_2$O(0.1% TFA) and the appropriate product fractions are concentrated in vacuo to provide 1-(2-aminoquinolin-6-ylmethyl)-piperazin-2-one ditrifluoroacetate (2.64 g, 5.45 mmol) as the major product in the form of a white solid. $^1$H NMR (d$^6$-DMSO, 300 MHz) δ8.78 (bs, 2H), 8.31 (d, 1H), 7.80 (s, 1H), 7.66 (m, 2H), 7.08 (d, 1H), 4.70 (s, 2H), 3.84 (s, 2H), 3.46 (bs, 4H). MS m/z 256, [M+]. Elemental analysis calculated with 0.25 mol of H$_2$O cal. C=44.25%, H=3.82%, N=11.47%, found C=44.23%, H=3.76%, N=11.23%.

The minor by-product 6-(2-oxo-piperazin-1-ylmethyl)-1H-quinolin-2-one (0.62 g, 1.28 mmol) is also isolated from the RP-HPLC separation as a white solid $^1$H NMR (d$^6$-DMSO, 300 MHz) δ11.76 (bs, 1H), 9.30 (bs, 2H), 7.85 (d, 1H), 7.55 (s, 1H), 7.42 (d, 1H), 7.28 (d, 1H), 6.50 (d, 1H), 4.60 (s, 2H), 3.80 (s, 2H), 3.38 (bs, 4H). MS m/z 257, [M+]. Elemental analysis calculated with 0.5 mol of H$_2$O cal. C=43.72%, H=3.68%, N=8.50%, found C=43.70%, H=3.62%, N=8.61%.

EXAMPLE 68

1-(1-Aminoisoquinolin-6-ylmethyl)piperazin-2-one

The title compound is prepared as described in EXAMPLE 67 substituting 6-bromomethyl-1-chloroisoquinoline for bromomethyl-2-chloroquinoline. $^1$H NMR (d6-DMSO, 300 MHz) δ (9.18 (bs, 2H), 8.53 (d, 1H), 7.81 (s, 1H), 7.63 (m, 2H), 7.14 (d, 1H), 4.77 (s, 2H), 3.88 (s, 2H), 3.50 (m, 4H).

EXAMPLE 69

2-(2-Oxopiperazin-1-ylmethyl)pyrrolo[3,2-c]pyridin-1-carboxylic acid tert-butyl ester A. 3-Iodopyridin-4ylamine.

A solution of potassium iodide (19.48 g, 117.4 mmol) and iodine (18.37 g, 72.3 mmol) in water (77 mL) is added dropwise via an addition funnel to a refluxing solution of 4-aminopyridine (9.21 g, 97.8 mmol) and sodium carbonate (6.12 g, 57.7 mmol) in water (35 mL). Upon complete addition the mixture is stirred for 2 hours at reflux then cooled to room temperature and extracted with ethyl acetate. The combined organic layers are washed with saturated sodium thiosulfate solution (3×) and brine then dried over $MgSO_4$, filtered and concentrated to give the title product (8.37 g, 38.0 mmol) and a trace of the di-iodo compound as an yellow/orange solid. This material is used in the subsequent step without further purification. $^1$H NMR ($CDCl_3$, 300 MHz) δ8.70 (s, 1H), 8.10 (d, 1H), 6.55 (d, 1H), 4.60 (bs, 2H).

B. (3-Iodopyridin-4-yl)-carbamic acid tert-butyl ester.

Di-tert-butyl dicarbonate (20.7 g, 94.8 mmol) is added to a solution of 3-iodopyridin-4-ylamine (19.0 g, 86.4 mmol) in THF (86 mL). The resulting solution is stirred for 2 hours at room temperature then concentrated. The residue is diluted with ethyl acetate and washed with saturated sodium bicarbonate solution and brine. The organic layer is dried over $MgSO_4$, filtered and concentrated. The residue is purified by column chromatography eluting with 1% EtOAc/$CH_2Cl_2$ to give the title product and a small amount of the BOC-protected di-iodo compound. Trituration of the mixture with ether/hexane removes the undesired compound leaving the title product in the solution. Filtration of the solid and concentration of the filtrate yields the title product (18.95 g, 59.2 mmol). $^1$H NMR ($CDCl_3$, 300 MHz) δ8.75 (s, 1H), 8.35 (d, 1H), 8.1 (d, 1H), 7.0 (bs, 1H), 1.55 (s, 9H).

C. 3-Oxo-4-prop-2-ynylpiperazine-1-carboxylic acid benzyl ester.

Sodium hydride (0.82 g, 23.0 mmol, 60% mineral oil dispersion) is added to a solution of 4-benzyloxycarbonylpiperazin-2-one (5.13 g, 21.9 mmol) in THF/DMF (75 mL, 3/1 v/v) at 0° C. The mixture is stirred for 5 minutes, then propargyl bromide (3.7 mL, 41.5 mmol) is added dropwise. The resulting solution is stirred for 1 hour then brought to room temperature and stirred for 2 hours. The reaction is quenched with saturated ammonium chloride solution then diluted with ethyl acetate and washed with water (4×) and brine. The organic layer is dried over $MgSO_4$, filtered and concentrated to dryness. The residue is purified by column chromatography eluting with 5% MeOH/$CH_2Cl_2$ to give the product (5.96 g, 21.9 mmol) as a white solid. $^1$H NMR ($CDCl_3$, 300 MHz) δ7.3 (m, 5H), 5.12 (s, 2H), 4.25 (s,2H), 4.16 (s, 2H), 3.75 (m, 2H), 3.47 (m, 2H), 2.22 (s, 1H).

D. 2-(4-Benzyloxycarbonyl-2-oxopiperazin-1-ylmethyl)pyrrolo[3,2-c]pyridin-1-carboxylic acid tert-butyl ester.

$Pd(PPh_3)_2Cl_2$ (0.29 g, 0.41 mmol), CuI (0.05 g, 0.25 mmol) and triethylamine (4.6 mL, 3.29 mmol) is added to a solution of 3-oxo-4-prop-2-ynylpiperazine-1-carboxylic acid benzyl ester (2.24 g, 8.23 mmol) and (3-iodopyridin-4-yl)-carbamic acid tert-butyl ester (2.63 g, 8.23 mmol) in DMF (30 mL) at room temperature. The mixture is heated to 100° C. and stirred for 1.5 hours. The reaction mixture is then cooled to 50° C. and DBU (2.5 mL, 16.5 mmol) is added. After 30 minutes the solution is cooled to room temperature, diluted with ethyl acetate and washed with saturated ammonium chloride, water and brine. The organic layer is dried over $MgSO_4$, filtered and concentrated in vacuo. The resulting solid is purified by column chromatography eluting with a gradient of 2% MeOH/$CH_2Cl_2$ to 5% MeOH/$CH_2Cl_2$ to give the product (2.93 g, 6.31 mmol) as a white solid. $^1$H NMR ($CDCl_3$, 300 MHz) δ8.75 (s, 1H), 8.4 (d, 1H), 7.85 (d, 1H), 7.35 (m, 5H), 6.38 (s, 1H), 5.2 (s, 2H), 5.00 (s, 2H), 4.29 (s, 2H), 3.85 (m, 2H), 3.52 (m, 2H), 1.7 (s, 9H). Ion spray MS, [M+H]$^+$=465.

E. 2-(2-Oxopiperazin-1-ylmethyl)pyrrolo[3,2-c]pyridin-1-carboxylic acid tert-butyl ester.

Palladium black (1.1 g, 10.3 mmol) is added to a solution of 2-(4-benzyloxycarbonyl-2-oxo-piperazin-1-ylmethyl)pyrrolo[3,2-c]pyridin-1-carboxylic acid tert-butyl ester (1.7 g, 3.7 mmol) in $HCO_2H$/MeOH (45 mL, 4.4% solution). After 40 minutes the catalyst is filtered through Celite and washed with MeOH. The filtrate is concentrated in vacuo to remove methanol then the resulting solution is diluted with methylene chloride and washed with saturated sodium bicarbonate, and brine. The organic layer is dried over $MgSO_4$, filtered and concentrated to dryness. The resulting solid is purified by column chromatography eluting with a gradient of 5% MeOH/$CH_2Cl_2$ to 10% MeOH/$CH_2Cl_2$ to give the product (0.8 g, 2.5 mmol) as a pale yellow foamy solid. $^1$H NMR ($CDCl_3$, 300 MHz) δ8.78 (s, 1H), 8.40 (d, 1H), 7.9 (d, 1H), 6.48 (s, 1H), 4.98 (s, 2H), 3.7 (s, 2H), 3.51 (t, 2H), 3.40 (t, 2H), 1.91 (bs, 1H), 1.70 (s, 9H).

EXAMPLE 70

2-(5-(±)-Methoxycarbonyl-2-oxo-piperazin-1-ylmethyl)-pyrrolo[3,2-c]pyridine-1-carboxylic acid tert-butyl ester A. 2-Benzyloxycarbonylamino-3-(prop-2-ynylamino)-propionic acid methyl ester.

Propargyl bromide (1.6 mL, 14.4 mmol) is added to a solution of 3-amino-2-benzyloxycarbonylamino-propionic acid methyl ester hydrochloride (4.0 g, 13.9 mmol) and triethylamine (4.1 mL, 29.4 mmol) in THF (46 mL). The resulting mixture is heated to 50° C. and stirred overnight then cooled to RT and concentrated in vacuo. The crude residue is diluted with methylene chloride, washed with saturated $NaHCO_3$ and brine then the organic layer is dried over $MgSO_4$, filtered and concentrated in vacuo. The crude material (4.0 g) is taken on to the subsequent step without further purification. $^1$H NMR ($CDCl_3$, 300 MHz) δ7.25-7.30 (m, 5H), 5.75 (bs, 1H), 5.20 (s, 2H), 4.45 (bs, 1H), 3.80 (s, 3H), 3.75 (m, 1H), 3.31 (s, 2H), 3.08 (dd, 1H), 2.98 (dd, 1H), 2.20 (t, 1H). EI MS, [M+H]$^+$=291.

B. 2-Benzyloxycarbonylamino-3-(bromoactyl-prop-2-ynylamino)-propionic acid methyl ester.

DCC (2.27 g, 11.0 mmol) and bromoacetic acid (1.48 g, 10.7 mmol) is added to a solution of 2-benzyloxycarbonylamino-3-(prop-2-ynylamino)-propionic acid methyl ester (3.10 g, 10.7 mmol) in $CH_2Cl_2$ at RT. The mixture is stirred overnight then diluted with ether. The white solid which precipitates out is filtered and the filtrate is concentrated to give a yellow oil. The crude product is purified by chromatography eluting with a gradient of 40% EtOAc/hexanes to 50% EtOAc/hexanes to yield the title product (2.1 g, 5.12 mmol) as an oil. $^1$H NMR ($CDCl_3$, 300 MHz) δ7.30 (m, 5H), 5.70 (d, 1H), 5.10 (s, 2H), 4.63 (m, 1H), 4.15 (d, 2H), 4.00 (m, 1H), 3.80 (s, 3H), 3.75 (s, 2H), 3.70 (dd, 1H), 2.27 (bs, 1H). Ion spray MS, [M+H]$^+$=411, 413, Br pattern.

C. 5-Oxo-4-prop-2-ynyl-piperazine-1,2-dicarboxylic acid 1-benzyl ester 2-methyl ester.

Sodium hydride (0.20 mg, 4.9 mmol) is added to a solution of 2-benzyloxycarbonylamino-3-(bromoactyl-prop-2-ynylamino)-propionic acid methyl ester (2.0 g, 4.8 mmol) in THF (50 mL) at 0° C. The solution is stirred for 40 minutes then quenched with saturated NH$_4$Cl solution. The reaction mixture is concentrated in vacuo then diluted with CH$_2$Cl$_2$ and washed with brine. The organic layer is dried over, filtered and concentrated in vacuo. The crude product is purified by chromatography eluting with 50% EtOAc/hexanes to give the title product (1.4 g, 4.1 mmol). $^1$H NMR (CDCl$_3$, 300 MHz) δ7.30 (m, 5H), 5.20 (s, 2H), 5.10 (m, 1H), 4.30 (dd, 1H), 4.25 (d, 2H), 4.08 (m, 1H), 4.00 (dd, 1H), 3.78 (dd, 1H), 3.78 (s, 3H), 2.25 (t, 1H).

D. 2-(5-(±)-Methoxycarbonyl-2-oxo-piperazin-1-ylmethyl)-pyrrolo[3,2-c]pyridine-1-carboxylic acid tert-butyl ester.

$^1$H NMR (CDCl$_3$, 300 MHz) δ8.75 (s, 1H), 8.41 (d, 1H), 7.90 (d, 1H), 6.42 (s, 1H), 5.00 (AB, 2H), 3.85-3.93 (m, 2H), 3.78 (s, 3H), 3.70-3.81 (m, 3H), 1.65 (s, 9H). Ion spray MS, [M+H]$^+$=389.

EXAMPLE 71

2-(2-(±)-Methoxycarbonyl-6-oxo-piperazin-1-ylmethyl)-pyrrolo[3,2-c]pyridine-1-carboxylic acid tert-butyl ester $^1$H NMR (CDCl$_3$, 300 MHz) δ8.81 (s, 1H), 8.43 (d, 1H), 7.90 (d, 1H), 6.48 (s, 1H), 5.63 (d, 1H), 4.40 (d, 1H), 4.20 (m, 1H), 3.78 (s, 3H), 3.70 (d, 1H), 3.52 (d, 1H), 3.33 (dd, 1H), 2.92 (s, 1H), 1.55 (s, 9H). Ion spray MS, [M+H]$^+$=389.

EXAMPLE 72

1-(4-Aminoquinazoline-7-ylmethyl)piperazine-2-one

A. 4-(4-Chloroquinazoline-7-ylmethyl)-3-oxopiperazine-1-carboxylic acid tert-butyl ester.

To a solution of 3-oxopiperazine-1-carboxylic acid tert-butyl ester (3.93 g, 19.6 mmol) and 7-bromomethyl-4-chloroquinazoline, EXAMPLE 7, (5.0 g, 19.6 mmol) in 150 mL of THF and 15 mL of DMF at 0° C. is added a 60% dispersion in mineral oil of NaH (0.79 g, 19.6 mmol). The solution is stirred at 0° C. for 0.5 hours and then is allowed to warm to ambient temperature. After 4 hours, the solution is poured into a saturated solution of NH$_4$Cl. The layers are separated and the organic layer is washed with H$_2$O, and saturated NaCl, dried over MgSO$_4$, filtered and concentrated. The title compound is obtained as a white solid (5.1 g, 13.4 mmol). MS (FAB) m/z 377, 379, (M+H), chlorine pattern.

B. 4-(4-Aminoquinazoline-7-ylmethyl-3-oxopiperazine-1-carboxylic acid tert-butyl ester.

A solution of 4-(4-chloroquinazoline-7-ylmethyl)-3-oxopiperazine-1-carboxylic acid tert-butyl ester (1.84 g, 4.9 mmol) in 120 mL of ethanol is saturated with NH$_3$ gas. To the resulting solution is added acetic acid (0.03 mL). The solution is heated to reflux. After 16 hours, the solution is concentrated. The resulting solid is dissolved in CH$_2$Cl$_2$ and the inorganic salts are filtered off. The organic solution is concentrated. The resulting solid is triturated with EtOAc. The title compound is obtained a a white solid (1.59 g, 4.5 mmol). MS (FAB) m/z 356, (M+H).

C. 1-(4-Aminoquinazoline-7-ylmethyl)piperazine-2-one.

A solution of 4-(4-aminoquinazoline-7-ylmethyl)-3-oxo-piperazine-1-carboxylic acid tert-butyl ester (1.92 g, 5.4 mmol) in EtOAc (200 mL) at 0° C. is saturated with HCl gas. The solution is stirred at 0° C. for 4 hours. After this time, the solution is concentrated. The title compound is obtained as a white solid (1.79 g, 5.4 mmol). $^1$H NMR (d$^6$-DMSO, 300 MHz) δ9.9 (bs, 3H), 9.7 (bs, 2H), 8.8 (s, 1H), 8.46 (d, 1H), 7.72 (s, 1H), 7.61 (d, 1H), 4.78 (s, 2H), 3.83 (s, 2H), 3.4 (m, 4H).

EXAMPLE 73

1-(4-Amino-thieno[2,3-d]pyrimidin-6-ylmethyl)-piperazin-2-one

A. 1-(4-Amino-thieno[2,3-d]pyrimidin-6-ylmethyl)-3-oxo-piperazine-1-carboxylic acid tert-butyl ester.

The title compound is prepared as described in EXAMPLE 72, Part A, substituting 6-bromomethyl-4-chlorothieno[2,3-d]pyrimidine. for 7-bromomethyl-4-chloroquinazoline. Followed by treatment as described in EXAMPLE 72, Part B, the title compound is obtained. $^1$H NMR (CD$_3$OD, 300 MHz) δ8.22 (s, 1H), 7.35 (s, 1H), 5.48 (s, 2H), 4.10 (s, 2H), 3.60 (m, 2H), 3.40 (m, 2H), 1.45 (s, 9H). MS (ion spray), 364, (M+H).

B. 1-(4-Amino-thieno[2,3-d]pyrimidin-6-ylmethyl)-piperazin-2-one.

The title compound is obtained by treatment of 1-(4-amino-thieno[2,3-d]pyrimidin-6-ylmethyl)-3-oxo-piperazine-1-carboxylic acid tert-butyl ester as described in EXAMPLE 72, Part C. MS (EI), 2634, (M+).

EXAMPLE 74

4-[3-(2-Oxo-piperazin-1-yl)-propyl]-piperidine-1-carboxylic acid tert-butyl ester A. 4-[3-(1-tert-butoxycarbonyl-piperidin-4-yl)-propyl]-3-oxo-piperazine-1-carboxylic acid benzyl ester.

The title compound is prepared as described in EXAMPLE 72, Part A, substituting 3-oxopiperazine-1-carboxylic acid benzyl ester for 3-oxopiperazine-1-carboxylic acid tert-butyl ester and 4-(3-bromopropyl)-piperidine-1-carboxylic acid tert-butyl ester for 7-bromomethyl-4-chloroquinazoline. The title compound is obtained as a white foam. $^1$H NMR (CDCl$_3$, 300 MHz) δ7.38 (m, 5H), 5.12 (s, 2H), 4.18 (m, 4H), 3.73 (m, 2H), 3.33 (m, 4H), 2.66 (m, 2H), 1.58 (m, 6H), 1.42 (s, 9H), 1.38 (m, 3H).

B. 4-[3-(2-Oxo-piperazin-1-yl)-propyl]-piperidine-1-carboxylic acid tert-butyl ester.

4-[3-(1-tert-butoxycarbonyl-piperidin-4-yl)-propyl]-3-oxo-piperazine-1-carboxylic acid benzyl ester is treated as described in EXAMPLE 67, Part D, to give the title compound as an oil.

EXAMPLE 75

1-(4-Amino-quinazoline-7-ylmethyl)-3-methoxymethyl-piperazine-2-one

A. 2-Methoxymethyl-3-oxo-piperazine-1-carboxylic acid benzyl ester.

To a solution of 2-oxo-3-(S)-methoxymethylpiperidine (5.36 g, 19.3 mmol), EXAMPLE 41, in 200 mL of 10:1

THF:DMF is added 2-(benzhydrylidene-amino)-4-bromomethyl-benzonitrile (12.6 g, 60% purity, 19.3 mmol), prepared as in EXAMPLE 13. The solution is cooled to 0° C. To the solution is added NaH (0.77 g of a 60% dispersion in mineral oil, 19.3 mmol). The solution is stirred for 16 hours. After this time, 1N HCl is added until the pH=1. The solution is stirred for 1 hour. After this time, the solution is diluted with EtOAc. The organic layer is washed with water and sat. NaCl. The organic layer is dried over $MgSO_4$, filtered and concentrated under vacuum. The resulting crude product is purified by column chromatography eluting with a gradient of 20%EtOAc/$CH_2C_2$ to 40%EtOAc/$CH_2Cl_2$. The title compound (6.8 g, 16.7 mmol) is obtained as a white solid. $^1$H NMR ($CDCl_3$, 300 MHz) δ7.34 (m, 5H), 6.61 (m, 2H), 5.13 (AB, 2H), 4.76 (m, 1H), 4.40 (AB, 2H), 4.08 (m, 5H), 3.74 (m, 2H), 3.32 (m, 1H), 3.30 (s, 3H), 3.10 (m, 1H).

B. 4-(4-Amino-quinazolin-7-ylmethyl)-2-methoxymethyl-3-oxo-piperazine-1-carboxylic acid benzyl ester.

To a solution of 2-methoxymethyl-3-oxo-piperazine-1-carboxylic acid benzyl ester (6.8 g, 16.7 mmol) in 100 mL of ethanol is added triazine (2.2 g, 26.4 mmol) and acetic acid (1.6 g, 26.4 mmol). The solution is heated to a reflux. After 36 h, the solution is concentrated. The resulting crude product is purified by column chromatography eluting with a gradient of 2%MeOH/$CH_2Cl_2$ to 5% MeOH/$CH_2Cl_2$. The title compound (5.8 g, 13.3 mmol) is obtained as a white solid. $^1$H NMR ($CDCl_3$, 300 MHz) δ8.55 (s, 1H), 7.72 (m, 2H), 7.48 (m, 1H), 7.35 (m, 5H), 6.40 (bs, 2H), 5.16 (AB, 2H), 5.06 (m, 1H), 4.72 (m, 1H), 4.59 (m, 1H), 4.09 (m, 2H), 3.74 (m, 2H), 3.44 (m, 1H), 3.30 (s, 3H), 3.12 (m, 1H). MS (ion spray) m/z 436, (M+H).

C. 1-(4-Amino-quinazoline-7-ylmethyl)-3-methoxymethyl-piperazine-2-one.

To a solution of 2-methoxymethyl-3-oxo-piperazine-1-carboxylic acid benzyl ester (5.8 g, 13.3 mmol) in 50 mL of acetic acid is added dropwise, 20 mL of a 30%HBr in AcOH solution. The solution is stirred for 1 hour. After this time, the solution is concentrated. The resulting crude product is purified by column chromatography eluting with $CH_2Cl_2$:MeOH: $NH_4OH$ (20:5:1). The title compound (2.0 g, 6.6 mmol) is obtained as a white solid. $^1$H NMR ($d^6$-DMSO, 300 MHz) δ8.60 (s, 1H), 7.72 (m, 2H), 7.48 (d, 1H), 5.60 (bs, 2H), 4.72 (AB, 2H), 3.87 (m, 2H), 3.71 (m, 1H), 3.42 (m, 1H), 3.40 (s, 3H), 3.19 (m, 2H), 3.02 (m, 1H). MS (ion spray) m/z 302, (M+H).

EXAMPLE 76

1-(4-Aminoquinazoline-7-ylmethyl)-3-butyl-piperazine-2-one

The title compound is prepared as described in EXAMPLE 75, substituting 2-butyl-3-oxo-piperazine-1-carboxylic acid benzyl ester, Example 42, for 2-methoxymethyl-3-oxo-piperazine-1-carboxylic acid benzyl ester. $^1$H NMR ($CD_3OD$, 300 MHz) δ8.35 (s, 1H), 8.09 (d, 1H), 7.54 (s, 1H), 7.41 (d, 1H), 4.74 (s, 2H), 3.43 (m, 2H), 3.28 (m, 1H), 3.09 (m, 1H), 2.95 (m, 1H), 1.92 (m, 1H), 1.70 (m, 1H), 1.39 (m, 4H), 0.93 (m, 3H). MS (ion spray) m/z 314, (M+H).

EXAMPLE 77

1-(4-Aminoquinazoline-7-ylmethyl)-3-ethyl-piperazine-2-one

The title compound is prepared as described in EXAMPLE 75, substituting 2-ethyl-3-oxo-piperazine-1-carboxylic acid benzyl ester r, Example 43, for 2-methoxymethyl-3-oxo-piperazine-1-carboxylic acid benzyl ester. $^1$H NMR ($CD_3OD$, 300 MHz) δ8.36 (s, 1H), 8.11 (d, 1H), 7.57 (s, 1H), 7.42 (d, 1H), 4.78 (s, 2H), 3.40 (m, 2H), 3.29 (m, 1H), 3.11 (m, 1H), 2.98 (m, 1H), 2.00 (m, 1H), 1.77 (m, 1H), 1.20 (m, 3H). MS (ion spray) m/z 286, (M+H).

EXAMPLE 78

1-(4-Aminoquinazoline-7-ylmethyl)-3-propyl-piperazine-2-one

The title compound is prepared as described in EXAMPLE 75, substituting 2-propyl-3-oxo-piperazine-1-carboxylic acid benzyl ester, Example 44, for 2-methoxymethyl-3-oxo-piperazine-1-carboxylic acid benzyl ester. $^1$H NMR ($CD_3OD$, 300 MHz) δ8.36 (s, 1H), 8.13 (d, 1H), 7.60 (s, 1H), 7.47 (d, 1H), 4.78 (s, 2H), 3.44 (m, 2H), 3.30 (m, 1H), 3.11 (m, 1H), 2.97 (m, 1H), 1.98 (m, 1H), 1.72 (m, 1H), 1.50 (m, 2H), 0.97 (m, 3H). MS (ion spray) m/z 300, (M+H).

EXAMPLE 79

1-(4-Amino-quinazoline-7-ylmethyl)-3-ethoxymethyl-piperazine-2-one

The title compound is prepared as described in EXAMPLE 75, substituting 2-ethoxymethyl-3-oxo-piperazine-1-carboxylic acid benzyl ester, Example 45, for 2-methoxymethyl-3-oxo-piperazine-1-carboxylic acid benzyl ester. $^1$H NMR ($CD_3OD$, 300 MHz) δ8.34 (s, 1H), 8.07 (d, 1H), 7.53 (s, 1H), 7.40 (d, 1H), 4.79 (AB, 2H), 3.90 (m, 1H), 3.72 (m, 1H), 3.68 (m, 1H), 3.52 (m, 2H), 3.20 (m, 1H), 3.00 (m, 1H), 1.92 (m, 3H). MS (ion spray) m/z 316, (M+H).

EXAMPLE 80

1-(4-Amino-quinazoline-7-ylmethyl)-3-methyl-piperazine-2-one

The title compound is prepared as described in EXAMPLE 75, substituting 2-methyl-3-oxo-piperazine-1-carboxylic acid benzyl ester, Example 46, for 2-methoxymethyl-3-oxo-piperazine-1-carboxylic acid benzyl ester. $^1$H NMR ($CD_3OD$, 300 MHz) δ8.36 (s, 1H), 8.11 (d, 1H), 7.57 (s, 1H), 7.44 (d, 1H), 4.79 (AB, 2H), 3.58 (m, 1H), 3.47 (m, 1H), 3.31 (m, 1H), 3.12 (m, 1H), 3.00 (m, 1H), 1.41 (d, 3H). MS (ion spray) m/z 272, (M+H).

EXAMPLE 81

1-(4-Amino-quinazoline-7-ylmethyl)-3-benzyl-piperazine-2-one

The title compound is prepared as described in EXAMPLE 75, substituting 2-benzyl-3-oxo-piperazine-1-carboxylic acid benzyl, Example 47, ester for 2-methoxymethyl-3-oxo-piperazine-1-carboxylic acid benzyl ester. $^1$H NMR ($CD_3OD$, 300 MHz) δ8.35 (s, 1H), 8.09 (d, 1H), 7.57 (s, 1H), 7.38 (d, 1H), 7.27 (m, 5H), 4.74 (AB, 2H), 3.76 (m, 1H), 3.47 (m, 1H), 3.30 (m, 3H), 3.08 (m, 1H), 2.96 (m, 1H). MS (ion spray) m/z 348, (M+H).

EXAMPLE 82

1-(4-Amino-quinazoline-7-ylmethyl)-3-(1-methoxyethyl)-piperazine-2-one

The title compound is prepared as described in EXAMPLE 75, substituting 2-(1-methoxyethyl)-3-oxo-piperazine-1-carboxylic acid benzyl ester, Example 48, for 2-methoxymethyl-3-oxo-piperazine-1-carboxylic acid benzyl ester. This compound is isolated as the bis hydrobromide salt. $^1$H NMR (CD$_3$OD, 300 MHz) δ8.70 (s, 1H), 8.40 (d, 1H), 7.88 (s, 1H), 7.71 (d, 1H), 4.94 (AB, 2H), 4.30 (m, 2H), 3.76 (m, 1H), 3.68 (m, 3H), 3.36 (s, 3H), 1.42 (d, 3H). MS (ion spray) m/z 316, (M+H).

EXAMPLE 83

1-(4-Amino-quinazoline-7-ylmethyl)-3,3-dimethyl-piperazine-2-one

The title compound is prepared as described in EXAMPLE 75, substituting 2,2-dimethyl-3-oxo-piperazine-1-carboxylic acid benzyl ester, Example 49, for 2-methoxymethyl-3-oxo-piperazine-1-carboxylic acid benzyl ester. $^1$H NMR (d$^6$-DMSO, 300 MHz) δ8.34 (s, 1H), 8.12 (d, 1H), 7.72 (bs, 2H) 7.41 (s, 1H), 7.26 (d, 1H), 4.60 (s, 2H), 3.33 (m, 2H), 2.98 (m, 2H), 1.27 (s, 6H).

EXAMPLE 84

1-(4-Amino-quinazoline-7-ylmethyl)-3-isopropyl-piperazine-2-one

The title compound is prepared as described in EXAMPLE 75, substituting 2-isopropyl-3-oxo-piperazine-1-carboxylic acid benzyl ester, Example 50, for 2-methoxymethyl-3-oxo-piperazine-1-carboxylic acid benzyl ester. $^1$H NMR (d$^6$-DMSO, 300 MHz) δ8.32 (s, 1H), 8.12 (d, 1H), 7.66 (bs, 2H), 7.42 (s, 1H), 7.27 (d, 1H), 4.60 (AB, 2H), 3.23 (m, 2H), 3.05 (m, 1H), 2.79 (m, 1H), 2.34 (m, 1H), 0.92 (s, 3H), 0.80 (s, 3H).

EXAMPLE 85

1-(4-Amino-quinazoline-7-ylmethyl)-3-isobutyl-piperazine-2-one

The title compound is prepared as described in EXAMPLE 75, substituting 2-isobutyl-3-oxo-piperazine-1-carboxylic acid benzyl ester, Example 51, for 2-methoxymethyl-3-oxo-piperazine-1-carboxylic acid benzyl ester. $^1$H NMR (d$^6$-DMSO, 300 MHz) δ8.65 (s, 1H), 7.70 (m, 2H), 7.48 (m, 1H), 5.61 (m, 2H), 4.82 (m, 1H), 4.65 (m, 1H), 3.52 (dd, 1H), 3.37 (m, 1H), 3.18 (m, 2H), 2.98 (m, 1H), 1.92 (m, 1H), 1.76 (m, 1H), 1.59 (m, 2H), 0.95 (m, 6H).

EXAMPLE 86

1-(4-Amino-quinazoline-7-ylmethyl)-3-(2-methoxyethyl)1-piperazine-2-one

The title compound is prepared as described in EXAMPLE 75, substituting 2-(2-methoxyethyl)-3-oxo-piperazine-1-carboxylic acid benzyl ester, Example 52, for 2-methoxymethyl-3-oxo-piperazine-1-carboxylic acid benzyl ester. $^1$H NMR (d$^6$-DMSO, 300 MHz) δ8.32 (s, 1H), 8.13 (d, 1H), 7.70 (bs, 2H), 7.42 (s, 1H), 7.28 (m, 1H), 4.60 (m, 2H), 3.32 (m, 8H), 3.11 (m, 1H), 2.95 (m, 1H), 2.78 (m, 1H), 2.07 (m, 1H), 1.72 (m, 1H).

EXAMPLE 87

1-(4-Amino-quinazoline-7-ylmethyl)-3-methoxymethyl-6-methyl-piperazine-2-one

The title compound is prepared as described in EXAMPLE 75, substituting 2-methoxymethyl-5-methyl-3-oxo-piperazine-1-carboxylic acid benzyl ester, Example 53, for 2-methoxymethyl-3-oxo-piperazine-1-carboxylic acid benzyl ester. $^1$H NMR (CD$_3$OD, 300 MHz) δ8.72 (s, 1H), 8.32 (d, 1H), 7.78 (m, 2H), 5.11 (m, 1H), 4.81 (m, 1H), 4.42 (m, 1H), 4.13 (m, 1H), 4.04 (m, 1H), 3.74 (m, 2H), 3.52 (m, 1H), 3.43 (s, 3H), 1.34 (d, 3H).

EXAMPLE 88

(3S,5RS)-1-(4-amino-quinazolin-7-ylmethyl)-3,5-dimethyl-piperazin-2-one

A. (2S,6RS)-4-[3-(benzhydryl-amino)-4-cyano-benzyl]-2,6-dimethyl-3-oxo-piperazine-1-carboxylic acid benzyl ester.

To a solution of the (2S,6RS)-2,6-dimethyl-3-oxo-piperazine-1-carboxylic acid benzyl ester (1.98 g, 7.56 mmol in 20 mL of tetrahydrofuran and 2 mL of DMF is added sodium hydride (60%, 289 mg, 12.6 mmol) at 0° C. The reaction is stirred for one hour at room temperature and the 2-benzhydrylidene-amino)-4-bromomethyl-benonitrile (4.24 mg, 11.34 mmol), Example 13, is added. After stirring at room temperature overnight, the tetrahydrofuran is removed. The residue is taken up in ethyl acetate. Excess sodium hydride is quenched with 5 mL of water, and normal aqueous work-up followed. The crude product is chromatographed on silica gel (50% EtOAc/Hexane) to give (2S,6RS)-4-[3-(benzhydryl-amino)-4-cyano-benzyl]-2,6-dimethyl-3-oxo-piperazine-1-carboxylic acid benzyl ester (2.6 g, 65%). C$_{35}$H$_{32}$N$_4$O$_3$ MS m/z: 557.

B. (2S,6RS)-4-(3-amino)-4-cyano-benzyl)-2,6-dimethyl-3-oxo-piperazine-1-carboxylic acid benzyl ester.

(2S,6RS)-4-[3-(Benzhydryl-amino)-4-cyano-benzyl]-2,6-dimethyl-3-oxo-piperazine-1-carboxylic acid benzyl ester (2.6 g, 5.21 mmol) is dissolved in 100 mL of ethyl acetate and cooled to 0° C. A 12N solution of hydrochloric acid (0.5 ml, 6.0 mmol) is added dropwise. The deprotection is complete in thirty minutes. The reaction mixture is washed with 10% sodium bicarbonate. The ethyl acetate layer is dried with magnesium sulfate, filtered and condensed. The resulting residue is purified by flash colunm (SiO$_2$, 60% ethyl acetate/hexane) to give the product (2S,6RS)-4-(3-amino)-4-cyano-benzyl)-2,6-dimethyl-3-oxo-piperazine-1-carboxylic acid benzyl ester (2.03 g, 99%).

C. (2S,6RS)-4-(4-Amino-quinazolin-7-ylmethyl)-2,6-dimethyl-3-oxo-piperazine-1-carboxylic acid benzyl ester.

Glacial acetic acid (0.9 ml, 15.54 mmol) and 1,3,5-triazine (840 mg, 10.36 mmol) is added to a solution of (2S,6RS)-4-(3-amino-4-cyano-benzyl)-2,6-dimethyl-3-oxo-piperazine-1-carboxylic acid benzyl ester (2.03 g, 5.18 mmol) in ethanol. The resulting mixture is heated to reflux overnight. Replaced the ethanol with ethyl acetate and washed with saturated sodium bicarbonate (5 mL). The ethyl acetate layer is dried with magnesium sulfate, filtered and condensed. The resulting residue is purified by flash colunm (SiO$_2$, 20% methanol/methylene chloride) to give the product (2S,6RS)-4-(4-amino-quinazolin-7-ylmethyl)-2,6-dimethyl-3-oxo-piperazine-1-carboxylic acid benzyl ester (1.85 g, 85%) as a yellow solid. C$_{23}$H$_{25}$N$_5$O$_3$ MS m/z: 420.

D. (3S,5RS)-1-(4-Amino-quinazolin-7-ylmethyl)-3,5-dimethyl-piperazin-2-one.

Palladium on carbon (10%, 700 mg) is added to a solution of (2S,6RS)-4-(4-amino-quinazolin-7-ylmethyl)-2,6-dimethyl-3-oxo-piperazine-1-carboxylic acid benzyl ester (1.62 g, 3.87 mmol) in 20 mL of methanol and 2 mL of acetic acid. The reaction mixture is left to stir in an atmosphere of hydrogen for eight hours. The palladium is filtered off, and the volitale solvents are removed on the rotovap. The crude product (1.7 g, 95%) is isolated as a white solid. The two epimers are separated on silica gel (1% triethylamine/15% methanol/methylene chloride). The minor epimer is assigned as (3S, 5R)-1-(4-amino-quinazolin-7-ylmethyl)-3,5-dimethyl-piperazin-2-one and the major epimer is assigned as (3S,5S)-1-(4-amino-quinazolin-7-ylmethyl)-3,5-dimethyl-piperazin-2-one.

EXAMPLE 89

1-(4-Chloroquinolin-7-ylmethyl)-piperazin-2-one 4-(Benzyloxycarbonyl)-piperazin-2-one (1.1 g, 4.6 mmol) is dissolved in THF (50 mL), cooled in an ice bath and treated with tretrabutylammonium iodide (0.18 g, mmol) and 60% sodium hydride (0.24 g, 6.0 mmol). The reaction mixture is stirred at 0° C. for 30 minutes then treated dropwise with a solution of 7-bromomethyl-4-chloroquinoline (1.2 g, 4.6 mmol), Example 14, in THF (50 mL). The resulting solution is stirred at 0° C. for 2 h then quenched with ammonium chloride solution and concentrated. Dilution with ethyl acetate is followed by a water wash; the organic layer is dried (sodium sulfate) and concentrated. The residue is chromatographed (4% methanol/methylene chloride) to yield solid 4-(benzyloxycarbonyl)-1-(4-chloroquinolin-7-ylmethyl)-piperazin-2-one (1.2 g, 2.9 mmol). A portion of this material (0.75 g, 1.8 mmol) is dissolved in acetonitrile (20 mL) and treated with iodo trimethylsilane (0.78 mL, 5.4 mmol) at room temperature for 3 hours. The reaction is quenched with methanol and concentrated to dryness. Methanol addition and concentration is repeated four times. The final residue is taken up is 2M aqueous HCl; the solution is washed with ether and concentrated. The residue is recrystallized from isopropanol and ether to yield the title compound (0.63 g, 2.3 mmol) MS m/z: M$^+$=275; $^1$HNMR (CD$_3$OD, 300 MHz) δ9.1 (d, 1H), 8.5 (d, 1H), 8.2-8.3 (m, 2H), 8.0 (d, 1H), 5.2 (s, 2H), 4.1 (s, 2H), 3.7-3.8 (m, 2H), 3.6-3.7 (m, 2H).

EXAMPLE 90

1-(4-Chlorocinnolin-7-ylmethyl)-piperazin-2-one 4-(t-Butyloxycarbonyl)-piperazin-2-one (0.6 g, 3.0 mmol), EXAMPLE 40, is dissolved in THF (80 mL), cooled in an ice bath and treated with tretrabutylammonium iodide (0.23 g, 0.62 mmol) and 60% sodium hydride (0.12 g, 3.0 mmol). The reaction mixture is stirred at ° C. for 40 minutes then treated dropwise with a solution of 7-bromomethyl-4-chlorocinnoline (10.7 g, 2.7 mmol), Example 15, in THF (20 mL). The resulting solution is warmed to ambient temperature over 2 hours. The solution is evaporated to dryness and the residue is taken up in ethyl acetate and 10% aqueous sodium bicarbonate solution. The organic layer is separated, washed with water, dried (sodium sulfate) and concentrated. The residue is chromatographed (ethyl acetate) to yield the title compound (0.6 g, 1.6 mmol). A portion of this material (0.21 g, 1.26 mmol) is dissolved in THF (~4 mL) and treated with a saturated solution of HCl in ethyl acetate (50 mL) at room temperature for 2 hours. The solution is filtered and concentrated to a residue (0.14 g, 0.4 mmol). MS m/z: M$^+$=275; $^1$H NMR (CD$_3$OD, 300 MHz) δ9.15 (d, 1H), 8.5 (d, 1H), 8.25 (s, 1H), 8.15 (d, 1H), 8.0 (d, 1H), 5.0 (s, 2H), 4.1 (s, 2H), 3.7-3.8 (m, 2H), 3.6-3.7 (m, 2H).

EXAMPLE 91

1-(4-Chloroquinolin-7-ylmethyl)-3-(S)-methylpiperazin-2-one 4-(Benzyloxycarbonyl)-3-(S)-methylpiperazin-2-one (1.0 g, 4.0 mmol), EXAMPLE 46, is dissolved in THF (60 mL), cooled in an ice bath and treated with tretrabutylammonium iodide (0.10 g, 0.27 mmol) and 60% sodium hydride (0.18 g, 4.4 mmol). The reaction mixture is stirred at 0° C. for 30 minutes then treated dropwise with a solution of 7-bromomethyl-4-chloroquinoline (1.12 g, 4.4 mmol), EXAMPLE 14, in THF (5 mL). The resulting solution warmed to room temperature over approximately 1 h then quenched with sodium bicarbonate solution and concentrated. The residue is partitioned between ethyl acetate and water; the organic layer is dried (sodium sulfate) and concentrated. The residue is chromatographed (5% methanol/methylene chloride) to yield solid 4-(Benzyloxycarbonyl)-1-(4-chloroquinolin-7-ylmethyl)-3-(S)-methyl-piperazin-2-one (1.32 g, 3.1 mmol). A portion of this material (0.10 g, 0.23 mmol) is dissolved in acetonitrile (6 mL) and treated with iodotrimethyl-silane (0.1 mL, 0.75 mmol) at room temperature for 2 hours. The reaction is quenched with methanol and concentrated to dryness. Methanol addition and concentration is repeated six times. The final residue is taken up is 2M aqueous HCl; the solution is washed with ether and concentrated to yield the title compound. MS m/z: M$^+$=289; $^1$H NMR (CD$_3$OD, 300 MHz) δ9.2 (d, 1H), 8.6 (d, 1H), 8.2-8.3 (m, 2H), 8.0 (d, 1H), 5.1 (q, 1H), 4.3-4.4 (m, 1H), 3.8-4.0 (m, 2H), 3.6-3.8 (m, 3H), 1.75 (d, 3H).

EXAMPLE 92

1-[2-(Pyridin-4-ylamino)-ethyl]-piperazin-2-one

A. 4-(tert-Butyloxycarbonyl)-1-(2-aminoethyl)-piperazin-2-one.

4-(tert-Butyloxycarbonyl)-piperazin-2-one (8.0 g, 40 mmol), EXAMPLE 40, is dissolved in THF (160 mL), cooled in an ice bath and treated with 60% sodium hydride (1.9 g, 48 mmol). The reaction mixture is stirred 40 minutes, then treated with tetra-butylammonium iodide (0.35 g, 0.95 mmol) and bromoacetonitrile (3.4 mL, 48 mmol). After 2 h the reaction is quenched with water, concentrated to a small volume and extracted with methylene chloride (3×). The combined organic extracts are concentrated and the residue is chromatographed (50% ethyl acetate/hexane) to give 4-(tert-butyloxycarbonyl)-1-cyanomethyl-piperazin-2-one (5.2 g, 21.7 mmol). This material is dissolved in ethanol (140 mL) and treated with platinum oxide (0.83 g) at 50 PSI of hydrogen gas for 24 hours. The catalyst is removed by filtration and the solution is concentrated to yield 4-(tert-butyloxycarbonyl)-1-(2-aminoethyl)-piperazin-2-one (5.2 g, 21.6 mmol). $^1$H NMR (CDCl$_3$, 300 MHz) δ4.08 (s, 2H), 3.62 (m, 2H), 3.44 (t, 2H), 3.38 (t, 2H), 2.89 (t, 2H).

B. 4-(tert-Butyloxycarbonyl)-1-[2-(2,3 5,6-tetrachloropyridin-4-ylamino)-ethyl]-piperazin-2-one.

4-(tert-Butyloxycarbonyl)-1-(2-aminoethyl)-piperazin-2-one (4.0 g, 16 mmol) is dissolved in methylene chloride (150 mL) and treated with 4-nitro-2,3,5,6-tetrachloro-pyridine (4.8 g, 18 mmol) and N-methylmorpholine (4.0 mL, 36 mmol). The reaction mixture is stirred for 5 h, concentrated and the residue is purified by chromatography (50% ethyl acetate/hexane) to give the title compound (4.8 g, 10.5 mmol). Fab MS m/z: 457, 469, 461, [M+1]+; $^1$H NMR (CDCl$_3$, 300 MHz) δ6.00 (t, 1H), 4.10 (s, 2H), 3.97 (m, 2H), 3.66 (m, 2H), 3.38 (m, 2H).

C. 1-[2-(Pyridin-4-ylamino)-ethyl]-piperazin-2-one.

4-(tert-Butyloxycarbonyl)-1-[2-(2,3,5,6-tetrachloropyridin-4-ylamino)-ethyl-piperazin-2-one (3.5 g, 7.6 mmol) is dissolved in methanol (20 mL) and 0.5 M sodium methoxide in methanol (150 mL, 75 mmol). The solution is treated with Pd/C (0.5 g) and agitated under 50 PSI of hydrogen gas for 16 hours. The solvent is removed and the residue is extracted with methylene chloride which is filtered. The filtrate is concentrated and loaded onto a silica flash column. The column is eluted with 5% MeOH/CH$_2$Cl$_2$ followed by NH$_4$OH/ MeOH/CH$_2$Cl$_2$ (1:5:95) and NH$_4$OH/MeOH/CH$_2$Cl$_2$ (1:10: 70) to yield 4-(tert-Butyloxycarbonyl)-1-[2-(pyridin-4-ylamino)-ethyl]-piperazin-2-one as a white foam (1.5 g, 4.7 mmol). This material (1.5 g, 4.7 mmol) is treated with 20% trifluoroacetic acid in methylene chloride (110 mL) at ambient temperature for 2 hours. The solution is concentrated and the residue is treated with saturated bicarbonate solution and ammonium hydroxide until a basic solution is obtained. The solution is applied to a silica column and eluted with NH$_4$OH/ MeOH/CH$_2$Cl$_2$ (1:10:60) and 1-[2-(pyridin-4-ylamino)-ethyl]-piperazin-2-one is isolated as a mixture of desired product and inorganic salts (estimate 25% by weight) EI MS m/z: 220, M+; $^1$H NMR (CD$_3$OD, 300 MHz) δ8.07 (d, 2H), 6.96 (d, 2H), 3.77 (s, 2H), 3,65 (m, 6H), 3.44 (t, 2H).

EXAMPLE 93

1-[2-{(Methyl)-(pyridin-4-yl)-amino}-ethyl]-piperazin-2-one trifluroacetate 4-(tert-Butyloxycarbonyl)-1-[2-(2,3,5,6-tetrachloropyridin-4-ylamino)-ethyl]-piperazin-2-one (0.19 g, 0.41 mmol), Example 92, Part B, is dissolved in DMF (3 ml) and treated with 60% NaH (20 mg, 0.5 mmol). After 10 minutes methyl iodide (0.025 ml, 0.40 mmol) is added and the yellow solution is stirred at r.t. overnight. The solution is diluted with EtOAc and washed with H$_2$O (6×). The organic layer is dried (MgSO4) and concentrated to a residue (0.19 g, 0.40 mmol). The residue is dissolved in methanol (2 ml) and treated with 0.5 M NaOMe in MeOH (8 ml, 4.0 mmol)). The solution is treated with Pd/C and agitated under 60 PSI of hydrogen gas overnight and filtered. The filtrate is concentrated and extracted several times with CH$_2$Cl$_2$; removal of solvent in vacuo gives 4-(tert-Butyloxycarbonyl)-1-[2-{(methyl)-(pyridin-4-yl)-amino}-ethyl]-piperazin-2-one as an amorphous residue (0.16 g). EI MS m/z: 335, [M+1]+; $^1$H NMR (CDCl$_3$, 300 MHz) δ8.21 (d, 2H), 6.56 (d, 2H), 3.99 (s, 2H), 3.60 (t, 2H), 3.53 (t, 2H), 3.47 (t, 2H), 3.28 (t, 2H), 2.98 (s, 3H), 1.46 (s, 9H). Treatment of the above product with 20% TFA/ CH$_2$Cl$_2$ (10 mL) at r.t. for 1 h gives, after concentration, the title compound as a residue which is used without further purification. $^1$H NMR (CD$_3$OD, 300 MHz) δ8.14 (d, 2H), 7.30 (br, 1H), 7.00 (br, 1H), 3.88-3.67 (m, 8H), 3.53 (t, 2H), 2.26 (s, 3H).

EXAMPLE 94

1-[2-(3-Methylpyridin-4-yl-amino)-ethyl]-piperazin-2-one

A. 4-[2-(3-Methylpyridin-4-ylamino)-ethyl]-3-oxo-piperazine-1-carboxlic acid benzyl ester.

4-(Benzyloxycarbonyl)-piperazin-2-one (4.7 g, 20 mmol) is dissolved in THF (50 mL) and treated with 1.5M LDA (20 mL, 30 mmol) at 0° C. The reaction mixture is treated with condensed ethylene oxide (3 mL, 40 mmol) and stirred at r.t. overnight. The mixture is neutralized with 2N HCl, concentrated, and extracted with EtOAc. The EtOAc layer is washed with H$_2$O and concentrated to a crude residue. Further extraction of the crude with Et$_2$O and concentration of the ethereal layer gives an oil (1.5 g). The above oil is dissolved in CH$_2$Cl$_2$ (25 mL) and added to the solution of 2M oxalyl chloride (7.5 mL, 15 mmol) and DMSO (2.3 mL, 29.7 mmol) in CH$_2$Cl$_2$ (25 mL) at −60° C. After 15 minutes, Et$_3$N (2.1 ml, 15 mmol) is added. The mixture is stirred at −50° C. for 10 minutes then warmed to r.t for 10 minutes. The reaction is quenched with 0.5 N HCl and extracted with CH$_2$Cl$_2$. The CH$_2$Cl$_2$ layer is washed with 0.5 N HCl, brine (2×), H$_2$O, and concentrated to a residue. The residue is purified by chromatography (2% MeOH/CH$_2$Cl$_2$) to give 4-amino-3-methyl pyridine as an oil (0.5 g, 1.6 mmol). A solution of the oil (0.2 g, 2 mmol), and (1R)-(−)-10-camphorsulfonic acid (15 mg) in toluene (100 ml) is refluxed with a Dean Stark set up overnight. The mixture is concentrated and the residue is purified by chromatography (2-4% MeOH/CH2Cl2) to give the title imine as a white foam (0.20 g, 0.54 mmol). Ion spray MS m/z: 367, [M+1]+; $^1$H NMR (CDCl$_3$, 300 MHz) δ8.20 (d, 1H), 8.14 (s, 1H), 7.35 (s, 5H), 6.60 (d, 1H), 6.18 (dd, 1H), 5.15 (s, 2H), 4.97 (d, 1H), 4.30 (s, 2H), 3.78 (t, 2H), 3.50 (bm, 2H), 2.15 (s, 3H).

B. 1-[2-(3-Methylpyridin-4-yl-amino)-ethyl]-piperazin-2-one.

4-[2-(3-Methylpyridin-4-ylamino)-ethyl]-3-oxo-piperazine-1-carboxlic acid benzyl ester (0.20 g, 0.54 mmol) is dissolved in anhydrous ethanol (20 mL) and hydrogenated at 50 PSI with 10% Pd/C overnight. After filtration, the filtrate is concentrated. The residue is treated with Pd black in 5% HCO$_2$H/CH$_2$Cl$_2$ (10 ml) for 10 minutes. Filtration and concentration gives crude residue, which is purified by chromatography using NH$_4$OH/MeOH/CH$_2$Cl$_2$ (1:5:95) to give the title compound as a clear syrup (0.078 g, 0.33 mmol). $^1$H NMR (CDCl$_3$, 300 MHz) δ8.17 (d, 1H), 8.03 (s, 1H), 7.35 (s, 5H), 6.36 (d, 1H), 5.30 (b, 1H), 3.74 (t, 2H), 3.53 (s, 2H), 3.38 (m, 4H), 3.08 (t, 2H), 2.02 (s, 3H).

EXAMPLE 95

1-[2-(Pyridazin-4-ylamino)-ethyl]-piperazin-2-one 1-(2-Aminoethyl)-4-(tert-butyloxycarbonyl)-piperazin-2-one from EXAMPLE 92, Part A (1.0 g, 4.1 mmol) is treated with 3,4,5-trichloropyridazine (0.81 g, 4.1 mmol), triethylamine (0.57 mL, 4.1 mmol), THF (25 mL) and heated to 120° C. in a sealed tube for 3 hours. Upon cooling, the solution is diluted with ethyl acetate and washed with aqueous sodium bicarbonate (25 mL), water and dried over sodium sulfate. The organic layer is concentrated and chromatographed (5% methanol/methylene chloride) to give a mixture of isomers (0.8 g, 20 mmol). The mixture is dissolved in 0.5 M sodium methoxide in methanol (200 mL), treated with 10% Pd/C (0.5 g) and agitated under 50 PSI of hydrogen for 20 hours. The reaction mixture is filtered; the filtrate is concentrated to a residue which is chromatographed (NH$_4$OH/H$_2$O/MeOH/ EtOAc, 1:1:2:90) to give crude 4-(tert-butyloxycarbonyl)-1-[2-(pyridazin-4-ylamino)-ethyl]-piperazin-2-one. This material is dissolved in a minimal amount of THF and treated with a saturated solution of HCl in ethyl acetate (50 mL). The solution is stirred at ambient temperature for 2 h and diluted with diethyl ether (50 mL). The precipitated title compound is collected and air dried (0.5 g, 1.7 mmol). MS m/z: 367, [M+1]$^+$; $^1$H NMR (CD$_3$OD, 300 MHz) δ8.8 (d, 1H), 8.5 (s, 1H), 7.4 (d, 1H), 4.1 (s, 2H), 3.5-3.8 (m, 8H).

EXAMPLE 96

4-[3-(4-tert-Butoxycarbonylamino-pyridin-3-yl)-propenyl]-3-oxo-piperazine-1-carboxylic acid tert-butyl ester and 4-[3-(4-tert-butoxycarbonylamino-pyridin-3-yl)-allyl]-3-oxo-piperazine-1-carboxylic acid tert-butyl ester A. 1-Allyl-4-(tert-butyloxycarbonyl)-piperazin-2-one.

4-(tert-Butyloxycarbonyl)-piperazin-2-one (1.0 g, 5.0 mmol), EXAMPLE 40, is alkylated with allyl bromide (0.48 ml, 5.5 mmol) in THF (20 ml) using the procedure described in Example 92, Part A. The title compound (0.92 g, 3.8 mmol) is obtained as a colorless liquid after chromatographed (50% ethyl acetate/hexane). EI MS m/z 240 (M+); $^1$H NMR (CDCl$_3$, 300 MHz) δ5.80-5.68 (m, 1H), 5.23-5.15 (m, 2H), 4.09 (s, 2H), 4.03 (d, 2H), 3.63 (t, 2H), 3,30 (t, 2H), 1.45 (s, 9H).

B. 4-[3-(4-tert-Butoxycarbonylamino-pyridin-3-yl)-propenyl]-3-oxo-piperazine-1-carboxylic acid tert-butyl ester and 4-[3-(4-tert-butoxycarbonylamino-pyridin-3-yl)-allyl]-3-oxo-piperazine-1-carboxylic acid tert-butyl ester 1-Allyl-4-(tert-butyloxycarbonyl)-piperazin-2-one (0.49 g, 2.0 mmol) is treated with (3-iodo-pyridin-4-yl)-carbamic acid tert-butyl ester (0.64 g, 2.0 mmol), Pd(OAc)$_2$ (14 mg, 0.06 mmol), P(o-tol)$_3$ (37 mg, 0.12 mmol), and Et$_3$N (0.56 mmol) in a seal tube. The mixture is stirred at 100° C. overnight, then diluted with CH$_2$Cl$_2$ and washed H$_2$O (2×). The CH$_2$Cl$_2$ layer is concentrated and the residue is chromatographed (5% MeOH/CH$_2$Cl$_2$) to give a mixture of two isomers (0.40 g, 0.92 mmol). The mixture is separated into its constituent isomers upon further chromatography (EtOAc) to give 4-[3-(4-tert-butoxycarbonylamino-pyridin-3-yl)-propenyl]-3-oxo-piperazine-1-carboxylic acid tert-butyl ester (90 mg, 0.21 mmol, higher R$_f$ value) and 4-[3-(4-tert-butoxycarbonylamino-pyridin-3-yl)-allyl]-3-oxo-piperazine-1-carboxylic acid tert-butyl ester_(0.24 g, 0.56 mmol, lower R$_f$ value). For the former: MS m/z 433 (M+1); $^1$H NMR (CDCl$_3$, 300 MHz) δ8.38 (d, 1H), 8.28 (s, 1H), 7.93 (d, 1H), 7.48 (d, 1H), 6.67 (s, 1H), 5.10 (m, 1H), 4.15 (s, 2H), 3.70 (t, 2H), 3,46 (t, 2H), 3.39 (d, 2H), 1.48 (s, 9H), 1.45 (s, 9H). For the latter: MS m/z 433 (M+1); $^1$H NMR (CDCl$_3$, 300 MHz) δ8.39 (s, 1H), 8.37 (d, 1H), 7.98 (d, 1H), 6.77 (s, 1H), 6.52 (d, 1H), 6.07 (m, 1H), 4.23 (d, 2H), 4.12 (s, 2H), 3,69 (t, 2H), 3.40 (t, 2H), 1.52 (s, 9H), 1.45 (s, 9H).

EXAMPLE 97

4-[3-(4-tert-Butoxycarbonylamino-pyridin-3-yl)-propyl]-3-oxo-piperazine-1-carboxylic acid tert-butyl ester A mixture of the two isomers from EXAMPLE 96, Part B. (0.11 g, 0.25 mmol) is dissolved in MeOH (7 ml), treated with with 10% Pd/C and is stirred under a balloon of hydrogen for 4 hours. Filtration and concentration gives a white foam (80 mg, 0.18 mmol). EI MS m/z 434 (M+); $^1$H NMR (CDCl$_3$, 300 MHz) δ8.33 (d, 1H), 8.30 (s, 1H), 8.05 (d, 1H), 4.08 (s, 2H), 3.64 (t, 2H), 3.50 (t, 2H), 3.35 (t, 2H), 2.58 (t, 2H), 1.90 (m, 2H), 1.57 (s, 9H), 1.48 (s, 9H).

EXAMPLE 98

4-(Benzyloxycarbonyl)-1-(2-pyrrolo[3,2-c]pyridin-1-ylethyl)-piperazin-2-one 4-(Benzyloxycarbonyl)-1-(2-hydroxyethyl)-piperazin-2-one, prepared as described in EXAMPLE 94, part A. (0.26 g, 0.94 mmol) in methylene chloride (6 mL) is treated with triphenyl phosphine (0.60 g, 2.3 mmol), imidazole (0.16 g, 2.3 mmol), and iodine (0.47 g, 1.9 mmol) for 0.5 h at 0° C. The reactin mixture is partitioned between water and methylene chloride; the organic layer is concentrated and the residue is chromatographed (15% EtOAc/methylene chloride) to give 4-(benzyloxycarbonyl)-1-(2-iodoethyl)-piperazin-2-one (0.24 g, 0.62 mmol). Pyrrolo[3,2-c]pyridine (0.073 g, g, 0.62 mmol) is dissolved in DMF (3 mL) and treated with 60% sodium hydride (0.03 g, 0.74 mmol) and all of the 4-(benzyloxycarbonyl)-1-(2-iodoethyl)-piperazin-2-one from the previous step; the reaction mixture is stirred at r.t. for 16 g. The reaction mixture is concentrated to dryness and the residue is partitioned between water and methylene chloride. The organic layer is concentrated and subjected to chromatography (2-5% MeOH/methylene chloride) to yield the title compound (0.028 g, 0.074 mmol) Ion Spray MS m/z: 379, [M+1]$^+$.

EXAMPLE 99

(±)-1-(3-Amino-4-cyano-benzyl)-4-(6-chloro-benzo[b]thiophene-2-sulfonyl)-6-oxo-piperazine-2-carboxylic acid methyl ester A. (±)-1-[3-(Benzhydrylidene-amino)-4-cyano-benzyl]-4-(6-chloro-benzo[b]thiophene-2-sulfonyl)-6-oxo-piperazine-2-carboxylic acid methyl ester A solution containing (±)-1-[3-(benzhydrylidene-amino)-4-cyano-benzyl]-6-oxo-piperazine-2-carboxylic acid methyl ester (55 mg, 0.12 mmol) in CH$_2$Cl$_2$ (1 mL) is cooled to 0° C. DIPEA (24 mg, 0.18 mmol) is then added followed by the addition of 6-chloro-benzo[b]thiophene-2-sulfonyl chloride (32 mg, 0.12 mmol), EXAMPLE 1. The reaction mixture is warmed to ambient temperature. After 16 h, the reaction mixture is absorbed directly onto silica gel and chromatographed (CH$_2$Cl$_2$ to 2% MeOH/CH$_2$Cl$_2$) to provide 60 mg (73%) of the title compound. $^1$H NMR (300 MHz, CDCl$_3$) δ2.77 (dd, J=12.3, 3.4 Hz, 1H), 3.50-3.72 (m, 3H), 3.79 (s, 3H), 4.15 (dd, J=12.3, 1.4 Hz, 1H), 4.24 (d, J=16.9 Hz, 1H), 5.41 (d, J=15.3 Hz, 1H), 6.50 (s, 1H), 6.76 (dd, J=7.9, 1.4 Hz, 1H), 7.11-7.86 (m, 15H) ppm; MS (ISP loop): m/z 683 (M+H).

B. (±)-1-(3-Amino-4-cyano-benzyl)-4-(6-chloro-benzo[b]thiophene-2-sulfonyl)-6-oxo-piperazine-2-carboxylic acid methyl ester Concentrated HCl (12M, one drop) is added at 0° C. to a mixture containing (±)-1-[3-(benzhydrylidene-amino)-4-cyano-benzyl]-4-(6-chloro-benzo[b]thiophene-2-sulfonyl)-6-oxo-piperazine-2-carboxylic acid methyl ester (60 mg, 0.08 mmol) in MeOH (5 mL). Added THF (2 mL) followed by a second drop of 12M HCl and warmed reaction mixture to ambient temperature. The reaction is quenched by pouring the reaction mixture onto a 1:1 mixture of CH$_2$Cl$_2$/aqueous NaHCO$_3$ and the layers are separated. The aqueous phase is washed with CH$_2$Cl$_2$ and then the combined organic phase is washed with brine, dried over anhydrous MgSO$_4$, filtered and concentrated. The crude residue is chromatographed on silica gel (CH$_2$Cl$_2$ to 4% MeOH/CH$_2$Cl$_2$) to provide 42 mg (93%)

of the title compound. $^1$H NMR (300 MHz, CDCl$_3$) δ2.98 (dd, J=12.5, 3.5 Hz, 1H), 3.60 (d, J=16.8 Hz, 1H), 3.69 (d, J=15.3 Hz, 1H), 3.79 (s, 3H), 3.98 (m, 1H), 4.21-4.31 (m, 2H), 4.44 (br s, 2H), 5.36 (d, J=15.3 Hz, 1H), 6.47 (dd, J=8.0, 1.4 Hz, 1H), 6.54 (s, 1H), 7.26 (d, J=8.0 Hz, 1H), 7.45 (dd, J=8.5, 1.8 Hz, 1H), 7.80-7.86 (m, 3H) ppm; MS (ISP loop): m/z 519 (M+H).

EXAMPLE 100

(±)-1-(3-Amino-4-cyano-benzyl)-4-(6-chloro-benzo[b]thiophene-2-sulfonyl)-6-oxo-piperazine-2-carboxylic acid Water (5 drops) is added to a solution containing (±)-1-(3-amino-4-cyano-benzyl)-4-(6-chloro-benzo[b]thiophene-2-sulfonyl)-6-oxo-piperazine-2-carboxylic acid methyl ester (30 mg, 0.05 mmol), EXAMPLE 99, in a 1:1 mixture of THF/MeOH (2 mL). At ambient temperature, LiOH monohydrate (7 mg, 1.66 mmol) is then added. After 16 h, the reaction mixture is diluted with water and purified by reverse-phase HPLC [Buffer A: water w/0.1% TFA; Buffer B: CH3CN w/0.1% TFA; Gradient: 0% B to 60% B over 30 min] to provide 10 mg (34%) of the title compound as a white solid. $^1$H NMR (300 MHz, d$_6$-DMSO) δ3.18 (dd, J=12.1, 3.5 Hz, 1H), 3.61 (d, J=16.0 Hz, 1H), 3.77 (d, J=16.0 Hz, 1H), 3.95 (d, J=16.0 Hz, 1H), 4.06 (d, J=12.1 Hz, 1H), 4.14 (m, 1H), 6.40 (d, J=8.0 Hz, 1H), 6.54 (s, 1H), 7.21 (d, J=8.0 Hz, 1H), 7.57 (dd, J=8.6, 1.9 Hz, 1H), 8.06 (d, J=8.6 Hz, 1H), 8.18 (s, 1H), 8.33 (s, 1H) ppm; MS (ISP loop): m/z 505 (M+H).

EXAMPLE 101

4-[4-(6-Chlorobenzo[b]thiophene-2-sulfonyl)-2-oxo-piperazine-1-ylmethyl]benzamidine To a solution of 4-(2-oxopiperazin-1-ylmethyl)benzamidine bistrifluoroacetate (0.38 g, 0.83 mmol), EXAMPLE 66, in CH$_2$Cl$_2$ (5 mL) is added Et$_3$N (0.35 mL, 2.6 mmol) and 6-chloro-benzo[b]thiophene-2-sulfonyl chloride (0.23 g, 0.85 mmol, EXAMPLE 1. After 6 hours, the solution is concentrated. The product is purified by RP-HPLC eluting in a gradient of 10% CH$_3$CN/H$_2$O(0.1% TFA) to 70% CH$_3$CN/H$_2$O(0.1% TFA). The appropriate collected fractions are lyophilized to afford the title compound as a white solid (0.37 g, 0.65 mmol). $^1$H NMR (d$^6$-DMSO, 300 MHz) δ9.33 (bs, 2H), 8.96 (bs, 1H), 8.30 (s, 1H), 8.18 (s, 1H), 8.04 (d, 1H), 7.70 (m, 2H), 7.50 (m, 1H), 7.28 (m, 2H), 4.55 (s, 2H), 3.86 (s, 2H), 3.44 (m, 2H), 3.22 (m, 2H).

The following compounds are prepared from 1-(4-Amino-quinazoline-7-ylmethyl)-3-ethyl-piperazine-2-one, Example 77, and the appropriate sulfonyl chloride using the method of Example 101.

| Example # | Name | m/z (M + H) |
| --- | --- | --- |
| 102 | 4-[4-(4-Methoxy-benzenesulfonyl)-2-oxo-piperazin-1-ylmethyl]-benzamidine | 403 |
| 103 | 4-[4-(5-Chloro-thieno[3,2-b]pyridine-2-sulfonyl)-2-oxo-piperazin-1-ylmethyl]-benzamidine | 463, 465 |
| 104 | 4-[4-(6-Chloro-thieno[2,3-b]pyridine-2-sulfonyl)-2-oxo-piperazin-1-ylmethyl]-benzamidine | 464, 466 Cl pattern |
| 105 | 4-[2-Oxo-4-(thieno[2,3-c]pyridine-2-sulfonyl)-piperazin-1-ylmethyl]-benzamidine | 430 |
| 106 | 4-[4-(7-Chloro-thieno[2,3-c]pyridine-2-sulfonyl)-2-oxo-piperazin-1-ylmethyl]-benzamidine | 464, 466 Cl pattern |
| 107 | 4-[4-(5'-Chloro-[2,2']bithiophenyl-5-sulfonyl)-2-oxo-piperazin-1-ylmethyl]-benzamidine | 495, 497 Cl pattern |
| 108 | 4-[4-(4-Chloro-thieno[3,2-c]pyridine-2-sulfonyl)-2-oxo-piperazin-1-ylmethyl]-benzamidine | 464, 466 Cl pattern |
| 109 | 4-[2-Oxo-4-(toluene-4-sulfonyl)-piperazin-1-ylmethyl]-benzamidine | 387 |
| 110 | 4-[4-(Benzo[b]thiophene-2-sulfonyl)-2-oxo-piperazin-1-ylmethyl]-benzamidine | 429 |
| 111 | 4-Amino-3-[4-(6-chloro-benzo[b]thiophene-2-sulfonyl)-2-oxo-piperazin-1-ylmethyl]-benzamidine | 478, 480 Cl pattern |
| 112 | 3-[2-Oxo-4-(toluene-4-sulfonyl)-piperazin-1-ylmethyl]-benzamidine | 387 |
| 113 | 3-[4-(6-Fluoro-benzo[b]thiophene-2-sulfonyl)-2-oxo-piperazin-1-ylmethyl]-benzamidine | 447 |
| 114 | 3-[4-(4-Chloro-benzo[b]thiophene-2-sulfonyl)-2-oxo-piperazin-1-ylmethyl]-benzamidine | 463, 465 Cl pattern |
| 115 | 3-[4-(5-Chloro-benzo[b]thiophene-2-sulfonyl)-2-oxo-piperazin-1-ylmethyl]-benzamidine | 463, 465 Cl pattern |
| 116 | 3-[4-(6-Methoxy-naphthalene-2-sulfonyl)-2-oxo-piperazin-1-ylmethyl]-benzamidine | 453 |
| 117 | 3-{4-[5-(5-Nitro-pyridine-2-sulfonyl)-thiophene-2-sulfonyl]-2-oxo-piperazin-1-ylmethyl}-benzamidine | 565 |
| 118 | 3-[4-(6-Chloro-benzo[b]thiophene-2-sulfonyl)-2-oxo-piperazin-1-ylmethyl]-benzamidine | 463, 465 Cl pattern |
| 119 | 3-{4-[2-(3-Chloro-phenyl)-ethenesulfonyl]-2-oxo-piperazin-1-ylmethyl}-benzamidine | 433, 435 Cl pattern |
| 120 | 3-[2-Oxo-4-(4-phenylazo-benzenesulfonyl)-piperazin-1-ylmethyl]-benzamidine | 477 |
| 121 | 3-[4-(Benzo[b]thiophene-2-sulfonyl)-2-oxo-piperazin-1-ylmethyl]-benzamidine | 429 |

EXAMPLE 122

4-[4-(6-Chloro-1H-benzoimidazol-2-ylmethyl)-2-oxo-piperazin-1-ylmethyl]-benzamidine Hydrogen chloride gas is bubbled into an ice-cooled solution of 4-[4-(6-chloro-1H-benzoimidazol-2-ylmethyl)-2-oxo-piperazin-1-ylmethyl]-benzonitrile (100 mg, 0.264 mmol), (prepared by deprotecting 4-(4-cyanobenzyl)-3-oxopiperazine-1-carboxylic acid benzyl ester, EXAMPLE 66, Part A, followed by alkylation with 6-chloro-2-chloromethylbenzimidazole) in 15 mL of methanol. The solution contained 3Å molecular sieves. The reaction mixture is stored at −30° C. The methanol is removed on the rotovap. Fresh methanol (20 ml) is added folowed by a stream of ammonia gas. The resulting mixture is heated to reflux for three hours. The reaction mixture is filtered at room temperature. The mother liquor is condensed and the resulting residue is purified by reverse phase HPLC (0-50% ACN/$H_2O$). The product is isolated as a white solid with a melting point of 91-95° C. MS $C_{20}H_{21}ClN_6O$ m/z: 397, 399. Anal. calcd. for $C_{20}H_{21}ClN_6O\cdot3C_2HF_3O_2$: C, 42.26; H, 3.27; N, 11.37. Found C, 42.20; H, 3.44; N, 11.36.

EXAMPLE 123

4-{4-[3-(5-Chloro-thiophen-2-yl)-(E)-acryloyl]-2-oxopiperazin-1-ylmethyl}benzamidine To a solution of 4-(2-oxopiperazin-1-ylmethyl)benzamidine bistrifluoroacetate (75 mg, 0.16 mmol), EXAMPLE 66, in 1.5 mL of DMF is added N,N-diisopropylethylamine (0.14 mL, 0.80 mmol). After stirring 10 min at room temperature, 3-(5-chloro-thiophen-2-yl)-(E)-acrylic acid (32 mg, 0.17 mmol), EXAMPLE 25, is added, followed by 2-(1H-benzotriazol-1-yl)-1,1,3,3-tetramethyluronium tetrafluoroborate (TBTU) (55 mg, 0.17 mmol). The resulting mixture is stirred at room temperature for 16 h and the solution is concentrated. The crude product is purified by RP-HPLC eluting in a gradient of 10% $CH_3CN/H_2O$ (0.1% TFA) to 70% $CH_3CN/H_2O$ (0.1% TFA) and the appropriate product fractions are combined and lyophelized to provide the title compound (77 mg, 0.15 mmol) as a white solid. $^1H$ NMR (d6-DMSO, 300 MHz) δ9.27 (bs, 2H), 9.10 (bs, 2H), 7.77 (d, 2H), 7.65 (d, 1H), 7.49 (dd, 2H), 7.39 (m, 1H), 7.15 (d, 1H), 6.89 (d, 1H), 4.65 (s, 2H), 4.45, 4.21 (m, 2H, rotamers), 3.80 (m, 2H), 3.35 (m, 2H). ESI MS, [M+H]$^+$=403,405 (Cl pattern).

EXAMPLE 124

3-{4-[3-(5-Chloro-thiophen-2-yl)-(E)-acryloyl]-2-oxopiperazin-1-ylmethyl}benzamidine The title compound is prepared as described in EXAMPLE 123 using 3-(5-chloro-thiophen-2-yl)-(E)-acrylic acid (EXAMPLE 25) and 3-(2-oxopiperazin-1-ylmethyl)benzamidine bistrifluoroacetate (prepared from 3-bromomethyl toluylnitrile as described in EXAMPLE 66). $^1H$ NMR (DMSO-$d_6$, 300 MHz) δ9.32 (bs, 2H), 9.16 (bs, 2H), 7.65 (m, 5H), 7.39 (m, 1H), 7.15 (d, 1H), 6.89 (d, 1H), 4.64 (s, 2H), 4.44, 4.21 (m, 2H, rotamers), 3.93, 3.79 (m, 2H, rotamers), 3.36 (m, 2H). ESI MS, [M+H]$^+$=403,405 (Cl pattern).

EXAMPLE 125

3-[4-(6-Chloro-1H-benzoimidazol-2-ylmethyl)-2-oxo-piperazin-1-ylmethyl]-benzamidine A white solid (13.0 mg, 13%). $C_{20}H_{21}ClN_6O$ MS m/z: 397, 399 Anal. calcd. for $C_{20}H_{21}ClN_6O\cdot3C_2HF_3O_2$: C, 42.26; H, 3.27; N, 11.37. Found C, 43.70; H, 3.71; N, 11.95.

EXAMPLE 126

1-(2-Aminoquinolin-6-ylmethyl)-4-(5'-chloro-[2,2'] bithiophenyl-5-sulfonyl)piperazin-2-one The title compound is prepared as described in Example 101 using 1-(2-aminoquinolin-6-ylmethyl)piperazin-2-one, EXAMPLE 67, and 5'-chloro-[2,2']bithiophenyl-5-sulfonyl chloride, EXAMPLE 2. The crude product is triturated in $CH_2Cl_2$ and filtered to provide the title compound as a white solid. $^1H$ NMR (d$_6$-DMSO, 300 MHz) δ7.82 (d, 1H), 7.68 (d, 1H), 7.42 (m, 3H), 7.36 (d, 1H), 7.25 (d, 1H), 7.20 (d, 1H), 6.70 (d, 1H), 6.43 (bs, 2H), 4.53 (s, 2H), 3.78 (s, 2H), 3.31 (m, 4H). MS (ion spray) m/z 519, 521, (M+H), Cl pattern.

EXAMPLE 127

6-[4-(6-Chlorobenzo[b]thiophene-2-sulfonyl)-2-oxopiperazin-1-ylmethyl]-1H-quinolin-2-one The title compound is prepared as described in EXAMPLE 101,using 6-(2-oxopiperazin-1-ylmethyl)-1H-quinolin-2-one, minor product from EXAMPLE 67, Part D, and 6-chlorobenzo[b]thiophene-2-sulfonyl chloride, EXAMPLE 1. The crude product is triturated in $CH_2Cl_2$ and filtered to provide the title compound as a white solid. $^1H$ NMR (d$_6$-DMSO, 300 MHz) δ11.72 (bs, 1H), 8.33 (s, 1H), 8.18 (s, 1H), 8.07 (d, 1H), 7.78 (d, 1H), 7.58 (dd, 1H), 7.45 (s, 1H), 7.30 (dd, 1H), 7.18 (d, 1H), 6.46 (d, 1H), 4.52 (s, 2H), 3.86 (s, 2H), 3.43 (m, 2H), 3.31 (m, 2H). MS (ion spray) m/z 488, 490, (M+H), Cl pattern.

The following compounds are prepared using starting materials prepared as described in Examples 67, 68 and 73 and the appropriate carboxylic acid according to the method of Example 123.

| Example # | Name | m/z (M + H) |
|---|---|---|
| 128 | 4-(6-Chloro-benzo[b]thiophene-2-sulfonyl)-1-thieno[2,3-c]pyridin-3-ylmethyl-piperazin-2-one | 478, 480 Cl pattern |
| 129 | 1-(2-Amino-quinoxalin-6-ylmethyl)-4-(6-chloro-benzo[b]thiophene-2-sulfonyl)-piperazin-2-one | |
| 130 | 4-(6-Chloro-benzo[b]thiophene-2-sulfonyl)-1-thieno[2,3-c]pyridin-2-ylmethyl-piperazin-2-one | 478, 480 Cl pattern |
| 131 | 4-(6-Chloro-benzo[b]thiophene-2-sulfonyl)-1-thieno[3,2-c]pyridin-2-ylmethyl-piperazin-2-one | 478, 480 Cl pattern |
| 132 | 1-(2-Amino-quinolin-6-ylmethyl)-4-(6-chloro-thieno[2,3-b]pyridine-2-sulfonyl)-piperazin-2-one | 488, 490 Cl pattern |

-continued

| Example # | Name | m/z (M + H) |
|---|---|---|
| 133 | 4-(6-Chloro-benzo[b]thiophene-2-sulfonyl)-1-(1-hydroxy-isoquinolin-6-ylmethyl)-piperazin-2-one | 488, 490 Cl pattern |
| 134 | 4-(6-Chloro-benzo[b]thiophene-2-sulfonyl)-1-(1-chloro-isoquinolin-6-ylmethyl)-piperazin-2-one | 506, 508 Cl pattern |
| 135 | 7-[4-(6-Chloro-benzo[b]thiophene-2-sulfonyl)-2-oxo-piperazin-1-ylmethyl]-2H-isoquinolin-1-one | 488, 490 Cl pattern |
| 136 | 4-(6-Chloro-benzo[b]thiophene-2-sulfonyl)-1-(1-chloro-isoquinolin-7-ylmethyl)-piperazin-2-one | 506, 508 Cl pattern |
| 137 | 1-(7-Amino-thieno[2,3-c]pyridin-2-ylmethyl)-4-(6-chloro-benzo[b]thiophene-2-sulfonyl)-piperazin-2-one | 493, 495 Cl pattern |
| 138 | 4-(6-Chloro-benzo[b]thiophene-2-sulfonyl)-1-(2-chloro-quinolin-6-ylmethyl)-piperazin-2-one | 506, 508 Cl pattern |
| 139 | 4-(6-Chloro-benzo[b]thiophene-2-sulfonyl)-1-quinolin-6-ylmethyl-piperazin-2-one | 472, 474 Cl pattern |
| 140 | 7-[4-(6-Chloro-benzo[b]thiophene-2-sulfonyl)-2-oxo-piperazin-1-ylmethyl]-1H-quinolin-2-one | 488, 490 Cl pattern |
| 141 | 1-(2-Amino-quinolin-7-ylmethyl)-4-(6-chloro-benzo[b]thiophene-2-sulfonyl)-piperazin-2-one | 487, 489 Cl pattern |
| 142 | 1-(4-Amino-thieno[3,2-c]pyridin-2-ylmethyl)-4-(6-chloro-benzo[b]thiophene-2-sulfonyl)-piperazin-2-one | 493, 495 Cl pattern |
| 143 | 4-(6-Chloro-benzo[b]thiophene-2-sulfonyl)-1-(1,2,3,4-tetrahydro-isoquinolin-6-ylmethyl)-piperazin-2-one | 475, 477 Cl pattern |
| 144 | 4-(6-Chloro-benzo[b]thiophene-2-sulfonyl)-1-isoquinolin-6-ylmethyl-piperazin-2-one | 472, 474 Cl pattern |
| 145 | 1-(2-Amino-quinolin-6-ylmethyl)-4-(6-chloro-benzo[b]thiophene-2-sulfonyl)-piperazin-2-one | 487, 489 Cl pattern |
| 146 | 4-(6-Chloro-benzo[b]thiophene-2-sulfonyl)-1-(decahydro-isoquinolin-6-ylmethyl)-piperazin-2-one | 482, 484 Cl pattern |
| 147 | 1-(1-Amino-isoquinolin-6-ylmethyl)-4-(6-chloro-benzo[b]thiophene-2-sulfonyl)-piperazin-2-one | 487, 489 Cl pattern |
| 148 | 4-(6-Chloro-benzo[b]thiophene-2-sulfonyl)-1-(decahydro-isoquinolin-7-ylmethyl)-piperazin-2-one | 482, 484 Cl pattern |
| 149 | 1-(1-Amino-isoquinolin-7-ylmethyl)-4-(6-chloro-benzo[b]thiophene-2-sulfonyl)-piperazin-2-one | 487, 489 Cl pattern |
| 150 | 1-(4-Amino-thieno[3,2-c]pyridin-3-ylmethyl)-4-(6-chloro-benzo[b]thiophene-2-sulfonyl)-piperazin-2-one | 493, 495 Cl pattern |
| 151 | (+/−)-[1-(6-Chloro-benzo[b]thiophene-2-sulfonyl)-3-oxo-4-thieno[3,2-c]pyridin-2-ylmethyl-piperazin-2-yl]-acetic acid | 536, 538 Cl pattern |
| 152 | (+/−)-[1-(6-Chloro-benzo[b]thiophene-2-sulfonyl)-3-oxo-4-thieno[2,3-c]pyridin-2-ylmethyl-piperazin-2-yl]-acetic acid | 536, 538 Cl pattern |
| 153 | 1-(1-Amino-isoquinolin-6-ylmethyl)-4-[3-(5-chloro-thiophen-2-yl)-(E)-acryloyl]-3-(S)-methoxymethyl-piperazin-2-one | 471, 473 Cl pattern |
| 154 | 1-(1-Amino-isoquinolin-6-ylmethyl)-4-[(5-chloro-thiophen-2-yloxy)-acetyl]-3-(S)-methoxymethyl-piperazin-2-one | 475, 477 Cl pattern |
| 155 | (3S)-1-(7-Chloro-isoquinolin-3-ylmethyl)-4-[(5-chloro-thiophen-2-yloxy)-acetyl]-3-methoxymethyl-piperazin-2-one | 494, 496, 498, Cl$_2$ pattern |
| 156 | (3S)-1-(7-Chloro-isoquinolin-3-ylmethyl)-4-[3-(5-chloro-thiophen-2-yl)-(E)-acryloyl]-3-methoxymethyl-piperazin-2-one | 490, 492, 494, Cl$_2$ pattern |
| 157 | (S)-4-[3-(5-Chloro-thiophen-2-yl)-acryloyl]-3-ethyl-1-(4-hydroxy-quinolin-7-ylmethyl)-piperazin-2-one | 456, 458 Cl pattern |
| 158 | 1-(2-Amino-quinolin-6-ylmethyl)-4-[3-(5-chloro-thiophen-2-yl)-(E)-acryloyl]-piperazin-2-one | 427, 429 Cl pattern |

The following compounds are prepared from starting materials prepared as described in Example 67 and the appropriate aryl-methyl bromide or allyl-methyl bromide using a K$_2$CO$_3$-mediated alkylation reaction.

| Example # | Name | m/z (M + H) |
|---|---|---|
| 159 | 1-(2-Aminoquinolin-6-ylmethyl)-4-(4-methoxybenzyl)piperazin-2-one | 377 |
| 160 | 1-(2-Aminoquinolin-6-ylmethyl)-4-6-chlorobenzo[b]thiophen-2-ylmethyl)piperazin-2-one | 436, 438 Cl pattern |
| 161 | 1-(2-Aminoquinolin-6-ylmethyl)-4-(5-methoxy-1H-benzoimidazol-2-ylmethyl)piperazin-2-one | 417 |
| 162 | 1-(2-Aminoquinolin-6-ylmethyl)-4-(5'-chloro-[2,2']bithiophenyl-5-ylmethyl)piperazin-2-one | 469, 471 Cl pattern |
| 163 | 1-(2-Aminoquinolin-6-ylmethyl)-4-[3-(5-chloro-thiophen-2-yl)-allyl]-piperazin-2-one | 413, 415 Cl pattern |

| Example # | Name | m/z (M + H) |
|---|---|---|
| 164 | 1-(2-Aminoquinolin-6-ylmethyl)-4-[3-(3,5-dibromo-4-methoxy-phenyl)-[1,2,4]oxadiazol-5-ylmethyl]piperazin-2-one | 601, 603, 605 Br$_2$ pattern |
| 165 | 3-[4-(2-Aminoquinolin-6-ylmethyl)-3-oxo-piperazin-1-ylmethyl]-7-fluoro-1H-quinolin-2-one | 431 |
| 166 | 1-(2-Aminoquinolin-6-ylmethyl)-4-(6-chloro-naphthalen-2-ylmethyl)-piperazin-2-one | 430 |

The following compounds are prepared from starting materials prepared as described in Examples 66, 67, 68 and 73 and the appropriate aryl-methyl bromide or allyl-methyl bromide using a K$_2$CO$_3$-mediated alkylation reaction.

| Example # | Name | m/z (M + H) |
|---|---|---|
| 167 | 3-(4-Biphenyl-3-ylmethyl-3-oxo-piperazin-1-ylmethyl)-benzamidine | 399 |
| 168 | 4-(5-Chloro-1H-indol-2-ylmethyl)-1-(4-chloro-quinolin-7-ylmethyl)-piperazin-2-one | 439, 441 Cl pattern |
| 169 | 1,4-Bis-(5-chloro-1H-indol-2-ylmethyl)-piperazin-2-one | 427 |
| 170 | 1-(4-Amino-thieno[3,2-d]pyrimidin-6-ylmethyl)-4-(7-chloro-isoquinolin-3-ylmethyl)-piperazin-2-one | 439, 441 Cl pattern |
| 171 | 1-(4-Amino-thieno[3,2-d]pyrimidin-6-ylmethyl)-4-(6-chloro-benzo[b]thiophen-2-ylmethyl)-piperazin-2-one | 444, 446 Cl pattern |
| 172 | 1-(4-Amino-thieno[3,2-d]pyrimidin-6-ylmethyl)-4-[3-(5-chloro-thiophen-2-yl)-allyl]-piperazin-2-one | 420, 422 Cl pattern |
| 173 | 1-(3-Amino-1H-indazol-6-ylmethyl)-4-[3-(5-chloro-thiophen-2-yl)-allyl]-piperazin-2-one | 401 |
| 174 | 1-(3-Amino-1H-indazol-6-ylmethyl)-4-(6-chloro-benzo[b]thiophen-2-ylmethyl)-piperazin-2-one | 426 |
| 175 | 1-(4-Amino-thieno[2,3-d]pyrimidin-6-ylmethyl)-4-(6-chloro-benzo[b]thiophen-2-ylmethyl)-piperazin-2-one | 443 |
| 176 | 4-[4-(6-Chloro-benzo[b]thiophen-2-ylmethyl)-2-oxo-piperazin-1-ylmethyl]-benzamidine | 413, 415 Cl pattern |
| 177 | 4-[4-(6-Chloro-benzo[b]thiophen-2-ylmethyl)-3-oxo-piperazin-1-ylmethyl]-benzamidine | 413, 415 Cl pattern |
| 178 | 4-(4-Cyclohexylmethyl-2-oxo-piperazin-1-ylmethyl)-benzamidine | 329 |
| 179 | 1-(1-Amino-isoquinolin-6-ylmethyl)-4-(6-chloro-benzo[b]thiophen-2-ylmethyl)-piperazin-2-one | 437, 439 Cl pattern |
| 180 | 1-(1-Amino-isoquinolin-6-ylmethyl)-4-[3-(5-chloro-thiophen-2-yl)-allyl]-3-(S)-methoxymethyl-piperazin-2-one | 457, 459 Cl pattern |
| 181 | 4-[3-(5-Chloro-thiophen-2-yl)-allyl]-1-[4-(6-methoxy-pyridin-3-yl)-benzyl]-3-(S)-methyl-piperazin-2-one | 468 |
| 182 | 4-[3-(5-Chloro-thiophen-2-yl)-allyl]-3-(S)-methyl-1-[4-(6-oxo-1,6-dihydro-pyridin-3-yl)-benzyl]-piperazin-2-one | 454 |
| 183 | (S)-4-(5-Chloro-1H-indol-2-ylmethyl)-1-(4-chloro-quinolin-7-ylmethyl)-3-methoxymethyl-piperazin-2-one | 483 |
| 184 | (S)-4-(5-Chloro-1H-indol-2-ylmethyl)-1-(4-chloro-quinolin-7-ylmethyl)-3-methyl-piperazin-2-one | 453 |

EXAMPLE 185

1-(4-Aminoquinazolin-7-ylmethyl)-4-(6-chlorobenzo[b]thiophene-2-sulfonyl)piperazin-2-one The title compound is prepared as described in EXAMPLE 101, substituting 1-(4-aminoquinazoline-7-ylmethyl)piperazine-2-one bishydrochloride, EXAMPLE 72, for 4-(2-oxopiperazin-1-ylmethyl)-benzamidine. The product is purified by RP-HPLC eluting in a gradient of 10% CH$_3$CN/H$_2$O (0.1% TFA) to 70% CH$_3$CN/H$_2$O (0.1% TFA). The appropriate collected fractions are lyopholized to afford the title compound as a white solid. MS (ion spray) m/z 488, 490, (M+H). $^1$H NMR (d$_6$-DMSO, 300 MHz) δ9.65 (s, 2H), 8.80 (s, 1H), 8.30 (m, 2H), 8.20 (s, 1H), 8.05 (d, 1H), 7.60 (m, 3H), 4.70 (s, 2H), 3.85 (s, 2H), 3.50-3.20 (m, 4H).

EXAMPLE 186

4-(4-Amino-quinazolin-7-ylmethyl)-3-oxo-piperazine-1-sulfonic acid 3-chloro-benzylamide To a solution of 1-(4-aminoquinazoline-7-ylmethyl)piperazine-2-one bishydrochloride, EXAMPLE 72, (0.10 g, 0.30 mmol) is 9 mL of DMF is added 3-chlorobenzyl sulfamyl catechol (0.09 g, 0.30 mmol), EXAMPLE 4, Et$_3$N (0.08 g, 0.75 mmol) and DMAP (0.001 g, 0.12 mmol). The solution is heated to 60° C. After 16 h, the solution is concentrated. The crude product is purified by RP-HPLC eluting with a gradient of 10% CH$_3$CN/H$_2$O (0.1%TFA) to 100% CH$_3$CN. The product fractions are lyophilized to give the title compound (0.077 g, 0.17 mmol) as the TFA salt. $^1$H NMR (d$_6$-DMSO, 300 MHz) δ9.82 (bs, 2H), 8.98 (s, 1H), 8.52 (d, 1H), 8.32 (d, 1H), 7.60 (m, 2H), 7.35 (m, 4H), 4.69 (AB, 2H), 4.11 (m, 2H), 3.77 (s, 2H), 3.38 (m, 2H), 3.27 (m, 2H). MS (ion spray) m/z 461, 463, (M+H), Cl pattern.

The following compounds are prepared from the compound of Example 72 and the appropriate sulfonyl choride using the method of Example 101.

| Example # | Name | m/z (M + H) |
|---|---|---|
| 187 | 1-(4-Amino-quinazolin-7-ylmethyl)-4-(6-chloro-thieno[2,3-b]pyridine-2-sulfonyl)-piperazin-2-one | 489, 491 Cl pattern |
| 188 | 1-(4-Amino-quinazolin-7-ylmethyl)-4-(5'-chloro-[2,2']bithiophenyl-5-sulfonyl)-piperazin-2-one | 520, 522 Cl pattern |
| 189 | 4-(4-Amino-quinazolin-7-ylmethyl)-3-oxo-piperazine-1-sulfonic acid 4-chloro-benzylamide | 460 |
| 190 | 1-(4-Amino-quinazolin-7-ylmethyl)-4-(5-isoxazol-3-yl-thiophene-2-sulfonyl)-piperazin-2-one | 471 |
| 191 | 1-(4-Amino-quinazolin-7-ylmethyl)-4-(thieno[3,2-b]pyridine-2-sulfonyl)-piperazin-2-one | 455 |
| 192 | 4-(4-Amino-quinazolin-7-ylmethyl)-3-oxo-piperazine-1-sulfonic acid [2-(3-chloro-phenyl)-ethyl]-amide | 474 |
| 193 | 4-(4-Amino-quinazolin-7-ylmethyl)-3-oxo-piperazine-1-sulfonic acid [2-(4-chloro-phenyl)-ethyl]-amide | 474 |
| 194 | 1-(4-Amino-quinazolin-7-ylmethyl)-4-(6-chloro-1H-benzoimidazole-2-sulfonyl)-piperazin-2-one | 472 |
| 195 | 1-(4-Amino-quinazolin-7-ylmethyl)-4-[2-(5-chloro-thiophen-2-yl)-ethenesulfonyl]-piperazin-2-one | 464, 466 Cl pattern |
| 196 | 4-(3-Amino-benzenesulfonyl)-1-(4-amino-quinazolin-7-ylmethyl)-piperazin-2-one | 413 |

The following compounds are prepared from starting materials obtained as described in Examples 75-88 and the appropriate sulfonyl chloride using the method of Example 101.

| Example # | Name | m/z (M + H) |
|---|---|---|
| 197 | 1-(4-Amino-quinazolin-7-ylmethyl)-4-[2-(5-chloro-thiophen-2-yl)-ethenesulfonyl]-3-(S)-ethyl-piperazin-2-one | 492, 494 Cl pattern |
| 198 | 1-(4-Amino-quinazolin-7-ylmethyl)-4-(6-chloro-benzo[b]thiophene-2-sulfonyl)-3-(S)-ethyl-piperazin-2-one | 516, 518 Cl pattern |
| 199 | 1-(4-Amino-quinazolin-7-ylmethyl)-4-(5'-chloro-[2,2']bithiophenyl-5-sulfonyl)-3-(S)-ethyl-piperazin-2-one | 548, 550 Cl pattern |
| 200 | 1-(4-Amino-quinazolin-7-ylmethyl)-4-(5'-chloro-[2,2']bithiophenyl-5-sulfonyl)-3-(S)-methyl-piperazin-2-one | 534, 536 Cl pattern |
| 201 | 1-(4-Amino-quinazolin-7-ylmethyl)-4-(6-chloro-benzo[b]thiophene-2-sulfonyl)-3-(S)-methyl-piperazin-2-one | 502, 504 Cl pattern |
| 202 | (+/−)-1-(4-Amino-quinazolin-7-ylmethyl)-4-(6-chloro-benzo[b]thiophene-2-sulfonyl)-6-methyl-piperazin-2-one | 502, 504 Cl pattern |
| 203 | (+/−)-[4-(4-Amino-quinazolin-7-ylmethyl)-1-(6-chloro-benzo[b]thiophene-2-sulfonyl)-3-oxo-piperazin-2-yl]-acetic acid | 546, 548 Cl pattern |

The following compounds are prepared from starting materials obtained as described in Examples 72 and 73 and the appropriate sulfonyl chloride according to the method of Example 101 or propriate carboxylic acid according to the method of Example 123.

| Example # | Name | m/z (M + H) |
|---|---|---|
| 204 | 1-(4-Amino-thieno[3,2-d]pyrimidin-6-ylmethyl)-4-[2-(5-chloro-thiophen-2-yl)-ethenesulfonyl]-piperazin-2-one | 470, 472 Cl pattern |
| 205 | 1-(4-Amino-thieno[3,2-d]pyrimidin-6-ylmethyl)-4-(6-chloro-benzo[b]thiophene-2-sulfonyl)-piperazin-2-one | 493, 495 Cl pattern |
| 206 | 1-(4-Amino-thieno[2,3-d]pyrimidin-6-ylmethyl)-4-(6-chloro-benzo[b]thiophene-2-sulfonyl)-piperazin-2-one | 494, 496 Cl pattern |
| 207 | 4-(6-Chloro-benzo[b]thiophene-2-sulfonyl)-1-(4-hydroxy-quinazolin-6-ylmethyl)-piperazin-2-one | 489, 491 Cl pattern |
| 208 | 1-(4-Amino-thieno[3,2-d]pyrimidin-7-ylmethyl)-4-(6-chloro-benzo[b]thiophene-2-sulfonyl)-piperazin-2-one | 494, 496 Cl pattern |
| 209 | 1-(4-Amino-quinazolin-6-ylmethyl)-4-(6-chloro-benzo[b]thiophene-2-sulfonyl)-piperazin-2-one | 488, 490 Cl pattern |
| 210 | 4-(6-Chloro-benzo[b]thiophene-2-sulfonyl)-1-(4-hydroxy-quinazolin-7-ylmethyl)-piperazin-2-one | 489, 491 Cl pattern |
| 211 | 1-(4-Amino-thieno[3,2-d]pyrimidin-6-ylmethyl)-4-[3-(4-bromo-thiophen-2-yl)-acryloyl]-piperazin-2-one | 478, 480 Br pattern |
| 212 | 1-(4-Amino-thieno[3,2-d]pyrimidin-6-ylmethyl)-4-[3-(5-chloro-thiophen-2-yl)-acryloyl]-piperazin-2-one | 434, 436 Cl pattern |

EXAMPLE 213

4-[2-(5-Chloro-thiophen-2-yl)-ethenesulfonyl]-1-(1H-pyrrolo[3,2-c]pyridin-2-ylmethyl)piperazin-2-one A. 2-{4-[2-(5-Chloro-thiophen-2-yl)-ethenesulfonyl]-2-oxopiperazin-1-ylmethyl}pyrrolo[3,2-c]pyridine-1-carboxylic acid tert-butyl ester.

To a solution of 2-(2-oxopiperazin-1-ylmethyl)pyrrolo[3,2-c]pyridine-1-carboxylic acid tert-butyl ester (0.71 g, 2.1 mmol), EXAMPLE 69, in $CH_3CN$ (7 mL) is added triethylamine (0.60 mL, 4.3 mmol) followed by 2-(5-chloro-thiophen-2-yl)-ethenesulfonyl chloride, EXAMPLE 3, (0.57 g, 2.1 mmol). The mixture is stirred overnight, then concentrated to dryness. The residue is diluted with $CH_2Cl_2$ and washed with saturated sodium bicarbonate and brine. The organic layer is dried over $MgSO_4$, filtered and concentrated in vacuo to give the title compound (1.2 g, 2.1 mmol) as a light yellow solid. The crude material can be used in the subsequent step without further purification. $^1$H NMR ($CDCl_3$, 300 MHz) δ8.80 (s, 1H), 8.42 (d, 1H), 7.88 (d, 1H), 7.55 (d, 1H), 7.14 (d, 1H), 6.98 (d, 1H), 6.41 (s, 1H), 6.36 (d, 1H), 5.00 (s, 2H), 3.98 (s, 2H), 3.61 (m, 4H), 1.71 (s, 9H). Ion spray MS, [M+H]$^+$=537, 539, Cl pattern.

B. 4-[2-(5-Chloro-thiophen-2-yl)-ethenesulfonyl]-1-(1H-pyrrolo[3,2-c]pyridin-2-ylmethyl)piperazin-2-one.

Trifluoroacetic acid (2.2 mL, 28.6 mmol) is added dropwise to a slurry of 2-[4-(6-chlorobenzo[b]thiophene-2-sulfonyl)-2-oxopiperazin-1-ylmethyl]pyrrolo[3,2-c]pyridine-1-carboxylic acid tert-butyl ester (1.32 g, 2.4 mmol) in $CH_2Cl_2$ (25 mL) at 0° C. After 1.5 hours, the ice bath is removed and the solution stirred at room temperature for 4 hours. The reaction mixture is diluted with methylene choride and washed with saturated sodium bicarbonate and brine. The organic layer is dried over $MgSO_4$, filtered and concentrated in vacuo to give the title compound as the free base. The crude product is purified by RP-HPLC eluting in a gradient of 10% $CH_3CN/H_2O$ (0.1% TFA) to 100% $CH_3CN$ and the appropriate product fractions are lyophilized to provide the title compound (1.29 g, 2.2 mmol) as a white solid. $^1$H NMR ($CDCl_3$, 300 MHz) δ14.90 (bs, 1H), 12.81 (s, 2H), 9.12 (s, 1H), 8.41 (d, 1H), 7.89 (d, 1H), 7.60 (d, 1H), 7.50 (d, 1H), 7.20 (d, 1H), 7.12 (d, 1H), 6.95 (s, 1H), 4.80 (s, 2H), 3.98 (s, 2H), 3.48 (s, 4H). Ion spray MS, [M+H]$^+$=437, 439, Cl pattern.

EXAMPLE 214

4-(6-Chlorobenzo[b]thiophene-2-sulfonyl)-1-(1H-pyrrolo[3,2-c]pyridin-2-ylmethyl)piperazin-2-one A. 2-[4-(6-Chlorobenzo[b]thiophene-2-sulfonyl)-2-oxopiperazin-1-ylmethyl]pyrrolo[3,2-c]pyridine-1-carboxylic acid tert-butyl ester.

$^1$H NMR ($CDCl_3$, 300 MHz) δ8.7 (s, 1H), 8.41 (d, 1H), 7.9-7.8 (m, 3H), 7.45 (d, 1H), 7.25 (d, 1H), 6.31 (s, 1H), 4.95 (s, 2H), 3.98 (s, 2H), 3.65 (m, 2H), 3.55 (m, 2H), 1.68 (s, 9H). Ion spray MS, [M+H]$^+$=561, 563, Cl pattern.

B. 4-(6-Chlorobenzo[b]thiophene-2-sulfonyl)-1-(1H-pyrrolo[3,2-c]pyridin-2-ylmethyl)piperazin-2-one trifluoroacetate.

$^1$H NMR (d6-DMSO, 300 MHz) δ14.68 (bs, 1H), 12.6 (s, 1H), 9.1 (s, 1H), 8.36 (d, 1H), 8.29 (d, 1H), 8.17 (s, 1H), 8.05 (d, 1H), 7.82 (d, 1H), 7.56 (m, 2H), 6.83 (s, 1H), 4.1 (s, 2H), 3.84 (s, 2H), 3.38 (m, 4H). Ion spray MS, [M+H]$^+$=461,463, Cl pattern.

EXAMPLE 215

4-(6-Chlorobenzo[b]thiophene-2-sulfonyl)-1-(5-oxy-1H-pyrrolo[3,2-c]pyridin-2-ylmethyl)piperazin-2-one 4-(6-Chlorobenzo[b]thiophene-2-sulfonyl)-1-(1H-pyrrolo[3,2-c]pyridin-2-ylmethyl)piperazin-2-one (0.06 g, 0.13 mmol) is dissolved in anhydrous methylene chloride (20 ml), treated with m-chloroperbenzoic acid (0.03 g, mmol) and stirred at room temperature for 4 hours. The solution is diluted with methylene chloride, washed with $NaHCO_3$, dried ($Na_2SO_4$) and concentrated. The residue is purified by flash chromatography (5-10% $MeOH/CH_2Cl_2$) and converted to the TFA salt to provide the title compound (0.015 g, 0.032 mmol). $^1$H NMR ($CDCl_3$, 300 MHz) δ9.14 (bs, 1H), 8.95 (d, 1H), 7.8-7.87 (m, 3H), 7.57 (d, 1H), 7.48 (dd, 1H), 6.87 (s, 1H), 4.90 (s, 2H), 3.95 (s, 2H), 3.86 (s, 3H), 3.49 (s, 3H). EI MS, [M$^+$]=474, 476, Cl pattern.

EXAMPLE 216

4-(6-Chlorobenzo[b]thiophene-2-sulfonyl)-1-(1-methyl-1H-pyrrolo[3,2-c]pyridin-2-ylmethyl)piperazin-2-one 4-(6-Chlorobenzo[b]thiophene-2-sulfonyl)-1-(1H-pyrrolo[3,2-c]pyridin-2-ylmethyl)piperazin-2-one (0.59 g, 1.28 mmol), EXAMPLE 214, is dissolved in anhydrous DMF (30 ml), cooled in an ice bath, treated with 60% sodium hydride (0.061 g, 1.53 mmol) and stirred at room temperature for 30 minutes. The solution is treated with methyl iodide (83 mL, 1.33 mmol) and warmed to room temperature over 4 hours. The reaction is quenched with ammonium chloride solution, diluted with ethyl acetate and separated. The organic layer is washed with brine (3×), dried ($Na_2SO_4$) and concentrated. The residue is purified by flash chromatography (5-10% MeOH/$CH_2Cl_2$) to provide the title compound (0.31 g, 0.65 mmol). $^1$H NMR ($CD_3OD$, 300 MHz) δ8.55 (d, 1H), 7.99 (dd, 1H), 7.82 (m, 3H), 7.49 (dd, 1H), 7.43 (d, 1H), 6.55 (s, 1H), 4.75 (s, 2H), 3.96 (s, 2H), 3.52 (m, 4H), 3.86 (s, 3H), 3.49 (s, 3H). Ion Spray MS, [M+H]$^+$=477.

The following compounds are prepared from starting materials obtained as described in Example 69 and the appropriate sulfonyl chlorides according to the method of Example 101.

| Example # | Name | m/z (M + H) |
|---|---|---|
| 217 | 4-(3-Chlorobenzo[b]thiophene-2-sulfonyl)-1-(1H-pyrrolo[3,2-c]pyridin-2-ylmethyl)piperazin-2-one | 460 |
| 218 | 4-(6-Chlorothieno[2,3-b]pyridine-2-sulfonyl)-1-(1H-pyrrolo[3,2-c]pyridin-2-ylmethyl)piperazin-2-one. | 462, 464 Cl pattern |
| 219 | 4-(6-Bromobenzo[b]thiophene-2-sulfonyl)-1-(1H-pyrrolo[3,2-c]pyridin-2-ylmethyl)piperazin-2-one | 505 |
| 220 | 2-[3-Oxo-4-(1H-pyrrolo[3,2-c]pyridin-2-ylmethyl)piperazine-1-sulfonyl]-benzo[b]thiophene-6-carbonitrile | 452 |
| 221 | 4-(5'-Chloro-[2,2']bithiophenyl-5-sulfonyl)-1-(1H-pyrrolo[3,2-c]pyridin-2-ylmethyl)piperazin-2-one | 493 |
| 222 | 4-[2-(4-Chlorophenyl)ethenesulfonyl]-1-(1H-pyrrolo[3,2-c]pyridin-2-ylmethyl)piperazin-2-one | 431 |
| 223 | {2-[4-(6-Chlorobenzo[b]thiophene-2-sulfonyl)-2-oxopiperazin-1-ylmethyl]pyrrolo[3,2-c]pyridin-1-yl} acetic acid | 519, 521 Cl pattern |
| 224 | 4-(5-Pyridin-4-ylthiophene-2-sulfonyl)-1-(1H-pyrrolo[3,2-c]pyridin-2-ylmethyl)piperazin-2-one | 454 |
| 225 | {2-[4-(6-Chlorobenzo[b]thiophene-2-sulfonyl)-2-oxopiperazin-1-ylmethyl]pyrrolo[3,2-c]pyridin-1-yl} acetic acid ethyl ester | 547, 549 Cl pattern |
| 226 | 4-(6-Chlorobenzo[b]thiophene-2-sulfonyl)-1-[1-(2-methoxyethyl)-1H-pyrrolo[3,2-c]pyridin-2-ylmethyl]piperazin-2-one | 519, 520 Cl pattern |
| 227 | 4-(6-Chlorothieno[3,2-b]pyridine-2-sulfonyl)-1-(1H-pyrrolo[3,2-c]pyridin-2-ylmethyl)piperazin-2-one | 462, 464 Cl pattern |
| 228 | {2-[4-(6-Chloro-benzo[b]thiophene-2-sulfonyl)-2-oxopiperazin-1-ylmethyl]pyrrolo[2,3-c]pyridin-1-yl} acetic acid methyl ester | 533, 535 Cl pattern |
| 229 | 2-[3-Oxo-4-(1H-pyrrolo[3,2-c]pyridin-2-ylmethyl)piperazine-1-sulfonyl]benzo[b]thiophene-5-carbonitrile | 452 |
| 230 | 4-(5-Aminomethylbenzo[b]thiophene-2-sulfonyl)-1-(1H-pyrrolo[3,2-c]pyridin-2-ylmethyl)piperazin-2-one | 456 |
| 231 | 2-{2-[4-(6-Chlorobenzo[b]thiophene-2-sulfonyl)-2-oxopiperazin-1-ylmethyl]pyrrolo[3,2-c]pyridin-1-yl}acetamide | 518, 520 Cl pattern |
| 232 | 4-(6-Chlorobenzo[b]thiophene-2-sulfonyl)-1-[1-(2-hydroxyethyl)-1H-pyrrolo[3,2-c]pyridin-2-ylmethyl]piperazin-2-one | 505 |
| 233 | 4-(6-Chloro-1H-benzoimidazole-2-sulfonyl)-1-(1H-pyrrolo[3,2-c]pyridin-2-ylmethyl)-piperazin-2-one | 445, 447 Cl pattern |
| 234 | 4-(1H-Benzoimidazole-2-sulfonyl)-1-(1H-pyrrolo[3,2-c]pyridin-2-ylmethyl)-piperazin-2-one | 411 |
| 235 | 4-(6-Aminomethyl-benzo[b]thiophene-2-sulfonyl)-1-(1H-pyrrolo[3,2-c]pyridin-2-ylmethyl)-piperazin-2-one | 456 |
| 236 | 1-(1H-Pyrrolo[3,2-c]pyridin-2-ylmethyl)-4-(thieno[2,3-b]pyridine-2-sulfonyl)-piperazin-2-one | 428 |
| 237 | 1-(1H-Pyrrolo[3,2-c]pyridin-2-ylmethyl)-4-(thieno[3,2-b]pyridine-2-sulfonyl)-piperazin-2-one | 428 |
| 238 | 4-[2-(5-Chloro-thiophen-2-yl)-ethanesulfonyl]-1-(1H-pyrrolo[3,2-c]pyridin-2-ylmethyl)-piperazin-2-one | 439, 441 Cl pattern |
| 239 | 4-(2-Benzo[b]thiophen-2-yl-ethenesulfonyl)-1-(1H-pyrrolo[3,2-c]pyridin-2-ylmethyl)-piperazin-2-one | 453 |
| 240 | 4-[2-(5-Chloro-4-methoxy-thiophen-2-yl)-ethenesulfonyl]-1-(1H-pyrrolo[3,2-c]pyridin-2-ylmethyl)-piperazin-2-one | 467, 469 |
| 241 | 4-(6-Chloro-benzo[b]thiophene-2-sulfonyl)-1-furo[3,2-c]pyridin-2-ylmethyl-piperazin-2-one | 462, 464 |
| 242 | 4-(6-Fluoro-benzo[b]thiophene-2-sulfonyl)-1-furo[3,2-c]pyridin-2-ylmethyl-piperazin-2-one | 446 |
| 243 | 4-(6-Chlorobenzo[b]thiophene-2-sulfonyl)-1-(1H-pyrrolo[2,3-c]pyridin-2-ylmethyl)piperazin-2-one | 460, 462 Cl pattern |
| 244 | 4-(6-Chlorothieno[2,3-b]pyridine-2-sulfonyl)-1-(1H-pyrrolo[2,3-c]pyridin-2-ylmethyl)piperazin-2-one | 462, 464 Cl pattern |
| 245 | {2-[4-(6-Chloro-benzo[b]thiophene-2-sulfonyl)-2-oxo-piperazin-1-ylmethyl]-pyrrolo[2,3-c]pyridin-1-yl}-acetic acid methyl ester | 533, 535 Cl pattern |
| 246 | 4-(6-Chloro-benzo[b]thiophene-2-sulfonyl)-1-(1H-pyrrolo[3,2-b]pyridin-2-ylmethyl)-piperazin-2-one | 461, 463 Cl pattern |

EXAMPLE 247

1-(4-Amino-1H-pyrrolo[3,2-c]pyridin-2-ylmethyl)-4-(6-chloro-benzo[b]thiophene-2-sulphonyl)-piperazin-2-one.

A. (2-Chloro-pyridin-4-yl)-carbamic acid tert-butyl ester.

NaHMDS (61.7 mL, 1.0M solution in THF) is rapidly added to a solution of 2-chloro-pyridin-ylamine (4.0 g, 30.9 mmol) amd BOC anhydride (6.74 g, 30.9 mmol) in THF (28 mL) at RT. The reaction mixture is cooled in an ice water bath (0° C.) for 1 h then stirred for 3 hr at RT. The gelatinous mixture is concentrated in vacuo and diluted with ethyl acetate and saturated $NH_4Cl$ solution. The organic layer is washed with 0.1N HCl, saturated $NaHCO_3$ and brine. The organic layer is then dried over $MgSO_4$, filtered and concentrated to dryness. The crude product is chromatographed eluting with 1% $MeOH/CH_2Cl_2$ to yield the title product (5.57 g, 24.4 mmol) as a yellow solid. $^1$H NMR ($CDCl_3$, 300 MHz), δ8.18 (d, 1H), 7.48 (d, 1H), 7.12 (dd, 1H), 1.60 (s, 9H). EI MS $[M]^+=228$.

B. (2-Chloro-3-iodo-pyridin-4-yl)-carbamic acid tert-butyl ester.

tert-Butyllithium (36.3 mL, 1.7M in pentane) is added dropwise to a solution of (2-chloro-pyridin-4-yl)-carbamic acid tert-butyl ester (6.00 g, 26.2 mmol) in THF (46 mL) at −78° C. under Ar. The yellow/orange mixture is stirred for 2 h at −78° C. then warmed to −40° C. for 1 h then cooled to −78° C. before dropwise addition of $I_2$ (15.65 g, 61.7 mmol) in THF (49 mL). The reaction mixture is stirred for 1.5 h at −78° C. then at −10° C. for 30 minutes. The reaction is quenched with saturated $NH_4Cl$ solution then diluted with $CH_2Cl_2$ and washed with saturated $NH_4Cl$, saturated sodium thiosulfate, water then brine. The organic layer is dried over $MgSO_4$, filtered and concentrated to dryness. The crude product is chromatographed eluting with 1-2% $MeOH/CH_2Cl_2$ to yield the title product (7.96 g, 22.5 mmol) as a bright yellow solid. $^1$H NMR ($CDCl_3$, 300 MHz) δ8.14 (d, 1H), 8.02 (d, 1H), 7.32 (bs, 1H), 1.60 (s, 9H). EI MS $[M]^+=354, 356$, Cl pattern.

C. 4-(4-Chloro-1H-pyrrolo[3.2-c]pyridin-2-ylmethyl)-3-oxo-piperazine-1-carboxylic acid benzyl ester.

Trifluoroacetic acid (10 mL) is added to a solution of 2-(4-benzyloxycarbonyl-2-oxo-piperazin-1-ylmethyl)-4-chloro-pyrrolo[3,2-c]pyridine-1-carboxylic acid tert-butyl ester (5.66 g, 11.3 mmol, prepared in the same manner as described previously) in $CH_2Cl_2$ (10 mL). The solution is stirred overnight then diluted with $CH_2Cl_2$ and washed with saturated $NaHCO_3$ and brine. The organic layer is dried over $MgSO_4$, filtered and concentrated to dryness. The crude product is chromatographed eluting with 1-5% $MeOH/CH_2Cl_2$ to yield the title product (3.81 g, 9.56 mmol) as a foamy yellow solid. $^1$H NMR ($CDCl_3$, 300 MHz) δ9.43 (bs, 1H), 8.08 (d, 1H), 7.38 (s, 5H), 7.18 (d, 1H), 6.51 (s, 1H), 5.15 (s, 2H), 4.58 (s, 2H), 4.20 (s, 2H), 3.71 (m, 2H), 3.50 (m, 2H). Ion spray $[M+H]^+=399, 401$, Cl pattern.

D. 4-(1-Benzenesulfonyl-4-chloro-1H-pyrrolo[3,2-c]pyridin-2-ylmethyl)-3-oxo-piperazine-1-carboxylic acid benzyl ester.

Powdered NaOH (0.96 g, 23.9 mmol) followed by $nBu_4NHSO_4$ (0.32 g, 0.96 mmol) and benzene sulfonyl chloride (1.8 mL, 14.1 mmol) is added to a solution of 4-(4-chloro-1H-pyrrolo[3,2-c]pyridin-2-ylmethyl)-3-oxo-piperazine-1-carboxylic acid benzyl ester (3.81 g, 9.56 mmol) in $CH_2Cl_2$ (32 mL) at RT. The resulting slurry is stirred for 3.5 h then diluted with $CH_2Cl_2$ and washed with saturated $NaHCO_3$ and brine. The organic layer is dried over $MgSO_4$, filtered and concentrated to dryness. The crude product is chromatographed eluting with 1-5% $MeOH/CH_2Cl_2$ to yield the title product (5.06 g, 9.38 mmol). $^1$H NMR ($CDCl_3$, 300 MHz) δ8.23 (d, 1H), 7.97 (d, 1H), 7.84 (d, 2H), 7.61 (d, 1H), 7.51 (m, 2H), 7.38 (s, 5H), 6.50 (s, 1H), 5.18 (s, 2H), 5.03 (s, 2H), 4.29 (s, 2H), 4.29 (s, 2H), 3.80 (m, 2H), 3.51 (m, 2H). Ion spray $[M+H]^+=539, 541$, Cl pattern.

E. 1-(1-Benzenesulfonyl-4-chloro-1H-pyrrolo[3,2-c]pyridin-2-ylmethyl)-piperazin-2-one.

TMSI (2.7 mL, 19.0 mmol) is added to a solution of 4-(1-benzenesulfonyl-4-chloro-1H-pyrrolo[3,2-c]pyridin-2-ylmethyl)-3-oxo-piperazine-1-carboxylic acid benzyl ester (5.06 g, 9.38 mmol) in $CH_3CN$ (134 mL) at 0° C. The reaction mixture is warmed to RT and stirred for 5 hours. The reaction mixture is concentrated to dryness and the red residue is diluted with MeOH and concentrated to dryness (this is repeated twice). The mixture is diluted with $CH_2Cl_2$ and washed with saturated $NaHCO_3$ and brine. The organic layer is dried over $MgSO_4$, filtered and concentrated to dryness. The crude product is chromatographed eluting with 1-5% $MeOH/CH_2Cl_2$ to yield the title product (0.70 g, 1.74 mmol) and unreacted starting material (3.58 g, 6.64 mmol). $^1$H NMR ($CDCl_3$, 300 MHz) δ8.20 (d, 1H), 7.93 (d, 1H), 7.85 (d, 2H), 7.60 (d, 1H), 7.51 (m, 2H), 6.50 (s, 1H), 5.01 (s, 2H), 3.45 (m, 2H), 3.18 (m, 2H). Ion spray $[M+H]^+=405, 407$, Cl pattern.

F. 1-(4-Amino-1H-pyrrolo[3 2-c]pyridin-2-ylmethyl)-4-(6-chlorobenzo[b]thiophene-2-sulfonyl)piperazin-2-one.

Anhydrous ammonium acetate (0.56 g, 7.2 mmol), phenol (0.45 g, 4.8 mmol) and 1-(1-benzenesulfonyl-4-chloro-1H-pyrrolo[3,2-c]pyridin-2-ylmethyl)-4-(6-chloro-benzo[b]thiophene-2-sulfonyl)-piperazin-2-one (0.31 g, 0.48 mmol, prepared as described previously) are heated to 100° C. for 3.5 days. The mixture is cooled to RT then the crude product is purified by RP-HPLC eluting in a gradient of 10% $CH_3CN/H_2O$ (0.1% TFA) to 100% $CH_3CN$ then the appropriate product fractions are lyophilized to provide the title compound (1.29 g, 2.2 mmol) as a white solid (22.4 mg, 0.038 mmol). $^1$H NMR (DMSO-$d_6$, 300 MHz) δ12.40 (bs, 1H), 12.00 (bs, 1H), 8.31 (d, 1H), 8.20 (s, 1H), 8.06 (d, 1H), 8.02 (bs, 2H), 7.57 (dd, 1H), 7.48 (m, 1H), 6.89 (d, 1H), 6.81 (s, 1H), 4.60 (s, 1H), 3.81 (s, 2H), 3.40 (m, 4H). LR-FAB MS, $[M+H]^+=476, 478$.

EXAMPLE 248

4-[2-(5-Chloro-thiophen-2-yl)-ethenesulfonyl]-5-(±)-hydroxymethyl-1-(1H-pyrrolo[3,2-c]pyridin-2-ylmethyl)-piperazin-2-one A. 2-{4-[2-(5-Chloro-thiophen-2-yl)-ethenesulfonyl]-2-(±)-hydroxymethyl-6-oxo-piperazin-1-ylmethyl}-pyrrolo[3,2-c]pyridine-1-carboxylic acid tert-butyl ester.

Sodium borohydride (0.005 g, 0.13 mmol) is added to a solution of 2-{4-[2-(5-chloro-thiophen-2-yl)-ethenesulfonyl]-2-(±)-methoxycarbonyl-6-oxo-piperazin-1-ylmethyl}-pyrrolo[3,2-c]pyridine-1-carboxylic acid tert-butyl ester (0.04 g, 0.07 mmol), (prepared from 2-(2-(±)-methoxycarbonyl-6-oxo-piperazin-1-ylmethyl)-pyrrolo[3,2-c]pyridine-1-carboxylic acid tert-butyl ester, EXAMPLE 71, and 2-(5-chloro-thiophen-2-yl)-ethenesulfonyl chloride, EXAMPLE 3, using the procedure described in EXAMPLE 214, Part A) in MeOH (3 mL) at RT. The reaction mixture is stirred for 6 h then quenched with water and concentrated in vacuo. The crude product (0.04 g) is taken onto the next step without further purification.

B. 4-[2-(5-Chloro-thiophen-2-yl)-ethenesulfonyl]-5-(±)-hydroxymethyl-1-(1H-pyrrolo[3,2-c]pyridin-2-ylmethyl)-piperazin-2-one.

Trifluoroacetic acid (1.8 mL) is added to a solution of 2-{4-[2-(5-chloro-thiophen-2-yl)-ethenesulfonyl]-2-(±)-hydroxymethyl-6-oxo-piperazin-1-ylmethyl}-pyrrolo[3,2-c]pyridine-1-carboxylic acid tert-butyl ester (0.04 g) in $CH_2Cl_2$ (4.2 mL) at RT. The reaction mixture is stirred for 4 h then concentrated in vacuo. The title compound is purified by RP-HPLC eluting in a gradient of 10% $CH_3CN/H_2O$ (0.1% TFA) to 100% $CH_3CN$ and lyophilizing the appropriate product fractions. $^1H$ NMR (DMSO-$d_6$, 300 MHz) δ9.10 (s, 1H), 8.46 (d, 1H), 7.82 (d, 1H), 7.50 (d, 1H) 7.43 (d, 1H), 7.14 (d, 1H), 7.01 (d, 1H), 6.94 (s, 1H), 5.12 (bs, 1H), 4.80 (AB, 2H), 3.98 (d, 2H0, 3.90 (m, 1H), 3.40-3.50 (m, 4H). APCI MS, [M+H]$^+$=467, 469.

The following compounds are prepared from starting materials obtained using the methods of Examples 69, 70 and 71 and the appropriate sulfonyl chorides according to the method of Example 101.

| Example # | Name | m/z |
|---|---|---|
| 249 | 1-(6-Chloro-benzo[b]thiophene-2-sulfonyl)-5-oxo-4-(1H-pyrrolo[3,2-c]pyridin-2-ylmethyl)-piperazine-2-(±)-carboxylic acid methyl ester | 519, 521 Cl pattern |
| 250 | 1-[2-(5-Chloro-thiophen-2-yl)-ethenesulfonyl]-5-oxo-4-(1H-pyrrolo[3,2-c]pyridin-2-ylmethyl)-piperazine-2-(±)-carboxylic acid methyl ester | 495, 497 Cl pattern |
| 251 | 1-(6-Chloro-benzo[b]thiophene-2-sulfonyl)-5-oxo-4-(1H-pyrrolo[3,2-c]pyridin-2-ylmethyl)-piperazine-2-(±)-carboxylic acid | 505, 507 Cl pattern |
| 252 | 4-(6-Chloro-benzo[b]thiophene-2-sulfonyl)-5-(±)-hydroxymethyl-1-(1H-pyrrolo[3,2-c]pyridin-2-ylmethyl)-piperazin-2-one | 491, 493 Cl pattern |

The following enantiomerically pure compounds are obtained by chiral resolution on a CHIRACEL OD prep column.

| Example # | Name | % ee | m/z |
|---|---|---|---|
| 253 | 1-[2-(5-Chloro-thiophen-2-yl)-ethenesulfonyl]-5-oxo-4-(1H-pyrrolo[3,2-c]pyridin-2-ylmethyl)-piperazine-2-(−)-carboxylic acid methyl ester | 99% (−) | 495, 497 Cl pattern |
| 254 | 1-[2-(5-Chloro-thiophen-2-yl)-ethenesulfonyl]-5-oxo-4-(1H-pyrrolo[3,2-c]pyridin-2-ylmethyl)-piperazine-2-(+)-carboxylic acid methyl ester | 95% (+) | 495, 497 Cl pattern |

EXAMPLE 255

4-[2-(5-Chloro-thiophen-2-yl)-ethenesulfonyl]-6-(R)-hydroxymethyl-1-(1H-pyrrolo[3 2-c]pyridin-2-ylmethyl)-piperazin-2-one A. 6-(R)-(tert-Butyl-dimethyl-silanyloxymethyl)-4-[2-(5-chloro-thiophen-2-yl)-ethenesulfonyl]-1-(1H-pyrrolo[3,2-c]pyridin-2-ylmethyl)-piperazin-2-one.

Trifluoroacetic acid (0.25 mL) is added to a solution of 2-{2-(R)-(tert-butyl-dimethyl-silanyloxymethyl)-4-[2-(5-chloro-thiophen-2-yl)-ethenesulfonyl]-6-oxo-piperazin-1-ylmethyl}-pyrrolo[3,2-c]pyridine-1-carboxylic acid tert-butyl ester (0.025 g, 0.037 mmol) in $CH_2Cl_2$(0.5 mL) at room temperature. The reaction mixture is stirred for 2 h then concentrated to dryness. The residue is diluted with $CH_2Cl_2$ and washed with saturated $NaHCO_3$ and brine. The organic layer is dried over $MgSO_4$, filtered and concentrated in vacuo. The crude product (0.019 g, 0.033 mmol) is used in the subsequent step without further purification.

B. 4-[2-(5-Chloro-thiophen-2-yl)-ethenesulfonyl]-6-(R)-hydroxymethyl-1-(1H-pyrrolo[3,2-c]pyridin-2-ylmethyl)-piperazin-2-one.

Glacial acetic acid (3 mL, 0.046 mmol) and tetrabutylammonium fluoride (92 mL, 0.092 mmol) is added to a solution of 6-(R)-(tert-butyl-dimethyl-silanyloxymethyl)-4-[2-(5-chloro-thiophen-2-yl)-ethenesulfonyl]-1-(1H-pyrrolo[3,2-c]pyridin-2-ylmethyl)-piperazin-2-one (0.019 g, 0.033 mmol) in THF (0.5 mL). The resulting solution is stirred for 4 h then concentrated in vacuo. The crude product is purified by RP-HPLC eluting in a gradient of 10% $CH_3CN/H_2O$ (0.1% TFA) to 100% $CH_3CN$ and the appropriate product fractions are lyophilized to provide the title compound (0.009 g, 0.016 mmol) as a white solid. $^1H$ NMR (DMSO-$d_6$, 300 MHz) δ14.50 (bs, 1H), 12.60 (bs, 1H), 9.18 (s, 1H), 8.38 (d, 1H), 7.89 (d, 1H), 7.61 (d, 1H), 7.50 (d, 1H), 7.21 (d, 1H), 7.08 (d, 1H), 6.90 (s, 1H), 5.03 (s, 2H), 4.63 (d, 2H), 3.70-3.90 (AB, 2H), 3.75 (m, 1H), 3.21 (m, 2H). Ion spray MS, [M+H]$^+$467, 469, Cl pattern.

The following compounds are prepared from starting materials obtained as described in Examples 69, 70 and 71 and the appropriate sulfonyl chloride according to the method of Example 101.

| Example # | Name | m/z |
|---|---|---|
| 256 | 4-(6-Chloro-benzo[b]thiophene-2-sulfonyl)-6-(R)-hydroxymethyl-1-(1H-pyrrolo[3,2-c]pyridin-2-ylmethyl)-piperazin-2-one | 491, 493 |
| 257 | 4-[2-(5-Chloro-thiophen-2-yl)-ethenesulfonyl]-6-oxo-1-(1H-pyrrolo[3,2-c]pyridin-2-ylmethyl)-piperazine-2-(±)-carboxylic acid methyl ester | 495, 497 Cl pattern |
| 258 | 4-(6-Chloro-benzo[b]thiophene-2-sulfonyl)-6-oxo-1-(1H-pyrrolo[3,2-c]pyridin-2-ylmethyl)-piperazine-2-(±)-carboxylic acid methyl ester | 519, 521 Cl pattern |
| 259 | 4-[2-(5-Chloro-thiophen-2-yl)-ethenesulfonyl]-6-oxo-1-(1H-pyrrolo[3,2-c]pyridin-2-ylmethyl)-piperazine-2-(±)-carboxylic acid | 481, 483 Cl pattern |
| 260 | 4-(6-Chloro-benzo[b]thiophene-2-sulfonyl)-6-oxo-1-(1H-pyrrolo[3,2-c]pyridin-2-ylmethyl)-piperazine-2-(±)-carboxylic acid | 505, 507 Cl pattern |
| 261 | 4-(6-Chloro-benzo[b]thiophene-2-sulfonyl)-6-(±)-hydroxymethyl-1-(1H-pyrrolo[3,2-c]pyridin-2-ylmethyl)-piperazin-2-one | 491, 493 Cl pattern |
| 262 | 4-[2-(5-Chloro-thiophen-2-yl)-ethenesulfonyl]-6-(±)-hydroxymethyl-1-(1H-pyrrolo[3,2-c]pyridin-2-ylmethyl)-piperazin-2-one | 467, 469 Cl pattern |
| 263 | 4-(6-Chloro-benzo[b]thiophene-2-sulfonyl)-6-oxo-1-(1H-pyrrolo[3,2-c]pyridin-2-ylmethyl)-piperazine-2-(±)-carboxylic acid amide | 504, 506 Cl pattern |
| 264 | 4-[2-(5-Chloro-thiophen-2-yl)-ethenesulfonyl]-3-(S)-methoxymethyl-1-(1H-pyrrolo[3,2-c]pyridin-2-ylmethyl)-piperazin-2-one | 481, 483 |
| 265 | 4-(6-Chloro-benzo[b]thiophene-2-sulfonyl)-3-(S)-methoxymethyl-1-(1H-pyrrolo[3,2-c]pyridin-2-ylmethyl)-piperazin-2-one | 505, 507 |
| 266 | 4-(5'-Chloro-[2,2']bithiophenyl-5-sulfonyl)-3-(S)-methoxymethyl-1-(1H-pyrrolo[3,2-c]pyridin-2-ylmethyl)-piperazin-2-one | 537, 539 |
| 267 | 4-[2-(4-Chloro-phenyl)-ethenesulfonyl]-3-(S)-methoxymethyl-1-(1H-pyrrolo[3,2-c]pyridin-2-ylmethyl)-piperazin-2-one | 475, 477 |

EXAMPLE 268

1-(4-Aminoquinazolin-7-ylmethyl)-4-(6-chlorobenzo[b]thiophene-2-ylmethyl)piperazin-2-one To a solution of 1-(4-aminoquinazoline-7-ylmethyl)piperazine-2-one bishydrochloride (1.84 g, 5.73 mmol), EXAMPLE 72, in DMF (20 mL) is added 2-bromomethyl-6-chloro-benzo[b]thiophene, EXAMPLE 5, (1.5 g, 5.73 mmol) and $K_2CO_3$ (4.0 g, 28.7 mmol). The solution is stirred for 16 hours. After this time, the solution is diluted with water. The solution is acidified with trifluoroacetic acid. The product is purified by RP-HPLC eluting in a gradient of 10% $CH_3CN$/$H_2O$ (0.1% TFA) to 50% $CH_3CN$/$H_2O$ (0.1% TFA). The appropriate collected fractions are lyopholized to afford the title compound as a white solid. $^1$H NMR (d$^6$-DMSO, 300 MHz) δ9.78 (bs, 3H), 8.82 (s, 1H), 8.34 (d, 1H), 8.07 (s, 1H), 7.81 (d, 1H), 7.63 (d, 1H), 7.51 (s, 1H), 7.32 (m, 2H), 4.71 (s, 2H), 3.95 (s, 2H), 3.28 (m, 4H), 2.80 (m, 2H).

EXAMPLE 269

1-(4-Aminoquinazolin-7-ylmethyl)-4-(6-chloro-1H-benzoimidazol-2-ylmethyl)piperazin-2-one A mixture of 1-(4-aminoquinazolin-7-ylmethyl)piperazin-2-one (50 mg, 0.15 mmol), EXAMPLE 72, 6-chloro-2-chloromethylbenzimidazole (30.5 mg, 0.15 mmol) and potassium carbonate (83 mg, 0.6 mmol) in 2 mL of DMF is stirred at ambient temperature overnight. The mixture is purified on reverse phase HPLC ($CH_3CN/H_2O$/TFA) to give the trifluoroacetic acid salt of 1-(4-aminoquinazolin-7-ylmethyl)-4-(6-chloro-1H-benzoimidazol-2-ylmethyl)piperazin-2-one (25 mg) as a solid. $^1$H NMR (CD$_3$OD, 300 MHz) δ8.69 (s, 1H), 8.33 (d, 1H), 7.79 (s, 1H), 7.75-7.69 (m, 3H), 7.57-7.54 (m, 1H), 4.86 (s, 2H), 4.22 (s, 2H), 3.31 (m, 4H), 2.99 (m, 2H). MS m/z 422 (M+H).

EXAMPLE 270

1-(4-Amino-quinazolin-7-ylmethyl)-4-(6-chloro-benzothioazol-2-ylmethyl)-piperazin-2-one To a solution of 1-(4-amino-quinazolin-7-ylmethyl)-piperazin-2-one (76 mg, 0.23 mmol), EXAMPLE 72, in 2 mL of DMF is added potassium carbonate (127 mg, 0.92 mmol) followed by 6-chloro-2-chloromethyl-benzothiazole (prepared according to the procedure of B. L. Mylari, Synthesis Comm. 1989, 16, 2921) (50 mg, 0.23 mmol). The resulting mixture is stirred overnight at room temperature. The undissolved potassium carbonate is removed by filtration and the mother liquor is purified by reverse phase HPLC (10-100% $CH_3CN/H_2O$). The desired is product is obtained as a white solid with a melting point of 123-126° C. $C_{21}H_{19}ClN_6OS$ MS m/z: 439, 441. Anal. cald. for $C_{21}H_{19}ClN_6OS.2C_2HF_3O_2$: C, 45.02; H, 3.17 N, 12.60. Found C, 44.15; H 3.19; N, 11.79.

EXAMPLE 271

1-(4-Amino-quinazolin-7-ylmethyl)-4-(6-chloro-benzooxazol-2-ylmethyl)-piperazin-2-one The desired product (10.0 mg, 7%) is isolated as a white solid. $C_{21}H_{19}ClN_6O_2$ MS m/z: 423, 425.

EXAMPLE 272

1-(4-Amino-quinazolin-7-ylmethyl)-4-(5-chloro-benzothioazol-2-ylmethyl)-piperazin-2-one The desired product (19.0 mg, 22%) is obtained as a white solid. $C_{21}H_{19}ClN_6OS$ MS m/z: 438,440. Anal. cald. for $C_{21}H_{19}ClN_6OS.2C_2HF_3O_2$: C, 45.02; H, 3.17 N, 12.60. Found C, 43.35; H, 3.26; N, 12.65.

EXAMPLE 273

3-[4-(4-Aminoquinazoline-7-ylmethyl)-3-oxopiperazin-1-ylmethyl]-7-chloro-1H-quinolin-2-one The title compound is prepared as described in EXAMPLE 268, substituting 3-bromomethyl-7-chloro-1H-quinoline-2-one, EXAMPLE 8, for 2-bromomethyl-6-chlorobenzo[b]thiophene. The product is purified by RP-HPLC eluting in a gradient of 10% $CH_3CN/H_2O$ (0.1% TFA) to 50% $CH_3CN/H_2O$ (0.1% TFA). The appropriate collected fractions are lyopholized to afford the title compound as a white solid. $^1H$ NMR ($d^6$-DMSO, 300 MHz) δ12.18 (bs, 1H), 9.75 (m, 1H), 8.86 (s, 1H), 8.40 (m, 1H), 8.11 (d, 1H), 8.10 (s, 1H), 7.78 (m, 1H), 7.69 (m, 2H), 7.37 (m, 1H), 4.80 (s, 2H), 4.10 (m, 2H), 3.30 (m, 2H). MS (ion spray) m/z 449, (M+H).

EXAMPLE 274

1-(4-Amino-quinazolin-7-ylmethyl)-4-(3-chloro-1H-indol-6-ylmethyl)-piperazin-2-one A. 1-(4-Amino-quinazolin-7-ylmethyl)-4-(3-chloro-1-(toluene-4-sulfonyl)-1H-indol-6-ylmethyl)-piperazin-2-one.

The title compound is prepared as described in EXAMPLE 268 using 6-bromomethyl-3-chloro-1-(toluene-4-sulfonyl)-1H-indole, EXAMPLE 16, in place of 2-bromomethyl-6-chloro-benzo[b]thiophene. The crude material is purified by RP-HPLC eluting in a gradient of 10% $CH_3CN/H_2O$ (0.1% TFA) to 80% $CH_3CN/H_2O$ (0.1% TFA) and the appropriate product fractions are combined and lyopholized to give a white solid. $^1H$ NMR (DMSO-$d_6$, 300 MHz) δ9.75 (bs, 2H), 8.82 (s, 1H), 8.40 (d, 1H), 7.64 (m, 2H), 7.60 (m, 2H), 7.40 (d, 1H), 7.23 (m, 1H), 7.19 (m, 2H), 6.99 (d, 2H), 5.09 (s, 2H), 4.78 (s, 2H), 4.10 (m, 2H), 3.40 (m, 4H), 2.49 (s, 3H).

B. 1-(4-Amino-quinazolin-7-ylmethyl)-4-(3-chloro-1H-indol-6-ylmethyl)-piperazin-2-one.

To a solution of 1-(4-amino-quinazolin-7-ylmethyl)-4-(3-chloro-1-(toluene-4-sulfonyl)-1H-indol-6-ylmethyl)-piperazin-2-one ditrifluoroacetate (31 mg, 0.04 mmol) in 2 mL of MeOH is added 0.3 mL of 1N NaOH solution. The solution is heated at 100° C. for 3 hours. After this time, the solution is diluted with water/acetonitrile and neutralized with trifluoroacetic acid. The crude material is purified by RP-HPLC eluting in a gradient of 10% $CH_3CN/H_2O$ (0.1% TFA) to 60% $CH_3CN/H_2O$ (0.1% TFA) and the appropriate product fractions are combined and lyopholized to give the title compound (21 mg, 0.03 mmol) as a white solid. $^1H$ NMR (DMSO-$d_6$, 300 MHz) δ9.71 (bs, 2H), 8.81 (s, 1H), 8.40 (d, 1H), 7.63 (m, 3H), 7.53 (d, 1H), 7.50 (s, 1H), 7.20 (d, 1H), 4.78 (s, 2H), 4.30-3.10 (m, 8H). ESI MS, [M+H]$^+$=421, 423 (Cl pattern).

EXAMPLE 275

1-(4-Amino-quinazolin-7-ylmethyl)-4-[3-(5-chloro-thiophen-2-yl)-(E)-allyl]-piperazin-2-one To a solution of 1-(4-amino-quinazolin-7-ylmethyl)-piperazin-2-one bishydrochloride (100 mg, 0.31 mmol), EXAMPLE 72, in 3 mL of DMF is added 2-(3-bromo-(E)-propenyl)-5-chloro-thiophene (73 mg, 0.31 mmol), prepared as described in EXAMPLE 17., and $K_2CO_3$ (0.21 g, 1.54 mmol). The solution is stirred at room temperature for 16 hours. After this time, the solution is diluted with water/acetonitrile and neutralized with trifluoroacetic acid. The crude material is purified by RP-HPLC eluting in a gradient of 10% $CH_3CN/H_2O$ (0.1% TFA) to 60% $CH_3CN/H_2O$ (0.1% TFA) and the appropriate product fractions are combined and lyopholized to give the title compound (80 mg, 0.12 mmol) as a white solid. $^1H$ NMR (DMSO-$d_6$, 300 MHz) δ9.76 (bs, 2H), 8.81 (s, 1H), 8.40 (d, 1H), 7.70 (s, 1H), 7.62 (dd, 1H), 7.10 (m, 2H), 6.90 (d, 1H), 6.05 (dt, 1H), 4.80 (s, 2H), 3.77 (m, 4H), 3.50 (m, 2H), 3.37 (m, 2H), ESI MS, [M+H]$^+$=414,416 (Cl pattern). Anal. ($C_{20}H_{20}ClN_5OS.2.0TFA.1.1H_2O$) C, H, N.

EXAMPLE 276

1-(4-Amino-quinazolin-7-ylmethyl)-4-[3-(5-chloro-thiophen-2-yl)-but-2-(E)-enyl]-piperazin-2-one ditrifluoroacetate $^1H$ NMR (DMSO-$d_6$, 300 MHz) δ9.70 (bs, 2H), 8.82 (s, 1H), 8.40 (d, 1H), 7.68 (s, 1H), 7.61 (d, 1H), 7.10 (m, 2H), 5.88 (t, 1H), 4.79 (s, 2H), 3.75 (m, 4H), 3.49 (m, 2H), 3.29 (m, 2H), 2.09 (s, 3H). EI MS, [M+H]$^+$=427, 429 (Cl pattern).

EXAMPLE 277

1-(4-Amino-quinazolin-7-ylmethyl)-4-[3-(5-chloro-thiophen-2-yl)-2-methyl-(E)-allyl]-piperazin-2-one ditrifluoroacetate $^1H$ NMR (DMSO-$d_6$, 300 MHz) δ9.80 (bs, 2H), 8.85 (s, 1H), 8.41 (d, 1H), 7.70 (s, 1H), 7.68 (d, 1H), 7.06 (d, 1H), 7.05 (d, 1H), 6.70 (bs, 1H), 4.80 (s, 2H), 4.30 (bs, 2H), 3.45 (m, 4H), 3.10 (m, 2H), 1.99 (s, 3H). ESI MS, [M+H]$^+$=428, 430 (Cl pattern).

EXAMPLE 278

1-(4-Amino-quinazolin-7-ylmethyl)-4-[3-(4-bromo-furan-2-yl)-(E)-allyl]-piperazin-2-one To a solution of 1-(4-amino-quinazolin-7-ylmethyl)-piperazin-2-one (50 mg, 0.20 mmol), EXAMPLE 72.in 3 mL of acetonitrile is added 3-(4-bromo-furan-2-yl)-(E)-propenal (43 mg, 0.22 mmol), prepared as described in EXAMPLE 18, 2 drops of HOAc and sodium triacetoxyborohydride (62 mg, 0.29 mmol). The solution is stirred at room temperature for 16 hours. After this time, the solution is diluted with water/acetonitrile. The crude material is purified by RP-HPLC eluting in a gradient of 10% $CH_3CN/H_2O$ (0.1% TFA) to 80% $CH_3CN/H_2O$ (0.1% TFA) and the appropriate product fractions are combined and lyopholized to give the title compound (48 mg, 0.07 mmol) as a white solid. $^1H$ NMR (DMSO-$d_6$, 300 MHz) δ9.75 (bs, 2H), 8.85 (s, 1H), 8.60 (d, 1H), 7.95 (s, 1H), 7.69 (s, 1H), 7.62 (d, 1H), 6.80 (s, 1H), 6.65 (d, 1H), 6.19 (dt, 1H), 4.80 (s, 2H), 3.70 (m, 4H), 3.50 (m, 2H), 3.28 (m, 2H), ESI MS [M+H]$^+$=441,443 (Br pattern).

EXAMPLE 279

1-(4-Amino-quinazolin-7-ylmethyl)-4-[3-(6-methoxy-pyridin-3-yl)-(E)-allyl]-piperazin-2-one Nitrogen (g) is bubbled through a solution of 1-(4-amino-quinazolin-7-ylmethyl)-piperazin-2-one (100 mg, 0.39 mmol), EXAMPLE 72, in 2 mL of $CH_3CN$. After 5 min, acetic acid 3-(6-methoxy-pyridin-3-yl)-(E)-allyl ester (75 mg, 0.36 mmol, prepared as described in EXAMPLE 19 in 2 mL of CH$_3$CN, palladium(II) acetate (catalytic amount), triphenylphosphine (catalytic amount), 2 mL of H$_2$O and 0.5 mL of triethylamine are added to the solution. The mixture is heated at 80° C. for 1 hours. At this time, the mixture is cooled, filtered and concentrated in vacuo. The crude material is purified by RP-HPLC eluting in a gradient of 10% CH$_3$CN/H$_2$O (0.1% TFA) to 60% CH$_3$CN/H$_2$O (0.1% TFA) and the appropriate product fractions are combined and lyopholized to give the title compound (44 mg, 0.07 mmol) as a white solid. $^1$H NMR (DMSO-d$_6$, 300 MHz) δ9.86 (s, 1H), 9.79 (s, 1H), 8.83 (s, 1H), 8.40 (d, 1H), 8.25 (s, 1H), 7.95 (d, 1H), 7.75 (s, 1H), 7.63 (d, 1H), 6.86 (d, 1H), 6.82 (d, 1H), 6.32 (dt, 1H), 4.78 (s, 2H), 3.98 (s, 2H), 3.93 (m, 2H), 3.85 (s, 3H), 3.53 (m, 4H). ESI MS, [M+H]$^+$=405.

EXAMPLE 280

1-(4-Amino-quinazolin-7-ylmethyl)-4-[3-(5-chloro-thiophen-2-yl)-(E)-allyl]-4-oxy-piperazin-2-one To a solution of 1-(4-amino-quinazolin-7-ylmethyl)-4-[3-(5-chloro-thiophen-2-yl)-(E)-allyl]-piperazin-2-one ditrifluoroacetate (0.60 g, 0.94 mmol), prepared as described in EXAMPLE 275, in 25 mL of CH$_2$Cl$_2$ is added m-chloroperoxybenzoic acid (0.30 g, 0.96 mmol, 55% pure grade). The mixture is stirred at room temperature for 3 h and then concentrated in vacuo. The crude material is purified by RP-HPLC eluting in a gradient of 10% CH$_3$CN/H$_2$O (0.1% TFA) to 60% CH$_3$CN/H$_2$O (0.1% TFA) and the appropriate product fractions are combined and lyopholized to give the title compound (0.5 mg, 0.76 mmol) as a white solid. $^1$H NMR (DMSO-d$_6$, 300 MHz) δ9.68 (bs, 2H), 8.79 (s, 1H), 8.39 (d, 1H), 7.68 (s, 1H), 7.60 (d, 1H), 7.17 (d, 1H), 7.12 (d, 1H), 7.06 (d, 1H), 6.17 (dt, 1H), 4.84 (s, 2H), 4.53 (m, 2H), 4.50 (AB, 2H), 4.04 (m, 2H), 3.78 (m, 1H), 3.60 (m, 1H). ESI MS, [M+H]$^+$430,432 (Cl pattern). Anal. (C$_{20}$H$_{20}$ClN$_5$O$_2$S.2.0TFA.1.4H$_2$O) C, H, N.

EXAMPLE 281

1-(4-Amino-quinazolin-7-ylmethyl)-4-[3-(5-chloro-thiophen-2-yl)-prop-2-ynyl]-piperazin-2-one The title compound is prepared as described in EXAMPLE 275 using 2-(3-bromo-prop-1-ynyl)-5-chloro-thiophene (prepared as described in EXAMPLE 20) in place of 2-(3-bromo-(E)-propenyl)-5-chloro-thiophene. The crude material is purified by RP-HPLC eluting in a gradient of 10% CH$_3$CN/H$_2$O (0.1% TFA) to 70% CH$_3$CN/H$_2$O (0.1% TFA) and the appropriate product fractions are combined and lyopholized to give the title compound as a white solid. $^1$H NMR (DMSO-d$_6$, 300 MHz) δ9.77 (bs, 2H), 8.83 (s, 1H), 8.38 (d, 1H), 7.63 (d, 1H), 7.58 (s, 1H), 7.25 (d, 1H), 7.13 (d, 1H), 4.74 (s, 2H), 3.74 (s, 2H), 3.32 (m, 4H), 2.85 (m, 2H). ESI MS, [M+H]$^+$=412, 414 (Cl pattern).

EXAMPLE 282

1-(4-Amino-quinazolin-7-ylmethyl)-4-[3-(5-chloro-thiophen-2-yl)-propyl]-piperazin-2-one The title compound is prepared as described in EXAMPLE 278 using 3-(5-chloro-thiophen-2-yl)-propionaldehyde (EXAMPLE 28, Part A) in place of 3-(4-bromo-furan-2-yl)-(E)-propenal. The crude material is purified by RP-HPLC eluting in a gradient of 10% CH$_3$CN/H$_2$O (0.1% TFA) to 60% CH$_3$CN/H$_2$O (0.1% TFA) and the appropriate product fractions are combined and lyopholized to give the title compound as a white solid. $^1$H NMR (DMSO-d$_6$, 300 MHz) δ9.77 (bs, 2H), 8.81 (s, 1H), 8.39 (d, 1H), 7.71 (s, 1H), 7.60 (d, 1H), 6.95 (d, 1H), 6.77 (d, 1H), 4.78 (s, 2H), 3.88 (m, 2H), 3.50 (m, 2H), 3.42 (m, 2H), 3.05 (m, 2H), 2.80 (t, 2H), 1.96 (m, 2H). ESI MS, [M+H]$^+$=416,418 (Cl pattern).

EXAMPLE 283

1-(4-Amino-quinazolin-7-ylmethyl)-4-prop-2-ynyl-piperazin-2-one

A. 1-(4-Amino-quinazolin-7-ylmethyl)-4-prop-2-ynyl-piperazin-2-one.

Propargyl bromide (0.29 g, 1.95 mmol) is added to a solution containing 1-(4-amino-quinazolin-7-ylmethyl)-piperazin-2-one (0.5 g, 1.95 mmol), EXAMPLE 72, and K$_2$CO$_3$ (0.40 g, 2.93 mmol) in DMSO (10 mL) at ambient temperature. After 15 min, the reaction mixture is partitioned between aqueous NaHCO$_3$ (100 mL) and CH$_2$Cl$_2$ (100 mL) and the layers are separated. The aqueous phase is subsequently saturated with NaCl and extracted three times with CHCl$_3$ (50 mL). The combined organic phase is washed with brine, dried over anhydrous Na$_2$SO$_4$, filtered and concentrated. The residue is purified by flash silica gel chromatography (CH$_2$Cl$_2$ to 10% MeOH/CH$_2$Cl$_2$) to provide 390 mg (68%) of the title compound as a white solid. $^1$H NMR (300 MHz, CDCl$_3$) δ2.68 (m, 1H), 3.13-3.37 (m, 6H), 4.07 (app q, J=5.2 Hz, 1H), 4.63 (s, 2H), 7.28 (dd, J=8.4, 1.4 Hz, 1H), 7.42 (s, 1H), 7.72 (br s, 2H), 8.14 (d, J=8.4 Hz, 1H), 8.34 (s, 1H) ppm; MS (ISP loop): m/z 296 (M+H).

EXAMPLE 284

1-(4-Amino-quinazolin-7-ylmethyl)-4-(3-biphenyl-2-yl-prop-2-ynyl)-piperazin-2-one A solution containing 1-(4-amino-quinazolin-7-ylmethyl)-4-prop-2-ynyl-piperazin-2-one (50 mg, 0.17 mmol), EXAMPLE 283, 2-bromobiphenyl (44 mg, 0.19 mmol), Et$_3$N (69 mg, 0.68 mmol), (Ph$_3$P)$_4$PdCl$_2$ (6 mg, 0.008 mmol), and CuI (1 mg, 0.005 mmol) in anhydrous DMF (2 mL) is warmed at 80° C. for 1 hours. The reaction mixture is cooled to 50° C. and the solvent is removed over 16 h under a stream of nitrogen. The crude residue is purified by flash silica gel chromatography (CH$_2$Cl$_2$ to 10% MeOH CH$_2$Cl$_2$) to afford a colorless gum which is triturated with ethyl alcohol to provide 4 mg (5%) of the title compound as a white solid. $^1$H NMR (300 MHz, d$_6$-DMSO) δ3.03 (s, 2H), 3.14 (m, 2H), 3.31 (m, 2H), 3.50 (s, 2H), 7.21-7.55 (m, 11H), 7.76 (br s, 2H), 8.18 (d, J=8.6 Hz, 1H), 8.36 (s, 1H) ppm; MS (ion spray): m/z 448 (M+H).

EXAMPLE 285

1-(4-Amino-quinazolin-7-ylmethyl)-4-(1H-pyrrolo[3,2-c]pyridin-2-ylmethyl)-piperazin-2-one A. (3-{3-[4-(4-Amino-quinazolin-7-ylmethyl)-3-oxo-piperazin-1-yl]-prop-1-ynyl}-pyridin-4-yl-carbamic acid tert-butyl ester.

A solution containing 1-(4-amino-quinazolin-7-ylmethyl)-4-prop-2-ynyl-piperazin-2-one (100 mg, 0.34 mmol), EXAMPLE 283, (3-iodo-pyridin-4-yl)-carbamic acid tert-butyl ester, EXAMPLE 69, Part B, (108 mg, 0.34 mmol), Et₃N (140 mg, 1.36 mmol), (Ph₃P)₄PdCl₂ (12 mg, 0.017 mmol), and CuI (2 mg, 0.01 mmol) in anhydrous DMF (5 mL) is stirred at ambient temperature. After 5 h, the reaction mixture is diluted with EtOAc (50 mL) and water (50 mL) and the layers are separated. The aqueous layer is extracted twice with EtOAc (25 mL) and the combined organic phase is washed with brine, dried over anhydrous Na₂SO₄, filtered and concentrated. The crude residue is purified by flash silica gel chromatography (CH₂Cl₂ to 10% MeOH CH₂Cl₂) to provide 59 mg (36%) of the title compound as a colorless oil. ¹H NMR (300 MHz, CDCl₃) δ 1.49 (s, 9H), 2.84 (m, 2H), 3.35 (m, 2H), 3.44 (s, 2H), 3.71 (s, 2H), 4.75 (s, 2H), 6.19 (br s, 2H), 7.24 (d, J=5.5 Hz, 1H), 7.41 (d, J=8.4 Hz, 1H), 7.66 (s, 1H), 7.79 (d, J=8.4 Hz, 1H), 8.05 (d, J=5.5 Hz, 1H), 8.37 (s, 1H), 8.49 (s, 1H), 8.58 (s, 1H) ppm; MS (ISP loop): m/z 488 (M+H).

B. 2-[4-(4-Amino-quinazolin-7-ylmethyl)-3-oxo-piperazin-1-ylmethyl]-pyrrolo[3,2-c]pyridine-1-carboxylic acid tert-butyl ester.

1,8-Diazabicyclo[5.4.0]undec-7-ene (37 mg, 0.24 mmol) is added to a suspension containing (3-{3-[4-(4-amino-quinazolin-7-ylmethyl)-3-oxo-piperazin-1-yl]-prop-1-ynyl}-pyridin-4-yl)-carbamic acid tert-butyl ester (59 mg, 0.12 mmol) in anhydrous CH₃CN (5 mL) and the mixture is warmed to 50° C. Dimethylformamide (1 mL) is added to solubilize and the homogeneous solution is maintained for 5 h at 50° C. The reaction mixture is diluted with EtOAc (50 mL) and water (50 mL) and the layers are separated. The aqueous layer is extracted twice with EtOAc (25 mL) and the combined organic phase is washed with brine, dried over anhydrous Na₂SO₄, filtered and concentrated to provide 50 mg of the product as a crude solid which is used directly without further purification. ¹H NMR (300 MHz, CDCl₃) δ 1.64 (s, 9H), 2.78 (m, 2H), 3.30 (m, 2H), 3.37 (s, 2H), 3.95 (s, 2H), 4.74 (s, 2H), 6.24 (br s, 2H), 6.63 (s, 1H), 7.40 (dd, J=8.5, 1.6 Hz, 1H), 7.64 (s, 1H), 7.81 (d, J=5.8 Hz, 1H), 7.83 (d, J=8.5 Hz, 1H), 7.99 (s, 1H), 8.39 (d, J=5.8 Hz, 1H), 8.58 (s, 1H), 8.77 (s, 1H) ppm.

C. 1-(4-Amino-quinazolin-7-ylmethyl)-4-(1H-pyrrolo[3,2-c]pyridin-2-ylmethyl)-piperazin-2-one.

To a solution containing 2-[4-(4-amino-quinazolin-7-ylmethyl)-3-oxo-piperazin-1-ylmethyl]-pyrrolo[3,2-c]pyridine-1-carboxylic acid tert-butyl ester (50 mg, 0.12 mmol) in CH₂Cl₂ (5 mL is added TFA (1 mL) at ambient temperature. After 16 h, the reaction mixture is concentrated to dryness, diluted with water and purified by reverse-phase HPLC [Buffer A: water w/0.1% TFA; Buffer B: CH3CN w/0.1% TFA; Gradient: 0% B to 45% B over 30 min] to provide 34 mg (73%, two steps) of the title compound as a white, lyophilized solid. ¹H NMR (300 MHz, CDCl₃) δ 2.77 (s, 3H), 3.23 (s, 2H), 3.31 (m, 2H), 3.89 (s, 2H), 4.00 (br s, 3H), 4.71 (s, 2H), 6.94 (s, 1H), 7.60 (m, 2H), 7.84 (d, J=6.5 Hz, 1H), 8.36 (m, 2H), 8.81 (s, 1H), 9.18 (s, 1H), 9.73 (br s, 2H), 12.87 (s, 1H) ppm; MS (ion spray): m/z 388 (M+H).

The following compounds are prepared from the compound of Example 72 using the procedures described above.

| Example # | Name | m/z (M + H) |
|---|---|---|
| 286 | 1-(4-Amino-quinazolin-7-ylmethyl)-4-[2-(5-chloro-thiophen-2-yloxy)-ethyl]-piperazin-2-one | 418, 420 Cl pattern |
| 287 | 1-(4-Amino-quinazolin-7-ylmethyl)-4-(5-chloro-1-methyl-1H-indol-2-ylmethyl)-piperazin-2-one | 435, 437 Cl pattern |
| 288 | 1-(4-Amino-quinazolin-7-ylmethyl)-4-[3-(4-chloro-thiophen-2-yl)-allyl]-piperazin-2-one | 414, 416 Cl pattern |
| 289 | 1-(4-Amino-quinazolin-7-ylmethyl)-4-[3-(6-chloro-benzo[b]thiophen-2-yl)-allyl]-piperazin-2-one | 464, 466 Cl pattern |
| 290 | 1-(4-Amino-quinazolin-7-ylmethyl)-4-[3-(5-chloro-4-methyl-thiophen-2-yl)-allyl]-piperazin-2-one | 428, 430 Cl pattern |
| 291 | 1-(4-Amino-quinazolin-7-ylmethyl)-4-(5-chloro-benzofuran-2-ylmethyl)-piperazin-2-one | 422, 424 Cl pattern |
| 292 | 1-(4-Amino-quinazolin-7-ylmethyl)-4-(3-chloro-1H-indol-5-ylmethyl)-piperazin-2-one | 421, 423 Cl pattern |
| 293 | 1-(4-Amino-quinazolin-7-ylmethyl)-4-(5-chloro-1H-indol-2-ylmethyl)-piperazin-2-one | 421, 423 Cl pattern |
| 294 | 1-(4-Amino-quinazolin-7-ylmethyl)-4-(5,7-dichloro-1H-indol-2-ylmethyl)-piperazin-2-one | 455, 457 Cl pattern |
| 295 | 1-(4-Amino-quinazolin-7-ylmethyl)-4-(6-chloro-1H-indol-2-ylmethyl)-piperazin-2-one | 421, 423 Cl pattern |
| 296 | 1-(4-Amino-quinazolin-7-ylmethyl)-4-(3-p-tolyl-prop-2-ynyl)-piperazin-2-one | 386 |
| 297 | 1-(4-Amino-quinazolin-7-ylmethyl)-4-(3-m-tolyl-prop-2-ynyl)-piperazin-2-one | 386 |
| 298 | 1-(4-Amino-quinazolin-7-ylmethyl)-4-[3-(4-chloro-phenyl)-prop-2-ynyl]-piperazin-2-one | 406, 408 Cl pattern |
| 299 | 1-(4-Amino-quinazolin-7-ylmethyl)-4-[3-(3-chloro-phenyl)-prop-2-ynyl]-piperazin-2-one | 406, 408 Cl pattern |
| 300 | 1-(4-Amino-quinazolin-7-ylmethyl)-4-[3-(2-chloro-phenyl)-prop-2-ynyl]-piperazin-2-one | 406 |
| 301 | 1-(4-Amino-quinazolin-7-ylmethyl)-4-(3-biphenyl-4-yl-prop-2-ynyl)-piperazin-2-one | 448 |
| 302 | 1-(4-Amino-quinazolin-7-ylmethyl)-4-[3-(4,5-dibromo-thiophen-2-yl)-allyl]-piperazin-2-one | 536, 538, 540 Br₂ pattern |
| 303 | 1-(4-Amino-quinazolin-7-ylmethyl)-4-(3-biphenyl-3-yl-prop-2-ynyl)-piperazin-2-one | 448 |
| 304 | 1-(4-Amino-quinazolin-7-ylmethyl)-4-[3-(2,5-dichloro-thiophen-3-yl)-prop-2-ynyl]-piperazin-2-one | 446, 448 Cl pattern |
| 305 | 1-(4-Amino-quinazolin-7-ylmethyl)-4-[3-(3-chloro-phenyl)-propyl]-piperazin-2-one | 410, 412 Cl pattern |
| 306 | 1,4-Bis-(4-amino-quinazolin-7-ylmethyl)-piperazin-2-one | 415 |

-continued

| Example # | Name | m/z (M + H) |
|---|---|---|
| 307 | 1-(4-Amino-quinazolin-7-ylmethyl)-4-(1H-pyrrolo[2,3-c]pyridin-2-ylmethyl)-piperazin-2-one | 388 |
| 308 | 1-(4-Amino-quinazolin-7-ylmethyl)-4-[3-(5-nitro-thiophen-2-yl)-allyl]-piperazin-2-one | 425 |
| 309 | 1-(4-Amino-quinazolin-7-ylmethyl)-4-[3-(6-chloro-pyridin-3-yl)-allyl]-piperazin-2-one | 409, 411 Cl pattern |
| 310 | 1-(4-Amino-quinazolin-7-ylmethyl)-4-(1H-pyrrolo[3,2-c]pyridin-2-ylmethyl)-piperazin-2-one | 388 |
| 311 | 1-(4-Amino-quinazolin-7-ylmethyl)-4-[3-(5-chloro-thiophen-3-yl)-allyl]-piperazin-2-one | 414, 416 Cl pattern |
| 312 | 1-(4-Amino-quinazolin-7-ylmethyl)-4-[3-(5-bromo-furan-2-yl)-allyl]-piperazin-2-one | 442, 444 Br pattern |
| 313 | 1-(4-Amino-quinazolin-7-ylmethyl)-4-[5-(5-methyl-thiophen-2-yl)-penta-2,4-dienyl]-piperazin-2-one | 420 |
| 314 | 1-(4-Amino-quinazolin-7-ylmethyl)-4-(2-chloro-benzo[b]thiophen-5-ylmethyl)-piperazin-2-one | 438, 440 Cl pattern |
| 315 | 1-(4-Amino-quinazolin-7-ylmethyl)-4-[3-(5-methyl-thiophen-2-yl)-allyl]-piperazin-2-one | 394 |
| 316 | 1-(4-Amino-quinazolin-7-ylmethyl)-4-[3-(5-methoxy-thiophen-2-yl)-allyl]-piperazin-2-one | 410 |
| 317 | 4-(1-Amino-7-chloro-isoquinolin-3-ylmethyl)-1-(4-amino-quinazolin-7-ylmethyl)-piperazin-2-one | 448, 450 Cl pattern |
| 318 | 2-[4-(4-Amino-quinazolin-7-ylmethyl)-3-oxo-piperazin-1-yl]-N-(5-chloro-thiophen-2-yl)-acetamide | 431 |
| 319 | 1-(4-Amino-quinazolin-7-ylmethyl)-4-(7-chloro-isoquinolin-3-ylmethyl)-piperazin-2-one | 433, 435 Cl pattern |
| 320 | 1-(4-Amino-quinazolin-7-ylmethyl)-4-[2-(3-chloro-phenyl)-2-(S)-hydroxy-ethyl]-piperazin-2-one | 412, 414 Cl pattern |
| 321 | 1-(4-Amino-quinazolin-7-ylmethyl)-4-[2-(3-chloro-phenylsulfanyl)-ethyl]-piperazin-2-one | 428, 430 Cl pattern |
| 322 | 1-(4-Amino-quinazolin-7-ylmethyl)-4-(2-methylene-1,1-dioxo-2,3-dihydro-1H-11 6-benzo[b]thiophen-3-yl)-piperazin-2-one | 470 |
| 323 | 1-(4-Amino-quinazolin-7-ylmethyl)-4-[3-(4-nitro-phenyl)-allyl]-piperazin-2-one | 419 |
| 324 | 1-(4-Amino-quinazolin-7-ylmethyl)-4-(2-chloro-benzo[b]thiophen-6-ylmethyl)-piperazin-2-one | 438, 440 Cl pattern |
| 325 | 2-[4-(4-Amino-quinazolin-7-ylmethyl)-3-oxo-piperazin-1-yl]-N-(4-chloro-phenyl)-acetamide | 425, 427 Cl pattern |
| 326 | 1-(4-Amino-quinazolin-7-ylmethyl)-4-[1-(4-chloro-phenyl)-pyrrolidin-3-yl]-piperazin-2-one | 437, 439 Cl pattern |
| 327 | 1-(4-Amino-quinazolin-7-ylmethyl)-4-[2-(5-chloro-thiophen-2-yl)-ethyl]-piperazin-2-one | 402, 404 Cl pattern |
| 328 | 1-(4-Amino-quinazolin-7-ylmethyl)-4-[3-(4-chloro-phenyl)-propyl]-piperazin-2-one | 410, 412 Cl pattern |
| 329 | 2-[4-(4-Aminoquinazoline-7-ylmethyl)-3-oxo-piperazin-1-ylmethyl]-3-(4-chlorophenyl)-acrylic acid | 452, 454 Cl pattern |
| 330 | 1-(4-Amino-quinazolin-7-ylmethyl)-4-(7-chloro-1-hydroxy-isoquinolin-3-ylmethyl)-piperazin-2-one | 449, 451 Cl pattern |
| 331 | 1-(4-Amino-quinazolin-7-ylmethyl)-4-(6-chloro-naphthalen-2-ylmethyl)-piperazin-2-one | 432, 434 Cl pattern |
| 332 | 1-(4-Amino-quinazolin-7-ylmethyl)-4-isoquinolin-3-ylmethyl-piperazin-2-one | 399 |
| 333 | 1-(4-Amino-quinazolin-7-ylmethyl)-4-[1-(3-chloro-phenyl)-pyrrolidin-3-yl]-piperazin-2-one | 437, 439 Cl pattern |
| 334 | 1-(4-Amino-quinazolin-7-ylmethyl)-4-(1,7-dichloro-isoquinolin-3-ylmethyl)-piperazin-2-one | 467, 469 Cl pattern |
| 335 | 4-(2-Amino-7-chloro-quinolin-3-ylmethyl)-1-(4-amino-quinazolin-7-ylmethyl)-piperazin-2-one | 448, 450 Cl pattern |
| 336 | 1-(4-Aminoquinazolin-7-ylmethyl)-4-(5-chloro-benzo[b]thiophene-2-ylmethyl)piperazin-2-one. | 438, 440 Cl pattern |
| 337 | 1-(4-Amino-quinazolin-7-ylmethyl)-4-[2-(4-chloro-phenylsulfanyl)-ethyl]-piperazin-2-one | 428, 430 Cl pattern |
| 338 | 1-(4-Amino-quinazolin-7-ylmethyl)-4-[2-(6-chloro-benzo[b]thiophen-2-yl)-ethyl]-piperazin-2-one | 452, 454 Cl pattern |
| 339 | 1-(4-Aminoquinazolin-7-ylmethyl)-4-[2-(4-chloro-phenoxy)-ethyl]-piperazine-2-one | 412, 414 Cl pattern |
| 340 | 2-[4-(4-Amino-quinazolin-7-ylmethyl)-3-oxo-piperazin-1-ylmethyl]-6-chloro-4H-benzo[1,4]thiazin-3-one | 469, 471 Cl pattern |
| 341 | 1-(4-Amino-quinazolin-7-ylmethyl)-4-(2,7-dichloro-quinolin-3-ylmethyl)-piperazin-2-on | 467, 469 Cl$_2$ pattern |
| 342 | 2-[[4-(4-Amino-quinazolin-7-ylmethyl)-3-oxo-piperazin-1-yl]-(4-chloro-phenyl)-methyl]-acrylic acid ethyl ester | 480, 482 Cl pattern |
| 343 | 2-[4-(4-Amino-quinazolin-7-ylmethyl)-3-oxo-piperazin-1-ylmethyl]-3-(4-chloro-phenyl)-acrylic acid ethyl ester | 480, 482 Cl pattern |
| 344 | 1-(4-Amino-quinazolin-7-ylmethyl)-4-[3-(4-chloro-phenyl)-allyl]-piperazin-2-one | 408, 410 Cl pattern |

-continued

| Example # | Name | m/z (M + H) |
|---|---|---|
| 345 | 1-(4-Amino-quinazolin-7-ylmethyl)-4-[3-(3-chloro-phenyl)-allyl]-piperazin-2-one | 408, 410 Cl pattern |
| 346 | 1-(4-Amino-quinazolin-7-ylmethyl)-4-[3-(5-bromo-thiophen-2-yl)-allyl]-piperazin-2-one | 458, 460 Br pattern |
| 347 | 1-(4-Amino-quinazolin-7-ylmethyl)-4-[3-(4-bromo-thiophen-2-yl)-allyl]-piperazin-2-one | 458, 460 Br pattern |
| 348 | 3-[4-(4-Amino-quinazolin-7-ylmethyl)-3-oxo-piperazin-1-ylmethyl]-7-fluoro-1H-quinolin-2-one | 433 |
| 349 | 3-[4-(4-Amino-quinazolin-7-ylmethyl)-3-oxo-piperazin-1-ylmethyl]-6-chloro-1H-quinoxalin-2-one | 450, 452 Cl pattern |
| 350 | 1-(4-Amino-quinazolin-7-ylmethyl)-4-(5-chloro-1-methyl-1H-benzoimidazol-2-ylmethyl)-piperazin-2-one | 436, 438 Cl pattern |
| 351 | 2-[4-(4-Amino-quinazolin-7-ylmethyl)-3-oxo-piperazin-1-ylmethyl]-6-chloro-3H-quinazolin-4-one | 492, 494 Cl pattern |
| 352 | 1-(4-Amino-quinazolin-7-ylmethyl)-4-(3-thiophen-2-yl-propyl)-piperazin-2-one | 382 |
| 353 | 1-(4-Amino-quinazolin-7-ylmethyl)-4-(7-chloro-quinolin-3-ylmethyl)-piperazin-2-one | 432, 434 Cl pattern |
| 354 | 3-[4-(4-Amino-quinazolin-7-ylmethyl)-3-oxo-piperazin-1-ylmethyl]-5,7-dichloro-1H-quinolin-2-one | 483, 485 Cl pattern |
| 355 | 1-(4-Amino-quinazolin-7-ylmethyl)-4-(6,7-dichloro-benzo[b]thiophen-2-ylmethyl)-piperazin-2-one | 472, 474 Cl$_2$ pattern |
| 356 | 3-[4-(4-Amino-quinazolin-7-ylmethyl)-3-oxo-piperazin-1-ylmethyl]-5-chloro-1H-quinolin-2-one | 449, 451 Cl pattern |
| 357 | 1-(4-Amino-quinazolin-7-ylmethyl)-4-(5-chloro-[2,3']bithiophenyl-5'-ylmethyl)-piperazin-2-one | 470, 472 Cl pattern |
| 358 | 4-(6-Amino-benzo[b]thiophen-2-ylmethyl)-1-(4-amino-quinazolin-7-ylmethyl)-piperazin-2-one | 419 |
| 359 | 1-(4-Amino-quinazolin-7-ylmethyl)-4-(2-chloro-quinolin-6-ylmethyl)-piperazin-2-one | 433, 435 Cl pattern |
| 360 | 1-(4-Amino-quinazolin-7-ylmethyl)-4-(6-bromo-1H-benzoimidazol-2-ylmethyl)-piperazin-2-one | 466, 468 Br pattern |
| 361 | 1-(4-Amino-quinazolin-7-ylmethyl)-4-(6-nitro-benzo[b]thiophen-2-ylmethyl)-piperazin-2-one | 449 |
| 362 | 1-(4-Amino-quinazolin-7-ylmethyl)-4-[5-(3-chloro-phenyl)-thiophen-2-ylmethyl]-piperazin-2-one | 464, 466 Cl pattern |
| 363 | 1-(4-Amino-quinazolin-7-ylmethyl)-4-(6-chloro-3-methoxy-benzo[b]thiophen-2-ylmethyl)-piperazin-2-one | 468, 470 Cl pattern |
| 364 | 3-[4-(4-Amino-quinazolin-7-ylmethyl)-3-oxo-piperazin-1-ylmethyl]-6-chloro-1H-quinolin-2-one | 449, 451 Cl pattern |
| 365 | 1-(4-Amino-quinazolin-7-ylmethyl)-4-(6-trifluoromethyl-1H-benzoimidazol-2-ylmethyl)-piperazin-2-one | 456 |
| 366 | 1-(4-Amino-quinazolin-7-ylmethyl)-4-(5'-methyl-[2,2']bithiophenyl-5-ylmethyl)-piperazin-2-one | 450 |
| 367 | 1-(4-Amino-quinazolin-7-ylmethyl)-4-(5-methyl-benzo[b]thiophen-2-ylmethyl)-piperazin-2-one | 418 |
| 368 | 1-(4-Amino-quinazolin-7-ylmethyl)-4-(5'-chloro-3,3'-dimethyl-[2,2']bithiophenyl-5-ylmethyl)-piperazin-2-one | 498, 500 Cl pattern |
| 369 | 1-(4-Amino-quinazolin-7-ylmethyl)-4-[3-(3,5-dibromo-4-methoxy-phenyl)-[1,2,4]oxadiazol-5-ylmethyl]-piperazin-2-one | 602, 604, 606 Br$_2$ pattern |
| 370 | 1-(4-Amino-quinazolin-7-ylmethyl)-4-(6-methyl-benzo[b]thiophen-2-ylmethyl)-piperazin-2-one | 418 |
| 371 | 1-(4-Amino-quinazolin-7-ylmethyl)-4-(4-methyl-benzo[b]thiophen-2-ylmethyl)-piperazin-2-one | 418 |
| 372 | 1-(4-Amino-quinazolin-7-ylmethyl)-4-(7-chloro-benzo[b]thiophen-2-ylmethyl)-piperazin-2-one | 438, 440 Cl pattern |
| 373 | 1-(4-Amino-quinazolin-7-ylmethyl)-4-(5'-chloro-3'-methyl-[2,2']bithiophenyl-5-ylmethyl)-piperazin-2-one | 484, 486 Cl pattern |
| 374 | 1-(4-Amino-quinazolin-7-ylmethyl)-4-(1H-benzoimidazol-2-ylmethyl)-piperazin-2-one | 388 |
| 375 | 1-(4-Amino-quinazolin-7-ylmethyl)-4-(5'-bromo-[2,2']bithiophenyl-5-ylmethyl)-piperazin-2-one | 514, 516 Br pattern |
| 376 | 1-(4-Amino-quinazolin-7-ylmethyl)-4-[5-(2,3-dihydro-benzo[1,4]dioxin-6-yl)-oxazol-2-ylmethyl]-piperazin-2-one | 473 |
| 377 | 1-(4-Amino-quinazolin-7-ylmethyl)-4-(5,6-dichloro-benzo[b]thiophen-2-ylmethyl)-piperazin-2-one | 472, 474 Cl pattern |
| 378 | 1-(4-Amino-quinazolin-7-ylmethyl)-4-(4,5-dichloro-benzo[b]thiophen-2-ylmethyl)-piperazin-2-one | 472, 474 Cl pattern |
| 379 | 1-(4-Amino-quinazolin-7-ylmethyl)-4-(5-chloro-benzooxazol-2-ylmethyl)-piperazin-2-one | 423, 425 Cl pattern |
| 380 | 1-(4-Amino-quinazolin-7-ylmethyl)-4-(6-chloro-5-fluoro-benzo[b]thiophen-2-ylmethyl)-piperazin-2-one | 456, 458 Cl pattern |
| 381 | 1-(4-Amino-quinazolin-7-ylmethyl)-4-(4-chloro-5-fluoro-benzo[b]thiophen-2-ylmethyl)-piperazin-2-one | 456, 458 Cl pattern |
| 382 | 1-(4-Amino-quinazolin-7-ylmethyl)-4-(5'-chloro-3-methyl-[2,2']bithiophenyl-5-ylmethyl)-piperazin-2-one | 484, 486 Cl pattern |

| Example # | Name | m/z (M + H) |
|---|---|---|
| 383 | 1-(4-Amino-quinazolin-7-ylmethyl)-4-(5-chloro-thieno[3,2-b]pyridin-2-ylmethyl)-piperazin-2-one | 439, 441 Cl pattern |
| 384 | 1-(4-Amino-quinazolin-7-ylmethyl)-4-(5,6-dichloro-1H-benzoimidazol-2-ylmethyl)-piperazin-2-one | 456 |
| 385 | 1-(4-Amino-quinazolin-7-ylmethyl)-4-(3-benzooxazol-2-yl-benzyl)-piperazin-2-one | 464 |
| 386 | 1-(4-Amino-quinazolin-7-ylmethyl)-4-[5-(4-chloro-phenyl)-thiophen-2-ylmethyl]-piperazin-2-one | 464, 466 Cl pattern |
| 387 | 1-(4-Amino-quinazolin-7-ylmethyl)-4-(6-methyl-1H-benzoimidazol-2-ylmethyl)-piperazin-2-one | 402 |
| 388 | 1-(4-Amino-quinazolin-7-ylmethyl)-4-[2,2']bithiophenyl-5-ylmethyl-piperazin-2-one | 435 |
| 389 | 1-(4-Amino-quinazolin-7-ylmethyl)-4-(4-fluoro-benzo[b]thiophen-2-ylmethyl)-piperazin-2-one | 422 |
| 390 | 1-(4-Aminoquinazolin-7-ylmethyl)-4-(6-fluoro-benzo[b]thiophene-2-ylmethyl)piperazin-2-one. | 422 |
| 391 | 1-(4-Amino-quinazolin-7-ylmethyl)-4-[5-(1-methyl-5-trifluoromethyl-1H-pyrazol-3-yl)-thiophen-2-ylmethyl]-piperazin-2-one | 501 |
| 392 | 1-(4-Amino-quinazolin-7-ylmethyl)-4-(3,4-dimethyl-thieno[2,3-b]thiophen-2-ylmethyl)-piperazin-2-one | 438 |
| 393 | 1-(4-Amino-quinazolin-7-ylmethyl)-4-(4-chloro-3-methyl-benzo[b]thiophen-2-ylmethyl)-piperazin-2-one | 452, 454 Cl pattern |
| 394 | 1-(4-Amino-quinazolin-7-ylmethyl)-4-(6-chloro-3-methyl-benzo[b]thiophen-2-ylmethyl)-piperazin-2-one | 452, 454 Cl pattern |
| 395 | 1-(4-Amino-quinazolin-7-ylmethyl)-4-[5-(2-methyl-5-trifluoromethyl-2H-pyrazol-3-yl)thiophen-2-ylmethyl]piperazin-2-one | 502 |
| 396 | 1-(4-Amino-quinazolin-7-ylmethyl)-4-[5-(3-nitro-phenyl)-furan-2-ylmethyl]-piperazin-2-one | 459 |
| 397 | 1-(4-Amino-quinazolin-7-ylmethyl)-4-(5-chloro-thieno[3,2-b]pyridin-6-ylmethyl)-piperazin-2-one | 439, 441 Cl pattern |
| 398 | 1-(4-Amino-quinazolin-7-ylmethyl)-4-[5-(4-methoxy-phenyl)-thiophen-2-ylmethyl]-piperazin-2-one | 460 |
| 399 | 1-(4-Amino-quinazolin-7-ylmethyl)-4-(4-hydroxy-2-pyridin-2-yl-pyrimidin-5-ylmethyl)-piperazin-2-one | 443 |
| 400 | 1-(4-Amino-quinazolin-7-ylmethyl)-4-[3-(4-fluoro-phenoxy)-benzyl]-piperazin-2-one | 458 |
| 401 | 1-(4-Amino-quinazolin-7-ylmethyl)-4-[2-(4-chloro-phenyl)-thiazol-4-ylmethyl]-piperazin-2-one | 465, 467 Cl pattern |
| 402 | 1-(4-Amino-quinazolin-7-ylmethyl)-4-(6-bromo-benzo[b]thiophen-2-ylmethyl)-piperazin-2-one | 482, 484 Br pattern |
| 403 | 1-(4-Amino-quinazolin-7-ylmethyl)-4-benzo[b]thiophen-2-ylmethyl-piperazin-2-one | 404 |
| 404 | 1-(4-Amino-quinazolin-7-ylmethyl)-4-(5'-chloro-[2,2']bithiophenyl-5-ylmethyl)-piperazin-2-one | 470, 472 Cl pattern |
| 405 | 1-(4-Amino-quinazolin-7-ylmethyl)-4-(3,5-bis-trifluoromethyl-benzyl)-piperazin-2-one | 488 |
| 406 | 1-(4-Amino-quinazolin-7-ylmethyl)-4-biphenyl-4-ylmethyl-piperazin-2-one | 423 (M+) |
| 407 | 1-(4-Amino-quinazolin-7-ylmethyl)-4-naphthalen-2-ylmethyl-piperazin-2-one | 397 (M+) |
| 408 | 1-(4-Amino-quinazolin-7-ylmethyl)-4-(5-chloro-benzo[b]thiophen-3-ylmethyl)-piperazin-2-one | 438, 440 Cl pattern |
| 409 | 1-(4-Amino-quinazolin-7-ylmethyl)-4-(6-chloro-thieno[2,3-b]pyridin-2-ylmethyl)-piperazin-2-one | 438, 440 Cl pattern |

EXAMPLE 410

1-(4-Aminoquinazolin-7-ylmethyl)-4-[3-(5-chloro-thiophen-2-yl)-(E)-acryloyl]piperazine-2-one The title compound is prepared as described in EXAMPLE 123 using 1-(4-aminoquinazoline-7-ylmethyl)piperazine-2-one bishydrochloride, EXAMPLE 72, in place of 4-(2-oxopiperazin-1-ylmethyl)benzamidine bistrifluoroacetate. $^1$H NMR (d6-DMSO, 300 MHz) δ9.77 (bs, 2H), 8.83 (s, 1H), 8.40 (dd, 1H), 7.68 (d, 1H), 7.65 (s, 1H), 7.58 (d, 2H), 7.15 (d, 2H), 4.80 (s, 2H), 4.33, 4.15 (m, 2H, rotamers), 3.70 (m, 2H), 3.49 (m, 2H). ESI MS, [M+H]$^+$=456, 458 (Br pattern).

The following compounds are prepared from the compound of Example 72 using the methods described above.

| Example # | Name | m/z [M + H] |
|---|---|---|
| 411 | 1-(4-Amino-quinazolin-7-ylmethyl)-4-(4-chloro-thiophene-2-carbonyl)-piperazin-2-one | 402, 404 Cl pattern |
| 412 | 4-[3-(3-Amino-4-chloro-phenyl)-(E)-acryloyl]-1-(4-amino-quinazolin-7-ylmethyl)-piperazin-2-one | 437, 439 Cl pattern |

-continued

| Example # | Name | m/z [M + H] |
|---|---|---|
| 413 | 1-(4-Amino-quinazolin-7-ylmethyl)-4-(3-chloro-1H-indole-6-carbonyl)-piperazin-2-one | 435, 437 Cl pattern |
| 414 | 1-(4-Amino-quinazolin-7-ylmethyl)-4-[(5-chloro-thiophen-2-yloxy)-acetyl]piperazin-2-one | 432, 434 Cl pattern |
| 415 | 1-(4-Amino-quinazolin-7-ylmethyl)-4-[3-(5-bromo-thiophen-2-yl)-(E)-acryloyl]-piperazin-2-one | 472, 474 Br pattern |
| 416 | 5-Chloro-thiophene-2-carboxylic acid {2-[4-(4-amino-quinazolin-7-ylmethyl)-3-oxo-piperazin-1-yl]-2-oxo-ethyl}-amide | 459, 461 Cl pattern |
| 417 | 1-(4-Amino-quinazolin-7-ylmethyl)-4-[3-(4-chloro-thiophen-2-yl)-(E)-acryloyl]-piperazin-2-one | 428, 430 Cl pattern |
| 418 | 1-(4-Amino-quinazolin-7-ylmethyl)-4-(5-chloro-1H-indole-2-carbonyl)-piperazin-2-one | 435, 437 Cl pattern |
| 419 | 1-(4-Amino-quinazolin-7-ylmethyl)-4-[3-(6-chloro-benzo[b]thiophen-2-yl)-(E)-acryloyl]-piperazin-2-one | 478, 480 Cl pattern |
| 420 | 1-(4-Amino-quinazolin-7-ylmethyl)-4-[3-(4-bromo-thiophen-2-yl)-(E)-acryloyl]-piperazin-2-one | 472, 474 Br pattern |
| 421 | 5-Chloro-thiophene-2-carboxylic acid {2-[4-(4-amino-quinazolin-7-ylmethyl)-3-oxo-piperazin-1-yl]-1-methyl-2-oxo-ethyl}-amide | 473, 475 Cl pattern |
| 422 | 5-Chloro-thiophene-2-carboxylic acid {3-[4-(4-amino-quinazolin-7-ylmethyl)-3-oxo-piperazin-1-yl]-3-oxo-propyl}-amide | 473, 475 Cl pattern |
| 423 | 1-(4-Amino-quinazolin-7-ylmethyl)-4-[(4-chloro-phenoxy)-acetyl]-piperazin-2-one | 426, 428 Cl pattern |
| 424 | 1-(4-Amino-quinazolin-7-ylmethyl)-4-[(4-chloro-2-methyl-phenoxy)-acetyl]-piperazin-2-one | 440, 442 Cl pattern |
| 425 | 1-(4-Amino-quinazolin-7-ylmethyl)-4-(5'-chloro-[2,2']bithiophenyl-5-carbonyl)-piperazin-2-one | 484, 486 Cl pattern |
| 426 | 1-(4-Amino-quinazolin-7-ylmethyl)-4-[3-(5-chloro-thiophen-2-yl)-propionyl]-piperazin-2-one | 430, 432 Cl pattern |
| 427 | 1-(4-Amino-quinazolin-7-ylmethyl)-4-[3-(3-chloro-phenyl)-(E)-acryloyl]-piperazin-2-one | 422, 424 Cl pattern |
| 428 | N-[2-[4-(4-Amino-quinazolin-7-ylmethyl)-3-oxo-piperazin-1-yl]-1-(5-chloro-thiophen-2-ylmethyl)-2-oxo-ethyl]-benzamide | 428, 430 Cl pattern |
| 429 | N-[1-[4-(4-Amino-quinazolin-7-ylmethyl)-3-oxo-piperazine-1-carbonyl]-2-(5-chloro-thiophen-2-yl)-vinyl]-benzamide | 549, 550 Cl pattern |
| 430 | N-[1-[4-(4-Amino-quinazolin-7-ylmethyl)-3-oxo-piperazine-1-carbonyl]-2-(5-chloro-thiophen-2-yl)-vinyl]-acetamide | 485, 487 Cl pattern |
| 431 | 1-(4-Amino-quinazolin-7-ylmethyl)-4-[3-(4-chloro-phenyl)-(E)-acryloyl]-piperazin-2-one | 422, 424 Cl pattern |
| 432 | 1-(4-Amino-quinazolin-7-ylmethyl)-4-[(5-chloro-thiophen-2-yl)-acetyl]-piperazin-2-one | 415, 417 Cl pattern |
| 433 | 1-(4-Amino-quinazolin-7-ylmethyl)-4-(6-chloro-benzo[b]thiophene-2-carbonyl)-piperazin-2-one | 451, 453 Cl pattern |
| 434 | 2-[4-(4-Amino-quinazolin-7-ylmethyl)-3-oxo-piperazine-1-carbonyl]-6-chloro-4H-benzo[1,4]thiazin-3-one | 483, 485 Cl pattern |
| 435 | 1-(4-Amino-quinazolin-7-ylmethyl)-4-[(6-chloro-benzo[b]thiophen-2-yl)-acetyl]-piperazin-2-one | 466, 468 Cl pattern |

EXAMPLE 436

4-(4-Aminoquinazolin-7-ylmethyl)-3-oxopiperazine-1-carboxylic acid 4-chloro-benzylamide To a solution of 1-(4-aminoquinazoline-7-ylmethyl)piperazine-2-one (25 mg, 0.097 mmol), EXAMPLE 72, in 1 mL of DMF is added 4-chloro-benzyl isocyanate (22 mg, 0.13 mmol, prepared as described in EXAMPLE 37). After stirring 1 h at room temperature, the solution is concentrated. The crude product is purified by RP-HPLC eluting in a gradient of 10% CH$_3$CN/H$_2$O (0.1% TFA) to 80% CH$_3$CN/H$_2$O (0.1% TFA) and the appropriate product fractions are combined and lyophilized to provide the title compound (36 mg, 0.067 mmol) as a white solid. $^1$H NMR (d6-DMSO, 300 MHz) δ9.76 (bs, 2H), 8.83 (s, 1H), 8.38 (d, 1H), 7.64 (d, 1H), 7.60 (s, 1H), 7.34 (d, 2H), 7.31 (m, 1H), 7.26 (d, 2H), 4.75 (s, 2H), 4.22 (d, 2H), 4.08 (s, 2H), 3.60 (m, 2H), 3.35 (m, 2H). ESI MS, [M+H]$^+$=425,427 (Cl pattern).

EXAMPLE 437

4-(4-Aminoquinazolin-7-ylmethyl)-3-oxopiperazine-1-carboxylic acid (5-chloro-thiophen-2-ylmethyl) amide To a solution of (5-chloro-thiophen-2-yl)-acetic acid (0.18 g, 1.04 mmol), prepared as described in EXAMPLE 27 in 6 mL of dry CH$_2$Cl$_2$ is added Et$_3$N (0.15 mL g, 1.04 mmol) and diphenylphosphoryl azide (0.24 mL, 1.04 mmol). The mixture is stirred at room temperature for 2.5 h, then heated at 50° C. for 2 hours. To the solution is added 1-(4-aminoquinazoline-7-ylmethyl)piperazine-2-one (0.10 g, 0.41 mmol), EXAMPLE 72, and Et$_3$N (0.15 mL g, 1.04 mmol) and the mixture is heated at 50° C. for 2 h, then stirred at room temperature for 16 hours. The resulting mixture is concentrated. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are combined and lyophilized to provide the title compound (10 mg, 0.02 mmol) as a white solid. $^1$H NMR (d6-DMSO, 300 MHz) δ9.69 (bs, 2H), 8.80 (s, 1H), 8.48 (d, 1H), 7.61 (d, 1H), 7.60 (s, 1H), 7.41 (t, 1H), 6.90 (d, 1H), 6.80 (d, 1H), 4.77 (d, 2H), 4.30 (d, 2H), 4.10 (s, 2H), 3.61 (m, 2H), 3.38 (m, 2H). ESI MS, [M+H]$^+$=431,433 (Cl pattern).

EXAMPLE 438

4-(4-Aminoquinazolin-7-ylmethyl)-3-oxopiperazine-1-carboxylic acid (5-chloro-thiophen-2-yl)amide A mixture of 5-chloro-thiophene-2-carbonyl azide (55 mg, 0.29 mmol, prepared as described in EXAMPLE 38) and 1-(4-aminoquinazoline-7-ylmethyl)piperazine-2-one (50 mg, 0.20 mmol), EXAMPLE 72, in 3 mL of dry toluene is heated at 105° C. for 1 hours. The resulting mixture is concentrated in vacuo. The crude product is purified by RP-HPLC eluting in a gradient of 10% CH$_3$CN/H$_2$O (0.1% TFA) to 60% CH$_3$CN/H$_2$O (0.1% TFA) and the appropriate product fractions are combined and lyopholized to provide the title compound (35 mg, 0.02 mmol) as a white solid. $^1$H NMR (DMSO-d$_6$, 300 MHz) δ10.04 (s, 1H), 9.71 (bs, 2H), 8.81 (s, 1H), 8.38 (dd, 1H), 7.64 (d, 1H), 7.61 (s, 1H), 6.77 (d, 1H), 6.42 (d, 1H), 4.76 (s, 2H), 4.21 (s, 2H), 3.73 (m, 2H), 3.40 (m, 2H). ESI MS, [M+H]$^+$=417,419 (Cl pattern).

The following compounds are prepared from the compound of Example 72 using the methods described above.

| Example # | Name | m/z [M + H] |
|---|---|---|
| 439 | 4-(4-Amino-quinazolin-7-ylmethyl)-3-oxo-piperazine-1-carboxylic acid(4-chloro-thiophen-2-yl)-amide | 417, 419 Cl pattern |
| 440 | 4-(4-Amino-quinazolin-7-ylmethyl)-3-oxo-piperazine-1-carboxylic acid(5-bromo-thiophen-2-yl)-amide | 461, 463 Br pattern |
| 441 | 4-(4-Amino-quinazolin-7-ylmethyl)-3-oxo-piperazine-1-carboxylic acid(3-amino-4-chloro-phenyl)-amide | 426, 428 Cl pattern |
| 442 | 4-(4-Amino-quinazolin-7-ylmethyl)-3-oxo-piperazine-1-carboxylic acid(4-bromo-phenyl)-amide | 455, 457 Br pattern |
| 443 | 4-(4-Amino-quinazolin-7-ylmethyl)-3-oxo-piperazine-1-carboxylic acid(4-chloro-phenyl)-amide | 411, 413 Cl pattern |
| 444 | 4-(4-Amino-quinazolin-7-ylmethyl)-3-oxo-piperazine-1-carboxylic acid(4-methoxy-phenyl)-amide | 407 |
| 445 | 4-(4-Amino-quinazolin-7-ylmethyl)-3-oxo-piperazine-1-carboxylic acid(3,4-dichloro-phenyl)-amide | 445, 447 Cl$_2$ pattern |

EXAMPLE 446

4-(4-Amino-quinazolin-7-ylmethyl)-3-oxo-piperazine-1-carboxylic acid 5-chloro-thiophen-2-ylmethyl ester To a solution of 5-chloro-2-thiophene-methanol (0.10 g, 0.67 mmol, prepared by NaBH$_4$ reduction of 5-chloro-2-thiophene-carboxaldehyde) in 6 mL of CH$_2$Cl$_2$ is added 1,1'-carbonyldiimidazole (0.11 g, 0.67 mmol). The mixture is stirred at room temperature for 3 hours. Then 1-(4-amino-quinazoline-7-ylmethyl)piperazine-2-one (0.17 g, 0.67 mmol, EXAMPLE 72) and a catalytic amount of DMAP is added to the solution and the resulting mixture is heated at 35° C. for 18 hours. The mixture is dissolved in water/MeOH and the crude product is purified by RP-HPLC eluting in a gradient of 10% CH$_3$CN/H$_2$O (0.1% TFA) to 100% CH$_3$CN. The appropriate fractions are combined and lyoppholized to provide the title compound as a white solid. ESI MS, [M+H]$^+$=432,434 (Cl pattern).

The following compounds are prepared from the compound of Example 72 using the methods described above.

| Example # | Name | m/z [M + H] |
|---|---|---|
| 447 | 4-(4-Amino-quinazolin-7-ylmethyl)-3-oxo-piperazin-1-carboxylic acid 6-chloro-benzooxazol-2-ylmethyl ester | 467, 469 Cl pattern |
| 448 | 4-(4-Amino-quinazolin-7-ylmethyl)-3-oxo-piperazine-1-carboxylic acid 1-(3-chloro-phenyl)-pyrrolidin-3-yl ester | 481, 483 Cl pattern |

EXAMPLE 449

1-(4-Amino-quinazolin-7-ylmethyl)-4-(7-chloro-isoquinolin-3-ylmethyl)-3-(S)-methyl-piperazin-2-one To a solution of 1-(4-amino-quinazoline-7-ylmethyl)-3-methyl-piperazine-2-one, EXAMPLE 80, (0.06 g, 0.2 mmol) in 2 mL of DMF is added 3-bromomethyl-7-chloroisoquinoline, EXAMPLE 11, 0.052 g, 0.20 mmol), and K$_2$CO$_3$ (0.08 g, 0.06 mmol). After 16 h, the reaction mixture is concentrated to dryness The crude product is purified by RP-HPLC eluting with a gradient of 5% CH$_3$CN/H$_2$O (0.1% TFA) to 50% CH$_3$CN/H$_2$O (0.1% TFA). The product fractions are lyophilized to give the title compound as a tristrisfluoroacetic acid salt (0.06 g, 0.08 mmol) as a white solid. $^1$H NMR (d6-DMSO, 300 MHz) δ9.79 (bs, 2H), 9.40 (s, 1H), 8.73 (s, 1H), 8.33 (d, 1H), 8.25 (s, 1H), 8.06 (s, 1H), 8.00 (d, 1H), 7.79 (d, 1H), 7.60 (m, 2H), 4.80 (AB, 2H), 4.72 (AB, 2H), 4.28 (m, 1H), 3.54 (m, 4H), 1.96 (d, 3H). MS (ion spray) 447, 449, (Cl pattern). Elemental analysis C$_{28}$H$_{25}$ClF$_6$N$_6$O$_6$.3CF$_3$CO$_2$H.0.28H$_2$O, cal C=45.38%, H=3.35%, N=10.58%; found C=45.38, H=3.35%, N=10.63%.

EXAMPLE 450

4-(4-Amino-quinazolin-7-ylmethyl)-4-(3-chloro-1H-indol-6-ylmethyl)-3-(S)-methyl-piperazin-2-one The title compound is prepared as described in EXAMPLE 274 using 1-(4-amino-quinazoline-7-ylmethyl)-3-methyl-piperazine-2-one, EXAMPLE 80. $^1$H NMR (DMSO-$d_6$, 300 MHz) δ9.79 (bs, 2H), 8.82 (s, 1H), 8.39 (d, 1H), 7.61 (m, 3H), 7.57 (d, 1H), 7.52 (d, 1H), 7.49 (d, 1H), 7.20 (d, 1H), 7.10 (d, 1H, 4.75 (AB, 2H), 4.57 (m, 1H), 4.23 (m, 1H), 3.97 (m, 1H), 3.50 (m, 3H),1.65 (d, 3H). ESI MS, [M+H]$^+$=435,437 (Cl pattern). Anal. ($C_{23}H_{23}ClN_6O.2.15TFA.0.25H_2O$) C, H, N.

The following compounds are prepared from the compound of Example 80 using the methods described above.

EXAMPLE 465

1-(4-Amino-quinazolin-7-ylmethyl)-4-[3-(4-chloro-thiophen-2-yl)-acryloyl]-3-(S)-methyl-piperazin-2-one The title compound is prepared as described in EXAMPLE 123, using 1-(4-amino-quinazoline-7-ylmethyl)-3-methyl-piperazine-2-one, EXAMPLE 80, and 3-(4-chloro-thiophen-2-yl)-(E)-acrylic acid, EXAMPLE 26. $^1$H NMR (d6-DMSO, 300 MHz) δ9.74 (bs, 2H), 8.82 (s, 1H), 8.40 (d, 1H), 7.62 (m, 5H), 7.05 (d, 1H), 4.92 (m, 1H), 4.80 (m, 2H), 4.73 (m, 1H), 4.50 (m, 1H), 3.40 (m, 2H), 1.42 (m, 3H). ESI MS, [M+H]$^+$ =442, 444 (Cl pattern).

The following compounds are prepared from the compound of Example 80 using the methods described above.

| Example # | Name | m/z [M + H] |
|---|---|---|
| 451 | 1-(4-Amino-quinazolin-7-ylmethyl)-4-[3-(4-chloro-thiophen-2-yl)-allyl]-3-(S)-methyl-piperazin-2-one | 428, 430 Cl pattern |
| 452 | 1-(4-Amino-quinazolin-7-ylmethyl)-4-[3-(6-chloro-benzo[b]thiophen-2-yl)-allyl]-3-(S)-methyl-piperazin-2-one | 478, 480 Cl pattern |
| 453 | 1-(4-Amino-quinazolin-7-ylmethyl)-4-[3-(5-chloro-thiophen-2-yl)-propyl]-3-(S)-methyl-piperazin-2-one | 429, 431 Cl pattern |
| 454 | 1-(4-Amino-quinazolin-7-ylmethyl)-4-(5-chloro-1H-indol-2-ylmethyl)-3-(S)-methyl-piperazin-2-one | 435, 437 Cl pattern |
| 455 | 1-(4-Amino-quinazolin-7-ylmethyl)-4-[3-(5-chloro-thiophen-2-yl)-but-2-enyl]-3-(S)-methyl-piperazin-2-one | 442, 444 Cl pattern |
| 456 | 1-(4-Amino-quinazolin-7-ylmethyl)-4-(5'-chloro-[2,2']bithiophenyl-5-ylmethyl)-3-(S)-methyl-piperazin-2-one | 483 (M+) (EI) |
| 457 | 1-(4-Amino-quinazolin-7-ylmethyl)-4-(5-chloro-1H-benzoimidazol-2-ylmethyl)-3-(S)-methyl-piperazin-2-one | 536, 538 Cl pattern |
| 458 | 1-(4-Amino-quinazolin-7-ylmethyl)-4-[3-(5-chloro-thiophen-2-yl)-allyl]-3-(S)-methyl-piperazin-2-one | 428, 430 Cl pattern |
| 459 | 1-(4-Amino-quinazolin-7-ylmethyl)-4-(6-chloro-naphthalen-2-ylmethyl)-3-(S)-methyl-piperazin-2-one | 446, 448 Cl pattern |
| 460 | 1-(4-Amino-quinazolin-7-ylmethyl)-4-(6-chloro-thieno[2,3-b]pyridin-2-ylmethyl)-3-(S)-methyl-piperazin-2-one | 453, 455 Cl pattern |
| 461 | 1-(4-Amino-quinazolin-7-ylmethyl)-4-(6-chloro-benzo[b]thiophen-2-ylmethyl)-3-(S)-methyl-piperazin-2-one | 452, 454 Cl pattern |
| 462 | 1-(4-Amino-quinazolin-7-ylmethyl)-4-(5-chloro-benzo[b]thiophen-2-ylmethyl)-3-(S)-methyl-piperazin-2-one | 452, 454 Cl pattern |
| 463 | 1-(4-Amino-quinazolin-7-ylmethyl)-4-(5-chloro-benzo[b]thiophen-2-ylmethyl)-3-(R)-methyl-piperazin-2-one | 452, 454 Cl pattern |
| 464 | 1-(4-Amino-quinazolin-7-ylmethyl)-4-(6-chloro-benzo[b]thiophen-2-ylmethyl)-3-(R)-methyl-piperazin-2-one | 452, 454 Cl pattern |

| Example # | Name | m/z [M + H] |
|---|---|---|
| 466 | 1-(4-Amino-quinazolin-7-ylmethyl)-4-[(5-chloro-thiophen-3-yloxy)-acetyl]-3-(S)-methyl-piperazin-2-one | 446, 448 Cl pattern |
| 467 | 1-(4-Amino-quinazolin-7-ylmethyl)-4-[(4-chloro-thiophen-2-yloxy)-acetyl]-3-(S)-methyl-piperazin-2-one | 446, 448 Cl pattern |
| 468 | 1-(4-Amino-quinazolin-7-ylmethyl)-4-[3-(5-bromo-thiophen-2-yl)-acryloyl]-3-(S)-methyl-piperazin-2-one | 486, 488 Br pattern |
| 469 | 1-(4-Amino-quinazolin-7-ylmethyl)-4-(3-chloro-1H-indole-6-carbonyl)-3-(S)-methyl-piperazin-2-one | 449, 451 Cl pattern |
| 470 | 1-(4-Amino-quinazolin-7-ylmethyl)-4-(7-chloro-isoquinoline-3-carbonyl)-3-(S)-methyl-piperazin-2-one | 461, 463 Cl pattern |
| 471 | 1-(4-Amino-quinazolin-7-ylmethyl)-4-[(5-chloro-thiophen-2-yloxy)-acetyl]-3-(S)-methyl-piperazin-2-one | 446, 448 Cl pattern |
| 472 | 1-(4-Amino-quinazolin-7-ylmethyl)-4-[3-(4-bromo-thiophen-2-yl)-acryloyl]-3-(S)-methyl-piperazin-2-one | 486, 488 Br pattern |
| 473 | 1-(4-Amino-quinazolin-7-ylmethyl)-4-[(4-chloro-phenoxy)-acetyl]-3-(S)-methyl-piperazin-2-one | 440, 442 Cl pattern |
| 474 | 1-(4-Amino-quinazolin-7-ylmethyl)-4-(5'-chloro-[2,2']bithiophenyl-5-carbonyl)-3-(S)-methyl-piperazin-2-one | 498, 500 Cl pattern |
| 475 | 1-(4-Amino-quinazolin-7-ylmethyl)-4-[3-(5-chloro-thiophen-2-yl)-but-2-enoyl]-3-(S)-methyl-piperazin-2-one | 456, 458 Cl pattern |
| 476 | 1-(4-Amino-quinazolin-7-ylmethyl)-4-(6-chloro-benzo[b]thiophene-2-carbonyl)-3-(S)-methyl-piperazin-2-one | 466, 468 Cl pattern |
| 477 | 1-(4-Amino-quinazolin-7-ylmethyl)-4-[3-(5-chloro-thiophen-2-yl)-acryloyl]-3-(S)-methyl-piperazin-2-one | 442, 444 Cl pattern |

EXAMPLE 478

1-(4-Amino-quinazolin-7-ylmethyl)-4-[3-(5-chloro-thiophen-2-yl)-2-propyl]-3-(S)-ethyl-piperazin-2-one The title compound is prepared as described in EXAMPLE 278 using 1-(4-aminoquinazoline-7-ylmethyl)-3-ethyl-piperazine-2-one, EXAMPLE 77 and 3-(5-chloro-thiophen-2-yl)-propionaldehyde, EXAMPLE 28. $^1$H NMR (d6-DMSO+1 drop TFA, 300 MHz) δ9.80 (bs, 2H), 8.79 (s, 1H), 8.32 (d, 1H), 7.58 (m, 2H), 6.88 (d, 1H), 6.70 (d, 1H), 4.72 (AB, 2H), 4.00 (m, 1H), 3.72 (m, 1H), 3.48 (m, 2H), 3.23 (m, 3H), 2.72 (m, 2H), 1.96 (m, 4H), 0.98 (m, 3H). MS (ion spray), m/z, (M+H)=444, 446 (Cl pattern).

The following compounds are prepared from the compound of Example 77 using the methods described above.

EXAMPLE 486

1-(4-Amino-quinazolin-7-ylmethyl)-4-[3-(5-chloro-thiophen-2-yl)-acryloyl]-3-(S)-ethyl-piperazin-2-one The title compound is prepared as described in EXAMPLE 123, using 1-(4-aminoquinazoline-7-ylmethyl)-3-ethyl-piperazine-2-one, EXAMPLE 77 and 3-(5-chloro-thiophen-2-yl)-(E)-acrylic acid, EXAMPLE 25. $^1$H NMR(d6-DMSO+1 drop TFA, 300 MHz) δ9.78 (bs, 2H), 8.79 (s, 1H), 8.37 (d, 1H), 7.65 (m, 2H), 7.50 (s, 1H), 7.41 (m, 1H), 7.11 (d, 1H), 6.98 (d, 1H), 4.88 (m, 2H), 4.60 (m, 1H), 4.31 (m, 1H), 3.52 (m, 1H), 3.30 (m, 2H), 1.96 (m, 2H), 0.88 (m, 3H). MS (ion spray), m/z, (M+H)=456, 458 (Cl pattern). Elemental analysis, cal $C_{22}H_{22}ClN_5O_2S.1.5C_2HF_3O_2$ % C=47.89, % H=3.78, % N=11.17; found % C=47.34, % H=4.00, % N=11.12.

| Example # | Name | m/z [M + H] |
|---|---|---|
| 479 | 1-(4-Amino-quinazolin-7-ylmethyl)-4-[3-(4-chloro-thiophen-2-yl)-allyl]-3-(S)-ethyl-piperazin-2-one | 442, 444 Cl pattern |
| 480 | 1-(4-Amino-quinazolin-7-ylmethyl)-4-[3-(5-chloro-thiophen-2-yl)-but-2-enyl]-3-(S)-ethyl-piperazin-2-one | 456, 458 Cl pattern |
| 481 | 1-(4-Amino-quinazolin-7-ylmethyl)-4-(7-chloro-isoquinolin-3-ylmethyl)-3-(S)-ethyl-piperazin-2-one | 461, 463 Cl pattern |
| 482 | 1-(4-Amino-quinazolin-7-ylmethyl)-4-[3-(5-chloro-thiophen-2-yl)-allyl]-3-(S)-ethyl-piperazin-2-one | 442, 444 Cl pattern |
| 483 | 1-(4-Amino-quinazolin-7-ylmethyl)-4-(6-chloro-naphthalen-2-ylmethyl)-3-(S)-ethyl-piperazin-2-one | 460, 462 Cl pattern |
| 484 | 1-(4-Amino-quinazolin-7-ylmethyl)-4-(6-chloro-benzo[b]thiophen-2-ylmethyl)-3-(S)-ethyl-piperazin-2-one | 466, 468 Cl pattern |
| 485 | 1-(4-Amino-quinazolin-7-ylmethyl)-4-(6-chloro-thieno[2,3-b]pyridin-2-ylmethyl)-3-(S)-ethyl-piperazin-2-one | 467, 469 Cl pattern |

The following compounds are prepared from the compound of Example 77 using the methods described above.

| Example # | Name | m/z [M + H] |
|---|---|---|
| 487 | 1-(4-Amino-quinazolin-7-ylmethyl)-4-[(4-chloro-thiophen-2-yloxy)-acetyl]-(S)-3-ethyl-piperazin-2-one | 460, 462 Cl pattern |
| 488 | 1-(4-Amino-quinazolin-7-ylmethyl)-4-[(5-chloro-thiophen-3-yloxy)-acetyl]-(S)-3-ethyl-piperazin-2-one | 460, 462 Cl pattern |
| 489 | 1-(4-Amino-quinazolin-7-ylmethyl)-4-[3-(5-chloro-thiophen-3-yl)-acryloyl]-(S)-3-ethyl-piperazin-2-one | 456, 458 Cl pattern |
| 490 | 2-(2-{2-[4-(4-Amino-quinazolin-7-ylmethyl)-(S)-2-ethyl-3-oxo-piperazin-1-yl]-2-oxo-ethoxy}-5-chloro-thiophen-3-yl)-acetamide | 517, 519 Cl pattern |
| 491 | (2-{2-[4-(4-Amino-quinazolin-7-ylmethyl)-(S)-2-ethyl-3-oxo-piperazin-1-yl]-2-oxo-ethoxy}-5-chloro-thiophen-3-yl)-acetic acid | 518, 520 Cl pattern |
| 492 | 1-(4-Amino-quinazolin-7-ylmethyl)-4-(2,3-dichloro-benzo[b]thiophene-6-carbonyl)-(S)-3-ethyl-piperazin-2-one | 514, 516, 518 $Cl_2$ pattern |
| 493 | 1-(4-Amino-quinazolin-7-ylmethyl)-4-(2-chloro-benzo[b]thiophene-6-carbonyl)-(S)-3-ethyl-piperazin-2-one | 480, 482 Cl pattern |
| 494 | (2-{2-[4-(4-Amino-quinazolin-7-ylmethyl)-(S)-2-ethyl-3-oxo-piperazin-1-yl]-2-oxo-ethoxy}-5-chloro-thiophen-3-yl)-acetic acid ethyl ester | 546, 548 Cl pattern |
| 495 | 1-(4-Amino-quinazolin-7-ylmethyl)-4-[(3,5-dichloro-thiophen-2-yloxy)-acetyl]-(S)-3-ethyl-piperazin-2-one | 494, 496 Cl pattern |
| 496 | (2-{2-[4-(4-Amino-quinazolin-7-ylmethyl)-(S)-2-ethyl-3-oxo-piperazin-1-yl]-2-oxo-ethoxy}-5-chloro-thiophen-3-yl)-acetic acid methyl ester | 532, 534 Cl pattern |
| 497 | 1-(4-Amino-quinazolin-7-ylmethyl)-4-(3-chloro-1H-indole-6-carbonyl)-(3S)-ethyl-piperazin-2-one | 463, 465 |
| 498 | 1-(4-Amino-quinazolin-7-ylmethyl)-4-(7-chloro-isoquinoline-3-carbonyl)-3-(S)-ethyl-piperazin-2-one | 475, 477 Cl pattern |
| 499 | 1-(4-Amino-quinazolin-7-ylmethyl)-4-[(5-chloro-thiophen-2-yloxy)-acetyl]-3-(S)-ethyl-piperazin-2-one | 460, 462 Cl pattern |
| 500 | 1-(4-Amino-quinazolin-7-ylmethyl)-4-[3-(5-bromo-thiophen-2-yl)-acryloyl]-3-(S)-ethyl-piperazin-2-one | 500, 502 Br pattern |
| 501 | 1-(4-Amino-quinazolin-7-ylmethyl)-4-[3-(4-chloro-thiophen-2-yl)-acryloyl]-3-(S)-ethyl-piperazin-2-one | 456, 458 Cl pattern |
| 502 | 1-(4-Amino-quinazolin-7-ylmethyl)-4-[3-(4-bromo-thiophen-2-yl)-acryloyl]-3-(S)-ethyl-piperazin-2-one | 500, 502 Br pattern |
| 503 | 1-(4-Amino-quinazolin-7-ylmethyl)-4-[3-(5-chloro-thiophen-2-yl)-propionyl]-3-(S)-ethyl-piperazin-2-one | 458, 460 Cl pattern |
| 504 | 1-(4-Amino-quinazolin-7-ylmethyl)-4-[1-(4-chloro-phenyl)-1H-pyrrole-2-carbonyl]-3-(S)-ethyl-piperazin-2-one | 489, 491 Cl pattern |
| 505 | 1-(4-Amino-quinazolin-7-ylmethyl)-4-[(4-chloro-phenylsulfanyl)-acetyl]-3-(S)-ethyl-piperazin-2-one | 470, 472 Cl pattern |
| 506 | 1-(4-Amino-quinazolin-7-ylmethyl)-4-[3-(5-chloro-thiophen-2-yl)-but-2-enoyl]-3-(S)-ethyl-piperazin-2-one | 470, 472 Cl pattern |
| 507 | 1-(4-Amino-quinazolin-7-ylmethyl)-4-[(4-chloro-phenoxy)-acetyl]-3-(S)-ethyl-piperazin-2-one | 454, 456 Cl pattern |
| 508 | 1-(4-Amino-quinazolin-7-ylmethyl)-4-[3-(4-chloro-phenyl)-acryloyl]-3-(S)-ethyl-piperazin-2-one | 450, 452 Cl pattern |
| 509 | 1-(4-Amino-quinazolin-7-ylmethyl)-4-(5-chloro-1H-indole-2-carbonyl)-3-(S)-ethyl-piperazin-2-one | 463, 465 Cl pattern |
| 510 | 1-(4-Amino-quinazolin-7-ylmethyl)-4-[3-(4-chloro-phenyl)-propionyl]-3-(S)-ethyl-piperazin-2-one | 452, 454 Cl pattern |
| 511 | 1-(4-Amino-quinazolin-7-ylmethyl)-3-(S)-ethyl-4-[3-(4-methoxy-phenyl)-propionyl]-piperazin-2-one | 448 |
| 512 | 1-(4-Amino-quinazolin-7-ylmethyl)-4-(6-chloro-benzo[b]thiophene-2-carbonyl)-3-(S)-ethyl-piperazin-2-one | 480, 482 Cl pattern |

EXAMPLE 513

1-(4-Amino-quinazolin-7-ylmethyl)-4-[(5-chloro-thiophen-2-yloxy)-acetyl]-3-(S)-propyl-piperazin-2-one The title compound is prepared as described in EXAMPLE 123, using 1-(4-aminoquinazoline-7-ylmethyl)-3-propyl-piperazine-2-one, EXAMPLE 78 and 5-chloro-2-thienyloxy-acetic acid, EXAMPLE 24. $^1$H NMR (d6-DMSO, 300 MHz) δ9.78 (bs, 2H), 8.81 (s, 1H), 8.35 (d, 1H), 7.60 (m, 2H), 7.51 (s, 1H), 6.69 (m, 1H), 6.21 (d, 1H), 4.91 (AB, 2H), 4.72 (m, 2H), 3.84 (m, 1H), 3.52 (m, 2H), 3.23 (m, 1H), 1.80 (m, 2H), 1.24 (m, 2H), 0.82 (m, 3H). MS (ion spray), m/z, 474, 476, (M+H) (Cl pattern). Elemental analysis, cal $C_{22}H_{22}ClN_5O_2S \cdot C_2HF_3O_2 \cdot 1.15H_2O$ % C=47.31, % H=4.52, % N=11.50; found % C=47.39, % H=4.140, % N=11.19.

EXAMPLE 514

4-[3-(6-Amino-pyridin-3-yl)-acryloyl]-1-(4-amino-quinazolin-7-ylmethyl)-3-(S)-propyl-piperazin-2-one The title compound is prepared as described in EXAMPLE 123, using 1-(4-aminoquinazoline-7-ylmethyl)-3-propyl-piperazine-2-one, EXAMPLE 78 and 3-(6-amino-pyridin-3-yl)-acrylic acid, EXAMPLE 36. $^1$H NMR (d6-DMSO, 300

MHz) δ9.73 (bs, 2H), 8.81 (s, 1H), 8.36 (m, 2H), 8.22 (m, 3H), 7.62 (d, 1H), 7.52 (m, 1H), 7.39 (m, 1H), 7.21 (m, 1H), 6.91 (d, 1H), 5.00 (m, 1H), 4.78 (m, 1H), 4.60 (m, 2H), 4.34 (m, 1H), 3.30 (m, 2H), 1.87 (m, 2H), 1.24 (m, 2H), 0.90 (m, 3H). MS (ion spray), m/z, 446, 448 (M+H), (Cl pattern).

The following compounds are prepared from the compound of Example 78 using the methods described above.

| Example # | Name | m/z [M + H] |
| --- | --- | --- |
| 515 | 1-(4-Amino-quinazolin-7-ylmethyl)-4-[(2,5-dichloro-thiophen-3-yloxy)-acetyl]-3-(S)-propyl-piperazin-2-one | 508, 509, 511, Cl$_2$ pattern |
| 516 | 1-(4-Amino-quinazolin-7-ylmethyl)-4-[(4-chloro-thiophen-2-yloxy)-acetyl]-3-(S)-propyl-piperazin-2-one | 474, 476 Cl pattern |
| 517 | 1-(4-Amino-quinazolin-7-ylmethyl)-4-[3-(4-bromo-thiophen-2-yl)-acryloyl]-3-(S)-propyl-piperazin-2-one | 514, 516 Br pattern |
| 518 | 1-(4-Amino-quinazolin-7-ylmethyl)-4-[3-(4-chloro-thiophen-2-yl)-acryloyl]-3-(S)-propyl-piperazin-2-one | 470, 472 Cl pattern |
| 519 | 1-(4-Amino-quinazolin-7-ylmethyl)-4-[(3-chloro-phenoxy)-acetyl]-3-(S)-propyl-piperazin-2-one | 468, 470 Cl pattern |
| 520 | 1-(4-Amino-quinazolin-7-ylmethyl)-4-[(5-chloro-thiophen-3-yloxy)-acetyl]-3-(S)-propyl-piperazin-2-one | 474, 476 Cl pattern |
| 521 | 1-(4-Amino-quinazolin-7-ylmethyl)-4-[(3-chloro-5-methoxy-phenoxy)-acetyl]-3-(S)-propyl-piperazin-2-one | 498, 500 Cl pattern |
| 522 | 1-(4-Amino-quinazolin-7-ylmethyl)-4-[3-(5-chloro-thiophen-3-yl)-acryloyl]-3-(S)-propyl-piperazin-2-one | 470, 472 Cl pattern |
| 523 | 1-(4-Amino-quinazolin-7-ylmethyl)-4-[3-(5-chloro-thiophen-2-yl)-acryloyl]-3-(S)-propyl-piperazin-2-one | 470, 472 Cl pattern |

EXAMPLE 524

1-(4-Amino-quinazolin-7-ylmethyl)-4-[3-(5-chloro-thiophen-2-yl)-allyl]-3-(S)-methyoxymethyl-piperazin-2-one The title compound is prepared as described in EXAMPLE 278 using 1-(4-amino-quinazoline-7-ylmethyl)-3-methoxymethyl-piperazine-2-one, EXAMPLE 75 and 2-(3-bromo-(E)-propenyl)-5-chloro-thiophene EXAMPLE 17. $^1$H NMR (d6-DMSO, 300 MHz) δ9.74 (bs, 2H), 8.80 (s, 1H), 8.38 (d, 1H), 7.69 (m, 2H), 7.02 (dd, 1H), 6.84 (d, 1H), 6.02 (m, 1H), 4.76 (AB, 2H), 3.86 (m, 4H), 3.30 (s, 3H), 3.23 (m, 2H), 3.02 (m, 2H). MS (ion spray), m/z, 458, 460, (M+H) (Cl pattern). Elemental analysis, cal C$_{22}$H$_{24}$ClN$_5$O$_2$S.2C$_2$HF$_3$O$_2$.1.45H$_2$O % C=43.85, % H=4.09, % N=9.83; found % C=43.92, % H=3.61, % N=9.63.

The following compounds are prepared from the compound of Example 75 using the methods described above.

EXAMPLE 532

1-(4-Amino-quinazolin-7-ylmethyl)-4-[(5-chloro-thiophen-2-yloxy)-acetyl]-3-(S)-methyoxymethyl-piperazin-2-one To a solution of 4-(4-amino-quinazoline-7-ylmethyl)-2-methoxymethyl-3-oxo-piperazine-1-carboxylic acid benzyl ester, EXAMPLE 75, (0.69 g, 2.29 mmol) in 9 mL of DMF is added N,N-diisopropylethyl amine (0.89 g, 6.87 mmol), TBTU (0.76 g, 2.36 mmol), and 5-chloro-2-thienyloxyacetic acid, EXAMPLE 24, (0.40 g, 2.08 mmol). The solution is stirred for 16 hours. After this time the solution is concentrated. The crude material is purified by RP-HPLC eluting with a gradient of 10% CH$_3$CN/H$_2$O (0.1% TFA) to 80% CH$_3$CN/H$_2$O (0.1% TFA). The product fractions are lyophilized to give product as a white solid (1.0 g, 1.57 mmol). $^1$H NMR (d6-DMSO, 300 MHz) δ9.70 (bs, 2H), 8.78 (s, 1H), 8.29 (m, 1H), 7.55 (m, 2H), 6.72 (m, 1H), 6.22 (m, 1H), 4.80 (m, 4H), 3.78 (m, 4H), 3.59 (m, 3H), 3.31 and 3.2 (s, 3H rotational isomers).MS (ion spray) M+H=476. Elemental

| Example # | Name | m/z [M + H] |
| --- | --- | --- |
| 525 | 1-(4-Amino-quinazolin-7-ylmethyl)-4-(3-chloro-1H-indol-6-ylmethyl)-3-(S)-methoxymethyl-piperazin-2-one | 465, 467 |
| 526 | 1-(4-Amino-quinazolin-7-ylmethyl)-4-[2-(5-chloro-thiophen-2-yloxy)-ethyl]-3-(S)-methoxymethyl-piperazin-2-one | 446, 448 Cl pattern |
| 527 | 1-(4-Amino-quinazolin-7-ylmethyl)-4-(5-chloro-1H-indol-2-ylmethyl)-3-(S)-methoxymethyl-piperazin-2-one | 446, 448 Cl pattern |
| 528 | 1-(4-Amino-quinazolin-7-ylmethyl)-4-(7-chloro-isoquinolin-3-ylmethyl)-3-(R)-methoxymethyl-piperazin-2-one | 477, 479 Cl pattern |
| 529 | 1-(4-Amino-quinazolin-7-ylmethyl)-4-(7-chloro-isoquinolin-3-ylmethyl)-3-(S)-methoxymethyl-piperazin-2-one | 477, 479 Cl pattern |
| 530 | 1-(4-Amino-quinazolin-7-ylmethyl)-4-(6-chloro-naphthalen-2-ylmethyl)-3-(S)-methoxymethyl-piperazin-2-one | 476, 478 Cl pattern |
| 531 | 1-(4-Amino-quinazolin-7-ylmethyl)-4-(6-chloro-benzo[b]thiophen-2-ylmethyl)-3-(S)-methoxymethyl-piperazin-2-one | 482, 484 Cl pattern |

Analysis: C21H22ClN5O4S.1.4CF3CO2H cal: C=45.03%, H=3.68%, N=11.04%; found C=44.98%, H=3.71%, N=11.02%.

EXAMPLE 533

1-(4-Amino-quinazolin-7-ylmethyl)-4-(6-chloro-1H-benzimidazole-2-carbonyl)-3-(S)-methoxymethyl-piperazin-2-one To a solution of 4-(4-amino-quinazoline-7-ylmethyl)-2-methoxymethyl-3-oxo-piperazine-1-carboxylic acid benzyl ester, EXAMPLE 75, (20 mg, 0.066 mmol) in 1.5 mL of DMF is added TBTU (923.4 mg, 0.073 mmol), diisopropylethylamine (0.013 ml, 0.073 mmol) and 6-chloro-1H-benzoimidazole-2-carboxylic acid (prepared from literature in Eur.J.med.Chem. 1993, 28, 71) (14.3 mg, 0.073 mmol). The resulting mixture is left to stir at room temperature overnight. The crude mixture is directly purified by reverse phase HPLC (10-70% ACN/H$_2$O). The product (30.1 mg, 55%) is isolated as a white powder. C$_{23}$H$_{22}$ClN$_7$O$_3$ MS m/z: 480, 481. Anal. cald. for C$_{23}$H$_{22}$ClN$_7$O$_3$. 2C$_2$HF$_3$O$_2$: C, 45.81; H, 3.42; N, 13.85. Found C, 45.19; H, 3.59; N, 13.76.

The following compounds are prepared from the compound of Example 75 using the methods described above.

| Example # | Name | m/z [M + H] |
|---|---|---|
| 534 | 1-(4-Amino-quinazolin-7-ylmethyl)-4-[(4-chloro-thiophen-2-yloxy)-acetyl]-3-(S)-methoxymethyl-piperazin-2-one | 476, 478 Cl pattern |
| 535 | 4-[3-(4-Amino-phenyl)-acryloyl]-1-(4-amino-quinazolin-7-ylmethyl)-3-(S)-methoxymethyl-piperazin-2-one | 447 |
| 536 | 1-(4-Amino-quinazolin-7-ylmethyl)-4-(3-3H-imidazol-4-yl-acryloyl)-3-(S)-methoxymethyl-piperazin-2-one | |
| 537 | 1-(4-Amino-quinazolin-7-ylmethyl)-4-[(2,5-dichloro-thiophen-3-yloxy)-acetyl]-3-(S)-methoxymethyl-piperazin-2-one | 510, 512, Cl$_2$ pattern |
| 538 | (1-(4-Amino-quinazolin-7-ylmethyl)-4-(6-chloro-1H-benzoimidazole-2-carbonyl)-3-(S)-methoxymethyl-piperazin-2-one | 480, 482 Cl pattern |
| 539 | 1-(4-Amino-quinazolin-7-ylmethyl)-4-(5-chloro-thiophene-2-carbonyl)-3-(S)-methoxymethyl-piperazin-2-one | 446, 448 Cl pattern |
| 540 | 1-(4-Amino-quinazolin-7-ylmethyl)-4-[3-(5-bromo-furan-2-yl)-acryloyl]-3-(S)-methoxymethyl-piperazin-2-one | 500, 502 Br pattern |
| 541 | 1-(4-Amino-quinazolin-7-ylmethyl)-4-[3-(4-bromo-phenyl)-acryloyl]-3-(S)-methoxymethyl-piperazin-2-one | 510, 512 Br pattern |
| 542 | 1-(4-Amino-quinazolin-7-ylmethyl)-4-[3-(4-chloro-phenyl)-acryloyl]-3-(S)-methoxymethyl-piperazin-2-one | 466, 468 Cl pattern |
| 543 | 1-(4-Amino-quinazolin-7-ylmethyl)-4-[3-(3-bromo-phenyl)-acryloyl]-3-(S)-methoxymethyl-piperazin-2-one | 576, 578 Br pattern |
| 544 | 1-(4-Amino-quinazolin-7-ylmethyl)-4-[3-(3-chloro-phenyl)-acryloyl]-3-(S)-methoxymethyl-piperazin-2-one | 466, 468 Cl pattern |
| 545 | 1-(4-Amino-quinazolin-7-ylmethyl)-4-[3-(5-bromo-thiophen-2-yl)-acryloyl]-3-(S)-methoxymethyl-piperazin-2-one | 576, 578 Br pattern |
| 546 | 1-(4-Amino-quinazolin-7-ylmethyl)-4-[(5-chloro-thiophen-3-yloxy)-acetyl]-3-(S)—methoxymethyl-piperazin-2-one | 476, 478 Cl pattern |
| 547 | 1-(4-Amino-quinazolin-7-ylmethyl)-4-[(5-chloro-pyridin-3-yloxy)-acetyl]-3-(S)-methoxymethyl-piperazin-2-one | 471, 473 Cl pattern |
| 548 | 1-(4-Amino-quinazolin-7-ylmethyl)-4-[(6-chloro-pyridin-2-yloxy)-acetyl]-3-(S)-methoxymethyl-piperazin-2-one | 471, 473 Cl pattern |
| 549 | 4-[3-(6-Amino-pyridin-3-yl)-acryloyl]-1-(4-amino-quinazolin-7-ylmethyl)-3-(S)-methoxymethyl-piperazin-2-one | 448 |
| 550 | 1-(4-Amino-quinazolin-7-ylmethyl)-4-[(3-chloro-5-methoxy-phenoxy)-acetyl]-3-(S)-methoxymethyl-piperazin-2-one | 500, 502 Cl pattern |
| 551 | 1-(4-Amino-quinazolin-7-ylmethyl)-4-[3-(5-chloro-thiophen-3-yl)-acryloyl]-3-(S)-methoxymethyl-piperazin-2-one | 472, 474 Cl pattern |
| 552 | 1-(4-Amino-quinazolin-7-ylmethyl)-4-[(2,5-dichloro-phenoxy)-acetyl]-3-(S)-methoxymethyl-piperazin-2-one | 504, 506, 508 Cl$_2$ pattern |
| 553 | 1-(4-Amino-quinazolin-7-ylmethyl)-4-[(5-fluoro-thiophen-2-yloxy)-acetyl]-3-(S)-methoxymethyl-piperazin-2-one | 460 |
| 554 | 1-(4-Amino-quinazolin-7-ylmethyl)-4-[(3-fluoro-phenoxy)-acetyl]-3-(S)-methoxymethyl-piperazin-2-one | 453 |
| 555 | 1-(4-Amino-quinazolin-7-ylmethyl)-4-[2-(3-chloro-phenoxy)-propionyl]-3-(S)-methoxymethyl-piperazin-2-one | 484, 486 Cl pattern |
| 556 | 1-(4-Amino-quinazolin-7-ylmethyl)-4-[(6-chloro-pyridin-3-yloxy)-acetyl]-3-(S)-methoxymethyl-piperazin-2-one | 471, 473 Cl pattern |
| 557 | 1-(4-Amino-quinazolin-7-ylmethyl)-3-(S)-methoxymethyl-4-[(4-trifluoromethylsulfanyl-phenoxy)-acetyl]-piperazin-2-one | 536 |
| 558 | 1-(4-Amino-quinazolin-7-ylmethyl)-4-[(3-chloro-phenylamino)-acetyl]-3-(S)-methoxymethyl-piperazin-2-one | 469, 471 Cl pattern |
| 559 | 1-(4-Amino-quinazolin-7-ylmethyl)-4-[(4-chloro-phenylamino)-acetyl]-3-(S)-methoxymethyl-piperazin-2-one | 469, 471 Cl pattern |
| 560 | 1-(4-Amino-quinazolin-7-ylmethyl)-4-[(3-chloro-phenoxy)-acetyl]-3-(S)-methoxymethyl-piperazin-2-one | 471, 473 Cl pattern |
| 561 | (2-{2-[4-(4-Amino-quinazolin-7-ylmethyl)-2-(S)-methoxymethyl-3-oxo-piperazin-1-yl]-2-oxo-ethoxy}-5-chloro-thiophen-3-yl)-acetic acid | 534, 536 Cl pattern |
| 562 | 1-(4-Amino-quinazolin-7-ylmethyl)-4-[(5-chloro-thiophen-2-ylsulfanyl)-acetyl]-3-(S)-methoxymethyl-piperazin-2-one | 492, 494 Cl pattern |

-continued

| Example # | Name | m/z [M + H] |
|---|---|---|
| 563 | 1-(4-Amino-quinazolin-7-ylmethyl)-4-[(6-chloro-pyridin-3-ylamino)-acetyl]-3-(S)-methoxymethyl-piperazin-2-one | 470, 472 Cl pattern |
| 564 | 2-(2-{2-[4-(4-Amino-quinazolin-7-ylmethyl)-2-(S)-methoxymethyl-3-oxo-piperazin-1-yl]-2-oxo-ethoxy}-5-chloro-thiophen-3-yl)- | 533, 535 Cl pattern |
| 565 | 1-(4-Amino-quinazolin-7-ylmethyl)-4-(2-chloro-benzo[b]thiophene-6-carbonyl)-3-(S)-methoxymethyl-piperazin-2-one | 496, 498 Cl pattern |
| 566 | 1-(4-Amino-quinazolin-7-ylmethyl)-4-(2,3-dichloro-benzo[b]thiophene-6-carbonyl)-3-(S)-methoxymethyl-piperazin-2-one | 530, 532, 534 $Cl_2$ pattern |
| 567 | 1-(4-Amino-quinazolin-7-ylmethyl)-4-[(3,5-dichloro-thiophen-2-yloxy)-acetyl]-3-(S)-methoxymethyl-piperazin-2-one | 510, 512, 514 $Cl_2$ pattern |
| 568 | (2-{2-[4-(4-Amino-quinazolin-7-ylmethyl)-2-(S)-methoxymethyl-3-oxo-piperazin-1-yl]-2-oxo-ethoxy}-5-chloro-thiophen-3-yl)-acetic acid methyl ester | 548, 550 Cl pattern |
| 569 | (2-{2-[4-(4-Amino-quinazolin-7-ylmethyl)-2-(S)-methoxymethyl-3-oxo-piperazin-1-yl]-2-oxo-ethoxy}-5-chloro-thiophen-3-yl)-acetic acid ethyl ester | 562, 564 Cl pattern |
| 570 | 1-(4-Amino-quinazolin-7-ylmethyl)-4-[(2-chloro-pyridin-3-ylamino)-acetyl]-3-(S)-methoxymethyl-piperazin-2-one | 470, 472 Cl pattern |
| 571 | 1-(4-Amino-quinazolin-7-ylmethyl)-4-[(2,3-dichloro-phenoxy)-acetyl]-3-(S)-methoxymethyl-piperazin-2-one | 504, 506, 508 $Cl_2$ pattern |
| 572 | 1-(4-Amino-quinazolin-7-ylmethyl)-4-[(4-fluoro-phenoxy)-acetyl]-3-(S)-methoxymethyl-piperazin-2-one | 454 |
| 573 | 1-(4-Amino-quinazolin-7-ylmethyl)-4-[(4-chloro-2-methyl-phenoxy)-acetyl]-3-(S)-methoxymethyl-piperazin-2-one | 484, 486 Cl pattern |
| 574 | 1-(4-Amino-quinazolin-7-ylmethyl)-4-[(2,4-dichloro-phenoxy)-acetyl]-3-(S)-methoxymethyl-piperazin-2-one | 504, 506, 508 $Cl_2$ pattern |
| 575 | 1-(4-Amino-quinazolin-7-ylmethyl)-4-(7-chloro-isoquinoline-3-carbonyl)-3-(S)-methoxymethyl-piperazin-2-one | 491, 493 Cl pattern |
| 576 | (1-(4-Amino-quinazolin-7-ylmethyl)-4-[3-(4-bromo-thiophen-2-yl)-acryloyl]-3-(S)-methoxymethyl-piperazin-2-one | 516, 518 Br pattern |
| 577 | 1-(4-Amino-quinazolin-7-ylmethyl)-4-[3-(4-chloro-thiophen-2-yl)-acryloyl]-3-(S)-methoxymethyl-piperazin-2-one | 472, 474 Cl pattern |
| 578 | 1-(4-Amino-quinazolin-7-ylmethyl)-4-[3-(5-chloro-thiophen-2-yl)-acryloyl]-3-(R)-methoxymethyl-piperazin-2-one | 472, 474 Cl pattern |
| 579 | 1-(4-Amino-quinazolin-7-ylmethyl)-4-[3-(5-chloro-thiophen-2-yl)-acryloyl]-3-(S)-methoxymethyl-piperazin-2-one | 472, 474 Cl pattern |
| 580 | 1-(4-Amino-quinazolin-7-ylmethyl)-4-(6-chloro-benzo[b]thiophene-2-carbonyl)-3-(S)-methoxymethyl-piperazin-2-one | 496, 498 Cl pattern |
| 581 | 1-(4-Amino-quinazolin-7-ylmethyl)-4-[(4-chloro-phenoxy)-acetyl]-3-(S)-methoxymethyl-piperazin-2-one | 470, 472 Cl pattern |

EXAMPLE 582

1-(4-Amino-quinazolin-7-ylmethyl)-4-[(6-chloro-pyridin-3-yloxy)-acetyl]-3-(S)-ethoxymethyl-piperazin-2-one The title compound is prepared as described in EXAMPLE 123, using 1-(4-aminoquinazoline-7-ylmethyl)-3-ethoxymethyl-piperazine-2-one, EXAMPLE 79 and, (6-chloro-pyridin-3-yloxy)-acetic acid, prepared similarly to the procedure described in EXAMPLE 29. $^1$H NMR (d6-DMSO, 300 MHz) δ 9.73 (bs, 2H), 8.81 (s, 1H), 8.37 (m, 1H), 8.10 (m, 1H), 7.61 (m, 2H), 7.40 (m, 2H), 4.98 (m, 2H), 4.65 (m, 2H), 4.50 (m, 1H), 3.91 (m, 1H), 3.75 (m, 1H), 3.59 (m, 2H), 3.31 (m, 2H), 1.07 (m, 3H). MS (ion spray), m/z, 485, 487 (M+H), (Cl pattern).

The following compounds are prepared from the compound of Example 79 using the methods described above.

| Example # | Name | m/z [M + H] |
|---|---|---|
| 583 | 1-(4-Amino-quinazolin-7-ylmethyl)-3-(S)-ethoxymethyl-4-[(3-fluoro-phenoxy)-acetyl]-piperazin-2-one | 454 |
| 584 | 1-(4-Amino-quinazolin-7-ylmethyl)-4-[3-(5-chloro-thiophen-2-yl)-acryloyl]-3-(S)-ethoxymethyl-piperazin-2-one | 486, 488 Cl pattern |
| 585 | 1-(4-Amino-quinazolin-7-ylmethyl)-4-[(2-chloro-pyridin-3-ylamino)-acetyl]-3-(S)-ethoxymethyl-piperazin-2-one | 484, 486 Cl pattern |
| 586 | 1-(4-Amino-quinazolin-7-ylmethyl)-4-[(6-chloro-pyridin-3-ylamino)-acetyl]-3-(S)-ethoxymethyl-piperazin-2-one | 484, 486 Cl pattern |
| 587 | 1-(4-Amino-quinazolin-7-ylmethyl)-4-[(5-chloro-thiophen-2-yloxy)-acetyl]-3-(S)-ethoxymethyl-piperazin-2-one | 490, 492 Cl pattern |

The following compounds are prepared from the compounds of Examples 81-85 using the methods described above.

2-bromomethyl-6-chloronaphthalene, EXAMPLE 12. $^1$H NMR (CDCl$_3$, 300 MHz) δ8.59 (s, 1H), 7.79 (d, 1H), 7.70-7.12 (m, 3H), 7.68-7.67 (m, 2H), 7.55 (d, 1H), 7.39 (d, 1H),

| Example # | Name | m/z [M + H] |
|---|---|---|
| 588 | 1-(4-Amino-quinazolin-7-ylmethyl)-3-(S)-benzyl-4-[3-(5-chloro-thiophen-2-yl)-acryloyl]-piperazin-2-one | 518, 520 Cl pattern |
| 589 | 1-(4-Amino-quinazolin-7-ylmethyl)-3-(S)-benzyl-4-(6-chloro-benzo[b]thiophene-2-carbonyl)-piperazin-2-one | 542, 544 Cl pattern |
| 590 | 1-(4-Amino-quinazolin-7-ylmethyl)-3-(S)-benzyl-4-[3-(5-chloro-thiophen-2-yl)-allyl]-piperazin-2-one | 504, 506 Cl pattern |
| 591 | 1-(4-Amino-quinazolin-7-ylmethyl)-3-(S)-benzyl-4-(6-chloro-benzo[b]thiophen-2-ylmethyl)-piperazin-2-one | 528, 530 Cl pattern |
| 592 | 1-(4-Amino-quinazolin-7-ylmethyl)-3-(S)-benzyl-4-[(4-chloro-phenoxy)-acetyl]-piperazin-2-one | 516, 518 Cl pattern |
| 593 | 1-(4-Amino-quinazolin-7-ylmethyl)-3-(S)-benzyl-4-(6-chloro-naphthalen-2-ylmethyl)-piperazin-2-one | 522, 524 Cl pattern |
| 594 | 1-(4-Amino-quinazolin-7-ylmethyl)-3-(S)-benzyl-4-[3-(5-chloro-thiophen-2-yl)-propyl]-piperazin-2-one | 506, 508 Cl pattern |
| 595 | 1-(4-Amino-quinazolin-7-ylmethyl)-4-[(5-chloro-thiophen-2-yloxy)-acetyl]-3-(S)-((R)-1-methoxy-ethyl)-piperazin-2-one | 490, 492 Cl pattern |
| 596 | 1-(4-Amino-quinazolin-7-ylmethyl)-4-[3-(5-chloro-thiophen-2-yl)-allyl]-3-(S)-((R)-1-methoxy-ethyl)-piperazin-2-one | 472, 474 Cl pattetn |
| 597 | 1-(4-Amino-quinazolin-7-ylmethyl)-4-[3-(5-chloro-thiophen-2-yl)-acryloyl]-3-(S)-((R)-1-methoxy-ethyl)-piperazin-2-one | 486, 488 Cl pattern |
| 598 | 1-(4-Amino-quinazolin-7-ylmethyl)-4-[3-(4-bromo-thiophen-2-yl)-acryloyl]-3-(S)-((R)-1-methoxy-ethyl)-piperazin-2-one | 530, 532 Br pattern |
| 599 | 1-(4-Amino-quinazolin-7-ylmethyl)-4-(7-chloro-isoquinolin-3-ylmethyl)-3-(S)-((R)-1-methoxy-ethyl)-piperazin-2-one | 491, 493 Cl pattern |
| 600 | 1-(4-Amino-quinazolin-7-ylmethyl)-4-(6-chloro-benzo[b]thiophen-2-ylmethyl)-3-(S)-isopropyl-piperazin-2-one | 480, 482 Cl, pattern |
| 601 | 1-(4-Amino-quinazolin-7-ylmethyl)-4-(6-chloro-benzo[b]thiophen-2-ylmethyl)-3,3-dimethyl-piperazin-2-one | 466, 468 Cl pattern |
| 602 | 1-(4-Amino-quinazolin-7-ylmethyl)-4-[3-(5-chloro-thiophen-2-yl)-allyl]-3,3-dimethyl-piperazin-2-one | 442, 444 Cl pattern |
| 603 | 1-(4-Amino-quinazolin-7-ylmethyl)-4-[3-(5-chloro-thiophen-2-yl)-acryloyl]-3,3-dimethyl-piperazin-2-one | 456, 458 Cl pattern |
| 604 | 1-(4-Amino-quinazolin-7-ylmethyl)-4-(6-chloro-benzo[b]thiophene-2-carbonyl)-3,3-dimethyl-piperazin-2-one | 480, 482 Cl pattern |
| 605 | 1-(4-Amino-quinazolin-7-ylmethyl)-4-[(5-chloro-thiophen-2-yloxy)-acetyl]-3-(S)-(2-methoxy-ethyl)-piperazin-2-one | 490, 492 Cl pattern |
| 606 | 4-(4-Amino-quinazolin-7-ylmethyl)-2-(S)-(2-methoxy-ethyl)-3-oxo-piperazine-1-carboxylic acid(4-chloro-phenyl)-amide | 469, 471 Cl pattern |
| 607 | 1-(4-Amino-quinazolin-7-ylmethyl)-4-[(5-chloro-thiophen-3-yloxy)-acetyl]-3-(S)-(2-methoxy-ethyl)-piperazin-2-one | 490, 492 Cl pattern |
| 608 | 1-(4-Amino-quinazolin-7-ylmethyl)-4-(6-chloro-benzo[b]thiophene-2-carbonyl)-3-(S)-(2-methoxy-ethyl)-piperazin-2-one | 510, 512 Cl pattern |

4.78 (d, 2H), 3.98 (d, 2H), 3.44 (s, 3H), 3.38 (t, 1H), 2.64 (m, 2H), 1.26 (d, 3H). MS (ISP) 490, 492, (M+H), Cl pattern.

EXAMPLE 609

1-(4-Amino-quinazolin-7-ylmethyl)-4-(6-chloro-naphthalen-2-ylmethyl)-3-(S)-methoxymethyl-6-(S)-methyl-piperazin-2-one The title compound is prepared as described in EXAMPLE 268, using 1-(4-amino-quinazoline-7-ylmethyl)-3-methoxymethyl-6-methyl-piperazine-2-one, EXAMPLE 87, and The following materials are prepared from starting materials obtained as described in Example 87 using the methods described above.

| Example # | Name | m/z [M + H] |
|---|---|---|
| 610 | 1-(4-Amino-quinazolin-7-ylmethyl)-4-[3-(5-chloro-thiophen-2-yl)-propyl]-3-(S)-ethyl-6-methyl-piperazin-2-one | 458, 460 Cl pattern |
| 611 | 1-(4-Amino-quinazolin-7-ylmethyl)-4-(6-chloro-naphthalen-2-ylmethyl)-3-(S)-methoxymethyl-6-(R)-methyl-piperazin-2-one | 490, 492 Cl pattern |
| 612 | 1-(4-Amino-quinazolin-7-ylmethyl)-4-[3-(5-chloro-thiophen-2-yl)-allyl]-3-(S)-methoxymethyl-6-methyl-piperazin-2-one | 472, 474 Cl pattern |
| 613 | (1-(4-Amino-quinazolin-7-ylmethyl)-4-(7-chloro-isoquinolin-3-ylmethyl)-3-(S)-methoxymethyl-6-methyl-piperazin-2-one | 490, 492 Cl pattern |
| 614 | 1-(4-Amino-quinazolin-7-ylmethyl)-4-[3-(5-chloro-thiophen-2-yl)-allyl]-3-(S)-6-dimethyl-piperazin-2-one | 491, 493 Cl pattern |

| Example # | Name | m/z [M + H] |
|---|---|---|
| 615 | 1-(4-Amino-quinazolin-7-ylmethyl)-4-(6-chloro-naphthalen-2-ylmethyl)-6-methyl-piperazin-2-one | 442, 446 Cl pattern |
| 616 | 1-(4-Amino-quinazolin-7-ylmethyl)-4-[3-(5-chloro-thiophen-2-yl)-allyl]-6-methyl-piperazin-2-one | 428, 430 Cl pattern |

EXAMPLE 617

1-(4-Amino-quinazolin-7-ylmethyl)-4-[(5-chloro-thiophen-2-yloxy)-acetyl]-3(S)-methoxymethyl-6-methyl-piperazin-2-one The title compound is prepared as described in EXAMPLE 123 using 1-(4-amino-quinazoline-7-ylmethyl)-3-methoxymethyl-6-methyl-piperazine-2-one, EXAMPLE 87, and 5-chloro-2-thienyloxyacetic acid, EXAMPLE 24. $^1$H NMR (CD$_3$OD 300 MHz) δ 8.68 (s, 1H), 8.27 (d, 1H), 7.62 (m, 2H), 6.54 (d, 1H), 6.18 (m, 1H), 7.39 (d, 1H), 4.94 (m, 4H), 4.15 (m, 2H), 3.76 (m, 2H), 3.44 (s, 3H), 3.10 (m, 2H), 1.28 (d, 3H).

The following compounds are prepared from compounds obtained as described Examples 75-87 using methods described above.

EXAMPLE 636

4-(4-Amino-quinazolin-7-ylmethyl)-2-(S)-methoxymethyl-3-oxo-piperazine-1-carboxylic acid (4-chloro-phenyl)-amide The title compound is prepared as described in EXAMPLE 436 using 1-(4-amino-quinazoline-7-ylmethyl)-3-methoxymethyl-piperazine-2-one, EXAMPLE 75, and 4-chlorophenyl isocyanate. $^1$H NMR (DMSO-d$_6$, 300 MHz) δ 9.77 (bs, 2H), 8.81 (s, 1H), 8.70 (s, 1H), 8.40 (d, 1H), 7.64 (d, 1H), 7.61 (s, 1H), 7.49 (d, 2H), 7.28 (d, 2H), 4.88 (m, 1H), 4.80 (AB, 2H), 4.19 (m, 1H), 3.96 (m, 1H), 3.74-3.42 (m, 4H),

| Example # | Name | m/z [M + H] |
|---|---|---|
| 618 | 1-(4-Amino-quinazolin-7-ylmethyl)-4-[(4-chloro-thiophen-2-yloxy)-acetyl]-(S)-3-methoxymethyl-6-methyl-piperazin-2-one | 490, 492 Cl pattern |
| 619 | 1-(4-Amino-quinazolin-7-ylmethyl)-4-[(5-chloro-thiophen-3-yloxy)-acetyl]-(S)-3-methoxymethyl-6-methyl-piperazin-2-one | 490, 492 Cl$_2$ pattern |
| 620 | 1-(4-Amino-quinazolin-7-ylmethyl)-4-[(3-chloro-4-fluoro-phenoxy)-acetyl]-3(S)-methoxymethyl-6-methyl-piperazin-2-one | 502, 504 Cl$_2$ pattern |
| 621 | 1-(4-Amino-quinazolin-7-ylmethyl)-4-[(3,5-dichloro-phenoxy)-acetyl]-3(S)-methoxymethyl-6-methyl-piperazin-2-one | 502, 504 Cl pattern |
| 622 | 1-(4-Amino-quinazolin-7-ylmethyl)-4-[3-(2,5-dichloro-phenyl)-acryloyl]-3(S)-methoxymethyl-6-methyl-piperazin-2-one | 514 |
| 623 | 1-(4-Amino-quinazolin-7-ylmethyl)-4-[(5-chloro-2-methyl-phenoxy)-acetyl]-3(S)-methoxymethyl-6-methyl-piperazin-2-one | 498, 500 Cl$_2$ pattern |
| 624 | 1-(4-Amino-quinazolin-7-ylmethyl)-4-[(2,5-dichloro-phenoxy)-acetyl]-3(S)-methoxymethyl-6-methyl-piperazin-2-one | 518 |
| 625 | 1-(4-Amino-quinazolin-7-ylmethyl)-4-[(3-chloro-phenoxy)-acetyl]-3-(S)-methoxymethyl-6-methyl-piperazin-2-one | 484 |
| 626 | 1-(4-Amino-quinazolin-7-ylmethyl)-4-[3-(5-chloro-thiophen-2-yl)-propionyl]-3(S)-ethyl-6-methyl-piperazin-2-one | 472, 474 Cl pattern |
| 627 | 1-(4-Amino-quinazolin-7-ylmethyl)-4-[(5-chloro-thiophen-2-yloxy)-acetyl]-3(S)-ethyl-6-methyl-piperazin-2-one | 474 |
| 628 | 1-(4-Amino-quinazolin-7-ylmethyl)-4-[3-(4-bromo-thiophen-2-yl)-acryloyl]-3(S)-ethyl-6-methyl-piperazin-2-one | 514, 516 Br pattern |
| 629 | 1-(4-Amino-quinazolin-7-ylmethyl)-4-[3-(5-chloro-thiophen-2-yl)-acryloyl]-3(S)-ethyl-6-methyl-piperazin-2-one | 470, 472 Cl pattern |
| 630 | (S)-1-(4-Amino-quinazolin-7-ylmethyl)-4-[3-(5-chloro-thiophen-2-yl)-acryloyl]-3-methoxymethyl-6-methyl-piperazin-2-one | 486, 488 Cl pattern |
| 631 | (S)-1-(4-Amino-quinazolin-7-ylmethyl)-4-[3-(4-bromo-thiophen-2-yl)-acryloyl]-3-methoxymethyl-6-methyl-piperazin-2-one | 530, 532 Br pattern |
| 632 | 1-(4-Amino-quinazolin-7-ylmethyl)-4-(6-chloro-benzo[b]thiophene-2-carbonyl)-3(S)-6-dimethyl-piperazin-2-one | 480 Cl pattern |
| 633 | 1-(4-Amino-quinazolin-7-ylmethyl)-4-[3-(4-bromo-thiophen-2-yl)-acryloyl]-3(S)-6-dimethyl-piperazin-2-one | 500, 502 Br pattern |
| 634 | 1-(4-Amino-quinazolin-7-ylmethyl)-4-[3-(5-chloro-thiophen-2-yl)-acryloyl]-3(S)-6-dimethyl-piperazin-2-one | 456, 458 Cl pattern |
| 635 | 1-(4-Amino-quinazolin-7-ylmethyl)-4-[3-(5-chloro-thiophen-2-yl)-acryloyl]-6-methyl-piperazin-2-one | 442, 444 Cl pattern |

3.28 (s, 3H). ESI MS, [M+H]⁺=455,457 (Cl pattern). Anal. (C$_{22}$H$_{23}$ClN$_6$O$_3$.TFA.1.5H$_2$O) C, H, N.

EXAMPLE 637

4-(4-Amino-quinazolin-7-ylmethyl)-2-(S)-methyl-3-oxo-piperazine-1-carboxylic acid (5-chloro-thiophen-2-yl)-amide The title compound is prepared as described in EXAMPLE 438 using 1-(4-amino-quinazoline-7-ylmethyl)-3-methyl-piperazine-2-one (EXAMPLE 80) and 5-chloro-thiophene-2-carbonyl azide (EXAMPLE 38). $^1$H NMR (DMSO-d$_6$, 300 MHz) δ10.01 (s, 1H), 9.73 (bs, 2H), 8.83 (s, 1H), 8.39 (d, 1H), 7.65 (d, 1H), 7.58 (s, 1H), 6.79 (d, 1H), 6.44 (d, 1H), 4.85 (d, 1H), 4.71 (m, 1H), 4.69 (d, 1H), 4.17 (d, 1H), 3.50 (m, 3H), 1.45 (d, 3H). ESI MS, [M+H]⁺=431,433 (Cl pattern). Anal. (C$_{19}$H$_{19}$ClN$_6$O$_2$S.TFA.1.9H$_2$O) C, H, N.

EXAMPLE 638

4-(4-Amino-4quinazolin-7-ylmethyl)-(2S)-methoxymethyl-3-oxo-piperazine-1-carboxylic acid (5-chloro-thiophen-2-yl)-amide The title compound is prepared as described in EXAMPLE 439 using 1-(4-amino-quinazoline-7-ylmethyl)-3-methoxymethyl-piperazine-2-one (EXAMPLE 75) and 5-chloro-thiophene-2-carbonyl azide (EXAMPLE 38). $^1$H NMR (DMSO-d$_6$, 300 MHz) δ10.00 (s, 1H), 9.73 (bs, 2H), 8.82 (s, 1H), 8.40 (d, 1H), 7.65 (d, 1H), 7.60 (s, 1H), 6.80 (d, 1H), 6.42 (d, 1H), 4.86 (d, 1H), 4.80 (m, 1H), 4.70 (d, 1H), 4.18 (d, 1H), 3.96 (dd, 1H), 3.60 (m, 4H), 3.30 (s, 3H). ESI MS, [M+H]⁺=461,463 (Cl pattern). Anal. (C$_{20}$H$_{21}$ClN$_6$O$_3$S.TFA.1.1H$_2$O) C, H, N.

The following compounds are prepared using the methods described above.

| Example # | Name | m/z [M + H] |
|---|---|---|
| 639 | 4-(4-Amino-quinazolin-7-ylmethyl)-2(S)-(2-methoxy-ethyl)-3-oxo-piperazine-1-carboxylic acid(4-chloro-phenyl)-amide | 469 |
| 640 | 4-(4-Amino-quinazolin-7-ylmethyl)-2-(S)-butyl-3-oxo-piperazine-1-carboxylic acid(4-chloro-phenyl)-amide | 467, 469 Cl pattern |
| 641 | 4-(4-Amino-quinazolin-7-ylmethyl)-(2S)-methoxymethyl-3-oxo-piperazine-1-carboxylic acid(5-bromo-thiophen-2-yl)-amide | 505, 507 |
| 642 | 4-(4-Amino-quinazolin-7-ylmethyl)-(2S)-methoxymethyl-3-oxo-piperazine-1-carboxylic acid(5-chloro-thiophen-3-yl)-amide | 461, 463 |
| 643 | 4-(4-Amino-quinazolin-7-ylmethyl)-(2S)-methoxymethyl-3-oxo-piperazine-1-carboxylic acid(4-chloro-thiophen-2-yl)-amide | 461 |
| 644 | 4-(4-Amino-quinazolin-7-ylmethyl)-3-oxo-(S)-2-propyl-piperazine-1-carboxylic acid(4-chloro-phenyl)-amide | 453, 455 Cl pattern |
| 645 | 4-(4-Amino-quinazolin-7-ylmethyl)-(2S)-methoxymethyl-3-oxo-piperazine-1-carboxylic acid(3-bromo-phenyl)-amide | 499 |
| 646 | 4-(4-Amino-quinazolin-7-ylmethyl)-3-oxo-(2S)-propyl-piperazine-1-carboxylic acid(4-chloro-thiophen-2-yl)-amide | 459, 461 |
| 647 | 4-(4-Amino-quinazolin-7-ylmethyl)-3-oxo-(S)-2-propyl-piperazine-1-carboxylic acid(5-chloro-2-methoxy-phenyl)-amide | 483, 485 Cl pattern |
| 648 | 4-(4-Amino-quinazolin-7-ylmethyl)-2-(S)-methoxymethyl-3-oxo-piperazine-1-carboxylic acid(4-bromo-2-chloro-phenyl)-amide | 533, 535 |
| 649 | 4-(4-Amino-quinazolin-7-ylmethyl)-2-(S)-methoxymethyl-3-oxo-piperazine-1-carboxylic acid(4-trifluoromethoxy-phenyl)-amide | 505 |
| 650 | 4-(4-Amino-quinazolin-7-ylmethyl)-2-(S)-metboxymethyl-3-oxo-piperazine-1-carboxylic acid(4-fluoro-phenyl)-amide | 439 |
| 651 | 4-(4-Amino-quinazolin-7-ylmethyl)-2-(S)-methoxymethyl-3-oxo-piperazine-1-carboxylic acid(2,4-dichloro-phenyl)-amide | 489, 491 |
| 652 | 4-(4-Amino-quinazolin-7-ylmethyl)-2-(S)-methoxymethyl-3-oxo-piperazine-1-carboxylic acid(2,4-difluoro-phenyl)-amide | 457 |
| 653 | 4-(4-Amino-quinazolin-7-ylmethyl)-(2S)-methoxymethyl-3-oxo-piperazine-1-carboxylic acid(3-chloro-phenyl)-amide | 455 |
| 654 | 4-(4-Amino-quinazolin-7-ylmethyl)-3-oxo-(2S)-propyl-piperazine-1-carboxylic acid(5-chloro-thiophen-2-yl)-amide | 459, 460 Cl pattern |
| 655 | 4-(4-Amino-quinazolin-7-ylmethyl)-(2S)-methyl-3-oxo-piperazine-1-carboxylic acid(6-chloro-pyridin-3-yl)-amide | 426, 428 |
| 656 | 4-(4-Amino-quinazolin-7-ylmethyl)-(2S)-methoxymethyl-3-oxo-piperazine-1-carboxylic acid(4-bromo-phenyl)-amide | 499, 501 |
| 657 | 4-(4-Amino-quinazolin-7-ylmethyl)-(2S)-methyl-3-oxo-piperazine-1-carboxylic acid(4-bromo-phenyl)-amide | 486, 488 |
| 658 | 4-(4-Amino-quinazolin-7-ylmethyl)-2-(S)-methoxymethyl-5-(R,S)-methyl-3-oxo-piperazine-1-carboxylic acid(4-chloro-phenyl)-amide | 469, 471 |
| 659 | 4-(4-Amino-quinazolin-7-ylmethyl)-(2S)-ethyl-3-oxo-piperazine-1-carboxylic acid(4-bromo-phenyl)-amide | 483, 485 |

-continued

| Example # | Name | m/z [M + H] |
|---|---|---|
| 660 | 4-(4-Amino-quinazolin-7-ylmethyl)-(2S)-methyl-3-oxo-piperazine-1-carboxylic acid(4-chloro-phenyl)-amide | 425, 427 |
| 661 | 4-(4-Amino-quinazolin-7-ylmethyl)-(2S)-ethyl-3-oxo-piperazine-1-carboxylic acid(4-chloro-phenyl)-amide | 439, 441 |
| 662 | 4-(4-Amino-quinazolin-7-ylmethyl)-(S)-2-methoxymethyl-3-oxo-piperazine-1-carboxylic acid(5-chloro-4-methoxy-thiophen-2-yl)-amide | 491, 493<br>Cl pattern |

EXAMPLE 663

(3S, 5RS)-1-(4-Amino-quinazolin-7-ylmethyl)-4-(6-chloro-benzo[b]thiophen-2-ylmethyl)-3,5-dimethyl-piperazin-2-one (3 S,5RS)-1-(4-Amino-quinazolin-7-ylmethyl)-3,5-dimethyl-piperazin-2-one (260 mg, 0.56 mmol), EXAMPLE 88, is dissolved in 5 mL of DMF. Potassium carbonate (193.4 mg, 1.4 mmol) is added followed by the addition of 2-bromomethyl-6-chloro-benzo[b]thiophene (218 mg, 0.84 mmol), EXAMPLE 5. Reaction is left to stir overnight. The crude mixture is purified by reverse phase HPLC (10-70% ACN/H$_2$O) to afford the product (27 mg, 6%) as a clear wax with a melting point of 130-131° C. $C_{24}H_{24}ClN_5OS$ MS m/z: 466, 468.

EXAMPLE 664

(3S, 5S)-1-(4-Amino-quinazolin-7-ylmethyl)-4-[3-(5-chloro-thiophen-2-yl-allyl]-3,5-dimethyl-piperazin-2-one and

EXAMPLE 665

(3S,5R)-1-(4-Amino-quinazolin-7-ylmethyl)-4-[3-(5-chloro-thiophen-2-yl)-allyl]-3,5-dimethyl-piperazin-2-one (3S,5RS)-1-(4-Amino-quinazolin-7-ylmethyl)-3,5-dimethyl-piperazin-2-one (60 mg, 0.13 mmol) is dissolved in 1 mL of DMF. Potassium carbonate (53 mg, 0.39 mmol) is added followed by the addition of 3-bromoallyl-5-chloro-thiophene (75 mg, 0.32 mmol). Reaction is left to stir overnight. The two epimers are separated by reverse phase HPLC (10-70% ACN) in 43% yield.

The major epimer is assigned as (3S, 5S)-1-(4-Amino-quinazolin-7-ylmethyl)-4-[3-(5-chloro-thiophen-2-yl)-allyl]-3,5-dimethyl-piperazin-2-one trifluoroacetic acid salt (30.8 mg) and is isolated as a yellow solid with a melting point of 69-72° C. $C_{22}H_{24}ClN_5OS$ MS m/z: 442, 444.

The minor epimer is assigned as (3S, 5R)-1-(4-Amino-quinazolin-7-ylmethyl)-4-[3-(5-chloro-thiophen-2-yl)-allyl]-3,5-dimethyl-piperazin-2-one trifluoroacetic acid salt (13.1 mg) with a melting point of 67-70° C. $C_{22}H_{24}ClN_5OS$ MS m/z: 442, 444. 1H NMR (CD$_3$OD) δ: 8.67 (s, 1H); 8.31 (d, 1H, J=8.56 Hz); 7.83 (s, 1H); 7.74 (d, 2H, J=8.56 Hz); 7.14 (d, 1H, J=15.6 Hz); 6.92 (d, 1H, J=3.74 Hz); 6.10-6.03 (m, 1H); 5.0-4.74 (m, 2H); 4.25-3.63 (m, 6H); 1.78 (d, 3H, J=7.03 Hz); 1.50 (d, 3H, J=6.47 Hz).

EXAMPLE 666

(3S, 5R)-1-(4-Amino-quinazolin-7-ylmethyl)-4-[2-(5-chloro-thiophen-2-yl)-ethenesulfonyl]-3,5-dimethyl-piperazin-2-one (3S,5R)-1-(4-Amino-quinazolin-7-ylmethyl)-3,5-dimethyl-piperazin-2-one (43 mg, 0.123 mmol), minor epimer from EXAMPLE 88, Part D, is taken up in methylene chloride to this is added triethylamine (0.034 ml, 0.25 mmol) followed by 2-(5-chloro-thiophen-2-yl)-ethenesulfonyl chloride (40 mg, 0.16 mmol), EXAMPLE 3. The reaction is stirred overnight, and the crude material is purified by preparative thin layer chromatography (15% methanol/CH$_2$Cl$_2$). The product (1.4 mg, 2.3%) is isolated as a yellow wax. $C_{21}H_{22}ClN_5O_3S_2$ MS m/z: 492, 494. 1H NMR (CD$_3$OD) δ8.36 (s, 1H); 8.03 (d, 1H, J=7.5 Hz); 7.61 (s, 1H); 7.49-7.44 (m, 2H); 7.19 (d, 1H, J=3.83 Hz); 6.98 (d, 1H, J=3.75 Hz); 6.76 (d, 1H, J=15.1 Hz); 4.86-4.71 (m, 2H); 4.45-4.39 (m, 1H); 4.13-4.09 (m, 1H); 3.64-3.7 (m, 2H); 1.63 (d, 3H, J=7.09 Hz); 1.33 (d, 3H, J=6.80 Hz).

EXAMPLE 667

(3S, 5S)-1-(4-Amino-quinazolin-7-ylmethyl)-4-[2-(5-chloro-thiophen-2-yl)-ethenesulfonyl]-3,5-dimethyl-piperazin-2-one The product (7 mg, 9.4%) is isolated as a yellow solid with a melting point of 218-221° C. $C_{21}H_{22}ClN_5O_3S_2$ MS m/z: 492, 494. 1H NMR (CD$_3$OD) δ8.37 (s, 1H); 8.10 (d, 1H, J=8.57 Hz); 7.61-7.45 (m, 3H); 7.24 (d, 1H, J=3.94 Hz); 6.98 (d, 1H, J=3.85 Hz); 6.71 (d, 1H, J=15.1 Hz); 4.76 (s, 2H); 4.32 (m, 1H); 3.71 (m, 1H); 3.36 (m, 2H); 1.62 (d, 3H, J=7.06 Hz); 1.20 (d, 3H, J=6.63 Hz).

EXAMPLE 668

(3S, 5S)-1-(4-Amino-quinazolin-7-ylmethyl)-4-(6-chloro-benzo[b]thiophen-2-sulfonyl)-3,5-dimethyl-piperazin-2-one The desired product (5.4 mg, 8.5%) is isolated as yellow solid with a melting point of 224-226° C. $C_{23}H_{22}ClN_5O_3S_2$ MS m/z: 516, 518.

EXAMPLE 669

(3S, 5S)-1-(4-Amino-quinazolin-7-ylmethyl)-4-[3-(5-chloro-thiophen-2-yl)-acryloyl]-3,5-dimethyl-piperazin-2-one To a solution of (3S,5S)-1-(4-amino-quinazolin-7-ylmethyl)-3,5-dimethyl-piperazin-2-one (42 mg, 0.147 mmol), major epimer from EXAMPLE 88, Part D, in 2 mL of DMF is added TBTU (52 mg, 0.162 mmol), triethylamine (0.02 mL, 0.162 mmol) and 3-(5-chloro-thiophen-2-yl)-acrylic acid (28 mg, 0.15 mmol), EXAMPLE 25. After stirring for two hours, the reaction mixture is directly purified by reverse phase HPLC (10-70% ACN/$H_2O$). The product (35.5 mg, 36%) is isolated as a yellow solid with a melting point of 116-120° C. $C_{22}H_{22}ClN_5O_2S$: MS m/z: 456, 458. Anal. calcd. for $C_{22}H_{22}ClN_5O_2S \cdot C_2HF_3O_2$: C, 50.57; H, 4.07; N, 12.29. Found: C, 46.48; H, 3.64; N, 11.04.

EXAMPLE 670

(3S, 5R)-4-(4-Amino-quinazolin-7-ylmethyl)-2,6-dimethyl-oxo-piperazine-1-carboxylic acid (4-bromo-phenyl)-amide 4-Bromo-phenyl isocyanate (20.8 mg, 0.105 mmol) is added to solution of (3S,5R)-1-(4-amino-quinazolin-7-ylmethyl)-3,5-dimethyl-piperazin-2-one (30 mg, 0.105 mmol), minor epimer from EXAMPLE 88, Part D, in 1 mL of DMF. The reaction is stirred for two hours at room temperature. The product (21.4 mg, 33%) is isolated from reverse phase HPLC (10-70% ACN/$H_2O$) as white solid. The melting of the compound is 142-144° C. $C_{22}H_{23}BrN_6O_2$ MS m/z: 483, 485. Anal. cald. for $C_{22}H_{23}BrN_6O_2 \cdot 2C_2HF_3O_2$: C, 43.90; H, 3.54; N, 11.81. Found: C, 44.52; H, 3.86; N, 12.44.

EXAMPLE 671

(3S, 5S)-4-(4-Amino-quinazolin-7-ylmethyl)-2,6-dimethyl-oxo-piperazine-1-carboxylic acid (4-bromo-phenyl)-amide The desired product (35 mg, 47%) is isolated as a white solid with a melting point of 142-144° C. $C_{22}H_{23}BrN_6O_2$ MS m/z: 483, 485. Anal. cald. for $C_{22}H_{23}BrN_6O_2 \cdot 2C_2HF_3O_2$:C, 43.90; H, 3.54; N, 11.81. Found: C, 44.73; H, 3.59; N, 12.38.

EXAMPLE 672

(3S, 5S)-4-(4-Amino-quinazolin-7-ylmethyl)-2,6-dimethyl-oxo-piperazine-1-carboxylic acid (4-chloro-phenyl)-amide The product (24.7 mg, 50%) is obtained as a white solid with a melting point of 123-125° C. $C_{22}H_{23}ClN_6O_2$ MS m/z: 439, 441. Anal. cald. for $C_{22}H_{23}ClN_6O_2 \cdot 2C_2HF_3O_2$: C, 46.82; H, 3.78; N, 12.60. Found: C, 47.69; H, 4.33; N, 13.32.

EXAMPLE 673

1-(4-Aminoquinolin-7-ylmethyl)-4-(6-chlorobenzo[b]thiophen-2-sulfonyl)-piperazin-2-one A. 1-(4-Chloroquinolin-7-ylmethyl)-4-(6-chlorobenzo[b]thiophen-2-sulfonyl)-piperazin-2-one.

1-(4-chloroquinolin-7-ylmethyl)-3-(S)-methylpiperazin-2-one hydrochloride (0.49 g, 1.4 mmol), EXAMPLE 89, is treated with acetonitrile (20 mL), triethyl amine (1.2 ml, 8.4 mmol) and a solution of 6-chlorobenzo[b]thiophen-2-sulfonyl chloride (0.41 g, 1.54 mmol), EXAMPLE 1, in acetonitrile (10 mL) at 0° C. After 2 h the solution is poured into water and extracted with ethyl acetate. The organic layer is washed with water, dried over sodium sulfate and concentrated to yielded the title compound (0.45 g, 0.95 mmol). MS m/z: 506, [M+1]$^+$; $^1$H NMR (CD$_3$OD, 300 MHz) δ8.8 (d, 1H), 8.15 (d, 1H), 7.9 (d, 2H), 7.85 (s, 1H), 7.4-7.5 (m, 2H), 6.8 (s, 1H), 4.8 (s, 2H), 4.0 (s, 2H), 3.4-3.45 (m, 4H).

B. 1-(4-Azidoquinolin-7-ylmethyl)-4-(6-chlorobenzo[b]thiophen-2-sulfonyl)-piperazin-2-one.

1-(4-Chloroquinolin-7-ylmethyl)-4-(6-chlorobenzo[b]thiophen-2-sulfonyl)-piperazin-2-one (0.52 g, 1.03 mmol) is dissolved in DMF (15 mL), treated with sodium azide (0.52 g, 8.0 mmol), tetrabutyl ammonium chloride (0.1 g, 0.36 mmol) and heated to 65° C. overnight. The reaction mixture is cooled, poured into water and extracted with ethyl acetate. The organic layer is washed with water, dried (sodium sulfate) and concentrated to give the title compound (0.5 g, 1.04 mmol). $^1$H NMR (CD$_3$OD, 300 MHz) δ9.0 (d, 1H), 8.2 (d, 1H), 8.0 (s, 1H), 7.9 (d, 2H), 7.8 (d, 1H), 7.6 (d, 1H), 7.5 (d, 1H), 6.9 (s, 1H), 4.85 (s, 2H), 4.0 (s, 2H), 3.5-3.7 (m, 4H).

C. 1-(4-Aminoquinolin-7-ylmethyl)-4-(6-chlorobenzo[b]thiophen-2-sulfonyl)-piperazin-2-one.

A suspension of 1-(4-azidoquinolin-7-ylmethyl)-4-(6-chlorobenzo[b]thiophen-2-sulfonyl)-piperazin-2-one (0.50 g, 1.04 mmol) in 100 mL of acetic acid/methanol (~1:10) is treated with 10% Pd/C (0.15 g) and stirred under hydrogen for 1.5 hours. The resulting solution is filtered through Celite and the filtrate is evaporated in vacuo. The organic layer is concentrated and the residue is purified by reverse phase HPLC (gradient elution of 30% of 0.1% aqueous TFA/acetonitrile to 100% acetonitrile) and lyopholized to give the title compound (0.39 g, 0.86 mmol). MS (ISP) m/z 487, 489, (M+H), Cl pattern.

The following compounds are prepared from the compound of Example 89 or 91 using the methods described above.

| Example # | Name | m/z [M + H] |
| --- | --- | --- |
| 674 | 1-(4-Amino-quinolin-7-ylmethyl)-4-[2-(5-chloro-thiophen-2-yl)-ethenesulfonyl]-piperazin-2-one | 463, 465 |
| 675 | (S)-1-(4-Amino-quinolin-7-ylmethyl)-4-(6-chloro-benzo[b]thiophene-2-sulfonyl)-3-methyl-piperazin-2-one | 501, 503 |
| 676 | (3S,5S)-1-(4-Amino-quinolin-7-ylmethyl)-4-[2-(5-chloro-thiophen-2-yl)-ethenesulfonyl]-3,5-dimethyl-piperazin-2-one | 491, 493 |
| 677 | (3S,5R)-1-(4-Amino-quinolin-7-ylmethyl)-4-[2-(5-chloro-thiophen-2-yl)-ethenesulfonyl]-3,5-dimethyl-piperazin-2-one | 491, 493 |

-continued

| Example # | Name | m/z [M + H] |
|---|---|---|
| 678 | (S,R)-1-(4-Amino-quinolin-7-ylmethyl)-4-(6-chloro-benzo[b]thiophene-2-sulfonyl)-6-oxo-piperazine-2-carboxylic acid | 531, 533 |
| 679 | 1-(4-Amino-quinolin-7-ylmethyl)-4-(6-chloro-benzo[b]thiophene-2-sulfonyl)-6-oxo-piperazine-2-carboxylic acid methylamide | 544 |
| 680 | 1-(4-Amino-quinolin-7-ylmethyl)-4-(6-chloro-benzo[b]thiophene-2-sulfonyl)-6-oxo-piperazine-2-carboxylic acid ethylamide | 558 |
| 681 | 1-(4-Amino-quinolin-7-ylmethyl)-4-(6-chloro-benzo[b]thiophene-2-sulfonyl)-6-oxo-piperazine-2-carboxylic acid dimethylamide | 558 |
| 682 | 1-(4-Amino-quinolin-7-ylmethyl)-4-(6-chloro-benzo[b]thiophene-2-sulfonyl)-6-(morpholine-4-carbonyl)-piperazin-2-one | 600 |

EXAMPLE 683

(S)-1-(4-Aminoquinolin-7-ylmethyl)-4-[3-(5-chlorothiophen-2-yl)-allyl]-3-methylpiperazin-2-one A.   (S)-1-(4-Chloroquinolin-7-ylmethyl)-4-[3-(5-chlorothiophen-2-yl)-allyl]-3-methylpiperazin-2-one.

(S)-1-(4-chloroquinolin-7-ylmethyl)-3-methylpiperazin-2-one hydrochloride (0.25 g, 1.0 mmol), EXAMPLE 91, is treated with 2-(3-Bromo-(E)-propenyl)-5-chloro-thiophene (0.35 g 1.2 mmol), EXAMPLE 17, and potassium carbonate (0.5 g, 3 mmol). The resulting suspension is sonicated for 10 minutes then stirred vigorously for 16 h at ambient temperature. The reaction mixture is poured into water and extracted with ethyl acetate (2×150 mL). The organic layer is washed with water (4×200 mL), dried over sodium sulfate and concentrated. The residue is chromatographed (3% methanol/methylene chloride) to give the title compound (0.31 g, 0.73 mmol).

B.   (S)-1-(4-Aminoquinolin-7-ylmethyl)-4-[3-(5-chlorothiophen-2-yl)-allyl]-3-methylpiperazin-2-one.

(S)-1-(4-Chloroquinolin-7-ylmethyl)-4-[3-(5-chlorothiophen-2-yl)-allyl]-3-methylpiperazin-2-one(0.35 g, 0.82 mmol) is treated with phenol (2 g) and ammonium acetate (0.7 g, 9.1 mmol) and heated to 120° C. in a sealed vessel for 1 hour. Upon cooling, the solution is partitioned between 2 N NaOH and ethyl acetate. The organic layer is separated and washed with fresh 2 N NaOH (3×100 mL) and water. The organic layer is concentrated and the residue is purified by reverse phase HPLC to give the title compound as a white solid (0.15 g, 0.35 mmol). MS (ISP) m/z 427, 429, (M+H), Cl pattern.

The following compounds are prepared from starting materials prepared as described in Examples 61-64, 89 or 91 using the methods described above.

| Example # | Name | m/z [M + H] |
|---|---|---|
| 684 | 1-(4-Amino-quinolin-7-ylmethyl)-4-[3-(5-chloro-thiophen-2-yl)-allyl]-piperazin-2-one | 413, 415 |
| 685 | (3S, 5R)-1-(4-Amino-quinolin-7-ylmethyl)-4-(6-chloro-benzo[b]thiophen-2-ylmethyl)-3,5-dimethyl-piperazin-2-one | 465, 467 |
| 686 | (3S, 5S)-1-(4-Amino-quinolin-7-ylmethyl)-4-(6-chloro-benzo[b]thiophen-2-ylmethyl)-3,5-dimethyl-piperazin-2-one | 464 |
| 687 | (S)-1-(4-Amino-quinolin-7-ylmethyl)-4-(7-chloro-isoquinolin-3-ylmethyl)-3-methyl-piperazin-2-one | 446, 448 |
| 688 | (S)-1-(4-Amino-quinolin-7-ylmethyl)-4-(6-chloro-naphthalen-2-ylmethyl)-3-methyl-piperazin-2-one | 444 |
| 689 | (3S,5S)-1-(4-Amino-quinolin-7-ylmethyl)-4-[3-(5-chloro-thiophen-2-yl)-allyl]-3,5-dimethyl-piperazin-2-one | 441, 443 |
| 690 | (3S,5R)-1-(4-Amino-quinolin-7-ylmethyl)-4-[3-(5-chloro-thiophen-2-yl)-allyl]-3,5-dimethyl-piperazin-2-one | 441, 443 |
| 691 | 1-(4-Amino-quinolin-7-ylmethyl)-4-(5-chloro-1H-indol-2-ylmethyl)-piperazin-2-one | 420, 422 |
| 692 | (S)-1-(4-Amino-quinolin-7-ylmethyl)-4-(6-chloro-naphthalen-2-ylmethyl)-3-ethyl-piperazin-2-one | 458 |
| 693 | 1-(4-Amino-quinolin-7-ylmethyl)-4-[3-(5-chloro-thiophen-2-yl)-allyl]-(S)-3-((R)-1-methoxy-ethyl)-piperazin-2-one | 470 |
| 694 | 1-(4-Amino-quinolin-7-ylmethyl)-4-(7-chloro-isoquinolin-3-ylmethyl)-(S)-3-((R)-1-methoxy-ethyl)-piperazin-2-one | 489 |
| 695 | (S)-1-(4-Amino-quinolin-7-ylmethyl)-4-(5-chloro-1H-indol-2-ylmethyl)-3-methoxymethyl-piperazin-2-one | 464, 466 |
| 696 | (S)-1-(4-Amino-quinolin-7-ylmethyl)-4-(5-chloro-1H-indol-2-ylmethyl)-3-methyl-piperazin-2-one | 434, 436 |
| 697 | 4-(5-Chloro-1H-indol-2-ylmethyl)-1-[4-(2-hydroxy-ethylamino)-quinolin-7-ylmethyl]-piperazin-2-one | 464 |
| 698 | (S)-4-(5-Chloro-1H-indol-2-ylmethyl)-1-(4-ethylamino-quinolin-7-ylmethyl)-3-methyl-piperazin-2-one | 462 |
| 699 | (S)-4-(5-Chloro-1H-indol-2-ylmethyl)-1-(4-ethylamino-quinolin-7-ylmethyl)-3-methoxymethyl-piperazin-2-one | 492 |

-continued

| Example # | Name | m/z [M + H] |
|---|---|---|
| 700 | (S)-4-(5-Chloro-1H-indol-2-ylmethyl)-3-methyl-1-(4-methylamino-quinolin-7-ylmethyl)-piperazin-2-one | 448 |
| 701 | (S)-4-(5-Chloro-1H-indol-2-ylmethyl)-3-methoxymethyl-1-(4-methylamino-quinolin-7-ylmethyl)-piperazin-2-one | 478 |
| 702 | (S)-1-(4-Amino-quinolin-7-ylmethyl)-4-[3-(5-chloro-thiophen-2-yl)-allyl]-3-methyl-4-oxy-piperazin-2-one | 443 |

EXAMPLE 703

(S)-1-(4-Aminoquinolin-7-ylmethyl)-4-[3-(4-bromothiophen-2-yl)acryloyl]-3-methyl-piperazin-2-one.

A.      (S)-1-(4-Chloroquinolin-7-ylmethyl)-4-[3-(4-bromothiophen-2-yl)acryloyl]-3-methyl piperazin-2-one.

(S)-1-(4-chloroquinolin-7-ylmethyl)-3-methylpiperazin-2-one hydrochloride (0.35 g, 1.4 mmol), EXAMPLE 91, is treated with DMF (20 mL), 3-(4-bromothiophen-2-yl)-(E)-acrylic acid (0.32 g, 1.4 mmol), prepared according to EXAMPLE 26, using 4-bromothiophene-2-carboxaldehyde, triethyl amine (0.21 ml, 1.4 mmol) and 2-(1H-benzotriazol-1-yl)1,1,3,3-tertamethyluronium tetrafluoroborate (0.45 g, 1.4 mmol) and heated to 50° C. for 5 minutes. The reaction mixture is stirred at ambient temperature for 16 h then partitioned between ethyl acetate and water. The organic layer is concentrated and the residue is chromatographed (5% methanol/methylene chloride) to give crude title compound (0.5 g, 0.9 mmol). MS m/z: [M+H]$^+$=504. $^1$H NMR (CDCl$_3$, 300 MHz) δ8.9 (d, 1H), 8.2-8.3 (m, 2H), 8.0 (s, 1H), 7.7-7.8 (m, 1H), 7.4 (s, 1H), 7.3-7.4 (m, 1H), 6.7-6.8 (m, 1H), 6.6 (d, 1H), 5.1-5.2 (m, 1H), 4.6-4.7 (m, 2H), 3.4-3.6 (m, 2H), 3.0-3.3 (m, 2H), 1.5 (d, 3H).

B.      (S)-1-(4-Aminoquinolin-7-ylmethyl)-4-[3-(4-bromothiophen-2-yl)acryloyl]-3-methyl-piperazin-2-one.

(S)-1-(4-Chloroquinolin-7-ylmethyl)-4-[3-(4-bromothiophen-2-yl)acryloyl]-3-methyl piperazin-2-one (0.50 g, 0.9 mmol) is treated with phenol (~2 g) and ammonium acetate (0.5 g, 6.4 mmol) and heated to 120° C. in a sealed vessel for 1 hour. Upon cooling, the solution is partitioned between 2 N NaOH and ethyl acetate. The organic layer is separated and washed with fresh 2 N NaOH (3×100 mL) and water. The organic layer is concentrated and the residue is purified by reverse phase HPLC (gradient elution of 10% of 0.1% aqueous TFA/acetonitrile to 100% acetonitrile) to give the title compound (0.22 g, 0.56 mmol). MS m/z: [M+H]$^+$ =485, 487, Cl pattern. $^1$H NMR (CD$_3$OD, 300 MHz) δ8.2-8.4 (m, 2H), 7.7-7.8 (m, 2H), 7.6 (d, 1H), 7.5 (s, 1H), 7.3 (s, 1H), 6.9-7.0 (m, 1H), 6.7 (d, 1H), 5.0-5.1 (m, 1H), 4.9 (q, 2H), 4.3-4.4 (m, 1H), 3.5-3.7 (m, 2H), 3.3-3.4 (m, 2H), 1.5 (d, 3H).

The following compounds are prepared from starting materials prepared as described in Examples 75-87 using the methods described above.

| Example # | Name | m/z [M + H] |
|---|---|---|
| 704 | 1-(4-Amino-quinolin-7-ylmethyl)-4-[3-(5-chloro-thiophen-2-yl)-acryloyl]-3(S)-ethyl-6-methyl-piperazin-2-one | 469 Cl pattern |
| 705 | 4-[3-(5-Chloro-thiophen-2-yl)-acryloyl]-(S)-3-ethyl-1-(4-hydroxyamino-quinolin-7-ylmethyl)-piperazin-2-one | 471, 473 |
| 706 | 1-(4-Amino-quinolin-7-ylmethyl)-4-[3-(5-chloro-thiophen-2-yl)-acryloyl]-piperazin-2-one | 427, 429 |
| 707 | (S)-1-(4-Amino-quinolin-7-ylmethyl)-4-[3-(5-chloro-thiophen-2-yl)-acryloyl]-3-ethyl-piperazin-2-one | 454 |
| 708 | (S)-1-(4-Amino-quinolin-7-ylmethyl)-4-[3-(5-chloro-thiophen-2-yl)-acryloyl]-3-methyl-piperazin-2-one | 441, 443 |
| 709 | 1-(4-Amino-quinolin-7-ylmethyl)-4-[3-(4-bromo-thiophen-2-yl)-acryloyl]-piperazin-2-one | 471, 473 |
| 710 | (S)-1-(4-Amino-quinolin-7-ylmethyl)-4-[3-(5-chloro-thiophen-2-yl)-acryloyl]-3-methoxymethyl-piperazin-2-one | 470 |
| 711 | (S)-1-(4-Amino-quinolin-7-ylmethyl)-4-[3-(4-bromo-thiophen-2-yl)-acryloyl]-3-ethyl-piperazin-2-one | 498 |
| 712 | (S)-1-(4-Amino-quinolin-7-ylmethyl)-4-[(5-chloro-thiophen-2-yloxy)-acetyl]-3-ethyl-piperazin-2-one | 458 |
| 713 | (S)-1-(4-Amino-quinolin-7-ylmethyl)-4-[(5-chloro-thiophen-2-yloxy)-acetyl]-3-methoxymethyl-6-methyl-piperazin-2-one | 488 |
| 714 | 1-(4-Amino-quinolin-7-ylmethyl)-4-[3-(5-chloro-thiophen-2-yl)-acryloyl]-(S)-3-(1-(R)-methoxy-ethyl)-piperazin-2-one | 484 |
| 715 | 1-(4-Aminoquinolin-7-ylmethyl)-4-[3-(4-bromothiophen-2-yl)-acryloyl]-3-(S)-(1-(R)-methoxyethyl)-piperazin-2-one trifluoroacetate | 528 |

-continued

| Example # | Name | m/z [M + H] |
|---|---|---|
| 716 | 1-(4-Aminoquinolin-7-ylmethyl)-4-[(5-chlorothiophen-2-yloxy-acetyl]-3-(S)-(1-(R)-methoxyethyl)-piperazin-2-one trifluoroacetate | 488 |
| 717 | (S)-1-(4-Amino-quinolin-7-ylmethyl)-4-[3-(5-chloro-thiophen-2-yl)-acryloyl]-3-ethyl-piperazin-2-one | 454 |

EXAMPLE 718

1-(4-Aminocinnolin-7-ylmethyl)-4-[2-(5-chlorothiophen-2-yl)-ethenesulfonyl]-piperazin-2-one A. 1-(4-Chlorocinnolin-7-ylmethyl)-4-[2-(5-chlorothiophen-2-yl)-ethenesulfonyl]-piperazin-2-one 1-(4-chlorocinnolin-7-ylmethyl)-piperazin-2-one hydrochloride (0.14 g, 0.4 mmol), EXAMPLE 90, is treated with acetonitrile (20 mL), triethylamine (2 mL, 14 mmol) and 2-(5-chlorothiophen-2-yl)ethene-sulfonyl chloride (0.097 g, 0.4 mmol), EXAMPLE 3, at 0° C. The solution is warmed to ambient temperature over 1.5 h and diluted with ethyl acetate. The solution is washed with 10% sodium bicarbonate solution and water, dried (sodium sulfate) and concentrated to yield the title compound (0.17 g, 0.35 mmol). MS m/z: [M+H]$^+$=483; $^1$H NMR (CDCl$_3$, 300 MHz) δ9.4 (s, 1H), 8.4 (s, 1H), 8.3 (d, 1H) 7.85 (d, 1H), 7.7 (d, 1H), 7.1 (d, 1H), 6.95 (d, 1H), 6.35 (d, 1H), 4.9 (s, 2H), 4.0 (s, 2H), 3.4-3.5 (m, 4H).

B. 1-(4-Aminocinnolin-7-ylmethyl)-4-[2-(5-chlorothiophen-2-yl)-ethenesulfonyl]-piperazin-2-one 1-(4-Chlorocinnolin-7-ylmethyl)-4-[2-(5-chlorothiophen-2-yl)-ethenesulfonyl]-piperazin-2-one (0.06 g, 0.12 mmol) is treated with phenol (0.20 g) and ammonium acetate (0.2 g, 2.6 mmol) and heated to 120° C. for 45 minutes. The reaction mixture is cooled, diluted with ethyl acetate and washed with 1 N NaOH (3×100 mL) and water. The organic layer is concentrated and the residue is purified by reverse phase HPLC (20% aqueous TFA (0.1%)/acetonitrile to 100% acetonitrile). Fractions containing the desired product are lyophilized to obtain the title compound (0.02 g, 0.043 mmol). MS m/z: [M+H]$^+$=464; $^1$H NMR (CD$_3$OD, 300 MHz) δ8.6 (s, 1H), 8.4 (d, 1H), 7.75 (d, 1H), 7.65 (d, 1H), 7.35 (d, 1H), 7.1 (d, 1H), 6.8 (d, 1H), 4.9 (s, 2H), 4.05 (s, 2H), 3.6 (m, 4H).

EXAMPLE 719

4-(6-Chloro-thieno[2,3-b]pyridine-2-sulfonyl)-1-[2-(pyridin-4-ylamino)-ethyl]-piperazin-2-one 1-[2-(Pyridin-4-ylamino)-ethyl]-piperazin-2-one (0.20 mmol), EXAMPLE 90, is dissolved in MeCN (5 mL) and treated with 4-methylmorphorline (0.055 ml, 0.50 mmol). 6-Chloro-thieno[2,3-b]2,3b]pyridine-2-sulfonyl chloride (54 mg, 0.20 mmol) in MeCN (2 mL) is added dropwise. The reaction mixture is stirred at r.t. for 1.5 h, then subjected to HPLC purification, to give the title compound as white solid (0.021 g, 0.037 mmol). MS m/z 452, 454 (M+1); $^1$H NMR (CD$_3$OD, 300 MHz) δ8.37 (d, 1H), 8.30 (b, 1H), 8.12 (d, 1H), 8.02 (s, 1H), 7.97 (d, 1H), 7.57 (d. 1H), 6.98 (d, 1H), 6.88 (d, 2H), 3.73 (s, 2H), 3.60-3.48 (m, 8H).

EXAMPLE 720

4-(6-Chloro-benzo[b]thiophene-2-sulfonyl)-1-[2-(methyl-pyridin-4-yl-amino)-ethyl]-piperazin-2-one A portion (~50%) of the crude 1-[2-{(Methyl)-(pyridin-4-yl)-amino}-ethyl]-piperazin-2-one, EXAMPLE 93 is reacted with 6-chloro-benzo[b]thiophene-2-sulfonyl chloride (54 mg, 0.20 mmol), EXAMPLE 1, using same procedure as described in EXAMPLE 719. The residue obtained after HPLC purification is subjected to silica gel chromatography using NH$_4$OH/MeOH/CH$_2$Cl$_2$ (1:4:95) as eluant to give title compound (30 mg, 0.064 mmol) as a white solid. MS m/z 465, 457 (M+1); $^1$H NMR (CDCl$_3$, 300 MHz) δ8.15 (d, 2H), 7.88 (s, 1H), 7.85 (d, 1H), 7.79 (s, 1H), 7.47 (d, 1H), 6.47 (d. 2H), 3.80 (s, 2H), 3.50 (m, 4H), 3.43 (d, 2H), 3.30 (d, 2H), 2.98 (s, 3H).

EXAMPLE 721

4-[2-(5-Chloro-thiophen-2-yl)-ethenesulfonyl]-1-[2-(3-methyl-pyridin-4-ylamino)-ethyl]-piperazin-2-one 1-[2-(3-Methylpyridin-4-yl-amino)-ethyl]-piperazin-2-one (38 mg, 0.16 mmol), EXAMPLE 94, is reacted with 2-(5-chloro-thiophen-2-yl)-ethenesulfonyl chloride (40 mg, 0.16 mmol), EXAMPLE 3, using the same procedure as described in EXAMPLE 719. Reverse phase HPLC purification gives the title compound (29 mg, 0.052 mmol) as a white solid. MS m/z 441, 443 (M+H); $^1$H NMR (CD$_3$OD, 300 MHz) δ8.08 (d, 1H), 7.98 (s, 1H), 7.56 (d, 1H), 7.30 (d, 1H), 7.02 (s, 1H), 7.00 (d. 1H), 6.78 (d, 1H), 3.87 (s, 2H), 3.70-3.50 (m, 8H), 2.15 (s, 3H).

The following compounds are prepared from starting materials obtained as described in Examples 92-97 using the methods described above.

| Example # | Name | m/z [M + H] |
|---|---|---|
| 722 | 4-(6-Chloro-benzo[b]thiophene-2-sulfonyl)-1-[2-(pyridin-4-ylamino)-ethyl]-piperazin-2-one | 520 (M+) |
| 723 | 1-[2-(Pyridin-4-ylamino)-ethyl]-4-(thieno[2,3-b]pyridine-2-sulfonyl)-piperazin-2-one | 417 |
| 724 | 4-(5'-Chloro-[2,2']bithiophenyl-5-sulfonyl)-1-[2-(pyridin-4-ylamino)-ethyl]-piperazin-2-one | 483, 485 |
| 725 | 1-[2-(Pyridin-4-ylamino)-ethyl]-4-(thieno[3,2-b]pyridine-2-sulfonyl)-piperazin-2-one | 418 |

-continued

| Example # | Name | m/z [M + H] |
|---|---|---|
| 726 | 4-[2-(5-Chloro-thiophen-2-yl)-ethenesulfonyl]-1-[2-(pyridin-4-ylamino)-ethyl]-piperazin-2-one | 427, 429 |
| 727 | 4-[2-(5-Chloro-thiophen-2-yl)-ethenesulfonyl]-1-[2-(methylpyridin-4-ylamino)-ethyl]-piperazin-2-one | 441 |
| 728 | 4-(2-Benzo[b]thiophen-2-yl-ethenesulfonyl)-1-[2-(pyridin-4-ylamino)-ethyl]-piperazin-2-one | 443 |
| 729 | 4-(6-Chloro-benzo[b]thiophene-2-sulfonyl)-1-[2-(3-methyl-pyridin-4-ylamino)-ethyl]-piperazin-2-one | 465, 467 |
| 730 | 4-[2-(5-Chloro-thiophen-2-yl)-ethenesulfonyl]-1-(2-pyrrolo[3,2-c]pyridin-1-yl-ethyl)-piperazin-2-one | 450, 452 |
| 731 | 1-[2-(2-Amino-3-chloro-pyridin-4-ylamino)-ethyl]-4-[2-(5-chloro-thiophen-2-yl)-ethenesulfonyl]-piperazin-2-one | 476, 478 |
| 732 | 1-[2-(2-Amino-5-chloro-pyridin-4-ylamino)-ethyl]-4-[2-(5-chloro-thiophen-2-yl)-ethenesulfonyl]-piperazin-2-one | 476, 478 |
| 733 | 4-[2-(5-Chloro-thiophen-2-yl)-ethenesulfonyl]-1-[2-(2,3,5,6-tetrachloro-pyridin-4-ylamino)-ethyl]-piperazin-2-one | 563, 565, 567, 569 |
| 734 | 1-[2-(2-Amino-3,5,6-trichloro-pyridin-4-ylamino)-ethyl]-4-[2-(5-chloro-thiophen-2-yl)-ethenesulfonyl]-piperazin-2-one | 544, 546, 548 |
| 735 | 4-[3-(5-Chloro-thiophen-2-yl)-acryloyl]-1-[2-(pyridin-4-ylamino)-ethyl]-piperazin-2-one | 391, 393 |

EXAMPLE 736

4-(6-Chloro-benzo[b]thiophene-2-sulfonyl)-1-[2-(pyridazin-4-yl-amino)-ethyl]-piperazin-2-one 1-[2-(Pyridazin-4-ylamino)-ethyl]-piperazin-2-one hydrochloride (0.5 g, 1.7 mmol), EXAMPLE 95, is reacted with 6-chloro-benzo[b]thiophene-2-sulfonyl chloride (0.40 g, 1.5 mmol), EXAMPLE 1, using essentially the same procedure as described in EXAMPLE 719. Reverse phase HPLC purification gives the title compound (0.34 g, 0.75 mmol) as a white solid. MS m/z (M+H=452); $^1$H NMR (CD$_3$OD, 300 MHz) δ8.6 (d, 1H), 8.4 (d, 1H), 8.05 (s, 1H), 8.05 (s, 1H), 7.9 (d, 1H), 7.5 (d, 1H), 7.2 (d, 1H), 3.8 (s, 2H), 3.4-3.7 (m, 8H).

EXAMPLE 737

1-[3-(4-Amino-pyridin-3-yl)-propenyl]-4-[2-(5-chloro-thiophen-2-yl)-ethenesulfonyl]-piperazin-2-one 4-[3-(4-tert-Butoxycarbonylamino-pyridin-3-yl)-propenyl]-3-oxo-piperazine-1-carboxylic acid tert-butyl ester from EXAMPLE 96, Part B (45 mg, 0.10 mmol) is dissolved in 20% TFA/CH$_2$Cl$_2$ and stirred at r.t. for 2 hours. The solution is concentrated to residue. The residue is dissolved in MeCN (2.5 ml) and treated with 4-methylmorphorline (0.027 ml, 0.25 mmol). 2-(5-Chloro-thiophen-2-yl)-ethenesulfonyl chloride (24 mg, 0.10 mmol), EXAMPLE 3, in MeCN (1 mL) is then added dropwise. The reaction mixture is stirred at r.t. for 1 h, then subjected to reverse phase HPLC purification, to give the title compound as white solid (0.040 g, 0.037 mmol). MS m/z 439, 441 (M+H); $^1$H NMR (CD$_3$OD, 300 MHz) δ8.20 (br, 1H), 8.10 (s, 1H), 8.08 (d, 1H), 7.60 (d, 1H), 7.53 (d. 1H), 7.35 (d, 1H), 7.21 (d, 1H), 7.07 (d, 1H), 6.82 (d, 1H), 5.27 (m, 1H), 3.88 (s, 2H), 3.60-3.50 (m, 4H), 3.30 (d, 2H).

The following compounds are prepared from starting materials obtained as described in Examples 92-97 using the methods described above.

| Example # | Name | m/z [M + H] |
|---|---|---|
| 738 | 1-[3-(4-Amino-pyridin-3-yl)-propenyl]-4-(6-chloro-benzo[b]thiophene-2-sulfonyl)-piperazin-2-one | 463, 465 |
| 739 | 1-[3-(4-Amino-pyridin-3-yl)-allyl]-4-(6-chloro-benzo[b]thiophene-2-sulfonyl)-piperazin-2-one | 463, 465 |
| 740 | 1-[3-(4-Amino-pyridin-3-yl)-allyl]-4-[2-(5-chloro-thiophen-2-yl)-ethenesulfonyl]-piperazin-2-one | 439, 441 |
| 741 | 1-[3-(4-Amino-pyridin-3-yl)-propyl]-4-(6-chloro-benzo[b]thiophene-2-sulfonyl)-piperazin-2-one | 465, 467 |
| 742 | 1-[3-(4-Amino-pyridin-3-yl)-propyl]-4-[2-(5-chloro-thiophen-2-yl)-ethenesulfonyl]-piperazin-2-one | 441, 443 |

EXAMPLE 743

4-[2-(5-Chlorothiophen-2-yl)-ethenesulfonyl]-1-(2-pyrrolo[3 2-c]pyridin-1-ylethyl)-piperazin-2-one 4-(Benzyloxycarbonyl)-1-(2-pyrrolo[3,2-c]pyridin-1-yl-ethyl)-piperazin-2-one (0.028 g, 0.074 mmol), EXAMPLE 98, is treated with 4% HCO$_2$H/MeOH (5 mL) and a catalytic amount of Pd black for 5 minutes. The reaction mixture is filtered washed with methanol and the filtrate is concentrated to a residue. The residue is treated with acetonitrile (3 mL) excess N-methylmorpholine (0.04 mL) and 2-(5-chlorothiophen-2-yl)ethene-sulfonyl chloride (0.018 g, 0.074 mmol), EXAMPLE 3, and processed as usual (EXAMPLE 719). Further chromatographic purification (NH$_4$OH/MeOH/CH$_2$Cl$_2$: 1/4/95) yields the title compound: MS m/z 451, 453 (M+H); $^1$H NMR (CDCl$_3$, 300 MHz) δ8.93 (bs, 1H), 8.24 (bs, 1H), 7.41 (d, 1H), 7.23 (d, 1H), 7.14 (m, 2H), 6.94 (d, 1H), 6.68 (d. 1H), 6.18 (d, 1H), 4.43 (t, 2H), 3.67 (t, 2H), 2.88 (t, 2H), 2.66 (t, 2H).

EXAMPLE 744

4-Prop-2-ynyl-1-(1H-pyrrolo[3,2-c]pyridin-2-ylmethyl)-piperazin-2-one

A. 2-(2-Oxo-4-prop-2-ynyl-piperazin-1-ylmethyl)-pyrrolo[3,2-c]pyridine-1-carboxylic acid tert-butyl ester.

A solution containing 2-(2-oxo-piperazin-1-ylmethyl)-pyrrolo[3,2-c]pyridine-1-carboxylic acid tert-butyl ester (4.3 g, 13.0 mmol), EXAMPLE 69, in $CH_3CN$ (250 mL) is cooled to 0° C. Potassium carbonate (1.98 g, 14.3 mmol) is added to the reaction mixture followed by propargyl bromide (1.55 g, 13.0 mmol). The mixture is slowly warmed to ambient temperature and maintained until complete consumption of starting material is observed by TLC (approx. 8 h). The mixture is concentrated to dryness and then partitioned between aqueous $NaHCO_3$ (200 mL) and $CH_2Cl_2$ (200 mL) and the layers are separated. The aqueous phase is extracted twice with $CH_2Cl_2$ (100 mL) and the combined organic phase is washed with brine, dried over anhydrous $Na_2SO_4$, filtered and concentrated. The crude residue is purified by flash silica gel chromatography ($CH_2Cl_2$ to 5% MeOH/$CH_2Cl_2$) to provide 3.38 g (70%) of the title compound as a pale yellow solid. $^1H$ NMR (300 MHz, $CDCl_3$) δ1.69 (s, 9H), 2.34 (t, J=2.4 Hz, 1H), 2.89 (m, 2H), 3.42 (s, 2H), 3.45 (d, J=2.4 Hz, 2H), 3.52 (m, 2H), 4.95 (d, J=1.4 Hz, 2H), 6.42 (br s, 1H), 7.88 (dd, J=5.8, 0.8 Hz, 1H), 8.41 (d, J=5.8 Hz, 1H), 8.78 (d, J=0.8 Hz, 1H) ppm; MS (EI): m/z 368 (M+).

B. 4-Prop-2-ynyl-1-(1H-pyrrolo[3,2-c]pyridin-2-ylmethyl)-piperazin-2-one.

To a solution containing 2-(2-oxo-4-prop-2-ynyl-piperazin-1-ylmethyl)-pyrrolo[3,2-c]pyridine-1-carboxylic acid tert-butyl ester (1.3 g, 3.53 mmol) in $CH_2Cl_2$ (100 mL) is added TFA (20 mL) at 0° C. After 6 h, the reaction mixture is concentrated to dryness and then partitioned between aqueous $NaHCO_3$ (500 mL) and $CH_2Cl_2$ (200 mL) and the layers are separated. The aqueous phase is extracted four times with $CH_2Cl_2$ (100 mL) and the combined organic phase is washed with brine, dried over anhydrous $Na_2SO_4$, filtered and concentrated. The crude residue is purified by flash silica gel chromatography ($CH_2Cl_2$ to 10% MeOH/$CH_2Cl_2$) to provide 616 mg (65%) of the title compound as a pale yellow solid.

$^1H$ NMR (300 MHz, $CDCl_3$) δ2.27 (app t, J=2.4 Hz, 1H), 2.76 (m, 2H), 3.33 (s, 2H), 3.83 (d, J=2.4 Hz, 2H), 3.45 (m, 2H), 4.57 (s, 2H), 6.47 (s, 1H), 7.23 (d, J=5.7 Hz, 1H), 8.28 (d, J=5.7 Hz, 1H), 8.85 (d, J=0.9 Hz, 1H), 9.34 (br s, 1H) ppm; MS (EI): m/z 268 (M+).

EXAMPLE 745

1,4-Bis-(1H-pyrrolo[3,2-c]pyridin-2-ylmethyl)-piperazin-2-one

A. 2-{4-[3-(4-tert-Butoxycarbonylamino-pyridin-3-yl)-prop-2-ynyl]-2-oxo-piperazin-1-ylmethyl}-pyrrolo[3,2-c]pyridine-1-carboxylic acid tert-butyl ester.

A solution containing 2-(2-oxo-4-prop-2-ynyl-piperazin-1-ylmethyl)-pyrrolo[3,2-c]pyridine-1-carboxylic acid tert-butyl ester (100 mg, 0.27 mmol), EXAMPLE 743, (3-iodo-pyridin-4-yl)-carbamic acid tert-butyl ester (87 mg, 0.27 mmol), EXAMPLE 69, Part B, $Et_3N$ (110 mg, 1.08 mmol), $(Ph_3P)_4PdCl_2$ (10 mg, 0.013 mmol), and CuI (1 mg, 0.008 mmol) in anhydrous DMF (5 mL) is stirred at ambient temperature. After 5 h, the reaction mixture is diluted with EtOAc (50 mL) and water (50 mL) and the layers are separated. The aqueous layer is extracted twice with EtOAc (25 mL) and the combined organic phase is washed with brine, dried over anhydrous $Na_2SO_4$, filtered and concentrated. The crude residue is purified by flash silica gel chromatography ($CH_2Cl_2$ to 10% MeOH $CH_2Cl_2$) to provide 77 mg (51%) of the title compound as a colorless oil. $^1H$ NMR (300 MHz, $CDCl_3$, ~2:1 mixture of rotamers) major rotamer: δ1.53 (s, 9H), 1.69 (s, 9H), 2.98 (m, 2H), 3.49 (s, 2H), 3.56 (m, 2H), 3.78 (s, 2H), 4.98 (s, 2H), 6.43 (s, 1H), 7.89 (m, 1H), 8.09 (m, 2H), 8.34 (m, 1H), 8.41 (m, 1H), 8.75 (m, 1H) ppm; MS (ISP loop): m/z 561 (M+H).

B. 2-[4-(1-tert-Butoxycarbonyl-1H-pyrrolo[3,2-c]pyridin-2-ylmethyl)-2-oxo-piperazin-1-ylmethyl]-pyrrolo[3,2-c]pyridine-1-carboxylic acid tert-butyl ester.

1,8-Diazabicyclo[5.4.0]undec-7-ene (42 mg, 0.27 mmol) is added to a suspension containing 2-{4-[3-(4-tert-butoxycarbonylamino-pyridin-3-yl)-prop-2-ynyl]-2-oxo-piperazin-1-ylmethyl}-pyrrolo[3,2-c]pyridine-1-carboxylic acid tert-butyl ester (77 mg, 0.14 mmol) in anhydrous $CH_3CN$ (10 mL) and the mixture is warmed to 50° C. After 4 h, the reaction mixture is concentrated to dryness and the residue is partitioned between $CH_2Cl_2$ (50 mL) and water (50 mL) and the layers are separated. The aqueous layer is extracted twice with $CH_2Cl_2$ (25 mL) and the combined organic phase is washed with brine, dried over anhydrous $Na_2SO_4$, filtered and concentrated to provide 85 mg of the title compound as a crude solid which is used directly without further purification. $^1H$ NMR (300 MHz, $CDCl_3$) δ1.68 (s, 9H), 1.70 (s, 9H), 2.91 (m, 2H), 3.41 (s, 2H), 3.49 (m, 2H), 4.26 (s, 2H), 4.95 (d, J=1.1 Hz, 2H), 6.39 (d, J=0.7 Hz, 1H), (d, J=0.7 Hz, 1H), 7.86 (m, 1H), 8.41 (m, 1H), 8.76 (br s, 1H), 8.82 (br s, 1H) ppm; MS (EI): m/z 561 (M+H).

C. 1,4-Bis-(1H-pyrrolo[3 2-c]pyridin-2-ylmethyl)-piperazin-2-one.

To a solution containing 2-[4-(1-tert-Butoxycarbonyl-1H-pyrrolo[3,2-c]pyridin-2-ylmethyl)-2-oxo-piperazin-1-ylmethyl]-pyrrolo[3,2-c]pyridine-1-carboxylic acid tert-butyl ester (85 mg, 0.14 mmol) in $CH_2Cl_2$ (5 mL) is added TFA (1 mL) at 0° C. and the solution is allowed to slowly warm to ambient temperature. After 16 h, the reaction mixture is concentrated to dryness, diluted with water and purified by reverse-phase HPLC [Buffer A: water w/0.1% TFA; Buffer B: $CH_3CN$ w/0.1% TFA; Gradient: 0% B to 45% B over 30 min] to provide 35 mg (36%, two steps) of the title compound as a pale yellow, lyophilized solid.

$^1H$ NMR (300 MHz, $d_6$-DMSO) δ2.80 (m, 2H), 3.25 (s, 2H), 3.37 (m, 2H), 3.93 (s, 2H), 4.76 (s, 2H), 6.88 (s, 1H), 6.94 (s, 1H), 7.85 (d, J=6.6 Hz, 1H), 7.89 (d, J=6.6 Hz, 1H), 8.37 (d, J=6.7 Hz, 1H), 8.38 (d, J=6.7 Hz, 1H), 9.17 (s, 1H), 9.19 (s, 1H), 12.80 (s, 1H), 12.96 (s, 1H), 14.91 (br s, 2H) ppm; MS (ion spray): m/z 361 (M+H). $C_{23}H_{25}ClN_4OS$ MS m/z: 441, 443.

The following compounds are prepared from starting materials obtained as described in Examples 69-71 using the methods described above.

| Example # | Name | m/z [M + H] |
| --- | --- | --- |
| 746 | 4-(6-Chloro-1H-benzoimidazol-2-ylmethyl)-1-(1H-pyrrolo[3,2-c]pyridin-2-ylmethyl)-piperazin-2-one | 395, 397 |
| 747 | 4-(5'-Chloro-[2,2']bithiophenyl-5-ylmethyl)-1-(1H-pyrrolo[3,2-c]pyridin-2-ylmethyl)-piperazin-2-one | 443, 445 |

-continued

| Example # | Name | m/z [M + H] |
|---|---|---|
| 748 | 4-[3-(5-Chloro-thiophen-2-yl)-allyl]-1-(1H-pyrrolo[3,2-c]pyridin-2-ylmethyl)-piperazin-2-one | 386, 388 |
| 749 | 4-(5-Chloro-1H-indol-2-ylmethyl)-1-(1H-pyrrolo[3,2-c]pyridin-2-ylmethyl)-piperazin-2-one | 394, 396 |
| 750 | 4-(6-Chloro-naphthalen-2-ylmethyl)-1-(1H-pyrrolo[3,2-c]pyridin-2-ylmethyl)-piperazin-2-one | 405, 407 |
| 751 | 4-(7-Chloro-isoquinolin-3-ylmethyl)-1-(1H-pyrrolo[3,2-c]pyridin-2-ylmethyl)-piperazin-2-one | 406, 408 |
| 752 | 4-(5'-Chloro-[2,2']bithiophenyl-5-ylmethyl)-6-oxo-1-(1H-pyrrolo[3,2-c]pyridin-2-ylmethyl)-piperazine-2-(±)-carboxylic acid methyl ester | 501, 503 |
| 753 | 1-(5-Chloro-1H-indol-2-ylmethyl)-5-oxo-4-(1H-pyrrolo[3,2-c]pyridin-2-ylmethyl)-piperazine-2-(±)-carboxylic acid methyl ester | 452, 454 |
| 754 | 1-[(5-Chloro-thiophen-2-yloxy)-acetyl]-5-oxo-4-(1H-pyrrolo[3,2-c]pyridin-2-ylmethyl)-piperazine-2-carboxylic acid methyl ester | 463, 465 |
| 755 | 1-(6-Chloro-benzo[b]thiophene-2-carbonyl)-5-oxo-4-(1H-pyrrolo[3,2-c]pyridin-2-ylmethyl)-piperazine-2-carboxylic acid methyl ester | 483, 485 |
| 756 | 1-[1-(3,5-Dichloro-phenyl)-2,5-dimethyl-1H-pyrrole-3-carbonyl]-5-oxo-4-(1H-pyrrolo[3,2-c]pyridin-2-ylmethyl)-piperazine-2-carboxylic acid methyl ester | 554, 556 |
| 757 | 1-(1H-Pyrrolo[3,2-c]pyridin-2-ylmethyl)-4-(1H-pyrrolo[2,3-c]pyridin-2-ylmethyl)-piperazin-2-one | 361 |
| 758 | 4-(3-Phenyl-prop-2-ynyl)-1-(1H-pyrrolo[3,2-c]pyridin-2-ylmethyl)-piperazin-2-one | 345 |
| 759 | 4-[3-(5-Chloro-thiophen-2-yl)-prop-2-ynyl]-1-(1H-pyrrolo[3,2-c]pyridin-2-ylmethyl)-piperazin-2-one | 384 |

The following compounds are prepared from 3-(S)-methoxymethyl-1-(1H-pyrrolo[3,2-c]pyridin-2-ylmethyl)-piperazin-2-one using the procedures described above.

| Example # | Name | m/z [M + H] |
|---|---|---|
| 760 | 4-[3-(5-Chloro-thiophen-2-yl)-allyl]-3-(S)-methoxymethyl-1-(1H-pyrrolo[3,2-c]pyridin-2-ylmethyl)-piperazin-2-one | 431, 433 |
| 761 | 4-(5-Chloro-1H-indol-2-ylmethyl)-3-(S)-methoxymethyl-1-(1H-pyrrolo[3,2-c]pyridin-2-ylmethyl)-piperazin-2-one | 438, 440 |
| 762 | 4-(5'-Chloro-[2,2']bithiophenyl-5-ylmethyl)-3-(S)-methoxymethyl-1-(1H-pyrrolo[3,2-c]pyridin-2-ylmethyl)-piperazin-2-one | 487, 489 |
| 763 | 4-(6-Chloro-benzo[b]thiophene-2-carbonyl)-3-(S)-methoxymethyl-1-(1H-pyrrolo[3,2-c]pyridin-2-ylmethyl)-piperazin-2-one | 469, 471 |
| 764 | 4-[1-(3,5-Dichloro-phenyl)-2,5-dimethyl-1H-pyrrole-3-carbonyl]-3-(S)-methoxymethyl-1-(1H-pyrrolo[3,2-c]pyridin-2-ylmethyl)-piperazin-2-one | 540, 542 |
| 765 | 4-[3-(4-Chloro-phenyl)-(E)-acryloyl]-3-(S)-methoxymethyl-1-(1H-pyrrolo[3,2-c]pyridin-2-ylmethyl)-piperazin-2-one | 439, 441 |
| 766 | (S)-2-Methoxymethyl-3-oxo-4-(1H-pyrrolo[3,2-c]pyridin-2-ylmethyl)-piperazine-1-carboxylic acid (4-chloro-phenyl)-amide | 428, 430 |
| 767 | (S)-4-[3-(5-Chloro-thiophen-2-yl)-(E)-acryloyl]-3-methoxymethyl-1-(1H-pyrrolo[3,2-c]pyridin-2-ylmethyl)-piperazin-2-one | 445, 447 |

EXAMPLE 768

4-(6-Chloro-benzo[b]thiophene-2-carbonyl)-1-(1H-pyrrolo[3,2-c]pyridin-2-ylmethyl)piperazin-2-one A. 2-[4-(6-Chloro-benzo[b]thiophene-2-carbonyl)-2-oxopiperazin-1-ylmethyl]-(pyrrolo[3,2-c]pyridin-1-carboxylic acid tert-butyl ester.

The title compound is prepared as described in EXAMPLE 123 using 6-chloro-benzo[b]thiophene-2-carboxylic acid, EXAMPLE 1 and 2-(2-oxopiperazin-1-ylmethyl)-pyrrolo[3,2-c]pyridin-1-carboxylic acid tert-butyl ester EXAMPLE 69. The mixture is stirred overnight, then concentrated to dryness. The residue is diluted with $CH_2Cl_2$ and washed with saturated sodium bicarbonate and brine. The organic layer is dried over $MgSO_4$, filtered and concentrated in vacuo to give the title compound as a solid. The crude material can be used in the subsequent step without further purification.

B. 4-(6-Chloro-benzo[b]thiophene-2-carbonyl)-1-(1H-pyrrolo[3,2-c]pyridin-2-ylmethyl)piperazin-2-one.

Trifluoroacetic acid (0.5 mL) is added dropwise to a solution of 2-[4-(6-chloro-benzo[b]thiophene-2-carbonyl)-2-oxopiperazin-1-ylmethyl]-(pyrrolo[3,2-c]pyridin-1-carboxylic acid tert-butyl ester (0.14 g, 0.27 mmol) in 6 mL $CH_2Cl_2$ at 0° C. After 1 h, the ice bath is removed and the solution stirred at room temperature for 2 hours. The reaction mixture is concentrated in vacuo. The crude residue is purified by RP-HPLC eluting in a gradient of 10% $CH_3CN/H_2O$ (0.1% TFA) to 100% $CH_3CN$ and the appropriate product fractions are combined and lyophilized to provide the title compound (0.07 g, 0.13 mmol) as a white solid. ESI MS, [M+H]+=425, 427 (Cl pattern).

The following compounds are prepared using starting materials obtained as described in Example 69 using the methods described above.

| Example # | Name | m/z [M + H] |
|---|---|---|
| 769 | 4-[3-(6-Chloro-benzo[b]thiophen-2-yl)-(E)-acryloyl]-1-(1H-pyrrolo[3,2-c]pyridin-2-ylmethyl)-piperazin-2-one | 451, 453 |
| 770 | 4-[(5-Chloro-thiophen-2-yloxy)-acetyl]-1-(1H-pyrrolo[3,2-c]pyridin-2-ylmethyl)-piperazin-2-one | 405, 407 |
| 771 | 4-[1-(3,5-Dichloro-phenyl)-2,5-dimethyl-1H-pyrrole-3-carbonyl]-1-(1H-pyrrolo[3,2-c]pyridin-2-ylmethyl)-piperazin-2-one | 497, 499 |
| 772 | 4-(5'-Chloro-[2,2']bithiophenyl-5-carbonyl)-1-(1H-pyrrolo[3,2-c]pyridin-2-ylmethyl)-piperazin-2-one | 457, 459 |
| 773 | 4-(5-Chloro-1H-indole-2-carbonyl)-1-(1H-pyrrolo[3,2-c]pyridin-2-ylmethyl)-piperazin-2-one | 364, 366 |
| 774 | 4-[4-(6-Methoxy-pyridin-3-yl)-benzoyl]-1-(1H-pyrrolo[3,2-c]pyridin-2-ylmethyl)-piperazin-2-one | 442 |
| 775 | 4-(4-Pyridin-3-yl-benzoyl)-1-(1H-pyrrolo[3,2-c]pyridin-2-ylmethyl)-piperazin-2-one | 412 |
| 776 | 4-[3-(4-Bromo-thiophen-2-yl)-(E)-acryloyl]-1-(1H-pyrrolo[3,2-c]pyridin-2-ylmethyl)-piperazin-2-one | 446 |
| 777 | 4-[3-(5-Chloro-thiophen-2-yl)-propionyl]-1-(1H-pyrrolo[3,2-c]pyridin-2-ylmethyl)-piperazin-2-one | 403, 405 |
| 778 | 4-[(5-Chloro-3-methyl-benzo[b]thiophen-2-yl)-acetyl]-1-(1H-pyrrolo[3,2-c]pyridin-2-ylmethyl)-piperazin-2-one | 453, 455 |
| 779 | 4-[2-(4-Chloro-phenyl)-2-methyl-propionyl]-1-(1H-pyrrolo[3,2-c]pyridin-2-ylmethyl)-piperazin-2-one | 411, 413 |
| 780 | 4-[3-(3,4-Dichloro-phenyl)-(E)-acryloyl]-1-(1H-pyrrolo[3,2-c]pyridin-2-ylmethyl)-piperazin-2-one | 431, 433 |
| 781 | 4-[(4-Chloro-phenyl)-acetyl]-1-(1H-pyrrolo[3,2-c]pyridin-2-ylmethyl)-piperazin-2-one | 383, 385 |
| 782 | 4-[3-(4-Chloro-phenyl)-(E)-acryloyl]-1-(1H-pyrrolo[3,2-c]pyridin-2-ylmethyl)-piperazin-2-one | 395, 397 |
| 783 | 4-[3-(5-Chloro-thiophen-2-yl)-(E)-acryloyl]-1-(1H-pyrrolo[3,2-c]pyridin-2-ylmethyl)-piperazin-2-one | 400, 402 |

EXAMPLE 784

(±)-1-(4-Amino-quinazolin-7-ylmethyl)-4-(5-chloro-1H-indol-2-ylmethyl)-6-oxo-piperazine-2-carboxylic acid methyl ester A. (±)-4-[3-(Benzhydrylidene-amino)-4-cyano-benzyl]-5-oxo-piperazine-1,3-dicarboxylic acid 1-allyl ester 3-methyl ester.

To a solution containing (S)-5-oxo-piperazine-1,3-dicarboxylic acid 1-allyl ester 3-methyl ester (0.43 g, 1.77 mmol), EXAMPLE 56, and 2-(benzhydrylidene-amino)-4-bromomethyl-benzonitrile (0.66 g, 1.77 mmol), EXAMPLE 13, in anhydrous DMF (5 mL) at 0° C. is added 60% NaH (78 mg, 1.95 mmol). After 30 min, the reaction mixture is warmed to ambient temperature and maintained for 6 hours. The reaction mixture is carefully quenched with water and then diluted with water and diethyl ether. The layers are separated and the organic phase is washed twice with water, brine, dried over anhydrous Na$_2$SO$_4$, filtered and concentrated. The crude residue is chromatographed on silica gel (2:1 hexane/ethyl acetate to 1:1 hexane/ethyl acetate) to provide 0.37 g (39%) of the title compound as a glassy solid.

$^1$H NMR (300 MHz, CDCl$_3$) δ3.01-3.22 (m, 2H), 3.58 (m, 2H), 3.73 (s, 3H), 3.86-3.92 (m, 1H), 4.42-4.58 (m, 4H), 5.25 (m, 2H), 5.93 (m, 1H), 6.57 (br s, 1H), 6.85 (d, J=8.2 Hz, 1H), 7.17-7.51 (m, 9H), 7.76 (m, 2H) ppm; MS (ion spray): m/z 537 (M+H).

B. (±)-1-[3-(Benzhydrylidene-amino)-4-cyano-benzyl]-6-oxo-piperazine-2-carboxylic acid methyl ester.

Tetrakis(triphenylphosphine)palladium(0) (237 mg, 0.2 mmol) is added to a solution containing (±)-4-[3-(benzhydrylidene-amino)-4-cyano-benzyl]-5-oxo-piperazine-1,3-dicarboxylic acid 1-allyl ester 3-methyl ester (1.10 g, 2.05 mmol) and morpholine (894 mg, 10.2 mmol) in CH$_2$Cl$_2$ (30 mL). After ~5 min, the reaction mixture is absorbed onto silica gel and chromatographed (CH$_2$Cl$_2$ to 10% MeOH/CH$_2$Cl$_2$) to provide 900 mg (97%) of the title compound as a viscous yellow oil. $^1$H NMR (300 MHz, CDCl$_3$) δ1.83 (br s, 1H), 2.95 (dd, J=13.5, 4.3 Hz, 1H), 3.27 (br d, J=13.5 Hz, 1H), 3.46-3.72 (m, 4H), 3.73 (s, 3H), 5.40 (d, J=15.3 Hz, 1H), 6.57 (br s, 1H), 6.83 (dd, J=8.0, 1.2 Hz, 1H), 7.17-7.50 (m, 9H), 7.75-7.77 (m, 2H) ppm; MS (ion spray): m/z 453 (M+H).

C. (±)-2-{4-[3-(Benzhydrylidene-amino)-4-cyano-benzyl]-3-methoxycarbonyl-5-oxo-piperazin-1-ylmethyl}-5-chloro-indole-1-carboxylic acid tert-butyl ester.

To a mixture of (±)-1-[3-(benzhydrylidene-amino)-4-cyano-benzyl]-6-oxo-piperazine-2-carboxylic acid methyl ester (630 mg, 1.39 mmol) and K$_2$CO$_3$ (380 mg, 2.78 mmol) in anhydrous CH$_3$CN (5 mL) at 0° C. is added 2-bromomethyl-5-chloro-indole-1-carboxylic acid tert-butyl ester (720 mg, 2.09 mmol), EXAMPLE 21, in CH$_3$CN (4 mL). The reaction mixture is allowed to warm to ambient temperature then maintained for 16 hours. The reaction mixture is diluted with diethyl ether/water and the layers are separated. The organic phase is washed twice with water, brine, dried over anhydrous Na$_2$SO$_4$, filtered and concentrated. The crude residue is chromatographed on silica (CH$_2$Cl$_2$ to 2% MeOH/CH$_2$Cl$_2$) to provide 550 mg (55%) of the title compound which is used directly in the next reaction without further characterization.

D. (±)-2-[4-(3-Amino-4-cyano-benzyl)-3-methoxycarbonyl-5-oxo-piperazin-1-ylmethyl]-5-chloro-indole-1-carboxylic acid tert-butyl ester.

Partially-purified (±)-2-{4-[3-(benzhydrylidene-amino)-4-cyano-benzyl]-3-methoxycarbonyl-5-oxo-piperazin-1-ylmethyl}-5-chloro-indole-1-carboxylic acid tert-butyl ester (550 mg, 0.76 mmol) is suspended in reagent grade MeOH (20 mL). To the heterogeneous mixture is added 12M HCl (5 drops) and the reaction mixture is maintained at ambient temperature until homogeneous (~30 min). The reaction mixture is partitioned between diethyl ether and water containing excess $NaHCO_3$ (500 mL). The layers are separated and the organic phase is washed with brine, dried over anhydrous $Na_2SO_4$, filtered and concentrated. The crude residue is chromatographed on silica gel ($CH_2Cl_2$ to 2% MeOH/$CH_2Cl_2$) to provide 400 mg (94%) of the title compound which is used directly in the next reaction. MS (ISP loop): 532 (M+H).

E. (±)-2-[4-(4-Amino-quinazolin-7-ylmethyl)-3-methoxycarbonyl-5-oxo-piperazin-1-ylmethyl]-5-chloro-indole-1-carboxylic acid tert-butyl ester.

A solution containing (±)-2-[4-(3-amino-4-cyano-benzyl)-3-methoxycarbonyl-5-oxo-piperazin-1-ylmethyl]-5-chloro-indole-1-carboxylic acid tert-butyl ester (100 mg, 0.18 mmol), 1,3,5-triazine (146 mg, 1.81 mmol), and glacial HOAc (99 mg, 1.81 mmol) in absolute EtOH (10 mL) is maintained at reflux for 16 hours. A second portion of 1,3,5-triazine (146 mg, 1.81 mmol) and glacial HOAc (99 mg, 1.81 mmol) is added and the reaction mixture is maintained at reflux for an additional 16 hours. The reaction mixture is concentrated in vacuo and the crude product is diluted with water/$CH_3CN$ and purified by reverse-phase HPLC [Buffer A: water w/0.1% TFA; Buffer B: $CH_3CN$ w/0.1% TFA; Gradient: 0% B to 60% B over 30 min] to provide 26 mg (20%) of the title compound as a white solid which is used directly in the next reaction without further characterization.

F. (±)-1-(4-Amino-quinazolin-7-ylmethyl)-4-(5-chloro-1H-indol-2-ylmethyl)-6-oxo-piperazine-2-carboxylic acid methyl ester.

To a solution containing (±)-2-[4-(4-amino-quinazolin-7-ylmethyl)-3-methoxycarbonyl-5-oxo-piperazin-1-ylmethyl]-5-chloro-indole-1-carboxylic acid tert-butyl ester (26 mg, 0.03 mmol) in $CH_2Cl_2$ (4 mL) is added trifluoroacetic acid (1 mL) at ambient temperature. After 4 h, the reaction mixture is concentrated in vacuo and then dissolved in water/$CH_3CN$ and purified by reverse-phase HPLC [Buffer A: water w/0.1% TFA; Buffer B: $CH_3CN$ w/0.1% TFA; Gradient: 0% B to 60% B over 30 min] to provide 10 mg (47%) of the title compound as a white solid. $^1$H NMR (300 MHz, $d_6$-DMSO) δ2.62 (m, 1H), 3.05-3.51 (m, 4H), 3.59 (s, 3H), 3.81 (d, J=14.0 Hz, 1H), 4.26 (m, 1H), 4.69 (ABq, $\Delta_{AB}$=310 Hz, $J_{AB}$=16.4 Hz, 2H), 6.26 (s, 1H), 7.02 (dd, J=8.6, 2.0 Hz, 1H), 7.31 (d, J=8.6 Hz, 1H), 7.49 (d, J=2.0 Hz, 1H), 7.52 (s, 1H), 7.61 (d, J=8.7 Hz, 1H), 8.30 (d, J=8.6 Hz, 1H), 8.47 (s, 1H), 8.77 (s, 1H), 9.69 (br s, 2H), 11.17 (s, 1H) ppm; MS (ion spray): m/z 479 (M+H).

EXAMPLE 785

(±)-1-(4-Amino-quinazolin-7-ylmethyl)-4-(5-chloro-1H-indol-2-ylmethyl)-6-oxo-piperazine-2-carboxylic acid.

A. (±)-1-(3-Amino-4-cyano-benzyl)-4-(5-chloro-1H-indol-2-ylmethyl)-6-oxo-piperazine-2-carboxylic acid.

LiOH monohydrate (380 mg, 9.06 mmol) is added at ambient temperature to a solution containing (±)-2-[4-(3-amino-4-cyano-benzyl)-3-methoxycarbonyl-5-oxo-piperazin-1-ylmethyl]-5-chloro-indole-1-carboxylic acid tert-butyl ester (1.0 g, 1.81 mmol), EXAMPLE 784, Part E, in 1:1:1 THF/MeOH/water (30 mL). After 16 h, HOAc (0.5 mL) is added and the reaction mixture is concentrated in vacuo. The residue is dissolved in $CH_3CN$/water and purified by reverse-phase HPLC [Buffer A: water w/0.1% TFA; Buffer B: $CH_3CN$ w/0.1% TFA; Gradient: 0% B to 60% B over 30 min] to provide 378 mg (48%) of the title compound as a white solid. $^1$H NMR (300 MHz, $d_6$-DMSO) δ3.03 (m, 1H), 3.48 (m, 1H), 3.51 (ABq, $\Delta_{AB}$=69.2 Hz, $J_{AB}$=16.4 Hz, 2H), 3.78 (d, J=15.9 Hz, 1H), 4.05-4.09 (m, 2H), 5.04 (d, J=15.9 Hz, 1H), 6.41 (m, 2H), 6.58 (s, 1H), 7.04 (dd, J=8.6, 2.0 Hz, 1H), 7.25 (d, J=8.0 Hz, 1H), 7.35 (d, J=8.6 Hz, 1H), 7.51, d, J=2.0 Hz, 1H) ppm; MS (ISP loop): m/z 438 (M+H).

B. (±)-1-(4-Amino-quinazolin-7-ylmethyl)-4-(5-chloro-1H-indol-2-ylmethyl)-6-oxo-piperazine-2-carboxylic acid A solution containing (±)-1-(3-amino-4-cyano-benzyl)-4-(5-chloro-1H-indol-2-ylmethyl)-6-oxo-piperazine-2-carboxylic acid (200 mg, 0.30 mmol), 1,3,5-triazine (244 mg, 3.00 mmol), and glacial HOAc (180 mg, 3.00 mmol) in absolute EtOH (20 mL) is maintained at reflux for 16 hours. The reaction mixture is cooled to ambient temperature and the solid is collected on a Buchner funnel and washed with EtOH followed by diethyl ether. Oven-drying in vacuo provided 13 mg (76%) of the title compound as an off-white solid. $^1$H NMR (300 MHz, $d_6$-DMSO) δ2.63 (m, 1H), 3.06 (d, J=16.4 Hz, 1H), 3.24-3.42 (m, 4H), 3.68 (ABq, $\Delta_{AB}$=34.5 Hz, $J_{AB}$=14.1 Hz, 2H), 3.96 (m, 1H), 4.63 (ABq, $\Delta_{AB}$=400 Hz, $J_{AB}$=15.8 Hz, 2H), 6.27 (s, 1H), 6.99 (dd, J=8.6, 2.0 Hz, 1H), 7.29 (d, J=8.5 Hz, 2H), 7.40 (s, 1H), 7.46 (s, 1H), 7.69 (br s, 2H), 8.10 (d, J=8.5 Hz, 1H), 8.32 (s, 1H), 11.20 (s, 1H) ppm; MS (ion spray): m/z 465 (M+H).

EXAMPLE 786

(±)-1-(4-Amino-quinazolin-7-ylmethyl)-4-(5-chloro-1H-indol-2-ylmethyl)-6-oxo-piperazine-2-carboxylic acid methylamide To a solution containing (±)-1-(4-amino-quinazolin-7-ylmethyl)-4-(5-chloro-1H-indol-2-ylmethyl)-6-oxo-piperazine-2-carboxylic acid (25 mg, 0.03 mmol), EXAMPLE 785, and N-methylmorpholine (36 mg, 0.36 mmol) in anhydrous DMF (1 mL) is added methylamine hydrochloride (10 mg, 0.14 mmol) followed by HATU (40 mg, 0.10 mmol) at ambient temperature. After 3 h, the solvent is removed under high vacuum and the residue is dissolved in $CH_3CN$/water and purified by reverse-phase HPLC [Buffer A: water w/0.1% TFA; Buffer B: $CH_3CN$ w/0.1% TFA; Gradient: 0% B to 60% B over 30 min] to provide 22 mg (88%) of the title compound as a white solid.

$^1$H NMR (300 MHz, $d_6$-DMSO) δ2.57 (d, J=4.4 Hz, 3H), 2.70 (m, 1H), 3.0 (m, 1H), 3.66 (d, J=14.2 Hz, 1H), 3.77 (d, J=14.2 Hz, 1H), 3.85 (m, 1H), 4.03 (d, J=16.3 Hz, 1H), 5.18 (d, J=16.3 Hz, 1H), 6.28 (s, 1H), 7.02 (dd, J=8.5, 2.0 Hz, 1H), 7.31 (d, J=8.5 Hz, 1H), 7.49 (d, J=2.0 Hz, 1H), 7.51 (s, 1H), 7.58 (d, J=8.6 Hz, 1H), 7.97 (m, 1H), 8.31 (d, J=8.6 Hz, 1H), 8.79 (s, 1H), 9.72 (br s, 2H), 11.18 (s, 1H) pm; MS (ISP loop): m/z 478 (M+H).

TABLE 1

Amide Analogs Derived From C-6 Carboxylic Acid.

| Example # | Name | m/z [M + H] |
| --- | --- | --- |
| 787 | (+/−)-1-(4-Amino-quinazolin-7-ylmethyl)-4-(5-chloro-1H-indol-2-ylmethyl)-6-oxo-piperazine-2-carboxylic acid ethylamide | 492 |
| 788 | (+/−)-1-(4-Amino-quinazolin-7-ylmethyl)-4-(5-chloro-1H-indol-2-ylmethyl)-6-oxo-piperazine-2-carboxylic acid dimethylamide | 492 |
| 789 | (+/−)-1-(4-Amino-quinazolin-7-ylmethyl)-4-(5-chloro-1H-indol-2-ylmethyl)-6-oxo-piperazine-2-carboxylic acid benzylamide | 554 |
| 790 | (+/−)-1-(4-Amino-quinazolin-7-ylmethyl)-4-(5-chloro-1H-indol-2-ylmethyl)-6-oxo-piperazine-2-carboxylic acid (2-hydroxy-ethyl)-amide | 508 |
| 791 | (+/−)-1-(4-Amino-quinazolin-7-ylmethyl)-4-(5-chloro-1H-indol-2-ylmethyl)-6-oxo-piperazine-2-carboxylic acid bis-(2-hydroxy-ethyl)-amide | 552 |
| 792 | (+/−)-1-(4-Amino-quinazolin-7-ylmethyl)-4-(5-chloro-1H-indol-2-ylmethyl)-6-(morpholine-4-carbonyl)-piperazin-2-one | 534 |
| 793 | (+/−)-1-(4-Amino-quinazolin-7-ylmethyl)-4-(5-chloro-1H-indol-2-ylmethyl)-6-oxo-piperazine-2-carboxylic acid methylcarbamoylmethyl-amide | 535 |

The following compounds are prepared using the procedures described above.

| Example # | Name | m/z [M + H] |
| --- | --- | --- |
| 794 | (+/−)-1-(4-Amino-quinazolin-7-ylmethyl)-4-[3-(5-chloro-thiopben-2-yl)-allyl]-6-oxo-piperazine-2-carboxylic acid | 458 |
| 795 | (+/−)-1-(4-Amino-quinazolin-7-ylmethyl)-4-[3-(5-chloro-thiophen-2-yl)-allyl]-6-oxo-piperazine-2-carboxylic acid methyl ester | 472 |
| 796 | (+/−)-1-(4-Amino-quinazolin-7-ylmethyl)-4-[3-(5-chloro-thiophen-2-yl)-allyl]-6-oxo-piperazine-2-carboxylic acid amide | 457 |
| 797 | (+/−)-1-(4-Amino-quinazolin-7-ylmethyl)-4-[3-(5-chloro-thiophen-2-yl)-allyl]-6-oxo-piperazine-2-carboxylic acid ethylamide | 458 |
| 798 | (+/−)-1-(4-Amino-quinazolin-7-ylmethyl)-4-[3-(5-chloro-thiophen-2-yl)-allyl]-6-(4-methyl-piperazine-1-carbonyl)-piperazin-2-one | 540 |

EXAMPLE 799

(±)-1-(4-Amino-quinazolin-7-ylmethyl)-4-(6-chloro-benzo[b]thiophene-2-sulfonyl)-6-oxo-piperazine-2-carboxylic acid methyl ester A solution containing (±)-1-(3-amino-4-cyano-benzyl)-4-(6-chloro-benzo[b]thiophene-2-sulfonyl)-6-oxo-piperazine-2-carboxylic acid methyl ester (42 mg, 0.08 mmol), EXAMPLE 99, 1,3,5-triazine (40 mg, 0.48 mmol), and glacial HOAc (30 mg, 0.48 mmol) in absolute EtOH (1 mL) is maintained at reflux for 16 hours. The reaction mixture is concentrated and then dissolved in water/CH$_3$CN and purified by reverse-phase HPLC [Buffer A: water w/0.1% TFA; Buffer B: CH$_3$CN w/0.1% TFA; Gradient: 0% B to 60% B over 30 min] to provide 17 mg (32%) of the title compound as a white solid.

$^1$H NMR (300 MHz, d$_6$-DMSO) δ3.47 (m, 1H), 3.67 (s, 3H), 3.71 (d, J=16.1 Hz, 1H), 4.00 (d, J=16.5 Hz, 1H), 4.05 (m, 1H), 4.52 (m, 1H), 4.72 (ABq, $\Delta_{AB}$=248 Hz, $J_{AB}$=16.5 Hz, 2H), 7.57 (m, 2H), 8.05 (d, J=8.6 Hz, 1H), 8.20 (s, 1H), 8.23 (d, J=8.5 Hz, 1H), 8.35 (d, J=1.9 Hz, 1H), 8.49 (s, 1H), 8.72 (s, 1H), 9.57 (br s, 2H) ppm; MS (ion spray): m/z 546 (M+H).

EXAMPLE 800

(±)-1-(4-Amino-quinazolin-7-ylmethyl)-4-(6-chloro-benzo[b]thiophene-2-sulfonyl)-6-oxo-piperazine-2-carboxylic acid Water (1 mL) is added to a solution containing (±)-1-(4-amino-quinazolin-7-ylmethyl)-4-(6-chloro-benzo[b]thiophene-2-sulfonyl)-6-oxo-piperazine-2-carboxylic acid methyl ester (20 mg, 0.03 mmol), EXAMPLE 799, in a 1:1 mixture of THF/MeOH (2 mL). At ambient temperature, LiOH monohydrate (15 mg, 0.35 mmol) is then added. After 16 h, the reaction mixture is diluted with water and purified by reverse-phase HPLC [Buffer A: water w/0.1% TFA; Buffer B: CH3CN w/0.1% TFA; Gradient: 0% B to 60% B over 30 min] to provide 12 mg (63%) of the title compound as a white solid.

$^1$H NMR (300 MHz, d$_6$-DMSO) δ3.69 (d, J=16.0 Hz, 1H), 3.97 (d, J=16.0 Hz, 1H), 4.08 (d, J=11.7 Hz 1H), 4.18 (d, J=16.2 Hz, 1H), 4.31 (d, J=2.7 Hz, 1H), 5.20 (d, J=16.2 Hz, 1H), 7.47 (d, J=8.7 Hz, 1H), 7.52 (s, 1H), 7.58 (dd, J=8.6, 1.9 Hz, 1H), 8.06 (d, J=8.7 Hz, 1H), 8.16 (d, J=8.6 Hz, 1H), 8.19

(s, 1H), 8.34 (d, J=1.9 Hz, 1H), 8.54 (s, 1H), 8.77 (br s, 1H) ppm; MS (ion spray): m/z 532 (M+H).

EXAMPLE 801

(±)-1-(4-Amino-quinazolin-7-ylmethyl)-4-(6-chloro-benzo[b]thiophene-2-sulfonyl)-6-oxo-piperazine-2-carboxylic acid amide To a mixture containing (±)-1-(4-amino-quinazolin-7-ylmethyl)-4-(6-chloro-benzo[b]thiophene-2-sulfonyl)-6-oxo-piperazine-2-carboxylic acid (45 mg, 0.08 mmol), EXAMPLE 800, N-methylmorpholine (18 mg, 0.18 mmol), and HATU (35 mg, 0.09 mmol) in anhydrous DMF (1 mL) is added $NH_3$ (7N in MeOH, 2 drops, approx. 0.5 mmol). The heterogeneous mixture is stirred 16 h at ambient temprature and then concentrated to dryness. The residue is dissolved in water and purified by reverse-phase HPLC [Buffer A: water w/0.1% TFA; Buffer B: CH3CN w/0.1% TFA; Gradient: 0% B to 60% B over 30 min] to provide 25 mg (46%) of the title compound as a white solid. $^1$H NMR (300 MHz, $d_6$-DMSO) δ3.63 (d, J=16.0 Hz, 1H), 4.01 (m, 4H), 5.17 (d, J=16.6 Hz, 1H), 7.58 (m, 3H), 8.08 (d, J=8.6 Hz, 1H), 8.17 (s, 1H), 8.26 (d, J=8.6 Hz, 1H), 8.34 (d, J=1.9 Hz, 1H), 8.74 (s, 1H), 9.63 (br s, 2H) ppm; MS (ISP loop): m/z 531 (M+H).

The following compounds are prepared using the procedures described above.

phase is washed four times with $CH_2Cl_2$ (100 mL) and the combined organic phase is washed once with brine, dried over anhydrous $Na_2SO_4$, filtered and concentrated. The crude amide is purified by flash silica gel chromatography (hexane/EtOAc, 4:1 to 1:2) to afford 1.5 g of the title compound which is used directly in the next reaction. $^1$H NMR (300 MHz, $CDCl_3$, ~2:1 mixture of rotomers) major rotomer: δ3.55 (d, J=15.2 Hz, 1H), 3.60 (m, 1H), 3.69 (m, 5H), 4.37 (d, J=17.7 Hz, 1H), 4.62 (m, 2H), 4.79 (d, J=13.3 Hz, 1H), 5.35 (d, J=15.2 Hz, 1H), 6.05 (d, J=3.9 Hz, 1H), 6.52 (m. 2H), 6.84 (d, J=8.1 Hz, 1H), 7.18-7.49 (m, 11H), 7.76 (m, 1H) ppm; MS (ISP loop): m/z 627 (M+H).

B.  (±)-1-3-Amino-4-cyano-benzyl)-4-[(5-chloro-thiophen-2-yloxy)-acetyl]-6-oxo-piperazine-2-carboxylic acid methyl ester.

Concentrated HCl (12M, 0.5 mL) is added at 0° C. to a solution containing (±)-1-[3-(benzhydrylidene-amino)-4-cyano-benzyl]-4-[(5-chloro-thiophen-2-yloxy)-acetyl]-6-oxo-piperazine-2-carboxylic acid methyl ester (1.5 g, 2.39 mmol) in 4:1 MeOH/THF (25 mL). After 1.5 h, the reaction mixture is concentrated to dryness and then partitioned between a 1:1 mixture of EtOAc/aqueous $NaHCO_3$ (200 mL) and the layers are separated. The aqueous phase is extracted with EtOAc and then the combined organic phase is washed with brine, dried over anhydrous $Na_2SO_4$, filtered and concentrated. The crude residue is chromatographed on silica gel (hexane/EtOAc, 4:1

| Example # | Name | m/z [M + H] |
|---|---|---|
| 802 | (+/−)-1-(4-Amino-quinazolin-7-ylmethyl)-4-(6-chloro-benzo[b]thiophene-2-sulfonyl)-6-oxo-piperazine-2-carboxylic acid ethyl ester | 560 |
| 803 | (+/−)-1-(4-Amino-quinolin-7-ylmethyl)-4-(6-chloro-benzo[b]thiophene-2-sulfonyl)-6-oxo-piperazine-2-carboxylic acid | 531 |
| 804 | (+/−)-1-(4-Amino-quinolin-7-ylmethyl)-4-(6-chloro-benzo[b]thiophene-2-sulfonyl)-6-oxo-piperazine-2-carboxylic acid methylamide | 544 |
| 805 | (+/−)-1-(4-Amino-quinolin-7-ylmethyl)-4-(6-chloro-benzo[b]thiophene-2-sulfonyl)-6-oxo-piperazine-2-carboxylic acid ethylamide | 558 |
| 806 | (+/−)-1-(4-Amino-quinolin-7-ylmethyl)-4-(6-chloro-benzo[b]thiophene-2-sulfonyl)-6-oxo-piperazine-2-carboxylic acid dimethylamide | 558 |
| 807 | (+/−)-1-(4-Amino-quinolin-7-ylmethyl)-4-(6-chloro-benzo[b]thiophene-2-sulfonyl)-6-(morpholine-4-carbonyl)-piperazin-2-one | 600 |

EXAMPLE 808

(±)-1-(4-Amino-quinazolin-7-ylmethyl)-4-[(5-chloro-thiophen-2-yloxy)-acetyl]-6-oxo-piperazine-2-carboxylic acid methyl ester A.  (±)-1-[3-(Benzhydrylidene-amino)-4-cyano-benzyl]-4-[(5-chloro-thiophen-2-yloxy)-acetyl]-6-oxo-piperazine-2-carboxylic acid methyl ester.

To a solution containing (±)-1-[3-(benzhydrylidene-amino)-4-cyano-benzyl]-6-oxo-piperazine-2-carboxylic acid methyl ester (1.17 g, 2.6 mmol), EXAMPLE 784, Part B, 5-chlorothiophen-2-yloxyacetic acid (0.5 g, 2.6 mmol), EXAMPLE 24, and N-methylmorpholine (0.58 g, 5.72 mmol) in anhydrous DMF (10 mL) is added HATU (1.09 g, 2.86 mmol) at ambient temperature. After 1.5 h, the reaction mixture is diluted with $CH_2Cl_2$ (100 mL) and aqueous $NaHCO_3$ (100 mL) and the layers are separated. The aqueous to 1:2) to provide 934 mg (84%, two steps) of the title compound. $^1$H NMR (300 MHz, $CDCl_3$, ~2:1 mixture of rotomers) selected peaks: δ3.16 (app. dd, J 14.0, 3.8 Hz, 1H), 3.68 (s, 3H), 3.96 (app. dd, J=3.8, 2.0 Hz, 1H), 4.17 (d, J=17.7 Hz, 1H), 4.45 (br s, 2H), 4.62 (m, 2H), 4.87 (d, J=14.1 Hz, 1H), 5.21 (d, J=15.1 Hz, 1H), 6.07 (m, 1H), 6.51 (d, J=3.8 Hz, 1H), 6.57 (d, J=7.9 Hz, 1H), 6.62 (br s, 1H), 7.35 (d, J=7.9 Hz, 1H) ppm; MS (ISP loop): m/z 463 (M+H).

C.  (±)-1-(4-Amino-quinazolin-7-ylmethyl)-4-[(5-chloro-thiophen-2-yloxy)-acetyl]-6-oxo-piperazine-2-carboxylic acid methyl ester.

A solution containing (±)-1-(3-amino-4-cyano-benzyl)-4-[(5-chloro-thiophen-2-yloxy)-acetyl]-6-oxo-piperazine-2-carboxylic acid methyl ester (110 mg, 0.25 mmol), 1,3,5-triazine (207 mg, 2.55 mmol), and glacial HOAc (157 mg, 2.55 mmol) in absolute EtOH (5 mL) is maintained at reflux for 16 hours. The reaction mixture is concentrated to dryness and then purified by reverse-phase HPLC [Buffer A: water w/0.1% TFA; Buffer B: CH3CN w/0.1% TFA; Gradient: 0%

B to 60% B over 30 min] to provide 50 mg (32%) of the title compound as a white solid. $^1$H NMR (300 MHz, d$_6$-DMSO) δ3.34-3.89 (m, 2H), 3.60 (s, 3H), 4.14-4.54 (m, 3H), 4.64 (br d, J=14.4 Hz, 1H), 4.78-5.11 (m, 3H), 6.19 (d, J=4.1 Hz, 1H), 6.73 (d, J=4.1 Hz, 1H), 7.64 (s, 1H), 7.65 (d, J=9.0 Hz, 1H), 8.34 (d, J=9.0 Hz, 1H), 8.79 (s, 1H), 9.71 (br s, 2H) ppm; MS (ion spray): m/z 490 (M+H).

EXAMPLE 809

(±)-1-(4-Amino-quinazolin-7-ylmethyl)-4-[(5-chloro-thiophen-2-yloxy)-acetyl]-6-oxo-piperazine-2-carboxylic acid methylamide Water (1 mL) is added to a solution containing (±)-1-(4-amino-quinazolin-7-ylmethyl)-4-[(5-chloro-thiophen-2-yloxy)-acetyl]-6-oxo-piperazine-2-carboxylic acid methyl ester (20 mg, 0.03 mmol), EXAMPLE 808, in a 1:1 mixture of THF/MeOH (2 mL). At ambient temperature, LiOH monohydrate (3 mg, 0.07 mmol) is then added. After 16 h, the reaction mixture is diluted with water and purified by reverse-phase HPLC [Buffer A: water w/0.1% TFA; Buffer B: CH3CN w/0.1% TFA; Gradient: 0% B to 60% B over 30 min] to provide 25 mg (>100%) of the associated acid as a white solid after lyophilization which is used directly in the next reaction. To a mixture containing (+/−)-1-(4-amino-quinazolin-7-ylmethyl)-4-[(5-chloro-thiophen-2-yloxy)-acetyl]-6-oxo-piperazine-2-carboxylic acid (12 mg, 0.02 mmol), N-methylmorpholine (19 mg, 0.19 mmol), and HATU (22 mg, 0.05 mmol) in anhydrous DMF (1 mL) is added MeNH$_2$ hydrochloride (5 mg, 0.19 mmol). The reaction mixture is stirred 1 h at ambient temperature and then concentrated to dryness. The residue is dissolved in water and purified by reverse-phase HPLC [Buffer A: water w/0.1% TFA; Buffer B: CH3CN w/0.1% TFA; Gradient: 0% B to 60% B over 30 min] to provide 7 mg (58%) of the title compound as a white solid.

$^1$H NMR (300 MHz, d$_6$-DMSO) mixture of rotamers: δ2.51 (m, 3H), 4.07-4.54 (m, 6H), 4.87 (m, 2H), 5.10 (m, 1H), 6.18 (m, 1H), 6.74 (m, 1H), 7.62 (m, 2H), 8.06 (br s, 1H), 8.32 (br d, J=8.8 Hz, 1H), 8.78 (s, 1H), 9.61 (br s, 2H) ppm; MS (ISP loop): 489 (M+H).

The following compound is prepared using the procedures described above.

| Example # | Name | m/z [M + H] |
|---|---|---|
| 810 | (+/−)-1-(4-Amino-quinazolin-7-ylmethyl)-4-[(5-chloro-thiophen-2-yloxy)-acetyl]-6-oxo-piperazine-2-carboxylic acid ethylamide | 503 |

EXAMPLE 811

(+/−)-1-(4-Amino-quinazolin-7-ylmethyl)-4-[(5-chloro-thiophen-2-yloxy)-acetyl]-6-oxo-piperazine-2-carboxylic acid Water (0.5 mL) is added to a solution containing (±)-1-(3-amino-4-cyano-benzyl)-4-[(5-chloro-thiophen-2-yloxy)-acetyl]-6-oxo-piperazine-2-carboxylic acid methyl ester (35 mg, 0.08 mmol), EXAMPLE 808, Part B, in a 1:1 mixture of THF/MeOH (1 mL). At ambient temperature, LiOH monohydrate (4 mg, 0.10 mmol) is then added. After 16 h, an additional portion of LiOH monohydrate (4 mg, 0.10 mmol) is added and the reaction mixture is stirred for another 2 h then diluted with water and purified by reverse-phase HPLC [Buffer A: water w/0.1% TFA; Buffer B: CH3CN w/0.1% TFA; Gradient: 0% B to 60% B over 30 min] to provide 40 mg (95%) of the associated acid as a white solid after lyophilization which is used directly in the next reaction. MS (ISP loop): m/z 449 (M+H).

A solution containing (+/−)-1-(3-amino-4-cyano-benzyl)-4-[(5-chloro-thiophen-2-yloxy)-acetyl]-6-oxo-piperazine-2-carboxylic acid (20 mg, 0.03 mmol), 1,3,5-triazine (28 mg, 0.34 mmol), and glacial HOAc (20 mg, 0.34 mmol) in absolute EtOH (6 mL) is maintained at reflux for 16 hours. The reaction mixture is concentrated to dryness and then purified by reverse-phase HPLC [Buffer A: water w/0.1% TFA; Buffer B: CH3CN w/0.1% TFA; Gradient: 0% B to 60% B over 30 min] to provide 15 mg (75%) of the title compound as a white solid. $^1$H NMR (300 MHz, d$_6$-DMSO) δ3.75-4.38 (m, 5H), 4.67 (d, J=14.8 Hz, 1H), 4.79 (d, J=15.3 Hz, 1H), 4.95 (m, 1H), 5.09 (br d, J=16.0 Hz, 1H), 6.18 (m, 1H), 6.71 (m, 1H), 7.64 (m, 2H), 8.31 (d, J=8.5 Hz, 1H), 8.75 (s, 1H), 9.64 (br s, 2H) ppm; MS (ISP loop): m/z 476 (M+H).

EXAMPLE 812

4-Prop-2-ynyl-1-(1H-pyrrolo[3,2-c]pyridin-2-ylmethyl)-piperazin-2-one

A. 2-(2-Oxo-4-prop-2-ynyl-piperazin-1-ylmethyl)-pyrrolo[3,2-c]pyridine-1-carboxylic acid tert-butyl ester.

A solution containing 2-(2-oxo-piperazin-1-ylmethyl)-pyrrolo[3,2-c]pyridine-1-carboxylic acid tert-butyl ester (4.3 g, 13.0 mmol), EXAMPLE 69, in CH$_3$CN (250 mL) is cooled to 0° C. Potassium carbonate (1.98 g, 14.3 mmol) is added to the reaction mixture followed by propargyl bromide (1.55 g, 13.0 mmol). The mixture is slowly warmed to ambient temperature and maintained until complete consumption of starting material is observed by TLC (approx. 8 h). The mixture is concentrated to dryness and then partitioned between aqueous NaHCO$_3$ (200 mL) and CH$_2$Cl$_2$ (200 mL) and the layers are separated. The aqueous phase is extracted twice with CH$_2$Cl$_2$ (100 mL) and the combined organic phase is washed with brine, dried over anhydrous Na$_2$SO$_4$, filtered and concentrated. The crude residue is purified by flash silica gel chromatography (CH$_2$Cl$_2$ to 5% MeOH/CH$_2$Cl$_2$) to provide 3.38 g (70%) of the title compound as a pale yellow solid. $^1$H NMR (300 MHz, CDCl$_3$) δ1.69 (s, 9H), 2.34 (t, J=2.4 Hz, 1H), 2.89 (m, 2H), 3.42 (s, 2H), 3.45 (d, J=2.4 Hz, 2H), 3.52 (m, 2H), 4.95 (d, J=1.4 Hz, 2H), 6.42 (br s, 1H), 7.88 (dd, J=5.8, 0.8 Hz, 1H), 8.41 (d, J=5.8 Hz, 1H), 8.78 (d, J=0.8 Hz, 1H) ppm; MS (EI): m/z 368 (M+).

B. 4-Prop-2-ynyl-1-(1H-pyrrolo[3,2-c]pyridin-2-ylmethyl)-piperazin-2-one.

To a solution containing 2-(2-oxo-4-prop-2-ynyl-piperazin-1-ylmethyl)-pyrrolo[3,2-c]pyridine-1-carboxylic acid tert-butyl ester (1.3 g, 3.53 mmol) in CH$_2$Cl$_2$ (100 mL) is added TFA (20 mL) at 0° C. After 6 h, the reaction mixture is concentrated to dryness and then partitioned between aqueous NaHCO$_3$ (500 mL) and CH$_2$Cl$_2$ (200 mL) and the layers are separated. The aqueous phase is extracted four times with CH$_2$Cl$_2$ (100 mL) and the combined organic phase is washed with brine, dried over anhydrous Na$_2$SO$_4$, filtered and concentrated. The crude residue is purified by flash silica gel chromatography (CH$_2$Cl$_2$ to 10% MeOH/CH$_2$Cl$_2$) to provide 616 mg (65%) of the title compound as a pale yellow solid.

$^1$H NMR (300 MHz, CDCl$_3$) δ2.27 (app t, J=2.4 Hz, 1H), 2.76 (m, 2H), 3.33 (s, 2H), 3.83 (d, J=2.4 Hz, 2H), 3.45 (m, 2H), 4.57 (s, 2H), 6.47 (s, 1H), 7.23 (d, J=5.7 Hz, 1H), 8.28 (d, J=5.7 Hz, 1H), 8.85 (d, J=0.9 Hz, 1H), 9.34 (br s, 1H) ppm; MS (EI): m/z 268 (M+).

EXAMPLE 813

1,4-Bis-(1H-pyrrolo[3,2-c]pyridin-2-ylmethyl)-piperazin-2-one

A. 2-{4-[3-(4-tert-Butoxycarbonylamino-pyridin-3-yl)-prop-2-ynyl]-2-oxo-piperazin-1-ylmethyl}-pyrrolo[3,2-c]pyridine-1-carboxylic acid tert-butyl ester.

A solution containing 2-(2-oxo-4-prop-2-ynyl-piperazin-1-ylmethyl)-pyrrolo[3,2-c]pyridine-1-carboxylic acid tert-butyl ester (100 mg, 0.27 mmol), EXAMPLE 812, (3-iodo-pyridin-4-yl)-carbamic acid tert-butyl ester (87 mg, 0.27 mmol), EXAMPLE 69, Part B, Et$_3$N (110 mg, 1.08 mmol), (Ph$_3$P)$_4$PdCl$_2$ (10 mg, 0.013 mmol), and CuI (1 mg, 0.008 mmol) in anhydrous DMF (5 mL) is stired at ambient temperature. After 5 h, the reaction mixture is diluted with EtOAc (50 mL) and water (50 mL) and the layers are separated. The aqueous layer is extracted twice with EtOAc (25 mL) and the combined organic phase is washed with brine, dried over anhydrous Na$_2$SO$_4$, filtered and concentrated. The crude residue is purified by flash silica gel chromatography (CH$_2$Cl$_2$ to 10% MeOH CH$_2$Cl$_2$) to provide 77 mg (51%) of the title compound as a colorless oil. $^1$H NMR (300 MHz, CDCl$_3$, ~2:1 mixture of rotamers) major rotamer: δ1.53 (s, 9H), 1.69 (s, 9H), 2.98 (m, 2H), 3.49 (s, 2H), 3.56 (m, 2H), 3.78 (s, 2H), 4.98 (s, 2H), 6.43 (s, 1H), 7.89 (m, 1H), 8.09 (m, 2H), 8.34 (m, 1H), 8.41 (m, 1H), 8.75 (m, 1H) ppm; MS (ISP loop): m/z 561 (M+H).

B. 2-[4-(1-tert-Butoxycarbonyl-1H-pyrrolo[3,2-c]pyridin-2-ylmethyl)-2-oxo-piperazin-1-ylmethyl]-pyrrolo[3,2-c]piperidine-1-carboxylic acid tert-butyl ester.

1,8-Diazabicyclo[5.4.0]undec-7-ene (42 mg, 0.27 mmol) is added to a suspension containing 2-{4-[3-(4-tert-butoxycarbonylamino-pyridin-3-yl)-prop-2-ynyl]-2-oxo-piperazin-1-ylmethyl}-pyrrolo[3,2-c]pyridine-1-carboxylic acid tert-butyl ester (77 mg, 0.14 mmol) in anhydrous CH$_3$CN (10 mL) and the mixture is warmed to 50° C. After 4 h, the reaction mixture is concentrated to dryness and the residue is partitioned between CH$_2$Cl$_2$ (50 mL) and water (50 mL) and the layers are separated. The aqueous layer is extracted twice with CH$_2$Cl$_2$ (25 mL) and the combined organic phase is washed with brine, dried over anhydrous Na$_2$SO$_4$, filtered and concentrated to provide 85 mg of the title compound as a crude solid which is used directly without further purification. $^1$H NMR (300 MHz, CDCl$_3$) δ1.68 (s, 9H), 1.70 (s, 9H), 2.91 (m, 2H), 3.41 (s, 2H), 3.49 (m, 2H), 4.26 (s, 2H), 4.95 (d, J=1.1 Hz, 2H), 6.39 (d, J=0.7 Hz, 1H), 6.68 (d, J=0.7 Hz, 1H), 7.86 (m, 1H), 8.41 (m, 1H), 8.76 (br s, 1H), 8.82 (br s, 1H) ppm: MS (EI): m/z 561 (M+H).

C. 1,4-Bis-(1H-pyrrolo[3,2-c]pyridin-2-ylmethyl)-piperazin-2-one.

To a solution containing 2-[4-(1-tert-Butoxycarbonyl-1H-pyrrolo[3,2-c]pyridin-2-ylmethyl)-2-oxo-piperazin-1-ylmethyl]-pyrrolo[3,2-c]pyridine-1-carboxylic acid tert-butyl ester (85 mg, 0.14 mmol) in CH$_2$Cl$_2$ (5 mL) is added TFA (1 mL) at 0° C. and the solution is allowed to slowly warm to ambient temperature. After 16 h, the reaction mixture is concentrated to dryness, diluted with water and purified by reverse-phase HPLC [Buffer A: water w/0.1% TFA; Buffer B: CH3CN w/0.1% TFA; Gradient: 0% B to 45% B over 30 min] to provide 35 mg (36%, two steps) of the title compound as a pale yellow, lyophilized solid.

$^1$H NMR (300 MHz, d$_6$-DMSO) δ2.80 (m, 2H), 3.25 (s, 2H), 3.37 (m, 2H), 3.93 (s, 2H), 4.76 (s, 2H), 6.88 (s, 1H), 6.94 (s, 1H), 7.85 (d, J=6.6 Hz, 1H), 7.89 (d, J=6.6 Hz, 1H), 8.37 (d, J=6.7 Hz, 1H), 8.38 (d, J=6.7 Hz, 1H), 9.17 (s, 1H), 9.19 (s, 1H), 12.80 (s, 1H), 12.96 (s, 1H), 14.91 (br s, 2H) ppm; MS (ion spray): m/z 361 (M+H). C$_{23}$H$_{25}$ClN$_4$OS MS m/z: 441, 443.

EXAMPLE 814

2-Amino-4-[4-(6-chloro-1H-benzoimidazol-2-ylmethyl)-2-oxo-piperidin-1-ylmethyl]-benzonitrile.

A. {1-[3-Benzhydrylidene-amino)-4-cyano-benzyl]-2-oxo-piperidin-4-yl}-acetic acid ethyl ester:

Sodium hydride (140 mg, 3.51 mmol) is added to a cooled solution of (2-oxo-piperidin-4-yl)-acetic acid ethyl ester (500 mg, 2.70 mmol) in 10 mL of THF. After stirring for forty five minutes, 2-(benzhydrylidene-amino)-4-bromomethyl-benzonitrile (1.43 g, 3.82 mmol), EXAMPLE 13, is added, and the reaction is left to stir overnight. THF is removed, and the residue is taken up in 250 mL of ethyl acetate. Excess sodium hydride is quenched with 5 mL of water, and normal aqueous work-up followed. The crude product is chromatographed on silica gel (50% EtOAc/Hexane) to give {1-[3-benzhydrylidene-amino)-4-cyano-benzyl]-2-oxo-piperidin-4-yl}-acetic acid ethyl ester (732 mg, 57%) as a light yellow solid. C$_{30}$H$_{29}$N$_3$O$_3$ MS m/z: 480, 482. Anal cald. for C$_{30}$H$_{29}$N$_3$O$_3$: C,75.13; H, 6.09; N, 8.76. found C, 73.01; H, 6.02; N, 8.46.

B. {1-[3-Benzhydrylidene-amino)-4-cyano-benzyl]-2-oxo-piperidin-4-yl}-acetic acid.

To a solution of {1-[3-benzhydrylidene-amino)-4-cyano-benzyl]-2-oxo-piperidin-4-yl}-acetic acid ethyl ester (732 mg, 1.53 mmol) in 5 mL of THF is added 1N sodium hydroxide (1.53 ml, 1.53 mmol). After stirring for four hours, the THF is removed and EtOAc (500 mL) is added. The reaction mixture is acidified to a pH of 6 and normal aqueous work-up followed. The desired carboxylic acid (571 mg, 83% yield) is isolated as a white solid.

C. N-(2-Amino-5-chloro-phenyl)-2-{1-[3-(benzhydrylidene-amino)-4-cyano-benzyl]-2-oxo-piperidin-4-yl}-acetamide.

To a slurry of the {1-[3-(benzhydrylidene-amino)-4-cyano-benzyl]-2-oxo-piperidin-4-yl}-acetic acid (190 mg, 0.422 mmol) in THF (5 mL) and methylene chloride (3 mL) is added triethylamine (0.09 ml, 0.633 mmol). The solution is cooled to 0° C., and 1M isopropyl chloroformate in toluene (0.422 mL, 0.422 mmol) is added. The homogenous mixture is allowed to warm to room temperature, and 4-chloro-1,2-phenylene-diamine (150 mg, 1.06 mmol) is added. The reaction is stirred at room temperature overnight. The volatile solvents are removed, and the resulting residue is chromatographed (SiO$_2$, 5% MeOH/EtOAc) to give N-(2-amino-5-chloro-phenyl)-2-{1-[3-(benzhydrylidene-amino)-4-cyano-benzyl]-2-oxo-piperidin-4-yl}-acetamide (200 mg, 82% yield). C$_{34}$H$_{30}$ClN$_5$O$_2$ MS m/z: 576, 578.

D. 2-(Benzhydrylidene-amino)-4-[4-(6-chloro-1H-benzoimidazol-2-ylmethyl)-2-oxo-piperidin-1-ylmethyl}-benzonitrile.

The acetamide (200 mg, 0.35 mmol) is dissolved in 2 mL of acetic acid and refluxed for three hours. The acetic acid is removed, and the residue taken up in ethyl acetate and washed with saturated sodium bicarbonate. Concentration of the solvent afforded 2-(benzhydrylidene-amino)-4-[4-(6-chloro-1 (H-benzoimidazol-2-ylmethyl)-2-oxo-piperidin-1-ylmethyl}-benzonitrile (200 mg, 100% yield) which is used without further purification. $C_{34}H_{28}ClN_5O_5$ MS m/z:+558, 560.

E. 2-Amino-4-[4-(6-chloro-1H-benzoimidazol-2-ylmethyl)-2-oxo-piperidin-1-ylmethyl]-benzonitrile hydrochloric acid salt The above benzonitrile (220 mg, 0.36 mmol) is dissolved in 5 ml of methanol. Hydrochloric acid is bubbled into the ice-cooled methanol solution followed by three drops of water. After stirring at room temperature for one hour, the MeOH is removed. The resulting white solid is titurated with EtOAc. After drying under high vacuum, 2-amino-4-[4-(6-chloro-1H-benzoimidazol-2-ylmethyl)-2-oxo-piperidin-1-ylmethyl]-benzonitrile hydrochloric acid salt (145.6 mg, 87% yield) is obtained as a white solid. $C_{21}H_{20}ClN_5O$: MS m/z: 394,396.

EXAMPLE 815

4-[4-(6-Chloro-1H-benzoimidazol-2-ylmethyl)-2-oxo-piperidin-1-ylmethyl]-benzamidine Hydrochloric acid is bubbled into an ice cooled solution of 4-[4-(6-chloro-1H-benzoimidazol-2-ylmethyl)-2-oxo-piperidin-1-ylmethyl]-benzonitrile (127 mg, 0.336 mmol) in 10 mL of methanol. The solution also contained 3Å molecular sieves. The reaction is stored at −30 for forty-eight hours. The methanol is condensed on the rotovap. Fresh methanol (15 mL) is added followed by a stream of ammonia gas. The reaction is heated to reflux for two and half hours. The reaction mixture is filtered at room temperature. Methanol is removed from the mother liquor. The resulting residue is purified by reverse phase HPLC (0-50% ACN/H$_2$O). The product is isolated as a white solid with a melting point of 105-110° C. $C_{21}H_{22}ClN_5O$ MS m/z: 396,398. Anal. calcd. for $C_{21}H_{22}ClN_5O.2C_2HF_3O_2$: C; 48.13; H, 3.88; N,11.22. Found: C, 45.05; H, 3.52; N, 9.89.

EXAMPLE 816

1-(4-Amino-quinazolin-7-ylmethyl)-4-(6-chloro-1H-benzoimidazol-2-ylmethyl)-piperidin-2-one To a solution of 2-Amino-4-[4-(6-chloro-1H-benzoimidazol-2-ylmethyl)-2-oxo-piperidin-1-ylmethyl]-benzonitrile hydrochloric acid salt (143 mg, 0.308 mmol), EXAMPLE 814, Part E, in 2 mL of ethanol is added triethylamine (0.05 mL, 0.366 mmol), glacial acetic acid (0.02 mL, 0.366 mmol) and triazine (15 mg, 0.183 mmol). The resulting mixture is refluxed overnight. The volatile solvents are removed on the rotovap, and the residue is purified by reverse phase HPLC (0-50% Acetonitrile/H$_2$O). The desired product (110 mg, 55% yield) is isolated as a white powder with a melting point of 128-132 ° C. $C_{22}H_{21}ClN_6O$ MS m/z: 421, 423. Anal. calcd. for $C_{22}H_{21}ClN_6O$: C, 48.12; H,3.57; N, 12.95. Found: C, 45.79; H, 3.68; N, 11.94. H NMR (CD$_3$OD) δ: 8.67 (s, 1H); 8.31 (d, 1H, J=4.0 Hz); 7.83-7.55 (m, 5H); 4.93-4.73 (m, 2H); 3.48-3.42 (m, 2H); 3.31-3.21 (m, 2H); 2.71-2.58 (m, 2H); 2.43-2.33 (m, 1H); 2.07-2.01 (m, 1H); 1.82-1.69 (m, 1H).

EXAMPLE 817

4-(6-Chloro-1H-benzoimidazol-2-ylmethyl)-1-(2,4-diamino-quinazolin-7-ylmethyl)-piperidin-2-one 2-Amino-4-[4-(6-chloro-1H-benzoimidazol-2-ylmethyl)-2-oxo-piperidin-1-ylmethyl]-benzonitrile hydrochloric acid salt (70 mg, 0.15 mmol), EXAMPLE 814, Part E, pyridine (1.0 mL) and freshly made chloroformamide hydrochloride (150 mg, 1.33 mmol) are placed in a sealed tube and heated to 200° C. The resulting mixture is heated for twenty four hours. The crude reaction mixture is directly purified by reverse phase HPLC (0-50% ACN/H$_2$O). The product (53 mg, 45% yield) is isolated as a tanish solid. $C_{22}H_{22}ClN_7O$ MS m/z: 436,438. Anal. calcd. for $C_{22}H_{22}ClN_7O$: C, 43.23; H, 3.24; N, 12.60. Found: C, 43.16; H, 3.44; N, 13.40.

EXAMPLE 818

1-(4-Amino-2-methyl-quinazolin-7-ylmethyl)-4-(6-chloro-1H-benzoimidazol-2-ylmethyl)-piperidin-2-one A stream of hydrogen chloride gas is bubbled intermittently through an ice-cold mixture of 2-amino-4-[4-(6-chloro-1H-benzoimidazol-2-ylmethyl)-2-oxo-piperidin-1-ylmethyl]-benzonitrile hydrochloric acid salt (57 mg, 0.123 mmol), EXAMPLE 814, Part E, and acetonitrile (0.03 mL, 0.93 mmol) in 1.5 mL of dioxane for six hours. The dioxane is removed; the residue is purified by reverse phase HPLC (0-40% ACN/H$_2$O). The desired product (9.5 mg, 12% yield) is isolated as a clear wax. $C_{23}H_{23}ClN_6O$ MS m/z: 435, 437.

The following compounds are prepared using the methods described above.

| Example # | Name | m/z [M + H] |
|---|---|---|
| 819 | (3S,5R)-4-[4-(6-Chloro-benzo[b]thiophen-2-ylmethyl)-3,5-dimethyl-2-oxo-piperazin-1-ylmethyl]-benzamidine | 441, 443 |
| 820 | (3S,5S)-4-[4-(6-Chloro-benzo[b]thiophen-2-ylmethyl)-3,5-dimethyl-2-oxo-piperazin-1-ylmethyl]-benzamidine | 441, 443 |
| 821 | 4-{4-[3-(5-Chloro-thiophen-2-yl)-acryloyl]-3,5-dimethyl-2-oxo-piperazin-1-ylmethyl}-benzamidine | 431, 433 |
| 822 | (3R,5S)-4-[4-(6-Chloro-benzo[b]thiophen-2-ylmethyl)-3,5-dimethyl-2-oxo-piperazin-1-ylmethyl]-benzamidine | 441, 443 |

EXAMPLE 823

2-[4-(6-Chlorobenzo[b]thiophene-2-sulfonyl)-2-oxopiperazin-1-yl]-N-[2-(3H-imidazol-4-yl)-ethyl] acetamide A. 4-tert-Butoxycarbonylmethyl-3-oxo-piperazine-1-carboxylic acid benzyl ester.

To a solution of 3-oxopiperazine-1-carboxylic acid benzyl ester (4.68 g, 20 mmol) in 20 mL of DMF at) 0° C. is added sodium hydride (60%, 880 mg, 22 mmol). The suspension is stirred at ambient temperature for one t-butyl bromoacetate (4.68 g, 24 mmol) is added. The resulting mixture is stirred at ambient temperature overnight. After dilution with ethyl acetate (200 mL), the mixture is washed with brine (3×50 mL). The crude residue obtained from concentration of the organic phase is chromatographied on silica gel (30% ethyl acetate/Hexane) to give 5.57 g (80%) of 4-tert-butoxycarbonylmethyl-3-oxopiperazine-1-carboxylic acid benzyl ester as a white solid.

B. (2-Oxo-piperazin-1-yl)acetic acid tert-butyl ester.
4-tert-Butoxycarbonylmethyl-3-oxopiperazine-1-carboxylic acid benzyl ester (2.0 g, 5.75 mmol) is dissolved in 20 mL of methanol and 2 mL of acetic acid. Palladium (5%) on carbon (100 mg) is added, and the reaction mixture is stirred in an atmosphere of hydrogen overnight. The mixture is filtered and concentrated. Ethyl acetate is added, and the mixture is neutralized to pH 7 using 1N NaOH. The organic layer is concentrated to give (2-oxo-piperazin-1-yl)acetic acid tert-butyl ester (1.22 g).

C. [4-(6-Chlorobenzo[b]thiophene-2-sulfonyl)-2-oxopiperazine-1-yl]acetic acid tert-butyl ester.

To a solution of (2-oxo-piperazin-1-yl)acetic acid tert-butyl ester (1.22 g, 5.7 mmol) in 10 ml of methylene chloride is added triethylamine (1.2 mL, 8.55 mmol) and 6-chlorobenzothiophenesulfonyl chloride (1.52 g, 5.7 mmol). The reaction mixture is stirred overnight at ambient temperature. Flash column chromatography (50% ethyl acetate/hexane) affords 2.3 g (92%) of [4-(6-chlorobenzo[b]thiophene-2-sulfonyl)-2-oxopiperazine-1-yl]acetic acid tert-butyl ester.

D. [4-(6-Chlorobenzo[b]thiophene-2-sulfonyl)-2-oxopiperazine-1-yl]-acetic acid.

[4-(6-Chlorobenzo[b]thiophene-2-sulfonyl)-2-oxopiperazine-1-yl]acetic acid tert-butyl ester (500 mg, 1.13 mmol) is dissolved in 1 mL of trifluoroacetic acid and 3 mL of $CH_2Cl_2$. The solvents are azeotropically removed with toluene. [4-(6-chlorobenzo[b]thiophene-2-sulfonyl)-2-oxopiperazine-1-yl] acetic acid (438 mg) is isolated as a white solid.

E. 2-[4-(6-Chlorobenzo[b]thiophene-2-sulfonyl)-2-oxopiperazin-1-yl]-N-[2-(3H-imidazol-4-yl)-ethyl]acetamide.

To a slurry of [4-(6-chlorobenzo[b]thiophene-2-sulfonyl)-2-oxopiperazine-1-yl]acetic acid (47 mg, 0.12 mmol) in 2 mL of tetrahydrofuran is added $Et_3N$ (0.025 mL, 0.18 mmol). The mixture is cooled to 0° C., and 1M solution of isopropyl chloroformate in toluene (0.12 mL, 0.12 mmol) is added. The mixture is stirred for fifteen minutes and histamine (13.3 mg, 0.12 mmol) is added. The mixture is stirred overnight at room temperature. Reverse phase HPLC (AcCN/$H_2$O/TFA) affords 2-[4-(6-Chlorobenzo[b]thiophene-2-sulfonyl)-2-oxopiperazin-1-yl]-N-[2-(3H-imidazol-4-yl)-ethyl]acetamide trifluoroacetic acid salt (17 mg, 25%) as a solid. mp 77-82° C.; MS m/z 482 (M+H).

The followin compounds are prepared from the appropriate starting materials using the method of EXAMPLE 823.

| Example # | Name | m/z [M + H] |
|---|---|---|
| 824 | 2-[4-(6-Chloro-benzo[b]thiophene-2-sulfonyl)-2-oxo-piperazin-1-yl]-N-pyridin-4-yl-acetamide | 465, 467 |
| 825 | 2-[4-(6-Chloro-benzo[b]thiophene-2-sulfonyl)-2-oxo-piperazin-1-yl]-N-pyridin-3-ylmethyl-acetamide | 479, 481 |
| 826 | 2-[4-(6-Chloro-benzo[b]thiophene-2-sulfonyl)-2-oxo-piperazin-1-yl]-N-piperidin-4-yl-acetamide | 471, 473 |
| 827 | N-(1-Carbamimidoyl-piperidin-4-yl)-2-[4-(6-chloro-benzo[b]thiophene-2-sulfonyl)-2-oxo-piperazin-1-yl]-acetamide | 513, 515 |
| 828 | 5-(2-{2-[4-(6-Chloro-benzo[b]thiophene-2-sulfonyl)-2-oxo-piperazin-1-yl]-acetylamino}-ethyl)-imidazole-1-carboxylic acid ethyl ester | 554, 556 |
| 829 | 2-[4-(6-Chloro-benzo[b]thiophene-2-sulfonyl)-2-oxo-piperazin-1-yl]-N-pyrimidin-4-yl-acetamide | 466, 468 |
| 830 | 2-[4-(6-Chloro-benzo[b]thiophene-2-sulfonyl)-2-oxo-piperazin-1-yl]-N-phenyl-acetamide | 464, 466 |
| 831 | 2-[4-(6-Chloro-benzo[b]thiophene-2-sulfonyl)-2-oxo-piperazin-1-yl]-N-(9H-purin-6-yl)-acetamide | 506, 508 |
| 832 | N-(4-Amino-2-methyl-pyrimidin-5-ylmethyl)-2-[4-(6-chloro-benzo[b]thiophene-2-sulfonyl)-2-oxo-piperazin-1-yl]-acetamide | 509, 511 |
| 833 | 2-[4-(6-Chloro-benzo[b]thiophene-2-sulfonyl)-2-oxo-piperazin-1-yl]-N-(3-imidazol-1-yl-propyl)-acetamide | 496, 498 |
| 834 | 2-[4-(6-Chloro-benzo[b]thiophene-2-sulfonyl)-2-oxo-piperazin-1-yl]-N-[2-(1-methyl-1H-imidazol-4-yl)-ethyl]-acetamide | 496, 498 |
| 835 | 2-[4-(6-Chloro-benzo[b]thiophene-2-sulfonyl)-2-oxo-piperazin-1-yl]-N-(2-pyridin-4-yl-ethyl)-acetamide | 493, 495 |
| 836 | 2-[4-(6-Chloro-benzo[b]thiophene-2-sulfonyl)-2-oxo-piperazin-1-yl]-N-[2-(3-methyl-3H-imidazol-4-yl)-ethyl]-acetamide | 496, 498 |
| 837 | 2-[4-(6-Chloro-benzo[b]thiophene-2-sulfonyl)-2-oxo-piperazin-1-yl]-N-(2-pyridin-2-yl-ethyl)-acetamide | 493, 495 |
| 838 | 2-[4-(6-Chloro-benzo[b]thiophene-2-sulfonyl)-2-oxo-piperazin-1-yl]-N-(2-pyridin-3-yl-ethyl)-acetamide | 493, 495 |
| 839 | 2-[4-(6-Chloro-benzo[b]thiophene-2-sulfonyl)-2-oxo-piperazin-1-yl]-N-(2-imidazol-1-yl-ethyl)-acetamide | 482, 484 |
| 840 | 2-[4-(6-Chloro-benzo[b]thiophene-2-sulfonyl)-2-oxo-piperazin-1-yl]-N-[2-(1-methyl-1H-pyrrol-2-yl)-ethyl]-acetamide | 495, 497 |
| 841 | 2-[4-(6-Chloro-benzo[b]thiophene-2-sulfonyl)-2-oxo-piperazin-1-yl]-N-[2-(5-methyl-1H-imidazol-4-yl)-ethyl]-acetamide | 496, 498 |
| 842 | 2-[4-(6-Chloro-benzo[b]thiophene-2-sulfonyl)-2-oxo-piperazin-1-yl]-N-(4-dimethylamino-[1,3,5]triazin-2-yl)-acetamide | 510, 512 |
| 843 | 2-[4-(6-Chloro-benzo[b]thiophene-2-sulfonyl)-2-oxo-piperazin-1-yl]-N-methyl-N-pyridin-4-yl-acetamide | 479, 481 |
| 844 | N-[2-(2-Amino-pyridin-4-yl)-ethyl]-2-[4-(6-chloro-benzo[b]thiophene-2-sulfonyl)-2-oxo-piperazin-1-yl]-acetamide | 508, 510 |
| 845 | 2-[4-(6-Chloro-benzo[b]thiophene-2-sulfonyl)-2-oxo-piperazin-1-yl]-N-[2-(4-methyl-thiazol-5-yl)-ethyl]-acetamide | 513, 515 |
| 846 | 2-[4-(6-Chloro-benzo[b]thiophene-2-sulfonyl)-2-oxo-piperazin-1-yl]-N-(2-thiazol-4-yl-ethyl)-acetamide | 499, 501 |

-continued

| Example # | Name | m/z [M + H] |
|---|---|---|
| 847 | 2-[4-(6-Chloro-benzo[b]thiophene-2-sulfonyl)-2-oxo-piperazin-1-yl]-N-(3-guanidino-propyl)-acetamide trifluoroacetic acid salt | 487, 489 |
| 848 | N-(3-Amino-propyl)-2-[4-(6-chloro-benzo[b]thiophene-2-sulfonyl)-2-oxo-piperazin-1-yl]-acetamide | 445, 447 |
| 849 | 2-[4-(6-Chloro-benzo[b]thiopbene-2-sulfonyl)-2-oxo-piperazin-1-yl]-N-[2-(2-mercapto-1H-imidazol-4-yl)-ethyl]-acetamide | 514, 516 |
| 850 | N-[2-(2-Amino-thiazol-4-yl)-ethyl]-2-[4-(6-chloro-benzo[b]thiophene-2-sulfonyl)-2-oxo-piperazin-1-yl]-acetamide | 514, 516 |
| 851 | 2-[4-(6-Chloro-benzo[b]thiophene-2-sulfonyl)-2-oxo-piperazin-1-yl]-N-methyl-N-(2-pyridin-4-yl-ethyl)-acetamide | 507, 509 |
| 852 | 2-[4-(6-Chloro-benzo[b]thiophene-2-sulfonyl)-2-oxo-piperazin-1-yl]-N-[2-(2-methylsulfanyl-1H-imidazol-4-yl)-ethyl]-acetamide | 528, 530 |

EXAMPLE 853

4-(6-Chloro-benzo[b]thiophene-2-sulfonyl)-1-[3-(3H-imidazol-4-yl)-propyl]-piperazin-2-one A. 3-Oxo-4-[3-(3-trityl-3H-imidazol-4-yl)-allyl-piperazine-1-carboxylic acid benzyl ester.

3-Oxo-piperazin-1-carboxylic acid benzyl ester (702 mg, 3.0 mmol) is dissolved in dimethylformamide (10 mL) and cooled to 0° C. Sodium hydride (60%, 148 mg, 3.7 mmol) is added, followed by the addition of 5-(3-chloro-propenyl)-1-trityl-1H-imidazole (473 mg, 1.2 mmol). The resulting mixture is left to stir at room temperature overnight. Most of the dimethylformamide is removed on the high vacuum. The reaction mixture is diluted with ethyl acetate (250 mL) and quenched with water. The two layers are separated and ethyl acetate (2×100 mL) is used to extract and dried over magnesium sulfate. The residue after filtration and concentration is chromatographed on silica gel (50% EtOAc/hexane) to give 3-oxo-4-[3-(3-trityl-3H-imidazol-4-yl)-allyl-piperazine-1-carboxylic acid benzyl ester (360 mg) as the desired product.

B. 4-[3-(3-tert-Butoxycarbonyl-3H-imidazol-4-yl)-allyl]-3-oxo-piperazine-1-carboxylic acid benzyl ester.

3-Oxo-4-[3-(3-trityl-3H-imidazol-4-yl)-allyl-piperazine-1-carboxylic acid benzyl ester (360 mg, 0.62 mmol) is stirred vigorously in a 30% solution of trifluoroacetic acid and methylene chloride (10 mL). After stirring for three hours, the trityl group is removed. The volatile solvents are removed in vacuo, and the crude product is taken-up in methylene chloride (10 mL). Pyridine (0.5 ml) and Di-tert-butyl dicarbonate (176 mg, 0.81 mmol) is added to the solution, and the resulting mixture is left to stir overnight. The reaction mixture is condensed and purified by flash column (SiO$_2$, 20% EtOAc/Hexane) to give 4-[3-(3-tert-butoxycarbonyl-3H-imidazol-4-yl)-allyl]-3-oxo-piperazine-1-carboxylic acid benzyl ester (100 mg).

C. 5-{3-[4-(6-Chloro-benzo[b]thiophene-2-sulfonyl)-2-oxo-piperazin-1-yl]-propyl}-imidazol-1-carboxylic acid tert-butyl ester.

Palladium on carbon (10%, 15 mg) is added to a solution of 4-[3-(3-tert-butoxycarbonyl-3H-imidazol-4-yl)-allyl]-3-oxo-piperazine-1-carboxylic acid benzyl ester (50 mg, 0.114 mmol) in 5 mL of methanol. The reaction mixture is left to stir in an atmosphere of hydrogen overnight. The palladium is filtered off, and the volatile solvents are removed on the rotovap. The crude product (50 mg, 0.114 mmol) is redissolved in methylene chloride (5 mL). Triethylamine (0.06 ml, 0.43 mmol) 6-chloro-benzo[b]thiophene-2-sulfonyl chloride (39 mg, 0.15 mmol) is added, and the resulting mixture is stirred overnight. The crude product is directly purified by flash column (SiO$_2$, 30% EtOAc/Hexane) to afford 5-{3-[4-(6-chloro-benzo[b]thiophene-2-sulfonyl)-2-oxo-piperazin-1-yl]-propyl}-imidazol-1-carboxylic acid butyl ester (30 mg).

D. 4-(6-Chloro-benzo[b]thiophene-2-sulfonyl)-1-[3-(3H-imidazol-4-yl)-propyl]-piperazin-2-one:

5-{3-[4-(6-Chloro-benzo[b]thiophene-2-sulfonyl)-2-oxo-piperazin-1-yl]-propyl}-imidazol-1carboxylic acid tert-butyl ester (30 mg, 0.055 mmol) is stirred vigorously in a 30% solution of trifluoroacetic acid and methylene chloride (2 mL). The reaction is complete after stirring for three hours. The volatile solvents are removed on the rotovap, and the gummy solid is titurated with ether several times to afford 4-(6-chloro-benzo[b]thiophene-2-sulfonyl)-1-[3-(3H-imidazol-4-yl)-propyl]-piperazin-2-one trifluoroacetic acid salt (30 mg) as a yellow solid. $C_{18}H_{19}ClN_4O_3S_2$ (m/z)+: 439, 441. Anal cald. for $C_{18}H_{19}ClN_4O_3S_2.C_2HF_3O_2$: C, 43.44; H, 3.65; N, 10.13. Found C, 42.03; H, 3.55; N, 8.26.

The following compounds are prepared using the methods described above.

| Example # | Name | m/z [M + H] |
|---|---|---|
| 854 | 4-[4-(6-Chloro-benzo[b]thiophene-2-sulfonyl)-2-oxo-piperazin-1-ylmethyl]-piperidine-1-carboxamidine | 470, 472 Cl pattern |
| 855 | 4-(6-Chloro-benzo[b]thiophene-2-sulfonyl)-1-(3-piperazin-1-yl-propyl)-piperazin-2-one | 457, 459 Cl pattern |
| 856 | 4-(6-Chloro-benzo[b]thiophene-2-sulfonyl)-1-(3-pyridin-4-yl-propyl)-piperazin-2-one | 450, 452 Cl pattern |
| 857 | 4-(6-Chloro-benzo[b]thiophene-2-sulfonyl)-1-(4-piperidin-4-yl-butyl)-piperazin-2-one | 470, 472 Cl pattern |

-continued

| Example # | Name | m/z [M + H] |
|---|---|---|
| 858 | 4-(6-Chloro-benzo[b]thiophene-2-sulfonyl)-1-(2-piperidin-4-yl-ethyl)-piperazin-2-one | 442 |
| 859 | 4-(6-Chloro-benzo[b]thiophene-2-sulfonyl)-1-(3-piperidin-4-yl-propyl)-piperazin-2-one | 456 |

EXAMPLE 860

4-[(5-Chloro-thiophen-2-yloxy)-acetyl]-3-(S)-methoxymethyl-1-[4-(6-methoxy-pyridin-3-yl)-benzyl]-piperazin-2-one A. 3-Methoxymethyl-4-[4-(6-methoxy-pyridin-3-yl)-benzyl]-3-oxo-piperazine-1-carboxylic acid benzyl ester.

The title compound is prepared by the method in EXAMPLE 66, Part A, substituting 5-(4-bromomethyl-phenyl)-2-methoxy-pyridine for 4-bromomethyl tolynitrile and 2-methoxymethyl-3-oxopiperazin-1-carboxylic acid benzyl ester for 3-oxopiperazin-1-carboxylic acid benzyl ester. MS (ISP) m/z 476, (M+H).

4-[(5-Chloro-thiophen-2-yloxy)-acetyl]-3-(S)-methoxymethyl-1-[4-(6-methoxy-pyridin-3-yl)-benzyl]-piperazin-2-one The title compound is prepared by deprotecting 3-methoxymethyl-4-[4-(6-methoxy-pyridin-3-yl)-benzyl]-3-oxo-piperazine-1-carboxylic acid benzyl ester as described in EXAMPLE 75, Part C. The crude amine is then coupled as described in EXAMPLE 123 with 3-(5-chloro-thiophen-2-yl)-(E)-acrylic acid, EXAMPLE 25. MS (ISP) m/z 516, 518, (M+H), Cl pattern.

The following compounds are prepared according to the method of Example 860.

EXAMPLE 874

1-(3-Amino-1H-indazol-6-ylmethyl)-4-(6-chloro-benzo[b]thiophen-2-ylmethyl)-piperazin-2-one A. 2-Amino-4-(2-oxo-piperazin-1-ylmethyl)-benzonitrile.

To a solution of 4-(3-Amino-4-cyano-benzyl)-3-oxo-piperazine-1-carboxylic acid benzyl ester hydrochloride (4.0 g, 10.0 mmol) in CH$_3$OH (45 ml) and CH$_2$Cl$_2$ (10 ml) is added 10% Pd on carbon (0.6 g). The mixture is stirred under an atmosphere of H$_2$ for 2 hours then is filtered through a pad of celite. The filtrate is concentrated and the residue purified by column chromatography eluting with 10% 7M NH$_3$ in CH$_3$OH/CH$_2$Cl$_2$ to yield the title compound (1.62 g, 7.0 mmol). $^1$H NMR (DMSO, 300 MHz) δ7.34 (d, 1H), 6.64 (s, 1H), 6.46 (d, 1H), 6.04 (bs, 2H), 4.40 (s, 2H), 3.28 (s, 2H), 3.14 (m, 2H), 2.87 (m, 2H), 2.77 (bs, 1H). MS (ion spray): m/z 231 (M+H)$^+$.

B. 2-Amino-4-[4-(6-chloro-benzo[b]thiophen-2-ylmethyl)-2-oxo-piperazin-1-ylmethyl]-benzonitrile.

To a cooled solution (0° C.) of 2-Amino-4-(2-oxo-piperazin-1-ylmethyl)-benzonitrile (0.345 g, 1.5 mmol) in DMF (2 ml) is added finely powdered anhydrous K$_2$CO$_3$ (0.311 g, 2.25 mmol) and allowed to stir for 20 minutes. To this mixture is added a solution of 2-bromomethyl-benzo[b]thiophene (0.392 g, 1.5 mmol) in DMF (3 ml), the cold bath removed and allowed to stir for 2 hours. The reaction mixture is con-

| Example # | Name | m/z [M + H] |
|---|---|---|
| 861 | 4'-[4-(6-Chloro-benzo[b]thiophene-2-sulfonyl)-2-oxo-piperazin-1-ylmethyl]-biphenyl-2-carbonitrile | 522, 524 Cl pattern |
| 862 | 4-(6-Chloro-benzo[b]thiophene-2-sulfonyl)-1-(4-chloro-3-hydroxy-benzyl)-piperazin-2-one | 471, 473 Cl pattern |
| 863 | 1-Benzyl-4-(6-chloro-benzo[b]thiophene-2-sulfonyl)-piperazin-2-one | 421, 423 Cl pattern |
| 864 | 4-(6-Chloro-benzo[b]thiophene-2-sulfonyl)-1-(4-chloro-benzyl)-piperazin-2-one | 455, 457 Cl pattern |
| 865 | 4-[(4-Chloro-thiophen-2-yloxy)-acetyl]-3-(S)-methoxymethyl-1-[4-(6-methoxy-pyridin-3-yl)-benzyl]-piperazin-2-one | 516, 518 Cl pattern |
| 866 | 4-[(5-Chloro-thiophen-3-yloxy)-acetyl]-1-[4-(6-hydroxy-pyridin-3-yl)-benzyl]-3-(S)-methoxymethyl-piperazin-2-one | 502, 504 Cl pattern |
| 867 | 4-[(5-Chloro-thiophen-3-yloxy)-acetyl]-3-(S)-methoxymethyl-1-[4-(6-methoxy-pyridin-3-yl)-benzyl]-piperazin-2-one | 516, 518 Cl pattern |
| 868 | 4-[(5-Chloro-thiophen-2-yloxy)-acetyl]-1-[4-(6-hydroxy-pyridin-3-yl)-benzyl]-3-(S)-methoxymethyl-piperazin-2-one | 502, 504 Cl pattern |
| 869 | 4-[3-(5-Chloro-thiophen-2-yl)-(E)-acryloyl]-1-[4-(6-methoxy-pyridin-3-yl)-benzyl]-3-(S)-methyl-piperazin-2-one | 482 |
| 870 | 4-[3-(5-Chloro-thiophen-2-yl)-(E)-acryloyl]-3-(S)-methyl-1-[4-(6-oxo-1,6-dihydro-pyridin-3-yl)-benzyl]-piperazin-2-one | 468 |
| 871 | 1-Biphenyl-4-ylmethyl-4-[3-(5-chloro-thiophen-2-yl)-(E)-acryloyl]-3(S)-ethyl-6-methyl-piperazin-2-one | |
| 872 | 4-[3-(5-Chloro-thiophen-2-yl)-(E)-acryloyl]-1-[4-(6-hydroxy-pyridin-3-yl)-benzyl]-3-(S)-methoxymethyl-piperazin-2-one | 498, 500 Cl pattern |
| 873 | 4-[3-(5-Chloro-thiophen-2-yl)-(E)-acryloyl]-3-(S)-methoxymethyl-1-[4-(6-methoxy-pyridin-3-yl)-benzyl]-piperazin-2-one | 512, 514 Cl pattern | centrated under high vacuum and the residue purified by column chromatography eluting with 55% EtOAc/5% CH$_3$OH/hexane to yield the title compound (0.477 g, 1.16 mmol) as a white solid. $^1$H NMR (DMSO, 300 MHz) δ8.06 (d, 1H), 7.78 (d, 1H), 7.37 (m, 3H), 6.64 (s, 1H), 6.44 (d, 1H), 6.09 (bs, 2H), 4.42 (s, 2H), 3.88 (s, 2H), 3.21 (m, 4H), 2.72 (m, 2H). MS (ion spray): m/z 411, 413 (M+H)$^+$, Cl pattern.

C. 1-(3-Amino-1H-indazol-6-ylmethyl)-4-(6-chloro-benzo[b]thiophen-2-ylmethyl)-piperazin-2-one.

To a cooled solution (0° C.) of 2-Amino-4-[4-(6-chloro-benzo[b]thiophen-2-ylmethyl)-2-oxo-piperazin-1-ylmethyl]-benzonitrile (0.365 g, 0.89 mmol) in concentrated HCl (2.1 ml) is added dropwise a solution of sodium nitrite (0.068 g, 0.98 mmol) in H$_2$O (0.2 ml). The reaction mixture is added to a cooled solution (0° C.) of tin (II) chloride dihydrate (1.61 g, 7.12 mmol) in concentrated HCl (0.62 ml) and H$_2$O (3 ml). The precipitate is collected by vacuum filtration and dried under high vacuum. The crude solid is purified by column chromatography eluting with 10% 7M NH$_3$ in CH$_3$OH/ CH$_2$Cl$_2$ to yield the title compound (0.144 g, 0.34 mmol) as a yellow solid. $^1$H NMR (DMSO, 300 MHz) δ11.35 (bs, 1H), 8.05 (d, 1H), 7.78 (d, 1H), 7.64 (d, 1H), 7.37 (m, 2H), 7.08 (s, 1H), 6.78 (d, 1H), 5.75 (s, 1H), 5.40 (bs, 1H), 4.58 (s, 2H), 3.88 (s, 2H), 3.20 (m, 4H), 2.70 (bt, 2H). MS (ion spray): m/z 426 (M+H)$^+$. Anal. cald. for C$_{21}$H$_{20}$N$_5$OSCl;(H$_2$O)$_{0.25}$: C, 58.6; H, 4.8; N, 16.3. Found C, 58.6; H, 4.7; N, 15.9. M.P.=246-248° C.

EXAMPLE 875

1-(3-Amino-1H-indazol-6-ylmethyl)-4-[3-(5-chloro-thiophen-2-yl)]-piperazin-2-one A. 2-Amino-4-{4-[3-(5-chloro-thiophen-2-yl)-allyl]-2-oxo-piperazin-1-ylmethyl}-benzonitrile.

Using essentially the same procedure as in EXAMPLE 874, Part B using 2-(3-bromo-propenyl)-5-chloro-thiophene is obtained the title compound. MS (EI): m/z 386, 388 (M$^+$), Cl pattern.

B. 1-(3-Amino-1H-indazol-6-ylmethyl)-4-[3-(5-chloro-thiophen-2-yl)]-piperazin-2-one.

Using essentially the same procedure as in EXAMPLE 874, Part C there is obtained the title compound. $^1$H NMR (DMSO, 300 MHz) δ11.32 (bs, 1H), 7.62 (d, 1H), 7.06 (s, 1H), 7.02 (d, 1H), 6.96 (d, 1H), 6.78 (d, 1H), 6.67 (d, 1H), 5.96 (m, 1H), 5.32 (bs, 2H), 4.57 (s, 2H), 3.19 (bt, 2H), 3.12 (m, 4H), 2.64 (bt, 2H). MS (EI): m/z 401, 403 (M$^+$), Cl pattern. Anal. cald. for C$_{19}$H$_{20}$ClN$_5$OS: C, 56.8; H, 5.0; N, 17.4. Found C, 56.6; H, 4.8; N, 17.2. M.P.=167-169° C.

EXAMPLE 876

1-(3-Amino-1H-indazol-6-ylmethyl)-4-(6-chloro-benzo[b]thiophene-2-sulfonyl)-piperazin-2-one A. 2-Amino-4-[4-(6-chloro-benzo[b]thiophene-2-sulfonyl)-2-oxo-piperazin-1-ylmethyl]-benzonitrile.

Using essentially the same procedure as in EXAMPLE 874, Part B except using 6-chloro-benzo[b]thiophene-2-sulfonyl chloride, EXAMPLE 1, is obtained the title compound. MS (ion spray): m/z 461, 463 (M+H)$^+$, Cl pattern.

B. 1-(3-Amino-1H-indazol-6-ylmethyl)-4-(6-chloro-benzo[b]thiophene-2-sulfonyl)-piperazin-2-one.

Using essentially the same procedure as in EXAMPLE 874, Part C there is obtained the title compound. $^1$H NMR (DMSO, 300 MHz) δ11.29 (s, 1H), 8.35 (s, 1H), 8.18 (s, 1H), 8.08 (d, 1H), 7.58 (m, 2H), 7.05 (s, 1H), 6.70 (d, 1H), 5.30 (bs, 2H), 4.56 (s, 2H), 3.84 (s, 2H), 3.40 (m, 2H), 3.30 (m, 2H). MS (ion spray): m/z 476, 478 (M+H)$^+$, Cl pattern. Anal. cald. for C$_{20}$H$_{18}$ClN$_5$O$_3$S$_2$: C, 50.5; H, 3.8; N, 14.7. Found C, 50.3; H, 3.6; N, 14.5. M.P.=274-276° C.

The following compounds are prepared using the procedures described above.

| Example # | Name | m/z |
| --- | --- | --- |
| 877 | 4-[4-(6-Chloro-benzo[b]thiophen-2-ylmethyl)-2-(S)-methyl-3,6-dioxo-piperazin-1-ylmethyl]-benzamidine | 441, 443 Cl pattern |
| 878 | 4-[4-(6-Chloro-benzo[b]thiophen-2-ylmethyl)-2-(R)-methyl-3,6-dioxo-piperazin-1-ylmethyl]-benzamidine | 441, 443 Cl pattern |
| 879 | 3-[4-(6-Chloro-benzo[b]thiophen-2-ylmethyl)-2,5-dioxo-piperazin-1-ylmethyl]-benzamidine | 427, 429 Cl pattern |
| 880 | 4-[4-(6-Chloro-benzo[b]thiophen-2-ylmethyl)-2,5-dioxo-piperazin-1-ylmethyl]-benzamidine | 427, 429 Cl pattern |

Example 881

5-Chloro-2-chlorosulfonyl-indole-1-carboxylic acid tert-butyl ester

A. 5-Chloro-indole-1-carboxylic acid tert-butyl ester:

To a suspension of NaH (60%, 1.0 g, 25.2 mmol) in anhydrous THF (50 mL) at 0° C. is added 5-chloro-indole (2.73 g, 18.0 mmol). After 20 min, di-t-butyl dicarbonate (4.71 g, 21.6 mmol) is added and the reaction mixture is maintained at 0° C. for 4 h. The reaction mixture is partitioned between diethyl ether (100 mL) and saturated aqueous NH$_4$Cl (100 mL) and the layers are separated. The aqueous phase is extracted twice with diethyl ether (2×50 mL) and then the combined organic extracts are washed once with brine, dried over anhydrous MgSO$_4$, filtered and concentrated. The crude product is purified by flash silica gel chromatography (hexane/EtOAc, 30:1 to 20:1) to provide 4.0 g (89%) of 5-chloro-indole-1-carboxylic acid tert-butyl ester as a colorless solid. $^1$H NMR (300 MHz, CDCl$_3$) δ1.66 (s, 9H), 6.50 (d, J=3.5 Hz, 1H), 7.27 (m, 1H), 7.52 (s, 1H), 7.60 (d, J=3.3 Hz, 1H), 8.06 (d, J=8.6 Hz, 1H) ppm.

B. 5-Chloro-2-chlorosulfonyl-indole-1-carboxylic acid tert-butyl ester.

To a solution containing 5-chloro-indole-1-carboxylic acid tert-butyl ester (4.0 g, 15.9 mmol) in anhydrous THF (60 mL) at −78° C. is added 1.7 M t-BuLi in pentane (11.2 mL, 19.0 mmol) dropwise from a syringe. After 1 h at −78° C., SO$_2$ gas is introduced into the reaction mixture for 5-10 min. The reaction mixture is warmed to ambient temperature and then concentrated to dryness in vacuo. The resulting solid is then suspended in hexane (80 mL), cooled to −60° C., and $SO_2Cl_2$ (2.6 g, 19.0 mmol) is added dropwise.

After 16 h, the reaction mixture is concentrated to dryness and the residue is partitioned between EtOAc (100 mL) and aqueous $NaHCO_3$ (100 mL). The layers are separated and the organic phase is washed once with brine, dried over anhydrous $MgSO_4$, filtered and concentrated. The crude product is purified by flash silica gel chromatography (hexane/EtOAc, 100:1 to 30:1) to afford 3.35 g (60%) of 5-chloro-2-chlorosulfonyl-indole-1-carboxylic acid tert-butyl ester as a off-white solid. $^1$H NMR (300 MHz, $CDCl_3$) δ1.73 (s, 9H), 7.52 (dd, J=9.1, 2.0 Hz, 1H), 7.60 (s, 1H), 7.69 (d, J=2.0 Hz, 1H), 8.19 (d, J=9.1 Hz, 1H) ppm.

Example 882

6-Chloro-2-chlorosulfonyl-indole-1-carboxylic acid tert-butyl ester

A. 6-Chloro-indole-1-carboxylic acid tert-butyl ester.

To a suspension of NaH (60%, 0.41 g, 10.3 mmol) in anhydrous THF (20 mL) at 0° C. is added 6-chloro-indole (1.2 g, 7.4 mmol). After 10 min, di-t-butyl dicarbonate (1.93 g, 8.88 mmol) is added and the reaction mixture is slowly warmed to ambient temperature overnight. The reaction mixture is concentrated to dryness and the residue is partitioned between diethyl ether (100 mL) and saturated aqueous $NH_4Cl$ (100 mL) and the layers are separated. The aqueous phase is extracted twice with diethyl ether (2×50 mL) and then the combined organic extracts are washed once with brine, dried over anhydrous $MgSO_4$, filtered and concentrated. The crude product is purified by flash silica gel chromatography (hexane/EtOAc, 10:1) to provide 6.0 g (82%) of 6-chloro-indole-1-carboxylic acid tert-butyl ester as a colorless solid. $^1$H NMR (300 MHz, $CDCl_3$) δ1.66 (s, 9H), 6.52 (d, J=3.6 Hz, 1H), 7.19 (dd, J=8.3, 1.8 Hz, 1H), 7.45 (d, J=8.3 Hz, 1H), 7.56 (d, J=3.6 Hz, 1H), 8.18 (s, 1H) ppm.

B. 6-Chloro-2-chlorosulfonyl-indole-1-carboxylic acid tert-butyl ester.

To a solution containing 6-chloro-indole-1-carboxylic acid tert-butyl ester (2.1 g, 8.34 mmol) in anhydrous THF (30 mL) at −78° C. is added 1.7 M t-BuLi in pentane (6 mL, 10.2 mmol) dropwise from a syringe. After 1 h at −78° C., $SO_2$ gas is introduced into the reaction mixture for 5-10 min. The reaction mixture is warmed to ambient temperature and then concentrated to dryness in vacuo. The resulting solid is then suspended in hexane (80 mL), cooled to −60° C., and $SO_2Cl_2$ (0.81 g, 10.0 mmol) is added dropwise. After 16 h, the reaction mixture is concentrated to dryness and the residue is partitioned between diethyl ether (100 mL) and aqueous $NaHCO_3$ (100 mL). The layers are separated and the organic phase is washed once with brine, dried over anhydrous $MgSO_4$, filtered and concentrated. The crude product is purified by flash silica gel chromatography (hexane/EtOAc, 100:1 to 30:1) to afford 5.34 g (64%) of 6-chloro-2-chlorosulfonyl-indole-1-carboxylic acid tert-butyl ester as a off-white solid.

$^1$H NMR (300 MHz, $CDCl_3$) δ1.74 (s, 9H), 7.35 (dd, J=8.5, 1.8 Hz, 1H), 7.63 (m, 2H), 8.31 (m, 1H) ppm.

EXAMPLE 883

3-(5-Chloro-thiophen-2-yl)-3-oxo-propionic acid tert-butyl ester

A 0.25M THF solution of tert-butyl acetate (2.90 g, 25 mmol) is added dropwise to a cold (−78° C.) solution of potassium bis(trimethylsilyl)amide (100 ml of a 0.5M toluene solution) and ethyl 5-chlorothiophene-2-carboxylate (Lancaster)(4.77 g, 25 mmol) in 50 ml of THF. The reaction is allowed to warm to 0° C. over one hour. After stirring an additional hour at 0° C., the reaction is poured into 100 ml of a 1M HCl solution. The organic layer is extracted with brine and evaporated in vacuo. The crude residue is purified by flash column chromatography eluting with 5% ethyl acetate/hexane to provide the product (4.54 g, 17 mmol) as an oil. $^1$H NMR ($CDCl_3$, 300 MHz) δ7,53 (d, 1H), 6.98 (d, 1H), 3.78 (3, 2H), 1.50 (s, 9H).

EXAMPLE 884

Methyl06-Chloro-benzofurancarboxylate

A. 4-Chloro-2-hydroxy-benzylalcohol.

To 7 g of $LiAlH_4$ in 200 ml of THF is added portionwise 15 g of 4-chlorosalicylic acid. The resulting mixture is heated under reflux for one hour, cooled and stirred at room temperature for 21 hours. Water (7 ml) in THF (50 ml) is added dropwise, followed by 1N hydrochloric acid (250 ml), concentrated hydrochloric acid (50 ml) and ethyl acetate (200 ml). After filtration on a pad of celite the two layers are separated, the organic layer washed with brine, dried over magnesium sulfate, concentrated. The brown oil is dissolved in iso-propyl ether and filtered on a short column of silica gel. After concentration the solid is crystallized in cyclohexane, filtered, washed and dried to give 4-chloro-2-hydroxy-benzylalcohol as a white solid (9.7 g, 70% yield) $C_7H_7ClO_2$ MS ($M^+$) m/z: 158, 160, Cl pattern.

B. Ethyl-(2-hydroxymethyl-5-chloro-phenoxy)-acetate.

To a solution of 4-chloro-2-hydroxy-benzylalcohol (9.7 g, 61.3 mmol) in 100 ml of DMF is added potassium carbonate (17 g, 123.1 mmol), and the resulting suspension is stirred for 15 minutes at room temperature. Ethyle bromoacetate (7.96 ml, 67 mmol) is added and the mixture is stirred at room temperature for two days. The mixture is poured in 500 ml of water, extracted with ethyl acetate (500 ml). The ethyl acetate layer is separated, washed with water (500 ml), brine (500 ml) and dried over magnesium sulfate. After concentration ethyl-(2-hydroxymethyl-5-chloro-phenoxy)-acetate is obtained as a white solid (13.7 g, 91% yield) $C_{11}H_{13}ClO_4$, MS ($M^+$) m/z: 244, 246, Cl pattern.

C. Ethyl-(2-formyl-5-chloro-phenoxy)-acetate.

Ethyl-(2-hydroxymethyl-5-chloro-phenoxy)-acetate (2.44 g, 10 mmol) is dissolved in 40 ml of chloroform. Activated manganese (IV) oxide (8.7 g, 100 mmol) is added in two portions and the resulting suspension is stirred at room temperature for 5 hours. After fitration on a pad of celite and concentration ethyl-(2-formyl-5-chloro-phenoxy)-acetate (2.18 g, 90% yield) is obtained as a pale yellow oil.

$C_{11}H_{11}ClO_4$, MS $(M+H)^+$: 243, Cl pattern.

D. Methyl-6-chloro-benzofurancarboxylate

Magnesium (1.2 g, 50 mmol) is dissolved in 40 ml of methanol. A solution of ethyl-(2-formyl-5-chloro-phenoxy)-acetate (2.1 g, 8.65 mmol) in 15 ml of methanol is added and the resulting mixture is heated under reflux for one hour, cooled, poured in 1N hydrochloric acid (150 ml). After stirring at room temperature the yellow solid is filtered, washed thoroughly with water and dried. Methyl-6-chloro-benzofurancarboxylate is obtained as a yellow solid (0.835 g, 46% yield). $C_{10}H_7ClO_3$, MS (M+): 210, Cl pattern

EXAMPLE 885

2-Cyclopentyl-3-oxo-piperazine-1-carboxylic acid benzyl ester

The title compound is prepared as in EXAMPLE 41, substituting CBZ-1-amino-cyclopentyl-1-caboxylic acid for Cbz-O-methyl-serine. $^1$H NMR (CD$_3$OD, 300 MHz) δ7.32 (m, 5H), 5.12 (s, 2H), 3.71 (m, 2H), 3.28 (m, 2H), 2.17 (m, 4H), 1.8 (m, 4H). MS (ion spray) m/z 289, (M+H).

EXAMPLE 886

(+/−)-cis-4-benzyloxycarbonyl-decahydroquinoxalin-2-one

A. (+/−)-cis-decahydroquinoxalin-2-one.

cis-1,2-Diaminocyclohexane (4.1 g, 36 mmol) is dissolved in 150 ml of H$_2$O. Chloroacetic acid (3.4 g, 36 mmol) in 50 ml of H$_2$O is added dropwise at 10° C. in 5 minutes, then potassium carbonate (7.9 g, 57 mmol) in 30 ml of H$_2$O is added dropwise at 10 C. The reaction mixture is allowed to warm slowly to room temperature and stirred 24 hours. The solution is heated at 90° C. for 2 hours, concentrated. The resulting solid is taken-up in boiling toluene (100 ml), filtered while hot, concentrated to give (+/−)-cis-decahydroquinoxalin-2-one (0.8 g, 14% yield) as a white solid. $C_8H_{14}N_2O$, MS (M+H)+: 155

B. (+/−)-cis-4-benzyloxycarbonyl-decahydroquinoxalin-2-one.

(+/−)-cis-decahydroquinoxalin-2-one (0.8 g, 5.19 mmol) is suspended in 25 ml of H$_2$O. NaHCO$_3$ (0.87 g, 10.35 mmol) is added and the reaction mixture is cooled to 10° C. Benzylchloroformate (1 ml, 6.68 mmol) is added dropwise to the vigorously stirred mixture. After 20 hours at room temperature the solid is filtered, washed thoroughly with H$_2$O, air-dried. The title compound (1.46 g, 98% yield) is obtained as a white solid. $C_{16}H_{20}N_2O_3$, MS (M+H)+:289

EXAMPLE 887

5-Methyl-3-oxo-2-propyl-piperazine-1-carboxylic acid tert-butyl ester

A. [1-(Methoxy-methoxyl-methyl-carbamoyl]-carbamic acid benzyl ester.

To a solution of N-Cbz-L-alanine (12.9 g, 66.7 mmol) and N,O-dimethyl hydroxyl amine hydrochloride (7.2 g, 73.8 mmol) in CH$_2$Cl$_2$ (200 mL) is added TBTU (21.43 g, 66.7 mmol) and diisopropyl ethyl amine (25.9 g, 231.5 mmol). After 6 h, the solution is diluted with CH$_2$Cl$_2$ (200 mL) and is washed with 1N HCl, H$_2$O, and sat. NaCl. The organic layer is dried over MgSO4, filtered and concentrated to give the title compound as an oil. MS (EI) m/z 266, (M+).

B. [1-Methyl-2-oxo-ethyl]-carbamic acid benzyl ester.

To a solution of [1-(methoxy-methoxyl-methyl-carbamoyl]-carbamic acid benzyl ester (66.7 mmol) in THF (160 mL) is added a 1.0M solution of lithium aluminum hydride in THF (81.1 mmol, 81.1 mL) dropwise at 0° C. After 20 min., 1N KHSO$_4$ is added dropwise. The solution is diluted with H$_2$O (200 mL) and the pH is adjusted to 3 with 1N KHSO$_4$. The resulting solution is extracted with Et$_2$O. The Et2O extracts are washed with H2O and sat. NaCl. The organic layer is dried over MgSO4, filtered and concentrated to give the title compound (12 g, 66 mmol) of the title compound. MS (EI) m/z 177, (M+).

C. 2-[2-Benzyloxycarbonylamino-propylamino]-pentanoic acid methyl ester.

To a solution of [1-methyl-2-oxo-ethyl]-carbamic acid benzyl ester (12.3 g, 69 mmol) and norvaline methylester hydrochloride (11.6 g, 69 mmol) in MeOH (300 mL) is added diisopropyl ethyl amine (9.4 g, 73 mmol) and 2 drops of acetic acid. After 10 min., ZnCl$_2$ (9.46 g, 69 mmol) and sodium cyanoborohydride (8.72 g, 14 mmol) is added. The solution is stirred at ambient for 16 h. The solution is then concentrated. The residue is dissolved in EtOAc and 1N KHSO$_4$. The organic layer is washed with 1N KHSO$_4$, H$_2$O, and sat. NaCl. The organic layer is dried over MgSO$_4$, filtered and concentrated. The crude product is purified by column chromatograghy eluting with a gradient of 20% EtOAc/hexane to 40% EtOAc/hexanes. The title compound (8.6 gm, 26.6 mmol) is obtained as a foam. MS (ion spray) m/z 323, (M+H).

D. 5-Methyl-3-oxo-2-propyl-piperazine-1-carboxylic acid tert-butyl ester.

A solution of 2-[2-benzyloxycarbonylamino-propylamino]-pentanoic acid methyl ester (6.6 g, 20.5 mmol) in MeOH (100 mL) is added 4 drops of AcOH and 0.65 g of 10% Pd/C. The atmosphere above the reaction is replaced by hydrogen. The reaction is stirred overnight. The solution is then filtered to give a clear solution. The solution is concentrated and the residue is dissolved in EtOH. The solution is heated to reflux for 2 h. After this time the ethanolic solution is concentrated. The residue is dissolved in CH$_2$Cl$_2$ (60 mL) and BOC$_2$O (3.3 g, 15.1 mmol) followed by DMAP (0.16 g, 1.3 mmol) are added. After 16 h, the reaction is diluted with CH$_2$Cl$_2$ (150 mL) and washed with 1N KHSO4, H2O and sat. NaCl. The organic layer is dried over MgSO$_4$, filtered and concentrated to give the title compound (3.1 g, 12.1 mmol) as a white solid. $^1$H NMR (CDCl$_3$, 300 MHz) δ7.78 (s, 1H), 4.36 (m, 1H), 4.02 (m, 1H), 3.48 (m, 2H), 2.49 (m, 1H), 1.77 (m, 1H), 1.55 (m, 1H), 1.39 (s, 9H), 1.02 (d, 3H), 0.8 (m, 3H). MS (ion spray) m/z 257, (M+H).

EXAMPLE 888

4-[4-Amino-quinazolin-7-ylmethyl]-5-methyl-3-oxo-2-propyl-piperazine

A. 3-[3-Amino-4-cyanobenzyl]-2-propyl-5-methyl-3-oxo-piperazine-1-carboxylic acid tert-butyl ester.

To a solution of 5-methyl-3-oxo-2-propyl-piperazine-1-carboxylic acid tert-butyl ester (3.07 g, 12 mmol), prepared as described in EXAMPLE 887, .in THF (150 mL) is added t-BuOK (1.3 g, 11 mmol). The solution is stirred at ambient temperatures for 25 min. After this time, the reaction mixture is cooled to 0° C. and 2-amino-4-bromomethyl-benzonitrile (2.9 g, 11.3 mmol) and 18-C-6 (15 mgs) are added. The solution is allowed to warm to ambient temperatures and is stirred for 16 h. After this time, 0.5 mL of a saturated NH$_4$Cl solution is added. The solution is concentrated. The residue is purified by column chromatograghy eluting with 20% EtOAc/CH₂Cl₂ to give the title compound as a white solid.

MS (ion spray) m/z 387, (M+H).

B. 4-[4-Amino-quinazolin-7-ylmethyl]-5-methyl-3-oxo-2-propyl-piperazine-1-carboxylic acid tert-butyl-ester.

To a solution of 3-[3-amino-4-cyanobenzyl]-2-propyl-5-methyl-3-oxo-piperazine-1-carboxylic acid tert-butyl ester (1.16 g, 3.0 mmol) in ethanol (30 mL) is added acetic acid (0.55 g, 9.0 mmol) and triazine (0.73 g, 9.0 mmol). The solution is refluxed overnight. After this time, the solution is concentrated. The residue is purified by column chromatography eluting with 5% MeOH/CH₂Cl₂ to give the title compound (0.91 g) as a white solid.

MS (ion spray) m/z 414, (M+H).

C. 4-[4-Amino-quinazolin-7-ylmethyl]-5-methyl-3-oxo-2-propyl-piperazine.

To a solution of 4-[4-amino-quinazolin-7-ylmethyl]-5-methyl-3-oxo-2-propyl-piperazine-1-carboxylic acid tert-butyl-ester (0.91 g, 2.2 mmol) in EtOAc (40 mL) is bubbled HCl (gas) for 5 min. at 0° C. After this time, the solution is stirred at ambient temperatures for 15 min. The solution is concentrated. The residue is purified by column chromatography eluting with 1:5:100 NH₄OH/MeOH/CH₂Cl₂. The title compound (0.5 g) is obtained as a white solid. $^1$H NMR (300 MHz, CDOD) δ8.40 (s, 1H), 8.04 (d, 1H), 7.52 (s, 1H), 7.36 (m, 1H), 5.10 (d, 1H), 4.45 (d, 1H), 3.55 (m, 2H), 3.10 (m, 1H), 2.81 (m, 1H), 1.90 (m, 1H), 1.72 (m, 1H), 1.44 (m, 2H), 1.29 (d, 3H), 0.96 (m, 3H).

MS (ion spray) m/z 314, (M+H).

EXAMPLE 889

(R)-3-Methoxymethyl-5-oxo-piperazine-1-carboxylic acid allyl ester

A. (S)-2-Benzyloxycarbonylamino-3-methoxy-propionic acid methyl ester.

A solution containing Z-L-serine (30 g, 0.126 mol) in anhydrous DMF (500 mL) is cooled to 0° C. Sodium hydride (60%, 11.05 g, 0.28 mol) is added portionwise over ~20 min and the mixture is left to stir for 1 h. Methyl iodide (23.5 mL, 0.38 mol) is added and the mixture is stirred for 30 min at 0° C. and then at room temperature for 2.5 h after which time TLC indicated complete consumption of starting material. Water (1200 mL) is added and the mixture is extracted with diethyl ether (4×200 mL). The combined organic extracts are washed with brine (2×200 mL), dried over anhydrous Na₂SO₄ and concentrated to afford 30 g of crude (S)-2-benzyloxycarbonylamino-3-methoxy-propionic acid methyl ester as a pale yellow oil.

B. (R)-(1-Hydroxymethyl-2-methoxy-ethyl)-carbamic acid benzyl ester.

Calcium chloride (16.63 g, 149.8 mmol) is added to a stirring suspension of sodium borohydride (11.33 g, 299.6 mmol) in ethanol (300 mL) at −40° C. The heterogeneous mixture is warmed to −20° C. and stirred for 1 h. (S)-2-Benzyloxycarbonylamino-3-methoxy-propionic acid methyl ester (20 g, 74.9 mmol) in abs EtOH (250 mL) is then added via cannula transfer. The heterogeneous mixture is stirred at −20° C. for 3 h. The reaction is quenched with water (400 mL) and carefully acidified with 1.0 M HCl. The aqueous layer is extracted with CH₂Cl₂ (4×200 mL) and the combined organic phases are washed with brine (200 mL), dried over anhydrous Na₂SO₄ and concentrated to afford a colorless oil. The mixture is absorbed onto the silica gel and chromatographed on silica gel (hexane:EtOAc, 4:1>2:1>1:1>1:2) to afford 11.5 g (64%) of (R)-(1-hydroxymethyl-2-methoxy-ethyl)-carbamic acid benzyl ester as a colorless oil.

C. (S)-(1-Formyl-2-methoxy-ethyl)-carbamic acid benzyl ester.

To a solution of DMSO (3.56 mL, 50.21 mmol) in anhydrous CH₂Cl₂ (50 mL) at −78° C. is added 2.0 M oxalyl chloride in CH₂Cl₂ (12.55 mL, 25.1 mmol) via syringe. The mixture is stirred at −78° C. for 10 min, then a solution of (R)-(1-hydroxymethyl-2-methoxy-ethyl)-carbamic acid benzyl ester (5 g, 20.92 mmol) in anhydrous CH₂Cl₂ (100 mL) is added via cannula transfer. The mixture is stirred at −78° C. for 30 min. Triethylamine (14.6 mL, 104.6 mmol) is added and the mixture is placed in a 0° C. bath. The reaction is complete in 10 min.

The mixture is quenched with saturated NaHSO₄ (200 mL) and the product is extracted with CH₂Cl₂ (4×100 mL). The combined organic extracts are washed with brine (100 mL), dried over Na₂SO₄, and concentrated to afford (S)-(1-formyl-2-methoxy-ethyl)-carbamic acid benzyl ester as a yellow oil which is used without further purification. $^1$H NMR (300 MHz, CDCl₃) δ3.32 (s, 3H), 3.63 (dd, J=9.6, 4.5 Hz, 1H), 3.93 (dd, J=9.6, 3.3 Hz, 1H), 4.36 (m, 1H), 5.13 (s, 2H), 5.68 (br d, 1H), 7.29-7.37 (m, 5H), 9.60 (s, 1H) ppm.

D. (R)-(2-Benzyloxycarbonylamino-3-methoxy-propylamino)-acetic acid methyl ester.

To a solution of glycine methyl ester HCl (10.51 g, 83.68 mmol) in anhydrous MeOH (100 mL) at 0° C. is added a solution of (S)-(1-formyl-2-methoxy-ethyl)-carbamic acid benzyl ester (20.92 mmol) in anhydrous MeOH (20 mL). The solution is stirred at 0° C. for 10 minutes, then 1.0 M NaBH₃CN in THF (31.38 mL, 31.38 mmol) is added and the now heterogeneous mixture is allowed to warm to room temperature and stir overnight. The mixture is concentrated to dryness, then partitioned between NaHCO₃ (200 mL) and EtOAc (200 mL). The layers are separated and the aqueous layer is extracted twice with EtOAc (100 mL) and the combined organic phases are washed with brine (100 mL), dried over Na₂SO₄, and concentrated to afford a yellow oil which is absorbed onto silica gel and chromatographed (CH₂Cl₂=>1% MeOH/CH₂Cl₂=>2% MeOH/CH₂Cl₂) to afford 3.9 g (60%) of R-(2-benzyloxycarbonylamino-3-methoxy-propylamino)-acetic acid methyl ester as a pale yellow oil. $^1$H NMR (300 MHz, CDCl₃) δ1.73 (br s, 1H), 2.71 (dd, J=12.1, 5.7 Hz, 1H), 2.84 (dd, J=12.2, 5.7 Hz, 1H), 3.32 (s, 3H), 3.39 (d, J=8.6 Hz, 2H), 3.40-3.52 (m, 2H), 3.70 (s, 3H), 3.82 (m, 1H), 5.09 (s, 2H), 5.35 (br d, 1H), 7.25-7.35 (m, 5H) ppm. Mass spectrum (ion spray): m/z 331 (M+H).

E. (R)-6-methoxymethyl-piperazin-2-one.

(R)-(2-Benzyloxycarbonylamino-3-methoxy-propylamino)-acetic acid methyl ester (3.9 g, 12.58 mmol) is dissolved in MeOH (~200 mL) and warmed in the presence of decolorizing charcoal for 1 h. The mixture is filtered through celite and the clear filtrate is concentrated. The residue is redissolved in MeOH (160 mL) and placed in a Parr bottle. Palladium-on-carbon (10%, 800 mg) is added and the mixture is hydrogenated for 5 h at 45 PSI. An additional portion of Pd-on-C (250 mg) is added and the mixture left is reacted for 16 h at 45 PSI. The mixture is filtered through celite and concentrated to afford 1.5 g (83%) of (R)-6-methoxymethyl-piperazin-2-one as a yellow solid which is used without further purification. $^1$H NMR (300 MHz, CDCl₃) δ1,77 (br s, 1H), 2.70 (dd, J=13.1, 7.2 Hz, 1H), 3.07 (dd, J=13.1, 4.5 Hz, 1H), 3.26 (dd, J=9.1, 7.7 Hz, 1H), 3.33 (s, 3H), 3.37-3.45 (m, 3H), 3.61 (m, 1H), 6.51 (br s, 1H) ppm.

F. (R)-3-Methoxymethyl-5-oxo-piperazine-1-carboxylic acid allyl ester.

(R)-6-methoxymethyl-piperazin-2-one (2.3 g, 16.0 mmol) is dissolved in anhydrous $CH_2Cl_2$ (60 mL) and cooled to 0° C. Triethylamine (3.4 mL, 24.0 mmol) is added, followed, after 5 minutes, by allyl chloroformate (2.0 mL, 19.2 mmol). The mixture is allowed to warm to room temperature over 2 h when TLC analysis indicated that the reaction is complete.

The mixture is partitioned between water (100 mL) and $CH_2Cl_2$ (100 mL) and the layers are separated. The aqueous phase is extracted twice with $CH_2Cl_2$ (2×75 mL) and the combined organic phases are washed with brine (100 mL), dried over anhydrous $Na_2SO_4$ and concentrated to afford the crude product which is purified by flash silica gel chromatography ($CH_2Cl_2$ to 1%, 2%, 4% $MeOH/CH_2Cl_2$) to afford 3.41 g (93%) of (R)-3-methoxymethyl-5-oxo-piperazine-1-carboxylic acid allyl ester as a colorless oil.

$^1$H NMR (300 MHz, CDCl$_3$) δ3.26 (dd, J=9.3, 7.4 Hz, 1H), 3.31 (s, 3H), 3.36 (m, 1H), 3.63 (m, 1H), 3.76 (m, 1H), 4.07 (ABq, $\Delta_{AB}$=39.9 Hz, $J_{AB}$=18.5 Hz, 2H), 4.58 (d, J=5.59 Hz, 2H), 5.21 (m, 2H), 5.88 (m, 1H), 7.05 (br, 1H) ppm.

EXAMPLE 890

6-Isopropyl-piperazin-2-one

A. (R)-2-Benzyloxycarbonylamino-3-methyl-thiobutyric acid S-ethyl ester.

To a solution containing (R)-2-benzyloxycarbonylamino-3-methyl-butyric acid (5.0 g, 20.0 mmol) in anhydrous $CH_2Cl_2$ (20 mL) is added DMAP (258 mg, 2.0 mmol) followed by chilled EtSH (1.6 mL, 22.0 mmol). Dicyclohexylcarbodiimide (4.5 g, 22.0 mmol) is added in one portion and the reaction is complete after 30 min. The solid material is removed by vacuum filtration and the filtrate is concentrated. The crude product is purified by flash silica gel chromatography (hexane to 8:1 hexane/EtOAc) to provide (R)-2-benzyloxycarbonylamino-3-methyl-thiobutyric acid S-ethyl ester (5.21 g, 88%) as a colorless oil. $^1$H NMR (300 MHz, CDCl$_3$) δ0.85 (d, J=6.8 Hz, 3H), 0.98 (d, J=6.8 Hz, 3H), 1.23 (t, J=7.5 Hz, 3H), 2.27 (m, 1H), 2.88 (q, J=7.5 Hz, 2H), 4.35 (dd, J=9.5, 4.6 Hz, 1H), 5.13 (s, 2H), 5.25 (br d, J=9.5 Hz, 1H), 7.30-7.36 (m, 5H) ppm.

B. (R)-(1-Formyl-2-methyl-propyl)-carbamic acid benzyl ester.

To a solution containing (R)-2-benzyloxycarbonylamino-3-methyl-thiobutyric acid S-ethyl ester (5.2 g, 17.6 mmol) in acetone (100 mL) is added Pd-on-C (10%, 233 mg). The heterogeneous mixture is cooled to 0° C. and Et$_3$SiH (8.4 mL, 53 mmol) is quickly added. After 30 min, the reaction mixture is filtered through a pad of celite and the clear filtrate is concentrated to a residue which is partitioned between hexane (200 mL) and acetonitrile (300 mL). The layers are separated and the ACN phase is washed once with hexane (100 mL) and then concentrated to afford crude (R)-(1-Formyl-2-methyl-propyl)-carbamic acid benzyl ester (4.13 g) which is used directly without further purification. $^1$H NMR (300 MHz, CDCl$_3$) δ2.30 (m, 1H), 4.31 (m, 1H), 5.09 (s, 2H), 5.45 (br, 1H), 7.30-7.45 (m, 5H), 9.65 (s, 1H) ppm.

C. (R)-(2-Benzyloxycarbonylamino-3-methyl-butylamino)-acetic acid ethyl ester.

To a solution containing crude (R)-(1-formyl-2-methyl-propyl)-carbamic acid benzyl ester (4.13 g, 17.6 mmol) in anhydrous MeOH (100 mL) at 0° C. is added glycine ethyl ester hydrochloride (9.5 g, 70.4 mmol). After 10 min, 1.0 M NaCNBH$_3$ in THF (27 mL, 27 mmol) is added and the heterogeneous reaction mixture is allowed to warm to ambient temperature overnight.

The reaction mixture is concentrated and the residue is partitioned between diethyl ether (200 mL) and saturated aqueous NaHCO$_3$ (200 mL). The layers are separated and the aqueous layer is extracted twice with diethyl ether (2×200 mL). The combined organic extracts are washed with brine, dried over anhydrous Na$_2$SO$_4$, filtered and concentrated to afford the crude product which is purified by flash silica gel chromatography (hexane/EtOAc, 2:1 to 1:1) which provided 4.2 g (74%) of (R)-(2-benzyloxycarbonylamino-3-methyl-butylamino)-acetic acid ethyl ester as a colorless oil. $^1$H NMR (300 MHz, CDCl$_3$) δ0.89 (d, J=7.0 Hz, 3H), 0.92 (d, J=7.0 Hz, 3H), 1.25 (t, J=8.4 Hz, 3H), 1.62 (br s, 1H), 1.80 (m, 1H), 2.65-2.70 (m, 2H), 3.37 (ABq, $\Delta_{AB}$=32.3 Hz, $J_{AB}$=17.4 Hz, 2H), 4.16 (q, J=8.4 Hz, 2H), 5.14 (s, 2H), 7.28-7.36 (m, 5H) ppm. Mass spectrum (ion spray): m/z 323 (M+H).

D. (R)-6-Isopropyl-piperazin-2-one.

To a Parr vessel charged with (R)-(2-benzyloxycarbonylamino-3-methyl-butylamino)-acetic acid ethyl ester (4.2 g, 13.0 mmol) in MeOH (130 mL) is added Pd-on-C (10%, 396 mmol). The reaction vessel is pressurized with 40 PSI hydrogen pressure and shaken for 4 h at ambient temperature. The reaction mixture is then filtered through celite and the filtrate is concentrated to provide 1.77 g (95%) of (R)-6-isopropyl-piperazin-2-one as an off-white solid which is used without further purification. $^1$H NMR (300 MHz, CDCl$_3$) δ0.93 (d, J=6.8 Hz, 3H), 0.97 (d, J=6.8 Hz, 3H), 1.68 (sept, J=6.7 Hz, 1H), 2.67 (dd, J=12.8, 8.9 Hz, 1H), 3.09-3.22 (m, 2H), 3.46 (ABq, $\Delta_{AB}$=34.3 Hz, $J_{AB}$=17.5 Hz, 2H), 5.97 (br s, 1H) ppm.

EXAMPLE 891

9-(4-Aminoquinazolin-7-ylmethyl)-6,9-diaza-spiro [4,5]decan-10-one

The title compound is prepared as described in EXAMPLE 75, substituting 2-cyclopentyl-3-oxo-piperazine-1-carboxylic acid benzyl ester, Example 885, for 2-methoxymethyl-3-oxo-piperazine-1-carboxylic acid benzyl ester. $^1$H NMR (CD$_3$OD, 300 MHz) δ8.38 (s, 1H), 8.09 (d, 1H), 7.56 (s, 1H), 7.39 (d, 1H), 4.72 (s, 2H), 3.38 (m, 2H), 3.07 (m, 2H), 2.21 (m, 2H), 1.72 (m, 6H).

EXAMPLE 892

(+/−)-cis-4-benzyloxycarbonyl-decahydroquinoxalin-2-one

A. (+/−)-cis-decahydroquinoxalin-2-one.

cis-1,2-Diaminocyclohexane (4.1 g, 36 mmol) is dissolved in 150 ml of H$_2$O. Chloroacetic acid (3.4 g, 36 mmol) in 50 ml of H$_2$O is added dropwise at 10° C. in 5 minutes, then potassium carbonate (7.9 g, 57 mmol) in 30 ml of H$_2$O is added dropwise at 10 C. The reaction mixture is allowed to warm slowly to room temperature and stirred 24 hours. The solution is heated at 90° C. for 2 hours, concentrated. The resulting solid is taken-up in boiling toluene (100 ml), filtered while hot, concentrated to give (+/−)-cis-decahydroquinoxalin-2-one (0.8 g, 14% yield) as a white solid.

$C_8H_{14}N_2O$, MS (M+H)+: 155

B. (+/−)-cis-4-benzyloxycarbonyl-decahydroquinoxalin-2-one.

(+/−)-cis-Decahydroquinoxalin-2-one (0.8 g, 5.19 mmol) is suspended in 25 ml of $H_2O$. $NaHCO_3$ (0.87 g, 10.35 mmol) is added and the reaction mixture is cooled to 10° C. Benzylchloroformate (1 ml, 6.68 mmol) is added dropwise to the vigorously stirred mixture. After 20 hours at room temperature the solid is filtered, washed thoroughly with $H_2O$, air-dried. The title compound (1.46 g, 98% yield) is obtained as a white solid.

$C_{16}H_{20}N_2O_3$, MS (M+H)$^+$: 289

EXAMPLE 893

(+/−)-cis-1-(4-Amino-quinazolin-7-ylmethyl)-decahydroquinoxalin-2-one

The title compound is prepared as described in EXAMPLE 75, subsituting (+/−)-cis-4-benzyloxycarbonyl-decahydroquinoxalin-2-one EXAMPLE 892 for 2-methoxymethyl-3-oxo-piperazine-1-carboxylic acid benzyl ester. $C_{17}H_{21}N_5O$, MS (M+H)$^+$: 312

EXAMPLE 894

(+/−)-trans-4-benzyloxycarbonyl-decahydroquinoxalin-2-one

A. (+/−)-trans-decahydroquinoxalin-2-one.

(+/−)-trans-1,2-Diaminocyclohexane (22.84 g, 200 mmol) is dissolved in 600 ml of $H_2O$. Chloroacetic acid (18.8 g, 200 mmol) in 200 ml of $H_2O$ is added dropwise at 10° C. in 30 minutes, then potassium carbonate (44 g, 320 mmol) in 120 ml of $H_2O$ is added dropwise at 10 C. The reaction mixture is allowed to warm slowly to room temperature and stirred 24 hours. The solution is heated at 90° C. for 2 hours, concentrated. The resulting solid is taken-up in boiling EtOH (800 ml), filtered while hot, concentrated. The off-white solid is recrystallized in boiling toluene (1000 ml), dried to give (1) (9.72 g, 31% yield) as a white solid.

$C_8H_{14}N_2O$, MS (M+H)+: 155

B. (+/−)-trans-4-benzyloxycarbonyl-decahydroquinoxalin-2-one.

(+/−)-trans-4-Benzyloxycarbonyl-decahydroquinoxalin-2-one (0.8 g, 5.19 mmol) is suspended in 25 ml of $H_2O$. $NaHCO_3$ (0.87 g, 10.35 mmol) is added and the reaction mixture is cooled to 10° C. Benzylchloroformate (1 ml, 6.68 mmol) is added dropwise to the vigorously stirred mixture. After 5 hours at room temperature the solid is filtered, washed thoroughly with $H_2O$, air-dried. The title compound (1.33 g, 89% yield) is obtained as a white solid.

EXAMPLE 895

(+/−)-trans-1-(4-Amino-quinazolin-7-ylmethyl)-decahydroquinoxalin-2-one

The title compound is prepared as described in EXAMPLE 75, subsituting trans-4-benzyloxycarbonyl -decahydroquinoxalin-2-one (EXAMPLE 894) for 2-methoxymethyl-3-oxo-piperazine-1-carboxylic acid benzyl ester.

$C_{17}H_{21}N_5O$, MS (M+H)$^+$: 312

EXAMPLE 896

4-Benzyloxycarbonyl-3-(S)-(2-methylsulfanyl-ethyl)-piperazin-2-one

A. [1-(2,2-Dimethoxy-ethylcarbamoyl)-3-(S)-methylsulfanyl-propyl]-carbamic acid benzyl ester To a solution of (L)-N-Benzyloxycarbonyl-methionine (25 g, 88.2 mmol) in 400 ml of $CH_2Cl_2$ is added TBTU (28.3 g, 88.2 mmol), followed by $NEt_3$ (36.6 ml, 264 mmol) and aminoacetaldehyde dimethylacetal (10.6 ml, 69.7 mmol). The solution is stirred for 16 hours, washed with $H_2O$, 1N hydrochloric acid, saturated aqueous $NaHCO_3$, brine, dried over magnesium sulfate and concentrated. The resulting crude product is purified by column chromatography eluting with a gradient of 1% MeOH:$CH_2Cl_2$ to 5% MeOH:$CH_2Cl_2$. The title compound (23.3 g, 71% yield) is obtained as a white solid.

$C_{17}H_{26}N_2O_5S$ MS (M+H)$^+$: 371

B. 4-Benzyloxycarbonyl-3-(S)-(2-methylsulfanyl-ethyl)-3,4-dihydro-1H-pyrazine-2-one To a solution of [1-(2,2-dimethoxy-ethylcarbamoyl)-3-(S)-methylsulfanyl-propyl]-carbamic acid benzyl ester (23.3 g, 63 mmol) in toluene (300 ml) is added p-toluenesulfonic acid monohydrate (1.14 g, 6.3 mmol). The resulting solution is stirred at 70° C. for 4 hours, cooled, washed with $H_2O$, brine, dried over magnesium sulfate and concentrated. The resulting crude product is purified by column chromatography eluting with a gradient of 2% MeOH:$CH_2Cl_2$ to 5% MeOH:$CH_2Cl_2$. The title compound (17.9 g, 93% yield) is obtained as an oil.

$C_{15}H_{18}N_2O_3S$ MS (M+H)$^+$: 307

C. 4-Benzyloxycarbonyl-3-(S)-(2-methylsulfanyl-ethyl)-piperazin-2-one.

To a solution of 4-benzyloxycarbonyl-3-(S)-(2-methylsulfanyl-ethyl)-3,4-dihydro-1H-pyrazine-2-one (0.3 g, 1 mmol) in $CH_2Cl_2$ is added $Et_3SiH$ (1.57 ml, 10 mmol). The resulting solution is cooled to 0° C. and $CF_3CO_2H$ (2.2 ml, 30 mmol) is added dropwise. The mixture is stirred 16 hours at room temperature, washed with a saturated aqueous $NaHCO_3$ solution, brine. The solution is dried over $MgSO_4$, concentrated. The resulting crude product is purified by column chromatography on silica gel eluting with a gradient of 50% AcOEt: Hexane to 100% AcOEt. The title compound (0.138 g, 46% yield) is obtained as an oil.

$C_{15}H_{20}N_2O_3S$ MS (M+H)$^+$: 309

EXAMPLE 897

1-(4-Amino-quinazolin-7-ylmethyl)-3-(S)-(2-methylsulfanyl-ethyl)-piperazin-2-one A. 4-Benzyloxycarbonyl-1-[3-(benzhydrylidene-amino)-4-cyano-benzyl]-3-(S)-(2-methylsulfanyl-ethyl)-piperazin-2-one.

To a solution of 4-benzyloxycarbonyl-3-(S)-(2-methylsulfanyl-ethyl)-piperazin-2-one (1.15 g, 3.74 mmol) in 10 ml of DMF is added at 0° C. sodium hydride (164 mg at 60% in oil, 4.12 mmol). The solution is stirred 10 minutes then 2-(benzhydrylidene-amino)-4-bromomethyl-benzonitrile (2.6 g at 52%, 3.74 mmol) in 25 ml of DMF is added dropwise. The resulting mixture is stirred for 20 hours at room temperature, diluted with ethyle acetate, washed with water, with a saturated aqueous $NaHCO_3$ solution, brine. The solution is dried over $MgSO_4$, concentrated. The resulting crude product is purified by column chromatography on silica gel eluting with 2% MeOH:CH$_2$Cl$_2$. The title compound (1.8 g, 80% yield) is obtained as a viscous oil.

C$_{36}$H$_{34}$N$_4$O$_3$S MS (M+H)$^+$: 603

B. 4-Benzyloxycarbonyl-1-[3-(benzhydrylidene-amino)-4-cyano-benzyl]-3-(S)-(2-methylsulfanyl-ethyl)-piperazin-2-one.

To a solution of 4-benzyloxycarbonyl-1-[3-(benzhydrylidene-amino)-4-cyano-benzyl]-3-(S)-(2-methylsulfanyl-ethyl)-piperazin-2-one (1.8 g, 3 mmol) in 20 ml of ethyle acetate is added concentrated hydrochloric acid (10 drops) and H$_2$O (10 drops). The resulting mixture is stirred for 1 hour, the ethyle acetate solution is decanted, washed with a saturated aqueous NaHCO$_3$ solution, with water, brine. The solution is dried over MgSO$_4$, concentrated. The resulting crude product is purified by column chromatography on silica gel eluting with 1% MeOH:CH$_2$Cl$_2$. The title compound (1.17 g, 89% yield) is obtained as a yellow foam.

C$_{23}$H$_{26}$N$_4$O$_3$S MS (M+H)$^+$: 439

C. 1-(4-Amino-quinazolin-7-ylmethyl)-4-benzyloxycarbonyl-3-(S)-(2-methylsulfanyl-ethyl)-piperazin-2-one.

To a solution of 4-benzyloxycarbonyl-1-[3-(benzhydrylidene-amino)-4-cyano-benzyl]-3-(S)-(2-methylsulfanyl-ethyl)-piperazin-2-one (1.17 g, 2.67 mmol) in 15 ml of ethanol is added 1,3,5-triazine and glacial acetic acid (3.1 ml, 53.4 mmol). The resulting solution is refluxed for 20 hours, concentrated under vacuum. The residue is dissolved in ethyle acetate, washed with 1N hydrochloric acid, a saturated aqueous NaHCO$_3$ solution, water, brine. The solution is dried over MgSO$_4$, concentrated. The resulting crude product is purified by column chromatography eluting with a gradient of 5% MeOH:CH$_2$Cl$_2$ to 10% MeOH:CH$_2$Cl$_2$. The title compound (489 mg, 39% yield) is obtained as a yellow solid.

C$_{24}$H$_{27}$N$_5$O$_3$S MS (M+H)$^+$: 466.

D. 1-(4-Amino-quinazolin-7-ylmethyl)-3-(S)-(2-methylsulfanyl-ethyl)-piperazin-2-one.

1-(4-Amino-quinazolin-7-ylmethyl)-4-benzyloxycarbonyl-3-(S)-(2-methylsulfanyl-ethyl)-piperazin-2-one (100 mg, 0.215 mmol) is dissolved in 5 ml of 30% hydrogen bromide in acetic acid. The mixture is stirred for 1 hour, diluted with ethyle ether. The ether is decanted and the resulting solid is washed thoroughly with ethyle ether. The resulting crude product is purified by column chromatography eluting with a 4/2/1 mixture of CH$_2$Cl$_2$/MeOH/NH$_4$OH (30% in H$_2$O). with a gradient of 5% MeOH:CH$_2$Cl$_2$ to 10% MeOH:CH$_2$Cl$_2$. The resulting product is purified by another column chromatography eluting with a gradient of 20% MeOH:CH$_2$Cl$_2$ to 50% MeOH:CH$_2$Cl$_2$. The title bound (30 mg, 42% yield) is obtained as an off-white solid.

C$_{16}$H$_{25}$N$_5$OS MS (M+H)$^+$: 332.

The following compounds are prepared from the templates described above, coupled with an amino-quinazoline group, and the appropriate sulfonyl chloride using the method of Example 101.

| Example # | Name | m/z (M + H) |
| --- | --- | --- |
| 898 | (R)-1-(4-Amino-quinazolin-7-ylmethyl)-4-(5-chloro-1H-indole-2-sulfonyl)-6-isopropyl-piperazin-2-one | 513 |
| 899 | (R)-1-(4-Amino-quinazolin-7-ylmethyl)-4-(6-chloro-benzo[b]thiophene-2-sulfonyl)-6-isopropyl-piperazin-2-one | 530 |
| 900 | (R)-1-(4-Amino-quinazolin-7-ylmethyl)-4-(6-chloro-1H-benzoimidazole-2-sulfonyl)-6-isopropyl-piperazin-2-one | 514 |
| 901 | (R/S)1-(4-Amino-quinazolin-7-ylmethyl)-4-(6-chloro-1H-benzoimidazole-2-sulfonyl)-6-oxo-piperazine-2-carboxylic acid ethyl ester | 544 |
| 902 | (R)-1-(4-Amino-quinazolin-7-ylmethyl)-4-(6-chloro-1H-indole-2-sulfonyl)-6-methoxymethyl-piperazin-2-one | 515 |
| 903 | (R)-1-(4-Amino-quinazolin-7-ylmethyl)-4-(6-chloro-1H-benzoimidazole-2-sulfonyl)-6-isopropyl-piperazin-2-one | 514 |
| 904 | (R)-1-(4-Amino-quinazolin-7-ylmethyl)-4-(6-chloro-1H-indole-2-sulfonyl)-6-isopropyl-piperazin-2-one | 513 |
| 905 | (4aRS,8aSR)-1-(4-Amino-quinazolin-7-ylmethyl)-4-(6-chloro-benzo[b]thiophene-2-sulfonyl)-octahydro-quinoxalin-2-one | 542 |
| 906 | (R)-1-(4-Amino-quinazolin-7-ylmethyl)-4-(5-chloro-1H-indole-2-sulfonyl)-6-methoxymethyl-piperazin-2-one | 515, 517 Cl pattern |
| 907 | 1-(4-Amino-quinazolin-7-ylmethyl)-4-(5-chloro-1H-indole-2-sulfonyl)-piperazin-2-one | 471 |
| 908 | 1-(4-Amino-quinazolin-7-ylmethyl)-4-(6-chloro-1H-indole-2-sulfonyl)-piperazin-2-one | 471 |
| 909 | [1-(4-Amino-quinazolin-7-ylmethyl)-4-(6-chloro-benzo[b]thiophene-2-sulfonyl)-6-oxo-piperazin-2-(S)-yl]-acetic acid | 546 |
| 910 | [1-(4-Amino-quinazolin-7-ylmethyl)-4-(6-chloro-benzo[b]thiophene-2-sulfonyl)-6-oxo-piperazin-2-(S)-yl]-acetic acid tert-butyl ester | 602 |
| 911 | (R)-1-(4-Amino-quinazolin-7-ylmethyl)-4-(6-chloro-1H-benzoimidazole-2-sulfonyl)-6-methoxymethyl-piperazin-2-one | 516 |
| 912 | (+/−)-1-(4-Amino-quinazolin-7-ylmethyl)-4-(6-chloro-benzo[b]thiophene-2-sulfonyl)-6-oxo-piperazine-2-carboxylic acid (2-pyrrolidin-1-yl-ethyl)-amide | 628 |
| 913 | (+/−)-1-(4-Amino-quinazolin-7-ylmethyl)-4-(6-chloro-benzo[b]thiophene-2-sulfonyl)-6-oxo-piperazine-2-carboxylic acid 2-pyrrolidin-1-yl-ethyl ester | 629 |

-continued

| Example # | Name | m/z (M + H) |
|---|---|---|
| 914 | (S)-1-(4-Amino-quinazolin-7-ylmethyl)-4-(6-chloro-benzo[b]thiophene-2-sulfonyl)-6-methoxymethyl-piperazin-2-one | 532 |
| 915 | (s)-1-(4-Amino-quinazolin-7-ylmethyl)-4-(6-chloro-benzo[b]thiophene-2-sulfonyl)-6-methoxymethyl-piperazin-2-one | 532 |
| 916 | 4-(4-Amino-quinazolin-7-ylmethyl)-(2S)-methoxymethyl-3-oxo-piperazine-1-sulfonic acid(4-chloro-phenyl)-amide | 491 |

The following compounds can be prepared from the templates described above, coupled with an amino-quinazoline group, and the appropriate sulfonyl chloride using the method of Example 101.

The following compounds are prepared from the templates described above, coupled with an amino-quinazoline group, and the appropriate alkylating reagent using the method of Example 268.

| Example # | Name |
|---|---|
| 917 | 1-(4-Amino-quinazolin-7-ylmethyl)-4-(6-chloro-benzo[b]thiophene-2-sulfonyl)-6-oxo-piperazine-2-carboxylic acid 2-imidazol-1-yl-ethyl ester |
| 918 | (+/−)-1-(4-Amino-quinazolin-7-ylmethyl)-4-(6-chloro-benzo[b]thiophene-2-sulfonyl)-6-oxo-piperazine-2-carboxylic acid 2-morpholin-4-yl-ethyl ester |
| 919 | (+/−)-1-(4-Amino-quinazolin-7-ylmethyl)-4-(6-chloro-benzo[b]thiophene-2-sulfonyl)-6-oxo-piperazine-2-carboxylic acid pyrrolidin-2-ylmethyl ester |
| 920 | (+/−)-1-(4-Amino-quinazolin-7-ylmethyl)-4-(6-chloro-benzo[b]thiophene-2-sulfonyl)-6-oxo-piperazine-2-carboxylic acid 2-methylamino-ethyl ester |
| 921 | (R)-1-(4-Amino-quinazolin-7-ylmethyl)-4-(6-chloro-benzo[b]thiophene-2-sulfonyl)-6-methyl-piperazin-2-one |
| 922 | (S)-1-(4-Amino-quinazolin-7-ylmethyl)-4-(6-chloro-benzo[b]thiophene-2-sulfonyl)-6-methyl-piperazin-2-one |
| 923 | (R)-1-(4-Amino-quinazolin-7-ylmethyl)-4-(6-chloro-benzo[b]thiophene-2-sulfonyl)-6-isopropyl-piperazin-2-one |
| 924 | (R)-1-(4-Amino-quinazolin-7-ylmethyl)-4-(6-chloro-benzo[b]thiophene-2-sulfonyl)-6-isobutyl-piperazin-2-one |
| 925 | (S)-1-(4-Amino-quinazolin-7-ylmethyl)-4-(6-chloro-benzo[b]thiophene-2-sulfonyl)-6-isobutyl-piperazin-2-one |
| 926 | (R)-1-(4-Amino-quinazolin-7-ylmethyl)-4-(5-chloro-1H-indole-2-sulfonyl)-6-methyl-piperazin-2-one |
| 927 | (S)-1-(4-Amino-quinazolin-7-ylmethyl)-4-(5-chloro-1H-indole-2-sulfonyl)-6-methyl-piperazin-2-one |
| 928 | (R)-1-(4-Amino-quinazolin-7-ylmethyl)-4-(5-chloro-1H-indole-2-sulfonyl)-6-isobutyl-piperazin-2-one |
| 929 | (S)-1-(4-Amino-quinazolin-7-ylmethyl)-4-(5-chloro-1H-indole-2-sulfonyl)-6-isobutyl-piperazin-2-one |
| 930 | (R)-1-(4-Amino-quinazolin-7-ylmethyl)-4-(6-chloro-1H-indole-2-sulfonyl)-6-methyl-piperazin-2-one |
| 931 | (S)-1-(4-Amino-quinazolin-7-ylmethyl)-4-(6-chloro-1H-indole-2-sulfonyl)-6-methyl-piperazin-2-one |
| 932 | (R)-1-(4-Amino-quinazolin-7-ylmethyl)-4-(6-chloro-1H-indole-2-sulfonyl)-6-isobutyl-piperazin-2-one |
| 933 | (S)-1-(4-Amino-quinazolin-7-ylmethyl)-4-(6-chloro-1H-indole-2-sulfonyl)-6-isobutyl-piperazin-2-one |
| 934 | (R)-1-(4-Amino-quinazolin-7-ylmethyl)-4-(6-chloro-1H-benzoimidazole-2-sulfonyl)-6-methyl-piperazin-2-one |
| 935 | (S)-1-(4-Amino-quinazolin-7-ylmethyl)-4-(6-chloro-1H-benzoimidazole-2-sulfonyl)-6-methyl-piperazin-2-one |
| 936 | (R)-1-(4-Amino-quinazolin-7-ylmethyl)-4-(6-chloro-1H-benzoimidazole-2-sulfonyl)-6-isobutyl-piperazin-2-one |
| 937 | (S)-1-(4-Amino-quinazolin-7-ylmethyl)-4-(6-chloro-1H-benzoimidazole-2-sulfonyl)-6-isobutyl-piperazin-2-one |

| Example # | Name | m/z (M + H) |
|---|---|---|
| 938 | 1-(4-Amino-quinazolin-7-ylmethyl)-4-(2-chloro-imidazo[1,2-a]pyridin-7-ylmethyl)-piperazin-2-one | 422 |
| 939 | 1-(4-Amino-quinazolin-7-ylmethyl)-4-(5-chloro-1H-indol-2-ylmethyl)-3(S)-(2-methylsulfanyl-ethyl)-piperazin-2-one | 495 |
| 940 | 1-(4-Amino-quinazolin-7-ylmethyl)-4-[3-(5-chloro-thiophen-2-yl)-allyl]-(S)-6-methyl-(S)-3-propyl-piperazin-2-one | 470, 472 Cl pattern |
| 941 | 1-(4-Amino-quinazolin-7-ylmethyl)-4-(6-chloro-thieno[2,3-b]pyridin-2-ylmethyl)-(S)-3-propyl-piperazin-2-one | 481, 483 Cl pattern |
| 942 | 2-[4-(4-Amino-quinazolin-7-ylmethyl)-3-oxo(S)—2-propyl-piperazin-1-ylmethyl]-5-chloro-indole-1-carboxylic acid tert-butyl ester | 563, 565 Cl pattern |
| 943 | 1-(4-Amino-quinazolin-7-ylmethyl)-4-(5-chloro-1H-indol-2-ylmethyl)-(S)-3-propyl-piperazin-2-one | 463, 465 Cl pattern |
| 944 | 1-(4-Amino-quinazolin-7-ylmethyl)-4-(6-chloro-benzofuran-2-ylmethyl)-3(S)-propyl-piperazin-2-one | 464 |
| 945 | 9-(4-Amino-quinazolin-7-ylmethyl)-6-[3-(5-chloro-thiophen-2-yl)-allyl]-6,9-diaza-spiro[4.5]decan-10-one | 468 |
| 946 | (4aRS,8aSR)-1-(4-Amino-quinazolin-7-ylmethyl)-4-[3-(5-chloro-thiophen-2-yl)-allyl]-octahydro-quinoxalin-2-one | 468, 470 Cl pattern |
| 947 | (4aRS,8aSR)-1-(4-Amino-quinazolin-7-ylmethyl)-4-(5-chloro-1H-indol-2-ylmethyl)-octahydro-quinoxalin-2-one | 475, 477 Cl pattern |
| 948 | 1-(4-Amino-quinazolin-7-ylmethyl)-4-(5-chloro-1H-indol-2-ylmethyl)-3(S)-isobutyl-piperazin-2-one | 477, 479 Cl pattern |
| 949 | 1-(4-Amino-quinazolin-7-ylmethyl)-4-(7-chloro-isoquinolin-3-ylmethyl)-3(S)-isobutyl-piperazin-2-one | 489, 491 Cl pattern |
| 950 | 3-[4-(4-Amino-quinazolin-7-ylmethyl)-(2S)-methoxymethyl-3-oxo-piperazin-1-ylmethyl]-benzamidine | 434 |
| 951 | (4aRS,8aRS)-1-(4-Amino-quinazolin-7-ylmethyl)-4-(5-chloro-1H-indol-2-ylmethyl)-octahydro-quinoxalin-2-one | 475, 477 Cl pattern |
| 952 | (4aRS,8aRS)-1-(4-Amino-quinazolin-7-ylmethyl)-4-[3-(5-chloro-thiophen-2-yl)-allyl]-octahydro-quinoxalin-2-one | 468, 470 Cl pattern |
| 953 | (4aRS,8aRS)-1-(4-Amino-quinazolin-7-ylmethyl)-4-(7-chloro-isoquinolin-3-ylmethyl)-octahydro-quinoxalin-2-one | 487, 489 Cl pattern |
| 954 | 2-[4-(4-Amino-quinazolin-7-ylmethyl)-1-(7-chloro-isoquinolin-3-ylmethyl)-3-oxo-piperazin-2-(S)-yl]-N-methyl-acetamide | 504, 506 Cl pattern |
| 955 | 2-[4-(4-Amino-quinazolin-7-ylmethyl)-1-(7-chloro-isoquinolin-3-ylmethyl)-3-oxo-piperazin-2-(S)-yl)]-acetamide | 490, 492 Cl pattern |
| 956 | 2-{4-(4-Amino-quinazolin-7-ylmethyl)-1-[3-(5-chloro-thiophen-2-yl)-allyl]-3-oxo-piperazin-2-(S)-yl}-acetamide | 471, 473 Cl pattern |
| 957 | 2-{4-(4-Amino-quinazolin-7-ylmethyl)-1-[3-(5-chloro-thiophen-2-yl)-allyl]-3-oxo-piperazin-2-(S)-yl}-N-methyl-acetamide | 485, 487 Cl pattern |
| 958 | 1-(4-Amino-quinazolin-7-ylmethyl)-4-[3-(5-chloro-thiophen-2-yl)-allyl]-3(S)-isobutyl-piperazin-2-one | 470, 472 Cl pattern |
| 959 | (s)-1-(4-Amino-quinazolin-7-ylmethyl)-4-[3-(5-chloro-thiophen-2-yl)-allyl]-6-methoxymethyl-piperazin-2-one | 458, 460 Cl pattern |
| 960 | 1-(4-Amino-quinazolin-7-ylmethyl)-4-(4-amino-thieno[3,2-d]pyrimidin-6-ylmethyl)-3(S)-methoxymethyl-piperazin-2-one | 465 |
| 961 | 1-(4-Amino-quinazolin-7-ylmethyl)-3-(S)-methoxymethyl-4-(4-pyrimidin-4-yl-benzyl)-piperazin-2-one | 470 |
| 962 | 4-[4-(2-Amino-pyrimidin-4-yl)-benzyl]-1-(4-amino-quinazolin-7-ylmethyl)-3-(S)-methoxymethyl-piperazin-2-one | 485 |
| 963 | 3-Amino-5-[4-(4-amino-quinazolin-7-ylmethyl)-2(S)-methoxymethyl-3-oxo-piperazin-1-ylmethyl]-thiophene-2-carbonitrile | 438 |
| 964 | 1-(4-Amino-quinazolin-7-ylmethyl)-4-[3-(5-chloro-thiophen-2-yl)-allyl]-3(S)-(2-methoxy-ethyl)-piperazin-2-one | 472 |

EXAMPLE 965

3-{3-[4-(4-Amino-quinazolin-7-ylmethyl)-(2S)-methoxymethyl-3-oxo-piperazin-1-yl]-3-oxo-propenyl}-benzonitrile To a solution of 1-(4-amino-quinazoline-7-ylmethyl)-3-(S)-methoxymethyl-piperazine-2-one, EXAMPLE 75, (50 mg, 0.16 mmol) and 3-cyanocinnamic acid (29 mg, 0.17 mmol, prepared from 3-cyanobenzaldehyde) in 1 mL of DMF is added N,N-diisopropylethylamine (0.07 mL, 0.38 mmol), followed by 2-(1H-benzotriazol-1-yl)-1,1,3,3-tetramethyluronium tetrafluoroborate (TBTU) (59 mg, 0.18 mmol). The resulting mixture is stirred at room temperature for 16 h and the solution is concentrated. The crude product is purified by RP-HPLC eluting in a gradient of 10% $CH_3CN/H_2O$ (0.1% TFA) to 60% $CH_3CN/H_2O$ (0.1% TFA) over 30 min and the appropriate product fractions are combined and lyopholized to provide the title compound (73 mg, 0.13 mmol) as a white solid. $^1$H NMR ($d_6$-DMSO, 300 MHz) δ9.72 (bs, 2H), 8.78 (s, 1H), 8.40 (s, 1H), 8.35 (d, 1H), 8.04 (m, 1H), 7.83 (d, 1H), 7.60 (m, 4H), 7.46 (d, 1H), 5.25-4.44 (m, 4H, rotamers), 4.02 (m, 1H), 3.66 (m, 1H), 3.51-3.40 (m, 3H), 3.27 (s, 3H). ISP MS, [M+H]$^+$=457.

EXAMPLE 966

3-{3-[4-(4-Amino-quinazolin-7-ylmethyl)-(2S)-methoxymethyl-3-oxo-piperazin-1-yl]-3-oxo-propenyl}-benzamidine 3-{3-[4-(4-Amino-quinazolin-7-ylmethyl)-(2S)-methoxymethyl-3-oxo-piperazin-1-yl]-3-oxo-propenyl}-benzonitrile (68 mg, 0.12 mmol) is dissolved in 9 mL of 2:1 ethanol/$CH_2Cl_2$. The solution is cooled to 0° C. and HCl gas is bubbled through the solution for 5 min. The ice bath is removed and the reaction mixture is stirred at room temperature overnight. After this time, the solution is concentrated. The residue is dissolved in 10 mL of methanol. The solution is cooled to 0° C. and $NH_3$ gas is bubbled through the solution for 5 min. The reaction mixture is heated at reflux for 2 h. After this time, the solution is concentrated. The residue is purified by RP-HPLC eluting with a gradient of 10% $CH_3CN$/$H_2O$ (0.1% TFA) to 60% $CH_3CN$/$H_2O$ (0.1% TFA) over 30 min. The appropriate fractions are lyophilized to give the title compound (55 mg, 0.08 mmol) as a solid. $^1$H NMR ($d_6$-DMSO, 300 MHz) δ9.75 (bs, 2H), 9.36 (bs, 4H), 8.80 (s, 1H), 8.42 (s, 1H), 8.13 (m, 1H), 8.10 (m, 1H), 7.79 (d, 1H), 7.62 (m, 4H), 7.42 (m, 1H), 5.20-4.46 (m, 4H, rotamers), 4.03 (m, 1H), 3.86 (m, 1H), 3.56-3.34 (m, 3H), 3.28 (s, 3H). ISP MS, $[M+H]^+$=474.

EXAMPLE 967

1-(4-Amino-quinazolin-7-ylmethyl)-4-[3-(4-hydroxy-phenyl)-acryloyl]-(3S)-propyl-piperazin-2-one The title compound is prepared as described in EXAMPLE 123 using 4-hydroxy-cinnamic acid and 1-(4-amino-quinazoline-7-ylmethyl)-3-(S)-methoxymethyl-piperazine-2-one (EXAMPLE 75).
$^1$H NMR ($d_6$-DMSO, 300 MHz) δ9.88 (s, 1H), 9.68 (bs, 2H), 8.80 (s, 1H), 8.36 (d, 1H), 7.58 (m, 4H), 7.48 (d, 1H), 7.07 (d, 1H), 6.76 (d, 2H), 5.06-4.41 (m, 3H, rotamers), 3.62-3.25 (m, 4H), 1.87 (m, 2H), 1.32 (m, 2H), 0.89 (t, 3H). ISP MS, $[M+H]^+$=446.

EXAMPLE 968

1-(4-Amino-quinazolin-7-ylmethyl)-4-[3-(3-chlorophenyl)-acryloyl]-(3S)-propyl-piperazin-2-one The title compound is prepared as described in EXAMPLE 123 using 3-chloro-cinnamic acid and 1-(4-amino-quinazoline-7-ylmethyl)-3-(S)-methoxymethyl-piperazine-2-one (EXAMPLE 75).
$^1$H NMR ($d_6$-DMSO, 300 MHz) δ9.64 (bs, 2H), 8.78 (s, 1H), 8.36 (d, 1H), 7.96 (m, 1H, rotamers), 7.66 (m, 2H), 7.53 (m, 2H), 7.40 (m, 3H), 5.10-4.42 (m, 3H, rotamers), 3.65 (m, 1H), 3.52-3.22 (m, 3H), 1.90 (m, 2H), 1.33 (m, 2H), 0.90 (t, 3H). ISP MS, $[M+H]^+$=464.

EXAMPLE 969

1-[4-(4-Aminoquinazoline-7-ylmethyl)-3-oxo-2-propyl-piperazine-1-yl]-3-(5-chloro-thiophen-2-yl)-propane-1,3,dione The titled compound is prepared by a modification of a procedure published by Witzeman and Nottingham. (J. Org. Chem. 1991, 56, 1713.). 1-(4-Aminoquinazoline-7-ylmethyl)-3-propyl-piperazine-2-one (0.299 g, 1 mmol) and 3-(5-chloro-thiophen-2-yl)-3-oxo-propionic acid tert-butyl ester (0.287 g, 1.1 mmol) are dissolved in 10 ml of pyridine. The flask containing the resulting solution is placed in an oil bath preheated to 125° C. The reaction is heated with stirring under a stream of nitrogen gas for one hour until most of the pyridine had evaporated. The remaining pyridine is evaporated in vacuo. The residue is purified by flash column chromatography eluting with a gradient of 5% $CH_3OH$/$H_2CCl_2$ to 10% $CH_3OH$/$H_2CCl_2$ to provide the product (0.48 g, 0.98 mmol). The product could be recrystallized from $CH_2Cl_2$/hexane to yield a yellow solid. M.P. 120-5° C. (dec). MS (ion spray) m/z 486, (M+H).

EXAMPLE 970

1-[4-(4-Aminoquinazoline-7-ylmethyl)-3-oxo-2-propyl-piperazine-1-yl]-3-(5-chloro-thiophen-2-yl)-2-fluoro-propane-1,3,dione Prepared by a procedure of Differding and Ofner. (*Synlett* 1991, 187.). A solution of 1-[4-(4-aminoquinazoline-7-ylmethyl)-3-oxo-2-propyl-piperazine-1-yl]-3-(5-chloro-thiophen-2-yl)-propane-1,3,dione (0.486 g, 1 mmol) in 40 ml of THF is added dropwise to an ice cold suspension of NaH (0.16 g of 60% NaH, 4 mmol) and 5 ml of THF. After the mixture had stirred one hour at 0° C., a solution of N-fluorobenzenesulfonimide (Aldrich) (0.378 g, 1.2 mmol) in 10 ml of THF is added dropwise. The reaction is stirred overnight at room temperature before quenching with glacial acetic acid (0.23 ml, 0.240 g, 4 mmol). The volatiles are evaporated in vacuo and the residue purified by flash column chromatography eluting with a gradient of 5% $CH_3OH$/$H_2CCl_2$ to 10% $CH_3OH$/$H_2CCl_2$ to provide the product as a white solid. The product could be recrystallized from THF/hexane. M.P. 194-6° C. MS (ion spray) m/z 504, (M+H).

EXAMPLE 971

1-(4-Amino-quinazolin-7-ylmethyl)-4-[(5-chloro-thiophen-2-yloxy)-acetyl-3-(S)-(2-methylsulfanyl-ethyl)-piperazin-2-one To a solution of 1-(4-amino-quinazolin-7-ylmethyl)-3-(S)-(2-methylsulfanyl-ethyl)-piperazin-2-one (100 mg, 0.3 mmol) in 2 ml of DMF is added DIPEA (158 ml, 0.9 mmol), TBTU (107 mg, 0.33 mmol) and 5-chlorothiophen-2-yloxy-acetic acid (61 mg, 0.32 mmol). The solution is stirred for 20 hours at room temperature, concentrated under vacuum. The product is purified by RP-HPLC eluting in a gradient of 10% $CH_3CN$/$H_2O$(0.1% TFA) to 80% $CH_3CN$/$H_2O$ (0.1% TFA). The appropriate collected fractions are lyophilized to afford the title compound as a white solid (63 mg, 33% yield).
$C_{22}H_{24}N_5O_3S_2Cl.CF_3CO_2H$ $(M+H)^+$: 506

EXAMPLE 972

1-(4-Amino-quinazolin-7-ylmethyl)-4-[(5-chloro-thiophen-2-yloxy)-acetyl-3-(S)-(2-methanesulfinyl-ethyl)-piperazin-2-one To a solution of 1-(4-amino-quinazolin-7-ylmethyl)-4-[(5-chloro-thiophen-2-yloxy)-acetyl-3-(S)-(2-methysulfanyl-ethyl)-piperazin-2-one (29 mg, 0.057 mmol) in 1 ml of $CH_2Cl_2$ is added at 0° C. 3-chloroperbenzoic acid (14 mg at 71%, 0.057 mmol). The resulting mixture is stirred at room temperature for 2 hours, concentrated. The product is purified by RP-HPLC eluting in a gradient of 10% $CH_3CN$/$H_2O$(0.1%

TFA) to 80% CH₃CN/H₂O(0.1% TFA). The appropriate collected fractions are lyophilized to afford the title compound as a white solid (10 mg, 27% yield).

$C_{22}H_{24}N_5O_4S_2Cl \cdot CF_3CO_2H$ (M+H)⁺: 522

EXAMPLE 973

1-(4-Amino-quinazolin-7-ylmethyl)-4-[(5-chloro-thiophen-2-yloxy)-acetyl-3-(S)-(2-methanesulfonyl-ethyl)-piperazin-2-one To solution of 1-(4-amino-quinazolin-7-ylmethyl)-4-[(5-chloro-thiophen-2-yloxy)-acetyl-3-(S)-(2-methylsulfanyl-ethyl)-piperazin-2-one (29 mg, 0.057 mmol) in 1 ml of CH₂Cl₂ is added at 0° C. 3-chloroperbenzoic acid (28 mg at 71%, 0.114 mmol). The resulting mixture is stirred at room temprature for 2 hours, concentrated. The product is purified by RP-HPLC eluting in a gradient of 10% CH₃CN/H₂O(0.1% TFA) to 80% CH₃CN/H₂O(0.1% TFA). The appropriate collected fractions are lyophilized to afford the title compound as a white solid (25 mg, 67% yield).

$C_{22}H_{24}N_5O_5S_2Cl \cdot CF_3CO_2H$ (M+H)⁺: 538

Using the methods and templates described above, coupled to an amino-quinazoline group, and methods described in EXAMPLE 123, the following compounds are prepared.

| Example # | Name | m/z (M + H) |
|---|---|---|
| 974 | 1-(4-Amino-quinazolin-7-ylmethyl)-4-[(5-chloro-thiophen-2-yloxy)-acetyl]-3-(S)-dimethylaminomethyl-piperazin-2-one | 449, 451 Cl pattern |
| 975 | 1-(4-Amino-quinazolin-7-ylmethyl)-4-(5-chloro-benzo-[b]thiophene-2-carbonyl)-(3S)-methoxymethyl-piperazin-2-one | 496 |
| 976 | 1-(4-Amino-2-methyl-quinazolin-7-ylmethyl)-4-[(5-chloro-thiophen-2-yloxy)-acetyl]-3-(S)-propyl-piperazin-2-one | 488, 490 Cl pattern |
| 977 | 1-(4-Amino-quinazolin-7-ylmethyl)-4-(6-chloro-benzofuran-2-carbonyl)-(S)-6-methyl-(S)-3-propyl-piperazin-2-one | 492, 494 Cl pattern |
| 978 | 1-(4-Amino-quinazolin-7-ylmethyl)-4-(6-chloro-benzofuran-2-carbonyl)-3(S)-(2-methylsulfanyl-ethyl)-piperazin-2-one | 510, 512 Cl pattern |
| 979 | 1-(4-Amino-quinazolin-7-ylmethyl)-4-(5-chlorobenzo[b]-thiophene-2-carbonyl)-(S)-3-propyl-piperazin-2-one | 494, 496 Cl pattern |
| 980 | 1-(4-Amino-quinazolin-7-ylmethyl)-4-(5-chloro-benzo[b]-thiophene-2-carbonyl)-(S)-6-methyl-(S)-3-propyl-piperazin-2-one | 508, 510 Cl pattern |
| 981 | 1-(4-Amino-quinazolin-7-ylmethyl)-4-(6-chloro-benzo[b]-thiophene-2-carbonyl)-(S)-6-methyl-(S)-3-propyl-piperazin-2-one | 508, 510 Cl pattern |
| 982 | 1-(4-Amino-quinazolin-7-ylmethyl)-4-[3-(4-chloro-thiophen-2-yl)-acryloyl]-(S)-6-methyl-(S)-3-propyl-piperazin-2-one | 484, 486 Cl pattern |
| 983 | 1-(4-Amino-quinazolin-7-ylmethyl)-4-[(5-chloro-thiophen-3-yloxy)-acetyl]-(S)-6-methyl-(S)-3-propyl-piperazin-2-one | 488, 490 Cl pattern |
| 984 | 1-(4-Amino-quinazolin-7-ylmethyl)-4-[3-(5-chloro-thiophen-2-yl)-acryloyl]-(S)-6-methyl-(S)-3-propyl-piperazin-2-one | 484, 486 Cl pattern |
| 985 | 1-(4-Amino-quinazolin-7-ylmethyl)-4-[(5-chloro-thiophen-2-yloxy)-acetyl]-(S)-6-methyl-(S)-3-propyl-piperazin-2-one | 488, 490 Cl pattern |
| 986 | 1-(4-Amino-quinazolin-7-ylmethyl)-4-(5-chloro-benzofuran-2-carbonyl)-3(S)-propyl-piperazin-2-one | 478, 480 Cl pattern |
| 987 | 3-{2-[4-(4-Amino-quinazolin-7-ylmethyl)-2-(S)-methoxymethyl-3-oxo-piperazin-1-yl]-2-oxo-ethyl}-benzamidine | 462 |
| 988 | 3-{2-[4-(4-Amino-quinazolin-7-ylmethyl)-3-oxo-piperazin-1-yl]-2-oxo-ethyl}-benzamidine | 418 |
| 989 | 4-[3-(4-Amino-cyclohexyl)-acryloyl]-1-(4-amino-quinazolin-7-ylmethyl)-(3S)-propyl-piperazin-2-one | 451 |
| 990 | 1-(4-Amino-quinazolin-7-ylmethyl)-4-(6-chloro-benzo[b]thiophene-2-carbonyl)-(S)-3-propyl-piperazin-2-one | 494, 496 Cl pattern |
| 991 | 1-(4-Amino-quinazolin-7-ylmethyl)-4-(6-chloro-benzofuran-2-carbonyl)-3(S)-propyl-piperazin-2-one trifluoroacetate | 478, 480 Cl pattern |
| 992 | 1-[4-(4-Amino-quinazolin-7-ylmethyl)-3-oxo-2-propyl-piperazin-1-yl]-3-(3-chloro-phenyl)-propane-1,3-dione | 480 |
| 993 | 4-[(5-Amino-pyridin-2-yloxy)-acetyl]-1-(4-amino-quinazolin-7-ylmethyl)-(S)-3-methoxymethyl-piperazin-2-one | 452 |
| 994 | 1-(4-Amino-quinazolin-7-ylmethyl)-4-[(5-chloro-thiophen-2-yloxy)-acetyl]-3-(R)-methoxymethyl-piperazin-2-one | 476, 478 Cl pattern |
| 995 | 3-{3-[4-(4-Amino-quinazolin-7-ylmethyl)-3-oxo-piperazin-1-yl]-3-oxo-propyl}-benzamidine | 432 |
| 996 | 3-{3-[4-(4-Amino-quinazolin-7-ylmethyl)-(2S)-methoxymethyl-3-oxo-piperazin-1-yl]-3-oxo-propyl}-benzamidine | 476 |
| 997 | 1-(4-Amino-quinazolin-7-ylmethyl)-4-(4-imidazol-1-yl-benzoyl)-3(S)-propyl-piperazin-2-one | 470 |
| 998 | (6-{2-[4-(4-Amino-quinazolin-7-ylmethyl)-(S)-2-methoxymethyl-3-oxo-piperazin-1-yl]-2-oxo-ethoxy}-pyridin-3-yl)-carbamic acid tert-butyl ester | 552 |
| 999 | (4aRS,8aSR)-1-(4-Amino-quinazolin-7-ylmethyl)-4-[(5-chloro-thiophen-2-yloxy)-acetyl]-octahydro-quinoxalin-2-one | 486, 488 Cl pattern |
| 1000 | (4aRS,8aRS)-1-(4-Amino-quinazolin-7-ylmethyl)-4-[(5-chloro-thiophen-2-yloxy)-acetyl]-octahydro-quinoxalin-2-one | 486, 488 Cl pattern |
| 1001 | (4aRS,8aRS)-1-(4-Amino-quinazolin-7-ylmethyl)-4-[3-(5-chloro-thiophen-2-yl)-acryloyl]-octahydro-quinoxalin-2-one | 482, 484 Cl pattern |
| 1002 | 1-(4-Amino-quinazolin-7-ylmethyl)-4-[3-(5-chloro-6-oxo-1,6-dihydro-pyridin-3-yl)-acryloyl]-(S)-3-propyl-piperazin-2-one | 481, 483 Cl pattern |

-continued

| Example # | Name | m/z (M + H) |
|---|---|---|
| 1003 | 1-[4-(4-Amino-quinazolin-7-ylmethyl)-3-oxo-2-propyl-piperazin-1-yl]-3-(4-hydroxy-phenyl)-propane-1,3-dione | 462 |
| 1004 | 2-{4-(4-Amino-quinazolin-7-ylmethyl)-1-[3-(4-chloro-thiophen-2-yl)-acryloyl]-3-oxo-piperazin-2-(S)-yl}-acetamide | 485, 487 Cl pattern |
| 1005 | 2-{4-(4-Amino-quinazolin-7-ylmethyl)-1-[3-(5-chloro-thiophen-2-yl)-acryloyl]-3-oxo-piperazin-2-(S)-yl}-acetamide | 485, 487 Cl pattern |
| 1006 | 2-{4-(4-Amino-quinazolin-7-ylmethyl)-1-[(5-chloro-thiophen-2-yloxy)-acetyl]-3-oxo-piperazin-2-(S)-yl}-acetamide | 489, 491 Cl pattern |
| 1007 | {4-(4-Amino-quinazolin-7-ylmethyl)-1-[(5-chloro-thiophen-2-yloxy)-acetyl]-3-oxo-piperazin-2-(S)-yl}-acetic acid methyl ester | 504, 506 Cl pattern |
| 1008 | 2-{4-(4-Amino-quinazolin-7-ylmethyl)-1-[3-(4-chloro-thiophen-2-yl)-acryloyl]-3-oxo-piperazin-2-(S)-yl}-N-methyl-acetamide | 499, 501 Cl pattern |
| 1009 | 2-{4-(4-Amino-quinazolin-7-ylmethyl)-1-[(5-chloro-thiophen-2-yloxy)-acetyl]-3-oxo-piperazin-2-(S)-yl}-N-methyl-acetamide | 503, 505 Cl pattern |
| 1010 | 2-{4-(4-Amino-quinazolin-7-ylmethyl)-1-[3-(5-chloro-thiophen-2-yl)-acryloyl]-3-oxo-piperazin-2-(S)-yl}-N-methyl-acetamide | 499, 501 Cl pattern |
| 1011 | 4-{3-[4-(4-Amino-quinazolin-7-ylmethyl)-(S)-2-methoxymethyl-3-oxo-piperazin-1-yl]-3-oxo-propenyl}-benzenesulfonamide | 511 |
| 1012 | N-(5-{3-[4-(4-Amino-quinazolin-7-ylmethyl)-2-(S)-methoxymethyl-3-oxo-piperazin-1-yl]-3-oxo-propyl}-pyridin-2-yl)-acetamide | 492 |
| 1013 | 1-(4-Amino-quinazolin-7-ylmethyl)-4-[(5-amino-[1,3,4]thiadiazol-2-ylsulfanyl)-acetyl]-(S)-3-propyl-piperazin-2-one | 473 |
| 1014 | 1-(4-Amino-quinazolin-7-ylmethyl)-4-[(5-amino-[1,3,4]thiadiazol-2-ylsulfanyl)-acetyl]-(S)-3-methoxymethyl-piperazin-2-one | 475 |
| 1015 | 3-[4-(4-Amino-quinazolin-7-ylmethyl)-(2S)-methoxymethyl-3-oxo-piperazine-1-carbonyl]-benzamidine | 448 |
| 1016 | 1-(4-Amino-quinazolin-7-ylmethyl)-4-[(piperidin-3-yloxy)-acetyl]-piperazin-2-one | 399 |
| 1017 | 1-(4-Amino-quinazolin-7-ylmethyl)-4-[3-(3-chloro-4-hydroxy-phenyl)-(E)-acryloyl]-(3S)-methoxymethyl-piperazin-2-one | 482 |
| 1018 | (3S)-1-(4-Amino-quinazolin-7-ylmethyl)-4-(6-hydroxy-naphthalene-2-carbonyl)-3-propyl-piperazin-2-one | 470 |
| 1019 | (3S)-1-(4-Amino-quinazolin-7-ylmethyl)-4-(5-hydroxy-1H-indole-2-carbonyl)-3-propyl-piperazin-2-one | 459 |
| 1020 | 1-(4-Amino-quinazolin-7-ylmethyl)-4-[(3-hydroxy-phenoxy)-acetyl]-(3S)-methoxymethyl-piperazin-2-one | 452 |
| 1021 | 1-(4-Amino-quinazolin-7-ylmethyl)-4-[3-(4-hydroxy-phenyl)-acryloyl]-(R)-6-methyl-(S)-3-propyl-piperazin-2-one | 460 |
| 1022 | N-(5-{3-[4-(4-Amino-quinazolin-7-ylmethyl)-3-oxo-2-(S)-propyl-piperazin-1-yl]-3-oxo-propenyl}-pyridin-2-yl)-acetamide | 488 |
| 1023 | 1-(4-Amino-quinazolin-7-ylmethyl)-4-[(5-chloro-thiophen-2-yloxy)-acetyl]-(R)-6-methyl-(S)-3-propyl-piperazin-2-one | 488, 490 Cl pattern |
| 1024 | 1-(4-Amino-quinazolin-7-ylmethyl)-4-[(3-chloro-phenoxy)-acetyl]-(R)-6-methyl-(S)-3-propyl-piperazin-2-one | 482, 484 Cl pattern |
| 1025 | 1-(4-Amino-quinazolin-7-ylmethyl)-4-[(5-chloro-thiophen-2-yloxy)-acetyl]-3,6-bis-methoxymethyl-piperazin-2-one | |
| 1026 | 1-(4-Amino-quinazolin-7-ylmethyl)-4-[3-(3-chloro-phenyl)-acryloyl]-(R)-6-methyl-(S)-3-propyl-piperazin-2-one | 478, 480 Cl pattern |
| 1027 | 1-(4-Amino-quinazolin-7-ylmethyl)-4-[3-(4-chloro-thiophen-2-yl)-acryloyl]-(R)-6-methyl-(S)-3-propyl-piperazin-2-one | 484, 486 Cl pattern |
| 1028 | 4-[3-(6-Amino-pyridin-3-yl)-acryloyl]-1-(4-amino-quinazolin-7-ylmethyl)-(R)-6-methyl-(S)-3-propyl-piperazin-2-one | 478 |
| 1029 | 2-[4-(4-Amino-quinazolin-7-ylmethyl)-3-oxo-(S)-2-propyl-piperazin-1-yl]-N-(5-chloro-thiophen-2-yl)-2-oxo-acetamide | 487, 489 Cl pattern |
| 1030 | 2-[4-(4-Amino-quinazolin-7-ylmethyl)-3-oxo-piperazin-1-yl]-N-(5-chloro-thiophen-2-yl)-2-oxo-acetamide | 445, 447 Cl pattern |
| 1031 | 1-(4-Amino-quinazolin-7-ylmethyl)-4-[3-(5-chloro-thiophen-3-yl)-acryloyl]-(R)-6-methyl-(S)-3-propyl-piperazin-2-one | 484, 490 Cl pattern |
| 1032 | 1-(4-Amino-quinazolin-7-ylmethyl)-4-[3-(5-chloro-thiophen-2-yl)-acryloyl]-(R)-6-methyl-(S)-3-propyl-piperazin-2-one | 484, 490 Cl pattern |
| 1033 | 2-[4-(4-Amino-quinazolin-7-ylmethyl)-(S)-2-methoxymethyl-3-oxo-piperazin-1-yl]-N-(5-chloro-thiophen-2-yl)-2-oxo-acetamide | 489, 491 Cl pattern |
| 1034 | (S)-1-(4-Amino-quinazolin-7-ylmethyl)-4-[(5-chloro-thiophen-2-yloxy)-acetyl]-6-methoxymethyl-piperazin-2-one | 476 |
| 1035 | 1-(4-Amino-quinazolin-7-ylmethyl)-4-[3-(3,4-dihydroxy-phenyl)-(E)-acryloyl]-(3S)-methoxymethyl-piperazin-2-one | 464 |
| 1036 | 4-[3-(6-Amino-pyridin-3-yl)-propionyl]-1-(4-amino-quinazolin-7-ylmethyl)-3-(S)-methoxymethyl-piperazin-2-one | 450 |
| 1037 | 4-[3-(6-Amino-pyridin-3-yl)-propionyl]-1-(4-amino-quinazolin-7-ylmethyl)-3-(S)-propyl-piperazin-2-one | 448 |
| 1038 | 1-(4-Amino-quinazolin-7-ylmethyl)-4-[3-(4-chloro-thiophen-2-yl)-acryloyl]-3-(S)-hydroxymethyl-piperazin-2-one | 458, 460 Cl pattern |
| 1039 | N-(5-{3-[4-(4-Amino-quinazolin-7-ylmethyl)-2-(S)-butyl-3-oxo-piperazin-1-yl]-3-oxo-propenyl}-6-methyl-pyridin-2-yl)-acetamide | 516 |
| 1040 | N-(5-{3-[4-(4-Amino-quinazolin-7-ylmethyl)-2-(S)-butyl-3-oxo-piperazin-1-yl]-3-oxo-propenyl}-pyridin-2-yl)-acetamide | 502 |

-continued

| Example # | Name | m/z (M + H) |
|---|---|---|
| 1041 | 4-[3-(6-Amino-2-methyl-pyridin-3-yl)-acryloyl]-1-(4-amino-quinazolin-7-ylmethyl)-3-(S)-butyl-piperazin-2-one | 474 |
| 1042 | 1-[4-(4-Aminoquinazoline-7-ylmethyl)-3-oxo-piperazin-1-yl]-3-(5-chloro-thiophen-2-yl)-propane-1,3,dione | 444 |
| 1043 | 4-[3-(3-Amino-4-chloro-phenyl)-acryloyl]-1-(4-amino-quinazolin-7-ylmethyl)-(3S)-methoxymethyl-piperazin-2-one | 481 |
| 1044 | 4-[3-(3-Amino-5-chloro-phenyl)-acryloyl]-1-(4-amino-quinazolin-7-ylmethyl)-(3S)-methoxymethyl-piperazin-2-one | 481 |
| 1045 | 1-(4-Amino-quinazolin-7-ylmethyl)-4-[(5-chloro-thiophen-3-yloxy)-acetyl]-(R)-6-methyl-(S)-3-propyl-piperazin-2-one | 488, 490 Cl pattern |
| 1046 | 1-(4-Amino-quinazolin-7-ylmethyl)-4-[(4-chloro-thiophen-2-yloxy)-acetyl]-(R)-6-methyl-(S)-3-propyl-piperazin-2-one | 488, 490 Cl pattern |
| 1047 | 1-(4-Amino-quinazolin-7-ylmethyl)-4-[(4-chloro-benzenesulfinyl)-acetyl]-(3-S)-propyl-piperazin-2-one | 500 |
| 1048 | 1-(4-Amino-quinazolin-7-ylmethyl)-4-[(4-hydroxy-phenoxy)-acetyl]-(3S)-methoxymethyl-piperazin-2-one | 452 |
| 1049 | 1-(4-Amino-quinazolin-7-ylmethyl)-4-[(4-chloro-phenylsulfanyl)-acetyl]-piperazin-2-one | 442 |
| 1050 | 1-(4-Amino-quinazolin-7-ylmethyl)-4-[(3-chloro-benzenesulfinyl)-acetyl]-(3S)-methoxymethyl-piperazin-2-one | 502 |
| 1051 | 1-(4-Amino-quinazolin-7-ylmethyl)-4-[3-(3-hydroxy-phenyl)-(E)-acryloyl]-3-(S)-methoxymethyl-piperazin-2-one | 448 |
| 1052 | 1-(4-Amino-quinazolin-7-ylmethyl)-4-[3-(4-hydroxy-phenyl)-(E)-acryloyl]-3-(S)-methoxymethyl-piperazin-2-one | 448 |
| 1053 | 1-(4-Amino-quinazolin-7-ylmethyl)-4-[(4-chloro-thiophen-2-yloxy)-acetyl]-3-(S)-hydroxymethyl-piperazin-2-one | 462, 464 Cl pattern |
| 1054 | 1-(4-Amino-quinazolin-7-ylmethyl)-4-[3-(5-chloro-thiophen-2-yl)-acryloyl]-3-(S)-hydroxymethyl-piperazin-2-one | 458, 460 Cl pattern |
| 1055 | 1-(4-Amino-quinazolin-7-ylmethyl)-4-[(5-chloro-thiophen-2-yloxy)-acetyl]-3,6-bis-methoxymethyl-piperazin-2-one | 521 |
| 1056 | (R)-1-(4-Amino-quinazolin-7-ylmethyl)-4-[(5-chloro-thiophen-2-yloxy)-acetyl]-6-methoxymethyl-piperazin-2-one | 476 |
| 1057 | 4-[(6-Amino-pyrimidin-4-yloxy)-acetyl]-1-(4-amino-quinazolin-7-ylmethyl)-3(S)-methoxymethyl-piperazin-2-one | 453 |
| 1058 | 1-(4-Amino-quinazolin-7-ylmethyl)-4-[(3-chloro-benzenesulfonyl)-acetyl]-piperazin-2-one | 474 |
| 1059 | 1-[4-(4-Amino-quinazolin-7-ylmethyl)-3-oxo-piperazin-1-yl]-3-(4-chloro-phenyl)-propane-1,3-dione | 438 |
| 1060 | 1-(4-Amino-quinazolin-7-ylmethyl)-4-[(3-chloro-phenylsulfanyl)-acetyl]-piperazin-2-one | 442 |
| 1061 | 4-[3-(6-Amino-2-methyl-pyridin-3-yl)-acryloyl]-1-(4-amino-quinazolin-7-ylmethyl)-3-(S)-propyl-piperazin-2-one | 460 |
| 1062 | 1-(4-Amino-quinazolin-7-ylmethyl)-4-[3-(3-chloro-phenyl)-3-hydroxy-acryloyl]-piperazin-2-one | 438 |
| 1063 | 1-(4-Amino-quinazolin-7-ylmethyl)-4-[3-(4-dimethylamino-phenyl)-acryloyl]-(3S)-propyl-piperazin-2-one | 473 |
| 1064 | 3-(S)-6-(S)-1-(4-Amino-quinazolin-7-ylmethyl)-4-[(5-chloro-thiophen-2-yloxy)-acetyl]-6-hydroxymethyl-3-methoxymethyl-piperazin-2-one | 506 |
| 1065 | 4-[3-(6-Amino-pyridin-3-yl)-acryloyl]-1-(4-amino-quinazolin-7-ylmethyl)-3(S)-isobutyl-piperazin-2-one | 460 |
| 1066 | 4-[3-(2-Amino-pyrimidin-5-yl)-acryloyl]-1-(4-amino-quinazolin-7-ylmethyl)-3(S)-propyl-piperazin-2-one | 447 |
| 1067 | 1-(4-Amino-quinazolin-7-ylmethyl)-4-[3-(3-hydroxy-phenyl)-acryloyl]-(3S)-propyl-piperazin-2-one | 446 |
| 1068 | 4-[3-(3-Amino-phenyl)-acryloyl]-1-(4-amino-quinazolin-7-ylmethyl)-(3S)-methoxymethyl-piperazin-2-one | 447 |
| 1069 | 4-[3-(4-Amino-3-chloro-phenyl)-acryloyl]-1-(4-amino-quinazolin-7-ylmethyl)-(3S)-methoxymethyl-piperazin-2-one | 481 |
| 1070 | 1-(4-Amino-quinazolin-7-ylmethyl)-4-[(6-chloro-pyrazin-2-yloxy)-acetyl]-(S)-3-methoxymethyl-piperazin-2-one | 472, 474 Cl pattern |
| 1071 | 1-(4-Amino-quinazolin-7-ylmethyl)-4-[(6-chloro-pyrazin-2-yloxy)-acetyl]-(S)-3-propyl-piperazin-2-one | 470, 472 Cl pattern |
| 1072 | 1-(4-Amino-quinazolin-7-ylmethyl)-4-[3-(5-chloro-thiophen-2-yl)-acryloyl]-3(S)-isobutyl-piperazin-2-one | 484, 486 Cl pattern |
| 1073 | 1-(4-Amino-quinazolin-7-ylmethyl)-4-[(5-chloro-thiophen-2-yloxy)-acetyl]-3(S)-isobutyl-piperazin-2-one | 488, 490 Cl pattern |
| 1074 | 1-(4-Amino-quinazolin-7-ylmethyl)-4-[(2-amino-thiazol-4-yl)-acetyl]-(S)-3-propyl-piperazin-2-one | 440 |
| 1075 | (+/−)-1-(4-Amino-quinazolin-7-ylmethyl)-4-[(5-chloro-thiophen-2-yloxy)-acetyl]-6-oxo-piperazine-2-carboxylic acid ethyl ester | 504, 506 Cl pattern |
| 1076 | 4-[3-(4-Amino-phenyl)-acryloyl]-1-(4-amino-quinazolin-7-ylmethyl)-(3S)-propyl-piperazin-2-one | 445 |
| 1077 | 1-(4-Amino-quinazolin-7-ylmethyl)-4-[(3,4-dichloro-thiophen-2-yloxy)-acetyl]-(S)-3-propyl-piperazin-2-one | 508, 510, 512 $Cl_2$ pattern |

-continued

| Example # | Name | m/z (M + H) |
|---|---|---|
| 1078 | 1-(4-Amino-quinazolin-7-ylmethyl)-4-[(3,4-dichloro-thiophen-2-yloxy)-acetyl]-(S)-3-methoxymethyl-piperazin-2-one | 510, 512, 514 Cl$_2$ pattern |
| 1079 | 4-[3-(6-Amino-pyridin-3-yl)-acryloyl]-1-(4-amino-quinazolin-7-ylmethyl)-3(S)-(2-methoxy-ethyl)-piperazin-2-one | 462 |
| 1080 | 1-(4-Amino-quinazolin-7-ylmethyl)-4-[3-(4-chloro-thiophen-2-yl)-acryloyl]-3(S)-(2-methoxy-ethyl)-piperazin-2-one | 486, 488 Cl pattern |
| 1081 | 1-(4-Amino-quinazolin-7-ylmethyl)-4-[3-(5-chloro-thiophen-2-yl)-acryloyl]-3(S)-(2-methoxy-ethyl)-piperazin-2-one | 486, 488 Cl pattern |

EXAMPLE 1082

4-(4-Amino-quinazolin-7-ylmethyl)-(S)-5-methyl-3-oxo-(S)-2-propyl-piperazine-1-carboxylic acid (4-chloro-phenyl)-amide To a solution of 4-[4-Amino-quinazolin-7-ylmethyl]-5-methyl-3-oxo-2-propyl-piperazine (12 mg, 0.04 mmol, EXAMPLE 888) in 2 mL of DMF is added 4-chlorophenyl isocyanate (9 mg, 0.06 mmol). After stirring at 100° C. for 1 h, the solution is concentrated. The crude product is purified by RP-HPLC eluting in a gradient of 10% CH$_3$CN/H$_2$O (0.1% TFA) to 70% CH$_3$CN/H$_2$O (0.1% TFA) and the appropriate product fractions are combined and lyophilized to provide the title compound (16 mg, 0.03 mmol) as a white solid. $^1$H NMR (d$_6$-DMSO, 300 MHz) δ9.74 (bs, 2H), 8.77 (m, 2H), 8.35 (m, 1H), 7.56 (m, 2H), 7.46 (d, 2H), 7.21 (d, 2H), 5.00-4.38 (m, 3H, rotamers), 4.20 (m, 1H, rotamers), 3.58 (m, 1H, rotamers), 3.10 (m, 1H), 1.86 (m, 2H), 1.33 (m, 2H), 1.08 (m, 3H, rotamers), 0.90 (t, 3H). ISP MS, [M+H]$^+$=467, 469 (Cl pattern).

EXAMPLE 1083

4-(4-Amino-quinazolin-7-ylmethyl)-(S)-5-methyl-3-oxo-(S)-2-propyl-piperazine-1-carboxylic acid (5-chloro-thiophen-2-yl)amide A mixture of 5-chloro-thiophene-2-carbonyl azide (28 mg, 0.15 mmol, EXAMPLE 38) and 4-[4-Amino-quinazolin-7-ylmethyl]-5-methyl-3-oxo-2-propyl-piperazine, EXAMPLE 888, (26 mg, 0.08 mmol) in 3 mL of dry DMF is heated at 100° C. for 1 h. The resulting mixture is concentrated in vacuo. The crude product is purified by RP-HPLC eluting in a gradient of 10% CH$_3$CN/H$_2$O (0.1% TFA) to 70% CH$_3$CN/H$_2$O (0.1% TFA) and the appropriate product fractions are combined and lyophilized to provide the title compound (18 mg, 0.03 mmol) as a white solid. $^1$H NMR (d$_6$-DMSO, 300 MHz) δ9.96 (bs, 1H), 9.70 (bs, 2H), 8.72 (s, 1H), 8.22 (d, 1H), 7.55 (d, 1H), 7.50 (s, 1H), 6.68 (d, 1H), 6.37 (d, 1H), 4.99-4.38 (m, 3H, rotamers), 4.15 (m, 1H, rotamers), 3.58 (m, 1H, rotamers), 3.10 (m, 1H), 1.85 (m, 2H), 1.32 (m, 2H), 1.07 (m, 3H, rotamers), 0.88 (t, 3H). ISP MS, [M+H]$^+$=473, 475 (Cl pattern).

Using the above procedures and templates described above, coupled with an amino-quinazoline, the following EXAMPLES are prepared;

| Example # | Name | m/z (M + H) |
|---|---|---|
| 1084 | 4-(4-Amino-quinazolin-7-ylmethyl)-2(S)-isobutyl-3-oxo piperazine-1-carboxylic acid(4-chloro-phenyl)-amide | 466 |
| 1085 | 4-(4-Amino-quinazolin-7-ylmethyl)-2-(S)-hydroxymethyl-3-oxo-piperazine-1-carboxylic acid(4-chloro-phenyl)-amide | 440 |
| 1086 | (2S)-4-(4-Amino-quinazolin-7-ylmethyl)-3-oxo-2-propyl-piperazine-1-carboxylic acid(5-bromo-thiazol-2-yl)-amide | 504 |
| 1087 | (2S)-4-(4-Amino-quinazolin-7-ylmethy)-3-methoxymethyl-3-oxo-piperazine-1-carboxylic acid(5-chloro-thiazol-2-yl)-amide | 462 |
| 1088 | (2S)-4-(4-Amino-quinazolin-7-ylmethyl)-3-oxo-2-propyl-piperazine-1-carboxylic acid(5-chloro-thiazol-2-yl)-amide | 460 |
| 1089 | 4-(4-Amino-quinazolin-7-ylmethyl)-(2S)-methoxymethyl-3-oxo piperazine-1-carboxylic acid(4-hydroxy-phenyl)-amide | 437 |
| 1090 | 4-(4-Amino-quinazolin-7-ylmethyl)-2-(S)-methylcarbamoylmethyl-3-oxo-piperazine-1-carboxylic acid(4-chloro-phenyl)-amide | 481 |
| 1091 | 4-(4-Amino-quinazolin-7-ylmethyl)-2-(S)-carbamoylmethyl-3-oxo-piperazine-1-carboxylic acid(4-chloro-phenyl)-amide | 467 |
| 1092 | (4aRS,8aRS)-4-(4-Amino-quinazolin-7-ylmethyl)-3-oxo-octahydro-quinoxaline-1-carboxylic acid(4-chloro-phenyl)-amide | 465 |
| 1093 | 4-(4-Amino-quinazolin-7-ylmethyl)-2(S)-(2-methylsulfanyl-ethyl)-3-oxo-piperazine-1-carboxylic acid(4-chloro-phenyl)-amide | 485, 487 Cl pattern |
| 1094 | 4-(4-Amino-quinazolin-7-ylmethyl)-(2S)-methoxymethyl-3-oxo-piperazine-1-carboxylic acid(5-chloro-furan-2-yl)-amide | 445 |
| 1095 | (2S)-4-(4-Amino-quinazolin-7-ylmethyl)-2-methoxymethyl-3-oxo-piperazine-1-carboxylic acid(5-bromo-thiazol-2-yl)-amide | 506 |
| 1096 | N-[4-(4-Amino-quinazolin-7-ylmethyl)-3-oxo-(S)-2-propyl-piperazine-1-carbonyl]-4-chloro-benzenesulfonamide | 517, 519 Cl pattern |

Using the templates described above with and amino-quinoline or an amino-cinnoline and the methods described in EXAMPLES 718-721;

| Example # | Name | m/z (M + H) |
|---|---|---|
| 1097 | 1-(S)-4-(4-Amino-quinolin-7-ylmethyl)-3-oxo-2-propyl-piperazine-1-carboxylic acid(4-chloro-phenyl)-amide | 452 |
| 1098 | 1-(S)-(4-Amino-quinolin-7-ylmethyl)-4-[3-(5-chloro-thiophen-2-yl)-allyl]-3-propyl-piperazin-2-one, | 455 |
| 1099 | 1-(S)-(4-Amino-quinolin-7-ylmethyl)-4-[3-(5-chloro-thiophen-2-yl)-allyl]-4-oxy-3-propyl-piperazin-2-one | 471 |
| 1100 | 1-(S)-4-(4-Amino-quinolin-7-ylmethyl)-2-methoxymethyl-3-oxo-2-piperazine-1-carboxylic acid(4-chloro-phenyl)-amide | 425 |
| 1101 | (S)-4-(4-Aminoquinolin-7-ylmethyl)-2-methoxylmethyl-3-oxo-2-piperazine-1-carboxylic acid(5-chlorothiophen-2-yl)-amide | 460 |
| 1102 | 1-(S)-4-(4-Amino-quinolin-7-ylmethyl)-2-methyl-3-oxo-2-piperazine-1-carboxylic acid phenylamide | 390 |
| 1103 | 1-(S)-4-(4-Amino-quinolin-7-ylmethyl)-2-methyl-3-oxo-2-piperazine-1-carboxylic acid(4-chloro-phenyl)-amide | 454 |
| 1104 | 1-(S)-4-(4-Amino-cinnolin-7-ylmethyl)-2-methyl-3-oxo-piperazine-1-carboxylic acid(4-chloro-phenyl)-amide, | 425 |
| 1105 | 1-(S)-(4-Amino-cinnolin-7-ylmethyl)-4-[3-(5-chloro-thiophen-2-yl)-acryloyl]-3-methyl-piperazin-2-one, | 442 |
| 1106 | 1-(4-Amino-cinnolin-7-ylmethyl)-4-[3-(5-chloro-thiophen-2-yl)-allyl]-3-methyl-piperazin-2-one | 428 |

The following compounds are prepared using the methods described above using the appropriate ketopiperazine and sulfonyl chloride. The racemates are separated on a CHIRALPAK AD 10 μm column.

| Example # | Name | m/z (M + H) |
|---|---|---|
| 1107 | 4-[2-(5-Chloro-thiophen-2-yl)-ethenesulfonyl]-6-oxo-1-(1H-pyrrolo[3,2-c]pyridin-2-ylmethyl)-piperazine-2-(+)-carboxylic acid methyl ester | 598, 600, Cl pattern |
| 1108 | 4-[2-(5-Chloro-thiophen-2-yl)-ethenesulfonyl]-6-oxo-1-(1H-pyrrolo[3,2-c]pyridin-2-ylmethyl)-piperazine-2-(−)-carboxylic acid methyl ester | 598, 600, Cl pattern |
| 1109 | 4-(6-Chloro-benzo[b]thiophene-2-sulfonyl)-6-oxo-1-(1H-pyrrolo[3,2-c]pyridin-2-ylmethyl)-piperazine-2-(+)-carboxylic acid amide | 504, 506, Cl pattern |
| 1110 | 4-(6-Chloro-benzo[b]thiophene-2-sulfonyl)-6-oxo-1-(1H-pyrrolo[3,2-c]pyridin-2-ylmethyl)-piperazine-2-(−)-carboxylic acid amide | 504, 506, Cl pattern |
| 1111 | 4-[2-(5-Chloro-thiophen-2-yl)-ethenesulfonyl]-6-methoxymethyl-1-(1H-pyrrolo[3,2-c]pyridin-2-ylmethyl)-piperazin-2-one | 481, 483, Cl pattern |
| 1112 | 4-(6-Chloro-benzo[b]thiophene-2-sulfonyl)-6-methoxymethyl-1-(1H-pyrrolo[3,2-c]pyridin-2-ylmethyl)-piperazin-2-one | 505, 507, Cl pattern |
| 1113 | 4-[2-(5-Chloro-thiophen-2-yl)-ethenesulfonyl]-6-hydroxymethyl-1-(1-methyl-1H-pyrrolo[3,2-c]pyridin-2-ylmethyl)-piperazin-2-one | 481, 483 Cl pattern |
| 1114 | 4-(6-Chloro-benzo[b]thiophene-2-sulfonyl)-6-hydroxymethyl-1-(1-methyl-1H-pyrrolo[3,2-c]pyridin-2-ylmethyl)-piperazin-2-one | 505, 507 Cl pattern |
| 1115 | 4-(5-Chloro-1H-indole-2-sulfonyl)-1-(1H-pyrrolo[3,2-c]pyridin-2-ylmethyl)-piperazin-2-one | 444 |
| 1116 | 4-(5-Chloro-1H-indole-2-sulfonyl)-6-methoxymethyl-1-(1H-pyrrolo[3,2-c]pyridin-2-ylmethyl)-piperazin-2-one | 488, 490 Cl pattern |
| 1117 | 4-(7-Methoxy-naphthalene-2-sulfonyl)-1-(1H-pyrrolo[3,2-c]pyridin-2-ylmethyl)-piperazin-2-one | 451 |
| 1118 | 4-(Benzo[b]thiophene-2-sulfonyl)-1-(1H-pyrrolo[3,2-c]pyridin-2-ylmethyl)-piperazin-2-one | 427 |

Representative Syntheses of Alkyl Azaindoles:

EXAMPLE 1119

4-[4-(5-Chloro-thiophen-2-yl)-benzyl]-1-(1H-pyrrolo[3,2-c]pyridin-2-ylmethyl)-piperazin-2-one A. (5-Chloro-thiophen-2-yl)-benzaldehyde 4-Formylphenylboronic acid (1.37 g, 9.15 mmol), 2-bromo-5-chlorothiophene (1 mL, 9.15 mmol), 2M Na$_2$CO$_3$ (9 mL, 18.3 mmol) and Pd(PPh$_3$)$_4$ (0.53 mg, 0.46 mmol) in DME (30 mL) are heated to reflux for 4 h after which time the reaction mixture is concentrated in vacuo and taken up in EtOAc. The organic solution is washed with water (×2) then brine and dried over MgSO$_4$, filtered and concentrated to dryness. The crude residue is purified by chromatography using 5% EtOAc/hexanes as the eluent to yield a yellow solid (1.8 g, 8.1 mmol) as the title compound. EI MS [M]+=222, 224, Cl pattern.

B. 2-{4-[4-(5-Chloro-thiophen-2-yl)-benzyl]-2-oxo-piperazin-1-ylmethyl}-pyrrolo[3,2-c]pyridine-1-carboxylic acid tert-butyl ester To a solution of 2-(2-oxo-piperazin-1-ylmethyl)-pyrrolo[3,2-c]pyridine-1-carboxylic acid tert-butyl ester (0.10 g, 0.30 mmol) in acetonitrile (5 mL) is added 4-(5-chloro-thiophen-2-yl)-benzaldehyde (0.067 g, 0.30 mmol) followed by triacetoxyborohydride (0.13 g, 0.60 mmol) and glacial acetic acid (1 drop). The resulting mixture is stirred at room temperature overnight then poured into EtOAc and washed with water (×2) and brine. The organic layer is dried over MgSO$_4$, filtered and concentrated to dryness then purified by column chromatography using EtOAc as the eluent to yield the title compound (0.90 g, 0.17 mmol). ESI MS [M+H]+ =537.

C. 4-[4-(5-Chloro-thiophen-2-yl)-benzyl]-1-(1H-pyrrolo[3,2-c]pyridin-2-ylmethyl)-piperazin-2-one 2-{4-[4-(5-Chloro-thiophen-2-yl)-benzyl]-2-oxo-piperazin-1-ylmethyl}-pyrrolo[3,2-c]pyridine-1-carboxylic acid tert-butyl ester (0.90 g, 0.17 mmol) is stirred in 30% TFA/CH$_2$Cl$_2$ (8 mL) for 1 h then concentrated to dryness and purified by RP-HPLC using 10-100% acetonitrile/0.1% TFA water as the eluent. The appropriate fractions are collected and lypholized to yield the title product as an amorphous white solid (0.44 mg, 0.08 mmol).

| Example # | Name | m/z (M + H) |
|---|---|---|
| 1120 | 4-[3-(5-Chloro-thiophen-2-yl)-benzyl]-3-(S)-propyl-1-(1H-pyrrolo[3,2-c]pyridin-2-ylmethyl)-piperazin-2-one | 479 |
| 1121 | 4-[3-(5-Chloro-thiophen-2-yl)-benzyl]-1-(1H-pyrrolo[3,2-c]pyridin-2-ylmethyl)-piperazin-2-one | 437 |
| 1122 | 4-[5-(5-Chloro-thiophen-2-yl)-pyridin-2-ylmethyl]-1-(1H-pyrrolo[3,2-c]pyridin-2-ylmethyl)-piperazin-2-one | 438 |
| 1123 | 4-[5-(5-Chloro-thiophen-2-yl)-pyridin-2-ylmethyl]-3-(S)-propyl-1-(1H-pyrrolo[3,2-c]pyridin-2-ylmethyl)-piperazin-2-one | 480 |
| 1124 | 4-[5-(5-Chloro-thiophen-2-yl)-pyridin-2-ylmethyl]-6-methoxymethyl-1-(1H-pyrrolo[3,2-c]pyridin-2-ylmethyl)-piperazin-2-one | 482 |
| 1125 | 4-[2-(4-Chloro-phenyl)-1H-indol-3-ylmethyl]-3-(S)-propyl-1-(1H-pyrrolo[3,2-c]pyridin-2-ylmethyl)-piperazin-2-one | 512 |
| 1126 | 4-[6-(5-Chloro-thiophen-2-yl)-pyridin-2-ylmethyl]-6-methoxymethyl-1-(1H-pyrrolo[3,2-c]pyridin-2-ylmethyl)-piperazin-2-one | 482 |
| 1127 | 4-[4-(5-Chloro-thiophen-2-yl)-benzyl]-6-methoxymethyl-1-(1H-pyrrolo[3,2-c]pyridin-2-ylmethyl)-piperazin-2-one | 481 |
| 1128 | 4-[6-(5-Chloro-thiophen-2-yl)-pyridin-2-ylmethyl]-1-(1H-pyrrolo[3,2-c]pyridin-2-ylmethyl)-piperazin-2-one | 438 |
| 1129 | 4-(5-Chloro-[2,3']bithiophenyl-5'-ylmethyl)-1-(1H-pyrrolo[3,2-c]pyridin-2-ylmethyl)-piperazin-2-one | 443 |
| 1130 | 4-(5'-Chloro-[2,2']bithiophenyl-5-ylmethyl)-6-methoxymethyl-1-(1H-pyrrolo[3,2-c]pyridin-2-ylmethyl)-piperazin-2-one | 487 |
| 1131 | 4-[2,2']Bithiophenyl-5-ylmethyl-6-methoxymethyl-1-(1H-pyrrolo[3,2-c]pyridin-2-ylmethyl)-piperazin-2-one | 453 |
| 1132 | 4-(5-Chloro-[2,3']bithiophenyl-5'-ylmethyl)-3-(S)-propyl-1-(1H-pyrrolo[3,2-c]pyridin-2-ylmethyl)-piperazin-2-one | 485 |
| 1133 | 4-[6-(5-Chloro-thiophen-2-yl)-pyridin-2-ylmethyl]-3-(S)-propyl-1-(1H-pyrrolo[3,2-c]pyridin-2-ylmethyl)-piperazin-2-one | 480 |
| 1134 | 4-[3-(5-Chloro-thiophen-2-yl)-4-fluoro-benzyl]-1-(1H-pyrrolo[3,2-c]pyridin-2-ylmethyl)-piperazin-2-one | 455 |
| 1135 | 4-[5-(3-Chloro-phenyl)-furan-2-ylmethyl]-1-(1H-pyrrolo[3,2-c]pyridin-2-ylmethyl)-piperazin-2-one | 421 |
| 1136 | 4-[4-(5-Chloro-thiophen-2-yl)-benzyl]-1-(1H-pyrrolo[3,2-c]pyridin-2-ylmethyl)-piperazin-2-one | 437 |
| 1137 | 4-[3-(5-Chloro-thiophen-2-yl)-4-fluoro-benzyl]-3-(S)-propyl-1-(1H-pyrrolo[3,2-c]pyridin-2-ylmethyl)-piperazin-2-one | 497 |
| 1138 | 4-[4-(5-Chloro-thiophen-2-yl)-benzyl]-3-(S)-propyl-1-(1H-pyrrolo[3,2-c]pyridin-2-ylmethyl)-piperazin-2-one | 479 |
| 1139 | 4-[5-(3-Chloro-phenyl)-furan-2-ylmethyl]-3-(S)-propyl-1-(1H-pyrrolo[3,2-c]pyridin-2-ylmethyl)-piperazin-2-one | 463 |
| 1140 | 4-[3-(5-Chloro-thiophen-2-yl)-allyl]-3-(S)-propyl-1-(1H-pyrrolo[3,2-c]pyridin-2-ylmethyl)-piperazin-2-one | 429, 431 Cl pattern |

-continued

| Example # | Name | m/z (M + H) |
|---|---|---|
| 1141 | 4-(5-Chloro-1H-indol-2-ylmethyl)-3-(S)-propyl-1-(1H-pyrrolo[3,2-c]pyridin-2-ylmethyl)-piperazin-2-one | 436 |
| 1142 | 4-(5'-Chloro-[2,2']bithiophenyl-5-ylmethyl)-3-(S)-propyl-1-(1H-pyrrolo[3,2-c]pyridin-2-ylmethyl)-piperazin-2-one | 485, 487 Cl pattern |
| 1143 | 4-[4-(5-Chloro-thiophen-2-yl)-benzyl]-3-(S)-methoxymethyl-1-(1H-pyrrolo[3,2-c]pyridin-2-ylmethyl)-piperazin-2-one | 481 |
| 1144 | 4-[5-(5-Chloro-thiophen-2-yl)-pyridin-2-ylmethyl]-3-(S)-methoxymethyl-1-(1H-pyrrolo[3,2-c]pyridin-2-ylmethyl)-piperazin-2-one | 482 |

The following compounds are prepared using the templates described above coupled with an amino-methyl-quinazoline, a quinazolinone, hydroxy-quinoline, an oxo-1,6-dihydro-pyridin-benzyl, a 6-methoxy-pyridin-3-yl)-benzyl or 3-imidazol-1-yl-benzyl group using the methods described in EXAMPLE 860 and the sulfonylation, alkylation or amide coupling reactions described above.

| Example # | Name | m/z (M + H) |
|---|---|---|
| 1145 | 1-(4-Amino-2-methyl-quinazolin-7-ylmethyl)-4-[(5-chloro-thiophen-2-yloxy)-acetyl]-3-(S)-propyl-piperazin-2-one | 487 |
| 1146 | 7-{4-[3-(5-Chloro-thiophen-2-yl)-acryloyl]-2-oxo-(S)-3-propyl-piperazin-1-ylmethyl}-3H-quinazolin-4-one | 471, 473 Cl pattern |
| 1147 | 7-{4-[(5-Chloro-thiophen-2-yloxy)-acetyl]-2-oxo-(S)-3-propyl-piperazin-1-ylmethyl}-3H-quinazolin-4-one | 475, 477 Cl pattern |
| 1148 | 1-(4-Amino-quinazolin-7-ylmethyl)-4-[3-(4-chloro-thiophen-2-yl)-acryloyl]-(S)-6-methyl-(S)-3-propyl-piperazin-2-one | 484, 486 Cl pattern |
| 1149 | 4-[3-(5-Chloro-thiophen-2-yl)-allyl]-(S)-3-ethyl-1-(4-hydroxy-quinolin-7-ylmethyl)-piperazin-2-one | 442, 444, Cl pattern |
| 1150 | 7-{4-[3-(5-Chloro-thiophen-2-yl)-allyl]-3-(S)-methoxymethyl-2-oxo-piperazin-1-ylmethyl}-2H-isoquinolin-1-one | 457 |
| 1151 | 7-[4-(7-Chloro-isoquinolin-3-ylmethyl)-3-(S)-methoxymethyl-2-oxo-piperazin-1-ylmethyl]-2H-isoquinolin-1-one | 477, 479 Cl pattern |
| 1152 | 4-(5-Chloro-1H-indol-2-ylmethyl)-1-[4-(6-oxo-1,6-dihydro-pyridin-3-yl)-benzyl]-3-(S)-propyl-piperazin-2-one | 489, 491 Cl pattern |
| 1153 | 4-(5-Chloro-1H-indol-2-ylmethyl)-3-(S)-methyl-1-[4-(6-oxo-1,6-dihydro-pyridin-3-yl)-benzyl]-piperazin-2-one | 561, 563 Cl pattern |
| 1154 | 6-{4-[(5-Chloro-thiophen-2-yloxy)-acetyl]-3-(S)-methoxymethyl-2-oxo-piperazin-1-ylmethyl}-3-methyl-3H-quinazolin-4-one | 491, 493 Cl pattern |
| 1155 | 6-{4-[(5-Chloro-thiophen-2-yloxy)-acetyl]-3-(S)-methoxymethyl-2-oxo-piperazin-1-ylmethyl}-3H-quinazolin-4-one | 477, 479 Cl pattern |
| 1156 | 4-(7-Chloro-isoquinolin-3-ylmethyl)-3-(S)-methyl-1-[4-(6-oxo-1,6-dihydro-pyridin-3-yl)-benzyl]-piperazin-2-one | 473, 475 Cl pattern |
| 1157 | 4-(7-Chloro-isoquinolin-3-ylmethyl)-1-[4-(6-oxo-1,6-dihydro-pyridin-3-yl)-benzyl]-piperazin-2-one | 459, 461 Cl pattern |
| 1158 | 4-(7-Chloro-isoquinolin-3-ylmethyl)-1-[4-(6-methoxy-pyridin-3-yl)-benzyl]-3-(S)-methyl-piperazin-2-one | 487, 489 Cl pattern |
| 1159 | 4-(7-Chloro-isoquinolin-3-ylmethyl)-1-[4-(6-oxo-1,6-dihydro-pyridin-3-yl)-benzyl]-3-(S)-propyl-piperazin-2-one | 501, 503 Cl pattern |
| 1160 | 4-(7-Chloro-isoquinolin-3-ylmethyl)-1-[4-(6-methoxy-pyridin-3-yl)-benzyl]-piperazin-2-one | 473, 475 Cl pattern |
| 1161 | 4-(7-Chloro-isoquinolin-3-ylmethyl)-1-[4-(6-methoxy-pyridin-3-yl)-benzyl]-3-(S)-propyl-piperazin-2-one | 515, 517 Cl pattern |
| 1162 | 4-(7-Chloro-isoquinolin-3-ylmethyl)-3-(S)-methoxymethyl-1-[4-(6-oxo-1,6-dihydro-pyridin-3-yl)-benzyl]-piperazin-2-one | 503 |
| 1163 | 4-[3-(6-Amino-pyridin-3-yl)-propionyl]-3-(S)-methoxymethyl-1-[4-(6-oxo-1,6-dihydro-pyridin-3-yl)-benzyl]-piperazin-2-one | 476 |
| 1164 | (S)-4-[(5-Chloro-thiophen-2-yloxy)-acetyl]-6-methoxymethyl-1-[4-(6-methoxy-pyridin-3-yl)-benzyl]-piperazin-2-one | 516 |
| 1165 | 4-[3-(5-Chloro-thiophen-2-yl)-acryloyl]-3(S)-isobutyl-1-[4-(6-oxo-1,6-dihydro-pyridin-3-yl)-benzyl]-piperazin-2-one | 510 |
| 1166 | 4-[(5-Chloro-thiophen-2-yloxy)-acetyl]-1-(3-imidazol-1-yl-benzyl)-3-(S)-methoxymethyl-piperazin-2-one | 475, 477 Cl pattern |
| 1167 | 4-[(5-Chloro-thiophen-2-yloxy)-acetyl]-3(S)-isobutyl-1-[4-(6-oxo-1,6-dihydro-pyridin-3-yl)-benzyl]-piperazin-2-one | 514 |
| 1168 | 4-[3-(6-Amino-pyridin-3-yl)-acryloyl]-3(S)-isobutyl-1-[4-(6-oxo-1,6-dihydro-pyridin-3-yl)-benzyl]-piperazin-2-one | 486 |
| 1169 | 4-[3-(6-Amino-pyridin-3-yl)-acryloyl]-1-[4-(6-oxo-1,6-dihydro-pyridin-3-yl)-benzyl]-3-(S)-propyl-piperazin-2-one | 472 |
| 1170 | 4-[(5-Chloro-thiophen-3-yloxy)-acetyl]-1-[4-(6-oxo-1,6-dihydro-pyridin-3-yl)-benzyl]-3-(S)-propyl-piperazin-2-one | 500, 502 Cl pattern |
| 1171 | 4-[(5-Chloro-thiophen-2-yloxy)-acetyl]-1-[4-(6-oxo-1,6-dihydro-pyridin-3-yl)-benzyl]-3-(S)-propyl-piperazin-2-one | 500, 502 Cl pattern |

| Example # | Name | m/z (M + H) |
|---|---|---|
| 1172 | 4-[3-(4-Chloro-thiophen-2-yl)-acryloyl]-1-[4-(6-oxo-1,6-dihydro-pyridin-3-yl)-benzyl]-3-(S)-propyl-piperazin-2-one | 496, 498 Cl pattern |
| 1173 | 4-[3-(5-Chloro-thiophen-2-yl)-acryloyl]-1-[4-(6-oxo-1,6-dihydro-pyridin-3-yl)-benzyl]-3-(S)-propyl-piperazin-2-one | 496, 498 Cl pattern |
| 1174 | 4-[3-(4-Chloro-thiophen-2-yl)-acryloyl]-1-[4-(6-methoxy-pyridin-3-yl)-benzyl]-3-(S)-propyl-piperazin-2-one | 510, 512 Cl pattern |
| 1175 | 4-[(5-Chloro-thiophen-2-yloxy)-acetyl]-1-[4-(6-methoxy-pyridin-3-yl)-benzyl]-3-(S)-propyl-piperazin-2-one | 514, 516 Cl pattern |
| 1176 | 4-[3-(5-Chloro-thiophen-2-yl)-acryloyl]-1-[4-(6-methoxy-pyridin-3-yl)-benzyl]-3-(S)-propyl-piperazin-2-one | 510, 512 Cl pattern |
| 1177 | 4-[(5-Chloro-thiophen-3-yloxy)-acetyl]-1-[4-(6-methoxy-pyridin-3-yl)-benzyl]-3-(S)-propyl-piperazin-2-one | 514, 516 Cl pattern |

EXAMPLE 1178

2-[4-(6-Chloro-benzo[b]thiophene-2-sulfonyl)-2-oxo-piperazin-1-ylmethyl]-6,7-dihydro-5H-benzothiazol-4-one A: 4-Cyanomethyl-piperazine-1-carboxylic acid tert-butyl ester To a partially dissolved solution of piperazine-1-carboxylic acid tert-butyl ester (2.0 g, 10 mmol) in THF (30 mL) is added 60% NaH (0.44 g, 11 mmol). The resulting solution is stirred for 5 min before the addition of bromoacetonitrile (0.9 mL, 13 mmol). The reaction is stirred for 4 h. MeOH (1 mL) is added and the solution is concentrated and the residue is diluted with EtOAc, washed with 1 N HCl, $H_2O$, $NaHCO_3$ and the solution is dried over $MgSO_4$. The filtrate is concentrated and the crude product is chromatographed using a silica column (50% EtOAc/PE-EtOAc) to yield 4-cyanomethyl-piperazine-1-carboxylic acid tert-butyl ester. $^1$H NMR (300 MHz, $CDCl_3$) δ4.41 (s, 2H), 4.16 (s, 2H), 3.75 (t, 2H), 3.51 (t, 2H), 1.47 (s, 9H).

B: Piperazin-1-yl-acetonitrile

To a solution of 30% $TFA/CH_2Cl_2$ (10 mL) is added 4-cyanomethyl-piperazine-1-carboxylic acid tert-butyl ester (1.7 g, 6.8 mmol) and the reaction is stirred for 14 h. The reaction is concentrated and chromatoghraphed using silica gel (%1 $NH_4OH$/7% $MeOH/CH_2Cl_2$) to isolate piperazin-1-yl-acetonitrile as the free base. $^1$H NMR (300 MHz, $CDCl_3$) δ4.36 (s, 2H), 3.54 (s, 2H), 3.45 (t, 2H), 3.13 (t, 2H).

C: [4-(6-Chloro-benzo[b]thiophene-2-sulfonyl)-piperazin-1-yl]-acetonitrile

To a solution of piperazin-1-yl-acetonitrile (0.32 g, 2.3 mmol) and $Et_3N$ (350 mg, 3.4 mmol) is added 6-chloro-benzo[b]thiophene-2-sulfonyl chloride (615 mg, 2.3 mmol) at 0° C. The reaction is warmed to room temperature and stirred 4 h. The reaction is diluted with $CH_2Cl_2$, washed with 1 N HCl, $NaHCO_3$ and dried over $MgSO_4$. The solution is concentrated and the residue is triturated with PE, triturated with $Et_2O$, and pumped to yield [4-(6-chloro-benzo[b]thiophene-2-sulfonyl)-piperazin-1-yl]-acetonitrile which can be used without further purification. $^1$H NMR (300 MHz, $CDCl_3$) δ7.89-7.84 (m, 3H), 7.48 (dd, 1H), 4.36 (s, 2H), 3.92 (s, 2H), 3.64-3.61 (m, 2H), 3.57-3.54 (m, 2H); MS (Ion Spray) 444 (M+H)$^+$.

D: 2-[4-(6-Chloro-benzo[b]thiophene-2-sulfonyl)-piperazin-1-yl]-thioacetamide

A suspension of [4-(6-chloro-benzo[b]thiophene-2-sulfonyl)-piperazin-1-yl]-acetonitrile (1.2 g, 3.2 mmol) is heated with diisopropylethylamine (0.65 g, 5.0 mmol) in a solution of ethanol saturated with hydrogen sulfide gas for 4 hours. The reaction is cooled, filtered and washed with cold ethanol to provide 2-[4-(6-chloro-benzo[b]thiophene-2-sulfonyl)-piperazin-1-yl]-thioacetamide. $^1$H NMR (300 MHz, DMSO-$d_6$) δ9.71 (bs, 1H), 9.01 (bs, 1H), 8.35 (d, 1H), 8.21 (s, 1H), 8.08 (d, 1H), 7.59 (dd, 1H), 4.15 (s, 2H), 3.73 (s, 2H), 3.43 (s, 4H).

E: 2-[4-(6-Chloro-benzo[b]thiophene-2-sulfonyl)-2-oxo-piperazin-1-ylmethyl]-6,7-dihydro-5H-benzothiazol-4-one To a solution of toluene/t-butanol (1:1) is added 2-[4-(6-chloro-benzo[b]thiophene-2-sulfonyl)-piperazin-1-yl]-thioacetamide (180 mg, 0.45 mmol) and 3-bromo-cyclohexane-1,2-dione (135 mg, 0.80 mmol). The reaction is heated at 90° C. for 4 h and is then concentrated and crude product is dissolved in $CH_2Cl_2$ and washed with $NaHCO_3$. The solution is concentrated and purified using 1% MeOH/EtOAc to provide 2-[4-(6-chloro-benzo[b]thiophene-2-sulfonyl)-2-oxo-piperazin-1-ylmethyl]-6,7-dihydro-5H-benzothiazol-4-one. $^1$H NMR (300 MHz, $CDCl_3$) δ7.87-7.82 (m, 3H), 7.47 (dd, 1H), 4.80 (s, 2H), 3.91 (s, 2H), 3.61 (t, 2H), 3.43 (t, 2H), 3.05 (t, 2H), 2.65 (t, 2H), 2.24 (dt, 2H); MS (Ion Spray) 496 (M+H)$^+$.

Using the corresponding α-haloketones, the following products can be produced:

EXAMPLE 1179

2-[4-(6-Chloro-benzo[b]thiophene-2-sulfonyl)-2-oxo-piperazin-1-ylmethyl]-4-methyl-thiazole-5-carboxylic acid methylamide $^1$H NMR (300 MHz, $CDCl_3$) δ7.87-7.82 (m, 3H), 7.46 (dd, 1H), 5.69 (br, 1H), 4.74 (s, 2H), 3.91 (s, 2H), 3.63-3.59 (m, 2H), 3.49-3.43 (m, 2H), 2.94 (d, 3H), 2.61 (s, 3H); MS (Ion Spray) 499 (M+H)$^+$.

EXAMPLE 1180

2-[4-(6-Chloro-benzo[b]thiophene-2-sulfonyl)-2-oxo-piperazin-1-ylmethyl]-4-methyl-thiazole-5-carboxylic acid dimethylamide $^1$H NMR (300 MHz, $CDCl_3$) δ7.88-7.82 (m, 3H), 7.46 (dd, 1H), 4.76 (s, 2H), 3.90 (s, 2H), 3.62-3.59 (m, 2H), 3.46-3.42 (m, 2H), 3.03 (br, 6H), 2.37 (s, 3H); MS (Ion Spray) 513 (M+H)$^+$.

EXAMPLE 1181

4-(6-Chloro-benzo[b]thiophene-2-sulfonyl)-1-(4-pyridin-4-yl-thiazol-2-ylmethyl)-piperazin-2-one hydrobromide $^1$H NMR (300 MHz, CDCl$_3$) δ 8.67 (br, 2H), 7.83-7.80 (m, 3H), 7.77 (br, 2H), 7.66 (s, 1H), 7.44 (dd, 1H), 4.87 (s, 2H), 3.96 (s, 2H), 3.70-3.66 (m, 2H), 3.52-3.49 (m, 2H); MS (Ion Spray) 505 (M+H)$^+$.

EXAMPLE 1182

2-[4-(6-Chloro-benzo[b]thiophene-2-sulfonyl)-2-oxo-piperazin-1-ylmethyl]-4,5,6,7-tetrahydro-benzothiazole-4-carboxylic acid amide $^1$H NMR (300 MHz, CDCl$_3$) δ 7.87-7.82 (m, 3H), 7.46 (dd, 1H), 6.84 (br, 1H), 5.60 (br, 1H), 4.85 (d, 1H), 4.66 (d, 1H), 3.91 (s, 2H), 3.64-3.52 (m, 3H), 3.47-3.44 (m, 2H), 2.76-2.62 (m, 2H), 2.41-2.33 (m, 1H), 1.93-2.81 (m, 3H); MS (Ion Spray) 525 (M+H)$^+$.

EXAMPLE 1183

{2-[4-(6-Chloro-benzo[b]thiophene-2-sulfonyl)-2-oxo-piperazin-1-ylmethyl]-thiazol-4-yl}-acetic acid methyl ester $^1$H NMR (300 MHz, CDCl$_3$) δ 7.86-7.82 (m, 3H), 7.46 (dd, 1H), 7.11 (s, 1H), 4.80 (s, 2H), 3.93 (s, 2H), 3.78 (s, 2H), 3.73 (s, 3H), 3.61-3.57 (m, 2H), 3.47-3.44 (m, 2H); MS (Ion Spray) 500 (M+H)$^+$.

EXAMPLE 1184

2-[4-(6-Chloro-benzo[b]thiophene-2-sulfonyl)-2-oxo-piperazin-1-ylmethyl]-thiazole-4-carboxylic acid ethyl ester $^1$H NMR (300 MHz, CDCl$_3$) δ 8.10 (s, 1H), 7.86-7.81 (m, 3H), 7.46 (dd, 1H), 4.86 (s, 2H), 4.41 (q, 2H), 3.93 (s, 2H), 3.63-3.59 (m, 2H), 3.48-3.44 (m, 2H), 1.39 (t, 3H); MS (Ion Spray) 500 (M+H)$^+$.

EXAMPLE 1185

2-[4-(6-Chloro-benzo[b]thiophene-2-sulfonyl)-2-oxo-piperazin-1-ylmethyl]-4-methyl-thiazole-5-carboxylic acid methyl ester $^1$H NMR (300 MHz, CDCl$_3$) δ 7.87-7.83 (m, 3H), 7.47 (dd, 1H), 4.76 (s, 2H), 3.93 (s, 2H), 3.84 (s, 3H), 3.64-3.60 (m, 2H), 3.49-3.45 (m, 2H) 2.66 (s, 3H); MS (Ion Spray) 500 (M+H)$^+$.

EXAMPLE 1186

1-(4-tert-Butyl-thiazol-2-ylmethyl)-4-(6-chloro-benzo[b]thiophene-2-sulfonyl)-piperazin-2-one $^1$H NMR (300 MHz, CDCl$_3$) δ 7.87-7.82 (m, 3H), 7.46 (dd, 1H), 6.79 (s, 1H), 4.81 (s, 2H), 3.93 (s, 2H), 3.61-3.58 (m, 2H), 3.48-3.44 (m, 2H), 1.29 (s, 9H); MS (Ion Spray) 484 (M+H)$^+$.

EXAMPLE 1187

4-(6-Chloro-benzo[b]thiophene-2-sulfonyl)-1-[4-(5-chloro-thiophen-2-yl)-thiazol-2-ylmethyl]-piperazin-2-one $^1$H NMR (300 MHz, CDCl$_3$) δ 7.83-7.81 (m, 3H), 7.45 (dd, 1H), 7.18 (s, 1H), 7.13 (d, 1H), 6.86 (d, 1H), 4.81 (s, 2H), 3.95 (s, 2H), 3.67-3.64 (m, 2H), 3.52-3.48 (m, 2H); MS (Ion Spray) 544 (M+H)$^+$.

EXAMPLE 1188

1-[4-(4-Bromo-phenyl)-thiazol-2-ylmethyl]-4-(6-chloro-benzo[b]thiophene-2-sulfonyl)-piperazin-2-one $^1$H NMR (300 MHz, CDCl$_3$) δ 7.83-7.80 (m, 3H), 7.70 (ddd, 2H), 7.53 (ddd, 2H), 7.45 (dd, 1H), 7.38 (s, 1H), 4.86 (s, 2H), 3.96 (s, 2H), 3.68-3.65 (m, 2H), 3.51-3.48 (m, 2H); MS (Ion Spray) 582 (M+H)$^+$.

EXAMPLE 1188

1-[4-(3-Bromo-phenyl)-thiazol-2-ylmethyl]-4-(6-chloro-benzo[b]thiophene-2-sulfonyl)-piperazin-2-one $^1$H NMR (300 MHz, CDCl$_3$) δ 8.00 (dd, 1H), 7.83-7.80 (m, 3H), 7.73 (dd, 1H), 7.48-7.40 (m, 3H), 7.28 (dd, 1H), 4.86 (s, 2H), 3.96 (s, 2H), 3.69-3.65 (m, 2H), 3.52-3.48 (m, 2H); MS (Ion Spray) 582 (M+H)$^+$.

EXAMPLE 1189

4-(6-Chloro-benzo[b]thiophene-2-sulfonyl)-1-(4-methyl-thiazol-2-ylmethyl)-piperazin-2-one $^1$H NMR (300 MHz, CDCl$_3$) δ 7.85-7.80 (m, 3H), 7.45 (dd, 1H), 6.79 (s, 1H), 4.78 (s, 2H), 3.92 (s, 2H), 3.59-3.56 (m, 2H), 3.47-3.43 (m, 2H) 2.38 (s, 3H); MS (Ion Spray) 442 (M+H)$^+$.

EXAMPLE 1190

4-(6-Chloro-benzo[b]thiophene-2-sulfonyl)-1-(4-pyridin-3-yl-thiazol-2-ylmethyl)-piperazin-2-one $^1$H NMR (300 MHz, CDCl$_3$) δ 9.07 (dd, 1H), 8.58 (dd, 1H), 8.11 (ddd, 1H), 7.83-7.79 (m, 3H), 7.43 (dd, 1H), 7.33 (dd, 1H), 4.86 (s, 2H), 3.95 (s, 2H), 3.67-3.64 (m, 2H), 3.51-3.47 (m, 2H); MS (Ion Spray) 505 (M+H)$^+$.

EXAMPLE 1191

1-(5-Acetyl-4-methyl-thiazol-2-ylmethyl)-4-(6-chloro-benzo[b]thiophene-2-sulfonyl)-piperazin-2-one $^1$H NMR (300 MHz, CDCl$_3$) δ 7.86-7.82 (m, 3H), 7.45 (dd, 1H), 4.75 (s, 2H), 3.92 (s, 2H), 3.65-3.61 (m, 2H), 3.48-3.45 (m, 2H), 2.65 (s, 3H), 2.61 (s, 3H); MS (Ion Spray) 499 (M+H)$^+$.

EXAMPLE 1192

3-{2-[4-(6-Chloro-benzo[b]thiophene-2-sulfonyl)-2-oxo-piperazin-1-ylmethyl]-thiazol-4-yl}-3-methyl-butyric acid ethyl ester $^1$H NMR (300 MHz, CDCl$_3$) δ 7.87-7.82 (m, 3H), 7.46 (dd, 1H), 6.85 (s, 1H), 4.80 (s, 2H), 3.98 (q, 2H), 3.92 (s, 2H), 3.60-3.57 (m, 2H), 3.46-3.43 (m, 2H), 2.66 (s, 2H), 1.40 (s, 6H), 1.12 (t, 3H); MS (Ion Spray) 556 (M+H)$^+$.

EXAMPLE 1193

1-(4-Adamantan-1-yl-thiazol-2-ylmethyl)-4-(6-chloro-benzo[b]thiophene-2-sulfonyl)-piperazin-2-one $^1$H NMR (300 MHz, CDCl$_3$) δ 7.86-7.82 (m, 3H), 7.46 (dd, 1H), 6.74 (s, 1H), 4.81 (s, 2H), 3.93 (s, 2H), 3.60-3.57 (m, 2H), 3.48-3.44 (m, 2H), 2.05 (m, 3H), 1.90 (m, 6H), 1.80-1.71 (m, 6H); MS (Ion spray) 562 (M+H)$^+$.

EXAMPLE 1194

1-(4-Adamantan-1-yl-thiazol-2-ylmethyl)-4-(6-chloro-benzo[b]thiophene-2-sulfonyl)-piperazin-2-one $^1$H NMR (300 MHz, CDCl$_3$) δ 7.86-7.82 (m, 3H), 7.46 (dd, 1H), 6.74 (s, 1H), 4.81 (s, 2H), 3.93 (s, 2H), 3.60-3.57 (m, 2H), 3.48-3.44 (m, 2H), 2.05 (m, 3H), 1.90 (m, 6H), 1.80-1.71 (m, 6H); MS (Ion Spray) 562 (M+H)$^+$.

EXAMPLE 1195

4-(6-Chloro-benzo[b]thiophene-2-sulfonyl)-1-(4-phenyl-thiazol-2-ylmethyl)-piperazin-2-one $^1$H NMR (300 MHz, CDCl$_3$) δ 7.83-7.79 (m, 5H), 7.45-7.31 (m, 5H), 4.87 (s, 2H), 3.95 (s, 2H), 3.69-3.65 (m, 2H), 3.51-3.47 (m, 2H); MS (Ion Spray) 504 (M+H)$^+$.

EXAMPLE 1195

4-(6-Chloro-benzo[b]thiophene-2-sulfonyl)-1-[4-(4-hydroxy-phenyl)-thiazol-2-ylmethyl]-piperazin-2-one $^1$H NMR (300 MHz, CDCl$_3$) δ 7.80-7.78 (m, 3H), 7.63 (ddd, 2H), 7.41 (dd, 1H), 7.17 (s, 1H), 6.83 (ddd, 1H), 4.81 (s, 2H), 3.92 (s, 2H), 3.68-3.61 (m, 2H), 3.48-3.44 (m, 2H); MS (Ion Spray) 520 (M+H)$^+$.

EXAMPLE 1196

4-(6-Chloro-benzo[b]thiophene-2-sulfonyl)-1-[4-(4-hydroxy-phenyl)-thiazol-2-ylmethyl]-piperazin-2-one $^1$H NMR (300 MHz, CDCl$_3$) δ 7.82-7.79 (m, 3H), 7.43 (dd, 1H), 7.36-7.34 (md, 3H), 7.25 (m, 1H), 6.83 (dd, 1H), 6.10 (br, 1H), 4.86 (s, 2H), 3.95 (s, 2H), 3.68-3.64 (m, 2H), 3.50-3.47 (m, 2H); MS (Ion Spray) 520 (M+H)$^+$.

EXAMPLE 1197

4-(6-Chloro-benzo[b]thiophene-2-sulfonyl)-1-(4,5,6,7-tetrahydro-benzothiazol-2-ylmethyl)-piperazin-2-one.

$^1$H NMR (300 MHz, CDCl$_3$) δ 7.87-7.82 (m, 3H), 7.46 (dd, 1H), 4.80 (s, 2H), 3.91 (s, 2H), 3.61-3.58 (m, 2H), 3.46-3.43 (m, 2H), 2.72 (bm, 4H), 1.83 (bs, 4H); MS (Ion Spray) 482 (M+H)$^+$.

EXAMPLE 1198

2-[4-(6-Chloro-benzo[b]thiophene-2-sulfonyl)-2-oxo-piperazin-1-ylmethyl]-thiazole-4-carboxylic acid dimethylamide $^1$H NMR (300 MHz, CDCl$_3$) δ 7.87-7.77 (m, 4H), 7.47 (dd, 1H), 4.83 (s, 2H), 3.92 (s, 2H), 3.63-3.60 (m, 2H), 3.47-3.43 (m, 2H), 3.18 (s, 3H), 3.10 (s, 3H); MS (Ion Spray) 499 (M+H)$^+$.

EXAMPLE 1199

2-[4-(6-Chloro-benzo[b]thiophene-2-sulfonyl)-2-oxo-piperazin-1-ylmethyl]-4,5,6,7-tetrahydro-benzothiazole-4-carboxylic acid ethyl ester $^1$H NMR (300 MHz, CDCl$_3$) δ 7.87-7.81 (m, 3H), 7.46 (dd, 1H), 4.81 (s, 2H), 4.17 (q, 2H), 3.91 (s, 1H), 3.89 (s, 1H), 3.80 (t, 0.5), 3.60-2.52 (m, 2.5H), 3.45-3.36 (m, 2H), 2.78-2.68 (m, 2H), 2.16-1.77 (m, 4H), 1.25 (t, 3H); MS (Ion Spray) 554 (M+H)$^+$.

EXAMPLE 1200

2-{2-[4-(6-Chloro-benzo[b]thiophene-2-sulfonyl)-2-oxo-piperazin-1-ylmethyl]-thiazol-4-yl}-benzoic acid $^1$H NMR (300 MHz, CDCl$_3$) δ 7.88 (d, 1H), 7.80-7.76 (m, 3H), 7.55-7.35 (m, 5H), (s, 2H), 3.94 (s, 2H), 3.55 (m, 2H), 3.43 (m, 2H); MS (ion spray) 548 (M+H)$^+$.

EXAMPLE 1201

4-(6-Chloro-benzo[b]thiophene-2-sulfonyl)-1-[4-(2-hydroxy-phenyl)-thiazol-2-ylmethyl]-piperazin-2-one $^1$H NMR (300 MHz, CDCl$_3$) δ 11.2 (s, 1H), 7.82-7.79 (m, 3H), 7.55 (dd, 1H), 7.45-7.40 (m, 2H), 7.24 (d, 1H), 6.97-6.89 (m, 2H), 4.87 (s, 2H), 3.95 (s, 2H), 3.61 (m, 2H), 3.50 (m, 2H); MS (ion spray) 520 (M+H)$^+$.

EXAMPLE 1202

4-(6-Chloro-benzo[b]thiophene-2-sulfonyl)-1-(4-pyridin-2-yl-thiazol-2-ylmethyl)-piperazin-2-one $^1$H NMR (300 MHz, CDCl$_3$) δ 8.61 (s, 1H), 7.99 (d, 1H), 7.96 (s, 1H), 7.83-7.74 (m, 4H), 7.43 (dd, 1H), 7.23-7.19 (m, 1H), 4.88 (s, 2H), 3.94 (s, 2H), 3.65 (m, 2H), 3.48 (m, 2H); MS (ion spray) 505 (M+H)$^+$.

EXAMPLE 1203

2-{2-[4-(6-Chloro-benzo[b]thiophene-2-sulfonyl)-2-oxo-piperazin-1-ylmethyl]-thiazol-4-yl}-benzamide $^1$H NMR (300 MHz, CDCl$_3$) δ 8.00 (s, 1H), 7.84-7.79 (m, 2H), 7.61-7.55 (m, 2H), 7.48-7.37 (m, 4H), 5.86 (d (broad), 2H), 4.83 (s, 2H), 3.92 (s, 2H), 3.65 (m, 2H), 3.47 (m, 2H) MS (ion spray) 547 (M+H)$^+$.

Using procedures described above the following compounds can be made;

EXAMPLE 1204

4-(6-Chloro-benzo[b]thiophene-2-sulfony)-1-(4,5,6,7-tetrahydro-thiazolo[5,4-c]pyridin-2-ylmethyl)-piperazin-2-one

EXAMPLE 1205

4-(6-Chloro-benzo[b]thiophene-2-sulfonyl)-1-(5-methyl-4,5,6,7-tetrahydro-thiazolo[5,4-c]pyridin-2-ylmethyl)-piperazin-2-one

EXAMPLE 1206

4-(6-Chloro-benzo[b]thiophene-2-sulfonyl)-1-(4,5,6,7-tetrahydro-thiazolo[4,5-c]pyridin-2-ylmethyl)-piperazin-2-one

EXAMPLE 1207

4-(6-Chloro-benzo[b]thiophene-2-sulfonyl)-1-(5-methyl-4,5,6,7-tetrahydro-thiazolo[4,5-c]pyridin-2-ylmethyl)-piperazin-2-one

EXAMPLE 1208

2-[4-(6-Chloro-benzo[b]thiophene-2-sulfonyl)-2-oxo-piperazin-1-ylmethyl]-4,7-dihydro-5H-thiazolo[4,5-c]pyridin-6-one The following compounds are prepared according to the methods described above;

| EXAMPLE # | Name | MS (m/z) (M + H) |
|---|---|---|
| 1209 | (R)-2-[4-(6-Chloro-benzo[b]thiophene-2-sulfonyl)-2-methoxymethyl-6-oxo-piperazin-1-ylmethyl]-4,5,6,7-tetrahydro-benzothiazole-4-carboxylic acid amide | 569 |
| 1210 | (R)-4-(6-Chloro-benzo[b]thiophene-2-sulfonyl)-6-methoxymethyl-1-(4,5,6,7-tetrahydro-benzothiazol-2-ylmethyl)-piperazin-2-one | 526 |
| 1211 | (R)-2-[4-(6-Chloro-benzo[b]thiophene-2-sulfonyl)-2-methoxymethyl-6-oxo-piperazin-1-ylmethyl]-thiazole-4-carboxylic acid ethyl ester | 544/546 |
| 1212 | (R)-2-[4-(6-Chloro-benzo[b]thiophene-2-sulfonyl)-2-methoxymethyl-6-oxo-piperazin-1-ylmethyl]-4-methyl-thiazole-5-carboxylic acid dimethylamide | 557 |
| 1213 | (R)-4-(6-Chloro-benzo[b]thiophene-2-sulfonyl)-6-methoxymethyl-1-(4-pyridin-3-yl-thiazol-2-ylmethyl)-piperazin-2-one | 549 |
| 1214 | (R)-3-{2-[4-(6-Chloro-benzo[b]thiophene-2-sulfonyl)-2-methoxymethyl-6-oxo-piperazin-1-ylmethyl]-thiazol-4-yl}-3-methyl-butyric acid ethyl ester | 600 |
| 1215 | (R)-2-[4-(6-Chloro-benzo[b]thiophene-2-sulfonyl)-2-methoxymethyl-6-oxo-piperazin-1-ylmethyl]-thiazole-4-carboxylic acid | 516 |
| 1216 | (R)-2-[4-(6-Chloro-benzo[b]thiophene-2-sulfonyl)-2-methoxymethyl-6-oxo-piperazin-1-ylmethyl]-thiazole-4-carboxylic acid dimethylamide | 543 |
| 1217 | (S)-2-{4-[(5-Chloro-thiophen-2-yloxy)-acetyl]-(3S)-methoxymethyl-2-oxo-piperazin-1-ylmethyl}-4,5,6,7-tetrahydro-benzothiazole-4-carboxylic acid amide | 513 |
| 1218 | (S)-2-{4-[(5-Chloro-thiophen-2-yloxy)-acetyl]-(3S)-methoxymethyl-2-oxo-piperazin-1-ylmethyl]-thiazole-4-carboxylic acid ethyl ester | 488 |
| 1219 | (S)-2-{4-[(5-Chloro-thiophen-2-yloxy)-acetyl]-3(S)-methoxymethyl-2-oxo-piperazin-1-ylmethyl}-thiazole-4-carboxylic acid dimethylamide | 487 |
| 1220 | (S)-(2-{4-[(5-Chloro-thiophen-2-yloxy)-acetyl]-3(S)-methoxymethyl-2-oxo-piperazin-1-ylmethyl}-thiazol-4-yl)-acetic acid methyl ester | 488 |
| 1221 | (S)-4-[(5-Chloro-thiophen-2-yloxy)-acetyl]-3(S)-methoxymethyl-1-(4,5,6,7-tetrahydro-benzothiazol-2-ylmethyl)-piperazin-2-one | 470 |

EXAMPLE 1222

4-(6-Chloro-benzo[b]thiophene-2-sulfonyl)-1-(4-hydroxy-4,5,6,7-tetrahydro-benzothiazol-2-ylmethyl)-piperazin-2-one To the suspension of 2-[4-(6-chloro-benzo[b]thiophene-2-sulfonyl)-2-oxo-piperazin-1-ylmethyl]-6,7-dihydro-5H-benzothiazol-4-one (7 mg, 0.01 mmol) in EtOH (1 mL) is added sodium borohydride (3 mg, 0.08 mmol). After 15 min the reaction is diluted with EtOAc and washed with 1N HCl, NaHCO$_3$ and brine. The solution is dried (MgSO4) and concentrated to provide 4-(6-chloro-benzo[b]thiophene-2-sulfonyl)-1-(4-hydroxy-4,5,6,7-tetrahydro-benzothiazol-2-ylmethyl)-piperazin-2-one. $^1$H NMR (300 MHz, CDCl$_3$) δ 7.88-7.82 (m, 3H), 7.46 (dd, 1H), 4.83-4.81 (m, 1H), 4.76 (s, 1H), 4.75 (s, 1H), 3.92 (s, 1H), 3.91 (s, 1H), 3.62-3.55 (m, 2H), 3.47-3.41 (m, 2H), 2.76-2.62 (m, 2H), 2.05-1.78 (m, 4H); MS (Ion Spray) 498 (M+H)$^+$.

EXAMPLE 1223

2-[4-(6-Chloro-benzo[b]thiophene-2-sulfonyl)-2-oxo-piperazin-1-ylmethyl]-6,7-dihydro-5H-benzothiazol-4-one oxime 2-[4-(6-Chloro-benzo[b]thiophene-2-sulfonyl)-2-oxo-piperazin-1-ylmethyl]-6,7-dihydro-5H-benzothiazol-4-one (24 mg, 0.05 mmol), hydroxylamine hydrochloride (20 mg, 0.3 mmol), sodium acetate (20 mg, 0.3 mmol) and EtOH (2 mL) are combined and stirred 3.5 h. The reaction is diluted with CH$_2$Cl$_2$ and washed with NH$_4$Cl, NaHCO$_3$ and concentrated to provide 2-[4-(6-chloro-benzo[b]thiophene-2-sulfonyl)-2-oxo-piperazin-1-ylmethyl]-6,7-dihydro-5H-benzothiazol-4-one oxime. $^1$H NMR (300 MHz, DMSO-d$_6$) δ 10.92 (s, 1H), 8.34 (d, 1H), 8.20 (s, 1H), 8.07 (d, 1H), 7.59 (dd, 1H), 4.70 (s, 2H), 3.87 (s, 2H), 3.49 (s, 4H), 2.74 (t, 2H), 2.61 (t, 2H), 1.81 (dt, 2H); (Ion Spray) 511 (M+H)$^+$.

EXAMPLE 1224a 1-(4-Amino-benzothiazol-2-ylmethyl)-4-(6-chloro-benzo[b]thiophene-2-sulfonyl)-piperazin-2-one and

EXAMPLE 1224b

2-[4-(6-Chloro-benzo[b]thiophene-2-sulfonyl)-2-oxo-piperazin-1-ylmethyl]-5,6,7,8-tetrahydro-thiazolo[4,5-c]azepin-4-one 2-[4-(6-Chloro-benzo[b]thiophene-2-sulfonyl)-2-oxo-piperazin-1-ylmethyl]-6,7-dihydro-5H-benzothiazol-4-one (60 mg, 0.12 mmol) is dissolved in CHCl$_3$ (4 mL) and sulfuric acid (0.5 mL) is added with vigorous stirring. Sodium azide (25 mg 0.4 mmol) is added and the reaction is stirred 1¾ h. The reaction is then added dropwise to a rapidly stirring mixture of K$_2$CO$_3$/H$_2$O/CH$_2$Cl$_2$. The organic phase is separated and washed with water, dried (MgSO$_4$) and concentrated. The residue is purified by column chromatography (silica, 2% to 6% MeOH/CH$_2$Cl$_2$) to provide a mixture of two products.

The faster eluting product is the Semler-Wolff aromatization product, 1-(4-amino-benzothiazol-2-ylmethyl)-4-(6-chloro-benzo[b]thiophene-2-sulfonyl)-piperazin-2-one. $^1$H NMR (300 MHz, DMSO-d$_6$) δ8.32 (d, 1H), 8.21 (s, 1H), 8.07 (d, 1H), 7.59 (dd, 1H), 7.08 (t, 1H), 6.98 (d, 1H), 6.13 (d, 1H), 5.59 (s, 2H), 4.84 (s, 2H), 3.93 (s, 2H), 3.54 (s, 4H); MS (Ion Spray) 493 (M+H)$^+$.

The slower eluting product is the ring expanded lactam, 2-[4-(6-chloro-benzo[b]thiophene-2-sulfonyl)-2-oxo-piperazin-1-ylmethyl]-5,6,7,8-tetrahydro-thiazolo[4,5-c]azepin-4-one. $^1$H NMR (300 MHz, CDCl$_3$) δ 7.87-7.82 (m, 3H), 7.47 (dd, 1H), 6.47 (bs, 1H), 4.80 (m, 2H), 3.91 (s, 2H), 3.65-3.61 (m, 2H), 3.46-3.42 (m, 2H), 3.37-3.32 (m, 2H), 3.07 (t, 2H) 2.17-2.10 (m, 2H); MS (Ion Spray) 511 (M+H)$^+$.

EXAMPLE 1225

2-[4-(6-Chloro-benzo[b]thiophene-2-sulfonyl)-2-oxo-piperazin-1-ylmethyl]-thiazole-4-carboxylic acid dimethylamide A: 2-[4-(6-Chloro-benzo[b]thiophene-2-sulfonyl)-2-oxo-piperazin-1-ylmethyl]-thiazol-4-yl-carboxylic acid A solution of 2-[4-(6-chloro-benzo[b]thiophene-2-sulfonyl)-2-oxo-piperazin-1-ylmethyl]-thiazol-4-yl-carboxylic acid ethyl ester (75 mg, 0.15 mmol) is dissolved in THF/MeOH –3:1 (2 mL) and a solution of 1N NaOH is added (0.5 mL). The reaction is stirred for 2 h and then diluted with EtOAc and washed with 2N HCl. The organic phase is dried (MgSO4) and concentrated to yield 2-[4-(6-chloro-benzo[b]thiophene-2-sulfonyl)-2-oxo-piperazin-1-ylmethyl]-thiazol-4-yl-carboxylic acid. $^1$H NMR (300 MHz, DMSO-d$_6$) δ 8.32 (d, 1H), 8.26 (s, 1H), 8.18 (s, 1H), 8.04 (d, 1H), 7.57 (dd, 1H), 4.74 (s, 2H), 3.87 (s, 2H), 3.49 (s, 4H); MS (Ion Spray) 471 (M)$^+$.

B: 2-[4-(6-Chloro-benzo[b]thiophene-2-sulfonyl)-2-oxo-piperazin-1-ylmethyl]-thiazole-4-carboxylic acid dimethylamide To a solution of 2-[4-(6-chloro-benzo[b]thiophene-2-sulfonyl)-2-oxo-piperazin-1-ylmethyl]-thiazol-4-yl-carboxylic acid (14 mg, 0.03 mmol) in N-methyl-pyrolidinone (0.3 mL) is added TBTU (0.05 mmol) and diisopropylethylamine (0.06 mmol) and dimethylamine hydrochloride (0.06). The reaction is stirred 3 h and an additional aliquot of TBTU, DIEA and amine are added. The reaction is stirred 1 h and the reaction is concentrated and purified by column chromatography (silica, 2% MeOH/EtOAc) to provide 2-[4-(6-chloro-benzo[b]thiophene-2-sulfonyl)-2-oxo-piperazin-1-ylmethyl]-thiazole-4-carboxylic acid dimethylamide. $^1$H NMR (300 MHz, CDCl$_3$) δ 7.87-7.77 (m, 4H), 7.47 (dd, 1H), 4.83 (s, 2H), 3.92 (s, 2H), 3.63-3.60 (m, 2H), 3.47-3.43 (m, 2H), 3.18 (s, 3H), 3.10 (s, 3H); MS (Ion Spray) 499 (M+H)$^+$.

When alternative amines are used in the above reaction the following products are isolated:

EXAMPLE 1226

4-(6-Chloro-benzo[b]thiophene-2-sulfonyl)-1-[4-(pyrrolidine-1-carbonyl)-thiazol-2-ylmethyl]-piperazin-2-one $^1$H NMR (300 MHz, CDCl$_3$) δ 7.99 (s, 1H), 7.87-7.81 (m, 3H), 7.47 (d, 1H), 4.81 (s, 2H), 3.92 (s, 2H), 3.82 (m, 2H), 3.72-3.61 (m, 4H), 3.46 (m, 2H), 1.97-1.87 (m, 4H); MS (ion spray) 525 (M+H)$^+$.

EXAMPLE 1227

4-(6-Chloro-benzo[b]thiophene-2-sulfonyl)-1-[4-(morpholine-4-carbonyl)-thiazol-2-ylmethyl]-piperazin-2-one $^1$H NMR (300 MHz, CDCl$_3$) δ 7.88-7.82 (m, 4H), 7.46 (dd, 1H), 4.82 (s, 2H), 3.93 (s, 2H), 3.88-3.67 (m, 8H), 3.61 (m, 2H), 3.46 (m, 2H); MS (ion spray) 541 (M+H)$^+$.

EXAMPLE 1228

4-(6-Chloro-benzo[b]thiophene-2-sulfonyl)-1-[4-(piperazine-1-carbonyl)-thiazol-2-ylmethyl]-piperazin-2-one As the TFA salt: $^1$H NMR (300 MHz, CDCl$_3$) δ 9.9 (s (broad), 1H), 7.99 (s, 1H), 7.87-7.82 (m, 3H), 7.46 (dd, 1H), 4.80 (s, 2H), 4.39-3.96 (m (broad), 4H), 3.90 (s, 2H), 3.59 (m, 2H), 3.47 (m, 2H), 3.28 (s (broad), 4H); MS (ion spray) 540 (M+H)$^+$.

EXAMPLE 1229

2-[4-(6-Chloro-benzo[b]thiophene-2-sulfonyl)-2-oxo-piperazin-1-ylmethyl]-thiazol-4-carboxylic acid N',N'-dimethyl-hydrazine $^1$H NMR (300 MHz, CDCl$_3$) δ 8.11 (s, 1H), 7.86-7.80 (m, 3H), 7.46-7.43 (m, 1H), 4.77 (s, 2H), 3.92 (s, 2H), 3.83 (m, 2H), 3.52 (m, 2H), 3.21 (s, 6H); MS (ion spray) 514 (M+H)$^+$.

EXAMPLE 1230

2-[4-(6-Chloro-benzo[b]thiophene-2-sulfonyl)-2-oxo-piperazin-1-ylmethyl]-thiazole-4-carboxylic acid (2-hydroxy-ethyl)-methyl-amide $^1$H NMR (300 MHz, CDCl$_3$) δ 7.91-7.81 (m, 4H), 7.46 (dd, 1H), 4.81 (s, 2H), 4.68 (t, 1H), 3.94 (s, 2H), 3.72 (m, 2H), 3.64-3.54 (m, 4H), 3.49 (m, 2H), 3.08 (s, 3H); MS (ion spray) 529 (M+H)$^+$.

EXAMPLE 1231

4-(6-Chloro-benzo[b]thiophene-2-sulfonyl)-1-[4-(3-hydroxy-pyrrolidine-1-carbonyl)-thiazol-2-ylmethyl]-piperazin-2-one $^1$H NMR (300 MHz, CDCl$_3$) δ 7.97 (d, 1H), 7.87-7.82 (m, 3H), 7.45 (dd, 1H), 4.85 (s, 2H), 4.62-4.55 (m, 1H), 4.08-3.42 (m, 10H), 2.12-1.92 (m, 2H); MS (ion spray) 541 (M+H)$^+$.

EXAMPLE 1232

2-(4-(6-Chloro-benzo[b]thiophene-2-sulfonyl)-2-oxo-piperazin-1-ylmethyl]-thiazole-4-carboxylic acid methoxy-methyl-amide $^1$H NMR (300 MHz, CDCl$_3$) δ 7.95 (s, 1H), 7.86-7.81 (m, 3H), 7.45 (dd, 1H), 4.85 (s, 2H), 3.92 (s, 2H), 3.72 (s, 3H), 3.62 (m, 2H), 3.45 (m, 2H), 3.39 (s, 3H); MS (ion spray) 515 (M+H)$^+$.

EXAMPLE 1233

2-[4-(6-Chloro-benzo[b]thiophene-2-sulfonyl)-2-oxo-piperazin-1-ylmethyl]-thiazole-4-carboxylic acid isopropyl-methyl-amide $^1$H NMR (300 MHz, CDCl$_3$) δ 7.87-7.81 (m, 3H), 7.66 (m, 1H), 7.45 (dd, 1H), 4.82 (s, 2H), 4.38-4.22 (m, 0.5), 3.91 (s, 2H), 3.68-3.59 (m, 2H), 3.48-3.42 (m, 2H), 2.92 (s (broad), 3H), 1.24-1.15 (m, 6H); MS (ion spray) 527 (M+H)$^+$.

EXAMPLE 1234

({2-[4-(6-Chloro-benzo[b]thiophene-2-sulfonyl)-2-oxo-piperazin-1-ylmethyl]-thiazole-4-carbonyl}-methyl-amino)-acetic acid ethyl ester $^1$H NMR (300 MHz, CDCl$_3$) δ 7.98-7.81 (m, 4H), 7.46 (dd, 1H), 4.83 (s, 1H), 4.75 (s, 1H), 4.44 (s, 1H), 4.26-4.13 (m, 3H), 3.91 (s, 1H), 3.63-3.58 (m, 2H), 3.46-3.43 (m, 2H), 3.31 (s, 1.5), 3.15 (s, 1.5), 1.32-1.22 (m, 3H); MS (ion spray) 571 (M+H)$^+$.

EXAMPLE 1235

2-[4-(6-Chloro-benzo[b]thiophene-2-sulfonyl)-2-oxo-piperazin-1-ylmethyl]-thiazole-4-carboxamide MS (ion spray) 471 (M+H)$^+$.

EXAMPLE 1236

2-[4-(6-Chloro-benzo[b]thiophene-2-sulfonyl)-2-oxo-piperazin-1-ylmethyl]-thiazole-4-carboxylic acid methylamide MS (ion spray) 485 (M+H)$^+$.

EXAMPLE 1237

2-[4-(6-Chloro-benzo[b]thiophene-2-sulfonyl)-2-oxo-piperazin-1-ylmethyl]-thiazole-4-carboxylic acid isopropylamide MS (ion spray) 513 (M+H)$^+$.

When a {2-[4-(6-Chloro-benzo[b]thiophene-2-sulfonyl)-2-oxo-piperazin-1-ylmethyl]-thiazol-4-yl}-acetic acid methyl ester is treated with NaOH under the conditions previously employed then the product obtained is:

EXAMPLE 1238

{2-[4-(6-Chloro-benzo[b]thiophene-2-sulfonyl)-2-oxo-piperazin-1-ylmethyl]-thiazol-4-yl}-acetic acid $^1$H NMR (300 MHz, CDCl$_3$+CD$_3$OD) δ 7.90-7.87 (m, 3H), 7.47 (dd, 1H), 7.17 (s, 1H), 4.80 (s, 2H), 3.93 (s, 2H), 3.75 (s, 2H), 3.60-3.58 (m, 2H), 3.50-3.48 (m, 2H); MS (Ion Spray) 486 (M+H)$^+$.

Amide bond formation using the conditions previously employed provides the following products using the amines shown

EXAMPLE 1239

2-{2-[4-(6-Chloro-benzo[b]thiophene-2-sulfonyl)-2-oxo-piperazin-1-ylmethyl]-thiazol-4-yl}-acetamide MS (ion spray) 485 (M+H)$^+$.

EXAMPLE 1240

2-{2-[4-(6-Chloro-benzo[b]thiophene-2-sulfonyl)-2-oxo-piperazin-1-ylmethyl]-thiazol-4-yl}-N-methyl-acetamide MS (ion spray) 499 (M+H)$^+$.

EXAMPLE 1241

2-{2-[4-(6-Chloro-benzo[b]thiophene-2-sulfonyl)-2-oxo-piperazin-1-ylmethyl]-thiazol-4-yl}-N-isopropyl-acetamide MS (ion spray) 527 (M+H)$^+$.

EXAMPLE 1242

2-{2-[4-(6-Chloro-benzo[b]thiophene-2-sulfonyl)-2-oxo-piperazin-1-ylmethyl]-thiazol-4-yl}-N,N-dimethyl-acetamide MS (ion spray) 513 (M+H)+.

EXAMPLE 1243

2-[4-(6-Chloro-benzo[b]thiophene-2-sulfonyl)-2-oxo-piperazin-1-ylmethyl]-4,7-dihydro-5H-thiazolo[5,4-c]pyridin-6-one.

A: 5-Benzyloxycarbonylamino-3-oxo-pentanoic acid ethyl ester

Cbz-β-Alanine (5.0 g, 21.6 mmol) is dissolved in THF (10 mL). To this is added dropwise a solution of carbonyl diimidazole (3.5 g, 21.6 mmol) in THF (50 mL) and allowed to stir 16 hrs. This solution is then reduced to ~30 mL by rotary evaporation. In a separate flask (oven dried), isopropyl magnesium chloride in THF (2M) (16.2 mL, 32 mmol) is added and cooled to 0° C. and hydrogen ethyl malonate (4.28 g, 32.4 mmol) is added dropwise. The contents are allowed to stir at 0° C. for 30 min, allowed to warm to 25° C. and continue stirring for another 30 min, and finally warmed to 40° C. for 30 min. The contents are then cooled to 0° C. and the contents of the first flask are added dropwise. The reaction is allowed to gradually come to 25° C. and continue stirring for 4 hrs. The reaction is poured into 100 mL of ice cold 1 N H$_3$PO$_4$ and allowed to stir for 30 min. The contents are extracted (3×100 mL) with ethyl acetate. The combined organic layers are then washed (3×100 mL) with saturated sodium bicarbonate followed by (3×100 mL) with brine. The organic layer is dried over MgSO$_4$, filtered and reduced to an oil by rotary evaporation to provide 5-benzyloxycarbonylamino-3-oxo-pentanoic acid ethyl ester. The product is used as is without further purification. $^1$H NMR (300 MHz, CDCl$_3$) δ 7.32 (s, 5H), 5.25 (bm, 1H), 5.06 (s, 2H), 4.17 (q, 2H), 3.42 (m, 5H), 2.78 (t, 2H), 1.25 (t, 3H); MS (ion spray) 294 (M+H)+.

B: 5-Benzyloxycarbonylamino-4-bromo-3-oxo-pentanoic acid ethyl ester

5-Benzyloxycarbonylamino-3-oxo-pentanoic acid ethyl ester (1.0 g, 3.4 mmol) is dissolved in glacial acetic acid (10 mL) and pyridinium bromide perbromide (1.1 g, 3.4 mmol) of is added. The reaction stirred 16 hrs and then poured into H$_2$O (100 mL) and extracted with ethyl acetate (2×100 mL). The organic layers are combined and washed with H$_2$O (2×100 mL) and with brine (2×100 mL). The organic layer is dried over MgSO4, filtered and reduced to an oil by rotary evaporation. The crude product is purified by flash chrom-atography on silica gel using 25% ethyl acetate/hexane as the eluent to provide 5-benzyloxycarbonylamino-4-bromo-3-oxo-pentanoic acid ethyl ester. $^1$H NMR (300 MHz, CDCl$_3$) δ 7.34 (s, 5H), 5.27 (m, 1H), 5.09 (s, 2H), 4.67 (t, 1H), 4.17 (q, 2H), 3.72 (m, 4H), 1.27 (t, 3H); MS (ion spray) 372 (M+H)+.

C: {5-(Benzyloxycarbonylamino-methyl)-2-[4-(6-chloro-benzo[b]thiophene-2-sulfonyl)-2-oxo-piperazin-1-ylmethyl]-thiazol-4-yl}-acetic acid ethyl ester A suspension of 2-[4-(6-chloro-benzo[b]thiophene-2-sulfonyl)-piperazin-1-yl]-thioacetamide (200 mg, 0.5 mmol) and 5-benzyloxycarbonylamino-4-bromo-3-oxo-pentanoic acid ethyl ester (370 mg, 1.0 mmol) is heated at 90° C. in a mixture of toluene/t-butanol, 1:1 (5 mL) for 16 h. The reaction is concentrated and purified using column chromatography (silica, 2%MeOH/CH$_2$Cl$_2$) to provide {5-(benzyloxycarbonylamino-methyl)-2-[4-(6-chloro-benzo[b]thiophene-2-sulfonyl)-2-oxo-piperazin-1-ylmethyl]-thiazol-4-yl}-acetic acid ethyl ester. $^1$H NMR (300 MHz, CDCl$_3$) δ 7.87-7.81 (m, 3H), 7.45 (dd, 1H), 7.32 (s, 5H), 7.45 (bt, 1H), 5.07 (s, 2H), 4.73 (s, 2H), 4.42 (d, 2H), 4.13 (q, 2H), 3.90 (s, 2H), 3.76 (s, 2H), 3.61-3.55 (m, 2H), 3.50-3.43 (m, 2H), 1.24 (t, 3H); MS (ion spray) 677 (M+H)+.

D: {5-Aminomethyl-2-[4-(6-chloro-benzo[b]thiophene-2-sulfonyl)-2-oxo-piperazin-1-ylmethyl]-thiazol-4-yl}-acetic acid ethyl ester {5-(Benzyloxycarbonylamino-methyl)-2-[4-(6-chloro-benzo[b]thiophene-2-sulfonyl)-2-oxo-piperazin-1-ylmethyl]-thiazol-4-yl}-acetic acid ethyl ester (40 mg, 0.06 mmol) is treated with 30% HBr/HOAc (1 mL) for 7 h. Ether (10 mL) is added and the resulting precipitate is washed twice with ether. The resulting salt is partitioned between EtOAc (15 mL) and NaHCO$_3$ solution (10 mL). The organic phase is washed with NaHCO3 and brine (2×10 mL), dried (MgSO$_4$) and concentrated to provide {5-aminomethyl-2-[4-(6-chloro-benzo[b]thiophene-2-sulfonyl)-2-oxo-piperazin-1-ylmethyl]-thiazol-4-yl}-acetic acid ethyl ester. $^1$H NMR (300 MHz, DMSO) δ 8.32 (d, 1H), 8.17 (s, 1H), 8.08-8.02 (m, 2H), 7.57 (dd, 1H), 4.62 (s, 2H), 4.02 (q, 2H), 3.81 (s, 2H), 3.74 (s, 2H), 3.64 (s, 2H), 3.48-3.35 (m, 4H), 2.48 (t, 3H); MS (ion spray) 543 (M+H)+.

E: 2-[4-(6-Chloro-benzo[b]thiophene-2-sulfonyl)-2-oxo-piperazin-1-ylmethyl]-4,7-dihydro-5H-thiazolo[5,4-c]pyridin-6-one {5-Aminomethyl-2-[4-(6-chloro-benzo[b]thiophene-2-sulfonyl)-2-oxo-piperazin-1-ylmethyl]-thiazol-4-yl}-acetic acid ethyl ester (12 mg, 0.02 mmol) is heated in EtOH (3 mL) for 3 days at 70° C. The precipitate which is formed is filtered to provide 2-[4-(6-chloro-benzo[b]thiophene-2-sulfonyl)-2-oxo-piperazin-1-ylmethyl]-4,7-dihydro-5H-thiazolo[5,4-c]pyridin-6-one. $^1$H NMR (300 MHz, DMSO) δ8.31 (d, 1H), 8.08-8.02 (m, 2H), 7.55 (dd, 1H), 4.67 (s, 2H), 4.36 (s (broad), 2H), 3.84 (s, 2H), 3.60-3.54 (m, 4H), 3.38 (t, 2H); MS (LC/MS-ESI) 496 (M+H)+.

EXAMPLE 1244

4-(6-Chloro-benzo[b]thiophene-2-sulfonyl)-1-piperidin-4-ylmethyl-piperazin-2-one A: 4-Hydroxymethyl-piperidine-1-carboxylic acid tert-butyl ester Isonipecotic acid (19.6 g, 76 mmol) is dissolved in THF (200 mL) and cooled to 0° C. and lithium aluminum hydride is added portionwise over 10 minutes. The reaction is allowed to stir at 25° C. for 16 h. The reaction is then cooled to 0° C. and water (6 mL) is added dropwise followed by 15% NaOH (6 mL). After 20 minutes, water (18 mL) is added and the reaction is stirred 30 min. The reaction is filtered, and the filtrate is concentrated and recrystallized from hexane to provide 4-hydroxymethyl-piperidine-1-carboxylic acid tert-butyl ester. mp 67-75° C.; $^1$H NMR (300 MHz, CDCl$_3$) δ 4.11 (bd, 2H), 3.50 (d, 2H), 2.70 (dd, 2H), 1.73-1.60 (m, 3H), 1.45 (s, 9H), 1.14 (ddd, 2H); MS (ion spray) 216 (M+H)+.

B: 4-Bromomethyl-piperidine-1-carboxylic acid tert-butyl ester

A solution of 4-hydroxymethyl-piperidine-1-carboxylic acid tert-butyl ester (2.30 g, 10.7 mmol) and carbon tetrabromide (4.43 g, 13.4 mmol) in CH$_2$Cl$_2$ (40 mL) is cooled to 0° C. Triphenylphosphine (4.21 g, 16.0 mmol) is added and the reaction is stirred at 25° C. for 1 h. The reaction is concentrated and ether is added to the residue. The mixture is filtered and washed with ether. The filtrate is concentrated and purified by column chromatography (silica, 20% EtOAc/hexane) to provide 4-bromomethyl-piperidine-1-carboxylic acid tert-butyl ester as a crystaline solid upon standing. Mp 48-50° C.; $^1$H NMR (300 MHz, CDCl$_3$) δ 4.13 (bm, 2H), 3.29 (d, 2H), 2.70 (dd, 2H), 1.85-1.73 (m, 3H), 1.46 (s, 9H), 1.28-1.13 (m, 2H); MS (EI) 277 (M)+.

C: 4-(1-tert-Butoxycarbonyl-piperidin-4-ylmethyl)-3-oxo-piperazine-1-carboxylic acid benzyl ester Sodium hydride (60%, 0.27 g, 6.7 mmol) is added to a solution of 4-benzyloxycarbonyl-2-oxo-piperazine (1.58 g, 6.7 mmol) in dry DMF (40 mL). After 30 minutes 4-bromomethyl-piperidine-1-carboxylic acid tert-butyl ester (1.87 g, 6.7 mmol) is added and the reaction is allowed to stir for 16 h. The solvent is removed in vacuo and the residue is dissolved in ether and washed with NH$_4$Cl. The aqueous phase is back-extracted with ether and the combined ether fractions are washed with water and brine to provide 4-(1-tert-butoxycarbonyl-piperidin-4-ylmethyl)-3-oxo-piperazine-1-carboxylic acid benzyl ester which is used without further purification. $^1$H NMR (300 MHz, CDCl$_3$) δ 7.36 (s, 5H), 5.16 (d, 2H), 4.16 (s, 2H), 4.13 (br, 2H), 3.73-3.69 (m, 2H), 3.44-3.30 (m, 6H), 2.68 (bt, 2H), 1.85-1.73 (m, 1H), 1.58 (bd, 2H), 1.46 (s, 9H), 1.25-1.10 (m, 2H); MS (ion spray) 432 (M+H)+.

D: 4-(2-Oxo-piperazin-1-ylmethyl)-piperidine-1-carboxylic acid tert-butyl ester

A solution of 4-(1-tert-butoxycarbonyl-piperidin-4-ylmethyl)-3-oxo-piperazine-1-carboxylic acid benzyl ester (2.3 g, 5.4 mmol) in methanol (75 mL) is purged with nitrogen and 10% Pd on carbon (0.3 g) is added, and the reaction is again purged with nitrogen. The reaction is placed on a Parr shaker under hydrogen for 16 h. After the system is purged of hydrogen, the catalyst is filtered and washed with methanol. The filtrate is concentrated to provide 4-(2-oxo-piperazin-1-ylmethyl)-piperidine-1-carboxylic acid tert-butyl ester which is used without further purification. MS (EI) 298 (M+H)+.

E: 4-[4-(6-Chloro-benzo[b]thiophene-2-sulfonyl)-2-oxo-piperazin-1-ylmethyl]-piperidine-1-carboxylic acid tert-butyl ester To a solution of 4-(2-oxo-piperazin-1-ylmethyl)-piperidine-1-carboxylic acid tert-butyl ester (1.44 g, 4.8 mmol) in CH$_2$Cl$_2$ (75 mL) and MeCN (10 mL) is added diisopropylethylamine (1.3 mL, 4.8 mmol) followed by 6-chloro-benzo[b]thiophene-2-sulfonyl chloride (1.29 g, 4.8 mmol), and the reaction is allowed to stir 16 h. The reaction is diluted with CH$_2$Cl$_2$ and washed with 1N HCl and NaHCO3, dried and concentrated. The residue is purified by column chromatography (silica, 40% EtOAc/CH$_2$Cl$_2$) to provide 4-[4-(6-chloro-benzo[b]thiophene-2-sulfonyl)-2-oxo-piperazin-1-ylmethyl]-piperidine-1-carboxylic acid tert-butyl ester. $^1$H NMR (300 MHz, CDCl$_3$) δ 7.88-7.83 (m, 3H), 7.47 (dd, 1H), 4.1 (br, 2H), 3.86 (s, 2H), 3.46 (bs, 4H), 3.25 (br, 2H), 2.61 (t, 2H), 1.87-1.75 (m, 1H), 1.51 (d, 2H), 1.41 (s, 9H), 1.10 (ddd, 2H); MS (Ion spray) 528 (M+H)+.

F: 4-(6-Chloro-benzo[b]thiophene-2-sulfonyl)-1-piperidin-4-ylmethyl-piperazin-2-one Trifluoroacetic acid (4 mL) is added to a solution of 4-[4-(6-chloro-benzo[b]thiophene-2-sulfonyl)-2-oxo-piperazin-1-ylmethyl]-piperidine-1-carboxylic acid tert-butyl ester (1.1 g, 2.0 mmol) in CH$_2$Cl$_2$ (15 mL). After 1 h the reaction is concentrated and the residue is dissolved in CH$_2$Cl$_2$ and washed with Na$_2$CO$_3$, dried (MgSO$_4$) and concentrated to provide 4-(6-chloro-benzo[b]thiophene-2-sulfonyl)-1-piperidin-4-ylmethyl-piperazin-2-one. $^1$H NMR (300 MHz, CDCl$_3$) δ 7.87-7.83 (m, 3H), 7.46 (dd, 1H), 3.86 (dd, 2H), 3.45 (s, 2H), 3.23 (d, 2H), 3.07 (d, 2H), 2.54 (dt, 2H), 2.39 (s, 1H), 1.83-1.75 (m, 1H), 1.56 (d, 2H), 1.24-1.11 (m, 2H); MS (Ion spray) 428 (M+H)+.

EXAMPLE 1245

4-[4-(6-Chloro-benzo[b]thiophene-2-sulfonyl)-2-oxo-piperazin-1-ylmethyl]-piperidine-1-carboxylic acid amide To a solution of 4-(6-chloro-benzo[b]thiophene-2-sulfonyl)-1-piperidin-4-ylmethyl-piperazin-2-one (20 mg, 0.047 mmol) in a mixture of 1,2-dichloroethane (1 mL) and THF (1 mL) is added trimethylsilyl isocyanate (0.006 mL, 0.05 mmol) and stirred 60 hours. The reaction is concentrated and purified by column chromatography (silica, 20% methanol/dichloromethane) to provide 4-[4-(6-chloro-benzo[b]thiophene-2-sulfonyl)-2-oxo-piperazin-1-ylmethyl]-piperidine-1-carboxylic acid amide. $^1$H NMR (300 MHz, CD$_3$OD) d 8.09 (s, 1H), 8.02 (d, 2H), 7.53 (dd, 1H), 3.90 (d, 4H), 3.49 (d, 4H), 3.30-3.24 (m, 2H), 2.65 (dt, 2H), 1.49 (d, 2H), 1.12-0.97 (m, 2H); MS (Ion spray) 471 (M+H).

EXAMPLE 1246

2-{4-[4-(6-Chloro-benzo[b]thiophene-2-sulfonyl)-2-oxo-piperazin-1-ylmethyl]-piperidin-1-yl}-acetamide To a solution of 4-(6-chloro-benzo[b]thiophene-2-sulfonyl)-1-piperidin-4-ylmethyl-piperazin-2-one (20 mg, 0.047 mmol) in N-methylpyrrolidinone (0.5 mL) is added 2-chloroacetamide (9 mg, 0.094 mmole) and diisopropylethylamine (0.016 mL, 0.094 mmole) and heated at 120° C. for 16 h. The reaction is concentrated and purified by column chromatography (silica, 5% methanol/dichloromethane) to provide 2-{4-[4-(6-chloro-benzo[b]thiophene-2-sulfonyl)-2-oxo-piperazin-1-ylmethyl]-piperidin-1-yl}-acetamide. $^1$H NMR (300 MHz, CDCl$_3$) d 7.88-7.83 (m, 3H), 7.47 (dd, 1H), 6.98 (bs, 1H), 5.30 (bs, 1H), 3.86 (s, 2H), 3.46 (s, 4H), 3.28 (d, 2H), 2.95 (s, 2H), 2.82 (d, 2H), 2.06 (t, 2H), 1.69-1.50 (m, 3H), 1.33-1.25 (m, 2H); MS (Ion spray) 485 (M+H)+.

EXAMPLE 1247

4-(6-Chloro-benzo[b]thiophene-2-sulfonyl)-1-[1-(2-chloro-pyrimidin-4-yl)-piperidin-4-ylmethyl]-piperazin-2-one To a solution of 4-(6-chloro-benzo[b]thiophene-2-sulfonyl)-1-piperidin-4-ylmethyl-piperazin-2-one (40 mg, 0.094 mmole) in n-butanol (1.0 mL) is added 2,4-dichloropyrimidine (14, 0.094 mmole) and diisopropylethylamine (0.016 mL, 0.094 mmole) and this mixture is heated at 110° C. for 4 hours. The reaction is concentrated and purified by column chromatography (silica, 25% ethyl acetate/dichloromethane) to yield 4-(6-chloro-benzo[b]thiophene-2-sulfonyl)-1-[1-(2-chloro-pyrimidin-4-yl)-piperidin-4-ylmethyl]-piperazin-2-one. $^1$H NMR (300 MHz, CDCl$_3$) d 8.01 (d, 1H), 7.89-7.87 (m, 3H), 7.48 (dd, 1H), 6.35 (d, 1H), 4.41-4.20 (m, 2H), 3.87 (s, 2H), 3.48 (s, 4H), 3.28 (dd, 2H), 2.05-1.95 (m, 1H), 1.67 (d, 2H), 1.31-1.20 (m, 2H); MS (Ion spray) 542 (M+H)+.

EXAMPLE 1248

4-(6-Chloro-benzo[b]thiophene-2-sulfonyl)-1-[1-(2-dimethylamino-pyrimidin-4-yl)-piperidin-4-ylmethyl]-piperazin-2-one To a solution of 4-(6-chloro-benzo[b]thiophene-2-sulfonyl)-1-[1-(2-chloro-pyrimidin-4-yl)-piperidin-4-ylmethyl]-piperazin-2-one (17 mg, 0.031 mmole) in ethanol (1 mL) is added a 40% solution of dimethylamine (11 mg, 0.094 mmole). This mixture is heated at 80° C. in a sealed tube 16 h. The reaction is concentrated and lyophilized to provide 4-(6-chloro-benzo[b]thiophene-2-sulfonyl)-1-[1-(2-dimethylamino-pyrimidin-4-yl)-piperidin-4-ylmethyl]-piperazin-2-one. $^1$H NMR (300 MHz, CDCl$_3$) d 7.93-7.84 (m, 4H), 7.48 (dd, 1H), 5.84 (d, 1H), 4.32 (d, 2H), 3.87 (s, 2H), 3.47 (s, 4H), 3.26 (d, 2H), 3.14 (s, 6H), 1.99-1.90 (m, 1H), 1.62 (d, 2H), 1.27-1.17 (m, 2H); MS (Ion spray) 549 (M+H)$^+$.

Using the procedures the following compounds can be prepared;

| EXAMPLE # | Name |
|---|---|
| 1249 | (R)-4-(5-chloro-1H-indole-2-sulfonyl)-1-[1-(2-dimethylamino-pyrimidin-4-yl)-piperidin-4-ylmethyl]-6-piperazin-2-one |
| 1250 | (R)-4-(6-chloro-1H-indole-2-sulfonyl)-1-[1-(2-dimethylamino-pyrimidin-4-yl)-piperidin-4-ylmethyl]-6-piperazin-2-one |
| 1251 | (R)-4-(6-chloro-1H-benzoimidazole-2-sulfonyl)-1-[1-(2-dimethylamino-pyrimidin-4-yl)-piperidin-4-ylmethyl]-6-piperazin-2-one |
| 1252 | (R)-4-(6-Chloro-benzo[b]thiophene-2-sulfonyl)-1-[1-(2-dimethylamino-pyrimidin-4-yl)-piperidin-4-ylmethyl]-6-methyl-piperazin-2-one |
| 1253 | (R)-4-(6-Chloro-benzo[b]thiophene-2-sulfonyl)-1-[1-(2-dimethylamino-pyrimidin-4-yl)-piperidin-4-ylmethyl]-6-methoxymethyl-piperazin-2-one |
| 1254 | 4-(6-Chloro-benzo[b]thiophene-2-sulfonyl)-1-[1-(2-dimethylamino-pyrimidin-4-yl)-piperidin-4-ylmethyl]-6-oxo-piperazine-2-carboxylic acid methyl ester |
| 1255 | (R)-4-(5-chloro-1H-indole-2-sulfonyl)-1-[1-(2-dimethylamino-pyrimidin-4-yl)-piperidin-4-ylmethyl]-6-methyl-piperazin-2-one |
| 1256 | (R)-4-(5-chloro-1H-indole-2-sulfonyl)-1-[1-(2-dimethylamino-pyrimidin-4-yl)-piperidin-4-ylmethyl]-6-methoxymethyl-piperazin-2-one |
| 1257 | 4-(5-chloro-1H-indole-2-sulfonyl)-1-[1-(2-dimethylamino-pyrimidin-4-yl)-piperidin-4-ylmethyl]-6-oxo-piperazine-2-carboxylic acid methyl ester |
| 1258 | (R)-4-(6-chloro-1H-indole-2-sulfonyl)-1-[1-(2-dimethylamino-pyrimidin-4-yl)-piperidin-4-ylmethyl]-6-methyl-piperazin-2-one |
| 1259 | (R)-4-(6-chloro-1H-indole-2-sulfonyl)-1-[1-(2-dimethylamino-pyrimidin-4-yl)-piperidin-4-ylmethyl]-6-methoxymethyl-piperazin-2-one |
| 1260 | 4-(6-chloro-1H-indole-2-sulfonyl)-1-[1-(2-dimethylamino-pyrimidin-4-yl)-piperidin-4-ylmethyl]-6-oxo-piperazine-2-carboxylic acid methyl ester |
| 1261 | (R)-4-(6-chloro-1H-benzoimidazole-2-sulfonyl)-1-[1-(2-dimethylamino-pyrimidin-4-yl)-piperidin-4-ylmethyl]-6-methyl-piperazin-2-one |
| 1262 | (R)-4-(6-chloro-1H-benzoimidazole-2-sulfonyl)-1-[1-(2-dimethylamino-pyrimidin-4-yl)-piperidin-4-ylmethyl]-6-methoxymethyl-piperazin-2-one |
| 1263 | 4-(6-chloro-1H-benzoimidazole-2-sulfonyl)-1-[1-(2-dimethylamino-pyrimidin-4-yl)-piperidin-4-ylmethyl]-6-oxo-piperazine-2-carboxylic acid methyl ester |

EXAMPLE 1264

4-(6-Chloro-benzo[b]thiophene-2-sulfonyl)-1-{1-[2-(2-hydroxy-ethylamino)-pyrimidin-4-yl]-piperidin-4-ylmethyl}-piperazin-2-one To a solution of 4-(6-chloro-benzo[b]thiophene-2-sulfonyl)-1-[1-(2-chloro-pyrimidin-4-yl)-piperidin-4-ylmethyl]-piperazin-2-one (0.40 g, 0.74 mmol) in EtOH is added ethanolamine (0.089 mL, 1.5 mmol). The solution is heated to reflux for 18 h and evaporated to dryness. The residue is chromatographed eluting successively with 1%, 2% and 4% MeOH in CH$_2$Cl$_2$. Fractions containing only product are combined and the solvent evaporated. Trituration with ether afforded the title compound as a yellow solid: MS (ESI): m/z 565 (M$^+$+H).

By substituting ethanolamine with the corresponding amine, the following products can similarly be prepared:

EXAMPLE 1265

4-(6-Chloro-benzo[b]thiophene-2-sulfonyl)-1-{1-[2-(4-dimethylamino-butylamino)-pyrimidin-4-yl]-piperidin-4-ylmethyl}-piperazin-2-one

EXAMPLE 1266

4-(6-Chloro-benzo[b]thiophene-2-sulfonyl)-1-{1-[2-(3-imidazol-1-yl-propylamino)-pyrimidin-4-yl]-piperidin-4-ylmethyl}-piperazin-2-one

EXAMPLE 1267

4-(6-Chloro-benzo[b]thiophene-2-sulfonyl)-1-{1-[2-(3-morpholin-4-yl-propylamino)-pyrimidin-4-yl]-piperidin-4-ylmethyl}-piperazin-2-one

EXAMPLE 1268

4-[(4-{4-[4-(6-Chloro-benzo[b]thiophene-2-sulfonyl)-2-oxo-piperazin-1-ylmethyl]-piperidin-1-yl}-pyrimidin-2-yl)-methyl-amino]-butyric acid

EXAMPLE 1269

4-(6-Chloro-benzo[b]thiophene-2-sulfonyl)-1-{1-[2-(2-dimethylamino-ethoxy)-pyrimidin-4-yl]-piperidin-4-ylmethyl}-piperazin-2-one

EXAMPLE 1270

4-(6-Chloro-benzo[b]thiophene-2-sulfonyl)-1-(1-{2-[2-(2-oxo-imidazolidin-1-yl)-ethylamino]-pyrimidin-4-yl}-piperidin-4-ylmethyl)-piperazin-2-one

EXAMPLE 1271

4-(6-Chloro-benzo[b]thiophene-2-sulfonyl)-1-{1-[2-(2-dimethylamino-ethylsulfanyl)-pyrimidin-4-yl]-piperidin-4-ylmethyl}-piperazin-2-one

EXAMPLE 1272

4-[4-(6-Chloro-benzo[b]thiophene-2-sulfonyl)-2-oxo-piperazin-1-ylmethyl]-3,4,5,6-tetrahydro-2H-[1,2']bipyridinyl-5'-carboxylic acid To a solution of 4-(6-chloro-benzo[b]thiophene-2-sulfonyl)-1-piperidin-4-ylmethyl-piperazin-2-one (20 mg, 0.047 mmol) in n-butanol (0.5 mL) is added 6-chloronicotinamide (15 mg, 0.094 mmole) and diisopropylethylamine (0.016 mL, 0.094 mmole) and heated at 110° C. 16 h. The reaction is concentrated and purified by column chromatography (silica, 20% methanol/dichloromethane) to provide 4-[4-(6-chloro-benzo[b]thiophene-2-sulfonyl)-2-oxo-piperazin-1-ylmethyl]-3,4,5,6-tetrahydro-2H-[1,2']bipyridinyl-5'-carboxylic acid. $^1$H NMR (300 MHz, CD$_3$OD) δ 8.59 (d, 1H), 8.11-7.92 (m, 3H), 7.54 (dd, 1H), 6.72 (d, 1H), 4.27 (d, 1H), 3.92 (s, 2H), 3.57-3.47 (m, 4H), 3.25 (d, 2H), 2.79-2.71 (dt, 2H), 1.96-1.80 (m, 1H), 1.50 (d, 2H), 1.29-1.06 (m, 2H); MS (Ion spray) 549 (M+H)$^+$.

Using the corresponding halide the following compounds can be similarly prepared:

EXAMPLE 1273

4-(6-Chloro-benzo[b]thiophene-2-sulfonyl)-1-(1-pyrimidin-2-yl-piperidin-4-ylmethyl)-piperazin-2-one $^1$H NMR (300 MHz, CDCl$_3$) δ 8.27 (d, 2H), 7.88-7.83 (m, 3H), 7.48 (d, 1H), 6.44 (t, 1H), 4.71 (d, 2H), 3.87 (s, 2H), 3.47 (s, 4H), 3.26 (d, 2H), 2.76 (dt, 2H), 2.00-1.91 (m, 1H), 1.62 (d, 2H), 1.26-1.21 (m, 2H); MS (Ion spray) 506 (M+H)$^+$.

EXAMPLE 1274

4-(6-Chloro-benzo[b]thiophene-2-sulfonyl)-1-(1-pyrazin-2-yl-piperidin-4-ylmethyl)-piperazin-2-one $^1$H NMR (300 MHz, CDCl$_3$) δ 8.07 (d, 2H), 7.89-7.84 (m, 4H), 7.48 (dd, 1H), 4.27 (d, 2H), 3.88 (s, 2H), 3.48 (s, 2H), 3.28 (d, 2H), 2.80 (t, 2H), 2.01-1.90 (m, 1H), 1.65 (d, 2H), 1.32 (m, 2H); MS (Ion spray) 506 (M+H)$^+$.

EXAMPLE 1275

4-(6-Chloro-benzo[b]thiophene-2-sulfonyl)-1-(3,4,5,6-tetrahydro-2H-[1,2']bipyridinyl-4-ylmethyl)-piperazin-2-one $^1$H NMR (300 MHz, CDCl$_3$) δ 8.15 (t, 1H), 7.89-7.84 (m, 3H), 7.49-7.41 (m, 2H), 6.63-6.56 (m, 2H), 4.23 (d, 2H), 3.88 (s, 2H), 3.48 (s, 4H), 3.27 (d, 2H), 2.73 (dt, 2H), 1.93-1.86 (m, 1H), 1.60 (t, 2H), 1.32-1.19 (m, 2H); MS (Ion spray) 505 (M+H)$^+$.

EXAMPLE 1276

4-[4-(6-Chloro-benzo[b]thiophene-2-sulfonyl)-2-oxo-piperazin-1-ylmethyl]-3,4,5,6-tetrahydro-2H-[1,2']bipyridinyl-3'-carboxylic acid $^1$H NMR (300 MHz, CDCl$_3$) δ 8.54 (s, 1H), 8.39-8.29 (m, 2H), 7.99-7.84 (m, 3H), 7.49-7.45 (m, 1H), 7.08 (q, 1H), 5.65 (s, 1H), 3.87 (d, 2H), 3.48 (d, 6H), 2.81 (t, 1H), 2.57 (dt, 1H), 1.85-1.76 (m, 1H), 1.73-1.69 (m, 2H), 1.43-1.37 (m, 2H); MS (Ion spray) 548 (M+H)$^+$.

EXAMPLE 1277

4-(6-Chloro-benzo[b]thiophene-2-sulfonyl)-1-(6'-methoxy-3,4,5,6-tetrahydro-2H-[1,2']bipyridinyl-4-ylmethyl)-piperazin-2-one $^1$H NMR (300 MHz, CDCl$_3$) δ 7.88-7.84 (m, 3H), 7.47 (dd, 1H), 7.37 (t, 1H), 6.12 (dd, 1H), 6.03 (dd, 1H), 4.24 (d, 2H), 3.88 (s, 2H), 3.84 (s, 3H), 3.48 (s, 4H), 3.27 (d, 2H), 2.71 (dt, 2H), 1.95-2.84 (m, 1H), 1.61 (d, 2H), 1.32-1.22 (m, 2H); MS (Ion spray) 535 (M+H)$^+$.

Preparation of the Intermediate

4-Bromomethyl-6'-methoxy-3,4,5,6-tetrahydro-2H-[1,3']bipyridinyl

A: 6'-Methoxy-3,4,5,6-tetrahydro-2H-[1,3']bipyridinyl-4-carboxylic acid ethyl ester In a round-bottom flask, 20 ml of anhydrous toluene is added and degassed several times from vacuum/N$_2$. 2-methoxy-5-bromopyridine (752 mg, 4.0 mmol), ethyl isonipecotate (740 mg, 4.8 mmol), sodium t-butoxide (537 mg, 5.6 mmol), Pd$_2$(DBA)$_3$ (73 mg, 2 mol %) and of BINAP (100 mg, 0.16 mmol) are added and heated to 70° C. under N$_2$ for 16 hrs. The reaction is cooled to r.t. and taken up in 100 ml of ethyl ether and washed with brine (2×50 ml). The ether is dried over MgSO$_4$, filtered and reduced to an oil under vacuum. The compound is purified by flash chromatography on silica gel using 20% ethyl acetate/hexane as the eluent to provide 6'-methoxy-3,4,5,6-tetrahydro-2H-[1,3']bipyridinyl-4-carboxylic acid ethyl ester. $^1$H NMR (300 MHz, CDCl$_3$) δ 7.78 (d, 1H), 7.28 (dd, 1H), 6.66 (d, 1H), 4.15 (q, 2H), 3.87 (s, 3H), 3.42 (dt, 2H), 2.71 (dt, 2H), 2.39 (m, 1H), 2.03 (m, 2H), 1.90 (m, 2H), 1.26 (t, 3H); MS (EI) 264 (M)$^+$.

B: (6'-Methoxy-3,4,5,6-tetrahydro-2H-[1,3']bipyridinyl-4-yl)-methanol

A round bottom flask is charged with anhydrous THF (8 mL) and LAH (122 mg, 3.17 mmol) is added. The contents are placed under N$_2$ and cooled to 0° C. To this is added a solution of 6'-methoxy-3,4,5,6-tetrahydro-2H-[1,3']bipyridinyl-4-carboxylic acid ethyl ester (400 mg, 1.51 mmol) in THF (2 ml) over 5 min. The reaction is allowed to come to r.t. and continue to stir for an additional hour. 4 drops of H$_2$O are added, followed by 4 drops of 15% NaOH$_{(aq)}$ and allowed to stir at r.t. for 20 min. 0.5 mL of H$_2$O are added, and the contents are filtered through a pad of celite and washed with THF. The solution is reduced to an oil under vacuum, and purified by flash chromatography on silica gel using 3% methanol/methylene chloride as the eluent to provide (6'-methoxy-3,4,5,6-tetrahydro-2H-[1,3']bipyridinyl-4-yl)-methanol. $^1$H NMR (300 MHz, CDCl$_3$) δ 7.95 (d, 1H), 7.29 (dd, 1H), 6.66 (d, 1H), 3.88 (s, 3H), 3.53 (m, 4H), 2.65 (dt, 2H), 1.85 (m, 2H), 1.65 (m, 1H), 1.42 (m, 2H); MS (EI) 222 (M)$^+$.

C: 4-Bromomethyl-6'-methoxy-3,4,5,6-tetrahydro-2H-[1,3']bipyridinyl (6'-methoxy-3,4,5,6-tetrahydro-2H-[1,3']bipyridinyl-4-yl)-methanol (300 mg, 1.35 mmol) is dissolved in methylene chloride (10 mL). carbon tetrabromide (561 mg, 1.69 mmol) is added and dissolved. The solution is cooled to 0° C. and triphenylphoshine (529 mg, 2.02 mmol) is added portionwise. The reaction is allowed to come to r.t. and is stirred for 30 min. The volume is then reduced under vacuum to ~2 ml and purified by flash chromatography on silica gel using 2% methanol/methylene chloride as the eluent to provide 4-bromomethyl-6'-methoxy-3,4,5,6-tetrahydro-2H-[1,3']bipyridinyl. $^1$H NMR (300 MHz, CD$_3$OD) δ 7.74 (d, 1H), 7.43 (dd, 1H), 6.72 (d, 1H), 3.83 (s, 3H), 3.54 (m, 2H), 3.38 (d, 2H), 2.65 (dt, 2H), 1.94 (m, 2H), 1.75 (m, 1H), 1.44 (m, 2H); MS (EI) 284 (M)$^+$.

The above alkylating reagent, 4-bromomethyl-6'-methoxy-3,4,5,6-tetrahydro-2H-[1,3']bipyridinyl, can be used to provide:

EXAMPLE 1278

4-(6-Chloro-benzo[b]thiophene-sulfonyl)-1-(6'-methoxy-3,4,5,6-tetrahydro-2H-[1,3']bipyridinyl-4-ylmethyl)-piperazin-2-one $^1$H NMR (300 MHz, CDCl$_3$) δ 7.87-7.81 (m, 3H), 7.50-7.43 (m, 2H), 6.88 (dd, 1H), (d, 1H), 3.85 (s, 5H), 3.48-3.15 (m, 7H), 3.29-3.17 (m, 2H), 2.89-2.81 (m, 1H), 2.25-2.12 (m, 1H), 1.65-1.56 (m, 4H); MS (ion spray) 535 (M+H)$^+$.

EXAMPLE 1279

O-Phenyl-1-cyano-3-{4-[(chlorobenzo[b]thiophene-2-sulfonyl)-2-(keto)piperazin-1-yl]methylpiperdinyl} isourea To a suspension of 4-(6-Chloro-benzo[b]thiophene-2-sulfonyl)-1-piperidin-4-ylmethyl-piperazin-2-one (0.90 g, 2.1 mmol) in 2-propanol (20 mL) is added diphenyl cyanocarbonimidate (0.50 g, 2.1 mmol). After stirring for 18 h, TLC (4% MeOH in CH$_2$Cl$_2$) indicated a mixture of starting material and primarily one faster migrating product. Additional diphenyl cyanocarbonimidate (0.50 g) is added and the reaction mixture is heated to 80° C. for 2 h. Upon cooling to rt the precipitate which formed is collected, washed with 2-propanol and air-dried to afford the title compound as an off-white solid; yield 0.48 g. A sample is further purified by chromatography eluting successively with 1%, 2% and 4% MeOH in CH$_2$Cl$_2$ to afford a chromatographically pure white solid: MS (ESI): m/z 572 (M$^+$+H).

EXAMPLE 1280

Preparation of N,N Dimethyl-2-{4-[6-(chlorobenzo[b]thiophene-2-sulfonyl)-2-(keto)piperazin-1-yl]methylpiperdin-1-yl]} cyanoformamidine To a solution of O-phenyl-1-cyano-3-{4-[(chlorobenzo[b]thiophene-2-sulfonyl)-2-(keto)piperazin-1-yl]methylpiperdinyl} isourea (0.10 g, 0.18 mmol) in MeOH (10 mL) is added 40% aqueous dimethylamine (10 mL) and the reaction is stirred at rt for 72 h. The solvents are evaporated and the residue is chromatographed eluting successively with 1% and 2% MeOH in CH$_2$Cl$_2$. Fractions containing only product are concentrated and the residue is triturated with ether to afford the title compound as a white solid; yield 17 mg: MS (ESI): m/z 523 (M$^+$+H).

EXAMPLE 1281

Preparation of N-Methyl-2-{4-[6-(chlorobenzo[b]thiophene-2-sulfonyl)-2-(keto)piperazin-1-yl]methylpiperdin-1-yl]} cyanoformamidine The title compound is prepared as a white solid using the procedure of Example 3 except substituting methylamine for dimethylamine: MS (ESI): m/z 509 (M$^+$+H).

Other, 4-(methylpiperin-1-yl) cyanoformamidine compounds can be prepared from intermediates having the structure of formula including but not limited to:

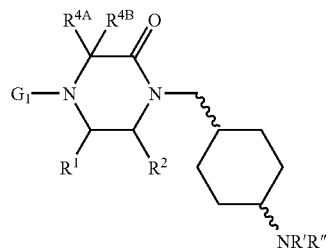

wherein G-1 includes but is not limited to

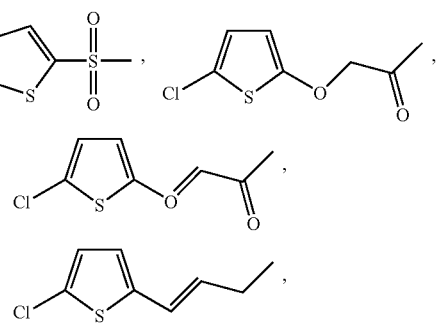

and

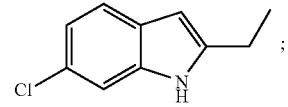

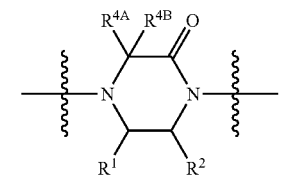

includes but is not limited to

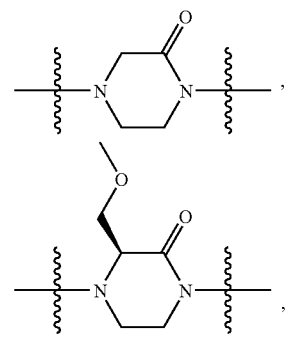

-continued

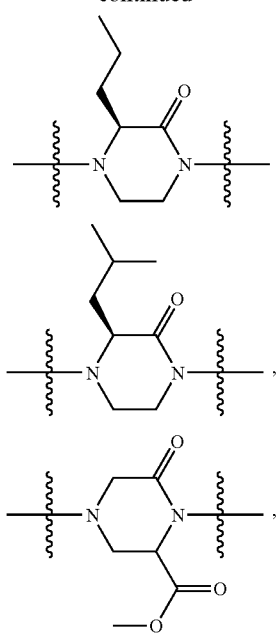

and

NRR' includes but is not limited to

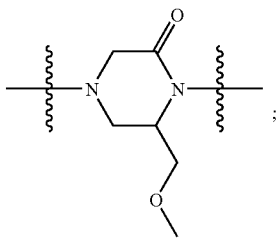

-continued and

Example 1282

Preparation of N-trans-[{4-(5-Chloro-thiophen-2-yloxy)-acetyl-2-keto-3-(S)-methoxymethyl}-piperazin-1-yl]methylcyclohexyl-cyanoguanidine a. Dimethoxymethyl-(2,3-dioxa-spiro[4.5]dec-8-ylmethyl)-amine 8-Carboxaldehyde-1,4-dioxa-spiro[4.5]decane (4.4 g, 26 mmol), prepared according to the method of Pearson et al. (*J. Org. Chem.* 62, 1997, 5284), aminoacetaldehyde dimethyl acetal (3.3 g, 0.31 mmol), acetic acid (1.6 g, 0.26 mmol) and sodium cyanoborohydride (2.0 g, 0.31 mmol) are stirred in methanol (140 mL) for 6 h. The methanol is evaporated and the residue is partitioned between ethyl acetate (200 mL) and 1 N NaOH (100 mL). The organic phase is dried ($Na_2SO_4$) and is evaporated to provide the intermediate title compound as a yellow oil (7.2 g) which is used without further purification. MS (EI), 259 [M]$^+$.

b. {1-[2,2-Dimethoxy-ethyl)-(2,3-dioxa-spiro[4.5]dec-8-yl-methyl)-carbamoyl]-2-(S)-methoxyethyl}-carbamic acid benzyl ester Dimethoxymethyl-(2,3-dioxa-spiro[4.5]dec-8-ylmethyl)-amine (6.6 g, 26 mmol), (S)-(2-benzyloxycarbonylamino-3-methoxy)-propionic acid (7.2 g, 28 mmol), [O-(7-azabenzo-triazol-1-yl)-1,1,3,3-tetramethyluronium hexafluorophosphate (12 g, 31 mmol) and N,N-diisopropylethylamine (7.7 g, 60 mmol) are stirred in DMF (200 mL) for 18 h. The DMF is evaporated and the residue diluted with ethyl acetate (200 mL). The organic phase is washed with water (50 mL), 2 N HCl (50 mL), 1 N NaOH (50 mL), is dried (MgSO$_4$) and is evaporated to provide the intermediate title compound as a yellow oil (13 g) which is used without further purification. MS (ES), 495 [M+H]$^+$.

c. 4-(1,4-Dioxa-spiro[4.5]dec-8-ylmethyl)-2-(S)-methoxymethyl-3-oxo-3,4-dihydro-2H-pyrazine-1-carboxylic acid benzyl ester {1-[2,2-Dimethoxy-ethyl)-(2,3-dioxa-spiro[4.5]dec-8-ylmethyl)-carbamoyl]-2-(S)-methoxyethyl}-carbamic acid benzyl ester (12.8 g, 26 mmole) and p-toluenesulphonic acid monohydrate (0.74 g, 3.9 mmol) are placed in toluene (150 mL) and stirred at 60-70° C. for 7 h. The mixture is evaporated and the residue is purified by flash chromatography (silica gel, 2:1 hexanes/ethyl acetate) to provide the intermediate title compound as a clear colorless oil (5.0 g, 45%). MS (ES), 431 [M+H]$^+$.

d. 1-(1,4-Dioxa-spiro[4.5]dec-8-ylmethyl)-2-(S)-methoxymethyl-piperazin-2-one 4-(1,4-Dioxa-spiro[4.5]dec-8-ylmethyl)-2-(S)-methoxymethyl-3-oxo-3,4-dihydro-2H-pyrazine-1-carboxylic acid benzyl ester (4.7 g, 11 mmol) and 10% Pd on carbon (1.0 g) are stirred in methanol (150 mL) under a hydrogen atmosphere for 18 h. The mixture is filtered through Celite@ and is evaporated to provide the intermediate title compound as a clear colorless oil (3.3 g, 11 mmol). MS (EI), 298 [M]$^+$.

e. 4-[(5-Chloro-thiophen-2-yloxy)-acetyl]-1-(1,4-dioxaspiro[4.5]dec-8-ylmethyl)-3-(S)-methoxymethyl-piperazin-2-one 1-(1,4-Dioxa-spiro[4.5]dec-8-ylmethyl)-2-(S)-methoxymethyl-piperazin-2-one (3.3 g, 11 mmol), (5-chlorothiophen-2-yloxy)-acetic acid (2.1 g, 11 mmol), 2-(1H-benzotriazol-1-yl)-1,1,3,3-tetramethyluronium tetrafluoroborate (3.9 g, 12 mmol) and triethylamine (3.3 g, 33 mmol) are stirred in DMF (100 mL) for 8 h. The mixture is evaporated and is diluted with ethyl acetate (200 mL). The organic phase is washed with water, 2 N HCl, 1 N NaOH and brine, is dried (MgSO$_4$) and is evaporated. The residue is purified by flash chromatography (silica gel, 4:1 ethyl acetate/hexanes) to provide the intermediate title compound as a clear colorless oil (2.8 g, 54%). MS (ES), 473 [M+H]$^+$.

f. 4-[(5-Chlorothiophen-2-yloxy)-acetyl]-3-(S)-methoxymethyl-1-(4-oxocyclohexylmethyl)-piperazin-2-one 4-[(5-Chloro-thiophen-2-yloxy)-acetyl]-1-(1,4-dioxaspiro[4.5]dec-8-ylmethyl)-3-(S)-methoxymethyl-piperazin-2-one (2.8 g, 5.9 mmol) is placed in 80:20 acetic acid/water and heated at 65° C. for 0.2 h. The mixture is evaporated and is diluted with ethyl acetate (200 mL). The organic phase is washed with 1 N NaOH, is dried (MgSO$_4$) and is evaporated to provide the intermediate title compound as a clear colorless oil (2.4 g, 95%). MS (ES), 429 [M+H]$^+$.

g. 1-cis-[4-(Amino)-cyclohexylmethyl]-4-[(5-chlorothiophen-2-yloxy)-acetyl]-3-(S)-methoxymethyl-piperazin-2-one and 1-trans-[4-(amino)-cyclohexylmethyl]-4-[(5-chloro-thiophen-2-yloxy)-acetyl]-3-(S)-methoxymethyl-piperazin-2-one Sodium cyanoborohydride (0.075 g, 1.2 mmol) is added to a mixture of 4-[(5-Chlorothiophen-2-yloxy)-acetyl]-3-(S)-methoxymethyl-1-(4-oxocyclohexylmethyl)-piperazin-2-one (0.5 g, 1.2 mmol) and ammonium acetate (0.9 g, 12 mmol) in anhydrous methanol (20 mL). The mixture is stirred 18 h and is concentrated in vacuo. The residue is diluted with EtOAc (20 mL) and is washed with 1N NaOH. The organic phase is dried (Na$_2$SO$_4$) and is evaporated to provide the intermediate title compound as a mixture of cis and trans isomers (0.49 g, 98%) which is used without further purification. MS (ES), 430 [M+H]$^+$.

h. N-trans-({[4-(5-Chloro-thiophen-2-yloxy)-acetyl]-3-(S)-methoxymethyl-2-oxo-piperazin-1-ylmethyl}-cyclohexyl)-N'-cyano-O-phenylisourea N-(cis/trans)-({[4-(5-Chloro-thiophen-2-yloxy)-acetyl]-3-(S)-methoxymethyl-2-oxo-piperazin-1-ylmethyl}-cyclohexyl)-N'-cyano-O-phenylisourea (0.49 g, 1.14 mmol) and diphenyl cyano-carbonimidate (0.28 g, 1.17 mmol) are stirred in i-propyl alcohol (5 mL) for 18 h. The mixture is concentrated in vacuo and is diluted with EtOAc (20 mL). The organic phase is washed with 2 N HCl, 1 N NaOH and brine, is dried (MgSO$_4$) and is evaporated. The residue is purified by flash chromatography (silica gel, EtOAc) to provide the intermediate title compound as a white solid (0.33 g, 50%). MS (ES), 574 [M+H]$^+$.

The cis isomer is also isolated (0.1 g, 15%). MS (ES), 574 [M+H]$^+$.

i. N-trans-[{4-(5-Chloro-thiophen-2-yloxy)-acetyl-2-keto-3-(S)-methoxymethyl}-piperazin-1-yl]methylcyclohexyl-cyanoguanidine N-trans-({[4-(5-Chloro-thiophen-2-yloxy)-acetyl]-3-(S)-methoxymethyl-2-oxo-piperazin-1-ylmethyl}-cyclohexyl)-N'-cyano-O-phenylisourea (0.025 g, 0.04 mmol) is stirred in a 7 N solution of ammonia in methanol (2 mL) for 18 h. The mixture is diluted with EtOAc (20 mL) and is washed with 1 N NaOH and brine. The organic phase is dried (MgSO$_4$) and is evaporated to provide the title compound as a colorless resin (0.014 g, 70%). MS (ES), 497 [M+H]$^+$.

The Following Compounds are also prepared in a similar manner to that described in Example 1282:

EXAMPLE 1283

N-trans-[{4-(5-Chloro-thiophen-2-yloxy)-acetyl-2-keto-3-(S)-methoxymethyl}-piperazin-1-yl]methyl-cyclohexyl-N',N'-dimethyl-cyanoguanidine: MS (ES), 510 [M+H]$^+$.

EXAMPLE 1284

N-trans-[{4-(5-Chloro-thiophen-2-yloxy)-acetyl-2-keto-3-(S)-methoxymethyl}-piperazin-1-yl]methyl-cyclohexyl-N'-methyl-cyanoguanidine: MS (ES), 524 [M+H]$^+$.

EXAMPLE 1285

N-trans-[{4-(5-Chloro-thiophen-2-yloxy)-acetyl-2-keto-3-(S)-methoxymethyl}-piperazin-1-yl]methyl-cyclohexyl-N'-(2-hydroxyethyl)-N'-methyl-cyanoguanidine: MS (ES), 554 [M+H]$^+$.

EXAMPLE 1286

Preparation of 4-[(5-Chlorothiophen-2-yloxy)-acetyl]-3-(S)-methoxymethyl-1-cis-(4-morpholin-4-yl-cyclohexylmethyl)-piperazin-2-one and 4-[(5-Chlorothiophen-2-yloxy)-acetyl]-3-(S)-methoxymethyl-1-trans-(4-morpholin-4-yl-cyclohexylmethyl)-piperazin-2-one A. Dimethoxymethyl-(2,3-dioxa-spiro[4.5]dec-8-ylmethyl)-amine 8-Carboxaldehyde-1,4-dioxa-spiro[4.5]decane (4.4 g, 26 mmol), prepared according to the method of Pearson et al. (J.

*Org. Chem.* 62, 1997, 5284), aminoacetaldehyde dimethyl acetal (3.3 g, 0.31 mmol), acetic acid (1.6 g, 0.26 mmol) and sodium cyanoborohydride (2.0 g, 0.31 mmol) are stirred in methanol (140 mL) for 6 h. The methanol is evaporated and the residue is partitioned between ethyl acetate (200 mL) and 1 N NaOH (100 mL). The organic phase is dried ($Na_2SO_4$) and is evaporated to provide the intermediate title compound as a yellow oil (7.2 g) which is used without further purification. MS (EI), 259 [M]$^+$.

B. {1-[2,2-Dimethoxy-ethyl)-(2,3-dioxa-spiro[4.5]dec-8-yl-methyl)-carbamoyl]-2-(S)-methoxyethyl}-carbamic acid benzyl ester Dimethoxymethyl-(2,3-dioxa-spiro[4.5]dec-8-ylmethyl)-amine (6.6 g, 26 mmol), (S)-(2-benzyloxycarbonylamino-3-methoxy)-propionic acid (7.2 g, 28 mmol), [O-(7-azabenzotriazol-1-yl)-1,1,3,3-tetramethyluronium hexafluorophosphate (12 g, 31 mmol) and N,N-diisopropylethylamine (7.7 g, 60 mmol) are stirred in DMF (200 mL) for 18 h. The DMF is evaporated and the residue diluted with ethyl acetate (200 mL). The organic phase is washed with water (50 mL), 2 N HCl (50 mL), 1 N NaOH (50 mL), is dried ($MgSO_4$) and is evaporated to provide the intermediate title compound as a yellow oil (13 g) which is used without further purification. MS (ES), 495 [M+H]$^+$.

C. 4-(1,4-Dioxa-spiro[4.5]dec-8-ylmethyl)-2-(S)-methoxymethyl-3-oxo-3,4-dihydro-2H-pyrazine-1-carboxylic acid benzyl ester {1-[2,2-Dimethoxy-ethyl)-(2,3-dioxa-spiro[4.5]dec-8-yl-methyl)-carbamoyl]-2-(S)-methoxyethyl}-carbamic acid benzyl ester (12.8 g, 26 mmole) and p-toluenesulphonic acid monohydrate (0.74 g, 3.9 mmol) are placed in toluene (150 mL) and stirred at 60-70° C. for 7 h. The mixture is evaporated and the residue is purified by flash chromatography (silica gel, 2:1 hexanes/ethyl acetate) to provide the intermediate title compound as a clear colorless oil (5.0 g, 45%). MS (ES), 431 [M+H]$^+$.

D. 1-(1,4-Dioxa-spiro[4.5]dec-8-ylmethyl)-2-(S)-methoxymethyl-piperazin-2-one 4-(1,4-Dioxa-spiro[4.5]dec-8-ylmethyl)-2-(S)-methoxymethyl-3-oxo-3,4-dihydro-2H-pyrazine-1-carboxylic acid benzyl ester (4.7 g, 11 mmol) and 10% Pd on carbon (1.0 g) are stirred in methanol (150 mL) under a hydrogen atmosphere for 18 h. The mixture is filtered through Celite@ and is evaporated to provide the intermediate title compound as a clear colorless oil (3.3 g, 11 mmol). MS (EI), 298 [M]$^+$.

E. 4-[(5-Chloro-thiophen-2-yloxy)-acetyl]-1-(1,4-dioxa-spiro[4.5]dec-8-ylmethyl)-3-(S)-methoxymethyl-piperazin-2-one 1-(1,4-Dioxa-spiro[4.5]dec-8-ylmethyl)-2-(S)-methoxymethyl-piperazin-2-one (3.3 g, 11 mmol), (5-chloro-thiophen-2-yloxy)-acetic acid (2.1 g, 11 mmol), 2-(1H-benzotriazol-1-yl)-1,1,3,3-tetramethyluronium tetrafluoroborate (3.9 g, 12 mmol) and triethylamine (3.3 g, 33 mmol) are stirred in DMF (100 mL) for 8 h. The mixture is evaporated and is diluted with ethyl acetate (200 mL). The organic phase is washed with water, 2 N HCl, 1 N NaOH and brine, is dried ($MgSO_4$) and is evaporated. The residue is purified by flash chromatography (silica gel, 4:1 ethyl acetate/hexanes) to provide the intermediate title compound as a clear colorless oil (2.8 g, 54%). MS (ES), 473 [M+H]$^+$.

F. 4-[(5-Chlorothiophen-2-yloxy)-acetyl]-3-(S)-methoxymethyl-1-(4-oxocyclohexylmethyl)-piperazin-2-one 4-[(5-Chloro-thiophen-2-yloxy)-acetyl]-1-(1,4-dioxa-spiro[4.5]dec-8-ylmethyl)-3-(S)-methoxymethyl-piperazin-2-one (2.8 g, 5.9 mmol) is placed in 80:20 acetic acid/water and heated at 65° C. for 0.2 h. The mixture is evaporated and is diluted with ethyl acetate (200 mL). The organic phase is washed with 1 N NaOH, is dried ($MgSO_4$) and is evaporated to provide the intermediate title compound as a clear colorless oil (2.4 g, 95%). MS (ES), 429 [M+H]$^+$.

G. 4-[(5-Chlorothiophen-2-yloxy)-acetyl]-3-(S)-methoxymethyl-1-cis-(4-morpholin-4-yl-cyclohexylmethyl)-piperazin-2-one and 4-[(5-Chlorothiophen-2-yloxy)-acetyl]-3-(S)-methoxymethyl-1-trans-(4-morpholin-4-yl-cyclohexylmethyl)-piperazin-2-one 4-[(5-Chlorothiophen-2-yloxy)-acetyl]-3-(S)-methoxymethyl-1-(4-oxocyclohexylmethyl)-piperazin-2-one (0.07 g, 0.14 mmol), morpholine (0.025 g, 0.28 mmol), acetic acid (0.008 g, 0.14 mmol) and sodium cyanoborohydride (0.01 g, 0.17 mmol) are stirred in methanol (1 mL) for 48 h. The solvent is removed in vacuo and the residue is purified by flash column chromatography (silica gel, 98:2 dichloromethane/methanol) to provide the cis isomer compound as a colorless resin (0.01 g, 15%). MS (ES), 500 [M+H]$^+$.

The trans isomer is also isolated (0.02, g, 29%). MS (ES), 500 [M+H]$^+$.

The following compounds are also prepared in a similar manner to that described in Example 1286.

EXAMPLE 1287

4-[(5-Chloro-thiophen-2-yloxy)-acetyl]-1-cis-{4-[(2-hydroxy-ethyl)-methyl-1-amino]-cyclohexylmethyl)-3-(S)-methoxymethyl-piperazin-2-one: MS (ES), 488 [M+H]$^+$.

EXAMPLE 1288

4-[(5-Chloro-thiophen-2-yloxy)-acetyl]-1-trans-{4-[(2-hydroxy-ethyl)-methyl-1-amino]-cyclohexylmethyl)-3-(S)-methoxymethyl-piperazin-2-one

MS (ES), 488 [M+H]$^+$.

EXAMPLE 1289

4-[(5-Chloro-thiophen-2-yloxy)-acetyl]-3-(S)-methoxymethyl-1-cis-{4-[2-(R,S)-(1-methyl-pyrrolidin-2-yl)-ethylamino]-cyclohexylmethyl}-piperazine-2-one: MS (ES), 541 [M+H]$^+$.

EXAMPLE 1290

4-[(5-Chloro-thiophen-2-yloxy)-acetyl]-3-(S)-methoxymethyl-1-trans-{4-[2-(R,S)-(1-methyl-pyrrolidin-2-yl)-ethylamino]-cyclohexylmethyl}-piperazine-2-one

MS (ES), 541 [M+H]$^+$.

EXAMPLE 1291

4-[(5-Chloro-thiophen-2-yloxy)-acetyl]-3-(S)-methoxymethyl-1-cis-[4-(2-pyridin-2-yl-ethylamino)-cyclohexylmethyl]-piperazin-2-one: MS (ES), 535 [M+H]+.

EXAMPLE 1292

4-[(5-Chloro-thiophen-2-yloxy)-acetyl]-3-(S)-methoxymethyl-1-trans-[4-(2-pyridin-2-yl-ethylamino)-cyclohexylmethyl]-piperazin-2-one

MS (ES), 535 [M+H]+.

EXAMPLE 1293

4-[(5-Chloro-thiophen-2-yloxy)-acetyl]-1-cis-[4-(2-dimethylamino-ethylamino)-cyclohexylmethyl]-3-(S)-methoxymethyl-piperazin-2-one: MS (ES), 501 [M+H]+.

EXAMPLE 1294

4-[(5-Chloro-thiophen-2-yloxy)-acetyl]-1-trans-[4-(2-dimethylamino-ethylamino)-cyclohexylmethyl]-3-(S)-methoxymethyl-piperazin-2-one

MS (ES), 501 [M+H]+.

EXAMPLE 1295

4-(4-cis-{4-[(5-Chloro-thiophen-2-yloxy)-acetyl]-3-(S)-methoxymethyl-2-oxo-piperazin-1-ylmethyl}-piperazine-1-carboxylic acid ethyl ester: MS (ES), 571 [M+H]+.

EXAMPLE 1296

4-(4-trans-{4-[(5-Chloro-thiophen-2-yloxy)-acetyl]-3-(S)-methoxymethyl-2-oxo-piperazin-1-ylmethyl}-piperazine-1-carboxylic acid ethyl ester

MS (ES), 571 [M+H]+.

EXAMPLE 1297

4-[(5-Chloro-thiophen-2-yloxy)-acetyl]-1-cis-([4-(4-hydroxy-piperidin-1-yl)-cyclohexylmethyl]-3-(S)-methoxymethyl-piperazin-2-one: MS (ES), 514 [M+H]+.

EXAMPLE 1398

4-[(5-Chloro-thiophen-2-yloxy)-acetyl]-1-trans-([4-(4-hydroxy-piperidin-1-yl)-cyclohexylmethyl]-3-(S)-methoxymethyl-piperazin-2-one

MS (ES), 514 [M+H]+.

EXAMPLE 1399

1-cis-(4-Azepan-1-yl-cyclohexylmethyl)-4-[(5-chloro-thiophen-2-yloxy)-acetyl]-3-(S)-methoxymethyl-piperazin-2-one MS (ES), 512 [M+H]+.

EXAMPLE 1300

1-trans-(4-Azepan-1-yl-cyclohexylmethyl)-4-[(5-chloro-thiophen-2-yloxy)-acetyl]-3-(S)-methoxymethyl-piperazin-2-one

MS (ES), 512 [M+H]+.

EXAMPLE 1301

4-[(5-chloro-thiophen-2-yloxy)-acetyl]-3-(S)-methoxymethyl-1-cis-{4-[(pyridin-2-ylmethyl)-amino]-cyclohexylmethyl}-piperazin-2-one MS (ES), 521 [M+H]+.

EXAMPLE 1302

4-[(5-chloro-thiophen-2-yloxy)-acetyl]-3-(S)-methoxymethyl-1-trans-{4-[(pyridin-2-ylmethyl)-amino]-cyclohexylmethyl}-piperazin-2-one

MS (ES), 521 [M+H]+.

EXAMPLE 1303

4-[(5-chloro-thiophen-2-yloxy)-acetyl]-3-(S)-methoxymethyl-1-cis-(4-phenylamino-cyclohexylmethyl)-piperazin-2-one: MS (ES), 506 [M+H]+.

EXAMPLE 1304

4-[(5-chloro-thiophen-2-yloxy)-acetyl]-3-(S)-methoxymethyl-1-trans-(4-phenylamino-cyclohexylmethyl)-piperazin-2-one

MS (ES), 506 [M+H]+.

EXAMPLE 1305

4-[(5-Chloro-thiophen-2-yloxy)-acetyl]-1-cis-{4-[2-(2-hydroxy-ethoxy)-ethylamino]-cyclohexylmethyl}-3-(S)-methoxymethyl-piperazin-2-one

MS (ES), 518 [M+H]+.

and

EXAMPLE 1306

4-[(5-Chloro-thiophen-2-yloxy)-acetyl]-1-trans-{4-[2-(2-hydroxy-ethoxy)-ethylamino]-cyclohexylmethyl}-3-(S)-methoxymethyl-piperazin-2-one

MS (ES), 518 [M+H]+.

Similarly, additional 1-(alkyl,aryl)amino-4-methylcyclohexyl compounds can be prepared from intermediates having a structure 311
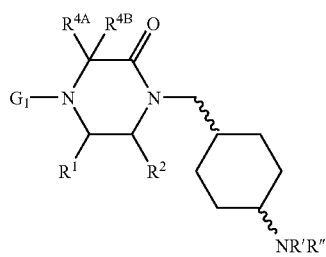
wherein:
G-1 includes but is not limited to
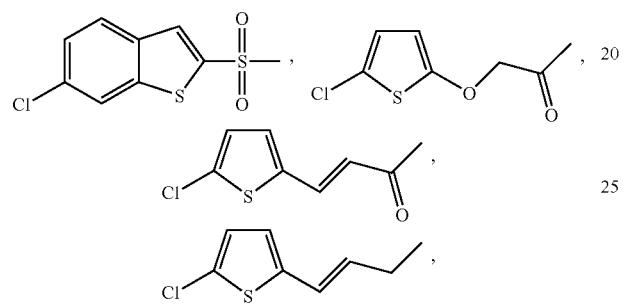
and
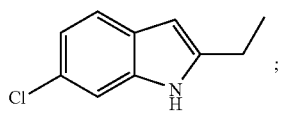
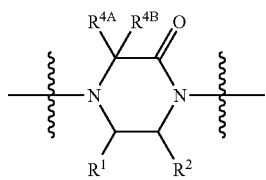
includes but is not limited to
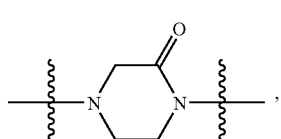
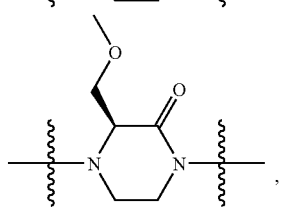
312
-continued
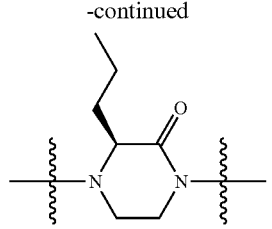
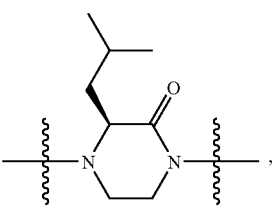
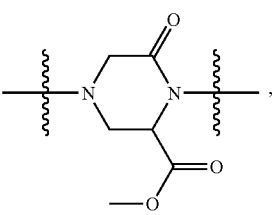
and
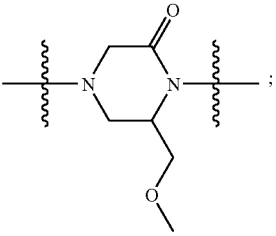
and
—NRR' includes but is not limited to
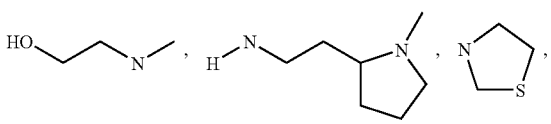
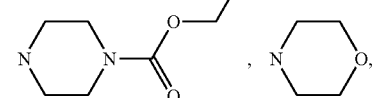
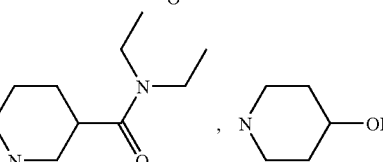
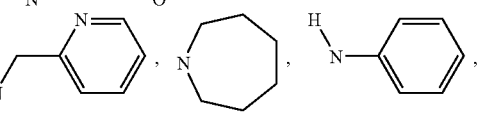

-continued

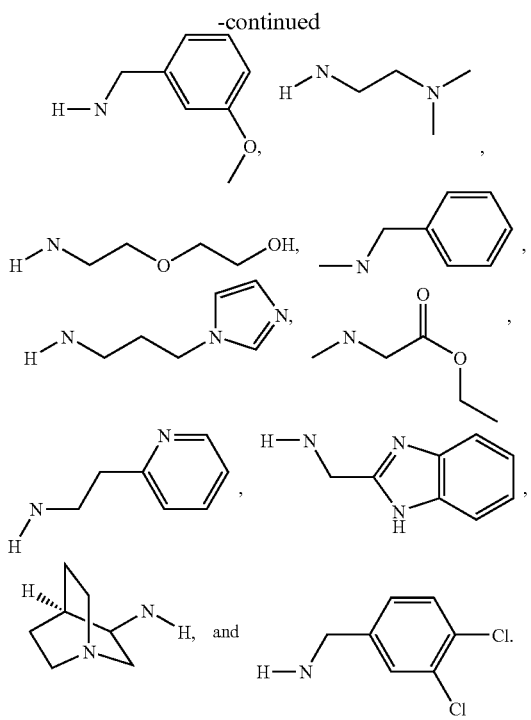

EXAMPLE 1307

4-[(5-Chlorothiophen-2-yloxy)-acetyl]-1-[(2-{[N,N-dimethylaminoethyl]-amino}-pyrimidin-5-yl)-methyl]-3-(S)-methoxymethyl-piperazine-2-one A. 5-hydroxymethyl-2-methylthiopyrimidine To a solution of 2-methylthiopyrimidine-5-carboxaldehyde (1.35 g, 8.7 mmol), prepared according to the method of Gupton et al. (J. Het. Chem. 28, 1991, 1281), in methanol (1 mL) at 0° C. is added sodium borohydride (0.3 g, 7.9 mmol). The mixture is stirred for 0.5 h and is concentrated in vacuo. The residue is partitioned between EtOAc and 1 N NaOH. The organic phase is dried (MgSO$_4$) and is evaporated to yield the intermediate title compound as a yellow solid (1.18 g, 87%). MS (ES), 157 [M+H]$^+$.

B. 5-bromomethyl-2-methylthiopyrimidine 5-hydroxymethyl-2-methylthiopyrimidine (0.1 g, 0.61 mmol), triphenylphosphine (0.45 g, 1.7 mmol) and carbon tetrabromide (0.28 g, 0.85 mmol) are stirred in benzene (5 mL) for 24 h. The mixture is evaporated and the residue is purified by flash chromatography (silica gel, 4:1 hexanes/ethyl acetate) to provide the intermediate title compound as a white solid (0.08 g, 61%). MS (ES), 219/221 [M+H]$^+$ (Br).

C. 4-benzyloxycarbonyl-3-(S)-methoxymethyl-1-[(2-methylthiopyrimidin-5-yl)-methyl]-piperazine-2-one 4-Benzyloxycarbonyl-3-(S)-methoxymethyl-piperazine-2-one (0.1 g 0.37 mmol), 5-bromomethyl-2-methylthiopyrimidine (0.08 g, 0.37 mmol) and tetra-n-butylammonium bromide (0.06 g, 0.19 mmol) are placed in dichloromethane (1 mL) and 50% aqueous NaOH (0.03 mL) and stirred for 4 h. The mixture is diluted with water and is extracted with dichloromethane (2×20 mL). The combined organic extracts are dried (MgSO$_4$) and are evaporated. The residue is purified by flash chromatography (silica gel, 98:2 dichloromethane/methanol) to provide the intermediate title compound as a colorless oil (0.05 g, 33%).

MS (ES), 417 [M+H]$^+$.

D. 4-benzyloxycarbonyl-1-[(2-{[N,N-dimethylaminoethyl]-amino}-pyrimidin-5-yl)-methyl]-3-(S)-methoxymethyl-piperazine-2-one 4-benzyloxycarbonyl-3-(S)-methoxymethyl-1-[(2-methylthiopyrimidin-5-yl)-methyl]-piperazine-2-one (0.045 g, 0.11 mmol) is dissolved in dichloromethane (3 mL) and cooled to −78° C. 57-86% 3-Chloroperoxybenzoic acid (0.095 g, 0.33 mmol) is added and the mixture is warmed to room temperature. The mixture is diluted with dichloromethane (20 mL) and is washed with dilute aqueous Na$_2$CO$_3$. The organic phase is dried (Na$_2$SO$_4$) and is evaporated. The crude residue is used without further purification. MS (ES), 449 [M+H]$^+$. The residue is placed in DMF (1 mL) and N,N-dimethylethylamine (0.05 g, 0.6 mmol) is added. The mixture is stirred for 4 h and is concentrated in vacuo. Purification by flash chromatography (silica gel, 9:1 dichloromethane/methanol) provided the intermediate title compound as a colorless resin (0.01 g, 20%). MS (ES), 457 [M+H]$^+$.

E. 1-[(2-{[N,N-dimethylaminoethyl]-amino}-pyrimidin-5-yl)-methyl]-3-(S)-methoxymethyl-piperazine-2-one 4-Benzyloxycarbonyl-1-[(2-{[N,N-dimethylaminoethyl]-amino}-pyrimidin-5-yl)-methyl]-3-(S)-methoxymethyl-piperazine-2-one (0.01 g, 0.02 mmol) and 10% Pd on carbon (0.01 g) are stirred in acetic acid (3 mL) under a hydrogen atmosphere for 18 h. The mixture is filtered through Celite@ and is evaporated to provide the intermediate title compound as a clear colorless oil (0.002 g). MS (ES), 323 [M+H]$^+$.

F. 4-[(5-Chlorothiophen-2-yloxy)-acetyl]-1-[(2-{[N,N-dimethylaminoethyl]-amino}-pyrimidin-5-yl)-methyl]-3-(S)-methoxymethyl-piperazine-2-one The title compound can be prepared by placing 1-[(2-{[N,N-dimethylaminoethyl]-amino}-pyrimidin-5-yl)-methyl]-3-(S)-methoxymethyl-piperazine-2-one, (5-chloro-thiophen-2-yloxy)-acetic acid, 2-(1H-benzotriazol-1-yl)-1,1,3,3-tetramethyluronium tetrafluoroborate and triethylamine in DMF and stirring 8-16 h. The mixture is evaporated and is diluted with ethyl acetate. The organic phase is washed with water, 2 N HCl, 1 N NaOH and brine, is dried (MgSO$_4$) and is evaporated. The residue is purified by flash chromatography (silica gel, 4:1 ethyl acetate/hexanes) to provide the title compound.

Similarly, 2-amino & alkoxy-4&5-substituted-methylpyrimidinyl compounds can be prepared from intermediates having a structure

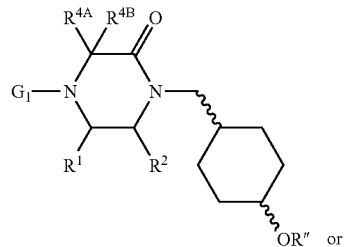

or

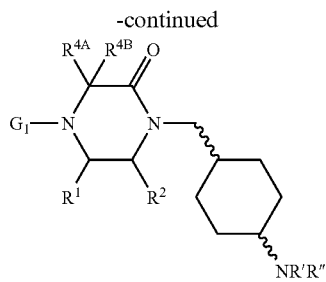
wherein:
G-1 includes but is not limited to
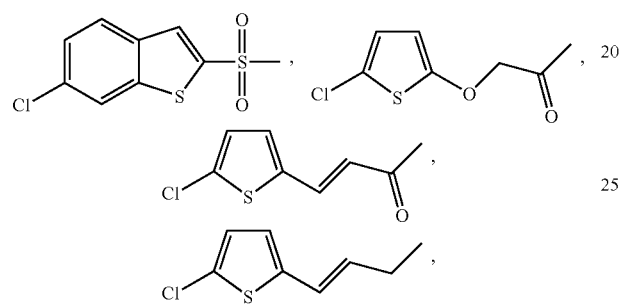
and
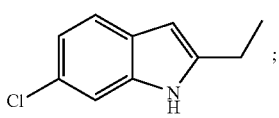
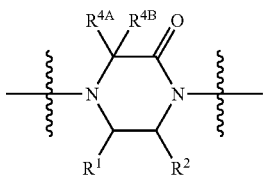
includes but is not limited to
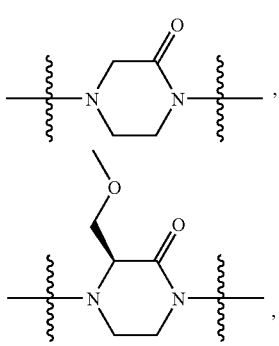
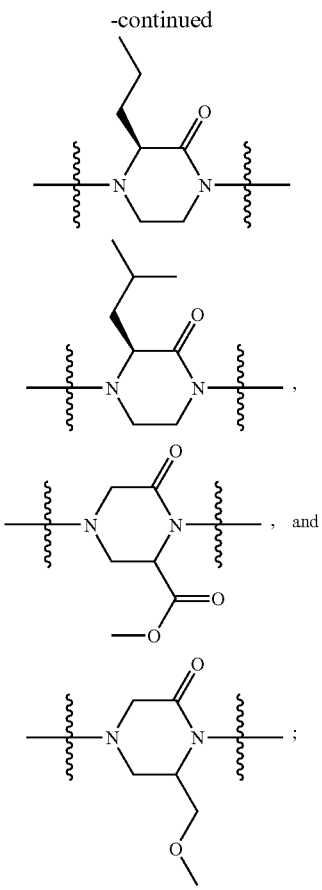
and
—NRR' includes but is not limited to
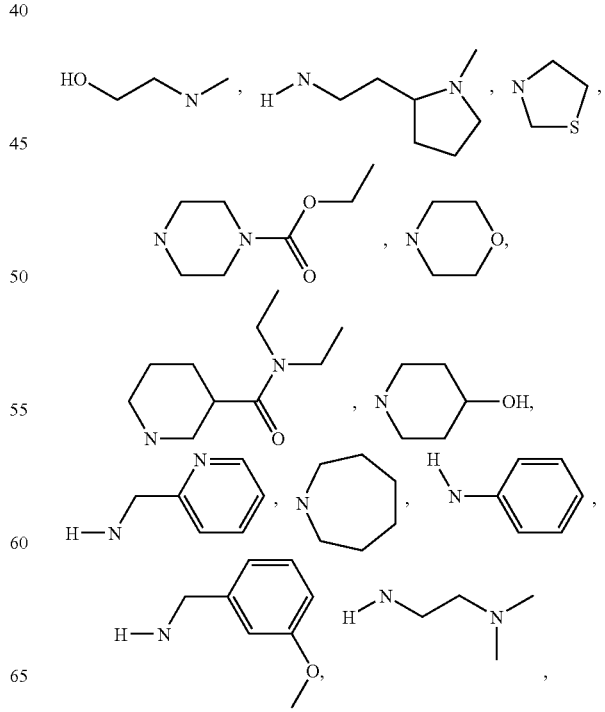

-continued

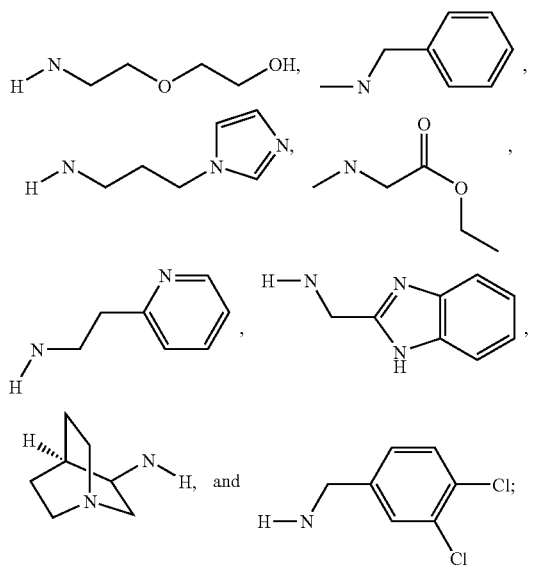

OR" includes but is not limited to

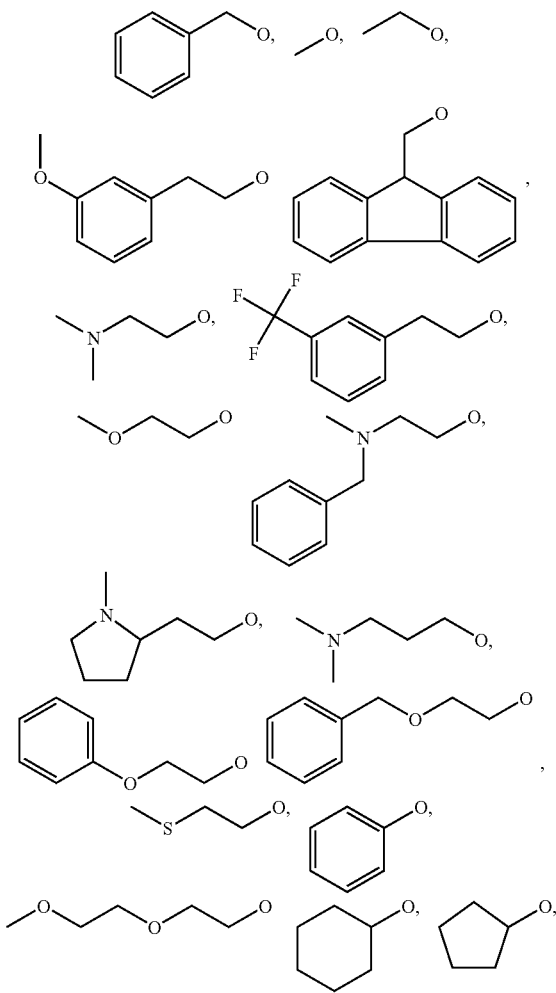

-continued

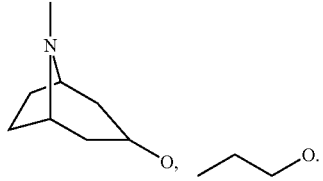

EXAMPLE 1308

1-(4-Amino-guinazolin-7-ylmethyl)-4-[3-(4-chlorophenyl)-allyl]-piperazine-2,3-dione A. Methyl 2-amino-4-hydroxymethlybenzoate.

To a solution of 16.0 g (76.6 mmole) of dimethyl aminoterephthalate in 200 ml of anhydrous THF cooled to −78° C. is added 250 ml (250 mmole) of 1 M Super Hydride dropwise over 1 hour. The mixture is stirred for an additional 1.5 hours warming to 0° C. (a little starting material on TLC is observed). The mixture is poured into 300 ml of cold water and extracted with ethyl acetate. The organic layer is washed with water and the two layers are allowed to stand for 30 minutes. The organic layer is dried over $MgSO_4$ and filtered. The filtrate is evaporated. The residue is dissolved in ethyl acetate and the solution is poured over a Buchner funnel containing silica gel, using 150 ml of ethyl acetate to wash the funnel. The filtrate is evaporated. The residue is dissolved in the minimum amount of ethyl acetate and the solution is diluted to the cloudy point with hexane. Additional hexane is added as the product precipitates. A total of 100 ml of hexane is added and the solid is collected and vacuum dried to give 8.4 g of the title intermediate material, 98-100° C. mp; 61% yield. $^1$H NMR ($CDCl_3$, 300 MHz) δ 7.82 (d, 1H), 6.67 (s, 1H), 6.60 (d, 1H), 5.75 (bs, 2H), 4.62 (s, 2H), 3.86 (s, 3H), 1.83 (bs, 1H). EI MS, $[M]^+$=181.

B. 7-Hydroxymethlyquinazolin-4-one.

A mixture of 2.0 g (19.1 mmole) of methyl 2-amino-4-hydroxymethlybenzoate in 4 ml of formamide is heated in an oil bath of 180° C. for three hours. The mixture is cooled and triturated with 70 ml of boiling ethyl acetate. The ethyl acetate is then decanted from the dark oil and cooled in a freezer overnight to precipitate 0.7 g 205-12° C. mp; 40% yield. $^1$H NMR ($d_6$-DMSO, 300 MHz) δ 8.08 (s, 1H), 8.06 (d, 1H), 7.60 (s, 1H), 7.45 (d, 1H), 5.48 (bs, 1H), 4.65 (s, 2H), 3.35 (bs, 1H). EI MS, $[M]^+$=176.

C. 4-Chloro-7-chloromethylquinazoline.

A mixture of 2.0 g (11.3 mmole) of 7-hydroxymethylquinazolin-4-one in 25 ml of phosphorus oxychloride is heated under reflux for 30 minutes. A very thick mixture is formed and the heating is continued for an additional 1.5 hours to give a solution. The phosphorus oxychloride is evaporated in a rotary evaporator and the residue is poured into ice water. The mixture is extracted with ether. The ether is dried over $MgSO_4$, filtered, and the filtrate evaporated. The residue is treated with 10 ml of ether and filtered. The filtrate is evaporated to afford 0.8 g of intermediate product which is used directly in the next step without further purification; 33% yield. $^1$H NMR ($CDCl_3$, 300 MHz) δ 9.07 (s, 1H), 8.30 (d, 1H), 8.06 (s, 1H), 7.78 (d, 1H), 4.78 (s, 2H). EI MS, $[M]^+$=212, 214, 216 ($Cl_2$ pattern).

D. 4-Amino-7-chloromethylquinazoline.

To 15 ml of a saturated ethanolic ammonia solution is added 1.0 g (4.7 mmole) of 4-chloro-7-chloromethylquinazoline. The mixture is stirred at room temperature overnight. The precipitate which forms is collected to give 0.7 g of the title intermediate product, mp>300° C.; 77% yield. $^1$H NMR (d$_6$-DMSO, 300 MHz) δ 8.38 (s, 1H), 8.20 (d, 1H), 7.78 (bs, 2H), 7.70 (s, 1H), 7.51 (d, 1H), 4.92 (s, 2H). EI MS, [M]$^+$ =193, 195 (Cl pattern).

E. 3-(4-Chloro-phenyl)-(E)-propenal.

To a solution of 3-(4-chloro-phenyl)-prop-2-(E)-en-1-ol (2.33 g, 13.8 mmol, prepared as described in *J. Med. Chem.* 1997, 1827) in 50 ml of CH$_2$Cl$_2$ is added activated manganese (IV) oxide (4.80 g, 55.3 mmol) in three portions over 3 hours and the resulting suspension is stirred at room temperature overnight. After filtration through a pad of celite and concentration in vacuo, the crude residue is purified by column chromatography eluting with 10% EtOAc/hexanes to provide the title intermediate compound (0.80 g, 4.80 mmol) as a pale yellow oil. $^1$H NMR (CDCl$_3$, 300 MHz) δ 9.71 (d, 1H), 7.48 (m, 3H), 7.41 (dd, 2H), 6.68 (dd, 1H).

F. {2-[3-(4-Chloro-phenyl)-allylamino]-ethyl}-carbamic acid tert-butyl ester.

To a solution of N-Boc-ethylenediamine (0.63 g, 4.80 mmol) in 20 mL of MeOH is added 3-(4-chloro-phenyl)-(E)-propenal (0.80 g, 4.80 mmol). After stirring for 3 hours at room temperature over 4A molecular sieves, NaBH$_4$ (0.19 g, 5.00 mmol) is added. The reaction mixture is stirred for 16 hours, then diluted with EtOAc and filtered through Celite plug. The solution is concentrated under reduced pressure. The residue is partitioned between EtOAc and H$_2$O and the layers are separated. The aqueous layer is extracted with EtOAc. The combined organic layers are washed with H$_2$O, brine, then dried over MgSO$_4$, filtered and concentrated. The crude title product is purified by column chromatography, eluting with a gradient of 25% EtOAc/CH$_2$Cl$_2$ to 50% EtOAc/CH$_2$Cl$_2$, to provide the title intermediate compound (0.80 g, 2.57 mmol). $^1$H NMR (CDCl$_3$, 300 MHz) δ 7.26 (s, 4H), 6.49 (d, 1H), 6.23 (dt, 1H), 4.96 (bs, 1H), 3.40 (m, 2H), 3.25 (m, 2H), 2.76 (m, 2H), 1.60 (bs, 1H), 1.45 (s, 9H).

G. N-(2-tert-Butoxycarbonylamino-ethyl)-N-[3-(4-chloro-phenyl)-allyl]-oxalamic acid methyl ester.

To a solution of {2-[3-(4-chloro-phenyl)-allylamino]-ethyl}-carbamic acid tert-butyl ester (0.80 g, 2.57 mmol) in 15 ml of CH$_2$Cl$_2$ at 0° C. is added triethylamine (0.54 mL, 3.85 mmol) and methyl chlorooxoacatate (0.25 mL, 2.70 mmol). The resulting mixture is stirred at 0° C. for 1 h, then at room temperature for 1 h. The solution is partitioned between EtOAc and H$_2$O and the layers separated. The organic layer is washed with 1N HCl solution, H$_2$O, saturated NaHCO$_3$ solution and brine, then dried over MgSO$_4$, filtered and concentrated. The crude product is purified by column chromatography eluting with 25% EtOAc/CH$_2$Cl$_2$ to provide the title intermediate compound (0.98 g, 2.47 mmol). $^1$H NMR (CDCl$_3$, 300 MHz) δ 7.31 (m, 4H), 6.55 (dd, 1H), 6.14 (m, 1H), 4.88 (bs, 1H), 4.21, 4.10 (d, 2H), rotamers), 3.91, 3.86 (s, 3H, rotamers), 3.55, 3.44 (m, 2H, rotamers), 3.36 (m, 2H), 1.43 (s, 9H).

H. 1-[3-(4-Chloro-phenyl)-allyl]-piperazine-2,3-dione.

A solution of N-(2-tert-butoxycarbonylamino-ethyl)-N-[3-(4-chloro-phenyl)-allyl]-oxalamic acid methyl ester (0.49 g, 1.23 mmol) in 6 mL of EtOAc at 0° C. is saturated with HCl gas. The ice-bath is removed and the solution is stirred at room temperature for 30 min as a white precipitate forms after about 5-10 min. After this time, the solution is concentrated to a white solid (0.41 g). The crude amine salt is suspended in 6 mL CH$_2$Cl$_2$ and 1.5 mL of MeOH. Triethylamine (0.5 mL, 3.53 mmol) is added and the resulting solution is stirred at room temperature overnight. The solution is concentrated under reduced pressure and partitioned between CH$_2$Cl$_2$ and H$_2$O. The aqueous layer is basified with 0.5N NaOH. The organic layer is washed with H$_2$O, brine, then dried over MgSO$_4$, filtered and concentrated. The title intermediate compound is obtained as a white solid (0.32 g, 1.21 mmol). $^1$H NMR (CDCl$_3$, 300 MHz) δ 7.82 (bs, 1H), 7.30 (s, 4H), 6.56 (d, 1H), 6.14 (dt, 1H), 4.27 (d, 2H), 3.58 (m, 4H).

I. 1-(4-Amino-quinazolin-7-ylmethyl)-4-[3-(4-chloro-phenyl)-allyl]-piperazine-2,3-dione.

To a solution of 1-[3-(4-chloro-phenyl)-allyl]-piperazine-2,3-dione (60 mg, 0.23 mmol) in 1.5 mL of DMF is added NaH (10 mg of a 60% dispersion in mineral oil, 0.24 mmol). The mixture is heated at 55° C. for 20 min. To the solution is added 4-amino-7-chloromethyl-quinazoline (49 mg, 0.25 mmol), and the resulting mixture is heated at 55° C. for 20 min as a white precipitate is formed. After this time, reaction mixture is quenched with a few drops of H$_2$O and MeOH, then concentrated. The crude product is purified by RP-HPLC, eluting in a gradient of 10% CH$_3$CN/H$_2$O (0.1% TFA) to 70% CH$_3$CN/H$_2$O (0.1% TFA) over 30 minutes, and the appropriate product fractions are combined and lyopholized to provide the title compound (56 mg, 0.10 mmol) as a white solid. $^1$H NMR (d$_6$-DMSO, 300 MHz) δ 9.78 (bs, 2H), 8.83 (s, 1H), 8.40 (s, 1H), 7.72 (d, 1H), 7.65 (s, 1H), 7.49 (d, 2H), 7.38 (d, 2H), 6.61 (d, 1H), 6.30 (dt, 1H), 4.80 (s, 2H), 4.18 (d, 2H), 3.59 (m, 4H). ISP MS, [M+H]$^+$=422.

The following 2,3-diketopiperazine compounds are prepared in a similar fashion using the procedures described above.

| Example # | Name | m/z [M + H] |
|---|---|---|
| 1309 | 1-(4-Amino-quinazolin-7-ylmethyl)-4-(6-chloro-benzo[b]thiophen-2-yl-methyl)-piperazine-2,3-dione | ISP-452, Cl |
| 1310 | 1-(4-Amino-quinolin-7-ylmethyl)-4-[3-(4-chloro-phenyl)-allyl]-piperazine-2,3-dione | ISP-421, Cl |
| 1311 | 1-(4-Amino-quinazolin-7-ylmethyl)-4-(5'-chloro-[2,2']bithiophenyl-5-ylmethyl)-piperazine-2,3-dione | ISP-484 |
| 1312 | 1-(3-carbamimidoyl-benzyl)-4-(4-carbamimidoyl-benzyl)-2,3 dioxopiperizine | ISP-379 |
| 1313 | Bis-1,4-(3-carbamimidoyl-benzyl)-2,3-dioxopiperizine | ISP-379 |
| 1314 | 1-(4-Amino-quinazolin-7-ylmethyl)-4-[3-(3-chloro-phenyl)-allyl]-piperazine-2,3-dione | |
| 1315 | 1-(4-Amino-quinazolin-7-ylmethyl)-4-[3-(5-chloro-thiophen-2-yl)-allyl]-piperazine-2,3-dione | |

-continued

| Example # | Name | m/z [M + H] |
|---|---|---|
| 1316 | 1-(4-Amino-quinolin-7-ylmethyl)-4-(6-chloro-benzo[b]thiophen-2-yl-methyl)-piperazine-2,3-dione | |
| 1317 | 1-(4-Amino-quinolin-7-ylmethyl)-4-(5'-chloro-[2,2']bithiophenyl-5-ylmethyl)-piperazine-2,3-dione | |
| 1318 | 1-(4-Amino-quinolin-7-ylmethyl)-4-[3-(5-chloro-thiophen-2-yl)-allyl]-piperazine-2,3-dione | |
| 1319 | 1-[3-(3-chloro-phenyl)-allyl]-4-(1H-pyrrolo[3,2-c]pyridin-2-ylmethyl)-piperazine-2,3-dione | |
| 1320 | 1-[3-(4-chloro-phenyl)-allyl]-4-(1H-pyrrolo[3,2-c]pyridin-2-ylmethyl)-piperazine-2,3-dione | |
| 1321 | 1-[3-(5-chloro-thiophen-2-yl)-allyl]-4-(1H-pyrrolo[3,2-c]pyridin-2-ylmethyl)-piperazine-2,3-dione | |
| 1322 | 1-(6-chloro-benzo[b]thiophen-2-yl-methyl)-4-(1H-pyrrolo[3,2-c]pyridin-2-ylmethyl)-piperazine-2,3-dione | |
| 1323 | 1-(5'-chloro-[2,2']bithiophenyl-5-ylmethyl)-4-(1H-pyrrolo[3,2-c]pyridin-2-ylmethyl)-piperazine-2,3-dione | |
| 1324 | 1-[3-(5-chloro-thiophen-2-yl)-allyl]-4-(1H-pyrrolo[2,3-c]pyridin-2-ylmethyl)-piperazine-2,3-dione | |
| 1325 | 1-[3-(5-chloro-thiophen-2-yl)-allyl]-4-(thieno[3,2-b]pyridin-2-ylmethyl)-piperazine-2,3-dione | |
| 1326 | 1-[3-(5-chloro-thiophen-2-yl)-allyl]-4-(4-pyridin-2-yl-benzyl)-piperazine-2,3-dione | |
| 1327 | 1-[3-(5-chloro-thiophen-2-yl)-allyl]-4-[4-(1-hydroxy-pyridin-2-yl)-benzyl]-piperazine-2,3-dione | |
| 1328 | 1-[3-(5-chloro-thiophen-2-yl)-allyl]-4-(4-pyridin-4-yl-benzyl)-piperazine-2,3-dione | |
| 1329 | 1-[3-(5-chloro-thiophen-2-yl)-allyl]-4-[4-(1-hydroxy-pyridin-4-yl)-benzyl]-piperazine-2,3-dione | |
| 1330 | 1-[3-(5-chloro-thiophen-2-yl)-allyl]-4-[4-(6-methoxy-pyridin-3-yl)-benzyl]-piperazine-2,3-dione | |
| 1331 | 1-[3-(5-chloro-thiophen-2-yl)-allyl]-4-[4-(6-oxo-1,6-dihydro-pyridin-3-yl)-benzyl]-piperazine-2,3-dione | |
| 1332 | 1-[3-(5-chloro-thiophen-2-yl)-allyl]-4-[4-(2-dimethylamino-pyrimidin-4-yl)-benzyl]-piperazine-2,3-dione | |
| 1333 | 1-[3-(5-chloro-thiophen-2-yl)-allyl]-4-(4-{2-[(2-dimethylamino-ethyl)-methyl-amino]-pyrimidin-4-yl}-benzyl)-piperazine-2,3-dione | |
| 1334 | 1-[3-(5-chloro-thiophen-2-yl)-allyl]-4-[4-(2-dimethylamino-pyrimidin-4-yl)-cyclohexymethyl]-piperazine-2,3-dione | |
| 1335 | 1-[3-(5-chloro-thiophen-2-yl)-allyl]-4-(4-{2-[(2-dimethylamino-ethyl)-methyl-amino]-pyrimidin-4-yl}-cyclohexylmethyl)-piperazine-2,3-dione | |
| 1336 | 1-(4-Amino-quinazolin-7-ylmethyl)-4-[3-(5-chloro-thiophen-2-yl)-allyl]-5-methyl-piperazine-2,3-dione | |
| 1337 | 1-(4-Amino-quinazolin-7-ylmethyl)-4-[3-(5-chloro-thiophen-2-yl)-allyl]-5-ethyl-piperazine-2,3-dione | |
| 1338 | 1-(4-Amino-quinazolin-7-ylmethyl)-4-[3-(5-chloro-thiophen-2-yl)-allyl]-5-propyl-piperazine-2,3-dione | |
| 1339 | 1-(4-Amino-quinazolin-7-ylmethyl)-4-[3-(5-chloro-thiophen-2-yl)-allyl]-5-butyl-piperazine-2,3-dione | |
| 1340 | 1-(4-Amino-quinazolin-7-ylmethyl)-4-[3-(5-chloro-thiophen-2-yl)-allyl]-5-isopropyl-piperazine-2,3-dione | |
| 1341 | 1-(4-Amino-quinazolin-7-ylmethyl)-4-[3-(5-chloro-thiophen-2-yl)-allyl]-5-isobutyl-piperazine-2,3-dione | |
| 1342 | 1-(4-Amino-quinazolin-7-ylmethyl)-4-[3-(5-chloro-thiophen-2-yl)-allyl]-5-methoxymethyl-piperazine-2,3-dione | |
| 1343 | 4-(4-Amino-quinazolin-7-ylmethyl)-1-[3-(5-chloro-thiophen-2-yl)-allyl]-5,6-dioxopiperazine-2-carboxylic acid | |
| 1344 | 4-(4-Amino-quinazolin-7-ylmethyl)-1-[3-(5-chloro-thiophen-2-yl)-allyl]-5,6-dioxopiperazine-2-carboxylic acid methyl ester | |
| 1345 | 4-(4-Amino-quinazolin-7-ylmethyl)-1-[3-(5-chloro-thiophen-2-yl)-allyl]-5,6-dioxopiperazine-2-carboxylic acid amide | |
| 1346 | 4-(4-Amino-quinazolin-7-ylmethyl)-1-[3-(5-chloro-thiophen-2-yl)-allyl]-5,6-dioxopiperazine-2-carboxylic acid methyl amide | |

Inhibition of Factor Xa

The compounds described herein inhibit blood coagulation by virtue of their ability to inhibit the penultimate enzyme in the coagulation cascade, controlling the activity of Factor Xa. Both the activity of free Factor Xa and Factor Xa assembled in the prothrombinase complex (Factor Xa, Factor Va, calcium and phospholipid) are inhibited by compounds of formula 1. The inhibition of the Factor Xa activity is obtained by direct complex formation between the inhibitor and the enzyme and is therefore independent of the plasma co-factor antithrombin III. Effective inhibition of the Factor Xa activity is achieved by administering the compounds either by oral administration, continuous intravenous infusion, bolus intravenous administration or any other parenteral route such that it achieves the desired effect of preventing the activity of Factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening thrombin throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

Accumulated experimental evidence has also reflected that prothrombin activation is only one of the biological activities of Factor Xa. EPR-1 (effector cell protease receptor-1, recognizing Factor Xa), is believed to mediate several of the vascular wall interactions by Factor Xa. It has been shown to be expressed on human umbilical vein endothelial cells, rat smooth muscle cells and platelets(C R McKenzie, et al., Arterioscler Thromb Vasc Biol 16 1285-91 (1996); also F Bono, et al., J Cell Physiol 172 36-43 (1997), A C Nicholson, et al., J Biol Chem 271 28407-13 (1996), J. M. Herbert, et al., J Clin Invest 101 993-1000 (1998)). This protease-receptor interaction could mediate not only prothrombinase-catalyzed thrombin generation, but also diverse cellular functions such as cell proliferation, release of PDGF and DNA syntheses. The mitogenic effect of Factor Xa has been reported to be dependent on Factor Xa enzymatic activity (F Bono, et al., J Cell Physiol 172 36-43 (1997), J. M. Herbert, et al., J Clin Invest 101 993-1000 (1998)). TAP for example inhibited the mitogenesis of human and rat cultured vascular smooth muscle cells (F Bono, et al., J Cell Physiol 172 36-43 (1997)). In a study of the rabbit carotid artery air-drying injury model, increased EPR-1 expression is detected after vascular injury. Animals treated with the specific Factor Xa inhibitor, DX-9065a, exhibited less neointimal proliferation. The important regulatory role of Factor Xa in the coagulation process coupled with its mitogenic effects points to Factor Xa's involvement in the formation of thrombin at the luminal surface of the vessel wall and contribution to the atherothrombotic process and abnormal proliferation of vascular cells resulting in restenosis or angiogenesis.

These compounds may be used alone or in combination with other diagnostic, anticoagulant, antiplatelet or fibrinolytic agents. For example adjunctive administration of inhibitors of the activity of Factor Xa with standard heparin, low molecular weight heparin(s), synthetic pentasaccharides, direct thrombin inhibitors (e.g. hirudin, Agratroban (Novastan®), aspirin, fibrinogen receptor antagonists, statins/fibrates streptokinase, urokinase and/or tissue plasminogen activator. The compounds described herein may be administered to treat thrombotic complications in a variety of animals such as primates including humans. Inhibition of factor Xa is useful not only in the anticoagulant therapy of individuals having thrombotic conditions but is useful whenever inhibition of blood coagulation is required such as to prevent coagulation of stored whole blood and to prevent coagulation in other biological samples for testing or storage. Thus, any inhibitor of Factor Xa activity can be added to or contacted with any medium containing or suspected of containing Factor Xa and in which it is desired that blood coagulation be inhibited.

In addition to their use in anticoagulant therapy, Factor Xa inhibitors may find utility in the treatment or prevention of other diseases in which the generation of thrombin has been implicated as playing a physiologic role. For example, thrombin has been proposed to contribute to the morbidity and mortality of such chronic and degenerative diseases as arthritis, cancer, atherosclerosis and Alzheimer's disease by virtue of its ability to regulate many different cell types through specific cleavage and activation of a cell surface thrombin receptor, mitogenic effects, diverse cellular functions such as cell proliferation, for example, abnormal proliferation of vascular cells resulting in restenosis or angiogenesis, release of PDGF and DNA syntheses. Inhibition of Factor Xa will effectively block thrombin generation and therefore neutralize any physiologic effects of thrombin on various cell types.

According to a further feature of the invention there is provided a method for the treatment of a human or animal patient suffering from, or subject to, a physiological condition which can be ameliorated by the administration of an inhibitor of the Factor Xa activity, for example conditions as hereinbefore described, which comprises the administration to the patient of a therapeutically effective amount of compound of formula I or formula II, or a composition containing a compound of formula I or formula II,. "Effective amount" is meant to describe an amount of compound of the present invention effective in inhibiting the activity of Factor Xa and thus producing the desired therapeutic effect.

The present invention also includes within its scope pharmaceutical formulations which comprise at least one of the compounds of formula I or formula II in association with a pharmaceutically acceptable carrier or coating.

The pharmaceutical compositions can be administered in a suitable formulation to humans and animals by topical or systemic administration, including oral, inhalational, rectal, nasal, buccal, sublingual, vaginal, parenteral (including subcutaneous, intramuscular, intravenous, intradermal, intrathecal and epidural), intracisternal and intraperitoneal. It will be appreciated that the preferred route may vary with for example the condition of the recipient.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I or formula II.

Actual dosage levels of active ingredients in the pharmaceutical compositions of this invention may be varied so as to obtain an amount of the active compound(s) that is effective to achieve the desired therapeutic response for a particular patient, composition, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved. In the adult, the doses are generally from about 0.01 to about 100, preferably about 0.01 to about 10, mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

Compounds within the scope of the present invention exhibit marked pharmacological activities according to tests described in the literature which tests results are believed to correlate to pharmacological activity in humans and other mammals. The following pharmacological test results are typical characteristics of compounds of the present invention.

Enzyme Assays:

The ability of the compounds in the present invention to act as inhibitors of factor Xa, thrombin, trypsin, tissue-plasminogen activator (t-PA), urokinase-plasminogen activator (u-PA), plasmin and activated protein C is evaluated by determining the concentration of inhibitor which resulted in a 50% loss in enzyme activity (IC50) using purified enzymes.

All enzyme assays are carried out at room temperature in 96-well microtiter plates using a final enzyme concentration of 1 nM. The concentrations of factor Xa and thrombin are determined by active site titration and the concentrations of all other enzymes are based on the protein concentration supplied by the manufacturer. Compounds according to the invention are dissolved in DMSO, diluted with their respective buffers and assayed at a maximal final DMSO concentration of 1.25%. Compound dilutions are added to wells containing buffer and enzyme and pre-equilibrated for between 5 and 30 minutes. The enzyme reactions are initiated by the addition of substrate and the color developed from the hydrolysis of the peptide-p-nitroanilide substrates is monitored continuously for 5 minutes at 405 nm on a Vmax microplate reader (Molecular Devices). Under these conditions, less than 10% of the substrate is utilized in all assays. The initial velocities measured are used to calculate the amount of inhibitor which resulted in a 50% reduction of the control velocity (IC50). The apparent Ki values are then determined according to the Cheng-Prusoff equation (IC50=Ki [1+[S]/Km]) assuming competitive inhibition kinetics.

An additional in vitro assay may be used to evaluate the potency of compounds according to the invention in normal human plasma. The activated partial thromboplastin time is a plasma-based clotting assay that relies on the in situ generation of factor Xa, its assembly into the prothrombinase complex and the subsequent generation of thrombin and fibrin which ultimately yields the formation of a clot as the assay endpoint. This assay is currently used clinically to monitor the ex vivo effects of the commonly used anticoagulant drug heparin as well as direct acting antithrombin agents undergoing clinical evaluation. Therefore, activity in this in vitro assay is considered as a surrogate marker for in vivo anticoagulant activity.

Human Plasma Based Clotting Assay:

Activated partial thromboplastin clotting times are determined in duplicate on a MLA Electra 800 instrument. A volume of 100 ml of citrated normal human pooled plasma (George King Biomedical) is added to a cuvette containing 100 ml of a compound according to the invention in Tris/NaCl buffer (pH 7.5) and placed in the instrument. Following a 3 minute warming period the instrument automatically adds 100 ml of activated cephaloplastin reagent (Actin, Dade) followed by 100 ml of 0.035 M $CaCl_2$ to initiate the clotting reaction. Clot formation is determined spectrophotometrically and measured in seconds. Compound potency is quantitated as the concentration required to double a control clotting time measured with human plasma in the absence of the compound according to the invention.

A compound according to the invention may also be evaluated for their in vivo antithrombotic efficacy in two well established animal experimental models of acute vascular thrombosis. A rabbit model of jugular vein thrombosis and a rat model of carotid artery thrombosis are used to demonstrate the antithrombotic activity of these compounds in distinct animal model paradigms of human venous thrombosis and arterial thrombosis, respectively.

Experimental Plazma Protein Binding Assay

Compounds are dissolved into DMSO to prepare a 10 mM stock. Serial dilutions of compounds are made in a buffer containing 0.05M Tris, 0.15M NaCl, 0.1% PEG-8000, PH 7.5. Human FXa and the substrate, Spectrozyme FXa, are prepared in the aforementioned buffer containing human Albumin and fibrinogen at 3.45 mg/ml and 2.3 mg/ml, respectively. The FXa assay is carried out at room temperature in the 96-well microtiter plates with a final enzyme concentration and substrate concentration of 1 nM and 200 µM, respectively. Compound dilutions are added to the wells containing buffer and FXa and preincubated for 30 minutes. The enzyme reactions are initiated by the addition of substrate, Spectrozyme FXa, and the color developed from the release of p-nitroanilide from each chromogenic substrate is monitored continuously for 5 minutes at 405 nm on a Thermomax microtiter plate reader (Molecular Devices, Sunnyvale, Calif.). In the final reaction mixture, the concentration of albumin and fibeinogen is 3 mg/ml and 2 mg/ml, respectively. Under the experimental conditions, less than 10% of the substrate is consumed in all assays. The initial velocities measured are used to determine the amount of inhibitor required to diminish 50% of the control velocity and defined as $IC_{50}$ of the inhibitor. Assuming the kinetic mechanisms are competitive inhibition, the apparent Ki values are then calculated according to the Cheng-Prusoff equation, $Ki=IC_{50}/(1+[S]/Km)$ Experimental in vivo Rabbit Venous Thrombosis Model:

This is a well characterized model of fibrin rich venous thrombosis that is validated in the literature and shown to be sensitive to several anticoagulant drugs including heparin (Antithrombotic Effect of Recombinant Truncated Tissue Factor Pathway Inhibitor (TFPI 1-161) in Experimental Venous Thrombosis-a Comparison with Low Molecular Weight Heparin, J. Holst, B. Lindblad, D. Bergqvist, O. Nordfang, P. B. Ostergaard, J. G. L. Petersen, G. Nielsen and U. Hedner. Thrombosis and Haemostasis, 71, 214-219 (1994). The purpose of utilizing this model is to evaluate the ability of compounds to prevent the formation of venous thrombi (clots) in vivo generated at a site of injury and partial stasis in the jugular vein.

Male and female New Zealand white rabbits weighing 1.5-2 kg are anesthetized with 35 mg/kg of ketamine and 5 mg/kg xylazine in a volume of 1 ml/kg (i.m.). The right jugular vein is cannulated for infusion of anesthetic (ketamine/xylazine 17/2.5 mg/kg/hr at a rate of approximately 0.5 ml/hr) and administration of test substances. The right carotid artery is cannulated for recording arterial blood pressure and collecting blood samples. Body temperature is maintained at 39° C. with a GAYMAR T-PUMP. The left external jugular vein is isolated and all side branches along an exposed 2-3 cm of vessel are tied off. The internal jugular vein is cannulated, just above the bifurcation of the common jugular, and the tip of the cannula is advanced just proximal to the common jugular vein. A 1 cm segment of the vein is isolated with non-traumatic vascular clamps and a relative stenosis is formed by tying a ligature around the vein with an 18 G needle just below the distal most clamp. This creates a region of reduced flow and partial stasis at the injury site. The isolated segment is gently rinsed with saline 2-3 times via the cannula in the internal jugular. Thereafter the isolated segment is filled with 0.5 ml of 0.5% polyoxyethylene ether (W-1) for 5 minutes. W-1 is a detergent which disrupts the endothelial cell lining of the segment, thus providing a thrombogenic surface for initiating clot formation. After 5 minutes the W-1 is withdrawn from the segment, and the segment is again gently rinsed with saline 2-3 times. The vascular clamps are then removed, restoring blood flow through this portion of the vessel. Clot formation is allowed to form and grow for 30 minutes after which the vein is cut just below the stenotic ligature and inspected for blood flow (the absence of blood flow is recorded as complete occlusion). The entire isolated segment of vein is then ligated and the formed clot is removed and weighed (wet weight). The effect of test agents on final clot weights is used as the primary end point. Animals are maintained for an additional thirty minutes to obtain a final pharmacodynamic measure of anticoagulation. Drug administration is initiated 15 minutes prior to vascular injury with W-1 and continued through the period of clot formation and maturation. Three blood samples (3 ml ea.) are obtained for evaluation of hemostatic parameters: one just prior to administration of W-1; a second 30 minutes after removal of the vascular clamps and a third at the termination of the experiment. Antithrombotic efficacy is expressed as a reduction in the final clot weight in preparations treated with a compound according to the invention relative to vehicle treated control animals.

Experimental in vivo Rat Arterial Thrombosis Model:

The antithrombotic efficacy of factor Xa inhibitors against platelet-rich arterial thrombosis may be evaluated using a well characterized rat carotid artery $FeCl_2$-induced thrombosis model (Superior Activity of a Thromboxane Receptor Antagonist as Compared with Aspirin in Rat Models of Arterial and Venous Thrombosis, W. A. Schumacher, C. L. Heran, T. E. Steinbacher, S. Youssef and M. L. Ogletree. Journal of Cardiovascular Pharmacology, 2, 526-533 (1993); Rat Model of Arterial Thrombosis Induced by Ferric Chloride, K. D. Kurtz, B. W. Main, and G. E. Sandusky. Thrombosis Research, 60, 269-280 (1990); The Effect of Thrombin Inhibition in a Rat Arterial Thrombosis Model, R. J. Broersma, L. W. Kutcher and E. F. Heminger. Thrombosis Research 64, 405-412 (1991). This model is widely used to evaluate the antithrombotic potential of a variety of agents including heparin and the direct acting thrombin inhibitors.

Sprague Dawley rats weighing 375-450 g are anesthetized with sodium pentobarbital (50 mg/kg i.p.). Upon reaching an acceptable level of anesthesia, the ventral surface of the neck is shaved and prepared for aseptic surgery. Electrocardiogram electrodes are connected and lead II is monitored throughout the experiment. The right femoral vein and artery are cannulated with PE-50 tubing for administration of a compound according to the invention and for obtaining blood samples and monitoring blood pressure, respectively. A midline incision is made in the ventral surface of the neck. The trachea is exposed and intubated with PE-240 tubing to ensure airway patency. The right carotid artery is isolated and two 4-0 silk sutures are placed around the vessel to facilitate instrumentation. An electromagnetic flow probe (0.95-1.0 mm lumen) is placed around the vessel to measure blood flow. Distal to the probe a 4×4 mm strip of parafilm is placed under the vessel to isolate it from the surrounding muscle bed. After baseline flow measurements are made, a 2×5 mm strip of filter paper previously saturated in 35% $FeCl_2$ is placed on top of the vessel downstream from the probe for ten minutes and then removed. The $FeCl_2$ is thought to diffuse into the underlying segment of artery and cause deendothelialization resulting in acute thrombus formation. Following application of the $FeCl_2$-soaked filter paper, blood pressure, carotid artery blood flow and heart rate are monitored for an observation period of 60 minutes. Following occlusion of the vessel (defined as the attainment of zero blood flow), or 60 minutes after filter paper application if patency is maintained, the artery is ligated proximal and distal to the area of injury and the vessel is excised. The thrombus is removed and weighed immediately and recorded as the primary end point of the study.

Following surgical instrumentation a control blood sample (B1) is drawn. All blood samples are collected from the arterial catheter and mixed with sodium citrate to prevent clotting. After each blood sample, the catheter is flushed with 0.5 ml of 0.9% saline. A compound according to the invention is administered intravenously (i.v.) starting 5 minutes prior to $FeCl_2$ application. The time between $FeCl_2$ application and the time at which carotid blood flow reached zero is recorded as time to occlusion (TTO). For vessels that did not occlude within 60 minutes, TTO is assigned a value of 60 minutes. Five minutes after application of $FeCl_2$, a second blood sample is drawn (B2). After 10 minutes of $FeCl_2$ exposure, the filter paper is removed from the vessel and the animal is monitored for the remainder of the experiment. Upon reaching zero blood flow blood a third blood sample is drawn (B3) and the clot is removed and weighed. Template bleeding time measurements are performed on the forelimb toe pads at the same time that blood samples are obtained. Coagulation profiles consisting of activated partial thromboplastin time (APTT) and prothrombin time (PT) are performed on all blood samples. In some instances a compound according to the invention may be administered orally. Rats are restrained manually using standard techniques and compounds are administered by intragastric gavage using a 18 gauge curved dosing needle (volume of 5 ml/kg). Fifteen minutes after intragastric dosing, the animal is anesthetized and instrumented as described previously. Experiments are then performed according to the protocol described above.

Experimental Canine Intravenous and Intragastric Dosing Experiments.

Beagle dogs (9-13 kg) of either sex are used to evaluate the pharmacodynamic effect of compounds of this invention after intravenous and intragastric dosing. Blood samples for these experiments are obtained via venipuncture of the cephalic vein. After discarding the first 0.5 ml of blood drawn, the control sample of 4.5 ml of blood is drawn into chilled plastic syringes containing 0.5 ml of trisodium citrate. After drug administration, 0.9 ml of blood is obtained at each time point (after discarding the first 0.5 ml of blood) by drawing the sample directly into chilled plastic syringes containing 0.1 ml trisodium citrate.

For the intravenous experiments, compounds are administered in the cephalic vein in the forelimb contralateral to that used for blood sampling. Compounds are dissolved in saline (0.5 ml/kg body weight) and administered as an i.v. bolus. Post-dosing blood samples are obtained at specific time points after dosing.

For the intragastric experiments, Compounds (in 0.5% methyl cellulose and 1% polysorbate-80, 1 ml/kg dosing volume) are administered via an intragastric feeding tube. A pre-dosing control blood sample is obtained as above and post-dosing samples are obtained at specific time points after dosing.

Coagulation times. Platelet-poor plasma is used for determination of activated partial thromboplastin time (APTT) and prothrombin time (PT), which are measured using a Microsample Coagulation Analyzer (MCA210, Bio Data Corp, Horsham, Pa.) and Dade® reagents (Thromboplastin-C Plus and Acting® FS Activated PTT reagent, Baxter Diagnostics, Inc., Deerfield, Ill.).

Ex vivo inhibition of Factor Xa. Factor-Xa inhibitory activity is analyzed by chromogenic methods using reagents (bovine factor Xa and spectrozyme Xa) supplied by American Diagnostica (Greenwich, Conn.). The rate of change of optical density (Vmax, 405 nm) is measured using a SPECTRAmax microtiter plate spectrophotometer and Softmax Pro software (Molecular Devices Corp., Sunnyvale, Calif.). Inhibition of Xa activity is determined as follows: percent inhibition of Xa activity=1-(Vmax of sample with inhibitor/Vmax of the pre-drug control sample) X 100.

One skilled in the art will readily appreciate that the present invention is well adapted to carry out the objects of the invention and obtain the ends and advantages mentioned, as well as those inherent therein. The compounds, compositions and methods described herein are presented as representative of the preferred embodiments, or intended to be exemplary and not intended as limitations on the scope of the present invention.

The present invention may be embodied in other specific forms without departing from the spirit or essential attributes thereof.

We claim:

1. A compound of formula

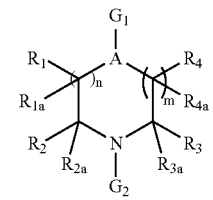

or a pharmaceutically acceptable salt thereof, pharmaceutically acceptable prodrug thereof, an N-oxide thereof, a hydrate thereof or a solvate thereof
wherein
$G_1$ is $L_1$-$Cy_1$;
$G_2$ is $L_2$-$Cy_2$;
$Cy_1$ and $Cy_2$ are independently selected from optionally substituted heteroaryl, optionally substituted fused arylheterocyclyl, optionally substituted fused arylheterocyclenyl, optionally substituted fused heteroarylcycloalkyl, optionally substituted fused heteroarylcycloalkenyl, optionally substituted fused heteroarylheterocyclyl and optionally substituted fused heteroarylheterocyclenyl;
$L_1$ is —S(O)$_2$—;
$L_2$ is $C_{(1-4)}$ alkylene;
A is N;
$R_1$, $R_{1a}$, $R_2$, $R_{2a}$, $R_4$ and $R_{4a}$ are independently selected from hydrogen, carboxy, alkoxycarbonyl, $Y_1Y_2NCO$, optionally substituted alkyl, optionally substituted aryl, optionally substituted aralkyl, optionally substituted heteroaryl and optionally substituted heteroaralkyl;

$R_3$ and $R_{3a}$ taken together form O;

m is 1;

n is 1; and $Y_1$ and $Y_2$ are independently hydrogen, optionally substituted alkyl, optionally substituted aryl, optionally substituted aralkyl or optionally substituted heteroaralkyl, or $Y_1$ and $Y_2$ taken together with the N through which $Y_1$ and $Y_2$ are linked form a monocyclic heterocyclyl.

2. A compound according to claim 1 wherein $Cy_2$ contains at least one nitrogen atom.

3. A compound according to claim 1 wherein $R_1$, $R_{1a}$, $R_2$, $R_{2a}$, and $R_4$ are hydrogen, and $R_{4a}$ is hydrogen or optionally substituted alkyl.

4. A compound according to claim 1 wherein $R_1$, $R_2$, $R_{2a}$, and $R_4$ are hydrogen; and $R_{1a}$ and $R_{4a}$ are independently selected from hydrogen, carboxy, alkoxycarbonyl, $Y_1Y_2NCO$ or optionally substituted alkyl.

5. A compound according to claim 1 wherein $L_2$ is alkylene of one to three carbon atoms.

6. A pharmaceutical composition comprising a pharmaceutically effective amount of a compound according to claim 1 and a pharmaceutically acceptable carrier.

7. A compound according to claim 1 wherein $Cy_2$ is optionally substituted with one or more groups selected from amino, carbamoyl, acylamino, heteroaryl, heterocyclenyl, heterocyclyl, alkyl, alkyloxycarbonyl, amidino, hydroxy, alkoxy, aryl, isourea, guanidino, acylhydrazino, acyl, cyano, carboxy, sulfamoyl, or halo.

8. A compound according to claim 1 wherein $Cy_2$ is optionally substituted with one or more groups selected from amino, hydroxy, or halo.

9. A compound according to claim 1 wherein $Cy_1$ is optionally substituted with one of more groups selected from amino, halo, hydroxyl, aryl, heteroaryl, amidino, alkyl, acylamino, carbamoyl, cyano, alkoxy, nitro, carbamate, sulfamyl.

10. A compound according to claim 1 wherein at least one of $R_1$ or $R_4$ is alkoxyalkyl, alkylthioalkyl, alkylsulfinylalkyl, alkylsulfonylalkyl, alkoxycarbonylalkyl, hydroxyalkyl, acylalkyl, acylaminoalkyl or carbamoylalkyl; and the corresponding $R_{1a}$ or $R_{4a}$ is hydrogen.

11. A compound according to claim 1 wherein at least one of $R_1$ or $R_4$ is lower alkyl, carboxy, alkoxycarbonyl or carbamoyl, and the corresponding $R_{1a}$ or $R_{4a}$ is hydrogen.

12. A compound according to claim 1 having the formula IIb

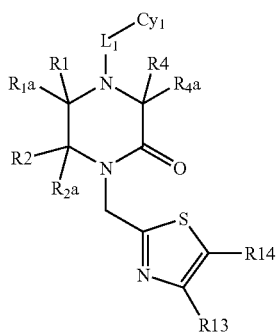

IIb or a pharmaceutically acceptable salt thereof, pharmaceutically acceptable prodrug thereof, an N-oxide thereof, a hydrate thereof or a solvate thereof, wherein $R_1$, $R_{1a}$, $R_2$, $R_{2a}$, $R_4$, $R_{4a}$, $L_1$ and $Cy_1$ are as defined in claim 1; and $R_{13}$ and $R_{14}$ are independently hydrogen, lower alkyl, aryl, heteroaryl, amino, acylaminoalkyl, alkoxycarbonylalkyl, carbamoylalkyl or alkoxyalkyl; or $R_{13}$ and $R_{14}$ together with the carbon atoms through which $R_{13}$ and $R_{14}$ are linked form a cycloalkyl group, cycloalkenyl group, heterocyclyl group, heterocyclenyl group, aryl group or heteroaryl group.

13. A compound according to claim 1 having the formula IIc

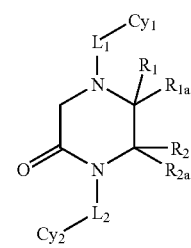

IIc or a pharmaceutically acceptable salt thereof, pharmaceutically acceptable prodrug thereof, an N-oxide thereof, a hydrate thereof or a solvate thereof, wherein:

$Cy_1$ is thiaheteroaryl or azaheteroaryl, $L_1$ is $-S(O)_2$;

$R_1$, $R_{1a}$, $R_2$, and $R_{2a}$ are independently hydrogen, alkyl, carboxyl, alkoxycarbonyl, or carbamoyl;

$L_2$ is methylene; and $Cy_2$ is azaheteroaryl, fused azaheteroarylcycloalkyl, fused azaheteroarylcycloalkenyl, fused heteroarylazacycloalkyl or fused heteroarylazacycloalkenyl.

14. A compound according to claim 1 having the formula IId

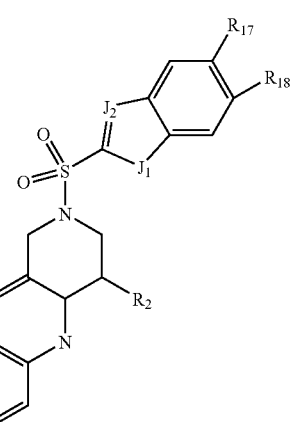

IId wherein $R_{17}$ and $R_{18}$ are independently hydrogen or halogen;

$J_1$ is S or NH;

$J_2$ is CH or N; and $R_2$ is hydrogen, alkyl, carboxyl, alkoxycarbonyl, or carbamoyl.

15. A compound according to claim 1 selected from the group consisting of 1-(2- Amino-quinoxalin-6-ylmethyl)-4-(6-chloro-benzo[b]thiopbene2sulfonyl)-piperazin-2-one, 4-(6-Chloro-benzo[b]thiophene-2-sulfonyl)-1-thieno[2,3-c]pyridin-2-ylmethyl-piperazin-2-one, 4-(6-Chloro-benzo[b]thiophene-2-sulfonyl)-1-thieno[3,2-c]pyridin-2-ylmethyl-piperazin-2-one, 1-(2-Amino-quinolin-6-ylmethyl)-4-(6-chloro-thieno[2,3-b]pyridine2sulfonyl)piperazin2one, 4-(6-Chloro-benzo[b]thiophene-2-sulfonyl)-1-(1-chloro-isoquinolin-6-ylmethyl)-piperazin-2-one, 1-(7-Amino-thieno[2,3-c]pyridin-2-ylmethyl)-4-(6-chloro-benzo[b]thiophene-2-sulfonyl)-piperazin-2-one, 4-(6-Chloro-benzo[b]thiophene-2-sulfonyl)-1-quinolin-6-ylmethyl-piperazin-2-one, 1-(2-Amino-quinoin-7-ylmethyl )-4-(6-chloro-benzo[b]thiophene-2sulfonyl)-piperazin-2-one, 1-(4-Amino-thieno[3,2-c]pyridin-2-ylmethyl)-4-(6-chloro-benzo[b]thiophene-2sulfonyl)-piperazin-2-one, 4-(6-Chloro-benzo[b]thiophene-2-sulfonyl)-1-isoquinolin-6-ylmethyl-piperazin-2-one, 1-(2-Amino-quinolin-6-ylmethyl)-4-(6-chloro-benzo[b]thiophene-2-sulfonyl)-piperazin-2-one, 1-(1-Amino-isoquinolin-6-ylmethyl)-4-(6-chloro-benzo[b]thiophene2sulfonyl)piperazin2one, 1-(1-Amino-isoquinolin-7-ylmethyl)-4-(6-chloro-benzo[b]thiophene2sulfonyl)-piperazin-2-one, 1-(4-Amino-thieno[3,2-c]pyridin-2-ylmethyl)-4-(6-chloro-benzo[b]thiophene-2-sulfonyly)-piperazin-2-one, 1-(4-Amino-quinazolin-7-ylmethyl)-4-(6-chloro-thieno[2,3-b]pyridine-2-sulfonyl)piperazin-2-one, 1-(4-Amino-quinazolin-7-ylmethyl)-4-(6-chloro-1H-benzoimidazole-2-sulfonyl)-piperazin-2-one, (S)-1-(4-Amino-quinazolin-7-ylmethyl)-4-(6-chloro-benzo[b]thiophene-2-sulfonyl)-3-ethyl-piperazin-2-one, (S)-1-(4-Amino-quinazolin-7-ylmethyl)-4-(6-chloro-benzo[b]thiophene-2-sulfonyl)-3-methyl-piperazin-2-one, (+/−)-1-(4-Amino-quinazolin-7-ylmethyl)-4-(6-chloro-benzo[b]thiophene-2-sulfonyl)-6-methyl-piperazin-2-one, 4-(6-Chloro-benzo[b]thiophene-2-sulfonyl)-1-(5-oxy-1H-pyrrolo[3,2-c]pyridin-2-ylmethyl)-piperazin-2-one, 4-(6-Chloro-benzo[b]thiophene-2-sulfonyl)-1-(1-methyl-1H-pyrrolo[3,2-c]pyridin-2-ylmethyl)-piperazin-2-one, 4-(6-Chloro-thieno[2,3-b]pyridine-2-sulfonyl)-1-(1H-pyrrolo[3,2-c]pyridin-2-ylmethyl)-piperazin-2-one, 4-(6- Bromo-benzo[b]thiophene-2-sulfonyl)-1-(1H-pyrrolo[3,2-c]pyridin-2-ylmethyl)-piperazin-2-one, 4-(5'-Chloro-[2,2']bithiophenyl-5-sulfonyl)-1-(1H-pyrrolo[3,2-c]pyridin-2-ylmethyl)-piperazin-2-one, 2-{2-[4-(6-Chloro-benzo[b]thiophene-2-sulfonyl)-2-oxo-piperazin-1-ylmethyl]-pyrrolo[3,2-c]pyridin-1-yl}-acetamide, 4-(6-Chloro-benzo[b]thiophene-2-sulfonyl)-1-[1-(2-hydroxy-ethyl)-1H-pyrrolo[3,2-c]pyridin-2-ylmethyl]-piperazin-2-one, 4-(6-Chloro-1H-benzoimidazole-2-sulfonyl)-1-(1H-pyrrolo[3,2-c]pyridin-2-ylmethyl)-piperazin-2-one, 4-(1H-Benzoimidazolc-2-sulfonyl)-1-(1H-pyrrolo[3,2-c]pyridin-2-ylmethyl)-piperazin-2-one, 4-(6-Chloro-benzo[b]thiophene-2-sulfonyl)-1-(1H-pyrrolo[2,3-c]pyridin-2-ylmethyl)-piperazin-2-one, 4-(6-Chloro-thieno[2,3-b]pyridine-2-sulfonyl)-1-(1H-pyrrolo[2,3-c]pyridin-2-ylmethyl)-piperazin-2-one, 4-(6-Chloro-benzo[b]thiophene-2-sulfonyl)-6-oxo-1-(1H-pyrrolo[3,2-c]pyridin-2-ylmethyl)-piperazine-2-carboxylic acid amide, (3S,5S)-1-(4-Amino-quinazolin-7-ylmethyl)-4-(6-chloro-benzo[b]thiophene-2-sulfonyl)-3,5-dimethyl-piperazin-2-one, 1-(4-Amino-quinolin-7-ylmethyl)-4-(6-chloro-benzo[b]thiophene-2-sulfonyl)-piperazin-2-one, 1-(S)-(4-Amino-quinolin-7-ylmethyl )-4-(6-chloro-benzo[b]thiophene-2-sulfonyl)-3-methyl-piperazin-2-one, 1-(4-Amino-quinolin-7-ylmethyl)-4-(6-chloro-benzo[b]thiophene-2-sulfonyl)-6-oxo-piperazine-2-carboxylic acid methylamide, 1-(4-Amino-quinolin-7-ylmethyl)-4-(6-chloro-benzo[b]thiophene-2-sulfonyl)-6-oxo-piperazine-2-carboxylic acid ethylamide, 1-(4-Amino-quinolin-7-ylmethyl)-4-(6-chloro-benzo[b]thiophene-2-sulfonyl)-6-oxo-piperazine-2-carboxylic acid dimethylamide, 1-(4-Amino-quinolin-7-ylmethyl)-4-(6-chloro-benzo[b]thiophene-2-sulfonyly)-6-(morpholine-4-carbonyl)-piperazin-2-one, (+/−)-1-(4-Amino-quinazolin-7-ylmethyl)-4-(6-chloro-benzo[b]thiophene-2-sulfonyl)-6-oxo-piperazine-2-carboxylic acid amide, 1-(4-Amino-quinolin-7-ylmethyl)-4-(6-chloro-benzo[b]thiophene-2-sulfonyl)-6-oxo-piperazine-2-carboxylic acid methylamide, 1-(4-Amino-quinolin-7-ylmethyl)-4-(6-chloro-benzo[b]thiophene-2-sulfonyl)-6-oxo-piperazine-2-carboxylic acid ethylamide, 1-(4-Amino-quinolin-7-ylmethyl)-4-(6-chloro-benzo[b]thiophene-2-sulfonyl)-6-oxo-piperazine-2-carboxylic acid dimethylamide, 1-(4-Amino-quinolin-7-ylmethyl)-4-(6-chloro-benzo[b]thiophene-2-sulfonyl)-(morpholine-4-carbonyl)-piperazin-2-one, and 1-(3-Amino-1H-indazol-6-ylmethyl)-4-(6-chloro-benzo[b]thiophene-2-sulfonyl)-piperazin-2-one, or a pharmaceutically acceptable salt thereof, pharmaceutically acceptable prodrug thereof, an N-oxide thereof, a hydrate thereof or a solvate thereof.

\* \* \* \* \*

UNITED STATES PATENT AND TRADEMARK OFFICE
CERTIFICATE OF CORRECTION

| | | |
|---|---|---|
| PATENT NO. | : 7,612,075 B2 | Page 1 of 1 |
| APPLICATION NO. | : 10/628093 | |
| DATED | : November 3, 2009 | |
| INVENTOR(S) | : Ewing et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (1162) days Delete the phrase "by 1162 days" and insert -- by 1830 days --

Signed and Sealed this

Twentieth Day of April, 2010

David J. Kappos
*Director of the United States Patent and Trademark Office*